US012077758B2

(12) United States Patent
Khvorova et al.

(10) Patent No.: US 12,077,758 B2
(45) Date of Patent: Sep. 3, 2024

(54) OLIGONUCLEOTIDES FOR SARS-COV-2 MODULATION

(71) Applicant: UNIVERSITY OF MASSACHUSETTS, Boston, MA (US)

(72) Inventors: Anastasia Khvorova, Westborough, MA (US); Jonathan Watts, Worcester, MA (US); Zachary Kennedy, Worcester, MA (US); Annabelle Biscans, Cambridge, MA (US); Bruno Miguel da Cruz Godinho, Worcester, MA (US); Chantal Ferguson, Worcester, MA (US); Dimas Echeverria Moreno, Worcester, MA (US); Ken Yamada, Boston, MA (US); Daniel O'Reilly, Boston, MA (US); Kathryn Monopoli, Boston, MA (US); Vignesh Narayan Hariharan, Boston, MA (US); Qi Tang, Boston, MA (US); Sarah Davis, Boston, MA (US); Samuel Hildebrand, Boston, MA (US); Socheata Ly, Boston, MA (US); Minwook Shin, Boston, MA (US); Pranathi Meda Krishnamurthy, Boston, MA (US); Nicholas McHugh, Boston, MA (US); Jacquelyn Sousa, Boston, MA (US); Jillian Caiazzi, Boston, MA (US); Yann Thillier, Boston, MA (US); Gitali Devi, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 17/333,839

(22) Filed: May 28, 2021

(65) Prior Publication Data

US 2023/0021431 A1 Jan. 26, 2023

Related U.S. Application Data

(60) Provisional application No. 63/084,817, filed on Sep. 29, 2020, provisional application No. 63/031,222, filed on May 28, 2020.

(51) Int. Cl.
*C12N 15/11* (2006.01)
*C12N 15/113* (2010.01)

(52) U.S. Cl.
CPC ...... *C12N 15/1131* (2013.01); *C12N 15/1136* (2013.01); *C12N 15/1137* (2013.01); *C12N 2310/14* (2013.01); *C12N 2310/315* (2013.01); *C12N 2310/321* (2013.01); *C12N 2310/351* (2013.01); *C12N 2310/3515* (2013.01); *C12N 2320/32* (2013.01)

(58) Field of Classification Search
CPC ............ C12N 15/1131; C12N 2310/14; C12N 2310/315; C12N 2310/351
See application file for complete search history.

(56) References Cited

U.S. PATENT DOCUMENTS

| | | | | |
|---|---|---|---|---|
| 5,328,470 | A | 7/1994 | Nabel et al. | |
| 5,684,143 | A | 11/1997 | Gryaznov et al. | |
| 5,858,988 | A | 1/1999 | Wang | |
| 6,177,403 | B1 | 1/2001 | Stedman | |
| 6,291,438 | B1 | 9/2001 | Wang | |
| 7,459,547 | B2 | 12/2008 | Zamore et al. | |
| 7,732,593 | B2 | 6/2010 | Zamore et al. | |
| 7,750,144 | B2 | 7/2010 | Zamore et al. | |
| 7,772,203 | B2 | 8/2010 | Zamore et al. | |
| 8,304,530 | B2 | 11/2012 | Zamore et al. | |
| 8,309,704 | B2 | 11/2012 | Zamore et al. | |
| 8,309,705 | B2 | 11/2012 | Zamore et al. | |
| 8,329,892 | B2 | 12/2012 | Zamore et al. | |
| 8,431,544 | B1 | 4/2013 | Agrawal et al. | |
| 2005/0100885 | A1 * | 5/2005 | Crooke | C12N 15/1137 435/5 |
| 2005/0220766 | A1 | 10/2005 | Amalfitano et al. | |
| 2006/0078542 | A1 | 4/2006 | Mah et al. | |
| 2007/0238681 | A1 | 10/2007 | Dobie et al. | |
| 2008/0269149 | A1 | 10/2008 | Bowles et al. | |
| 2009/0226921 | A1 | 9/2009 | Afar et al. | |
| 2010/0119489 | A1 * | 5/2010 | Stoffel | C12N 15/8509 435/375 |
| 2010/0186103 | A1 | 7/2010 | Gao et al. | |
| 2011/0287025 | A1 | 11/2011 | Boylan et al. | |
| 2014/0296486 | A1 | 10/2014 | Gao et al. | |
| 2017/0312367 | A1 | 11/2017 | Khvorova et al. | |

(Continued)

FOREIGN PATENT DOCUMENTS

| | | | |
|---|---|---|---|
| WO | WO 1997/005256 | A2 | 2/1997 |
| WO | WO 2004/092383 | A2 | 10/2004 |

(Continued)

OTHER PUBLICATIONS

Appendix to 63021399, pp. 1-307 (Year: 2020).*

(Continued)

*Primary Examiner* — Ekaterina Poliakova-Georgantas

(74) *Attorney, Agent, or Firm* — LATHROP GPM LLP; James H. Velema, Esq.; Michael J. Spellberg, Esq.

(57) ABSTRACT

This disclosure relates to novel SARS-CoV-2 targeting sequences. Novel SARS-CoV-2 targeting oligonucleotides for the treatment of SARS-CoV-2 infection are also provided.

18 Claims, 56 Drawing Sheets

Specification includes a Sequence Listing.

(56) References Cited

U.S. PATENT DOCUMENTS

2020/0123543 A1 4/2020 Khvorova et al.
2021/0277489 A1 9/2021 Donati et al.

FOREIGN PATENT DOCUMENTS

WO WO 2017/030973 A1 2/2017
WO WO 2017/132669 A1 8/2017
WO WO 2018/031933 A2 2/2018
WO WO 2020/198509 A2 10/2020
WO WO 2021/188841 A2 9/2021
WO WO-2021224918 A1 * 11/2021
WO WO 2021/243291 A2 12/2021

OTHER PUBLICATIONS

Ambros, et al., MicroRNAs and Other Tiny Endogenous RNAs in C. elegans, Current Biology, vol. 13, Issue 10, pp. 807-818, May 13, 2003.

Atwell, et al., Stable Heterodimers From Remodeling the Domain Interface of a Homodimer Using a Phage Display Library, Journal of Molecular Biology, vol. 270, Issue 1, pp. 26-35, Jul. 4, 1997.

Billy, et al., Specific Interference With Gene Expression Induced by Long, Double-Stranded RNA in Mouse Embryonal Teratocarcinoma Cell Lines, Proceedings of the National Academy of Sciences, vol. 98, No. 25, pp. 14428-14433, Dec. 4, 2001.

Braasch, et al., "RNA Interference in Mammalian Cells by Chemically-Modified RNA", Biochemistry, vol. 42, No. 26, pp. 7967-7975, Jun. 11, 2003.

Brummelkamp, et al., A System for Stable Expression of Short Interfering RNAs in Mammalian Cells, Science, vol. 296, Issue 5567, pp. 550-553, Apr. 19, 2002.

Carter, "Handbook of Parvoviruses", ed., P. Tijsser, CRC Press, pp. 155-168, 1990.

Chen, et al., "Gene Therapy for Brain Tumors: Regression of Experimental Gliomas by Adenovirus-Mediated Gene Transfer In Vivo", Proceedings of the National Academy of Sciences, vol. 91, No. 8, pp. 3054-3057, 1994.

Coutard, et al., The Spike Glycoprotein of the New Coronavirus 2019-nCoV Contains a Furin-like Cleavage Site Absent in CoV of the Same Clade, Antiviral Research, vol. 176, Article No. 104742, pp. 1-5, Apr. 2020.

Doench, et al., siRNAs Can Function as miRNAs, Genes & Development, vol. 17, pp. 438-442, 2003.

Ducruix et al., "Crystallization of Nucleic Acids and Proteins: A Practical Approach", Second Edition, Oxford University Press, New York, pp. 201-216, 1999.

Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.

Elmen, et al., Locked Nucleic Acid (LNA) Mediated Improvements in siRNA Stability and Functionality, Nucleic Acids Research, vol. 33, Issue 1, pp. 439-447, Jan. 14, 2005.

Fattal, et al., Biodegradable Polyalkylcyanoacrylate Nanoparticles for the Delivery of Oligonucleotides, Journal of Controlled Release, vol. 53, pp. 137-143, May 1998.

Fisher, et al., Transduction With Recombinant Adeno-Associated Virus for Gene Therapy Is Limited by Leading-Strand Synthesis, Journal of virology, vol. 70, No. 1, pp. 520-532, Jan. 1996.

Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.

Grad, et al., Computational and Experimental Identification of C. elegans microRNAs, Molecular Cell, vol. 11, Issue 5, pp. 1253-1263, May 2003.

Griffiths-Jones, San, The microRNA Registry, Nucleic Acids Research, vol. 32, Issue Supplement 1, pp. D109-D111, Jan. 1, 2004.

Hammerling et al., Monoclonal Antibodies and T-Cell Hybridomas, Research Monographs in Immunology, vol. 3, pp. 563-681, 1981.

Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.

Hutvagner, et al., A microRNA in a Multiple-Turnover RNAi Enzyme Complex, Science, vol. 297, Issue 5589, pp. 2056-2060, Sep. 20, 2002.

Institut Pasteur, Protocol: Real-time RT-PCR assays for the detection of SARS-CoV-2, Retrieved Nov. 2, 2021 from: <<https://www.who.int/docs/default-source/coronaviruse/real-time-rt-pcr-assays-for-the-detection-of-sars-cov-2-institut-pasteur-paris.pdf>>, pp. 1-3.

International Search Report & Written Opinion for PCT International Patent Application No. PCT/US2021/035002, mailed Jan. 6, 2022.

Iwata-Yoshikawa, et al., TMPRSS2 Contributes to Virus Spread and Immunopathology in the Airways of Murine Models after Coronavirus Infection, Journal of Virology, vol. 93, No. 6, pp. e01815-e01818, Mar. 5, 2019.

Jung, et al., Comparative Analysis of Primer-probe Sets for the Laboratory Confirmation of SARS-CoV-2, Feb. 27, 2020, Retrieved from: <<https://web.archive.org/web/20200715075740id_/https://www.biorxiv.org/content/biorxiv/early/2020/Feb. 27, 2020.02.25.964775.full.pdf>>, 13 Pages.

Karlin, et al., Applications and Statistics for Multiple High-Scoring Segments in Molecular Sequences, Proceedings of the National Academy of Sciences of the USA, vol. 90, pp. 5873-5877, Jun. 1993.

Karlin, et al., Methods for Assessing the Statistical Significance of Molecular Sequence Features by Using General Scoring Schemes, Proceedings of the National Academy of science of the USA, vol. 87, No. 6, pp. 2264-2268, Mar. 1990.

Lagos-Quintana, et al., Identification of Novel Genes Coding for Small Expressed RNAs, Science, vol. 294, Issue 5543, pp. 853-858, Oct. 26, 2001.

Lagos-Quintana, et al., Identification of Tissue-Specific MicroRNAs from Mouse, Current Biology, vol. 12, Issue 9, pp. 735-739, Apr. 30, 2002.

Lai, et al., Computational Identification of *Drosophila* microRNA Genes, Genome Biology, vol. 4, No. 7, pp. 1-20, Jun. 30, 2003.

Lam, et al., "A New Type of Synthetic Peptide Library for Identifying Ligand-Binding Activity", Nature, vol. 354, pp. 82-84, Nov. 7, 1991.

Lambert, et al., "Nanoparticulate Systems for the Delivery of Antisense Oligonucleotides", Advanced Drug Delivery Reviews, vol. 47, pp. 99-112, 2001.

Langer, et al., Medical Applications of Controlled Release, CRC Press, Boca Raton, Florida, pp. 115-138, 1974.

Lim, et al., The microRNAs of Caenorhabditis elegans, Genes & Development, vol. 17, No. 8, pp. 991-1008, 2003.

Lim, et al., Vertebrate MicroRNA Genes, Science, vol. 299, Issue 5612, p. 1540, Mar. 7, 2003.

Liu, et al., Can we use Interleukin-6 (IL-6) Blockade for Coronavirus Disease 2019 (COVID-19)-Induced Cytokine Release Syndrome (CRS)?, Journal of Autoimmunity, vol. 111, Article No. 102452, pp. 1-8, Jul. 2020.

Miyagishi, et al., U6 promoter-driven siRNAs With Four Uridine 3' Overhangs Efficiently Suppress Targeted Gene Expression in Mammalian Cells, Nature Biotechnology, vol. 20, No. 5, pp. 497-500, May 1, 2002.

Mourelatos, et al., miRNPs: A Novel Class of Ribonucleoproteins Containing Numerous microRNAs, Genes & Development, vol. 16, No. 6, pp. 720-728, 2002.

Nielsen, et al., Sequence-Selective Recognition of DNA by Strand Displacement With a Thymine-Substituted Polyamide, Science, vol. 254, Issue 5037, pp. 1497-1500, Dec. 6, 1991.

Petersen, et al., LNA: A Versatile Tool for Therapeutics and Genomics, Trends in Biotechnology, vol. 21, Issue 2, pp. 74-81, Feb. 2003.

Reinhart, et al., Small RNAs Correspond to Centromere Heterochromatic Repeats, Science, vol. 297, No. 5588, 1 Page, Sep. 13, 2002.

Rusckowski, et al., Biodistribution and Metabolism of a Mixed Backbone Oligonucleotide (GEM 231) Following Single and Mul-

(56) References Cited

OTHER PUBLICATIONS tiple Dose Administration in Mice, Antisense and Nucleic Acid Drug Development, vol. 10, Issue 5, pp. 333-345, Jan. 30, 2009.
Schwab, et al., An Approach for New Anticancer Drugs:Oncogene-Targeted Antisense DNA, Annals of Oncology, vol. 5, Issue 4, pp. 55-58, 1994.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wright, et al., Identification of Factors That Contribute to Recombinant AAV2 Particle Aggregation and Methods to Prevent Its Occurrence During Vector Purification and Formulation, Molecular Therapy, vol. 12, Issue 1,, pp. 171-178, Jul. 2005.
Wu, et al., A New Coronavirus Associated With Human Respiratory Disease in China, Nature, vol. 579, pp. 265-269, Feb. 3, 2020.
Yekta et al., MicroRNA-directed cleavage of HOXB8 mRNA, Science, 304(5670):594-596, doi: 10.1126/science.1097434, (Apr. 23, 2004).
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Chowdury et al., “A computational approach to design potential siRNA molecules as a prospective tool for silencing nucleocapsid phosphoprotein and surface glycopretoein gene of SARS-CoV-2”, Genomics, Jan. 2021, 113(1 Pt. 1): 331-343.
Partial Supplementary European Search Report for European Patent Application No. 21814500.1, dated Jun. 13, 2024.

* cited by examiner

ACE2
human genomic sequence ENST00000427411

Transcripts
human NM_021804 mouse NM_001130513

FURIN
human genomic sequence ENST00000268171.8

Transcripts
human NM_002569 mouse isoform 1 NM_001081454 mouse isoform 2 NM_011046

Intratracheal; 20 nmol for mono, 40 nmol for di; n=2, 24h, 40x, Scale=50 um

Intratracheal; 20 nmol for mono, 40 nmol for di; n=2, 24h, 40x, Scale=50 um

Intratracheal; 20 nmol for mono, 40 nmol for di; n=2, 24h, 40x, Scale=50 um

Subcutaneous; 40 nmol; n=3, 24h, 40x, Scale=50 um

Subcutaneous; 40 nmol; n=3, 24h, 40x, Scale=50 um

Subcutaneous; 40 nmol; n=3, 24h, 40x, Scale=50 um

| oligo | alveoli cells / total cells |
|---|---|
| PBS | 29/261 = 11% |
| mono | 64/544 = 12% |
| dio | 55/556 = 10% |
| EPA | 99/675 = 15% |
| DCA | 36/354 = 10% |

| oligo | club cells / total cells |
|---|---|
| PBS | 64/251 = 25% |
| mono | 134/627 = 21% |
| dio | 97/615 = 16% |
| EPA | 142/601 = 24% |
| DCA | 101/691 = 15% |

Plate 1

Plate 2

OLIGONUCLEOTIDES FOR SARS-COV-2 MODULATION

CROSS-REFERENCE TO RELATED APPLICATIONS

This application claims the benefit of U.S. Provisional Application Ser. No. 63/031,222, filed May 28, 2020, and U.S. Provisional Application Ser. No. 63/084,817, filed Sep. 29, 2020, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Sep. 8, 2021, is named 718622_UM9-258_ST25.txt and is 520,824 bytes in size.

FIELD OF THE INVENTION

This disclosure relates to novel SARS-CoV-2 targeting sequences, novel branched oligonucleotides, and novel methods for treating and preventing SARS-CoV-2-related infection.

BACKGROUND

SARS-CoV-2 (severe acute respiratory syndrome coronavirus 2) is a highly infectious virus that causes severe respiratory illness. The SARS-CoV-2 genome encodes for four structural proteins, S (spike), E (envelope), M (membrane) and N (nucleocapsid). The spike protein plays a critical role in viral entry into a host cell. SARS-CoV-2 is the causative agent of the COVID-19 epidemic that has infected and kills millions of people worldwide.

RNAi-based therapeutics are revolutionizing human medicine. Currently, a single subcutaneous injection of chemically modified oligonucleotide compounds supports up to 12-months of target silencing in the liver with a clean adverse events profile. The ability to develop RNAi-based drugs is dependent on efficient delivery to the targeted tissues. Currently, the liver is the only tissue validated for clinical delivery.

With the current clinical approaches, it is not possible to halt or cure SARS-CoV-2 infection. The highly infectious virus is spreading throughout the world, leaving a path of destruction and death. Survivors of a severe infection with SARS-CoV-2 often present with long lasting lung injury and scarring.

There is a clear need for a therapeutic that can effectively neutralize SARS-CoV-2 particles from causing infection, and especially to selectively do so in the lung. This could be accomplished using optimized RNAi-based therapeutics, which is addressed in the present application.

SUMMARY

In one aspect, the disclosure provides an RNA molecule having a length of from about 8 nucleotides to about 80 nucleotides; and a nucleic acid sequence that is substantially complementary to a SARS-CoV-2 nucleic acid sequence of SEQ ID NO: 1. In certain embodiments, the RNA molecule is from 8 nucleotides to 80 nucleotides in length (e.g., 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, 50 nucleotides, 51 nucleotides, 52 nucleotides, 53 nucleotides, 54 nucleotides, 55 nucleotides, 56 nucleotides, 57 nucleotides, 58 nucleotides, 59 nucleotides, 60 nucleotides, 61 nucleotides, 62 nucleotides, 63 nucleotides, 64 nucleotides, 65 nucleotides, 66 nucleotides, 67 nucleotides, 68 nucleotides, 69 nucleotides, 70 nucleotides, 71 nucleotides, 72 nucleotides, 73 nucleotides, 74 nucleotides, 75 nucleotides, 76 nucleotides, 77 nucleotides, 78 nucleotides, 79 nucleotides, or 80 nucleotides in length).

In certain embodiments, the RNA molecule is from 10 to 50 nucleotides in length (e.g., 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, or 50 nucleotides in length).

In certain embodiments, the RNA molecule comprises about 15 nucleotides to about 25 nucleotides in length. In certain embodiments, the RNA molecule is from 15 to 25 nucleotides in length (e.g., 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, or 25 nucleotides in length).

In one aspect, the disclosure provides an oligonucleotide compound comprising 15 to 35 bases in length, comprising a sequence substantially complementary to a SARS-CoV-2 nucleic acid sequence of SEQ ID NO: 1.

In certain embodiments, the oligonucleotide compound comprises a sequence substantially complementary to a SARS-CoV-2 nucleic acid sequence of any one of SEQ ID NOs: 2-10.

In certain embodiments, the oligonucleotide compound comprises a sequence substantially complementary to a SARS-CoV-2 nucleic acid sequence of any one of the 45-nucleotide target gene regions in Table 6A.

In certain embodiments, the oligonucleotide compound comprises a sequence substantially complementary to a SARS-CoV-2 nucleic acid sequence of any one of the 20-nucleotide targets in Table 6A.

In certain embodiments, the oligonucleotide compound comprises a sequence substantially complementary to a SARS-CoV-2 nucleic acid sequence of any one of the 45-nucleotide target gene regions of 7a_27751, N_29293, Orf1a_2290, and Orf1ab_18571 in Table 6A.

In certain embodiments, the oligonucleotide compound comprises a sequence substantially complementary to a SARS-CoV-2 nucleic acid sequence of any one of the 20-nucleotide targets of 7a_27751, N_29293, Orf1a_2290, and Orf1ab_18571 in Table 6A.

In certain embodiments, the oligonucleotide compound comprises complementarity to at least 10, 11, 12 or 13 contiguous nucleotides of the SARS-CoV-2 nucleic acid sequence of any one of SEQ ID NOs: 1-10. In certain embodiments, the oligonucleotide compound comprises no more than 3 mismatches with the SARS-CoV-2 nucleic acid sequence of any one of SEQ ID NOs: 1-10. In certain embodiments, the oligonucleotide compound comprises full complementarity to the SARS-CoV-2 nucleic acid sequence of any one of SEQ ID NOs: 1-10.

In another aspect, the disclosure provides an oligonucleotide compound comprising 15 to 35 bases in length, comprising a sequence substantially complementary to an Angiotensin I Converting Enzyme 2 (ACE2) nucleic acid sequence of any one of the 45-nucleotide target gene regions in Table 1 ID or Table 12C.

In certain embodiments, the oligonucleotide compound comprises a sequence substantially complementary to an ACE2 nucleic acid sequence of any one of the 45-nucleotide target gene regions of ACE2_119, ACE2_336, ACE2_349, ACE_1034, ACE_1775, ACE_784, ACE_908, and ACE_1071, as recited in Table 12C.

In another aspect, the disclosure provides an oligonucleotide compound comprising 15 to 35 bases in length, comprising a sequence substantially complementary to a FURIN nucleic acid sequence of any one of the 45-nucleotide target gene regions in Table 1 IC or Table 12D.

In certain embodiments, the oligonucleotide compound comprises a sequence substantially complementary to a FURIN nucleic acid sequence of any one of the 45-nucleotide target gene regions of FURIN_443, FURIN_1959, FURIN_2711, FURIN_2712, FURIN_3524, and FURIN_3526, as recited in Table 12D.

In one aspect, the disclosure provides an oligonucleotide compound comprising 15 to 35 bases in length, comprising a sequence substantially complementary to an Interleukin 6 (IL-6) nucleic acid sequence of any one of the 45-nucleotide target gene regions in Table 11B or Table 12B.

In one aspect, the disclosure provides an oligonucleotide compound comprising 15 to 35 bases in length, comprising a sequence substantially complementary to an Interleukin 6 Receptor (IL-6R) nucleic acid sequence of any one of the 45-nucleotide target gene regions in Table 12E.

In one aspect, the disclosure provides an oligonucleotide compound comprising 15 to 35 bases in length, comprising a sequence substantially complementary to a Transmembrane Serine Protease 2 (TMPRSS2) nucleic acid sequence of any one of the 45-nucleotide target gene regions in Table 11A or Table 12A.

In certain embodiments, the oligonucleotide compound comprises one or more naturally occurring nucleotides.

In certain embodiments, the oligonucleotide compound comprises one or more modified nucleotide.

In certain embodiments, the one or more modified nucleotides each independently comprise a modification of a ribose group, a phosphate group, a nucleobase, or a combination thereof.

In certain embodiments, each modification of the ribose group is independently selected from the group consisting of 2'-O-methyl, 2'-fluoro, 2'-deoxy, 2'-O-(2-methoxyethyl) (MOE), 2'-O-alkyl, 2'-O-alkoxy, 2'-O-alkylamino, 2'-$NH_2$, and a constrained nucleotide.

In certain embodiments, the constrained nucleotide is selected from the group consisting of a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid (2',4'-$BNA^{NC}$), an alpha-L-locked nucleic acid, a tricyclo-DNA, and any combination thereof.

In certain embodiments, the constrained nucleotide is a locked nucleic acid (LNA), a 2'-(S)-constrained ethyl (S-cEt) nucleotide, and a combination thereof.

In certain embodiments, each modification of the nucleobase group is independently selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, and halogenated aromatic groups.

In certain embodiments, each modification of the phosphate group is independently selected from the group consisting of a phosphorothioate, phosphonoacetate (PACE), thiophosphonoacetate (thioPACE), amide, triazole, phosphonate, and phosphotriester modification.

In certain embodiments, the modification of the phosphate group is phosphorothioate.

In certain embodiments, the oligonucleotide compound comprises 4-16 phosphorothioate modifications. In certain embodiments, the oligonucleotide compound comprises 6-13 phosphorothioate modifications.

In certain embodiments, the oligonucleotide compound comprises at least one modified internucleotide linkage.

In certain embodiments, the oligonucleotide compound comprises at least one modified internucleotide linkage of Formula I:

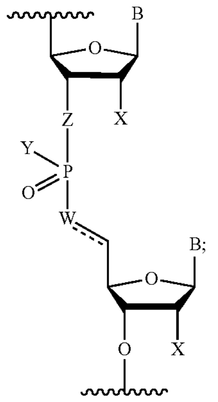
(I)

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and $\equiv$ is an optional double bond.

In certain embodiments, the oligonucleotide compound comprises at least 80% chemically modified nucleotides. In certain embodiments, the oligonucleotide compound is fully chemically modified.

In certain embodiments, the oligonucleotide compound comprises an antisense oligonucleotide or a double stranded (ds) RNA.

In certain embodiments, the dsRNA comprises an antisense strand and a sense strand. In certain embodiments, the antisense strand comprises about 15 nucleotides to 25 nucleotides in length. In certain embodiments, the sense strand comprises about 15 nucleotides to 25 nucleotides in length. In certain embodiments, the antisense strand is 20 nucleotides in length, 21 nucleotides in length, or 22 nucleotides in length. In certain embodiments, the sense strand is 15 nucleotides in length, 16 nucleotides in length, 18 nucleotides in length, or 20 nucleotides in length.

In certain embodiments, the dsRNA comprises a double-stranded region of 15 base pairs to 20 base pairs. In certain embodiments, the dsRNA comprises a double-stranded region of 15 base pairs, 16 base pairs, 18 base pairs, or 20 base pairs.

In certain embodiments, the dsRNA comprises a blunt-end. In certain embodiments, the dsRNA comprises at least one single stranded nucleotide overhang. In certain embodiments, the dsRNA comprises about a 2-nucleotide to 5-nucleotide single stranded nucleotide overhang. In certain embodiments, the dsRNA comprises a 2-nucleotide single stranded nucleotide overhang or a 5-nucleotide single stranded nucleotide overhang.

In certain embodiments, the dsRNA comprises at least 70% 2'-O-methyl nucleotide modifications.

In certain embodiments, the antisense strand comprises at least 70% 2'-O-methyl nucleotide modifications. In certain embodiments, the antisense strand comprises about 70% to 90% 2'-O-methyl nucleotide modifications. In certain embodiments, the sense strand comprises at least 65% 2'-O-methyl nucleotide modifications. In certain embodiments, the sense strand comprises 100% 2'-O-methyl nucleotide modifications.

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand.

In certain embodiments, the antisense strand comprises a 5' phosphate, a 5'-alkyl phosphonate, a 5' alkylene phosphonate, or a 5' alkenyl phosphonate. In certain embodiments, the antisense strand comprises a 5' vinyl phosphonate.

In certain embodiments, the dsRNA comprises an antisense strand and a sense strand, each strand with a 5' end and a 3' end, wherein: (1) the antisense strand comprises a sequence substantially complementary to a SARS-CoV-2 nucleic acid sequence of any one of the 45-nucleotide target gene regions in Table 6A; (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a SARS-CoV-2 nucleic acid sequence of any one of the 45-nucleotide target gene regions in Table 6A; (2) the antisense strand comprises at least 70% 2'-O-methyl modifications; (3) the nucleotides at positions 2, 6, 14, and 16 from the 5' end of the antisense strand are not a 2'-methoxy-ribonucleotide; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; (7) the nucleotides at positions 6, 7, 8 and 10 from the 5' end of the sense strand are not a 2'-methoxy-ribonucleotide; and (8) the nucleotides at positions 1-2 from the 5' end of the sense strand are connected to each other via phosphorothioate internucleotide linkages.

In certain embodiments, the dsRNA further comprises 1 to 5 internucleotide linkages of Formula I. In certain embodiments, the 3' end of the antisense strand comprises 1 to 5 internucleotide linkages of Formula I. In certain embodiments, the 3' end of the antisense strand comprises 4 consecutive internucleotide linkages of Formula I.

In certain embodiments, a functional moiety is linked to one or both of the 5' end and 3' end of the antisense strand. In certain embodiments, a functional moiety is linked to one or both of the 5' end and 3' end of the sense strand. In certain embodiments, a functional moiety is linked to the 3' end of the sense strand.

In certain embodiments, the functional moiety comprises a hydrophobic moiety. In certain embodiments, the hydrophobic moiety is selected from the group consisting of fatty acids, steroids, secosteroids, lipids, gangliosides, nucleoside analogs, endocannabinoids, vitamins, and a mixture thereof. In certain embodiments, the steroid selected from the group consisting of cholesterol and Lithocholic acid (LCA). In certain embodiments, the fatty acid selected from the group consisting of Eicosapentaenoic acid (EPA), Docosahexaenoic acid (DHA) and Docosanoic acid (DCA). In certain embodiments, the vitamin is selected from the group consisting of choline, vitamin A, vitamin E, and derivatives or metabolites thereof. In certain embodiments, the vitamin is selected from the group consisting of retinoic acid and alpha-tocopheryl succinate.

In certain embodiments, the functional moiety is linked to one or both of the antisense strand and sense strand by a linker. In certain embodiments, the linker comprises a divalent or trivalent linker. In certain embodiments, the divalent or trivalent linker is selected from the group consisting of

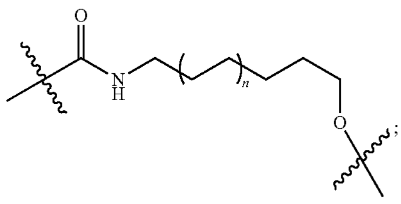;
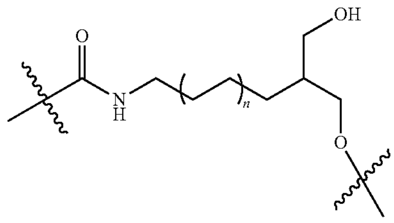;

-continued

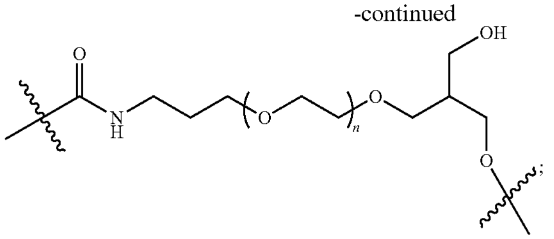

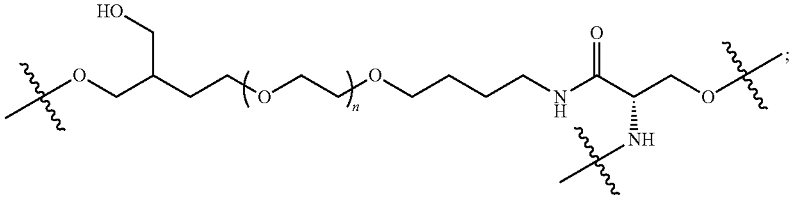

and

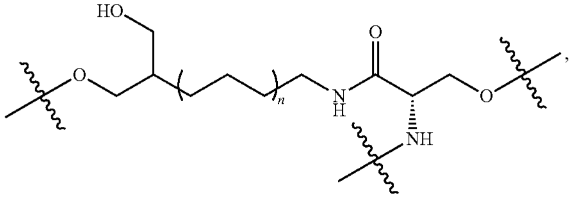

wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, the linker comprises a dTdT dinucleotide.

In certain embodiments, the functional moiety is linked to the 3' end of the sense strand by a dTdT dinucleotide followed by the linker

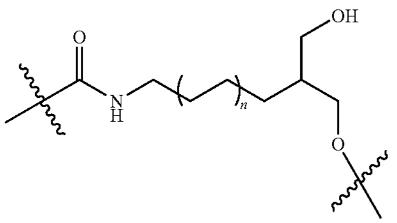

wherein n is 1.

In certain embodiments, the trivalent linker further links a phosphodiester or phosphodiester derivative.

In certain embodiments, the phosphodiester or phosphodiester derivative is selected from the group consisting of (Zc1)

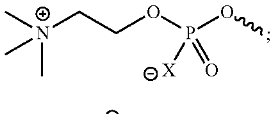

(Zc2)

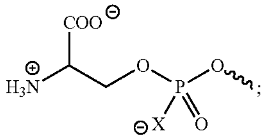

-continued (Zc3)

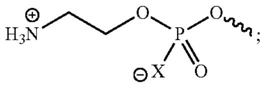

and (Zc4)

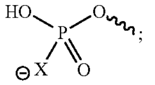

wherein X is O, S or $BH_3$.

In certain embodiments, the nucleotides at positions 1 and 2 from the 5' end of antisense strand are connected to adjacent ribonucleotides via phosphorothioate linkages.

In one aspect, the disclosure provides a double stranded (ds) RNA, comprising an antisense strand and a sense strand, each strand with a 5' end and a 3' end, wherein: (1) the antisense strand comprises a sequence substantially complementary to a SARS-CoV-2 nucleic acid sequence of any one of the 45-nucleotide target gene regions in Table 6A; (2) the antisense strand comprises at least 70% 2'-O-methyl modifications; (3) the nucleotides at positions 2, 6, 14, and 16 from the 5' end of the antisense strand are not a 2'-methoxy-ribonucleotide; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; (7) the nucleotides at positions 6, 7, 8 and 10 from the 5' end of the sense strand are not a 2'-methoxy-ribonucleotide; (8) the nucleotides at positions 1-2 from the 5' end of the sense strand are connected to each other via phosphorothioate internucleotide linkages; and (9) the antisense strand comprises at least one modified intersubunit linkages of Formula II:

(II)

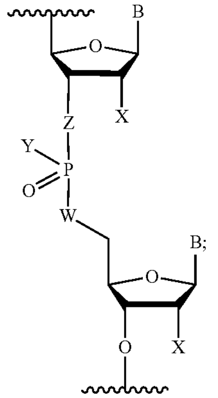

wherein:

B is a base pairing moiety;

W is O or $O(CH_2)_{n^1}$, wherein $n^1$ is 1 to 10;

X is selected from the group consisting of H, OH, $OR^1$, F, SH, SR, $NR^2_2$ and $C_{1-6}$-alkoxy;

Y is selected from the group consisting of $O^-$, OH, OR, $OR^2$, $NH^-$, $NH_2$, $NR^2_2$, $BH_3$, $S^-$, $R^1$, and SH;

Z is O or $O(CH_2)_{n^2}$ wherein $n^2$ is 1 to 10;

$R^1$ is alkyl, allyl or aryl; and $R^2$ is alkyl, allyl or aryl.

In certain embodiments, the 3' end of the antisense strand comprises four consecutive modified intersubunit linkages of Formula II.

In certain embodiments, the antisense strand comprises a 5' vinyl phosphonate.

In certain embodiments, the antisense strand is 20 nucleotides in length, 21 nucleotides in length, or 22 nucleotides in length. In certain embodiments, the sense strand is 15 nucleotides in length, 16 nucleotides in length, 18 nucleotides in length, or 20 nucleotides in length.

In certain embodiments, a functional moiety is linked to the 3' end of the sense strand.

In certain embodiments, the functional moiety comprises Eicosapentaenoic acid (EPA) or Docosanoic acid (DCA).

In certain embodiments, a functional moiety is linked to the 3' end of the sense strand by a linker.

In certain embodiments, the linker comprises a dTdT dinucleotide.

In certain embodiments, the functional moiety is linked to the 3' end of the sense strand by a dTdT dinucleotide followed by the linker

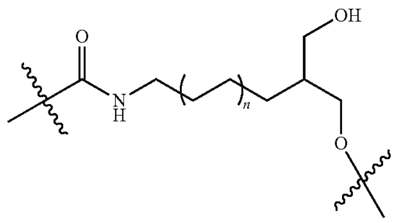

wherein n is 1.

In one aspect, the disclosure provides a combination comprising two or more oligonucleotide compounds or dsRNA recited above, wherein each oligonucleotide compound or dsRNA in the combination comprises complementarity to a different SARS-CoV-2 nucleic acid sequence.

In certain embodiments, the combination comprises two, three, four, or five oligonucleotide compounds or dsRNA.

In one aspect, the disclosure provides a combination comprising two or more oligonucleotide compounds for inhibiting the expression of a SARS-CoV-2 gene in a cell of an organism, wherein each oligonucleotide compound in the combination comprises complementarity to a different SARS-CoV-2 nucleic acid sequence.

In certain embodiments, the combination comprises a first oligonucleotide compound, a second oligonucleotide compound, and a third oligonucleotide compound, wherein:

i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region orf1a_9679, as recited in Table 6A; and iii) the third oligonucleotide compound comprises a sequence substantially complementary to the 45-nucleotide target gene region orf1ab_21391, as recited in Table 6A; or i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region orf1a_8744, as recited in Table 6A; and iii) the third oligonucleotide compound comprises a sequence substantially complementary to the 45-nucleotide target gene region orf1ab_21391, as recited in Table 6A; or i) the first oligonucleotide compound comprises a sequence substantially complementary to the 45-nucleotide target gene region orf1a_9679, as recited in Table 6A;

ii) the second oligonucleotide compound comprises a sequence substantially complementary to the 45-nucleotide target gene region orf1a_8744, as recited in Table 6A; and iii) the third oligonucleotide compound comprises a sequence substantially complementary to the 45-nucleotide target gene region orf1ab_21391, as recited in Table 6A; or i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region orf1a_9679, as recited in Table 6A; and iii) the third oligonucleotide compound comprises a sequence substantially complementary to the 45-nucleotide target gene region 7a_27565, as recited in Table 6A; or i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region orf1ab_21391, as recited in Table 6A; and iii) the third oligonucleotide compound comprises a sequence substantially complementary to the 45-nucleotide target gene region 7a_27565, as recited in Table 6A; or i) the first oligonucleotide compound comprises a sequence substantially complementary to the 45-nucleotide target gene region orf1ab_21391, as recited in Table 6A;

ii) the second oligonucleotide compound comprises a sequence substantially complementary to the 45-nucleotide target gene region 7a_27656, as recited in Table 6A; and iii) the third oligonucleotide compound comprises a sequence substantially complementary to the 45-nucleotide target gene region 7a_27751, as recited in Table 6A; or i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region S_23174, as recited in Table 6A; and iii) the third oligonucleotide compound comprises a sequence substantially complementary to the 45-nucleotide target gene region E_26305, as recited in Table 6A; or i) the first oligonucleotide compound comprises a sequence substantially complementary to the 45-nucleotide target gene region orf1a_9679, as recited in Table 6A;

ii) the second oligonucleotide compound comprises a sequence substantially complementary to the 45-nucleotide target gene region S_23174, as recited in Table 6A; and iii) the third oligonucleotide compound comprises a sequence substantially complementary to the 45-nucleotide target gene region N_29293, as recited in Table 6A; or i) the first oligonucleotide compound comprises a sequence substantially complementary to the 45-nucleotide target gene region orf1ab_21391, as recited in Table 6A;

ii) the second oligonucleotide compound comprises a sequence substantially complementary to the 45-nucleotide target gene region E_26305, as recited in Table 6A; and iii) the third oligonucleotide compound comprises a sequence substantially complementary to the 45-nucleotide target gene region N_29293, as recited in Table 6A; or i) the first oligonucleotide compound comprises a sequence substantially complementary to the 45-nucleotide target gene region S_23174, as recited in Table 6A;

ii) the second oligonucleotide compound comprises a sequence substantially complementary to the 45-nucleotide target gene region E_26470, as recited in Table 6A; and iii) the third oligonucleotide compound comprises a sequence substantially complementary to the 45-nucleotide target gene region 7a_27565, as recited in Table 6A; or i) the first oligonucleotide compound comprises a sequence substantially complementary to the 45-nucleotide target gene region S_23174, as recited in Table 6A;

ii) the second oligonucleotide compound comprises a sequence substantially complementary to the 45-nucleotide target gene region M_27123, as recited in Table 6A; and iii) the third oligonucleotide compound comprises a sequence substantially complementary to the 45-nucleotide target gene region 7a_27656, as recited in Table 6A; or i) the first oligonucleotide compound comprises a sequence substantially complementary to the 45-nucleotide target gene region S_23174, as recited in Table 6A;

ii) the second oligonucleotide compound comprises a sequence substantially complementary to the 45-nucleotide target gene region M_27032, as recited in Table 6A; and iii) the third oligonucleotide compound comprises a sequence substantially complementary to the 45-nucleotide target gene region 7a_27751, as recited in Table 6A; or i) the first oligonucleotide compound comprises a sequence substantially complementary to the 45-nucleotide target gene region orf1a_416, as recited in Table 6A;

ii) the second oligonucleotide compound comprises a sequence substantially complementary to the 45-nucleotide target gene region E_26305, as recited in Table 6A; and iii) the third oligonucleotide compound comprises a sequence substantially complementary to the 45-nucleotide target gene region 7a_27565, as recited in Table 6A; or i) the first oligonucleotide compound comprises a sequence substantially complementary to the 45-nucleotide target gene region orf1a_9679, as recited in Table 6A;

ii) the second oligonucleotide compound comprises a sequence substantially complementary to the 45-nucleotide target gene region E_26369, as recited in Table 6A; and iii) the third oligonucleotide compound comprises a sequence substantially complementary to the 45-nucleotide target gene region 7a_27656, as recited in Table 6A; or i) the first oligonucleotide compound comprises a sequence substantially complementary to the 45-nucleotide target gene region orf1ab_21391, as recited in Table 6A;

ii) the second oligonucleotide compound comprises a sequence substantially complementary to the 45-nucleotide target gene region M_27032, as recited in Table 6A; and iii) the third oligonucleotide compound comprises a sequence substantially complementary to the 45-nucleotide target gene region 7a_27751, as recited in Table 6A; or i) the first oligonucleotide compound comprises a sequence substantially complementary to the 45-nucleotide target gene region 3a_25868, as recited in Table 6A;

ii) the second oligonucleotide compound comprises a sequence substantially complementary to the 45-nucleotide target gene region 7a_27751, as recited in Table 6A; and iii) the third oligonucleotide compound comprises a sequence substantially complementary to the 45-nucleotide target gene region S_23774, as recited in Table 6A.

In one aspect, the disclosure provides a combination comprising one or more oligonucleotide compounds for inhibiting the expression of a SARS-CoV-2 gene and one or more oligonucleotide compounds for inhibiting the expression of one or more of an ACE2 gene, a FURIN gene, an IL-6 gene, a TMPRSS2 gene, and a IL-6R gene.

In one aspect, the disclosure provides a pharmaceutical composition for inhibiting the expression of one or more of a SARS-CoV-2 gene, an ACE2 gene, a FURIN gene, an IL-6 gene, a TMPRSS2 gene, and a IL-6R gene in a cell of an organism, comprising the oligonucleotide compound, dsRNA, or combination recited above and a pharmaceutically acceptable carrier.

In certain embodiments, the oligonucleotide compound, dsRNA, or combination inhibits the expression of one or more of the SARS-CoV-2 genes, the ACE2 gene, the FURIN gene, the IL-6 gene, the TMPRSS2 gene, and the IL-6R gene by at least 50%. In certain embodiments, the oligonucleotide compound, dsRNA, or combination inhibits the expression of one or more of the SARS-CoV-2 genes, the ACE2 gene, the FURIN gene, the IL-6 gene, the TMPRSS2 gene, and the IL-6R gene by at least 75%.

In one aspect, the disclosure provides a pharmaceutical composition for inhibiting the expression of one or more SARS-CoV-2 genes in a cell of an organism, comprising the oligonucleotide compound, dsRNA, or combination recited above and a pharmaceutically acceptable carrier.

In certain embodiments, the oligonucleotide compound, dsRNA, or combination inhibits the expression of one or more SARS-CoV-2 genes by at least 50%. In certain embodiments, the oligonucleotide compound, dsRNA, or combination inhibits the expression of one or more SARS-CoV-2 genes by at least 75%.

In one aspect, the disclosure provides a method for inhibiting expression of a SARS-CoV-2 gene in a cell of an organism, the method comprising: (a) introducing into the cell an oligonucleotide compound, dsRNA, or combination recited above; and (b) maintaining the cell produced in step (a) for a time sufficient to obtain degradation of the mRNA transcript of the SARS-CoV-2 gene, thereby inhibiting expression of the SARS-CoV-2 gene in the cell.

In one aspect, the disclosure provides a method for inhibiting expression of one or more of a SARS-CoV-2 gene, an ACE2 gene, a FURIN gene, an IL-6 gene, a TMPRSS2 gene, and an IL-6R gene in a cell, the method comprising: (a) introducing into the cell an oligonucleotide compound, dsRNA, or combination recited above; and (b) maintaining the cell produced in step (a) for a time sufficient to obtain degradation of the mRNA transcript of the SARS-CoV-2 gene, the ACE2 gene, the FURIN gene, the IL-6 gene, the TMPRSS2 gene, and the IL-6R gene thereby inhibiting expression of the SARS-CoV-2 gene, the ACE2 gene, the FURIN gene, the IL-6 gene, the TMPRSS2 gene, and the IL-6R gene in the cell.

In one aspect, the disclosure provides a method of treating or managing a SARS-CoV-2 infection, comprising administering to a patient in need of such treatment a therapeutically effective amount of the oligonucleotide compound, dsRNA, or combination recited above.

In certain embodiments, the oligonucleotide compound, dsRNA, or combination is administered by intratracheal (IT) injection, intravenous (IV) injection, subcutaneous (SQ) injection, or a combination thereof.

In certain embodiments, the oligonucleotide compound, dsRNA, or combination is administered sequentially or simultaneously.

In certain embodiments, administering the oligonucleotide compound, dsRNA, or combination causes a decrease in one or more of SARS-CoV-2 gene mRNA, ACE2 gene mRNA, FURIN gene mRNA, IL-6 gene mRNA, TMPRSS2 gene mRNA, and IL-6R gene mRNA in the lung.

In certain embodiments, the oligonucleotide compound, dsRNA, or combination inhibits the expression of one or more of the SARS-CoV-2 gene, the ACE2 gene, the FURIN gene, the IL-6 gene, the TMPRSS2 gene, and the IL-6R gene by at least 50%. In certain embodiments, the oligonucleotide compound, dsRNA, or combination inhibits the expression of one or more of the SARS-CoV-2 gene, the ACE2 gene, the FURIN gene, the IL-6 gene, the TMPRSS2 gene, and the IL-6R gene by at least 75%.

In one aspect, the disclosure provides a vector comprising a regulatory sequence operably linked to a nucleotide sequence that encodes an oligonucleotide compound recited above.

In certain embodiments of the vector, the oligonucleotide compound inhibits the expression of one or more of the SARS-CoV-2 gene, the ACE2 gene, the FURIN gene, the IL-6 gene, the TMPRSS2 gene, and the IL-6R gene by at least 30%. In certain embodiments of the vector, the oligonucleotide compound inhibits the expression of one or more of the SARS-CoV-2 gene, the ACE2 gene, the FURIN gene, the IL-6 gene, the TMPRSS2 gene, and the IL-6R gene by at least 50%. In certain embodiments of the vector, the oligonucleotide compound inhibits the expression of one or more of the SARS-CoV-2 gene, the ACE2 gene, the FURIN gene, the IL-6 gene, the TMPRSS2 gene, and the IL-6R gene by at least 75%.

In one aspect, the disclosure provides a cell comprising the vector recited above.

In one aspect, the disclosure provides a recombinant adeno-associated virus (rAAV) comprising the vector recited above and an AAV capsid.

In one aspect, the disclosure provides a branched oligonucleotide compound comprising two or more of the oligonucleotide compounds or dsRNA recited above covalently bound to one another.

In certain embodiments, the oligonucleotide compounds are covalently bound to one another by way of a linker, spacer, a branching point, or a mixture thereof.

In one aspect, the disclosure provides a method of treating or managing a SARS-CoV-2 infection, comprising administering to a patient in need of such treatment a therapeutically effective amount of the branched oligonucleotide compound recited above.

In certain embodiments, the branched oligonucleotide compound is administered by intratracheal (IT) injection, intravenous (IV) injection, subcutaneous (SQ) injection, or a combination thereof.

In certain embodiments, the branched oligonucleotide compound accumulates in lung tissue to a greater extent than a non-branched oligonucleotide compound when administered by intratracheal (IT) injection.

In one aspect, the disclosure provides a branched RNA compound comprising: two or more RNA molecules comprising 15 to 35 nucleotides in length, and a sequence substantially complementary to a SARS-CoV-2 nucleic acid sequence, wherein the two or more RNA molecules are connected to one another by one or more moieties independently selected from a linker, a spacer and a branching point.

In certain embodiments, the branched RNA compound comprises a sequence substantially complementary to a SARS-CoV-2 nucleic acid sequence of any one of the 45-nucleotide target gene regions in Table 6A.

In certain embodiments of the branched RNA compound, each RNA molecule comprises 15 to 25 nucleotides in length.

In certain embodiments of the branched RNA compound, each RNA molecule comprises a dsRNA comprising a sense strand and an antisense strand, wherein each antisense strand independently comprises a sequence substantially complementary to a SARS-CoV-2 nucleic acid sequence of any one of the 45-nucleotide target gene regions in Table 6A.

In certain embodiments, the branched RNA compound comprises complementarity to at least 10, 11, 12 or 13 contiguous nucleotides of a SARS-CoV-2 nucleic acid sequence of any one of the 45-nucleotide target gene regions in Table 6A. In certain embodiments of the branched RNA compound, each RNA molecule comprises no more than 3 mismatches with a SARS-CoV-2 nucleic acid sequence of any one of the 45-nucleotide target gene regions in Table 6A. In certain embodiments, the branched RNA compound comprises full complementary to a SARS-CoV-2 nucleic acid sequence of any one of the 45-nucleotide target gene regions in Table 6A.

In certain embodiments of the branched RNA compound, the antisense strand comprises a portion having the nucleic acid sequence of any one of the antisense strands recited in Table 6B.

In certain embodiments of the branched RNA compound, the antisense strand and/or sense strand comprises about 15 nucleotides to 25 nucleotides in length. In certain embodiments of the branched RNA compound, the antisense strand is 20 nucleotides in length, 21 nucleotides in length, or 22 nucleotides in length. In certain embodiments of the branched RNA compound, the sense strand is 15 nucleotides in length, 16 nucleotides in length, 18 nucleotides in length, or 20 nucleotides in length.

In certain embodiments of the branched RNA compound, the dsRNA comprises a double-stranded region of 15 base pairs to 20 base pairs. In certain embodiments of the branched RNA compound, the dsRNA comprises a double-stranded region of 15 base pairs, 16 base pairs, 18 base pairs, or 20 base pairs.

In certain embodiments of the branched RNA compound, the dsRNA comprises a blunt-end. In certain embodiments of the branched RNA compound, the dsRNA comprises at least one single stranded nucleotide overhang. In certain embodiments of the branched RNA compound, the dsRNA comprises between a 2-nucleotide to 5-nucleotide single stranded nucleotide overhang.

In certain embodiments of the branched RNA compound, the dsRNA comprises naturally occurring nucleotides.

In certain embodiments of the branched RNA compound, the dsRNA comprises at least one modified nucleotide.

In certain embodiments of the branched RNA compound, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In certain embodiments of the branched RNA compound, the dsRNA comprises at least one modified internucleotide linkage. In certain embodiments of the branched RNA compound, the modified internucleotide linkage comprises a phosphorothioate internucleotide linkage. In certain embodiments, the branched RNA compound comprises 4-16 phosphorothioate internucleotide linkages. In certain embodiments, the branched RNA compound comprises 6-13 phosphorothioate internucleotide linkages.

In certain embodiments of the branched RNA compound, the dsRNA comprises at least one modified internucleotide linkage of Formula I:

(I)

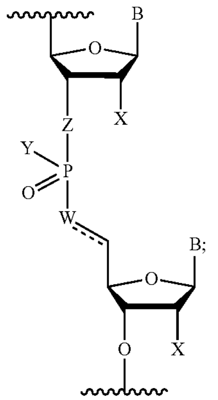

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and $\equiv$ is an optional double bond.

In certain embodiments of the branched RNA compound, the dsRNA comprises at least 80% chemically modified nucleotides. In certain embodiments of the branched RNA compound, the dsRNA is fully chemically modified. In certain embodiments of the branched RNA compound, the dsRNA comprises at least 70% 2'-O-methyl nucleotide modifications. In certain embodiments of the branched RNA compound, the antisense strand comprises at least 70% 2'-O-methyl nucleotide modifications. In certain embodiments of the branched RNA compound, the antisense strand comprises about 70% to 90% 2'-O-methyl nucleotide modifications. In certain embodiments of the branched RNA compound, the sense strand comprises at least 65% 2'-O-methyl nucleotide modifications. In certain embodiments of the branched RNA compound, the sense strand comprises 100% 2'-O-methyl nucleotide modifications.

In certain embodiments of the branched RNA compound, the sense strand comprises one or more nucleotide mismatches between the antisense strand and the sense strand. In certain embodiments of the branched RNA compound, the one or more nucleotide mismatches are present at positions 2, 6, and 12 from the 5' end of sense strand. In certain embodiments of the branched RNA compound, the nucleotide mismatches are present at positions 2, 6, and 12 from the 5' end of the sense strand.

In certain embodiments of the branched RNA compound, the antisense strand comprises a 5' phosphate, a 5'-alkyl phosphonate, a 5' alkylene phosphonate, a 5' alkenyl phosphonate, or a mixture thereof. In certain embodiments of the branched RNA compound, the antisense strand comprises a 5' vinyl phosphonate.

In certain embodiments of the branched RNA compound, the dsRNA comprises an antisense strand and a sense strand, each strand with a 5' end and a 3' end, wherein: (1) the antisense strand comprises a sequence substantially complementary to a SARS-CoV-2 nucleic acid sequence of any one of the 45-nucleotide target gene regions in Table 6A; (2) the antisense strand comprises at least 70% 2'-O-methyl modifications; (3) the nucleotides at positions 2, 6, 14, and 16 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 70% 2'-O-methyl modifications; (7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments of the branched RNA compound, the antisense strand comprises a 5' vinyl phosphonate.

In certain embodiments of the branched RNA compound, the antisense strand is 20 nucleotides in length, 21 nucleotides in length, or 22 nucleotides in length. In certain embodiments of the branched RNA compound, the sense strand is 15 nucleotides in length, 16 nucleotides in length, 18 nucleotides in length, or 20 nucleotides in length.

In certain embodiments of the branched RNA compound, a functional moiety is linked to one or both of the 5' end and 3' end of the antisense strand. In certain embodiments of the branched RNA compound, a functional moiety is linked to one or both of the 5' end and 3' end of the sense strand. In certain embodiments of the branched RNA compound, a functional moiety is linked to the 3' end of the sense strand.

In certain embodiments of the branched RNA compound, the functional moiety comprises a hydrophobic moiety. In certain embodiments of the branched RNA compound, the hydrophobic moiety is selected from the group consisting of fatty acids, steroids, secosteroids, lipids, gangliosides, nucleoside analogs, endocannabinoids, vitamins, and a mixture thereof. In certain embodiments of the branched RNA compound, the steroid is selected from the group consisting of cholesterol and Lithocholic acid (LCA). In certain embodiments of the branched RNA compound, the fatty acid is selected from the group consisting of Eicosapentaenoic acid (EPA), Docosahexaenoic acid (DHA) and Docosanoic acid (DCA). In certain embodiments of the branched RNA compound, the vitamin is selected from the group consisting of choline, vitamin A, vitamin E, derivatives thereof, and metabolites thereof. In certain embodiments of the branched RNA compound, the vitamin is selected from the group consisting of retinoic acid and alpha-tocopheryl succinate.

In certain embodiments of the branched RNA compound, the functional moiety is linked to one or both of the antisense strand and sense strand by a linker. In certain embodiments of the branched RNA compound, the linker comprises a divalent or trivalent linker.

In certain embodiments of the branched RNA compound, the divalent or trivalent linker is selected from the group consisting of:

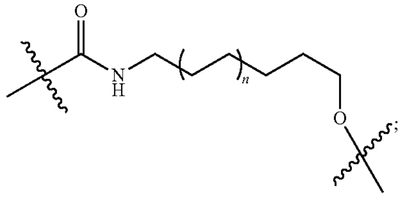
;
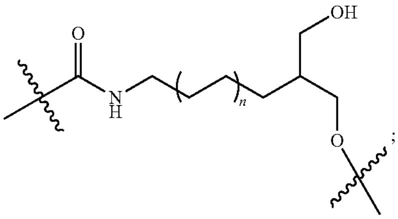
;
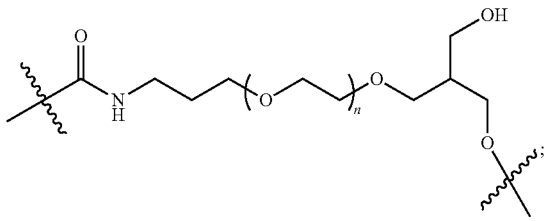
;
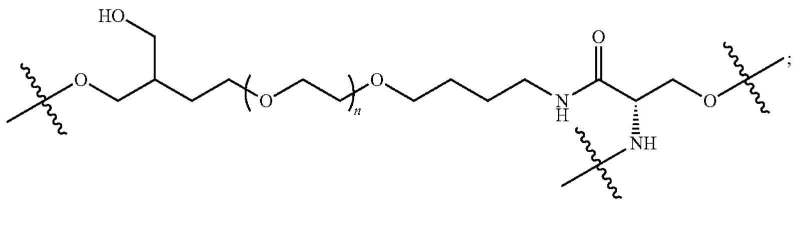
; and

-continued

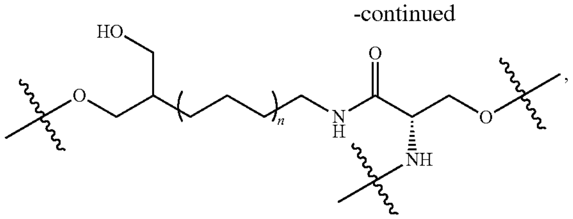, wherein n is 1, 2, 3, 4, or 5.

In certain embodiments of the branched RNA compound, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments of the branched RNA compound, the trivalent linker further links a phosphodiester or phosphodiester derivative. In certain embodiments of the branched RNA compound, the phosphodiester or phosphodiester derivative is selected from the group consisting of:

(Zc1)

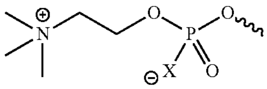 ;

(Zc2)

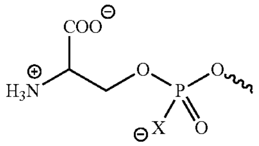 ;

(Zc3)

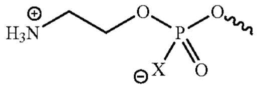 ; and (Zc4)

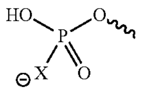 ;

wherein X is O, S or $BH_3$.

In certain embodiments of the branched RNA compound, the nucleotides at positions 1 and 2 from the 3' end of sense strand, and the nucleotides at positions 1 and 2 from the 5' end of antisense strand, are connected to adjacent ribonucleotides via phosphorothioate linkages.

In one aspect, the disclosure provides compound of formula (I):

$$L\text{-}(N)_n \quad \text{(I)}$$

wherein:

L comprises an ethylene glycol chain, an alkyl chain, a peptide, an RNA, a DNA, a phosphate, a phosphonate, a phosphoramidate, an ester, an amide, a triazole, or combinations thereof, and wherein formula (I) optionally further comprises one or more branch point B, and one or more spacer S, wherein B is independently for each occurrence a polyvalent organic species or derivative thereof;

S comprises independently for each occurrence an ethylene glycol chain, an alkyl chain, a peptide, an RNA, a DNA, a phosphate, a phosphonate, a phosphoramidate, an ester, an amide, a triazole, or a combination thereof; and N is a double stranded nucleic acid comprising 15 to 35 bases in length comprising a sense strand and an antisense strand; wherein the antisense strand comprises a sequence substantially complementary to a SARS-CoV-2 nucleic acid sequence of any one of the 45-nucleotide target gene regions in Table 6A;

the sense strand and antisense strand each independently comprise one or more chemical modifications; and n is 2, 3, 4, 5, 6, 7 or 8.

In certain embodiments, the compound has a structure selected from formulas (I-1)-(I-9):

(I-1)

N—L—N (I-2)

N—S—L—S—N (I-3)

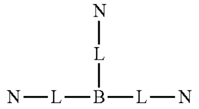

(I-4)

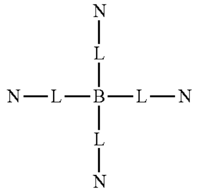

(I-5)

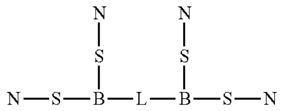

(I-6)

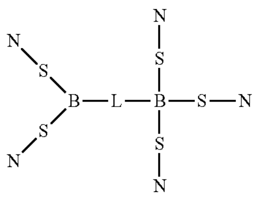

(I-7)

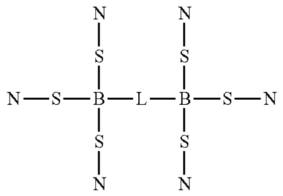

-continued
(I-8)
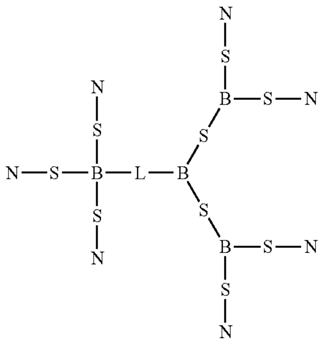
(I-9)
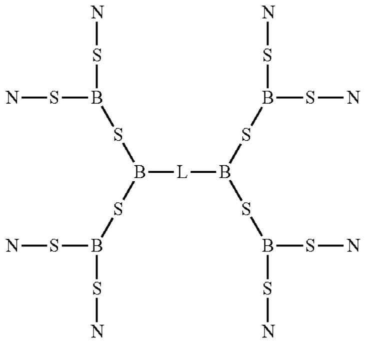
In certain embodiments, the antisense strand comprises a 5' terminal group R selected from the group consisting of:
$R^1$
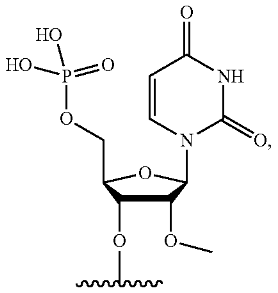
$R^2$
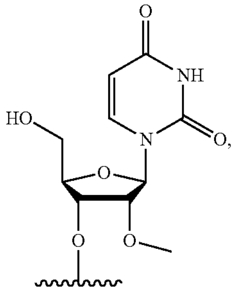
-continued
$R^3$
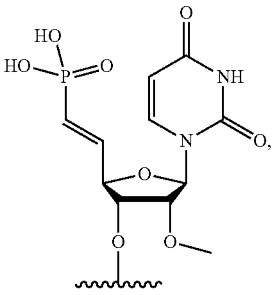
$R^4$
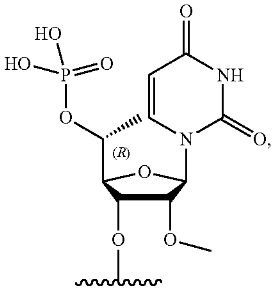
$R^5$
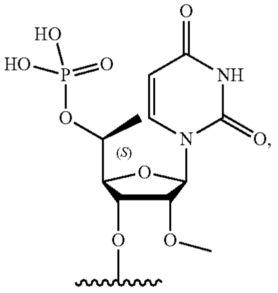
$R^6$
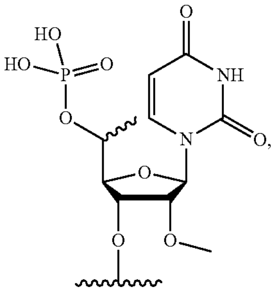
$R^7$
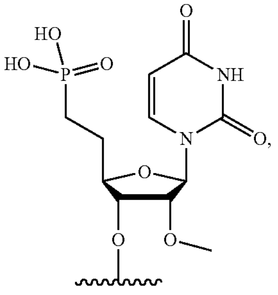
and -continued $R^8$

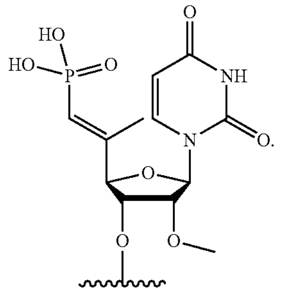

In certain embodiments, the compound comprises the structure of formula (II):

(II)

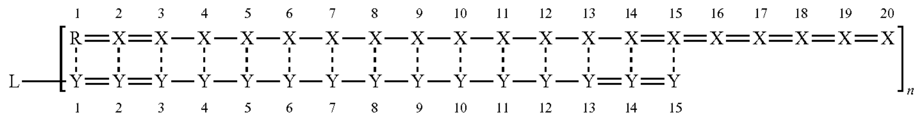

wherein:

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester internucleoside linkage;

= represents a phosphorothioate internucleoside linkage; and

--- represents, individually for each occurrence, a base-pairing interaction or a mismatch.

In certain embodiments, the compound comprises structure of formula (IV):

(IV)

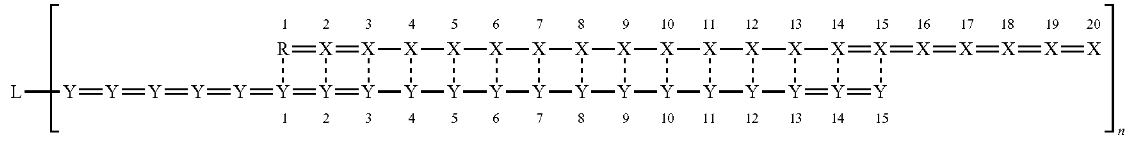

wherein:

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester internucleoside linkage;

= represents a phosphorothioate internucleoside linkage; and

--- represents, individually for each occurrence, a base-pairing interaction or a mismatch.

In certain embodiments, L is structure L1:

(L1)

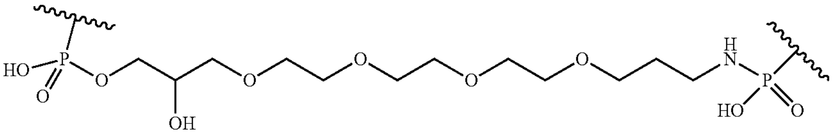

In certain embodiments, R is $R^3$ and n is 2.

In certain embodiments, L is structure L2:

(L2)

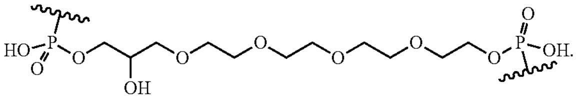

In certain embodiments, R is $R^3$ and n is 2.

In one aspect, the disclosure provides a delivery system for therapeutic nucleic acids having the structure of Formula (VI):

$$L\text{-}(cNA)_n \quad (VI)$$

wherein:

L comprises an ethylene glycol chain, an alkyl chain, a peptide, an RNA, a DNA, a phosphate, a phosphonate, a phosphoramidate, an ester, an amide, a triazole, or combinations thereof, wherein formula (VI) optionally further comprises one or more branch point B, and one or more spacer S, wherein B comprises independently for each occurrence a polyvalent organic species or a derivative thereof;

S comprises independently for each occurrence an ethylene glycol chain, an alkyl chain, a peptide, RNA, DNA, a phosphate, a phosphonate, a phosphoramidate, an ester, an amide, a triazole, or combinations thereof;

each cNA, independently, is a carrier nucleic acid comprising one or more chemical modifications;

each cNA, independently, comprises at least 15 contiguous nucleotides of a SARS-CoV-2 nucleic acid sequence of any one of the 45-nucleotide target gene regions in Table 6A; and n is 2, 3, 4, 5, 6, 7 or 8.

In certain embodiments, the delivery system has a structure selected from formulas (VI-1)-(VI-9):

(VI-1)

ANc—L—cNA (VI-2)

ANc—S—L—S—cNA (VI-3)

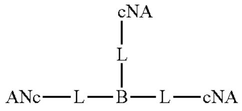

(VI-4)

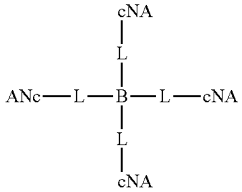

(VI-5)

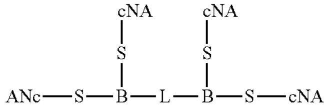

(VI-6)

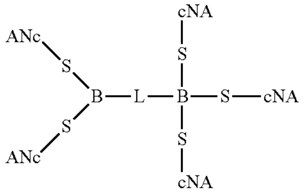

-continued (VI-7)

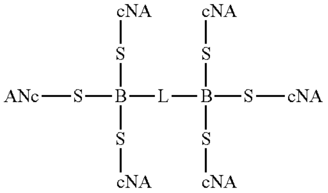

(VI-8)

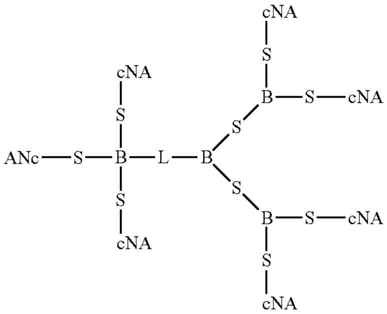

(VI-9)

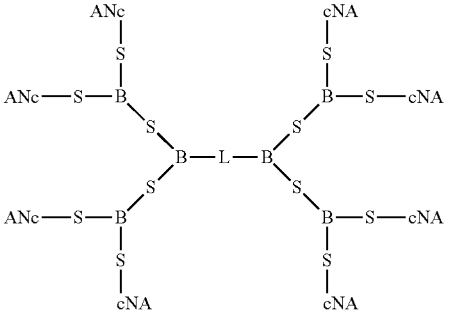

In certain embodiments, each cNA independently comprises a chemically-modified nucleotide.

In certain embodiments, the delivery system further comprises n therapeutic nucleic acids (NA), wherein each NA is hybridized to at least one cNA.

In certain embodiments, each NA independently comprises at least 16 contiguous nucleotides. In certain embodiments, each NA independently comprises 16-20 contiguous nucleotides.

In certain embodiments, each NA comprises an unpaired overhang of at least 2 nucleotides. In certain embodiments, the nucleotides of the overhang are connected via phosphorothioate linkages.

In certain embodiments, each NA, independently, is selected from the group consisting of DNAs, siRNAs, antagomiRs, miRNAs, gapmers, mixmers, and guide RNAs.

In certain embodiments, each NA is substantially complementary to a SARS-CoV-2 nucleic acid sequence of any one of the 45-nucleotide target gene regions in Table 6A.

In one aspect, the disclosure provides a pharmaceutical composition for inhibiting the expression of a SARS-CoV-2 gene in an organism, comprising a compound or a system recited above, and a pharmaceutically acceptable carrier.

In certain embodiments, the compound or system inhibits the expression of the SARS-CoV-2 gene by at least 50%. In certain embodiments, the compound or system inhibits the expression of the SARS-CoV-2 gene by at least 75%.

In one aspect, the disclosure provides a method for inhibiting expression of a SARS-CoV-2 gene in a cell, the method comprising: (a) introducing into the cell a compound or a system recited above; and (b) maintaining the cell produced in step (a) for a time sufficient to obtain degradation of the mRNA transcript of the SARS-CoV-2 gene, thereby inhibiting expression of the SARS-CoV-2 gene in the cell.

In one aspect, the disclosure provides a method of treating or managing a SARS-CoV-2 infection comprising administering to a patient in need of such treatment or management a therapeutically effective amount of a compound or a system recited above.

In certain embodiments, the compound or system is administered to the lung of the patient.

In certain embodiments, the compound or system is administered by intratracheal (IT) injection, intravenous (IV) injection, subcutaneous (SQ) injection, or a combination thereof.

In certain embodiments, administering the compound or system causes a decrease in SARS-CoV-2 gene mRNA in one or more of the club cells and alveoli cells of the lung.

In certain embodiments, the compound or system inhibits the expression of the SARS-CoV-2 gene by at least 50%. In certain embodiments, the compound or system inhibits the expression of the SARS-CoV-2 gene by at least 75%.

In certain embodiments, the compound or system accumulates in lung tissue to a greater extent than a non-branched oligonucleotide compound when administered by intratracheal (IT) injection.

In one aspect, the disclosure provides a method of delivering an oligonucleotide compound to the lung of a patient, comprising administering the oligonucleotide compound, wherein the oligonucleotide compound is conjugated to a functional moiety selected from Eicosapentaenoic acid (EPA) and Docosanoic acid (DCA).

In certain embodiments, the oligonucleotide compound is a dsRNA comprising an antisense strand and a sense strand, each strand with a 5' end and a 3' end. In certain embodiments, the dsRNA is conjugated to the sense strand 3' end.

In certain embodiments, the functional moiety is conjugated to the sense strand by a linker. In certain embodiments, the linker comprises a divalent or trivalent linker.

In certain embodiments, the divalent or trivalent linker is selected from the group consisting of:

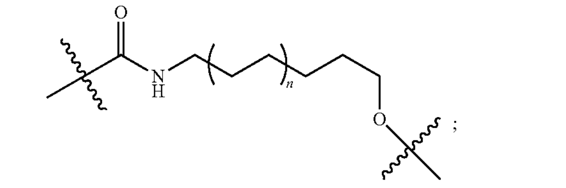

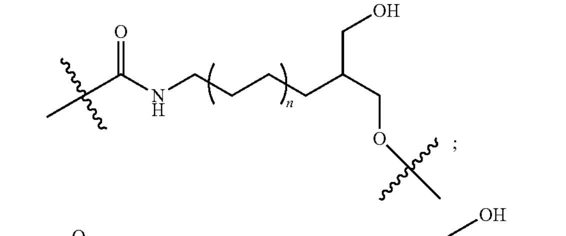

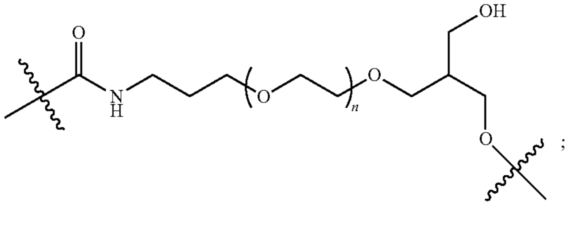

-continued

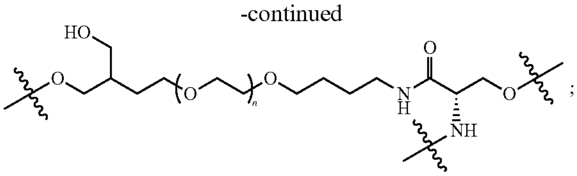

and

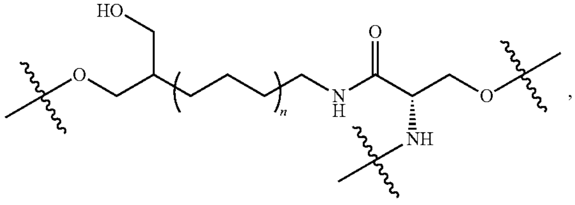

wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, the trivalent linker further links a phosphodiester or phosphodiester derivative.

In certain embodiments, the phosphodiester or phosphodiester derivative is selected from the group consisting of:

(Zc1)

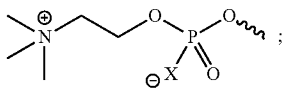

(Zc2)

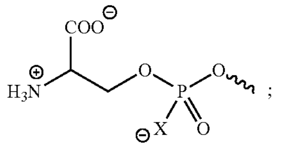

(Zc3)

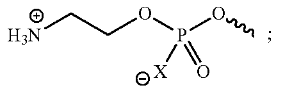

and (Zc4)

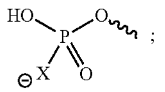

wherein X is O, S or $BH_3$.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 4A, siRNAs and ASOs were selected to target regions of the 9 selection genes with low mutation rates in other coronaviruses. FIG. 4B, the proportion of SARS-CoV-2 variants from patient isolates targeted by all selected siRNAs. FIG.

FIG. 5A, gene orf1a, FIG. 5B, gene 3a; FIG. 5C, gene 7a, FIG. 5D, gene orf1ab, FIG. 5E, gene E, FIG. 5F, gene 8b, FIG. 5G, gene S, FIG. 5H, gene M, FIG. 5I, gene N. SiRNAs were tested in Hela cells and silencing was assessed using the psi-check reporter system. Concentration: 1.5 uM; Time point: 72 hours.

FIG. 6A, gene orf1a, FIG. 6B, gene Orf1ab; FIG. 6C, gene S, FIG. 6D, gene 3a, FIG. 6E, gene E, FIG. 6F, gene M, FIG. 6G, gene 7a, FIG. 6H, gene 8b, FIG. 6I, gene N. ASOs were tested in Hela cells and silencing was assessed using the psi-check reporter system. Concentration: 1.5 uM; Time point: 72 hours.

FIG. 7A, SARS-CoV-2 genome. FIG. 7B, siRNAs targeting different genes in the SARS-CoV2 genome tested for silencing efficacy. siRNAs were tested in Hela cells and silencing was assessed using the psi-check reporter system. Concentration: 1.5 uM; Time point: 72 hours.

FIG. 8A, SARS-CoV-2 genome. FIG. 8B, LNA gapmers targeting different genes in the SARS-CoV-2 genome were tested for silencing efficacy. ASOs were tested in Hela cells and silencing was assessed using the psi-check reporter system. Concentration: 1.5 μM; Time point: 72 hours.

FIG. 9A, gene orf1a, FIG. 9B, gene Orf1ab; FIG. 9C, gene Spike, FIG. 9D, gene 3a, FIG. 9E, gene Envelope, FIG. 9F, gene Membrane, FIG. 9G, gene Orf7a, FIG. 9H, gene Orf8a, FIG. 9I, gene Nucleocapsid. siRNAs were tested in Hela cells and silencing was assessed using the psi-check reporter system. Concentration: Top=1.5 μM; Time point: 72 hours.

FIG. 11A, replication cocktails; FIG. 11B, Replication/immuno cocktails; FIG. 11C, Replication/Capsid cocktails; FIG. 11D, Immuno/Capsid cocktails; and FIG. 11E, Replication/Immuno/Capsid cocktails. siRNAs were tested in Hela cells and silencing was assessed using the psi-check reporter system. Concentration: Top=1.5 uM; Time point: 72 hours.

FIG. 15A, 2711; FIG. 15B, 2712; FIG. 15C, 3524; FIG. 15D, 3526. siRNAs were tested in HaCat cells and silencing was assessed using QuantiGene. Concentration: Top=1.5 μM; Time point: 72 hours.

FIG. 20A, effect on huntingtin mRNA expression. FIG. 20B, effect on cyclophilin B mRNA expression. The presence of a two-thymidine linker increases DCA-conjugated siRNA silencing in multiple tissues. SC injection (FVB/N mice); 20 mg/kg; collection of tissues one week after injection; n=6 per group. Huntingtin (Htt) (A.) or Cyclophilin B (Ppib) (B.) mRNA levels were measured using QuantiGene® (Affymetrix), normalized to a housekeeping gene, Hprt (Hypoxanthine-guanine phosphoribosyl transferase), and presented as percent of PBS (Phosphate buffered saline) control (mean±SD). Data analysis: t test (**P<0.0001, *P<0.001, **P<0.01, *P<0.1).

FIG. 23A, liver; FIG. 23B, kidney; FIG. 23C, spleen; FIG. 23D, muscle; FIG. 23E, lung; FIG. 23F, heart; FIG. 23G, adrenal glands; FIG. 23H, Fat. These data show increased silencing of DCA-conjugated siRNAs with exNA modifications compared to those without exNAs in all tissues including the lungs. SC, 20 mg/kg, n=5, 1 week, bDNA QuantiGene assay.

FIG. 25A, Distribution and delivery throughout the lung of mono and divalent siRNAs (Cy-3) compared to PBS controls; FIG. 25B, distribution and delivery throughout the lung of EPA and DCA conjugated siRNAs (Cy-3) compared to PBS controls. Intratracheal; 20 nmol for mono, 40 nmol for di; n=2, 24 h, 5×, Scale=1 mm. Subcutaneous; 40 nmol; n=3, 48 h, 5×, Scale=1 mm.

FIG. 26A, distribution and delivery throughout the lung of mono and divalent siRNAs (Cy-3) compared to PBS controls; FIG. 26B, distribution and delivery throughout the lung of mono and divalent siRNAs (Red, Cy3) to club cells (epithelial) (green) of the lungs compared to PBS controls; FIG. 26C, distribution and delivery throughout the lung of mono and divalent siRNAs (Red, Cy3) to alveoli type II cells (green) in the lung compared to PBS controls. Divalent siRNAs distribute to all cells of the lungs and saturate both alveolar and epithelial (club) cells 24 hours after intratracheal administration.

FIG. 27A, distribution and delivery throughout the lung of EPA and DCA conjugated siRNAs (Cy-3) compared to PBS controls; FIG. 27B, distribution of EPA and DCA conjugated siRNAs (Red, Cy3) to club cells (epithelial) (green) of the lungs compared to PBS controls; FIG. 27C, distribution of EPA and DCA conjugated siRNAs (Red, Cy3) to alveoli cells (green) in the lung compared to PBS controls.

FIG. 28A, fluorescence uptake in alveolar cells; FIG. 28B, percent in alveoli cells/total cells; FIG. 28C, fluorescence uptake in club cells; FIG. 28D, percent in club cells/total cells.

FIG. 29A, distribution in various lung cells; FIG. 29B, distribution by cell type; FIG. 29C-29G, CY3 signals in total cells, immune cells, endothelial cells, epithelial cells and fibroblasts, respectively. Using flow cytometry siRNA accumulation was quantified after systemic (SC) administration of EPA and DCA conjugated siRNAs.

FIG. 30A, distribution in various lung cells; FIG. 30B, distribution by cell type; FIG. 30C-30G, CY3 signals in total cells, immune cells, endothelial cells, epithelial cells and fibroblasts, respectively. Divalent siRNAs showed the highest amount of uptake in all cell types compared to other siRNAs.

FIG. 31A, di-siRNAs after intratracheal administration; FIG. 31B, di-siRNAs after intratracheal administration and DAC/EPA siRNA after SC injection. Intratracheal or SC, 7.5 and 15 nmol and 40 nmol, n=3, 1 week, PNA hybridization assay.

FIG. 32A, liver; FIG. 32B, kidney; FIG. 32C, spleen; FIG. 32D, lung; FIG. 32E, heart, FIG. 32F, adrenal glands; FIG. 32G, muscle; FIG. 32H, fat. Low dose of di-siRNA achieved the best silencing in lungs without silence the gene in other tissues. Intratracheal, 7.5 or 15 nmol, n=5, 1 week, bDNA QuantiGene assay.

DETAILED DESCRIPTION

Figure 1A:
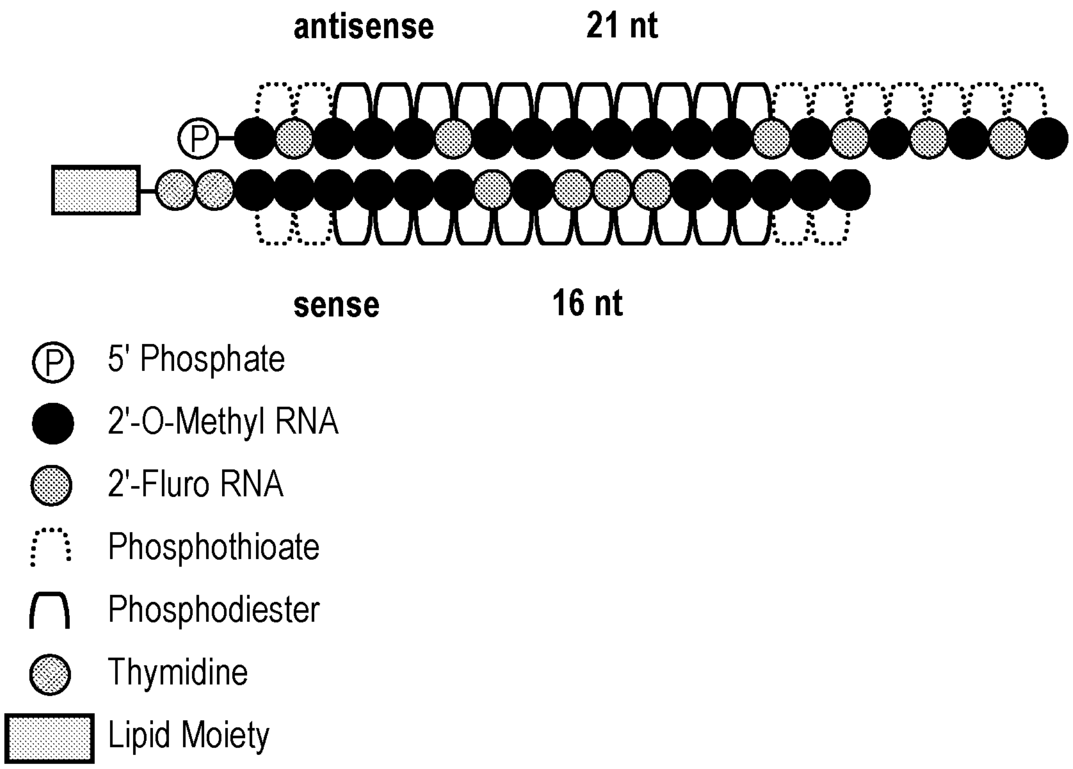
FIG. 1A-1B depict an exemplary chemically modified siRNA (FIG. 1A), and a schematic of the SARS-CoV-2 genome (FIG. 1B).

Novel SARS-CoV-2 target sequences are provided. Also provided are novel RNA molecules, such as siRNAs and branched RNA compounds containing the same, that target one or more SARS-CoV-2 genes mRNA, such as one or more target sequences of the disclosure. Also provided are novel ACE2, FURIN, IL-6, and TMPRSS2 target sequences.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N2,N2-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs), which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include: the 5 position, e.g., 5-(2-amino)propyl uridine, 5-bromo uridine, 5-propyne uridine, 5-propenyl uridine, etc.; the 6 position, e.g., 6-(2-amino)propyl uridine; and the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs, such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function, such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a short polymer of nucleotides and/or nucleotide analogs.

The term "RNA analog" refers to a polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. As discussed above, the oligonucleotides may be linked with linkages, which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Some RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand, which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) and causes or contributes to a disease or disorder. The gain-of-function mutation can be a deletion, addition, or substitution of a nucleotide or nucleotides in the gene, which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

As described herein, the term "SARS-CoV-2" refers to the severe acute respiratory syndrome coronavirus 2, which can cause severe respiratory illness. The SARS-CoV-2 genome contains nine genes. Four genes encode for four structural proteins, S (spike), E (envelope), M (matrix) and N (nucleocapsid). The five other genes are orf1a, orf1ab, 3a, 8b, and 7a. The sequence of the SARS-CoV-2 and the nine genes are recited in Table 1 and Table 2, respectively.

The phrase "examining the function of a gene in a cell or organism" refers to examining or studying the expression, activity, function or phenotype arising therefrom.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small noncoding RNAs can be generated. Exemplary RNA silencing agents include siRNAs, miRNAs, siRNA-like duplexes, antisense oligonucleotides, GAPMER molecules, and dual-function oligonucleotides, as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also known in the art as "small temporal RNAs" ("stRNAs"), refers to a small (10-50 nucleotide) RNA, which are genetically encoded (e.g., by viral, mammalian, or plant genomes) and are capable of directing or mediating RNA silencing. An "miRNA disorder" shall refer to a disease or disorder characterized by an aberrant expression or activity of a miRNA.

As used herein, the term "dual functional oligonucleotide" refers to a RNA silencing agent having the formula T-L-μ, wherein T is an mRNA targeting moiety, L is a linking moiety, and p is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA).

As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like, between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term “bond strength” or “base pair strength” refers to the strength of the base pair.

As used herein, the term “mismatched base pair” refers to a base pair consisting of non-complementary or non-Watson-Crick base pairs, for example, not normal complementary G:C, A:T or A:U base pairs. As used herein the term “ambiguous base pair” (also known as a non-discriminatory base pair) refers to a base pair formed by a universal nucleotide.

As used herein, term “universal nucleotide” (also known as a “neutral nucleotide”) include those nucleotides (e.g. certain destabilizing nucleotides) having a base (a “universal base” or “neutral base”) that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms “sufficient complementarity” or “sufficient degree of complementarity” mean that the RNA silencing agent has a sequence (e.g. in the antisense strand, mRNA targeting moiety or miRNA recruiting moiety), which is sufficient to bind the desired target RNA, respectively, and to trigger the RNA silencing of the target mRNA.

As used herein, the term “translational repression” refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include a step that involves comparing a value, level, feature, characteristic, property, etc. to a “suitable control,” referred to interchangeably herein as an “appropriate control.” A “suitable control” or “appropriate control” is any control or standard familiar to one of ordinary skill in the art useful for comparison purposes. In one embodiment, a “suitable control” or “appropriate control” is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a “suitable control” or “appropriate control” is a value, level, feature, characteristic, property, etc. determined in a cell or organism, e.g., a control or normal cell or organism, exhibiting, for example, normal traits. In yet another embodiment, a “suitable control” or “appropriate control” is a predefined value, level, feature, characteristic, property, etc.

As used herein, the terms “extended nucleic acid” or “exNA” or ex-NA” refer to a novel oligonucleotide backbone modification. This chemical modification of the backbone significantly enhances oligonucleotide metabolic stability. The chemical modification includes one or more carbon atoms or chains inserted in the backbone at the 5'-position, 3'-position, or both. This structural modulation forms non-canonical stretched/flexible structure on oligo-backbones, which protect oligonucleotides from cleavage by various nucleases.

The novel exNA-modification is widely compatible in any oligonucleotide, such as an siRNA, antisense oligonucleotide, and mRNA. The combination of an exNA-phosphorothioate (exNA-PS) backbone enables drastic enhancement of metabolic stability (10-50 orders of magnitude as compared to unmodified oligonucleotides) without compromising the function of the oligonucleotide (e.g., siRNA-mediated silencing efficacy). For example, 5'-[exNA-PS]4-3' modification induce NO negative impact on siRNA efficacy while inducing drastically high exonuclease stability, as will be shown below. Moreover, an exNA-phosphodiester (exNA-PO) backbone also enables drastic enhancement of metabolic stability without compromising the function of the oligonucleotide. It has been previously shown that phosphorothioate-containing backbones in oligonucleotides are toxic when administered in vivo. Accordingly, the exNA-PO backbone can be employed to enhancement of metabolic stability while decreasing toxicity. Thus, this metabolically stabilizing exNA modification is widely and robustly improves the performance of therapeutic oligonucleotide candidates in vivo.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the invention are described in further detail in the following subsections.

I. Novel Target Sequences

In certain exemplary embodiments, RNA silencing agents of the invention are capable of targeting a SARS-CoV-2 nucleic acid sequence of any one of SEQ ID NOs: 1-10, as recited in Table 4 and Table 5.

In certain exemplary embodiments, RNA silencing agents of the invention are capable of targeting one or more of a SARS-CoV-2 nucleic acid sequence of any one of the 45-nucleotide target gene regions recited in Table 6A. In certain exemplary embodiments, RNA silencing agents of the invention are capable of targeting one or more of a SARS-CoV-2 nucleic acid sequence of any one of the 20-nucleotide target regions recited in Table 6A.

In certain exemplary embodiments, RNA silencing agents of the invention are capable of targeting one or more of a SARS-CoV-2 nucleic acid sequence of any one of the 45-nucleotide target gene regions recited in Table 7. In certain exemplary embodiments, RNA silencing agents of the invention are capable of targeting one or more of a SARS-CoV-2 nucleic acid sequence of any one of the 20-nucleotide target regions recited in Table 7.

In certain exemplary embodiments, RNA silencing agents of the invention are capable of targeting one or more of a SARS-CoV-2 nucleic acid sequence of any one of the 45-nucleotide target gene regions recited in Table 8. In certain exemplary embodiments, RNA silencing agents of the invention are capable of targeting one or more of a SARS-CoV-2 nucleic acid sequence of any one of the 20-nucleotide target regions recited in Table 8.

In certain exemplary embodiments, RNA silencing agents of the invention comprise an antisense strand as recited in Table 6B. In certain exemplary embodiments, RNA silencing agents of the invention comprise a sense strand as recited in Table 6C. In certain exemplary embodiments, RNA silencing agents of the invention comprise a sense strand as recited in Table 6D.

In one embodiment, the RNA silencing agents of the invention capable of targeting one or more of a SARS-CoV-2 nucleic acid sequence can be combined with RNA silencing agents of the invention capable of targeting one or more of an ACE2, FURIN, TMPRSS2, IL-6, and IL-6R nucleic acid sequence. The endogenous genes ACE2, FURIN, TMPRSS2, IL-6, and IL-6R each may play a role in SARS-CoV-2 infection and pathogenesis.

"ACE2", as described herein, refers to angiotensin I converting enzyme 2. ACE2 belongs to a family of dipeptidyl carboxydipeptidases and is a zinc-containing metallo protease. ACE2 cleaves angiotensin I into angiotensin II, which has vasoconstrictive properties. It also is a functional receptor of the spike glycoprotein of the human corona viruses. ACE2 expression is age and disease state dependent. Children have lower ACE2 expression, which may explain their decreased susceptibility and milder disease symptoms upon SARS-CoV-2 infection. As such, a reduction in ACE2 expression is a viable therapeutic approach.

"FURIN", as described herein, refers to a subtilisin-like proprotein belonging to the convertase family of proteases. They include proteases that process protein and peptides precursors as they traffic through the constitute branches of the secretory pathway. Furin is exploited by viruses for cleaving envelope proteins. The spike protein of the SARS-CoV-2 virus must be cleaved by furin to become functional, and as such furin represents an attractive target for siRNA (Coutard et al. Antiviral Research. 176: 104727. April 2020).

"TMPRSS2", as described herein, refers to Transmembrane Serine Protease 2. TMPRSS2 has been shown to contribute to virus spread and immunopathology in the airways of murine models after coronavirus infection (Iwata-Yoshikawa et al. J. Virol. 93 (6): e01815-18. March 2019).

"IL-6", as described herein, refers to interleukin-6. "IL-6R", as described herein, refers to interleukin-6 receptor. IL-6 is an inflammatory agent that contributes to cytokine release syndrome (CRS), a severe and potentially deadly response to an infection. IL-6 stimulates inflammation through an interaction with IL-6R (Liu et al. J Autoimmun. 10: 102452. April 2020). Inhibition of IL-6 or its receptor, IL-6R may prevent or reduce the cytokine release syndrome that occurs during a SARS-CoV-2 infection.

In certain exemplary embodiments, RNA silencing agents of the invention are capable of targeting an ACE2 nucleic acid sequence of any one of the 45-nucleotide target gene regions recited in Table 11D and Table 12C. In certain exemplary embodiments, RNA silencing agents of the invention are capable of targeting an ACE2 nucleic acid sequence of any one of the 20-nucleotide target regions recited in Table 1 ID and Table 12C.

In certain exemplary embodiments, RNA silencing agents of the invention are capable of targeting an FURIN nucleic acid sequence of any one of the 45-nucleotide target gene regions recited in Table 11C and Table 12D. In certain exemplary embodiments, RNA silencing agents of the invention are capable of targeting an FURIN nucleic acid sequence of any one of the 20-nucleotide target regions recited in Table 1 IC and Table 12D.

In certain exemplary embodiments, RNA silencing agents of the invention are capable of targeting an TMPRSS2 nucleic acid sequence of any one of the 45-nucleotide target gene regions recited in Table 11A and Table 12A. In certain exemplary embodiments, RNA silencing agents of the invention are capable of targeting an TMPRSS2 nucleic acid sequence of any one of the 20-nucleotide target regions recited in Table 11A and Table 12A.

In certain exemplary embodiments, RNA silencing agents of the invention are capable of targeting an IL-6 nucleic acid sequence of any one of the 45-nucleotide target gene regions recited in Table 11B and Table 12B. In certain exemplary embodiments, RNA silencing agents of the invention are capable of targeting an IL-6 nucleic acid sequence of any one of the 20-nucleotide target regions recited in Table 11B and Table 12B.

In certain exemplary embodiments, RNA silencing agents of the invention are capable of targeting an IL-6R nucleic acid sequence of any one of the 45-nucleotide target gene regions recited in Table 12E. In certain exemplary embodiments, RNA silencing agents of the invention are capable of targeting an IL-6R nucleic acid sequence of any one of the 20-nucleotide target regions recited in Table 12E.

Genomic sequence for each target sequence can be found in, for example, the publicly available database maintained by the NCBI.

II. siRNA Design

In some embodiments, siRNAs are designed as follows. First, a portion of the target gene (e.g., the SARS-CoV-2 gene), e.g., one or more of the target sequences set forth in Table 4, Table 5, Table 6A, Table 7, or Table 8 is selected. Cleavage of mRNA at these sites should eliminate translation of corresponding protein. Antisense strands were designed based on the target sequence and sense strands were designed to be complementary to the antisense strand. Hybridization of the antisense and sense strands forms the siRNA duplex. The antisense strand includes about 19 to 25 nucleotides, e.g., 19, 20, 21, 22, 23, 24 or 25 nucleotides. In other embodiments, the antisense strand includes 20, 21, 22 or 23 nucleotides. The sense strand includes about 14 to 25 nucleotides, e.g., 14, 15, 16, 17, 18, 19, 20, 21, 22, 23, 24 or 25 nucleotides. In other embodiments, the sense strand is 15 nucleotides. In other embodiments, the sense strand is 18 nucleotides. In other embodiments, the sense strand is 20 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention, provided that they retain the ability to mediate RNAi. Longer RNAi agents have been demonstrated to elicit an interferon or PKR response in certain mammalian cells, which may be undesirable. In certain embodiments, the RNAi agents of the invention do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence can be designed such that the target sequence is essentially in the middle of the strand. Moving the target sequence to an off-center position can, in some instances, reduce efficiency of cleavage by the siRNA. Such compositions, i.e., less efficient compositions, may be desirable for use if off-silencing of the wild-type mRNA is detected.

The antisense strand can be the same length as the sense strand and includes complementary nucleotides. In one embodiment, the strands are fully complementary, i.e., the strands are blunt-ended when aligned or annealed. In another embodiment, the strands align or anneal such that 1-, 2-, 3-, 4-, 5-, 6-, 7-, or 8-nucleotide overhangs are generated, i.e., the 3' end of the sense strand extends 1, 2, 3, 4, 5, 6, 7, or 8 nucleotides further than the 5' end of the antisense strand and/or the 3' end of the antisense strand extends 1, 2, 3, 4, 5, 6, 7, or 8 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled “Methods and Compositions for Controlling Efficacy of RNA Silencing” (filed Jun. 2, 2003) and U.S. Pat. Nos. 8,309,704, 7,750,144, 8,304,530, 8,329,892 and 8,309,705, entitled “Methods and Compositions for Enhancing the Efficacy and Specificity of RNAi” (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the SARS-CoV-2 target sequences set forth in Table 4, Table 5, Table 6A, Table 7, or Table 8 is described in detail below. siRNAs can be designed according to the above exemplary teachings for any other target sequences found in the SARS-CoV-2 gene. Moreover, the technology is applicable to targeting any other target sequences, e.g., non-disease-causing target sequences.

To validate the effectiveness by which siRNAs destroy mRNAs (e.g., SARS-CoV-2 mRNA), the siRNA can be incubated with cDNA (e.g., SARS-CoV-2 cDNA) in a *Drosophila*-based in vitro mRNA expression system. Radiolabeled with $^{32}P$, newly synthesized mRNAs (e.g., SARS-CoV-2 mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

III. RNAi Agents

The present invention includes RNAi molecules, such as siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategyl.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems, such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., SARS-CoV-2 genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding SARS-CoV-2, targeting the same gene or multiple genes, and can be driven, for example, by separate PolIII promoter sites.

Animal cells express a range of noncoding RNAs of approximately 22 nucleotides termed micro RNA (miRNAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., lung (e.g., endothelial cells, epithelial cells, fibroblasts, and immune cells in the lungs, e.g. clara cells, alveolar cells, and club cells)

The nucleic acid compositions of the invention include both unmodified siRNAs and modified siRNAs, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative, as compared to the corresponding siRNA, and are useful for tracing the siRNA derivative in the cell, or improving the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA, which will be targeted by the siRNA generated from the engineered RNA precursor, and will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53 (1-3): 137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3H$, $^{32}P$ or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis), generated (e.g., enzymatically generated), or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, such as about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-SARS-CoV-2 RNA Silencing Agents

In certain embodiment, the present invention provides novel anti-SARS-CoV-2 RNA silencing agents (e.g., siRNA, shRNA, and antisense oligonucleotides), methods of making said RNA silencing agents, and methods (e.g., research and/or therapeutic methods) for using said improved RNA silencing agents (or portions thereof) for RNA silencing of SARS-CoV-2 protein. The RNA silencing agents comprise an antisense strand (or portions thereof), wherein the antisense strand has sufficient complementary to a target SARS-CoV-2 mRNA to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-20 base pair duplexes; (4) greater than 50% 2'-methoxy modifications, such as 70%-100% 2'-methoxy modifications, although an alternating pattern of chemically-modified nucleotides (e.g., 2'-fluoro and 2'-methoxy modifications), are also contemplated; and (5) single-stranded, fully phosphorothioated tails of 5-8 bases. In certain embodiments, the number of phosphorothioate modifications is varied from 4 to 16 total. In certain embodiments, the number of phosphorothioate modifications is varied from 8 to 13 total.

In certain embodiments, the siRNA compounds described herein can be conjugated to a variety of targeting agents, including, but not limited to, docosanoic acid (DCA), cholesterol, docosahexaenoic acid (DHA), phenyltropanes, cortisol, vitamin A, vitamin D, N-acetylgalactosamine (GalNac), and gangliosides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts. lung epithelial cells).

Certain compounds of the invention having the structural properties described above and herein may be referred to as "hsiRNA-ASP" (hydrophobically-modified, small interfering RNA, featuring an advanced stabilization pattern). In addition, siRNAs conjugated to DCA or EPA and containing different numbers of 3' exNA modifications and phosphorothioates showed a dramatically improved distribution through the lung, making them accessible for therapeutic intervention.

In certain embodiments, the siRNA comprises between 6 and 13 total phosphorothioate modifications. In certain embodiments, the siRNA comprises 6 phosphorothioate modifications. In certain embodiments, the siRNA comprises 8 phosphorothioate modifications. In certain embodiments, the siRNA antisense strand comprises 6 phosphorothioate modifications. In certain embodiments, the siRNA antisense strand comprises 4 phosphorothioate modifications. In certain embodiments, the siRNA sense strand comprises 2 phosphorothioate modifications.

In certain embodiments, the siRNA sense strand 3' end is conjugated to DCA. In certain embodiments, the siRNA sense strand 3' end is conjugated to EPA.

In certain embodiments, the siRNA antisense strand comprises two to five 3' exNA modifications. In certain embodiments, the siRNA antisense strand comprises two 3' exNA modifications. In certain embodiments, the siRNA antisense strand comprises three 3' exNA modifications. In certain embodiments, the siRNA antisense strand comprises four 3' exNA modifications. In certain embodiments, the siRNA antisense strand comprises five 3' exNA modifications. In certain embodiments, the siRNA antisense strand comprises four consecutive 3' exNA modifications.

In certain embodiments, the siRNA antisense strand comprises two to five 3' exNA modifications and 6 phosphorothioate modifications. In certain embodiments, the siRNA antisense strand comprises two to five 3' exNA modifications and 4 phosphorothioate modifications. In certain embodiments, the siRNA antisense strand comprises four 3' exNA modifications and 6 phosphorothioate modifications. In certain embodiments, the siRNA antisense strand comprises four 3' exNA modifications and 4 phosphorothioate modifications.

The compounds of the invention can be described in the following aspects and embodiments.

In a first aspect, provided herein is a double stranded RNA (dsRNA) comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;
(2) the antisense strand comprises alternating 2'-methoxy-ribonucleotides and 2'-fluoro-ribonucleotides;
(3) the nucleotides at positions 2 and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises alternating 2'-methoxy-ribonucleotides and 2'-fluoro-ribonucleotides; and
(7) the nucleotides at positions 1-2 from the 5' end of the sense strand are connected to each other via phosphorothioate internucleotide linkages.

In a second aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;
(2) the antisense strand comprises at least 70% 2'-O-methyl modifications;
(3) the nucleotide at position 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 70% 2'-O-methyl modifications; and
(7) the nucleotides at positions 1-2 from the 5' end of the sense strand are connected to each other via phosphorothioate internucleotide linkages.

In a third aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;
(2) the antisense strand comprises at least 85% 2'-O-methyl modifications;
(3) the nucleotides at positions 2 and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises 100% 2'-O-methyl modifications; and (7) the nucleotides at positions 1-2 from the 5' end of the sense strand are connected to each other via phosphorothioate internucleotide linkages.

In a fourth aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;

(2) the antisense strand comprises at least 75% 2'-O-methyl modifications;

(3) the nucleotides at positions 4, 5, 6, and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises 100% 2'-O-methyl modifications; and (7) the nucleotides at positions 1-2 from the 5' end of the sense strand are connected to each other via phosphorothioate internucleotide linkages.

In a fifth aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;

(2) the antisense strand comprises at least 75% 2'-O-methyl modifications;

(3) the nucleotides at positions 2, 4, 5, 6, and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises 100% 2'-O-methyl modifications; and (7) the nucleotides at positions 1-2 from the 5' end of the sense strand are connected to each other via phosphorothioate internucleotide linkages.

In a sixth aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;

(2) the antisense strand comprises at least 75% 2'-O-methyl modifications;

(3) the nucleotides at positions 2, 6, 14, and 16 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 70% 2'-O-methyl modifications;

(7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In a seventh aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SARS-CoV-2 nucleic acid sequence of any one of the 45-nucleotide target gene regions in Table 6A;

(2) the antisense strand comprises at least 75% 2'-O-methyl modifications;

(3) the nucleotides at positions 2, 6, and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 80% 2'-O-methyl modifications;

(7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

a) Design of Anti-SARS-CoV-2 siRNA Molecules

An siRNA molecule of the application is a duplex made of a sense strand and complementary antisense strand, the antisense strand having sufficient complementary to a SARS-CoV-2 mRNA to mediate RNAi. In certain embodiments, the siRNA molecule has a length from about 10-50 or more nucleotides, i.e., each strand comprises 10-50 nucleotides (or nucleotide analogs). In other embodiments, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In certain embodiments, the strands are aligned such that there are at least 1, 2, 3, 4, 5, 6, 7, 8, 9, or 10 bases at the end of the strands, which do not align (i.e., for which no complementary bases occur in the opposing strand), such that an overhang of 1, 2, 3, 4, 5, 6, 7, 8, 9, or 10 residues occurs at one or both ends of the duplex when strands are annealed.

Usually, siRNAs can be designed by using any method known in the art, for instance, by using the following protocol:

1. The siRNA should be specific for a target sequence, e.g., a target sequence set forth in the Examples. The first strand should be complementary to the target sequence, and the other strand is substantially complementary to the first strand. (See Examples for exemplary sense and antisense strands.) Exemplary target sequences are selected from any region of the target gene that leads to potent gene silencing.

Regions of the target gene include, but are not limited to, the 5' untranslated region (5'-UTR) of a target gene, the 3' untranslated region (3'-UTR) of a target gene, an exon of a target gene, or an intron of a target gene. Cleavage of mRNA at these sites should eliminate translation of corresponding SARS-CoV-2 protein. Target sequences from other regions of the SARS-CoV-2 gene are also suitable for targeting. A sense strand is designed based on the target sequence.

2. The sense strand of the siRNA is designed based on the sequence of the selected target site. In certain embodiments, the sense strand includes about 15 to 25 nucleotides, e.g., 15, 16, 17, 18, 19, 20, 21, 22, 23, 24 or 25 nucleotides. In certain embodiments, the sense strand includes 15, 16, 17, 18, 19, or 20 nucleotides. In certain embodiments, the sense strand is 15 nucleotides in length. In certain embodiments, the sense strand is 18 nucleotides in length. In certain embodiments, the sense strand is 20 nucleotides in length. The skilled artisan will appreciate, however, that siRNAs having a length of less than 15 nucleotides or greater than 25 nucleotides can also function to mediate RNAi. Accordingly, siRNAs of such length are also within the scope of the instant invention, provided that they retain the ability to mediate RNAi. Longer RNA silencing agents have been demonstrated to elicit an interferon or Protein Kinase R (PKR) response in certain mammalian cells which may be undesirable. In certain embodiments, the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently complementary to a target sequence portion of the target gene to effect RISC-mediated cleavage of the target gene are contemplated. Accordingly, in a certain embodiment, the antisense strand of the siRNA is designed to have a sequence sufficiently complementary to a portion of the target. For example, the antisense strand may have 100% complementarity to the target site. However, 100% complementarity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% complementarity, between the antisense strand and the target RNA sequence is contemplated. The present application has the advantage of being able to tolerate certain sequence variations to enhance efficiency and specificity of RNAi. In one embodiment, the antisense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and the percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2 (# of A+T bases)+4 (# of G+C bases). For hybrids between 18 and 49 base pairs in length, $T_m$(° C.)=81.5+16.6 (log 10[Na+])+0.41 (% G+C)−(600/N), where N is the number of bases in the hybrid, and [Na+] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant SARS-CoV-2 mRNA), the siRNA may be incubated with target cDNA (e.g., SARS-CoV-2 cDNA) in a *Drosophila*-based in vitro mRNA expression system. Radiolabeled with $^{32}P$, newly synthesized target mRNAs (e.g., SARS-CoV-2 mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-SARS-CoV-2 siRNAs may be designed to target any of the target sequences described supra. Said siRNAs comprise an antisense strand, which is sufficiently complementary with the target sequence to mediate silencing of the target sequence. In certain embodiments, the RNA silencing agent is a siRNA.

In certain embodiments, the siRNA comprises a sense strand comprising a sequence set forth in Table 6C or Table 6D, and an antisense strand comprising a sequence set forth in Table 6B.

Sites of siRNA-mRNA complementation are selected, which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of an SARS-CoV-2 mRNA to direct gene silencing either by RNAi or translational repression. siRNA-like molecules are designed in the same way as siRNA molecules, but the degree of sequence identity between the sense strand and target RNA approximates that observed between a miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an SARS-CoV-2 target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides, which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the present application are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the SARS-CoV-2 target sequence. In certain embodiments, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are about 15 to about 50 nucleotides in length. In certain embodiments, the two stem portions are about 18 or 19 to about 21, 22, 23, 24, 25, 30, 35, 37, 38, 39, or 40 or more nucleotides in length. In certain embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. In certain embodiments, a loop consists of or comprises a "tetraloop" sequence. Exemplary tetraloop sequences include, but are not limited to, the sequences GNRA, where N is any nucleotide and R is a purine nucleotide, GGGG, and UUUU.

In certain embodiments, shRNAs of the present application include the sequences of a desired siRNA molecule described supra. In other embodiments, the sequence of the antisense portion of a shRNA can be designed essentially as described above or generally by selecting an 18, 19, 20, 21 nucleotides, or longer, sequence from within the target RNA (e.g., SARS-CoV-2 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include, in the duplex stem, the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between a miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In certain embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), a miRNA, to mediate RNA silencing. Accordingly, the methods described herein obviate the need to introduce foreign molecules (e.g., siRNAs) to mediate RNA silencing. Second, the RNA-silencing agents and the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In certain embodiments, the tethers have the formula T-L-μ, wherein T is an mRNA targeting moiety, L is a linking moiety, and is a miRNA recruiting moiety. Any one or more moiety may be double stranded. In certain embodiments, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly, depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a certain embodiment, the targeting moiety is about 15 to about 25 nucleotides in length.

The miRNA recruiting moiety, as described above, is capable of associating with a miRNA. According to the present application, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties can be oligonucleotide moieties comprising a sufficient number of nucleotides, such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., SARS-CoV-2 gene expression) can be modulated using oligonucleotide-based compounds comprising two or more single stranded antisense oligonucleotides that are linked through their 5'-ends that allow the presence of two or more accessible 3'-ends to effectively inhibit or decrease SARS-CoV-2 gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of a gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula $HO—(CH_2)_o—CH(OH)—(CH_2)_p—OH$, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula $HO—(CH_2)_m—C(O)NH—CH_2—CH(OH)—CH_2—NHC(O)—(CH_2)_m—OH$, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods, such as phosphoramidate or H-phosphonate chemistry, which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate, carboxymethyl ester, or a combination of these and other internucleotide linkages between the 5' end of one nucleotide and the 3' end of another nucleotide, in which the 5' nucleotide phosphodiester linkage has been replaced with any number of chemical groups.

V. Modified Anti-SARS-CoV-2 RNA Silencing Agents

In certain aspects of the invention, an RNA silencing agent (or any portion thereof) of the present application, as described supra, may be modified, such that the activity of the agent is further improved. For example, the RNA silencing agents described in Section II supra, may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the present application may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is contemplated because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In certain embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide.

In certain embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In certain embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the present application may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In certain embodiments, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In certain embodiments, the base pair is selected from the group consisting of an I:A, I:U and I:C. In yet another embodiment, the asymmetry of an RNA silencing agent of the invention may be enhanced such that there is at least one base pair comprising a modified nucleotide. In certain embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. In order to enhance the stability, the 3'-residues may be stabilized against degradation, e.g., they may be selected such that they consist of purine nucleotides, such as adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an “internal” nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified. In certain embodiments, the RNA silencing agents may be fully chemically modified, i.e., 100% of the nucleotides are chemically modified. In another aspect, the present application features RNA silencing agents comprising 2'-OH ribose groups that are at least 80% chemically modified. In certain embodiments, the RNA silencing agents comprise 2'-OH ribose groups that are about 80%, 85%, 90%, 95%, or 100% chemically modified.

In certain embodiments, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Moreover, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphorothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In certain embodiments, the modifications are 2'-fluoro, 2'-amino and/or 2'-thio modifications. Modifications include 2'-fluoro-cytidine, 2'-fluoro-uridine, 2'-fluoro-adenosine, 2'-fluoro-guanosine, 2-amino-cytidine, 2-amino-uridine, 2-amino-adenosine, 2'-amino-guanosine, 2,6-diaminopurine, 4-thio-uridine, and/or 5-amino-allyl-uridine. In a certain embodiment, the 2'-fluoro ribonucleotides are every uridine and cytidine. Additional exemplary modifications include 5-bromo-uridine, 5-iodo-uridine, 5-methyl-cytidine, ribothymidine, 2-aminopurine, 2'-amino-butyryl-pyrene-uridine, 5-fluoro-cytidine, and 5-fluoro-uridine. 2'-deoxy-nucleotides and 2'-O-Me nucleotides can also be used within modified RNA-silencing agents of the instant invention. Additional modified residues include, deoxy-abasic, inosine, N3-methyl-uridine, N6,N6-dimethyl-adenosine, pseudouridine, purine ribonucleoside and ribavirin. In a certain embodiment, the 2' moiety is a methyl group such that the linking moiety is a 2'-O-methyl oligonucleotide.

In a certain embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone, which is highly resistant to nuclease digestion and imparts improved binding specificity to the molecule (Nielsen, et al., Science, (2001), 254: 1497-1500).

Also contemplated are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a O with an S; (c) replacement of the U with a $C_5$ amino linker; (d) replacement of an A with a G (sequence changes can be located on the sense strand and not the antisense strand in certain embodiments); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications. In certain embodiments, the RNA silencing agent is a dsRNA comprising an antisense strand and sense strand. In certain embodiments, the antisense strand comprises at least about 70% 2'-O-methyl nucleotide modifications. In certain embodiments, the antisense strand comprises between about 70% and about 90% 2'-O-methyl nucleotide modifications. In certain embodiments, the sense strand comprises at least about 70% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications.

2'-O-methyl rich RNA silencing agents and specific chemical modification patterns are further described in U.S. Ser. No. 16/550,076 (filed Aug. 23, 2019) and U.S. Ser. No. 62/891,185 (filed Aug. 23, 2019), each of which is incorporated herein by reference.

Internucleotide Linkage Modifications

In certain embodiments, at least one internucleotide linkage, intersubunit linkage, or nucleotide backbone is modified in the RNA silencing agent. In certain embodiments, all of the internucleotide linkages in the RNA silencing agent are modified. In certain embodiments, the modified internucleotide linkage comprises a phosphorothioate internucleotide linkage. In certain embodiments, the RNA silencing agent comprise 1, 2, 3, 4, 5, 6, 7, 8, 9, 10, 11, 12, 13, 14, 15, 16, 17, 18, 19, 20, 21, 22, 23, 24, or 25 phosphorothioate internucleotide linkages. In certain embodiments, the RNA silencing agent comprises 4-16 phosphorothioate internucleotide linkages. In certain embodiments, the RNA silencing agent comprises 8-13 phosphorothioate internucleotide linkages. In certain embodiments, the RNA silencing agent is a dsRNA comprising an antisense strand and a sense strand, each comprising a 5' end and a 3' end. In certain embodiments, the nucleotides at positions 1 and 2 from the 5' end of sense strand are connected to adjacent ribonucleotides via phosphorothioate internucleotide linkages. In certain embodiments, the nucleotides at positions 1 and 2 from the 3' end of sense strand are connected to adjacent ribonucleotides via phosphorothioate internucleotide linkages. In certain embodiments, the nucleotides at positions 1 and 2 from the 5' end of antisense strand are connected to adjacent ribonucleotides via phosphorothioate internucleotide linkages. In certain embodiments, the nucleotides at positions 1-2 to 1-8 from the 3' end of antisense strand are connected to adjacent ribonucleotides via phosphorothioate internucleotide linkages. In certain embodiments, the nucleotides at positions 1-2, 1-3, 1-4, 1-5, 1-6, 1-7, or 1-8 from the 3' end of antisense strand are connected to adjacent ribonucleotides via phosphorothioate internucleotide linkages. In certain embodiments, the nucleotides at positions 1-2 to 1-7 from the 3' end of antisense strand are connected to adjacent ribonucleotides via phosphorothioate internucleotide linkages.

In one aspect, the disclosure provides a modified oligonucleotide, said oligonucleotide having a 5' end, a 3' end, that is complementary to a target, wherein the oligonucleotide comprises a sense and antisense strand, and at least one modified intersubunit linkage of Formula (I):

(I)

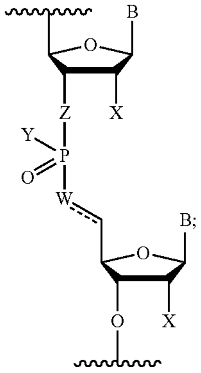

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and $\overline{\overline{---}}$ is an optional double bond.

In an embodiment of Formula (I), when W is CH, $\overline{\overline{---}}$ is a double bond.

In an embodiment of Formula (I), when W selected from the group consisting of O, $OCH_2$, OCH, $CH_2$, $\overline{\overline{---}}$ is a single bond.

In an embodiment of Formula (I), when Y is $O^-$, either Z or W is not O.

In an embodiment of Formula (I), Z is $CH_2$ and W is $CH_2$. In another embodiment, the modified intersubunit linkage of Formula (I) is a modified intersubunit linkage of Formula (II):

(II)

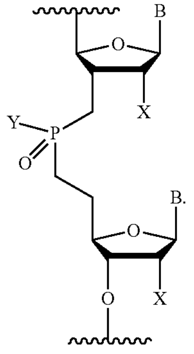

In an embodiment of Formula (I), Z is $CH_2$ and W is O. In another embodiment, wherein the modified intersubunit linkage of Formula (I) is a modified intersubunit linkage of Formula (III):

(III)

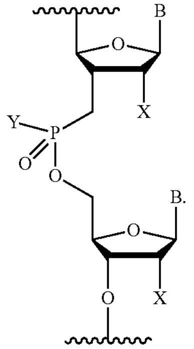

In an embodiment of Formula (I), Z is O and W is $CH_2$. In another embodiment, the modified intersubunit linkage of Formula (I) is a modified intersubunit linkage of Formula (IV):

(IV)

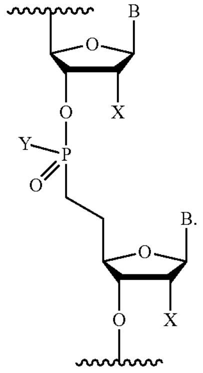

In an embodiment of Formula (I), Z is O and W is CH. In another embodiment, the modified intersubunit linkage of Formula (I) is a modified intersubunit linkage of Formula V:

(V)

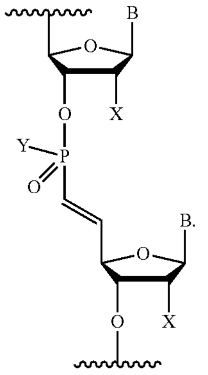

In an embodiment of Formula (I), Z is O and W is $OCH_2$. In another embodiment, the modified intersubunit linkage of Formula (I) is a modified intersubunit linkage of Formula VI:

(VI)

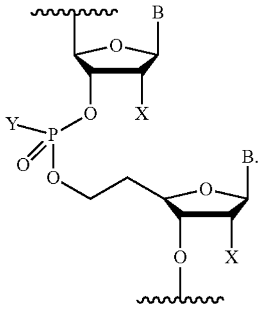

In an embodiment of Formula (I), Z is $CH_2$ and W is CH. In another embodiment, the modified intersubunit linkage of Formula (I) is a modified intersubunit linkage of Formula VII:

(VII)

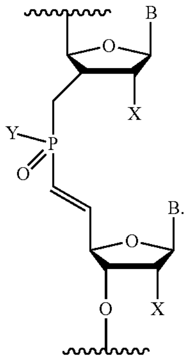

In an embodiment of Formula (I), the base pairing moiety B is selected from the group consisting of adenine, guanine, cytosine, and uracil.

In an embodiment, the modified oligonucleotide is incorporated into siRNA, said modified siRNA having a 5' end, a 3' end, that is complementary to a target, wherein the siRNA comprises a sense and antisense strand, and at least one modified intersubunit linkage of any one or more of Formula (I), Formula (II), Formula (III), Formula (IV), Formula (V), Formula (VI), or Formula (VII).

In an embodiment, the modified oligonucleotide is incorporated into siRNA, said modified siRNA having a 5' end, a 3' end, that is complementary to a target and comprises a sense and antisense strand, wherein the siRNA comprises at least one modified intersubunit linkage is of Formula VIII:

(VIII)

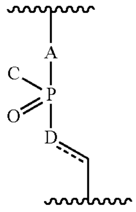

;

wherein:

- D is selected from the group consisting of O, $OCH_2$, OCH, $CH_2$, and CH;
- C is selected from the group consisting of $O^-$, OH, $OR^1$, $NH^-$, $NH_2$, $S^-$, and SH;
- A is selected from the group consisting of O and $CH_2$;
- $R^1$ is a protecting group;
- $\equiv$ is an optional double bond; and
- the intersubunit is bridging two optionally modified nucleosides.

In an embodiment, when C is $O^-$, either A or D is not O.

In an embodiment, D is $CH_2$. In another embodiment, the modified intersubunit linkage of Formula VIII is a modified intersubunit linkage of Formula (IX):

(IX)

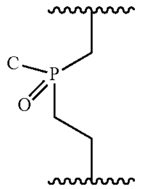

In an embodiment, D is O. In another embodiment, the modified intersubunit linkage of Formula VIII is a modified intersubunit linkage of Formula (X):

(X)

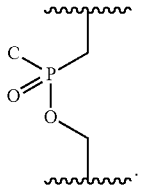

In an embodiment, D is $CH_2$. In another embodiment, the modified intersubunit linkage of Formula (VIII) is a modified intersubunit linkage of Formula (XI):

(XI)

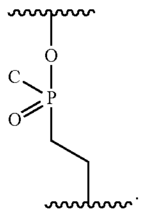

In an embodiment, D is CH. In another embodiment, the modified intersubunit linkage of Formula VIII is a modified intersubunit linkage of Formula (XII):

(XII)

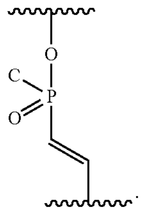

In another embodiment, the modified intersubunit linkage of Formula (VII) is a modified intersubunit linkage of Formula (XIV):

(XIV)

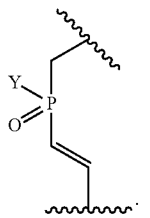

In an embodiment, D is $OCH_2$. In another embodiment, the modified intersubunit linkage of Formula (VII) is a modified intersubunit linkage of Formula (XIII):

(XIII)

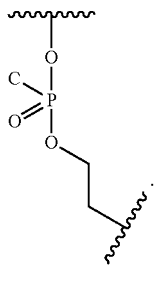

In another embodiment, the modified intersubunit linkage of Formula (VII) is a modified intersubunit linkage of Formula (XXa):

(XXa)

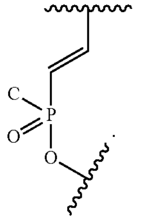

In an embodiment of the modified siRNA linkage, each optionally modified nucleoside is independently, at each occurrence, selected from the group consisting of adenosine, guanosine, cytidine, and uridine.

In certain exemplary embodiments of Formula (I), W is O. In another embodiment, W is $CH_2$. In yet another embodiment, W is CH.

In certain exemplary embodiments of Formula (I), X is OH. In another embodiment, X is $OCH_3$. In yet another embodiment, X is halo.

In a certain embodiment of Formula (I), the modified siRNA does not comprise a 2'-fluoro substituent.

In an embodiment of Formula (I), Y is O. In another embodiment, Y is OH. In yet another embodiment, Y is OR. In still another embodiment, Y is $NH^-$. In an embodiment, Y is $NH_2$. In another embodiment, Y is $S^-$. In yet another embodiment, Y is SH.

In an embodiment of Formula (I), Z is O. In another embodiment, Z is $CH_2$.

In an embodiment, the modified intersubunit linkage is inserted on position 1-2 of the antisense strand. In another embodiment, the modified intersubunit linkage is inserted on position 6-7 of the antisense strand. In yet another embodiment, the modified intersubunit linkage is inserted on position 10-11 of the antisense strand. In still another embodiment, the modified intersubunit linkage is inserted on position 19-20 of the antisense strand. In an embodiment, the modified intersubunit linkage is inserted on positions 5-6 and 18-19 of the antisense strand.

In an exemplary embodiment of the modified siRNA linkage of Formula (VIII), C is $O^-$. In another embodiment, C is OH. In yet another embodiment, C is $OR^1$. In still another embodiment, C is $NH^-$. In an embodiment, C is $NH_2$. In another embodiment, C is $S^-$. In yet another embodiment, C is SH.

In an exemplary embodiment of the modified siRNA linkage of Formula (VIII), A is O. In another embodiment, A is $CH_2$. In yet another embodiment, C is $OR^1$. In still another embodiment, C is $NH^-$. In an embodiment, C is $NH_2$. In another embodiment, C is $S^-$. In yet another embodiment, C is SH.

In a certain embodiment of the modified siRNA linkage of Formula (VIII), the optionally modified nucleoside is adenosine. In another embodiment of the modified siRNA linkage of Formula (VIII), the optionally modified nucleoside is guanosine. In another embodiment of the modified siRNA linkage of Formula (VIII), the optionally modified nucleoside is cytidine. In another embodiment of the modified siRNA linkage of Formula (VIII), the optionally modified nucleoside is uridine.

In an embodiment of the modified siRNA linkage, wherein the linkage is inserted on position 1-2 of the antisense strand. In another embodiment, the linkage is inserted on position 6-7 of the antisense strand. In yet another embodiment, the linkage is inserted on position 10-11 of the antisense strand. In still another embodiment, the linkage is inserted on position 19-20 of the antisense strand. In an embodiment, the linkage is inserted on positions 5-6 and 18-19 of the antisense strand.

In certain embodiments of Formula (I), the base pairing moiety B is adenine. In certain embodiments of Formula (I), the base pairing moiety B is guanine. In certain embodiments of Formula (I), the base pairing moiety B is cytosine. In certain embodiments of Formula (I), the base pairing moiety B is uracil.

In an embodiment of Formula (I), W is O. In an embodiment of Formula (I), W is $CH_2$. In an embodiment of Formula (I), W is CH.

In an embodiment of Formula (I), X is OH. In an embodiment of Formula (I), X is $OCH_3$. In an embodiment of Formula (I), X is halo.

In an exemplary embodiment of Formula (I), the modified oligonucleotide does not comprise a 2'-fluoro substituent.

In an embodiment of Formula (I), Y is $O^-$. In an embodiment of Formula (I), Y is OH. In an embodiment of Formula (I), Y is OR. In an embodiment of Formula (I), Y is $NH^-$. In an embodiment of Formula (I), Y is $NH_2$. In an embodiment of Formula (I), Y is $S^-$. In an embodiment of Formula (I), Y is SH.

In an embodiment of Formula (I), Z is O. In an embodiment of Formula (I), Z is $CH_2$.

In an embodiment of the Formula (I), the linkage is inserted on position 1-2 of the antisense strand. In another embodiment of Formula (I), the linkage is inserted on position 6-7 of the antisense strand. In yet another embodiment of Formula (I), the linkage is inserted on position 10-11 of the antisense strand. In still another embodiment of Formula (I), the linkage is inserted on position 19-20 of the antisense strand. In an embodiment of Formula (I), the linkage is inserted on positions 5-6 and 18-19 of the antisense strand.

Modified intersubunit linkages are further described in WO20200198509 and PCT/US2021/024425, each of which is incorporated herein by reference.

4) Conjugated Functional Moieties

In other embodiments, RNA silencing agents may be modified with one or more functional moieties. A functional moiety is a molecule that confers one or more additional activities to the RNA silencing agent. In certain embodiments, the functional moieties enhance cellular uptake by target cells (e.g., lung cells). Thus, the invention includes RNA silencing agents which are conjugated or unconjugated (e.g., at its 5' and/or 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53 (1-3): 137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a certain embodiment, the functional moiety is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, a cationic dye (e.g., Cy3). In an exemplary embodiment, the lipophilic moiety is cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

In certain embodiments, the functional moieties may comprise one or more ligands tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These can be located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or a metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine, has an increased affinity for the HIV Rev-response element (RRE). In some embodiments, the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, either directly or indirectly, via an intervening tether, to a ligand-conjugated carrier. In certain embodiments, the coupling is through a covalent bond. In certain embodiments, the ligand is attached to the carrier via an intervening tether. In certain embodiments, a ligand alters the distribution, targeting or lifetime of an RNA silencing agent into which it is incorporated. In certain embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNAc) or derivatives thereof, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycosides, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP. In certain embodiments, the ligand is GalNAc or a derivative thereof.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF D), interleukin-1 beta, or gamma interferon. In one aspect, the ligand is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a certain embodiment, the lipid based ligand binds HSA. A lipid-based ligand can bind HSA with a sufficient affinity such that the conjugate will be distributed to a non-kidney tissue. However, it is contemplated that the affinity not be so strong that the HSA-ligand binding cannot be reversed. In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These can be useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent can be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

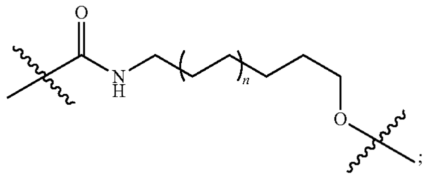
;

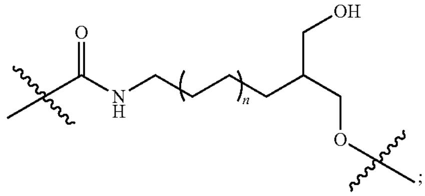
;

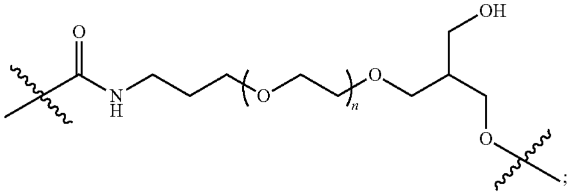
;

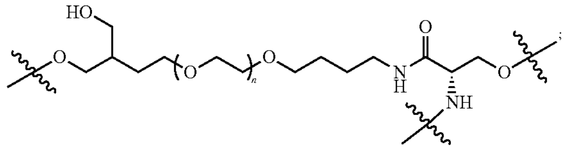
;

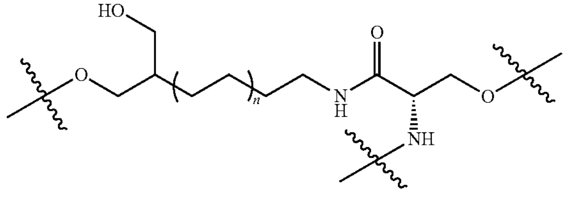

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of.

(Zc1)

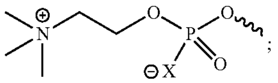

(Zc2)

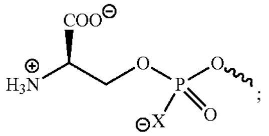

(Zc3)

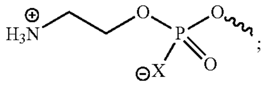

and (Zc4)

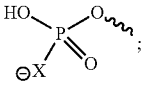

wherein X is O, S or $BH_3$.

The various functional moieties of the disclosure and means to conjugate them to RNA silencing agents are described in further detail in WO2017/030973A1 and WO2018/031933A2, incorporated herein by reference.

VI. Branched Oligonucleotides

Two or more RNA silencing agents as disclosed supra, for example oligonucleotide constructs such as anti-SARS-CoV-2 siRNAs, may be connected to one another by one or more moieties independently selected from a linker, a spacer and a branching point, to form a branched oligonucleotide RNA silencing agent. In certain embodiments, the branched oligonucleotide RNA silencing agent consists of two siRNAs to form a di-branched siRNA ("di-siRNA") scaffolding for delivering two siRNAs. In representative embodiments, the nucleic acids of the branched oligonucleotide each comprise an antisense strand (or portions thereof), wherein the antisense strand has sufficient complementarity to a target mRNA (e.g., SARS-CoV-2 mRNA) to mediate an RNA-mediated silencing mechanism (e.g. RNAi).

In exemplary embodiments, the branched oligonucleotides may have two to eight RNA silencing agents attached through a linker. The linker may be hydrophobic. In an embodiment, branched oligonucleotides of the present application have two to three oligonucleotides. In an embodiment, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has two to ten nucleotides.

In certain embodiments, branched oligonucleotides are characterized by three properties: (1) a branched structure, (2) full metabolic stabilization, and (3) the presence of a single-stranded tail comprising phosphorothioate linkers. In certain embodiments, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. In some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm ~37° C.) for fast dissociation upon internalization of the branched structure into the cell.

The Di-siRNA branched oligonucleotides may comprise chemically diverse conjugates, such as the functional moieties described above. Conjugated bioactive ligands may be used to enhance cellular specificity and to promote membrane association, internalization, and serum protein binding. Examples of bioactive moieties to be used for conjugation include DHA, GalNAc, and cholesterol. These moieties can be attached to Di-siRNA either through the connecting linker or spacer, or added via an additional linker or spacer attached to another free siRNA end.

Branched oligonucleotides comprise a variety of therapeutic nucleic acids, including siRNAs, ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

VII. Compound of Formula (I)

In another aspect, provided herein is a branched oligonucleotide compound of formula (I):

$$L\text{-}(N)_n \qquad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof, S is independently for each occurrence selected from an ethylene glycol chain, an alkyl chain, a peptide, RNA, DNA, a phosphate, a phosphonate, a phosphoramidate, an ester, an amide, a triazole, and combinations thereof.

Moiety N is an RNA duplex comprising a sense strand and an antisense strand; and n is 2, 3, 4, 5, 6, 7 or 8. In an embodiment, the antisense strand of N comprises a sequence substantially complementary to a SARS-CoV-2 nucleic acid sequence of any one of SEQ ID NOs: 1-10, as recited in Table 4 and Table 5.

In an embodiment, the antisense strand of N comprises a sequence substantially complementary to a SARS-CoV-2 nucleic acid sequence of any one of the 45-nucleotide target gene regions recited in Table 6A.

The sense strand and antisense strand may each independently comprise one or more chemical modifications.

In an embodiment, the compound of formula (I) has a structure selected from formulas (I-1)-(I-9) of Table 1.

TABLE 1

N—L—N (I-1)

N—S—L—S—N (I-2)

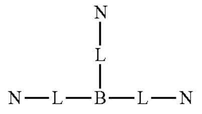

(I-3)

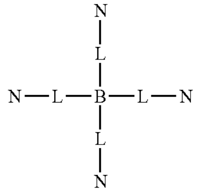

(I-4)

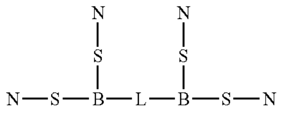

(I-5)

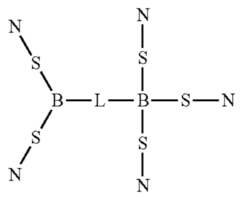

(I-6)

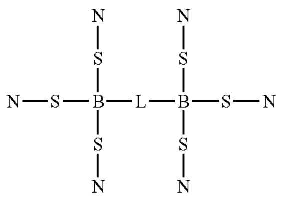

(I-7)

TABLE 1-continued

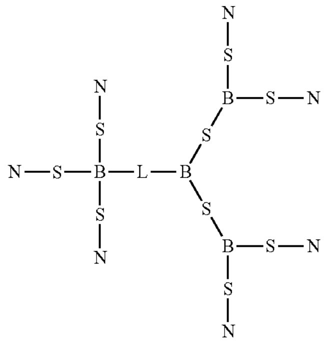

(I-8)

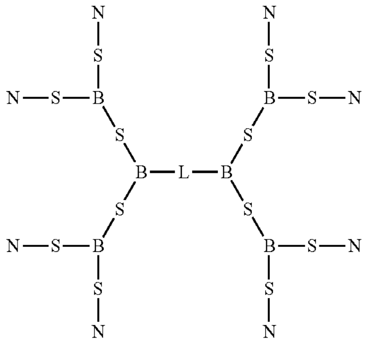

(I-9)

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of.

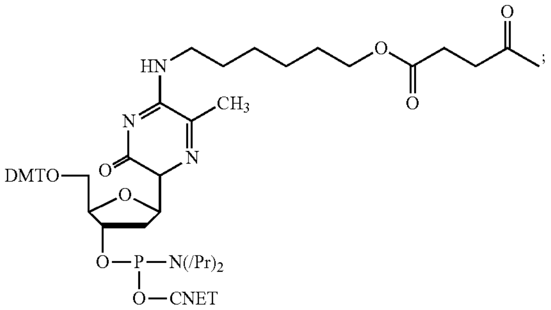

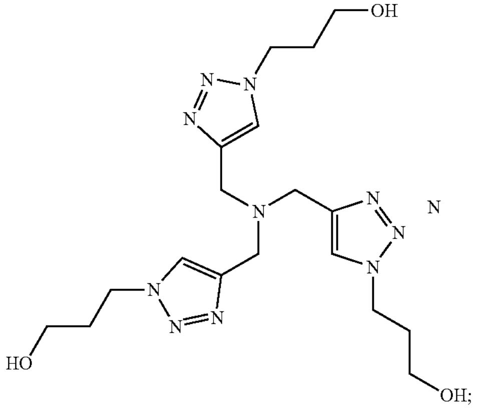

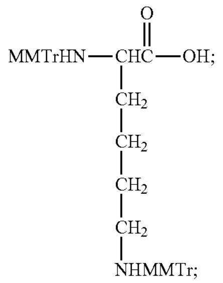

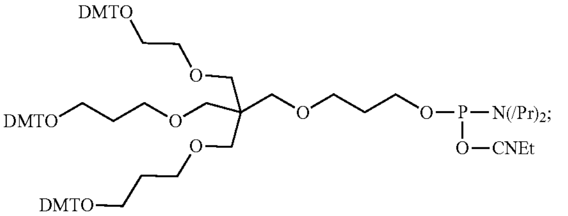

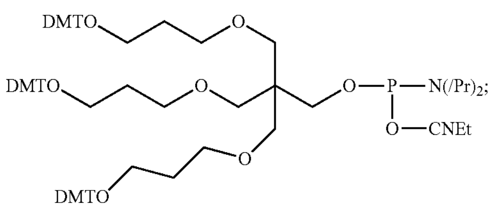

or

-continued

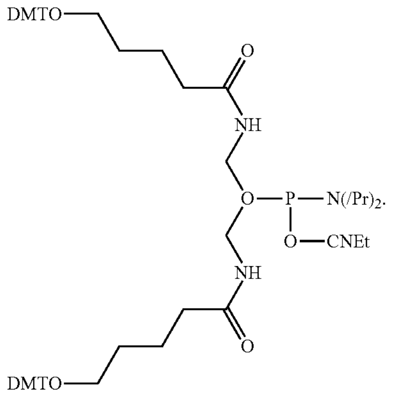

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

| $R^1$ |
|---|
| 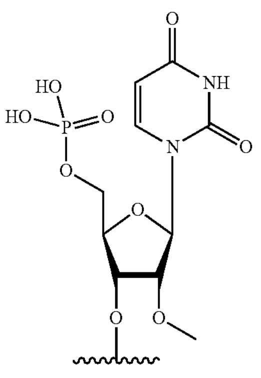 |

TABLE 2-continued $R^2$

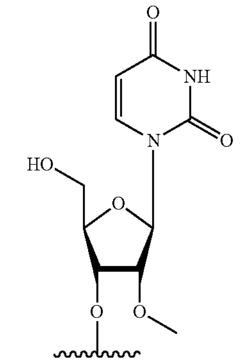

$R^3$

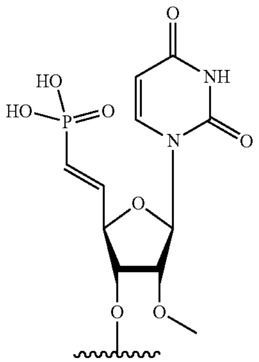

$R^4$

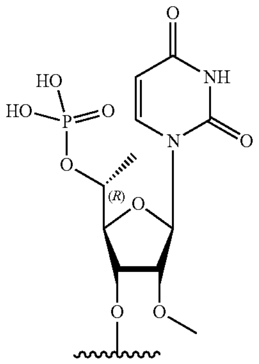

$R^5$

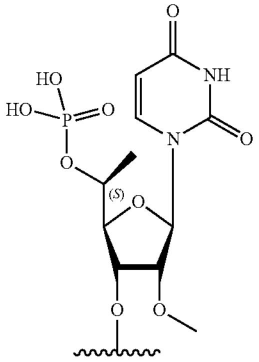

TABLE 2-continued $R^6$

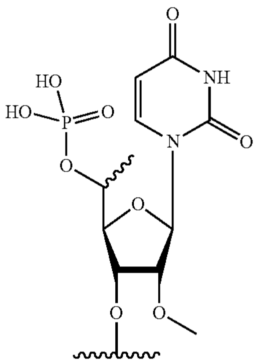

$R^7$

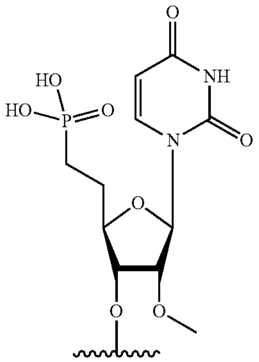

$R^8$

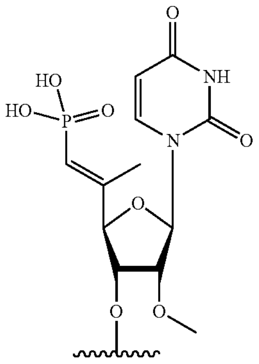

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) has the structure of formula (II):

(II)

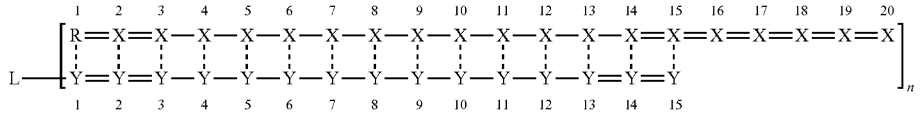

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; = represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III):

(III)

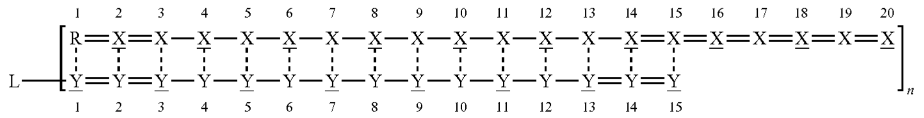

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

(IV)

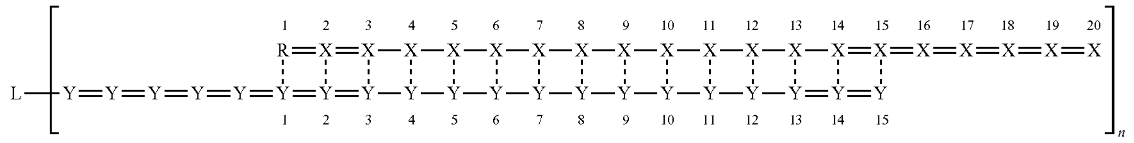

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; =represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (IV) are chemically-modified nucleotides. In other embodiments, >95%, >90%, >85%, >80%, >75%, >70%, >65%, >60%, >55% or >50% of X's of the structure of formula (IV) are chemically-modified nucleotides.

Structure of Formula (V)

In an embodiment, the compound of formula (I) has the structure of formula (V):

(V)

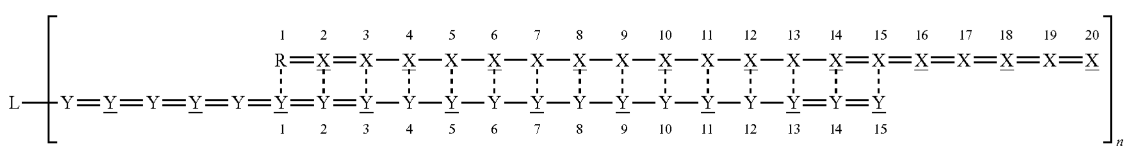

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

(L1)

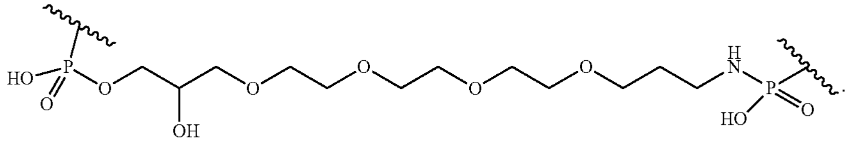

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

(L2)

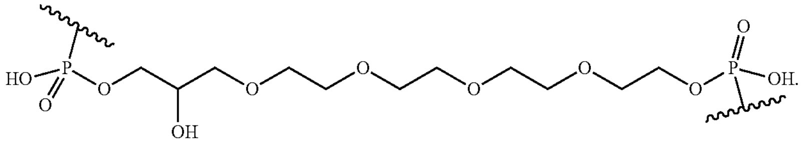

In an embodiment of L2, R is R3 and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

Delivery System

In a third aspect, provided herein is a delivery system for therapeutic nucleic acids having the structure of formula (VI):

$$L\text{-}(cNA)_n \qquad (VI)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >5500 or >5000 chemically-modified nucleotides.

In an embodiment, the compound of formula (VI) has a structure selected from formulas (VI-1)-(VI-9) of Table 3:

TABLE 3

ANc—L—cNA (VI-1)

ANc—S—L—S—cNA (VI-2)

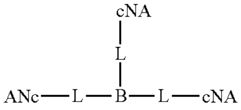
(VI-3)

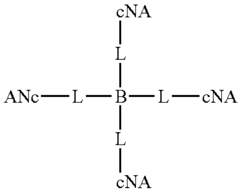
(VI-4)

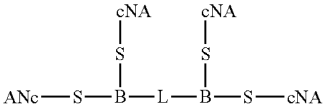
(VI-5)

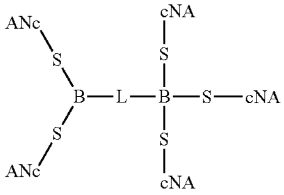
(VI-6)

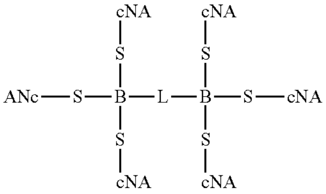
(VI-7)

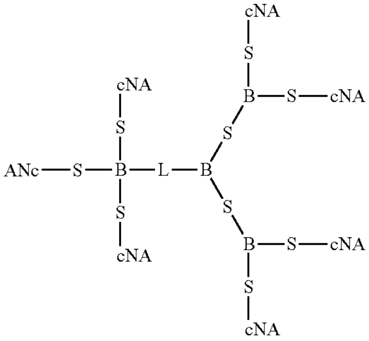
(VI-8)

TABLE 3-continued (VI-9)

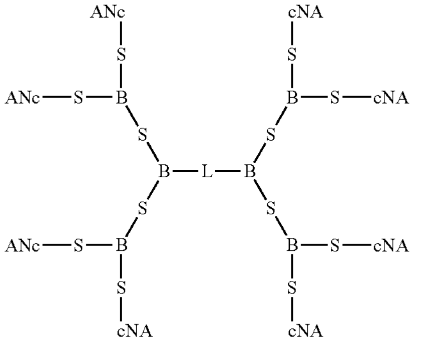

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a sequence substantially complementary to a SARS-CoV-2 nucleic acid sequence of any one of SEQ ID NOs: 1-10, as recited in Table 4 and Table. In further embodiments, NA includes strands that are capable of targeting one or more SARS-CoV-2 nucleic acid sequences of any one of the 45-nucleotide target gene regions recited in Table 6A.

Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 15 contiguous nucleotides. In an embodiment, each NA independently comprises 15-25 contiguous nucleotides. In an embodiment, each NA independently comprises 15 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides. In an embodiment, each NA independently comprises 21 contiguous nucleotides. In an embodiment, each NA independently comprises 22 contiguous nucleotides. In an embodiment, each NA independently comprises 23 contiguous nucleotides. In an embodiment, each NA independently comprises 24 contiguous nucleotides. In an embodiment, each NA independently comprises 25 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is $R^3$ and n is 2. In another embodiment, the delivery system has a structure selected from formulas (I), (II), (III), (IV), (V), (VI), further comprising a linker of structure L1 wherein R is $R^3$ and n is 2. In another embodiment, the delivery system has a structure selected from formulas (I), (II), (III), (IV), (V), (VI), further comprising a linker of structure L2 wherein R is $R^3$ and n is 2.

In an embodiment of the delivery system, the target of delivery is selected from the group consisting of: lung, brain, liver, skin, kidney, spleen, pancreas, colon, fat, muscle, adrenal glands, and thymus. In one embodiment, the target of delivery is the lung. In another embodiment, the target of delivery are alveolar cells in the lung. In another embodiment, the target of delivery are club cells in the lung. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery are the adrenal glands. In one embodiment, the target of delivery is the muscle. In one embodiment, the target of delivery is the thymus. In one embodiment, the target of delivery is the spinal cord.

In one embodiment, efficacy of delivery to lung cells is achieved through combinations of unique conjugates, optimization of siRNA stability, structural configuration, cleavable linker, and Phosphorothioate (PS) content. In another embodiment, three conjugates, EPA, DCA and PC-DCA, have different distribution profiles. In one embodiment, DCA and PC-DCA are being cleared mostly by the liver and EPA is being cleared mostly by the kidneys. In another embodiment the two classes of conjugates show different cell-type preferences in the lung, where EPA accumulation is higher in epithelial (Clara) cells of the lung.

In certain embodiments, compounds of the invention are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phoshorothioated single oligonucleotides containing at least 3, phosphorothioated bonds. In certain embodiments, the phoshorothioated single oligonucleotides contain 4-20 phosphorothioated bonds.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

Branched oligonucleotides, including synthesis and methods of use, are described in greater detail in WO2017/132669, incorporated herein by reference.

Methods of Introducing Nucleic Acids, Vectors and Host Cells

RNA silencing agents of the invention may be directly introduced into the cell (e.g., a cell in the lung) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an SARS-CoV-2 target sequence) is tested for its ability to specifically degrade mutant mRNA (e.g., SARS-CoV-2 mRNA and/or the production of SARS-CoV-2 protein) in cells, such as cells in the lung. In certain embodiments, cells in the lung include, but are not limited to, clara cells, alveolar cells, and club cells. Also suitable for cell-based validation assays are other readily transfectable cells, for example, HeLa cells or COS cells. Cells are transfected with human wild type or mutant cDNAs (e.g., human wild type or mutant SARS-CoV-2 cDNA). Standard siRNA, modified siRNA or vectors able to produce siRNA from U-looped mRNA are co-transfected. Selective reduction in target mRNA (e.g., SARS-CoV-2 mRNA) and/or target protein (e.g., SARS-CoV-2 protein) is measured. Reduction of target mRNA or protein can be compared to levels of target mRNA or protein in the absence of an RNAi agent or in the presence of an RNAi agent that does not target SARS-CoV-2 mRNA. Exogenously-introduced mRNA or protein (or endogenous mRNA or protein) can be assayed for comparison purposes. When utilizing lung cells, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., lung cells (e.g., clara cells, alveolar cells or club cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In certain embodiments, widespread lung delivery can be achieved by intratracheal (IT) delivery of recombinant adeno-associated virus 7 (rAAV7), RAAV9 and rAAV10, or other suitable rAAVs. rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the lung of a subject. By "lung" is meant all cells and tissue of the lung of a vertebrate. Thus, the term includes, but is not limited to, clara cells, alveolar cells, club cells, and the like. Recombinant AAVs may be delivered directly to the lung by injection, e.g., intratracheal injection.

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about 109 to $10^{16}$ genome copies. In some cases, a dosage between about $10^{11}$ to $10^{12}$ rAAV genome copies is appropriate. In certain embodiments, $10^{12}$ rAAV genome copies is effective to target lung, heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VIII. Methods of Treatment

In one aspect, the present invention provides for both prophylactic and therapeutic methods of treating a subject at risk of (or susceptible to) SARS-CoV-2 infection. In one embodiment, the disease or disorder is such that SARS-CoV-2 levels in blood or another biological sample have been found to be a marker of infection. In another embodiment, the infection with SARS-CoV-2 is characterized by a clinical manifestation of viral infection, e.g. an increase in body temperature. In a certain embodiment, a reduction in SARS-CoV-2 mRNA reduces clinical manifestations of SARS-CoV-2 infection.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a lung cell with a therapeutic agent (e.g., a RNAi agent or vector or transgene encoding same) that is specific for a target sequence within the gene (e.g., SARS-CoV-2 target sequences of Tables 4, 5, 6A, 7, and 8), such that sequence specific interference with the gene is achieved. These methods can be performed in vitro (e.g., by culturing the cell with the agent) or, alternatively, in vivo (e.g., by administering the agent to a subject).

IX. Pharmaceutical Compositions and Methods of Administration

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain embodiments, a composition that includes a compound of the invention can be delivered to the lungs of a subject by a variety of routes. Exemplary routes include intratracheal or nasal delivery. The composition can also be delivered systemically, e.g., by intravenous, subcutaneous or intramuscular injection.

For example, compositions can include one or more species of a compound of the invention and a pharmaceutically acceptable carrier. The pharmaceutical compositions of the present invention may be administered in a number of ways depending upon whether local or systemic treatment is desired and upon the area to be treated.

As used herein "intratracheal administration" refers to the direct administration to the lung through the trachea. Intratracheal administration includes, but is not limited to, intratracheal inhalation and intratracheal instillation. Intratracheal administration (IT) is non-invasive and can be used in the field. Both the chemical architectures of the siRNAs and routes of administration might have benefits in different clinical contexts and disease stages. The chemical architectures optimal for different routes of administration is different. For example, DCA-conjugated siRNAs or divalent siRNAs can be effective for delivery of siRNA to the lung.

In one embodiment, divalent siRNAs are delivered to lung tissues. A variety of lung delivery systems can be employed to accomplish delivery to the lung tissues, for example, but not limited to, direct intrathecal instillation, or by using a nebulizer. Formulations in which the siRNA can be delivered are, for example, but not limited to, dry powder, direct powder, vapor droplets, etc.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. In Vitro Identification of SARS-CoV-2 Targeting Sequences

Hyper functional siRNAs targeting all 9 genes (regions) of SARS-CoV2 were identified. A combination of bioinformatic approaches were employed to identify regions of conservation (based on 718 patients isolates) in combination with features essential for RISC entry and tolerance of chemical modifications. Over 100 chemically optimized compounds were synthesized, and reporter systems developed to test these compounds in cells, screened at 1.5 μM concentration. Selected hits were further screened in dose response studies, and at least two lead compounds were identified per gene with $IC_{50}$ values <20 nM.

Target sequences were derived from the severe acute respiratory syndrome coronavirus 2 (SARS CoV-2) isolate Wuhan-Hu-1 (NCBI accession: NC_045512). Fully chemically modified and conjugated oligonucleotides targeting SARS-CoV-2 and the human host receptors of SARS-CoV2 could potentially prevent and treat viral infections from viruses within the family Coronaviridiae.

Figure 1B:
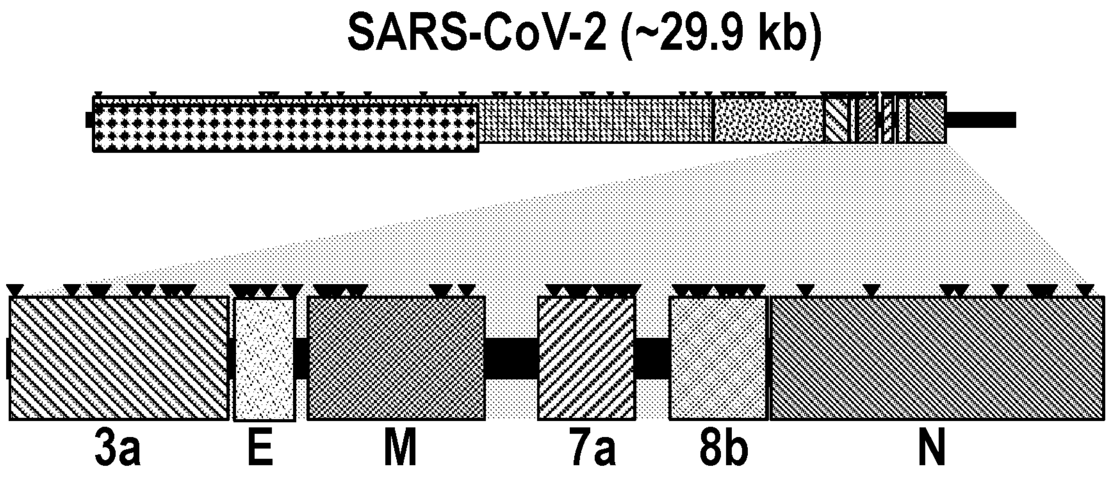
Figure 2:
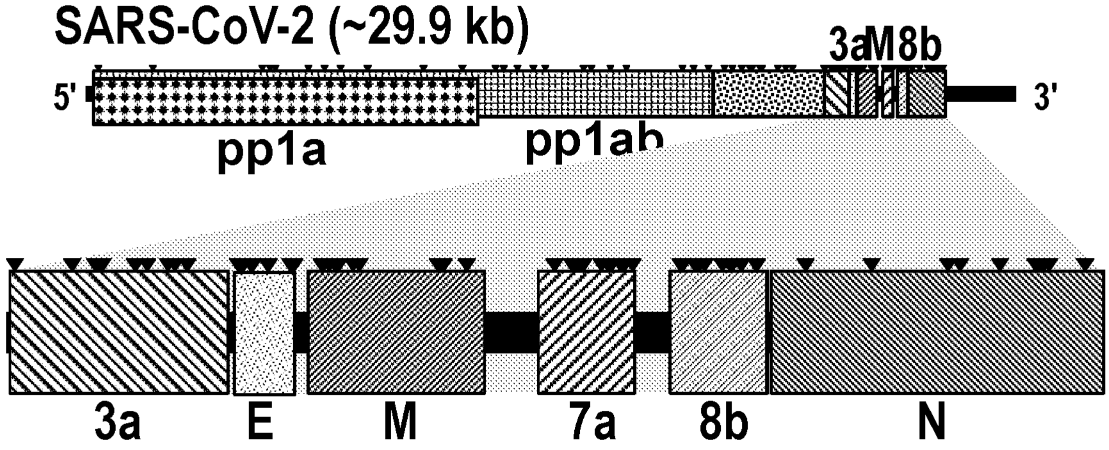
FIG. 2 depicts a diagram of siRNA and ASO target positions on encoded proteins in the SARS-CoV-2 Genome. siRNAs were designed to target nine genes encoding SARS-CoV-2 proteins: orf1a, orf1ab, spike surface glycoprotein (S), small envelope protein (E), matrix protein (M), nucleocapsid protein (N), and accessory proteins 3a, 8b, 7a. Grey arrows indicate siRNA and ASO target positions. Inset shows detailed view of siRNA target positions on genes in the 3' region of the genome.

Nine SARS-CoV-2 transcripts were selected for knockdown: the genes coding for the four major structural proteins spike surface glycoprotein (S), small envelope protein (E), matrix protein (M), and nucleocapsid protein (N), as well as genes coding for pp1a, pp1ab, which make up the 16 non-structural proteins of SARS-CoV-2, and genes coding for the accessory proteins 3a, 8b, 7a (FIG. 1). Table 4 shows the full-length sequence of the SARS-CoV-2 genome, Table 5 the sequences of the SARS-CoV-2 genes. FIG. 2 depicts a diagram of siRNA and antisense oligonucleotides (ASOs) target positions on encoded proteins in the SARS-CoV-2 genome. siRNAs were designed to target nine genes encoding SARS-CoV-2 proteins: orf1a, orf1ab, spike surface glycoprotein (S), small envelope protein (E), matrix protein (M), nucleocapsid protein (N), and accessory proteins 3a, 8b, 7a. Grey arrows indicate siRNA and ASO target positions. Inset in FIG. 2 shows a detailed view of siRNA target positions on genes in the 3' region of the genome.

TABLE 4

| SARS-CoV2 genomic sequence (NCBI Accession Number NC 045512) |
|---|
| SARS-CoV2 genome sequence<br>ATTAAAGGTTTATACCTTCCCAGGTAACAAACCAACCAACTTTCGATCTC<br>TTGTAGATCTGTTCTCTAAACGAACTTTAAAATCTGTGTGGCTGTCACTC<br>GGCTGCATGCTTAGTGCACTCACGCAGTATAATTAATAACTAATTACTGT<br>CGTTGACAGGACACGAGTAACTCGTCTATCTTCTGCAGGCTGCTTACGGT<br>TTCGTCCGTGTTGCAGCCGATCATCAGCACATCTAGGTTTCGTCCGGGTG<br>TGACCGAAAGGTAAGATGGAGAGCCTTGTCCCTGGTTTCAACGAGAAAAC<br>ACACGTCCAACTCAGTTTGCCTGTTTTACAGGTTCGCGACGTGCTCGTAC<br>GTGGCTTTGGAGACTCCGTGGAGGAGGTCTTATCAGAGGCACGTCAACAT<br>CTTAAAGATGGCACTTGTGGCTTAGTAGAAGTTGAAAAAGGCGTTTTGCC |

TABLE 4-continued

| SARS-CoV2 genomic sequence (NCBI Accession Number NC 045512) |
|---|
| TCAACTTGAACAGCCCTATGTGTTCATCAAACGTTCGGATGCTCGAACTG |
| CACCTCATGGTCATGTTATGGTTGAGCTGGTAGCAGAACTCGAAGGCATT |
| CAGTACGGTCGTAGTGGTGAGACACTTGGTGTCCTTGTCCCTCATGTGGG |
| CGAAATACCAGTGGCTTACCGCAAGGTTCTTCTTCGTAAGAACGGTAATA |
| AAGGAGCTGGTGGCCATAGTTACGGCGCCGATCTAAAGTCATTTGACTTA |
| GGCGACGAGCTTGGCACTGATCCTTATGAAGATTTTCAAGAAAACTGGAA |
| CACTAAACATAGCAGTGGTGTTACCCGTGAACTCATGCGTGAGCTTAACG |
| GAGGGGCATACACTCGCTATGTCGATAACAACTTCTGTGGCCCTGATGGC |
| TACCCTCTTGAGTGCATTAAAGACCTTCTAGCACGTGCTGGTAAAGCTTC |
| ATGCACTTTGTCCGAACAACTGGACTTTATTGACACTAAGAGGGGTGTAT |
| ACTGCTGCCGTGAACATGAGCATGAAATTGCTTGGTACACGGAACGTTCT |
| GAAAAGAGCTATGAATTGCAGACACCTTTTGAAATTAAATTGGCAAAGAA |
| ATTTGACACCTTCAATGGGGAATGTCCAAATTTTGTATTTCCCTTAAATT |
| CCATAATCAAGACTATTCAACCAAGGGTTGAAAAGAAAAAGCTTGATGGC |
| TTTATGGGTAGAATTCGATCTGTCTATCCAGTTGCGTCACCAAATGAATG |
| CAACCAAATGTGCCTTTCAACTCTCATGAAGTGTGATCATTGTGGTGAAA |
| CTTCATGGCAGACGGGCGATTTTGTTAAAGCCACTTGCGAATTTTGTGGC |
| ACTGAGAATTTGACTAAAGAAGGTGCCACTACTTGTGGTTACTTACCCCA |
| AAATGCTGTTGTTAAAATTTATTGTCCAGCATGTCACAATTCAGAAGTAG |
| GACCTGAGCATAGTCTTGCCGAATACCATAATGAATCTGGCTTGAAAACC |
| ATTCTTCGTAAGGGTGGTCGCACTATTGCCTTTGGAGGCTGTGTGTTCTC |
| TTATGTTGGTTGCCATAACAAGTGTGCCTATTGGGTTCCACGTGCTAGCG |
| CTAACATAGGTTGTAACCATACAGGTGTTGTTGGAGAAGGTTCCGAAGGT |
| CTTAATGACAACCTTCTTGAAATACTCCAAAAAGAGAAAGTCAACATCAA |
| TATTGTTGGTGACTTTAAACTTAATGAAGAGATCGCCATTATTTTGGCAT |
| CTTTTTCTGCTTCCACAAGTGCTTTTGTGGAAACTGTGAAAGGTTTGGAT |
| TATAAAGCATTCAAACAAATTGTTGAATCCTGTGGTAATTTTAAAGTTAC |
| AAAAGGAAAAGCTAAAAAAGGTGCCTGGAATATTGGTGAACAGAAATCAA |
| TACTGAGTCCTCTTTATGCATTTGCATCAGAGGCTGCTCGTGTTGTACGA |
| TCAATTTTCTCCCGCACTCTTGAAACTGCTCAAAATTCTGTGCGTGTTTT |
| ACAGAAGGCCGCTATAACAATACTAGATGGAATTTCACAGTATTCACTGA |
| GACTCATTGATGCTATGATGTTCACATCTGATTTGGCTACTAACAATCTA |
| GTTGTAATGGCCTACATTACAGGTGGTGTTGTTCAGTTGACTTCGCAGTG |
| GCTAACTAACATCTTTGGCACTGTTTATGAAAAACTCAAACCCGTCCTTG |
| ATTGGCTTGAAGAGAAGTTTAAGGAAGGTGTAGAGTTTCTTAGAGACGGT |
| TGGGAAATTGTTAAATTTATCTCAACCTGTGCTTGTGAAATTGTCGGTGG |
| ACAAATTGTCACCTGTGCAAAGGAAATTAAGGAGAGTGTTCAGACATTCT |
| TTAAGCTTGTAAATAAATTTTTGGCTTTGTGTGCTGACTCTATCATTATT |
| GGTGGAGCTAAACTTAAAGCCTTGAATTTAGGTGAAACATTTGTCACGCA |

TABLE 4-continued

| SARS-CoV2 genomic sequence (NCBI Accession Number NC 045512) |
|---|
| CTCAAAGGGATTGTACAGAAAGTGTGTTAAATCCAGAGAAGAAACTGGCC |
| TACTCATGCCTCTAAAAGCCCCAAAAGAAATTATCTTCTTAGAGGGAGAA |
| ACACTTCCCACAGAAGTGTTAACAGAGGAAGTTGTCTTGAAAACTGGTGA |
| TTTACAACCATTAGAACAACCTACTAGTGAAGCTGTTGAAGCTCCATTGG |
| TTGGTACACCAGTTTGTATTAACGGGCTTATGTTGCTCGAAATCAAAGAC |
| ACAGAAAAGTACTGTGCCCTTGCACCTAATATGATGGTAACAAACAATAC |
| CTTCACACTCAAAGGCGGTGCACCAACAAAGGTTACTTTTGGTGATGACA |
| CTGTGATAGAAGTGCAAGGTTACAAGAGTGTGAATATCACTTTTGAACTT |
| GATGAAAGGATTGATAAAGTACTTAATGAGAAGTGCTCTGCCTATACAGT |
| TGAACTCGGTACAGAAGTAAATGAGTTCGCCTGTGTTGTGGCAGATGCTG |
| TCATAAAAACTTTGCAACCAGTATCTGAATTACTTACACCACTGGGCATT |
| GATTTAGATGAGTGGAGTATGGCTACATACTACTTATTTGATGAGTCTGG |
| TGAGTTTAAATTGGCTTCACATATGTATTGTTCTTTCTACCCTCCAGATG |
| AGGATGAAGAAGAAGGTGATTGTGAAGAAGAAGAGTTTGAGCCATCAACT |
| CAATATGAGTATGGTACTGAAGATGATTACCAAGGTAAACCTTTGGAATT |
| TGGTGCCACTTCTGCTGCTCTTCAACCTGAAGAAGAGCAAGAAGAAGATT |
| GGTTAGATGATGATAGTCAACAAACTGTTGGTCAACAAGACGGCAGTGAG |
| GACAATCAGACAACTACTATTCAAACAATTGTTGAGGTTCAACCTCAATT |
| AGAGATGGAACTTACACCAGTTGTTCAGACTATTGAAGTGAATAGTTTTA |
| GTGGTTATTTAAAACTTACTGACAATGTATACATTAAAAATGCAGACATT |
| GTGGAAGAAGCTAAAAAGGTAAAACCAACAGTGGTTGTTAATGCAGCCAA |
| TGTTTACCTTAAACATGGAGGAGGTGTTGCAGGAGCCTTAAATAAGGCTA |
| CTAACAATGCCATGCAAGTTGAATCTGATGATTACATAGCTACTAATGGA |
| CCACTTAAAGTGGGTGGTAGTTGTGTTTTAAGCGGACACAATCTTGCTAA |
| ACACTGTCTTCATGTTGTCGGCCCAAATGTTAACAAAGGTGAAGACATTC |
| AACTTCTTAAGAGTGCTTATGAAAATTTTAATCAGCACGAAGTTCTACTT |
| GCACCATTATTATCAGCTGGTATTTTTGGTGCTGACCCTATACATTCTTT |
| AAGAGTTTGTGTAGATACTGTTCGCACAAATGTCTACTTAGCTGTCTTTG |
| ATAAAAATCTCTATGACAAACTTGTTTCAAGCTTTTTGGAAATGAAGAGT |
| GAAAAGCAAGTTGAACAAAAGATCGCTGAGATTCCTAAAGAGGAAGTTAA |
| GCCATTTATAACTGAAAGTAAACCTTCAGTTGAACAGAGAAAACAAGATG |
| ATAAGAAAATCAAAGCTTGTGTTGAAGAAGTTACAACAACTCTGGAAGAA |
| ACTAAGTTCCTCACAGAAAACTTGTTACTTTATATTGACATTAATGGCAA |
| TCTTCATCCAGATTCTGCCACTCTTGTTAGTGACATTGACATCACTTTCT |
| TAAAGAAAGATGCTCCATATATAGTGGGTGATGTTGTTCAAGAGGGTGTT |
| TTAACTGCTGTGGTTATACCTACTAAAAAGGCTGGTGGCACTACTGAAAT |
| GCTAGCGAAAGCTTTGAGAAAAGTGCCAACAGACAATTATATAACCACTT |
| ACCCGGGTCAGGGTTTAAATGGTTACACTGTAGAGGAGGCAAAGACAGTG |

TABLE 4-continued

| SARS-CoV2 genomic sequence (NCBI Accession Number NC 045512) |
|---|
| CTTAAAAAGTGTAAAAGTGCCTTTTACATTCTACCATCTATTATCTCTAA |
| TGAGAAGCAAGAAATTCTTGGAACTGTTTCTTGGAATTTGCGAGAAATGC |
| TTGCACATGCAGAAGAAACACGCAAATTAATGCCTGTCTGTGTGGAAACT |
| AAAGCCATAGTTTCAACTATACAGCGTAAATATAAGGGTATTAAAATACA |
| AGAGGGTGTGGTTGATTATGGTGCTAGATTTTACTTTTACACCAGTAAAA |
| CAACTGTAGCGTCACTTATCAACACACTTAACGATCTAAATGAAACTCTT |
| GTTACAATGCCACTTGGCTATGTAACACATGGCTTAAATTTGGAAGAAGC |
| TGCTCGGTATATGAGATCTCTCAAAGTGCCAGCTACAGTTTCTGTTTCTT |
| CACCTGATGCTGTTACAGCGTATAATGGTTATCTTACTTCTTCTTCTAAA |
| ACACCTGAAGAACATTTTATTGAAACCATCTCACTTGCTGGTTCCTATAA |
| AGATTGGTCCTATTCTGGACAATCTACACAACTAGGTATAGAATTTCTTA |
| AGAGAGGTGATAAAAGTGTATATTACACTAGTAATCCTACCACATTCCAC |
| CTAGATGGTGAAGTTATCACCTTTGACAATCTTAAGACACTTCTTTCTTT |
| GAGAGAAGTGAGGACTATTAAGGTGTTTACAACAGTAGACAACATTAACC |
| TCCACACGCAAGTTGTGGACATGTCAATGACATATGGACAACAGTTTGGT |
| CCAACTTATTTGGATGGAGCTGATGTTACTAAAATAAAACCTCATAATTC |
| ACATGAAGGTAAAACATTTTATGTTTTACCTAATGATGACACTCTACGTG |
| TTGAGGCTTTTGAGTACTACCACACAACTGATCCTAGTTTTCTGGGTAGG |
| TACATGTCAGCATTAAATCACACTAAAAAGTGGAAATACCCACAAGTTAA |
| TGGTTTAACTTCTATTAAATGGGCAGATAACAACTGTTATCTTGCCACTG |
| CATTGTTAACACTCCAACAAATAGAGTTGAAGTTTAATCCACCTGCTCTA |
| CAAGATGCTTATTACAGAGCAAGGGCTGGTGAAGCTGCTAACTTTTGTGC |
| ACTTATCTTAGCCTACTGTAATAAGACAGTAGGTGAGTTAGGTGATGTTA |
| GAGAAACAATGAGTTACTTGTTTCAACATGCCAATTTAGATTCTTGCAAA |
| AGAGTCTTGAACGTGGTGTGTAAAACTTGTGGACAACAGCAGACAACCCT |
| TAAGGGTGTAGAAGCTGTTATGTACATGGGCACACTTTCTTATGAACAAT |
| TTAAGAAAGGTGTTCAGATACCTTGTACGTGTGGTAAACAAGCTACAAAA |
| TATCTAGTACAACAGGAGTCACCTTTTGTTATGATGTCAGCACCACCTGC |
| TCAGTATGAACTTAAGCATGGTACATTTACTTGTGCTAGTGAGTACACTG |
| GTAATTACCAGTGTGGTCACTATAAACATATAACTTCTAAAGAAACTTTG |
| TATTGCATAGACGGTGCTTTACTTACAAAGTCCTCAGAATACAAAGGTCC |
| TATTACGGATGTTTTCTACAAAGAAAACAGTTACACAACAACCATAAAAC |
| CAGTTACTTATAAATTGGATGGTGTTGTTTGTACAGAAATTGACCCTAAG |
| TTGGACAATTATTATAAGAAAGACAATTCTTATTTCACAGAGCAACCAAT |
| TGATCTTGTACCAAACCAACCATATCCAAACGCAAGCTTCGATAATTTTA |
| AGTTTGTATGTGATAATATCAAATTTGCTGATGATTTAAACCAGTTAACT |
| GGTTATAAGAAACCTGCTTCAAGAGAGCTTAAAGTTACATTTTTCCCTGA |
| CTTAAATGGTGATGTGGTGGCTATTGATTATAAACACTACACACCCTCTT |
| TTAAGAAAGGAGCTAAATTGTTACATAAACCTATTGTTTGGCATGTTAAC |

TABLE 4-continued

| SARS-CoV2 genomic sequence (NCBI Accession Number NC 045512) |
|---|
| AATGCAACTAATAAAGCCACGTATAAACCAAATACCTGGTGTATACGTTG |
| TCTTTGGAGCACAAAACCAGTTGAAACATCAAATTCGTTTGATGTACTGA |
| AGTCAGAGGACGCGCAGGGAATGGATAATCTTGCCTGCGAAGATCTAAAA |
| CCAGTCTCTGAAGAAGTAGTGGAAAATCCTACCATACAGAAAGACGTTCT |
| TGAGTGTAATGTGAAAACTACCGAAGTTGTAGGAGACATTATACTTAAAC |
| CAGCAAATAATAGTTTAAAAATTACAGAAGAGGTTGGCCACACAGATCTA |
| ATGGCTGCTTATGTAGACAATTCTAGTCTTACTATTAAGAAACCTAATGA |
| ATTATCTAGAGTATTAGGTTTGAAAACCCTTGCTACTCATGGTTTAGCTG |
| CTGTTAATAGTGTCCCTTGGGATACTATAGCTAATTATGCTAAGCCTTTT |
| CTTAACAAAGTTGTTAGTACAACTACTAACATAGTTACACGGTGTTTAAA |
| CCGTGTTTGTACTAATTATATGCCTTATTTCTTTACTTTATTGCTACAAT |
| TGTGTACTTTTACTAGAAGTACAAATTCTAGAATTAAAGCATCTATGCCG |
| ACTACTATAGCAAAGAATACTGTTAAGAGTGTCGGTAAATTTTGTCTAGA |
| GGCTTCATTTAATTATTTGAAGTCACCTAATTTTTCTAAACTGATAAATA |
| TTATAATTTGGTTTTTACTATTAAGTGTTTGCCTAGGTTCTTTAATCTAC |
| TCAACCGCTGCTTTAGGTGTTTTAATGTCTAATTTAGGCATGCCTTCTTA |
| CTGTACTGGTTACAGAGAAGGCTATTTGAACTCTACTAATGTCACTATTG |
| CAACCTACTGTACTGGTTCTATACCTTGTAGTGTTTGTCTTAGTGGTTTA |
| GATTCTTTAGACACCTATCCTTCTTTAGAAACTATACAAATTACCATTTC |
| ATCTTTTAAATGGGATTTAACTGCTTTTGGCTTAGTTGCAGAGTGGTTTT |
| TGGCATATATTCTTTTCACTAGGTTTTTCTATGTACTTGGATTGGCTGCA |
| ATCATGCAATTGTTTTTCAGCTATTTTGCAGTACATTTTATTAGTAATTC |
| TTGGCTTATGTGGTTAATAATTAATCTTGTACAAATGGCCCCGATTTCAG |
| CTATGGTTAGAATGTACATCTTCTTTGCATCATTTTATTATGTATGGAAA |
| AGTTATGTGCATGTTGTAGACGGTTGTAATTCATCAACTTGTATGATGTG |
| TTACAAACGTAATAGAGCAACAAGAGTCGAATGTACAACTATTGTTAATG |
| GTGTTAGAAGGTCCTTTTATGTCTATGCTAATGGAGGTAAAGGCTTTTGC |
| AAACTACACAATTGGAATTGTGTTAATTGTGATACATTCTGTGCTGGTAG |
| TACATTTATTAGTGATGAAGTTGCGAGAGACTTGTCACTACAGTTTAAAA |
| GACCAATAAATCCTACTGACCAGTCTTCTTACATCGTTGATAGTGTTACA |
| GTGAAGAATGGTTCCATCCATCTTTACTTTGATAAAGCTGGTCAAAAGAC |
| TTATGAAAGACATTCTCTCTCTCATTTTGTTAACTTAGACAACCTGAGAG |
| CTAATAACACTAAAGGTTCATTGCCTATTAATGTTATAGTTTTTGATGGT |
| AAATCAAAATGTGAAGAATCATCTGCAAAATCAGCGTCTGTTTACTACAG |
| TCAGCTTATGTGTCAACCTATACTGTTACTAGATCAGGCATTAGTGTCTG |
| ATGTTGGTGATAGTGCGGAAGTTGCAGTTAAAATGTTTGATGCTTACGTT |
| AATACGTTTTCATCAACTTTTAACGTACCAATGGAAAAACTCAAAACACT |
| AGTTGCAACTGCAGAAGCTGAACTTGCAAAGAATGTGTCCTTAGACAATG |

TABLE 4-continued

SARS-CoV2 genomic sequence (NCBI Accession Number NC 045512)

TCTTATCTACTTTTATTTCAGCAGCTCGGCAAGGGTTTGTTGATTCAGAT

GTAGAAACTAAAGATGTTGTTGAATGTCTTAAATTGTCACATCAATCTGA

CATAGAAGTTACTGGCGATAGTTGTAATAACTATATGCTCACCTATAACA

AAGTTGAAAACATGACACCCCGTGACCTTGGTGCTTGTATTGACTGTAGT

GCGCGTCATATTAATGCGCAGGTAGCAAAAAGTCACAACATTGCTTTGAT

ATGGAACGTTAAAGATTTCATGTCATTGTCTGAACAACTACGAAAACAAA

TACGTAGTGCTGCTAAAAAGAATAACTTACCTTTTAAGTTGACATGTGCA

ACTACTAGACAAGTTGTTAATGTTGTAACAACAAAGATAGCACTTAAGGG

TGGTAAAATTGTTAATAATTGGTTGAAGCAGTTAATTAAAGTTACACTTG

TGTTCCTTTTTGTTGCTGCTATTTTCTATTTAATAACACCTGTTCATGTC

ATGTCTAAACATACTGACTTTTCAAGTGAAATCATAGGATACAAGGCTAT

TGATGGTGGTGTCACTCGTGACATAGCATCTACAGATACTTGTTTTGCTA

ACAAACATGCTGATTTTGACACATGGTTTAGCCAGCGTGGTGGTAGTTAT

ACTAATGACAAAGCTTGCCCATTGATTGCTGCAGTCATAACAAGAGAAGT

GGGTTTTGTCGTGCCTGGTTTGCCTGGCACGATATTACGCACAACTAATG

GTGACTTTTTGCATTTCTTACCTAGAGTTTTTAGTGCAGTTGGTAACATC

TGTTACACACCATCAAAACTTATAGAGTACACTGACTTTGCAACATCAGC

TTGTGTTTTGGCTGCTGAATGTACAATTTTTAAAGATGCTTCTGGTAAGC

CAGTACCATATTGTTATGATACCAATGTACTAGAAGGTTCTGTTGCTTAT

GAAAGTTTACGCCCTGACACACGTTATGTGCTCATGGATGGCTCTATTAT

TCAATTTCCTAACACCTACCTTGAAGGTTCTGTTAGAGTGGTAACAACTT

TTGATTCTGAGTACTGTAGGCACGGCACTTGTGAAAGATCAGAAGCTGGT

GTTTGTGTATCTACTAGTGGTAGATGGGTACTTAACAATGATTATTACAG

ATCTTTACCAGGAGTTTTCTGTGGTGTAGATGCTGTAAATTTACTTACTA

ATATGTTTACACCACTAATTCAACCTATTGGTGCTTTGGACATATCAGCA

TCTATAGTAGCTGGTGGTATTGTAGCTATCGTAGTAACATGCCTTGCCTA

CTATTTTATGAGGTTTAGAAGAGCTTTTGGTGAATACAGTCATGTAGTTG

CCTTTAATACTTTACTATTCCTTATGTCATTCACTGTACTCTGTTTAACA

CCAGTTTACTCATTCTTACCTGGTGTTTATTCTGTTATTTACTTGTACTT

GACATTTTATCTTACTAATGATGTTTCTTTTTTAGCACATATTCAGTGGA

TGGTTATGTTCACACCTTTAGTACCTTTCTGGATAACAATTGCTTATATC

ATTTGTATTTCCACAAAGCATTTCTATTGGTTCTTTAGTAATTACCTAAA

GAGACGTGTAGTCTTTAATGGTGTTTCCTTTAGTACTTTTGAAGAAGCTG

CGCTGTGCACCTTTTTGTTAAATAAAGAAATGTATCTAAAGTTGCGTAGT

GATGTGCTATTACCTCTTACGCAATATAATAGATACTTAGCTCTTTATAA

TAAGTACAAGTATTTTAGTGGAGCAATGGATACAACTAGCTACAGAGAAG

CTGCTTGTTGTCATCTCGCAAAGGCTCTCAATGACTTCAGTAACTCAGGT

TCTGATGTTCTTTACCAACCACCACAAACCTCTATCACCTCAGCTGTTTT

GCAGAGTGGTTTTAGAAAAATGGCATTCCCATCTGGTAAAGTTGAGGGTT

GTATGGTACAAGTAACTTGTGGTACAACTACACTTAACGGTCTTTGGCTT

GATGACGTAGTTTACTGTCCAAGACATGTGATCTGCACCTCTGAAGACAT

GCTTAACCCTAATTATGAAGATTTACTCATTCGTAAGTCTAATCATAATT

TCTTGGTACAGGCTGGTAATGTTCAACTCAGGGTTATTGGACATTCTATG

CAAAATTGTGTACTTAAGCTTAAGGTTGATACAGCCAATCCTAAGACACC

TAAGTATAAGTTTGTTCGCATTCAACCAGGACAGACTTTTTCAGTGTTAG

CTTGTTACAATGGTTCACCATCTGGTGTTTACCAATGTGCTATGAGGCCC

AATTTCACTATTAAGGGTTCATTCCTTAATGGTTCATGTGGTAGTGTTGG

TTTTAACATAGATTATGACTGTGTCTCTTTTTGTTACATGCACCATATGG

AATTACCAACTGGAGTTCATGCTGGCACAGACTTAGAAGGTAACTTTTAT

GGACCTTTTGTTGACAGGCAAACAGCACAAGCAGCTGGTACGGACACAAC

TATTACAGTTAATGTTTTAGCTTGGTTGTACGCTGCTGTTATAAATGGAG

ACAGGTGGTTTCTCAATCGATTTACCACAACTCTTAATGACTTTAACCTT

GTGGCTATGAAGTACAATTATGAACCTCTAACACAAGACCATGTTGACAT

ACTAGGACCTCTTTCTGCTCAAACTGGAATTGCCGTTTTAGATATGTGTG

CTTCATTAAAAGAATTACTGCAAAATGGTATGAATGGACGTACCATATTG

GGTAGTGCTTTATTAGAAGATGAATTTACACCTTTTGATGTTGTTAGACA

ATGCTCAGGTGTTACTTTCCAAAGTGCAGTGAAAAGAACAATCAAGGGTA

CACACCACTGGTTGTTACTCACAATTTTGACTTCACTTTTAGTTTTAGTC

CAGAGTACTCAATGGTCTTTGTTCTTTTTTTTGTATGAAAATGCCTTTTT

ACCTTTTGCTATGGGTATTATTGCTATGTCTGCTTTTGCAATGATGTTTG

TCAAACATAAGCATGCATTTCTCTGTTTGTTTTTGTTACCTTCTCTTGCC

ACTGTAGCTTATTTTAATATGGTCTATATGCCTGCTAGTTGGGTGATGCG

TATTATGACATGGTTGGATATGGTTGATACTAGTTTGTCTGGTTTTAAGC

TAAAAGACTGTGTTATGTATGCATCAGCTGTAGTGTTACTAATCCTTATG

ACAGCAAGAACTGTGTATGATGATGGTGCTAGGAGAGTGTGGACACTTAT

GAATGTCTTGACACTCGTTTATAAAGTTTATTATGGTAATGCTTTAGATC

AAGCCATTTCCATGTGGGCTCTTATAATCTCTGTTACTTCTAACTACTCA

GGTGTAGTTACAACTGTCATGTTTTTGGCCAGAGGTATTGTTTTTATGTG

TGTTGAGTATTGCCCTATTTTCTTCATAACTGGTAATACACTTCAGTGTA

TAATGCTAGTTTATTGTTTCTTAGGCTATTTTTGTACTTGTTACTTTGGC

CTCTTTTGTTTACTCAACCGCTACTTTAGACTGACTCTTGGTGTTTATGA

TTACTTAGTTTCTACACAGGAGTTTAGATATATGAATTCACAGGGACTAC

TCCCACCCAAGAATAGCATAGATGCCTTCAAACTCAACATTAAATTGTTG

GGTGTTGGTGGCAAACCTTGTATCAAAGTAGCCACTGTACAGTCTAAAAT

GTCAGATGTAAAGTGCACATCAGTAGTCTTACTCTCAGTTTTGCAACAAC

TCAGAGTAGAATCATCATCTAAATTGTGGGCTCAATGTGTCCAGTTACAC

AATGACATTCTCTTAGCTAAAGATACTACTGAAGCCTTTGAAAAAATGGT

TABLE 4-continued

| SARS-CoV2 genomic sequence (NCBI Accession Number NC 045512) |
|---|
| TTCACTACTTTCTGTTTTGCTTTCCATGCAGGGTGCTGTAGACATAAACA |
| AGCTTTGTGAAGAAATGCTGGACAACAGGGCAACCTTACAAGCTATAGCC |
| TCAGAGTTTAGTTCCCTTCCATCATATGCAGCTTTTGCTACTGCTCAAGA |
| AGCTTATGAGCAGGCTGTTGCTAATGGTGATTCTGAAGTTGTTCTTAAAA |
| AGTTGAAGAAGTCTTTGAATGTGGCTAAATCTGAATTTGACCGTGATGCA |
| GCCATGCAACGTAAGTTGGAAAAGATGGCTGATCAAGCTATGACCCAAAT |
| GTATAAACAGGCTAGATCTGAGGACAAGAGGGCAAAAGTTACTAGTGCTA |
| TGCAGACAATGCTTTTCACTATGCTTAGAAAGTTGGATAATGATGCACTC |
| AACAACATTATCAACAATGCAAGAGATGGTTGTGTTCCCTTGAACATAAT |
| ACCTCTTACAACAGCAGCCAAACTAATGGTTGTCATACCAGACTATAACA |
| CATATAAAAATACGTGTGATGGTACAACATTTACTTATGCATCAGCATTG |
| TGGGAAATCCAACAGGTTGTAGATGCAGATAGTAAAATTGTTCAACTTAG |
| TGAAATTAGTATGGACAATTCACCTAATTTAGCATGGCCTCTTATTGTAA |
| CAGCTTTAAGGGCCAATTCTGCTGTCAAATTACAGAATAATGAGCTTAGT |
| CCTGTTGCACTACGACAGATGTCTTGTGCTGCCGGTACTACACAAACTGC |
| TTGCACTGATGACAATGCGTTAGCTTACTACAACACAACAAAGGGAGGTA |
| GGTTTGTACTTGCACTGTTATCCGATTTACAGGATTTGAAATGGGCTAGA |
| TTCCCTAAGAGTGATGGAACTGGTACTATCTATACAGAACTGGAACCACC |
| TTGTAGGTTTGTTACAGACACACCTAAAGGTCCTAAAGTGAAGTATTTAT |
| ACTTTATTAAAGGATTAAACAACCTAAATAGAGGTATGGTACTTGGTAGT |
| TTAGCTGCCACAGTACGTCTACAAGCTGGTAATGCAACAGAAGTGCCTGC |
| CAATTCAACTGTATTATCTTTCTGTGCTTTTGCTGTAGATGCTGCTAAAG |
| CTTACAAAGATTATCTAGCTAGTGGGGGACAACCAATCACTAATTGTGTT |
| AAGATGTTGTGTACACACACTGGTACTGGTCAGGCAATAACAGTTACACC |
| GGAAGCCAATATGGATCAAGAATCCTTTGGTGGTGCATCGTGTTGTCTGT |
| ACTGCCGTTGCCACATAGATCATCCAAATCCTAAAGGATTTTGTGACTTA |
| AAAGGTAAGTATGTACAAATACCTACAACTTGTGCTAATGACCCTGTGGG |
| TTTTACACTTAAAAACACAGTCTGTACCGTCTGCGGTATGTGGAAAGGTT |
| ATGGCTGTAGTTGTGATCAACTCCGCGAACCCATGCTTCAGTCAGCTGAT |
| GCACAATCGTTTTTAAACGGGTTTGCGGTGTAAGTGCAGCCCGTCTTACA |
| CCGTGCGGCACAGGCACTAGTACTGATGTCGTATACAGGGCTTTTGACAT |
| CTACAATGATAAAGTAGCTGGTTTTGCTAAATTCCTAAAAACTAATTGTT |
| GTCGCTTCCAAGAAAAGGACGAAGATGACAATTTAATTGATTCTTACTTT |
| GTAGTTAAGAGACACACTTTCTCTAACTACCAACATGAAGAAACAATTTA |
| TAATTTACTTAAGGATTGTCCAGCTGTTGCTAAACATGACTTCTTTAAGT |
| TTAGAATAGACGGTGACATGGTACCACATATATCACGTCAACGTCTTACT |
| AAATACACAATGGCAGACCTCGTCTATGCTTTAAGGCATTTTGATGAAGG |
| TAATTGTGACACATTAAAAGAAATACTTGTCACATACAATTGTTGTGATG |
| ATGATTATTTCAATAAAAAGGACTGGTATGATTTTGTAGAAAACCCAGAT |

TABLE 4-continued

| SARS-CoV2 genomic sequence (NCBI Accession Number NC 045512) |
|---|
| ATATTACGCGTATACGCCAACTTAGGTGAACGTGTACGCCAAGCTTTGTT |
| AAAAACAGTACAATTCTGTGATGCCATGCGAAATGCTGGTATTGTTGGTG |
| TACTGACATTAGATAATCAAGATCTCAATGGTAACTGGTATGATTTCGGT |
| GATTTCATACAAACCACGCCAGGTAGTGGAGTTCCTGTTGTAGATTCTTA |
| TTATTCATTGTTAATGCCTATATTAACCTTGACCAGGGCTTTAACTGCAG |
| AGTCACATGTTGACACTGACTTAACAAAGCCTTACATTAAGTGGGATTTG |
| TTAAAATATGACTTCACGGAAGAGAGGTTAAAACTCTTTGACCGTTATTT |
| TAAATATTGGGATCAGACATACCACCCAAATTGTGTTAACTGTTTGGATG |
| ACAGATGCATTCTGCATTGTGCAAACTTTAATGTTTTATTCTCTACAGTG |
| TTCCCACCTACAAGTTTTGGACCACTAGTGAGAAAAATATTTGTTGATGG |
| TGTTCCATTTGTAGTTTCAACTGGATACCACTTCAGAGAGCTAGGTGTTG |
| TACATAATCAGGATGTAAACTTACATAGCTCTAGACTTAGTTTTAAGGAA |
| TTACTTGTGTATGCTGCTGACCCTGCTATGCACGCTGCTTCTGGTAATCT |
| ATTACTAGATAAACGCACTACGTGCTTTTCAGTAGCTGCACTTACTAACA |
| ATGTTGCTTTTCAAACTGTCAAACCCGGTAATTTTAACAAAGACTTCTAT |
| GACTTTGCTGTGTCTAAGGGTTTCTTTAAGGAAGGAAGTTCTGTTGAATT |
| AAAACACTTCTTCTTTGCTCAGGATGGTAATGCTGCTATCAGCGATTATG |
| ACTACTATCGTTATAATCTACCAACAATGTGTGATATCAGACAACTACTA |
| TTTGTAGTTGAAGTTGTTGATAAGTACTTTGATTGTTACGATGGTGGCTG |
| TATTAATGCTAACCAAGTCATCGTCAACAACCTAGACAAATCAGCTGGTT |
| TTCCATTTAATAAATGGGGTAAGGCTAGACTTTATTATGATTCAATGAGT |
| TATGAGGATCAAGATGCACTTTTCGCATATACAAAACGTAATGTCATCCC |
| TACTATAACTCAAATGAATCTTAAGTATGCCATTAGTGCAAAGAATAGAG |
| CTCGCACCGTAGCTGGTGTCTCTATCTGTAGTACTATGACCAATAGACAG |
| TTTCATCAAAAATTATTGAAATCAATAGCCGCCACTAGAGGAGCTACTGT |
| AGTAATTGGAACAAGCAAATTCTATGGTGGTTGGCACAACATGTTAAAAA |
| CTGTTTATAGTGATGTAGAAAACCCTCACCTTATGGGTTGGGATTATCCT |
| AAATGTGATAGAGCCATGCCTAACATGCTTAGAATTATGGCCTCACTTGT |
| TCTTGCTCGCAAACATACAACGTGTTGTAGCTTGTCACACCGTTTCTATA |
| GATTAGCTAATGAGTGTGCTCAAGTATTGAGTGAAATGGTCATGTGTGGC |
| GGTTCACTATATGTTAAACCAGGTGGAACCTCATCAGGAGATGCCACAAC |
| TGCTTATGCTAATAGTGTTTTTAACATTTGTCAAGCTGTCACGGCCAATG |
| TTAATGCACTTTTATCTACTGATGGTAACAAAATTGCCGATAAGTATGTC |
| CGCAATTTACAACACAGACTTTATGAGTGTCTCTATAGAAATAGAGATGT |
| TGACACAGACTTTGTGAATGAGTTTTACGCATATTTGCGTAAACATTTCT |
| CAATGATGATACTCTCTGACGATGCTGTTGTGTGTTTCAATAGCACTTAT |
| GCATCTCAAGGTCTAGTGGCTAGCATAAAGAACTTTAAGTCAGTTCTTTA |
| TTATCAAAACAATGTTTTTATGTCTGAAGCAAAATGTTGGACTGAGACTG |

TABLE 4-continued

| SARS-CoV2 genomic sequence (NCBI Accession Number NC 045512) |
|---|
| ACCTTACTAAAGGACCTCATGAATTTTGCTCTCAACATACAATGCTAGTT |
| AAACAGGGTGATGATTATGTGTACCTTCCTTACCCAGATCCATCAAGAAT |
| CCTAGGGGCCGGCTGTTTTGTAGATGATATCGTAAAAACAGATGGTACAC |
| TTATGATTGAACGGTTCGTGTCTTTAGCTATAGATGCTTACCCACTTACT |
| AAACATCCTAATCAGGAGTATGCTGATGTCTTTCATTTGTACTTACAATA |
| CATAAGAAAGCTACATGATGAGTTAACAGGACACATGTTAGACATGTATT |
| CTGTTATGCTTACTAATGATAACACTTCAAGGTATTGGGAACCTGAGTTT |
| TATGAGGCTATGTACACACCGCATACAGTCTTACAGGCTGTTGGGGCTTG |
| TGTTCTTTGCAATTCACAGACTTCATTAAGATGTGGTGCTTGCATACGTA |
| GACCATTCTTATGTTGTAAATGCTGTTACGACCATGTCATATCAACATCA |
| CATAAATTAGTCTTGTCTGTTAATCCGTATGTTTGCAATGCTCCAGGTTG |
| TGATGTCACAGATGTGACTCAACTTTACTTAGGAGGTATGAGCTATTATT |
| GTAAATCACATAAACCACCCATTAGTTTTCCATTGTGTGCTAATGGACAA |
| GTTTTTGGTTTATATAAAAATACATGTGTTGGTAGCGATAATGTTACTGA |
| CTTTAATGCAATTGCAACATGTGACTGGACAAATGCTGGTGATTACATTT |
| TAGCTAACACCTGTACTGAAAGACTCAAGCTTTTTGCAGCAGAAACGCTC |
| AAAGCTACTGAGGAGACATTTAAACTGTCTTATGGTATTGCTACTGTACG |
| TGAAGTGCTGTCTGACAGAGAATTACATCTTTCATGGGAAGTTGGTAAAC |
| CTAGACCACCACTTAACCGAAATTATGTCTTTACTGGTTATCGTGTAACT |
| AAAAACAGTAAAGTACAAATAGGAGAGTACACCTTTGAAAAAGGTGACTA |
| TGGTGATGCTGTTGTTTACCGAGGTACAACAACTTACAAATTAAATGTTG |
| GTGATTATTTTGTGCTGACATCACATACAGTAATGCCATTAAGTGCACCT |
| ACACTAGTGCCACAAGAGCACTATGTTAGAATTACTGGCTTATACCCAAC |
| ACTCAATATCTCAGATGAGTTTTCTAGCAATGTTGCAAATTATCAAAAGG |
| TTGGTATGCAAAAGTATTCTACACTCCAGGGACCACCTGGTACTGGTAAG |
| AGTCATTTTGCTATTGGCCTAGCTCTCTACTACCCTTCTGCTCGCATAGT |
| GTATACAGCTTGCTCTCATGCCGCTGTTGATGCACTATGTGAGAAGGCAT |
| TAAAATATTTGCCTATAGATAAATGTAGTAGAATTATACCTGCACGTGCT |
| CGTGTAGAGTGTTTTGATAAATTCAAAGTGAATTCAACATTAGAACAGTA |
| TGTCTTTTGTACTGTAAATGCATTGCCTGAGACGACAGCAGATATAGTTG |
| TCTTTGATGAAATTTCAATGGCCACAAATTATGATTTGAGTGTTGTCAAT |
| GCCAGATTACGTGCTAAGCACTATGTGTACATTGGCGACCCTGCTCAATT |
| ACCTGCACCACGCACATTGCTAACTAAGGGCACACTAGAACCAGAATATT |
| TCAATTCAGTGTGTAGACTTATGAAAACTATAGGTCCAGACATGTTCCTC |
| GGAACTTGTCGGCGTTGTCCTGCTGAAATTGTTGACACTGTGAGTGCTTT |
| GGTTTATGATAATAAGCTTAAAGCACATAAAGACAAATCAGCTCAATGCT |
| TTAAAATGTTTTATAAGGGTGTTATCACGCATGATGTTTCATCTGCAATT |
| AACAGGCCACAAATAGGCGTGGTAAGAGAATTCCTTACACGTAACCCTGC |
| TTGGAGAAAAGCTGTCTTTATTTCACCTTATAATTCACAGAATGCTGTAG |

TABLE 4-continued

| SARS-CoV2 genomic sequence (NCBI Accession Number NC 045512) |
|---|
| CCTCAAAGATTTTGGGACTACCAACTCAAACTGTTGATTCATCACAGGGC |
| TCAGAATATGACTATGTCATATTCACTCAAACCACTGAAACAGCTCACTC |
| TTGTAATGTAAACAGATTTAATGTTGCTATTACCAGAGCAAAAGTAGGCA |
| TACTTTGCATAATGTCTGATAGAGACCTTTATGACAAGTTGCAATTTACA |
| AGTCTTGAAATTCCACGTAGGAATGTGGCAACTTTACAAGCTGAAAATGT |
| AACAGGACTCTTTAAAGATTGTAGTAAGGTAATCACTGGGTTACATCCTA |
| CACAGGCACCTACACACCTCAGTGTTGACACTAAATTCAAAACTGAAGGT |
| TTATGTGTTGACATACCTGGCATACCTAAGGACATGACCTATAGAAGACT |
| CATCTCTATGATGGGTTTTAAAATGAATTATCAAGTTAATGGTTACCCTA |
| ACATGTTTATCACCCGCGAAGAAGCTATAAGACATGTACGTGCATGGATT |
| GGCTTCGATGTCGAGGGGTGTCATGCTACTAGAGAAGCTGTTGGTACCAA |
| TTTACCTTTACAGCTAGGTTTTTCTACAGGTGTTAACCTAGTTGCTGTAC |
| CTACAGGTTATGTTGATACACCTAATAATACAGATTTTTCCAGAGTTAGT |
| GCTAAACCACCGCCTGGAGATCAATTTAAACACCTCATACCACTTATGTA |
| CAAAGGACTTCCTTGGAATGTAGTGCGTATAAAGATTGTACAAATGTTAA |
| GTGACACACTTAAAAATCTCTCTGACAGAGTCGTATTTGTCTTATGGGCA |
| CATGGCTTTGAGTTGACATCTATGAAGTATTTTGTGAAAATAGGACCTGA |
| GCGCACCTGTTGTCTATGTGATAGACGTGCCACATGCTTTTCCACTGCTT |
| CAGACACTTATGCCTGTTGGCATCATTCTATTGGATTTGATTACGTCTAT |
| AATCCGTTTATGATTGATGTTCAACAATGGGGTTTTACAGGTAACCTACA |
| AAGCAACCATGATCTGTATTGTCAAGTCCATGGTAATGCACATGTAGCTA |
| GTTGTGATGCAATCATGACTAGGTGTCTAGCTGTCCACGAGTGCTTTGTT |
| AAGCGTGTTGACTGGACTATTGAATATCCTATAATTGGTGATGAACTGAA |
| GATTAATGCGGCTTGTAGAAAGGTTCAACACATGGTTGTTAAAGCTGCAT |
| TATTAGCAGACAAATTCCCAGTTCTTCACGACATTGGTAACCCTAAAGCT |
| ATTAAGTGTGTACCTCAAGCTGATGTAGAATGGAAGTTCTATGATGCACA |
| GCCTTGTAGTGACAAAGCTTATAAAATAGAAGAATTATTCTATTCTTATG |
| CCACACATTCTGACAAATTCACAGATGGTGTATGCCTATTTTGGAATTGC |
| AATGTCGATAGATATCCTGCTAATTCCATTGTTTGTAGATTTGACACTAG |
| AGTGCTATCTAACCTTAACTTGCCTGGTTGTGATGGTGGCAGTTTGTATG |
| TAAATAAACATGCATTCCACACACCAGCTTTTGATAAAAGTGCTTTTGTT |
| AATTTAAAACAATTACCATTTTTCTATTACTCTGACAGTCCATGTGAGTC |
| TCATGGAAAACAAGTAGTGTCAGATATAGATTATGTACCACTAAAGTCTG |
| CTACGTGTATAACACGTTGCAATTTAGGTGGTGCTGTCTGTAGACATCAT |
| GCTAATGAGTACAGATTGTATCTCGATGCTTATAACATGATGATCTCAGC |
| TGGCTTTAGCTTGTGGGTTTACAAACAATTTGATACTTATAACCTCTGGA |
| ACACTTTTACAAGACTTCAGAGTTTAGAAAATGTGGCTTTTAATGTTGTA |
| AATAAGGGACACTTTGATGGACAACAGGGTGAAGTACCAGTTTCTATCAT |

TABLE 4-continued

| SARS-CoV2 genomic sequence (NCBI Accession Number NC 045512) |
|---|
| TAATAACACTGTTTACACAAAAGTTGATGGTGTTGATGTAGAATTGTTTG |
| AAAATAAAACAACATTACCTGTTAATGTAGCATTTGAGCTTTGGGCTAAG |
| CGCAACATTAAACCAGTACCAGAGGTGAAAATACTCAATAATTTGGGTGT |
| GGACATTGCTGCTAATACTGTGATCTGGGACTACAAAAGAGATGCTCCAG |
| CACATATATCTACTATTGGTGTTTGTTCTATGACTGACATAGCCAAGAAA |
| CCAACTGAAACGATTTGTGCACCACTCACTGTCTTTTTTGATGGTAGAGT |
| TGATGGTCAAGTAGACTTATTTAGAAATGCCCGTAATGGTGTTCTTATTA |
| CAGAAGGTAGTGTTAAAGGTTTACAACCATCTGTAGGTCCCAAACAAGCT |
| AGTCTTAATGGAGTCACATTAATTGGAGAAGCCGTAAAAACACAGTTCAA |
| TTATTATAAGAAAGTTGATGGTGTTGTCCAACAATTACCTGAAACTTACT |
| TTACTCAGAGTAGAAATTTACAAGAATTTAAACCCAGGAGTCAAATGGAA |
| ATTGATTTCTTAGAATTAGCTATGGATGAATTCATTGAACGGTATAAATT |
| AGAAGGCTATGCCTTCGAACATATCGTTTATGGAGATTTTAGTCATAGTC |
| AGTTAGGTGGTTTACATCTACTGATTGGACTAGCTAAACGTTTTAAGGAA |
| TCACCTTTTGAATTAGAAGATTTTATTCCTATGGACAGTACAGTTAAAAA |
| CTATTTCATAACAGATGCGCAAACAGGTTCATCTAAGTGTGTGTGTTCTG |
| TTATTGATTTATTACTTGATGATTTTGTTGAAATAATAAAATCCCAAGAT |
| TTATCTGTAGTTTCTAAGGTTGTCAAAGTGACTATTGACTATACAGAAAT |
| TTCATTTATGCTTTGGTGTAAAGATGGCCATGTAGAAACATTTTACCCAA |
| AATTACAATCTAGTCAAGCGTGGCAACCGGGTGTTGCTATGCCTAATCTT |
| TACAAAATGCAAAGAATGCTATTAGAAAAGTGTGACCTTCAAAATTATGG |
| TGATAGTGCAACATTACCTAAAGGCATAATGATGAATGTCGCAAAATATA |
| CTCAACTGTGTCAATATTTAAACACATTAACATTAGCTGTACCCTATAAT |
| ATGAGAGTTATACATTTTGGTGCTGGTTCTGATAAAGGAGTTGCACCAGG |
| TACAGCTGTTTTAAGACAGTGGTTGCCTACGGGTACGCTGCTTGTCGATT |
| CAGATCTTAATGACTTTGTCTCTGATGCAGATTCAACTTTGATTGGTGAT |
| TGTGCAACTGTACATACAGCTAATAAATGGGATCTCATTATTAGTGATAT |
| GTACGACCCTAAGACTAAAAATGTTACAAAAGAAAATGACTCTAAAGAGG |
| GTTTTTTCACTTACATTTGTGGGTTTATACAACAAAAGCTAGCTCTTGGA |
| GGTTCCGTGGCTATAAAGATAACAGAACATTCTTGGAATGCTGATCTTTA |
| TAAGCTCATGGGACACTTCGCATGGTGGACAGCCTTTGTTACTAATGTGA |
| ATGCGTCATCATCTGAAGCATTTTTAATTGGATGTAATTATCTTGGCAAA |
| CCACGCGAACAAATAGATGGTTATGTCATGCATGCAAATTACATATTTTG |
| GAGGAATACAAATCCAATTCAGTTGTCTTCCTATTCTTTATTTGACATGA |
| GTAAATTTCCCCTTAAATTAAGGGGTACTGCTGTTATGTCTTTAAAAGAA |
| GGTCAAATCAATGATATGATTTTATCTCTTCTTAGTAAAGGTAGACTTAT |
| AATTAGAGAAAACAACAGAGTTGTTATTTCTAGTGATGTTCTTGTTAACA |
| ACTAAACGAACAATGTTTGTTTTTCTTGTTTTATTGCCACTAGTCTCTAG |
| TCAGTGTGTTAATCTTACAACCAGAACTCAATTACCCCCTGCATACACTA |

TABLE 4-continued

| SARS-CoV2 genomic sequence (NCBI Accession Number NC 045512) |
|---|
| ATTCTTTCACACGTGGTGTTTATTACCCTGACAAAGTTTTCAGATCCTCA |
| GTTTTACATTCAACTCAGGACTTGTTCTTACCTTTCTTTTCCAATGTTAC |
| TTGGTTCCATGCTATACATGTCTCTGGGACCAATGGTACTAAGAGGTTTG |
| ATAACCCTGTCCTACCATTTAATGATGGTGTTTATTTTGCTTCCACTGAG |
| AAGTCTAACATAATAAGAGGCTGGATTTTTGGTACTACTTTAGATTCGAA |
| GACCCAGTCCCTACTTATTGTTAATAACGCTACTAATGTTGTTATTAAAG |
| TCTGTGAATTTCAATTTTGTAATGATCCATTTTTGGGTGTTTATTACCAC |
| AAAAACAACAAAAGTTGGATGGAAAGTGAGTTCAGAGTTTATTCTAGTGC |
| GAATAATTGCACTTTTGAATATGTCTCTCAGCCTTTTCTTATGGACCTTG |
| AAGGAAAACAGGGTAATTTCAAAAATCTTAGGGAATTTGTGTTTAAGAAT |
| ATTGATGGTTATTTTAAAATATATTCTAAGCACACGCCTATTAATTTAGT |
| GCGTGATCTCCCTCAGGGTTTTTCGGCTTTAGAACCATTGGTAGATTTGC |
| CAATAGGTATTAACATCACTAGGTTTCAAACTTTACTTGCTTTACATAGA |
| AGTTATTTGACTCCTGGTGATTCTTCTTCAGGTTGGACAGCTGGTGCTGC |
| AGCTTATTATGTGGGTTATCTTCAACCTAGGACTTTTCTATTAAAATATA |
| ATGAAAATGGAACCATTACAGATGCTGTAGACTGTGCACTTGACCCTCTC |
| TCAGAAACAAAGTGTACGTTGAAATCCTTCACTGTAGAAAAAGGAATCTA |
| TCAAACTTCTAACTTTAGAGTCCAACCAACAGAATCTATTGTTAGATTTC |
| CTAATATTACAAACTTGTGCCCTTTTGGTGAAGTTTTTAACGCCACCAGA |
| TTTGCATCTGTTTATGCTTGGAACAGGAAGAGAATCAGCAACTGTGTTGC |
| TGATTATTCTGTCCTATATAATTCCGCATCATTTTCCACTTTTAAGTGTT |
| ATGGAGTGTCTCCTACTAAATTAAATGATCTCTGCTTTACTAATGTCTAT |
| GCAGATTCATTTGTAATTAGAGGTGATGAAGTCAGACAAATCGCTCCAGG |
| GCAAACTGGAAAGATTGCTGATTATAATTATAAATTACCAGATGATTTTA |
| CAGGCTGCGTTATAGCTTGGAATTCTAACAATCTTGATTCTAAGGTTGGT |
| GGTAATTATAATTACCTGTATAGATTGTTTAGGAAGTCTAATCTCAAACC |
| TTTTGAGAGAGATATTTCAACTGAAATCTATCAGGCCGGTAGCACACCTT |
| GTAATGGTGTTGAAGGTTTTAATTGTTACTTTCCTTTACAATCATATGGT |
| TTCCAACCCACTAATGGTGTTGGTTACCAACCATACAGAGTAGTAGTACT |
| TTCTTTTGAACTTCTACATGCACCAGCAACTGTTTGTGGACCTAAAAAGT |
| CTACTAATTTGGTTAAAAACAAATGTGTCAATTTCAACTTCAATGGTTTA |
| ACAGGCACAGGTGTTCTTACTGAGTCTAACAAAAAGTTTCTGCCTTTCCA |
| ACAATTTGGCAGAGACATTGCTGACACTACTGATGCTGTCCGTGATCCAC |
| AGACACTTGAGATTCTTGACATTACACCATGTTCTTTTGGTGGTGTCAGT |
| GTTATAACACCAGGAACAAATACTTCTAACCAGGTTGCTGTTCTTTATCA |
| GGATGTTAACTGCACAGAAGTCCCTGTTGCTATTCATGCAGATCAACTTA |
| CTCCTACTTGGCGTGTTTATTCTACAGGTTCTAATGTTTTTCAAACACGT |
| GCAGGCTGTTTAATAGGGGCTGAACATGTCAACAACTCATATGAGTGTGA |

TABLE 4-continued

| SARS-CoV2 genomic sequence (NCBI Accession Number NC 045512) |
|---|
| CATACCCATTGGTGCAGGTATATGCGCTAGTTATCAGACTCAGACTAATT |
| CTCCTCGGCGGGCACGTAGTGTAGCTAGTCAATCCATCATTGCCTACACT |
| ATGTCACTTGGTGCAGAAAATTCAGTTGCTTACTCTAATAACTCTATTGC |
| CATACCCACAAATTTTACTATTAGTGTTACCACAGAAATTCTACCAGTGT |
| CTATGACCAAGACATCAGTAGATTGTACAATGTACATTTGTGGTGATTCA |
| ACTGAATGCAGCAATCTTTTGTTGCAATATGGCAGTTTTTGTACACAATT |
| AAACCGTGCTTTAACTGGAATAGCTGTTGAACAAGACAAAAACACCCAAG |
| AAGTTTTTGCACAAGTCAAACAAATTTACAAAACACCACCAATTAAAGAT |
| TTTGGTGGTTTTAATTTTTCACAAATATTACCAGATCCATCAAAACCAAG |
| CAAGAGGTCATTTATTGAAGATCTACTTTTCAACAAAGTGACACTTGCAG |
| ATGCTGGCTTCATCAAACAATATGGTGATTGCCTTGGTGATATTGCTGCT |
| AGAGACCTCATTTGTGCACAAAAGTTTAACGGCCTTACTGTTTTGCCACC |
| TTTGCTCACAGATGAAATGATTGCTCAATACACTTCTGCACTGTTAGCGG |
| GTACAATCACTTCTGGTTGGACCTTTGGTGCAGGTGCTGCATTACAAATA |
| CCATTTGCTATGCAAATGGCTTATAGGTTTAATGGTATTGGAGTTACACA |
| GAATGTTCTCTATGAGAACCAAAAATTGATTGCCAACCAATTTAATAGTG |
| CTATTGGCAAAATTCAAGACTCACTTTCTTCCACAGCAAGTGCACTTGGA |
| AAACTTCAAGATGTGGTCAACCAAAATGCACAAGCTTTAAACACGCTTGT |
| TAAACAACTTAGCTCCAATTTTGGTGCAATTTCAAGTGTTTTAAATGATA |
| TCCTTTCACGTCTTGACAAAGTTGAGGCTGAAGTGCAAATTGATAGGTTG |
| ATCACAGGCAGACTTCAAAGTTTGCAGACATATGTGACTCAACAATTAAT |
| TAGAGCTGCAGAAATCAGAGCTTCTGCTAATCTTGCTGCTACTAAAATGT |
| CAGAGTGTGTACTTGGACAATCAAAAAGAGTTGATTTTTGTGGAAAGGGC |
| TATCATCTTATGTCCTTCCCTCAGTCAGCACCTCATGGTGTAGTCTTCTT |
| GCATGTGACTTATGTCCCTGCACAAGAAAAGAACTTCACAACTGCTCCTG |
| CCATTTGTCATGATGGAAAAGCACACTTTCCTCGTGAAGGTGTCTTTGTT |
| TCAAATGGCACACACTGGTTTGTAACACAAAGGAATTTTTATGAACCACA |
| AATCATTACTACAGACAACACATTTGTGTCTGGTAACTGTGATGTTGTAA |
| TAGGAATTGTCAACAACACAGTTTATGATCCTTTGCAACCTGAATTAGAC |
| TCATTCAAGGAGGAGTTAGATAAATATTTTAAGAATCATACATCACCAGA |
| TGTTGATTTAGGTGACATCTCTGGCATTAATGCTTCAGTTGTAAACATTC |
| AAAAAGAAATTGACCGCCTCAATGAGGTTGCCAAGAATTTAAATGAATCT |
| CTCATCGATCTCCAAGAACTTGGAAAGTATGAGCAGTATATAAAATGGCC |
| ATGGTACATTTGGCTAGGTTTTATAGCTGGCTTGATTGCCATAGTAATGG |
| TGACAATTATGCTTTGCTGTATGACCAGTTGCTGTAGTTGTCTCAAGGGC |
| TGTTGTTCTTGTGGATCCTGCTGCAAATTTGATGAAGACGACTCTGAGCC |
| AGTGCTCAAAGGAGTCAAATTACATTACACATAAACGAACTTATGGATTT |
| GTTTATGAGAATCTTCACAATTGGAACTGTAACTTTGAAGCAAGGTGAAA |
| TCAAGGATGCTACTCCTTCAGATTTTGTTCGCGCTACTGCAACGATACCG |

TABLE 4-continued

| SARS-CoV2 genomic sequence (NCBI Accession Number NC 045512) |
|---|
| ATACAAGCCTCACTCCCTTTCGGATGGCTTATTGTTGGCGTTGCACTTCT |
| TGCTGTTTTTCAGAGCGCTTCCAAAATCATAACCCTCAAAAAGAGATGGC |
| AACTAGCACTCTCCAAGGGTGTTCACTTTGTTTGCAACTTGCTGTTGTTG |
| TTTGTAACAGTTTACTCACACCTTTTGCTCGTTGCTGCTGGCCTTGAAGC |
| CCCTTTTCTCTATCTTTATGCTTTAGTCTACTTCTTGCAGAGTATAAACT |
| TTGTAAGAATAATAATGAGGCTTTGGCTTTGCTGGAAATGCCGTTCCAAA |
| AACCCATTACTTTATGATGCCAACTATTTTCTTTGCTGGCATACTAATTG |
| TTACGACTATTGTATACCTTACAATAGTGTAACTTCTTCAATTGTCATTA |
| CTTCAGGTGATGGCACAACAAGTCCTATTTCTGAACATGACTACCAGATT |
| GGTGGTTATACTGAAAAATGGGAATCTGGAGTAAAAGACTGTGTTGTATT |
| ACACAGTTACTTCACTTCAGACTATTACCAGCTGTACTCAACTCAATTGA |
| GTACAGACACTGGTGTTGAACATGTTACCTTCTTCATCTACAATAAAATT |
| GTTGATGAGCCTGAAGAACATGTCCAAATTCACACAATCGACGGTTCATC |
| CGGAGTTGTTAATCCAGTAATGGAACCAATTTATGATGAACCGACGACGA |
| CTACTAGCGTGCCTTTGTAAGCACAAGCTGATGAGTACGAACTTATGTAC |
| TCATTCGTTTCGGAAGAGACAGGTACGTTAATAGTTAATAGCGTACTTCT |
| TTTTCTTGCTTTCGTGGTATTCTTGCTAGTTACACTAGCCATCCTTACTG |
| CGCTTCGATTGTGTGCGTACTGCTGCAATATTGTTAACGTGAGTCTTGTA |
| AAACCTTCTTTTTACGTTTACTCTCGTGTTAAAAATCTGAATTCTTCTAG |
| AGTTCCTGATCTTCTGGTCTAAACGAACTAAATATTATATTAGTTTTTCT |
| GTTTGGAACTTTAATTTTAGCCATGGCAGATTCCAACGGTACTATTACCG |
| TTGAAGAGCTTAAAAAGCTCCTTGAACAATGGAACCTAGTAATAGGTTTC |
| CTATTCCTTACATGGATTTGTCTTCTACAATTTGCCTATGCCAACAGGAA |
| TAGGTTTTTGTATATAATTAAGTTAATTTTCCTCTGGCTGTTATGGCCAG |
| TAACTTTAGCTTGTTTTGTGCTTGCTGCTGTTTACAGAATAAATTGGATC |
| ACCGGTGGAATTGCTATCGCAATGGCTTGTCTTGTAGGCTTGATGTGGCT |
| CAGCTACTTCATTGCTTCTTTCAGACTGTTTGCGCGTACGCGTTCCATGT |
| GGTCATTCAATCCAGAAACTAACATTCTTCTCAACGTGCCACTCCATGGC |
| ACTATTCTGACCAGACCGCTTCTAGAAAGTGAACTCGTAATCGGAGCTGT |
| GATCCTTCGTGGACATCTTCGTATTGCTGGACACCATCTAGGACGCTGTG |
| ACATCAAGGACCTGCCTAAAGAAATCACTGTTGCTACATCACGAACGCTT |
| TCTTATTACAAATTGGGAGCTTCGCAGCGTGTAGCAGGTGACTCAGGTTT |
| TGCTGCATACAGTCGCTACAGGATTGGCAACTATAAATTAAACACAGACC |
| ATTCCAGTAGCAGTGACAATATTGCTTTGCTTGTACAGTAAGTGACAACA |
| GATGTTTCATCTCGTTGACTTTCAGGTTACTATAGCAGAGATATTACTAA |
| TTATTATGAGGACTTTTAAAGTTTCCATTTGGAATCTTGATTACATCATA |
| AACCTCATAATTAAAAATTTATCTAAGTCACTAACTGAGAATAAATATTC |
| TCAATTAGATGAAGAGCAACCAATGGAGATTGATTAAACGAACATGAAAA |

TABLE 4-continued

| SARS-CoV2 genomic sequence (NCBI Accession Number NC 045512) |
|---|
| TTATTCTTTTCTTGGCACTGATAACACTCGCTACTTGTGAGCTTTATCAC |
| TACCAAGAGTGTGTTAGAGGTACAACAGTACTTTTAAAAGAACCTTGCTC |
| TTCTGGAACATACGAGGGCAATTCACCATTTCATCCTCTAGCTGATAACA |
| AATTTGCACTGACTTGCTTTAGCACTCAATTTGCTTTTGCTTGTCCTGAC |
| GGCGTAAAACACGTCTATCAGTTACGTGCCAGATCAGTTTCACCTAAACT |
| GTTCATCAGACAAGAGGAAGTTCAAGAACTTTACTCTCCAATTTTTCTTA |
| TTGTTGCGGCAATAGTGTTTATAACACTTTGCTTCACACTCAAAAGAAAG |
| ACAGAATGATTGAACTTTCATTAATTGACTTCTATTTGTGCTTTTTAGCC |
| TTTCTGCTATTCCTTGTTTTAATTATGCTTATTATCTTTTGGTTCTCACT |
| TGAACTGCAAGATCATAATGAAACTTGTCACGCCTAAACGAACATGAAAT |
| TTCTTGTTTTCTTAGGAATCATCACAACTGTAGCTGCATTTCACCAAGAA |
| TGTAGTTTACAGTCATGTACTCAACATCAACCATATGTAGTTGATGACCC |
| GTGTCCTATTCACTTCTATTCTAAATGGTATATTAGAGTAGGAGCTAGAA |
| AATCAGCACCTTTAATTGAATTGTGCGTGGATGAGGCTGGTTCTAAATCA |
| CCCATTCAGTACATCGATATCGGTAATTATACAGTTTCCTGTTTACCTTT |
| TACAATTAATTGCCAGGAACCTAAATTGGGTAGTCTTGTAGTGCGTTGTT |
| CGTTCTATGAAGACTTTTTAGAGTATCATGACGTTCGTGTTGTTTTAGAT |
| TTCATCTAAACGAACAAACTAAAATGTCTGATAATGGACCCCAAAATCAG |
| CGAAATGCACCCCGCATTACGTTTGGTGGACCCTCAGATTCAACTGGCAG |
| TAACCAGAATGGAGAACGCAGTGGGGCGCGATCAAAACAACGTCGGCCCC |
| AAGGTTTACCCAATAATACTGCGTCTTGGTTCACCGCTCTCACTCAACAT |
| GGCAAGGAAGACCTTAAATTCCCTCGAGGACAAGGCGTTCCAATTAACAC |
| CAATAGCAGTCCAGATGACCAAATTGGCTACTACCGAAGAGCTACCAGAC |
| GAATTCGTGGTGGTGACGGTAAAATGAAAGATCTCAGTCCAAGATGGTAT |
| TTCTACTACCTAGGAACTGGGCCAGAAGCTGGACTTCCCTATGGTGCTAA |
| CAAAGACGGCATCATATGGGTTGCAACTGAGGGAGCCTTGAATACACCAA |
| AAGATCACATTGGCACCCGCAATCCTGCTAACAATGCTGCAATCGTGCTA |
| CAACTTCCTCAAGGAACAACATTGCCAAAAGGCTTCTACGCAGAAGGGAG |
| CAGAGGCGGCAGTCAAGCCTCTTCTCGTTCCTCATCACGTAGTCGCAACA |
| GTTCAAGAAATTCAACTCCAGGCAGCAGTAGGGGAACTTCTCCTGCTAGA |
| ATGGCTGGCAATGGCGGTGATGCTGCTCTTGCTTTGCTGCTGCTTGACAG |
| ATTGAACCAGCTTGAGAGCAAAATGTCTGGTAAAGGCCAACAACAACAAG |
| GCCAAACTGTCACTAAGAAATCTGCTGCTGAGGCTTCTAAGAAGCCTCGG |
| CAAAAACGTACTGCCACTAAAGCATACAATGTAACACAAGCTTTCGGCAG |
| ACGTGGTCCAGAACAAACCCAAGGAAATTTTGGGGACCAGGAACTAATCA |
| GACAAGGAACTGATTACAAACATTGGCCGCAAATTGCACAATTTGCCCCC |
| AGCGCTTCAGCGTTCTTCGGAATGTCGCGCATTGGCATGGAAGTCACACC |
| TTCGGGAACGTGGTTGACCTACACAGGTGCCATCAAATTGGATGACAAAG |
| ATCCAAATTTCAAAGATCAAGTCATTTTGCTGAATAAGCATATTGACGCA |
| TACAAAACATTCCCACCAACAGAGCCTAAAAAGGACAAAAAGAAGAAGGC |
| TGATGAAACTCAAGCCTTACCGCAGAGACAGAAGAAACAGCAAACTGTGA |
| CTCTTCTTCCTGCTGCAGATTTGGATGATTTCTCCAAACAATTGCAACAA |
| TCCATGAGCAGTGCTGACTCAACTCAGGCCTAAACTCATGCAGACCACAC |
| AAGGCAGATGGGCTATATAAACGTTTTCGCTTTTCCGTTTACGATATATA |
| GTCTACTCTTGTGCAGAATGAATTCTCGTAACTACATAGCACAAGTAGAT |
| GTAGTTAACTTTAATCTCACATAGCAATCTTTAATCAGTGTGTAACATTA |
| GGGAGGACTTGAAAGAGCCACCACATTTTCACCGAGGCCACGCGGAGTAC |
| GATCGAGTGTACAGTGAACAATGCTAGGGAGAGCTGCCTATATGGAAGAG |
| CCCTAATGTGTAAAATTAATTTTAGTAGTGCTATCCCCATGTGATTTTAA |
| TAGCTTCTTAGGAGAATGACAAAAAAAAAAAAAAAAAAAAAAAAAAAAAA |
| AAA (SEQ ID NO: 1) |

TABLE 5

| SARS-CoV2 gene sequences | | | |
|---|---|---|---|
| Gene | Start | End | Sequence |
| orf1a (SEQ ID NO: 2) | 266 | 13483 | ATGGAGAGCCTTGTCCCTGGTTTCAACGAGAAAACAC ACGTCCAACTCAGTTTGCCTGTTTTACAGGTTCGCGAC GTGCTCGTACGTGGCTTTGGAGACTCCGTGGAGGAGG TCTTATCAGAGGCACGTCAACATCTTAAAGATGGCAC TTGTGGCTTAGTAGAAGTTGAAAAAGGCGTTTTGCCTC AACTTGAACAGCCCTATGTGTTCATCAAACGTTCGGAT GCTCGAACTGCACCTCATGGTCATGTTATGGTTGAGCT GGTAGCAGAACTCGAAGGCATTCAGTACGGTCGTAGT GGTGAGACACTTGGTGTCCTTGTCCCTCATGTGGGCGA AATACCAGTGGCTTACCGCAAGGTTCTTCTTCGTAAGA ACGGTAATAAAGGAGCTGGTGGCCATAGTTACGGCGC CGATCTAAAGTCATTTGACTTAGGCGACGAGCTTGGC ACTGATCCTTATGAAGATTTTCAAGAAAACTGGAACA CTAAACATAGCAGTGGTGTTACCCGTGAACTCATGCG TGAGCTTAACGGAGGGGCATACACTCGCTATGTCGAT AACAACTTCTGTGGCCCTGATGGCTACCCTCTTGAGTG CATTAAAGACCTTCTAGCACGTGCTGGTAAAGCTTCAT |

TABLE 5-continued

SARS-CoV2 gene sequences

| Gene | Start | End | Sequence |
|---|---|---|---|
| | | | GCACTTTGTCCGAACAACTGGACTTTATTGACACTAAG AGGGGTGTATACTGCTGCCGTGAACATGAGCATGAAA TTGCTTGGTACACGGAACGTTCTGAAAAGAGCTATGA ATTGCAGACACCTTTTGAAATTAAATTGGCAAAGAAA TTTGACACCTTCAATGGGGAATGTCCAAATTTTGTATT TCCCTTAAATTCCATAATCAAGACTATTCAACCAAGGG TTGAAAAGAAAAAGCTTGATGGCTTTATGGGTAGAAT TCGATCTGTCTATCCAGTTGCGTCACCAAATGAATGCA ACCAAATGTGCCTTTCAACTCTCATGAAGTGTGATCAT TGTGGTGAAACTTCATGGCAGACGGGCGATTTTGTTA AAGCCACTTGCGAATTTTGTGGCACTGAGAATTTGACT AAAGAAGGTGCCACTACTTGTGGTTACTTACCCCAAA ATGCTGTTGTTAAAATTTATTGTCCAGCATGTCACAAT TCAGAAGTAGGACCTGAGCATAGTCTTGCCGAATACC ATAATGAATCTGGCTTGAAAACCATTCTTCGTAAGGGT GGTCGCACTATTGCCTTTGGAGGCTGTGTGTTCTCTTA TGTTGGTTGCCATAACAAGTGTGCCTATTGGGTTCCAC GTGCTAGCGCTAACATAGGTTGTAACCATACAGGTGT TGTTGGAGAAGGTTCCGAAGGTCTTAATGACAACCTT CTTGAAATACTCCAAAAAGAGAAAGTCAACATCAATA TTGTTGGTGACTTTAAACTTAATGAAGAGATCGCCATT ATTTTGGCATCTTTTTCTGCTTCCACAAGTGCTTTTGT GGAAACTGTGAAAGGTTTGGATTATAAAGCATTCAAAC AAATTGTTGAATCCTGTGGTAATTTTAAAGTTACAAAA GGAAAAGCTAAAAAAGGTGCCTGGAATATTGGTGAAC AGAAATCAATACTGAGTCCTCTTTATGCATTTGCATCA GAGGCTGCTCGTGTTGTACGATCAATTTTCTCCCGCAC TCTTGAAACTGCTCAAAATTCTGTGCGTGTTTTACAGA AGGCCGCTATAACAATACTAGATGGAATTTCACAGTA TTCACTGAGACTCATTGATGCTATGATGTTCACATCTG ATTTGGCTACTAACAATCTAGTTGTAATGGCCTACATT ACAGGTGGTGTTGTTCAGTTGACTTCGCAGTGGCTAAC TAACATCTTTGGCACTGTTTATGAAAAACTCAAACCCG TCCTTGATTGGCTTGAAGAGAAGTTTAAGGAAGGTGT AGAGTTTCTTAGAGACGGTTGGGAAATTGTTAAATTTA TCTCAACCTGTGCTTGTGAAATTGTCGGTGGACAAATT GTCACCTGTGCAAAGGAAATTAAGGAGAGTGTTCAGA CATTCTTTAAGCTTGTAAATAAATTTTTGGCTTTGTGT GCTGACTCTATCATTATTGGTGGAGCTAAACTTAAAGC CTTGAATTTAGGTGAAACATTTGTCACGCACTCAAAG GGATTGTACAGAAAGTGTGTTAAATCCAGAGAAGAAA CTGGCCTACTCATGCCTCTAAAAGCCCCAAAAGAAAT TATCTTCTTAGAGGGAGAAACACTTCCCACAGAAGTG TTAACAGAGGAAGTTGTCTTGAAAACTGGTGATTTAC AACCATTAGAACAACCTACTAGTGAAGCTGTTGAAGC TCCATTGGTTGGTACACCAGTTTGTATTAACGGGCTTA TGTTGCTCGAAATCAAAGACACAGAAAAGTACTGTGC CCTTGCACCTAATATGATGGTAACAAACAATACCTTCA CACTCAAAGGCGGTGCACCAACAAAGGTTACTTTTGG TGATGACACTGTGATAGAAGTGCAAGGTTACAAGAGT GTGAATATCACTTTTGAACTTGATGAAAGGATTGATA AAGTACTTAATGAGAAGTGCTCTGCCTATACAGTTGA ACTCGGTACAGAAGTAAATGAGTTCGCCTGTGTTGTG GCAGATGCTGTCATAAAAACTTTGCAACCAGTATCTG AATTACTTACACCACTGGGCATTGATTTAGATGAGTGG AGTATGGCTACATACTACTTATTTGATGAGTCTGGTGA GTTTAAATTGGCTTCACATATGTATTGTTCTTTCTACC CTCCAGATGAGGATGAAGAAGAAGGTGATTGTGAAGA AGAAGAGTTTGAGCCATCAACTCAATATGAGTATGGT ACTGAAGATGATTACCAAGGTAAACCTTTGGAATTTG GTGCCACTTCTGCTGCTCTTCAACCTGAAGAAGAGCA AGAAGAAGATTGGTTAGATGATGATAGTCAACAAACT GTTGGTCAACAAGACGGCAGTGAGGACAATCAGACAA CTACTATTCAAACAATTGTTGAGGTTCAACCTCAATTA GAGATGGAACTTACACCAGTTGTTCAGACTATTGAAG TGAATAGTTTTAGTGGTTATTTAAAACTTACTGACAAT GTATACATTAAAAATGCAGACATTGTGGAAGAAGCTA AAAAGGTAAAACCAACAGTGGTTGTTAATGCAGCCAA TGTTTACCTTAAACATGGAGGAGGTGTTGCAGGAGCC TTAAATAAGGCTACTAACAATGCCATGCAAGTTGAAT CTGATGATTACATAGCTACTAATGGACCACTTAAAGT GGGTGGTAGTTGTGTTTTAAGCGGACACAATCTTGCTA AACACTGTCTTCATGTTGTCGGCCCAAATGTTAACAAA GGTGAAGACATTCAACTTCTTAAGAGTGCTTATGAAA ATTTTAATCAGCACGAAGTTCTACTTGCACCATTATTA TCAGCTGGTATTTTTGGTGCTGACCCTATACATTCTTT |

TABLE 5-continued

SARS-CoV2 gene sequences

| Gene | Start | End | Sequence |
|---|---|---|---|
| | | | AAGAGTTTGTGTAGATACTGTTCGCACAAATGTCTACT |
| | | | TAGCTGTCTTTGATAAAAATCTCTATGACAAACTTGTT |
| | | | TCAAGCTTTTTGGAAATGAAGAGTGAAAAGCAAGTTG |
| | | | AACAAAAGATCGCTGAGATTCCTAAAGAGGAAGTTAA |
| | | | GCCATTTATAACTGAAAGTAAACCTTCAGTTGAACAG |
| | | | AGAAAACAAGATGATAAGAAAATCAAAGCTTGTGTTG |
| | | | AAGAAGTTACAACAACTCTGGAAGAAACTAAGTTCCT |
| | | | CACAGAAAACTTGTTACTTTATATTGACATTAATGGCA |
| | | | ATCTTCATCCAGATTCTGCCACTCTTGTTAGTGACATT |
| | | | GACATCACTTTCTTAAAGAAAGATGCTCCATATATAGT |
| | | | GGGTGATGTTGTTCAAGAGGGTGTTTTAACTGCTGTGG |
| | | | TTATACCTACTAAAAAGGCTGGTGGCACTACTGAAAT |
| | | | GCTAGCGAAAGCTTTGAGAAAAGTGCCAACAGACAAT |
| | | | TATATAACCACTTACCCGGGTCAGGGTTTAAATGGTTA |
| | | | CACTGTAGAGGAGGCAAAGACAGTGCTTAAAAAGTGT |
| | | | AAAAGTGCCTTTTACATTCTACCATCTATTATCTCTAA |
| | | | TGAGAAGCAAGAAATTCTTGGAACTGTTTCTTGGAATT |
| | | | TGCGAGAAATGCTTGCACATGCAGAAGAAACACGCAA |
| | | | ATTAATGCCTGTCTGTGTGGAAACTAAAGCCATAGTTT |
| | | | CAACTATACAGCGTAAATATAAGGGTATTAAAATACA |
| | | | AGAGGGTGTGGTTGATTATGGTGCTAGATTTTACTTTT |
| | | | ACACCAGTAAAACAACTGTAGCGTCACTTATCAACAC |
| | | | ACTTAACGATCTAAATGAAACTCTTGTTACAATGCCAC |
| | | | TTGGCTATGTAACACATGGCTTAAATTTGGAAGAAGC |
| | | | TGCTCGGTATATGAGATCTCTCAAAGTGCCAGCTACA |
| | | | GTTTCTGTTTCTTCACCTGATGCTGTTACAGCGTATAA |
| | | | TGGTTATCTTACTTCTTCTTCTAAAACACCTGAAGAAC |
| | | | ATTTTATTGAAACCATCTCACTTGCTGGTTCCTATAAA |
| | | | GATTGGTCCTATTCTGGACAATCTACACAACTAGGTAT |
| | | | AGAATTTCTTAAGAGAGGTGATAAAAGTGTATATTAC |
| | | | ACTAGTAATCCTACCACATTCCACCTAGATGGTGAAGT |
| | | | TATCACCTTTGACAATCTTAAGACACTTCTTTCTTTGA |
| | | | GAGAAGTGAGGACTATTAAGGTGTTTACAACAGTAGA |
| | | | CAACATTAACCTCCACACGCAAGTTGTGGACATGTCA |
| | | | ATGACATATGGACAACAGTTTGGTCCAACTTATTTGGA |
| | | | TGGAGCTGATGTTACTAAAATAAAACCTCATAATTCA |
| | | | CATGAAGGTAAAACATTTTATGTTTTACCTAATGATGA |
| | | | CACTCTACGTGTTGAGGCTTTTGAGTACTACCACACAA |
| | | | CTGATCCTAGTTTTCTGGGTAGGTACATGTCAGCATTA |
| | | | AATCACACTAAAAAGTGGAAATACCCACAAGTTAATG |
| | | | GTTTAACTTCTATTAAATGGGCAGATAACAACTGTTAT |
| | | | CTTGCCACTGCATTGTTAACACTCCAACAAATAGAGTT |
| | | | GAAGTTTAATCCACCTGCTCTACAAGATGCTTATTACA |
| | | | GAGCAAGGGCTGGTGAAGCTGCTAACTTTTGTGCACT |
| | | | TATCTTAGCCTACTGTAATAAGACAGTAGGTGAGTTA |
| | | | GGTGATGTTAGAGAAACAATGAGTTACTTGTTTCAAC |
| | | | ATGCCAATTTAGATTCTTGCAAAAGAGTCTTGAACGTG |
| | | | GTGTGTAAAACTTGTGGACAACAGCAGACAACCCTTA |
| | | | AGGGTGTAGAAGCTGTTATGTACATGGGCACACTTTCT |
| | | | TATGAACAATTTAAGAAAGGTGTTCAGATACCTTGTA |
| | | | CGTGTGGTAAACAAGCTACAAAATATCTAGTACAACA |
| | | | GGAGTCACCTTTTGTTATGATGTCAGCACCACCTGCTC |
| | | | AGTATGAACTTAAGCATGGTACATTTACTTGTGCTAGT |
| | | | GAGTACACTGGTAATTACCAGTGTGGTCACTATAAAC |
| | | | ATATAACTTCTAAAGAAACTTTGTATTGCATAGACGGT |
| | | | GCTTTACTTACAAAGTCCTCAGAATACAAAGGTCCTAT |
| | | | TACGGATGTTTTCTACAAAGAAAACAGTTACACAACA |
| | | | ACCATAAAACCAGTTACTTATAAATTGGATGGTGTTGT |
| | | | TTGTACAGAAATTGACCCTAAGTTGGACAATTATTATA |
| | | | AGAAAGACAATTCTTATTTCACAGAGCAACCAATTGA |
| | | | TCTTGTACCAAACCAACCATATCCAAACGCAAGCTTC |
| | | | GATAATTTTAAGTTTGTATGTGATAATATCAAATTTGC |
| | | | TGATGATTTAAACCAGTTAACTGGTTATAAGAAACCT |
| | | | GCTTCAAGAGAGCTTAAAGTTACATTTTTCCCTGACTT |
| | | | AAATGGTGATGTGGTGGCTATTGATTATAAACACTAC |
| | | | ACACCCTCTTTTAAGAAAGGAGCTAAATTGTTACATA |
| | | | AACCTATTGTTTGGCATGTTAACAATGCAACTAATAAA |
| | | | GCCACGTATAAACCAAATACCTGGTGTATACGTTGTCT |
| | | | TTGGAGCACAAAACCAGTTGAAACATCAAATTCGTTT |
| | | | GATGTACTGAAGTCAGAGGACGCGCAGGGAATGGATA |
| | | | ATCTTGCCTGCGAAGATCTAAAACCAGTCTCTGAAGA |
| | | | AGTAGTGGAAAATCCTACCATACAGAAAGACGTTCTT |
| | | | GAGTGTAATGTGAAAACTACCGAAGTTGTAGGAGACA |
| | | | TTATACTTAAACCAGCAAATAATAGTTTAAAAATTAC |
| | | | AGAAGAGGTTGGCCACACAGATCTAATGGCTGCTTAT |
| | | | GTAGACAATTCTAGTCTTACTATTAAGAAACCTAATGA |

TABLE 5-continued

SARS-CoV2 gene sequences

| Gene | Start | End | Sequence |
|---|---|---|---|
| | | | ATTATCTAGAGTATTAGGTTTGAAAACCCTTGCTACTC |
| | | | ATGGTTTAGCTGCTGTTAATAGTGTCCCTTGGGATACT |
| | | | ATAGCTAATTATGCTAAGCCTTTTCTTAACAAAGTTGT |
| | | | TAGTACAACTACTAACATAGTTACACGGTGTTTAAACC |
| | | | GTGTTTGTACTAATTATATGCCTTATTTCTTTACTTTA |
| | | | TTGCTACAATTGTGTACTTTTACTAGAAGTACAAATTC |
| | | | TAGAATTAAAGCATCTATGCCGACTACTATAGCAAAGA |
| | | | ATACTGTTAAGAGTGTCGGTAAATTTTGTCTAGAGGCT |
| | | | TCATTTAATTATTTGAAGTCACCTAATTTTTCTAAACT |
| | | | GATAAATATTATAATTTGGTTTTTACTATTAAGTGTTT |
| | | | GCCTAGGTTCTTTAATCTACTCAACCGCTGCTTTAGGT |
| | | | GTTTTAATGTCTAATTTAGGCATGCCTTCTTACTGTAC |
| | | | TGGTTACAGAGAAGGCTATTTGAACTCTACTAATGTCA |
| | | | CTATTGCAACCTACTGTACTGGTTCTATACCTTGTAGT |
| | | | GTTTGTCTTAGTGGTTTAGATTCTTTAGACACCTATCC |
| | | | TTCTTTAGAAACTATACAAATTACCATTTCATCTTTTA |
| | | | AATGGGATTTAACTGCTTTTGGCTTAGTTGCAGAGTGG |
| | | | TTTTTGGCATATATTCTTTTCACTAGGTTTTTCTATGT |
| | | | ACTTGGATTGGCTGCAATCATGCAATTGTTTTTCAGCT |
| | | | ATTTTGCAGTACATTTTATTAGTAATTCTTGGCTTAT |
| | | | GTGGTTAATAATTAATCTTGTACAAATGGCCCCGATTT |
| | | | CAGCTATGGTTAGAATGTACATCTTCTTTGCATCATT |
| | | | TTATTATGTATGGAAAAGTTATGTGCATGTTGTAGACG |
| | | | GTTGTAATTCATCAACTTGTATGATGTGTTACAAACGT |
| | | | AATAGAGCAACAAGAGTCGAATGTACAACTATTGTTAA |
| | | | TGGTGTTAGAAGGTCCTTTTATGTCTATGCTAATGGAG |
| | | | GTAAAGGCTTTTGCAAACTACACAATTGGAATTGTGTT |
| | | | AATTGTGATACATTCTGTGCTGGTAGTACATTTATTAG |
| | | | TGATGAAGTTGCGAGAGACTTGTCACTACAGTTTAAA |
| | | | AGACCAATAAATCCTACTGACCAGTCTTCTTACATCGT |
| | | | TGATAGTGTTACAGTGAAGAATGGTTCCATCCATCTTT |
| | | | ACTTTGATAAAGCTGGTCAAAAGACTTATGAAAGACATTC |
| | | | TCTCTCTCATTTTGTTAACTTAGACAACCTGAGAGCTAA |
| | | | TAACACTAAAGGTTCATTGCCTATTAATGTTATAGTTT |
| | | | TTGATGGTAAATCAAAATGTGAAGAATCATCTGCAAA |
| | | | ATCAGCGTCTGTTTACTACAGTCAGCTTATGTGTCAAC |
| | | | CTATACTGTTACTAGATCAGGCATTAGTGTCTGATGTT |
| | | | GGTGATAGTGCGGAAGTTGCAGTTAAAATGTTTGATG |
| | | | CTTACGTTAATACGTTTTCATCAACTTTTAACGTACCA |
| | | | ATGGAAAAACTCAAAACACTAGTTGCAACTGCAGAAG |
| | | | CTGAACTTGCAAAGAATGTGTCCTTAGACAATGTCTTA |
| | | | TCTACTTTTATTTCAGCAGCTCGGCAAGGGTTTGTTGA |
| | | | TTCAGATGTAGAAACTAAAGATGTTGTTGAATGTCTTA |
| | | | AATTGTCACATCAATCTGACATAGAAGTTACTGGCGA |
| | | | TAGTTGTAATAACTATATGCTCACCTATAACAAAGTTG |
| | | | AAAACATGACACCCCGTGACCTTGGTGCTTGTATTGAC |
| | | | TGTAGTGCGCGTCATATTAATGCGCAGGTAGCAAAAA |
| | | | GTCACAACATTGCTTTGATATGGAACGTTAAAGATTTC |
| | | | ATGTCATTGTCTGAACAACTACGAAAACAAATACGTA |
| | | | GTGCTGCTAAAAAGAATAACTTACCTTTTAAGTTGACA |
| | | | TGTGCAACTACTAGACAAGTTGTTAATGTTGTAACAAC |
| | | | AAAGATAGCACTTAAGGGTGGTAAAATTGTTAATAAT |
| | | | TGGTTGAAGCAGTTAATTAAAGTTACACTTGTGTTCCT |
| | | | TTTTGTTGCTGCTATTTTCTATTTAATAACACCTGTTCA |
| | | | TGTCATGTCTAAACATACTGACTTTTCAAGTGAAATCA |
| | | | TAGGATACAAGGCTATTGATGGTGGTGTCACTCGTGA |
| | | | CATAGCATCTACAGATACTTGTTTTGCTAACAAACATG |
| | | | CTGATTTTGACACATGGTTTAGCCAGCGTGGTGGTAGT |
| | | | TATACTAATGACAAAGCTTGCCCATTGATTGCTGCAGT |
| | | | CATAACAAGAGAAGTGGGTTTTGTCGTGCCTGGTTTGC |
| | | | CTGGCACGATATTACGCACAACTAATGGTGACTTTTTG |
| | | | CATTTCTTACCTAGAGTTTTTAGTGCAGTTGGTAACAT |
| | | | CTGTTACACACCATCAAAACTTATAGAGTACACTGACT |
| | | | TTGCAACATCAGCTTGTGTTTTGGCTGCTGAATGTACA |
| | | | ATTTTTAAAGATGCTTCTGGTAAGCCAGTACCATATTG |
| | | | TTATGATACCAATGTACTAGAAGGTTCTGTTGCTTATG |
| | | | AAAGTTTACGCCCTGACACACGTTATGTGCTCATGGAT |
| | | | GGCTCTATTATTCAATTTCCTAACACCTACCTTGAAGG |
| | | | TTCTGTTAGAGTGGTAACAACTTTTGATTCTGAGTACT |
| | | | GTAGGCACGGCACTTGTGAAAGATCAGAAGCTGGTGT |
| | | | TTGTGTATCTACTAGTGGTAGATGGGTACTTAACAATG |
| | | | ATTATTACAGATCTTTACCAGGAGTTTTCTGTGGTGTA |
| | | | GATGCTGTAAATTTACTTACTAATATGTTTACACCACT |
| | | | AATTCAACCTATTGGTGCTTTGGACATATCAGCATCTA |
| | | | TAGTAGCTGGTGGTATTGTAGCTATCGTAGTAACATGC |
| | | | CTTGCCTACTATTTTATGAGGTTTAGAAGAGCTTTTGG |

TABLE 5-continued

| SARS-CoV2 gene sequences | | | |
|---|---|---|---|
| Gene | Start | End | Sequence |
| | | | TGAATACAGTCATGTAGTTGCCTTTAATACTTTACTAT TCCTTATGTCATTCACTGTACTCTGTTTAACACCAGTTT ACTCATTCTTACCTGGTGTTTATTCTGTTATTTACTTGT ACTTGACATTTTATCTTACTAATGATGTTTCTTTTTTAG CACATATTCAGTGGATGGTTATGTTCACACCTTTAGTA CCTTTCTGGATAACAATTGCTTATATCATTTGTATTTCC ACAAAGCATTTCTATTGGTTCTTTAGTAATTACCTAAA GAGACGTGTAGTCTTTAATGGTGTTTCCTTTAGTACTT TTGAAGAAGCTGCGCTGTGCACCTTTTTGTTAAATAAA GAAATGTATCTAAAGTTGCGTAGTGATGTGCTATTACC TCTTACGCAATATAATAGATACTTAGCTCTTTATAATA AGTACAAGTATTTTAGTGGAGCAATGGATACAACTAG CTACAGAGAAGCTGCTTGTTGTCATCTCGCAAAGGCTC TCAATGACTTCAGTAACTCAGGTTCTGATGTTCTTTAC CAACCACCACAAACCTCTATCACCTCAGCTGTTTTGCA GAGTGGTTTTAGAAAAATGGCATTCCCATCTGGTAAA GTTGAGGGTTGTATGGTACAAGTAACTTGTGGTACAA CTACACTTAACGGTCTTTGGCTTGATGACGTAGTTTAC TGTCCAAGACATGTGATCTGCACCTCTGAAGACATGCT TAACCCTAATTATGAAGATTTACTCATTCGTAAGTCTA ATCATAATTTCTTGGTACAGGCTGGTAATGTTCAACTC AGGGTTATTGGACATTCTATGCAAAATTGTGTACTTAA GCTTAAGGTTGATACAGCCAATCCTAAGACACCTAAG TATAAGTTTGTTCGCATTCAACCAGGACAGACTTTTTC AGTGTTAGCTTGTTACAATGGTTCACCATCTGGTGTTT ACCAATGTGCTATGAGGCCCAATTTCACTATTAAGGGT TCATTCCTTAATGGTTCATGTGGTAGTGTTGGTTTTAA CATAGATTATGACTGTGTCTCTTTTTGTTACATGCACC ATATGGAATTACCAACTGGAGTTCATGCTGGCACAGA CTTAGAAGGTAACTTTTATGGACCTTTTGTTGACAGGC AAACAGCACAAGCAGCTGGTACGGACACAACTATTAC AGTTAATGTTTTAGCTTGGTTGTACGCTGCTGTTATAA ATGGAGACAGGTGGTTTCTCAATCGATTTACCACAACT CTTAATGACTTTAACCTTGTGGCTATGAAGTACAATTA TGAACCTCTAACACAAGACCATGTTGACATACTAGGA CCTCTTTCTGCTCAAACTGGAATTGCCGTTTTAGATAT GTGTGCTTCATTAAAAGAATTACTGCAAAATGGTATG AATGGACGTACCATATTGGGTAGTGCTTTATTAGAAG ATGAATTTACACCTTTTGATGTTGTTAGACAATGCTCA GGTGTTACTTTCCAAAGTGCAGTGAAAAGAACAATCA AGGGTACACACCACTGGTTGTTACTCACAATTTTGACT TCACTTTTAGTTTTAGTCCAGAGTACTCAATGGTCTTT GTTCTTTTTTTTGTATGAAAATGCCTTTTTACCTTTTGC TATGGGTATTATTGCTATGTCTGCTTTTGCAATGATGT TTGTCAAACATAAGCATGCATTTCTCTGTTTGTTTTTGT TACCTTCTCTTGCCACTGTAGCTTATTTTAATATGGTCT ATATGCCTGCTAGTTGGGTGATGCGTATTATGACATGG TTGGATATGGTTGATACTAGTTTGTCTGGTTTTAAGCT AAAAGACTGTGTTATGTATGCATCAGCTGTAGTGTTAC TAATCCTTATGACAGCAAGAACTGTGTATGATGATGG TGCTAGGAGAGTGTGGACACTTATGAATGTCTTGACA CTCGTTTATAAAGTTTATTATGGTAATGCTTTAGATCA AGCCATTTCCATGTGGGCTCTTATAATCTCTGTTACTT CTAACTACTCAGGTGTAGTTACAACTGTCATGTTTTTG GCCAGAGGTATTGTTTTTATGTGTGTTGAGTATTGCCC TATTTTCTTCATAACTGGTAATACACTTCAGTGTATAA TGCTAGTTTATTGTTTCTTAGGCTATTTTTGTACTTGTT ACTTTGGCCTCTTTTGTTTACTCAACCGCTACTTTAGAC TGACTCTTGGTGTTTATGATTACTTAGTTTCTACACAG GAGTTTAGATATATGAATTCACAGGGACTACTCCCAC CCAAGAATAGCATAGATGCCTTCAAACTCAACATTAA ATTGTTGGGTGTTGGTGGCAAACCTTGTATCAAAGTAG CCACTGTACAGTCTAAAATGTCAGATGTAAAGTGCAC ATCAGTAGTCTTACTCTCAGTTTTGCAACAACTCAGAG TAGAATCATCATCTAAATTGTGGGCTCAATGTGTCCAG TTACACAATGACATTCTCTTAGCTAAAGATACTACTGA AGCCTTTGAAAAAATGGTTTCACTACTTTCTGTTTTGC TTTCCATGCAGGGTGCTGTAGACATAAACAAGCTTTGT GAAGAAATGCTGGACAACAGGGCAACCTTACAAGCTA TAGCCTCAGAGTTTAGTTCCCTTCCATCATATGCAGCT TTTGCTACTGCTCAAGAAGCTTATGAGCAGGCTGTTGC TAATGGTGATTCTGAAGTTGTTCTTAAAAAGTTGAAGA AGTCTTTGAATGTGGCTAAATCTGAATTTGACCGTGAT GCAGCCATGCAACGTAAGTTGGAAAAGATGGCTGATC AAGCTATGACCCAAATGTATAAACAGGCTAGATCTGA GGACAAGAGGGCAAAAGTTACTAGTGCTATGCAGACA |

TABLE 5-continued

SARS-CoV2 gene sequences

| Gene | Start | End | Sequence |
|---|---|---|---|
| | | | ATGCTTTTCACTATGCTTAGAAAGTTGGATAATGATGC |
| | | | ACTCAACAACATTATCAACAATGCAAGAGATGGTTGT |
| | | | GTTCCCTTGAACATAATACCTCTTACAACAGCAGCCAA |
| | | | ACTAATGGTTGTCATACCAGACTATAACACATATAAA |
| | | | AATACGTGTGATGGTACAACATTTACTTATGCATCAGC |
| | | | ATTGTGGGAAATCCAACAGGTTGTAGATGCAGATAGT |
| | | | AAAATTGTTCAACTTAGTGAAATTAGTATGGACAATTC |
| | | | ACCTAATTTAGCATGGCCTCTTATTGTAACAGCTTTAA |
| | | | GGGCCAATTCTGCTGTCAAATTACAGAATAATGAGCT |
| | | | TAGTCCTGTTGCACTACGACAGATGTCTTGTGCTGCCG |
| | | | GTACTACACAAACTGCTTGCACTGATGACAATGCGTT |
| | | | AGCTTACTACAACACAACAAAGGGAGGTAGGTTTGTA |
| | | | CTTGCACTGTTATCCGATTTACAGGATTTGAAATGGGC |
| | | | TAGATTCCCTAAGAGTGATGGAACTGGTACTATCTATA |
| | | | CAGAACTGGAACCACCTTGTAGGTTTGTTACAGACAC |
| | | | ACCTAAAGGTCCTAAAGTGAAGTATTTATACTTTATTA |
| | | | AAGGATTAAACAACCTAAATAGAGGTATGGTACTTGG |
| | | | TAGTTTAGCTGCCACAGTACGTCTACAAGCTGGTAATG |
| | | | CAACAGAAGTGCCTGCCAATTCAACTGTATTATCTTTC |
| | | | TGTGCTTTTGCTGTAGATGCTGCTAAAGCTTACAAAGA |
| | | | TTATCTAGCTAGTGGGGGACAACCAATCACTAATTGT |
| | | | GTTAAGATGTTGTGTACACACACTGGTACTGGTCAGG |
| | | | CAATAACAGTTACACCGGAAGCCAATATGGATCAAGA |
| | | | ATCCTTTGGTGGTGCATCGTGTTGTCTGTACTGCCGTT |
| | | | GCCACATAGATCATCCAAATCCTAAAGGATTTTGTGA |
| | | | CTTAAAAGGTAAGTATGTACAAATACCTACAACTTGT |
| | | | GCTAATGACCCTGTGGGTTTTACACTTAAAAACACAGT |
| | | | CTGTACCGTCTGCGGTATGTGGAAAGGTTATGGCTGTA |
| | | | GTTGTGATCAACTCCGCGAACCCATGCTTCAGTCAGCT |
| | | | GATGCACAATCGTTTTTAAACGGGTTTGCGGTGTA |
| orf1ab (SEQ ID NO: 3) | 266 | 21555 | ATGGAGAGCCTTGTCCCTGGTTTCAACGAGAAAACAC |
| | | | ACGTCCAACTCAGTTTGCCTGTTTTACAGGTTCGCGAC |
| | | | GTGCTCGTACGTGGCTTTGGAGACTCCGTGGAGGAGG |
| | | | TCTTATCAGAGGCACGTCAACATCTTAAAGATGGCAC |
| | | | TTGTGGCTTAGTAGAAGTTGAAAAAGGCGTTTTGCCTC |
| | | | AACTTGAACAGCCCTATGTGTTCATCAAACGTTCGGAT |
| | | | GCTCGAACTGCACCTCATGGTCATGTTATGGTTGAGCT |
| | | | GGTAGCAGAACTCGAAGGCATTCAGTACGGTCGTAGT |
| | | | GGTGAGACACTTGGTGTCCTTGTCCCTCATGTGGGCGA |
| | | | AATACCAGTGGCTTACCGCAAGGTTCTTCTTCGTAAGA |
| | | | ACGGTAATAAAGGAGCTGGTGGCCATAGTTACGGCGC |
| | | | CGATCTAAAGTCATTTGACTTAGGCGACGAGCTTGGC |
| | | | ACTGATCCTTATGAAGATTTTCAAGAAAACTGGAACA |
| | | | CTAAACATAGCAGTGGTGTTACCCGTGAACTCATGCG |
| | | | TGAGCTTAACGGAGGGGCATACACTCGCTATGTCGAT |
| | | | AACAACTTCTGTGGCCCTGATGGCTACCCTCTTGAGTG |
| | | | CATTAAAGACCTTCTAGCACGTGCTGGTAAAGCTTCAT |
| | | | GCACTTTGTCCGAACAACTGGACTTTATTGACACTAAG |
| | | | AGGGGTGTATACTGCTGCCGTGAACATGAGCATGAAA |
| | | | TTGCTTGGTACACGGAACGTTCTGAAAAGAGCTATGA |
| | | | ATTGCAGACACCTTTTGAAATTAAATTGGCAAAGAAA |
| | | | TTTGACACCTTCAATGGGGAATGTCCAAATTTTGTATT |
| | | | TCCCTTAAATTCCATAATCAAGACTATTCAACCAAGGG |
| | | | TTGAAAAGAAAAAGCTTGATGGCTTTATGGGTAGAAT |
| | | | TCGATCTGTCTATCCAGTTGCGTCACCAAATGAATGCA |
| | | | ACCAAATGTGCCTTTCAACTCTCATGAAGTGTGATCAT |
| | | | TGTGGTGAAACTTCATGGCAGACGGGCGATTTTGTTA |
| | | | AAGCCACTTGCGAATTTTGTGGCACTGAGAATTTGACT |
| | | | AAAGAAGGTGCCACTACTTGTGGTTACTTACCCCAAA |
| | | | ATGCTGTTGTTAAAATTTATTGTCCAGCATGTCACAAT |
| | | | TCAGAAGTAGGACCTGAGCATAGTCTTGCCGAATACC |
| | | | ATAATGAATCTGGCTTGAAAACCATTCTTCGTAAGGGT |
| | | | GGTCGCACTATTGCCTTTGGAGGCTGTGTGTTCTCTTA |
| | | | TGTTGGTTGCCATAACAAGTGTGCCTATTGGGTTCCAC |
| | | | GTGCTAGCGCTAACATAGGTTGTAACCATACAGGTGT |
| | | | TGTTGGAGAAGGTTCCGAAGGTCTTAATGACAACCTT |
| | | | CTTGAAATACTCCAAAAAGAGAAAGTCAACATCAATA |
| | | | TTGTTGGTGACTTTAAACTTAATGAAGAGATCGCCATT |
| | | | ATTTTGGCATCTTTTTCTGCTTCCACAAGTGCTTTTGTG |
| | | | GAAACTGTGAAAGGTTTGGATTATAAAGCATTCAAAC |
| | | | AAATTGTTGAATCCTGTGGTAATTTTAAAGTTACAAAA |
| | | | GGAAAAGCTAAAAAAGGTGCCTGGAATATTGGTGAAC |
| | | | AGAAATCAATACTGAGTCCTCTTTATGCATTTGCATCA |
| | | | GAGGCTGCTCGTGTTGTACGATCAATTTTCTCCCGCAC |
| | | | TCTTGAAACTGCTCAAAATTCTGTGCGTGTTTTACAGA |

TABLE 5-continued

SARS-CoV2 gene sequences

| Gene | Start | End | Sequence |
|---|---|---|---|
| | | | AGGCCGCTATAACAATACTAGATGGAATTTCACAGTA |
| | | | TTCACTGAGACTCATTGATGCTATGATGTTCACATCTG |
| | | | ATTTGGCTACTAACAATCTAGTTGTAATGGCCTACATT |
| | | | ACAGGTGGTGTTGTTCAGTTGACTTCGCAGTGGCTAAC |
| | | | TAACATCTTTGGCACTGTTTATGAAAAACTCAAACCCG |
| | | | TCCTTGATTGGCTTGAAGAGAAGTTTAAGGAAGGTGT |
| | | | AGAGTTTCTTAGAGACGGTTGGGAAATTGTTAAATTTA |
| | | | TCTCAACCTGTGCTTGTGAAATTGTCGGTGGACAAATT |
| | | | GTCACCTGTGCAAAGGAAATTAAGGAGAGTGTTCAGA |
| | | | CATTCTTTAAGCTTGTAAATAAATTTTTGGCTTTGTGT |
| | | | GCTGACTCTATCATTATTGGTGGAGCTAAACTTAAAGC |
| | | | CTTGAATTTAGGTGAAACATTTGTCACGCACTCAAAG |
| | | | GGATTGTACAGAAAGTGTGTTAAATCCAGAGAAGAAA |
| | | | CTGGCCTACTCATGCCTCTAAAAGCCCCAAAAGAAAT |
| | | | TATCTTCTTAGAGGGAGAAACACTTCCCACAGAAGTG |
| | | | TTAACAGAGGAAGTTGTCTTGAAAACTGGTGATTTAC |
| | | | AACCATTAGAACAACCTACTAGTGAAGCTGTTGAAGC |
| | | | TCCATTGGTTGGTACACCAGTTTGTATTAACGGGCTTA |
| | | | TGTTGCTCGAAATCAAAGACACAGAAAAGTACTGTGC |
| | | | CCTTGCACCTAATATGATGGTAACAAACAATACCTTCA |
| | | | CACTCAAAGGCGGTGCACCAACAAAGGTTACTTTTGG |
| | | | TGATGACACTGTGATAGAAGTGCAAGGTTACAAGAGT |
| | | | GTGAATATCACTTTTGAACTTGATGAAAGGATTGATA |
| | | | AAGTACTTAATGAGAAGTGCTCTGCCTATACAGTTGA |
| | | | ACTCGGTACAGAAGTAAATGAGTTCGCCTGTGTTGTG |
| | | | GCAGATGCTGTCATAAAAACTTTGCAACCAGTATCTG |
| | | | AATTACTTACACCACTGGGCATTGATTTAGATGAGTGG |
| | | | AGTATGGCTACATACTACTTATTTGATGAGTCTGGTGA |
| | | | GTTTAAATTGGCTTCACATATGTATTGTTCTTTCTACCC |
| | | | TCCAGATGAGGATGAAGAAGAAGGTGATTGTGAAGA |
| | | | AGAAGAGTTTGAGCCATCAACTCAATATGAGTATGGT |
| | | | ACTGAAGATGATTACCAAGGTAAACCTTTGGAATTTG |
| | | | GTGCCACTTCTGCTGCTCTTCAACCTGAAGAAGAGCA |
| | | | AGAAGAAGATTGGTTAGATGATGATAGTCAACAAACT |
| | | | GTTGGTCAACAAGACGGCAGTGAGGACAATCAGACAA |
| | | | CTACTATTCAAACAATTGTTGAGGTTCAACCTCAATTA |
| | | | GAGATGGAACTTACACCAGTTGTTCAGACTATTGAAG |
| | | | TGAATAGTTTTAGTGGTTATTTAAAACTTACTGACAAT |
| | | | GTATACATTAAAAATGCAGACATTGTGGAAGAAGCTA |
| | | | AAAAGGTAAAACCAACAGTGGTTGTTAATGCAGCCAA |
| | | | TGTTTACCTTAAACATGGAGGAGGTGTTGCAGGAGCC |
| | | | TTAAATAAGGCTACTAACAATGCCATGCAAGTTGAAT |
| | | | CTGATGATTACATAGCTACTAATGGACCACTTAAAGT |
| | | | GGGTGGTAGTTGTGTTTTAAGCGGACACAATCTTGCTA |
| | | | AACACTGTCTTCATGTTGTCGGCCCAAATGTTAACAAA |
| | | | GGTGAAGACATTCAACTTCTTAAGAGTGCTTATGAAA |
| | | | ATTTTAATCAGCACGAAGTTCTACTTGCACCATTATTA |
| | | | TCAGCTGGTATTTTTGGTGCTGACCCTATACATTCTTT |
| | | | AAGAGTTTGTGTAGATACTGTTCGCACAAATGTCTACT |
| | | | TAGCTGTCTTTGATAAAAATCTCTATGACAAACTTGTT |
| | | | TCAAGCTTTTTGGAAATGAAGAGTGAAAAGCAAGTTG |
| | | | AACAAAAGATCGCTGAGATTCCTAAAGAGGAAGTTAA |
| | | | GCCATTTATAACTGAAAGTAAACCTTCAGTTGAACAG |
| | | | AGAAAACAAGATGATAAGAAAATCAAAGCTTGTGTTG |
| | | | AAGAAGTTACAACAACTCTGGAAGAAACTAAGTTCCT |
| | | | CACAGAAAACTTGTTACTTTATATTGACATTAATGGCA |
| | | | ATCTTCATCCAGATTCTGCCACTCTTGTTAGTGACATT |
| | | | GACATCACTTTCTTAAAGAAAGATGCTCCATATATAGT |
| | | | GGGTGATGTTGTTCAAGAGGGTGTTTTAACTGCTGTGG |
| | | | TTATACCTACTAAAAAGGCTGGTGGCACTACTGAAAT |
| | | | GCTAGCGAAAGCTTTGAGAAAAGTGCCAACAGACAAT |
| | | | TATATAACCACTTACCCGGGTCAGGGTTTAAATGGTTA |
| | | | CACTGTAGAGGAGGCAAAGACAGTGCTTAAAAAGTGT |
| | | | AAAAGTGCCTTTTACATTCTACCATCTATTATCTCTAA |
| | | | TGAGAAGCAAGAAATTCTTGGAACTGTTTCTTGGAATT |
| | | | TGCGAGAAATGCTTGCACATGCAGAAGAAACACGCAA |
| | | | ATTAATGCCTGTCTGTGTGGAAACTAAAGCCATAGTTT |
| | | | CAACTATACAGCGTAAATATAAGGGTATTAAAATACA |
| | | | AGAGGGTGTGGTTGATTATGGTGCTAGATTTTACTTTT |
| | | | ACACCAGTAAAACAACTGTAGCGTCACTTATCAACAC |
| | | | ACTTAACGATCTAAATGAAACTCTTGTTACAATGCCAC |
| | | | TTGGCTATGTAACACATGGCTTAAATTTGGAAGAAGC |
| | | | TGCTCGGTATATGAGATCTCTCAAAGTGCCAGCTACA |
| | | | GTTTCTGTTTCTTCACCTGATGCTGTTACAGCGTATAA |
| | | | TGGTTATCTTACTTCTTCTTCTAAAACACCTGAAGAAC |
| | | | ATTTTATTGAAACCATCTCACTTGCTGGTTCCTATAAA |

TABLE 5-continued

SARS-CoV2 gene sequences

| Gene | Start | End | Sequence |
|---|---|---|---|
| | | | GATTGGTCCTATTCTGGACAATCTACACAACTAGGTAT |
| | | | AGAATTTCTTAAGAGAGGTGATAAAAGTGTATATTAC |
| | | | ACTAGTAATCCTACCACATTCCACCTAGATGGTGAAGT |
| | | | TATCACCTTTGACAATCTTAAGACACTTCTTTCTTTGA |
| | | | GAGAAGTGAGGACTATTAAGGTGTTTACAACAGTAGA |
| | | | CAACATTAACCTCCACACGCAAGTTGTGGACATGTCA |
| | | | ATGACATATGGACAACAGTTTGGTCCAACTTATTTGGA |
| | | | TGGAGCTGATGTTACTAAAATAAAACCTCATAATTCA |
| | | | CATGAAGGTAAAACATTTTATGTTTTACCTAATGATGA |
| | | | CACTCTACGTGTTGAGGCTTTTGAGTACTACCACACAA |
| | | | CTGATCCTAGTTTTCTGGGTAGGTACATGTCAGCATTA |
| | | | AATCACACTAAAAAGTGGAAATACCCACAAGTTAATG |
| | | | GTTTAACTTCTATTAAATGGGCAGATAACAACTGTTAT |
| | | | CTTGCCACTGCATTGTTAACACTCCAACAAATAGAGTT |
| | | | GAAGTTTAATCCACCTGCTCTACAAGATGCTTATTACA |
| | | | GAGCAAGGGCTGGTGAAGCTGCTAACTTTTGTGCACT |
| | | | TATCTTAGCCTACTGTAATAAGACAGTAGGTGAGTTA |
| | | | GGTGATGTTAGAGAAACAATGAGTTACTTGTTTCAAC |
| | | | ATGCCAATTTAGATTCTTGCAAAAGAGTCTTGAACGTG |
| | | | GTGTGTAAAACTTGTGGACAACAGCAGACAACCCTTA |
| | | | AGGGTGTAGAAGCTGTTATGTACATGGGCACACTTTCT |
| | | | TATGAACAATTTAAGAAAGGTGTTCAGATACCTTGTA |
| | | | CGTGTGGTAAACAAGCTACAAAATATCTAGTACAACA |
| | | | GGAGTCACCTTTTGTTATGATGTCAGCACCACCTGCTC |
| | | | AGTATGAACTTAAGCATGGTACATTTACTTGTGCTAGT |
| | | | GAGTACACTGGTAATTACCAGTGTGGTCACTATAAAC |
| | | | ATATAACTTCTAAAGAAACTTTGTATTGCATAGACGGT |
| | | | GCTTTACTTACAAAGTCCTCAGAATACAAAGGTCCTAT |
| | | | TACGGATGTTTTCTACAAAGAAAACAGTTACACAACA |
| | | | ACCATAAAACCAGTTACTTATAAATTGGATGGTGTTGT |
| | | | TTGTACAGAAATTGACCCTAAGTTGGACAATTATTATA |
| | | | AGAAAGACAATTCTTATTTCACAGAGCAACCAATTGA |
| | | | TCTTGTACCAAACCAACCATATCCAAACGCAAGCTTC |
| | | | GATAATTTTAAGTTTGTATGTGATAATATCAAATTTGC |
| | | | TGATGATTTAAACCAGTTAACTGGTTATAAGAAACCT |
| | | | GCTTCAAGAGAGCTTAAAGTTACATTTTTCCCTGACTT |
| | | | AAATGGTGATGTGGTGGCTATTGATTATAAACACTAC |
| | | | ACACCCTCTTTTAAGAAAGGAGCTAAATTGTTACATA |
| | | | AACCTATTGTTTGGCATGTTAACAATGCAACTAATAAA |
| | | | GCCACGTATAAACCAAATACCTGGTGTATACGTTGTCT |
| | | | TTGGAGCACAAAACCAGTTGAAACATCAAATTCGTTT |
| | | | GATGTACTGAAGTCAGAGGACGCGCAGGGAATGGATA |
| | | | ATCTTGCCTGCGAAGATCTAAAACCAGTCTCTGAAGA |
| | | | AGTAGTGGAAAATCCTACCATACAGAAAGACGTTCTT |
| | | | GAGTGTAATGTGAAAACTACCGAAGTTGTAGGAGACA |
| | | | TTATACTTAAACCAGCAAATAATAGTTTAAAAATTAC |
| | | | AGAAGAGGTTGGCCACACAGATCTAATGGCTGCTTAT |
| | | | GTAGACAATTCTAGTCTTACTATTAAGAAACCTAATGA |
| | | | ATTATCTAGAGTATTAGGTTTGAAAACCCTTGCTACTC |
| | | | ATGGTTTAGCTGCTGTTAATAGTGTCCCTTGGGATACT |
| | | | ATAGCTAATTATGCTAAGCCTTTTCTTAACAAAGTTGT |
| | | | TAGTACAACTACTAACATAGTTACACGGTGTTTAAACC |
| | | | GTGTTTGTACTAATTATATGCCTTATTTCTTTACTTTAT |
| | | | TGCTACAATTGTGTACTTTTACTAGAAGTACAAATTCT |
| | | | AGAATTAAAGCATCTATGCCGACTACTATAGCAAAGA |
| | | | ATACTGTTAAGAGTGTCGGTAAATTTTGTCTAGAGGCT |
| | | | TCATTTAATTATTTGAAGTCACCTAATTTTTCTAAACT |
| | | | GATAAATATTATAATTTGGTTTTTACTATTAAGTGTTT |
| | | | GCCTAGGTTCTTTAATCTACTCAACCGCTGCTTTAGGT |
| | | | GTTTTAATGTCTAATTTAGGCATGCCTTCTTACTGTACT |
| | | | GGTTACAGAGAAGGCTATTTGAACTCTACTAATGTCA |
| | | | CTATTGCAACCTACTGTACTGGTTCTATACCTTGTAGT |
| | | | GTTTGTCTTAGTGGTTTAGATTCTTTAGACACCTATCCT |
| | | | TCTTTAGAAACTATACAAATTACCATTTCATCTTTTAA |
| | | | ATGGGATTTAACTGCTTTTGGCTTAGTTGCAGAGTGGT |
| | | | TTTTGGCATATATTCTTTTCACTAGGTTTTTCTATGTAC |
| | | | TTGGATTGGCTGCAATCATGCAATTGTTTTTCAGCTAT |
| | | | TTTGCAGTACATTTTATTAGTAATTCTTGGCTTATGTG |
| | | | GTTAATAATTAATCTTGTACAAATGGCCCCGATTTCAG |
| | | | CTATGGTTAGAATGTACATCTTCTTTGCATCATTTTATT |
| | | | ATGTATGGAAAAGTTATGTGCATGTTGTAGACGGTTGT |
| | | | AATTCATCAACTTGTATGATGTGTTACAAACGTAATAG |
| | | | AGCAACAAGAGTCGAATGTACAACTATTGTTAATGGT |
| | | | GTTAGAAGGTCCTTTTATGTCTATGCTAATGGAGGTAA |
| | | | AGGCTTTTGCAAACTACACAATTGGAATTGTGTTAATT |
| | | | GTGATACATTCTGTGCTGGTAGTACATTTATTAGTGAT |

TABLE 5-continued

SARS-CoV2 gene sequences

| Gene | Start | End | Sequence |
|---|---|---|---|
| | | | GAAGTTGCGAGAGACTTGTCACTACAGTTTAAAAGAC<br>CAATAAATCCTACTGACCAGTCTTCTTACATCGTTGAT<br>AGTGTTACAGTGAAGAATGGTTCCATCCATCTTTACTT<br>TGATAAAGCTGGTCAAAAGACTTATGAAAGACATTCT<br>CTCTCTCATTTTGTTAACTTAGACAACCTGAGAGCTAA<br>TAACACTAAAGGTTCATTGCCTATTAATGTTATAGTTT<br>TTGATGGTAAATCAAAATGTGAAGAATCATCTGCAAA<br>ATCAGCGTCTGTTTACTACAGTCAGCTTATGTGTCAAC<br>CTATACTGTTACTAGATCAGGCATTAGTGTCTGATGTT<br>GGTGATAGTGCGGAAGTTGCAGTTAAAATGTTTGATG<br>CTTACGTTAATACGTTTTCATCAACTTTTAACGTACCA<br>ATGGAAAAACTCAAAACACTAGTTGCAACTGCAGAAG<br>CTGAACTTGCAAAGAATGTGTCCTTAGACAATGTCTTA<br>TCTACTTTTATTTCAGCAGCTCGGCAAGGGTTTGTTGA<br>TTCAGATGTAGAAACTAAAGATGTTGTTGAATGTCTTA<br>AATTGTCACATCAATCTGACATAGAAGTTACTGGCGA<br>TAGTTGTAATAACTATATGCTCACCTATAACAAAGTTG<br>AAAACATGACACCCCGTGACCTTGGTGCTTGTATTGAC<br>TGTAGTGCGCGTCATATTAATGCGCAGGTAGCAAAAA<br>GTCACAACATTGCTTTGATATGGAACGTTAAAGATTTC<br>ATGTCATTGTCTGAACAACTACGAAAACAAATACGTA<br>GTGCTGCTAAAAAGAATAACTTACCTTTTAAGTTGACA<br>TGTGCAACTACTAGACAAGTTGTTAATGTTGTAACAAC<br>AAAGATAGCACTTAAGGGTGGTAAAATTGTTAATAAT<br>TGGTTGAAGCAGTTAATTAAAGTTACACTTGTGTTCCT<br>TTTTGTTGCTGCTATTTTCTATTTAATAACACCTGTTCA<br>TGTCATGTCTAAACATACTGACTTTTCAAGTGAAATCA<br>TAGGATACAAGGCTATTGATGGTGGTGTCACTCGTGA<br>CATAGCATCTACAGATACTTGTTTTGCTAACAAACATG<br>CTGATTTTGACACATGGTTTAGCCAGCGTGGTGGTAGT<br>TATACTAATGACAAAGCTTGCCCATTGATTGCTGCAGT<br>CATAACAAGAGAAGTGGGTTTTGTCGTGCCTGGTTTGC<br>CTGGCACGATATTACGCACAACTAATGGTGACTTTTTG<br>CATTTCTTACCTAGAGTTTTTAGTGCAGTTGGTAACAT<br>CTGTTACACACCATCAAAACTTATAGAGTACACTGACT<br>TTGCAACATCAGCTTGTGTTTTGGCTGCTGAATGTACA<br>ATTTTTAAAGATGCTTCTGGTAAGCCAGTACCATATTG<br>TTATGATACCAATGTACTAGAAGGTTCTGTTGCTTATG<br>AAAGTTTACGCCCTGACACACGTTATGTGCTCATGGAT<br>GGCTCTATTATTCAATTTCCTAACACCTACCTTGAAGG<br>TTCTGTTAGAGTGGTAACAACTTTTGATTCTGAGTACT<br>GTAGGCACGGCACTTGTGAAAGATCAGAAGCTGGTGT<br>TTGTGTATCTACTAGTGGTAGATGGGTACTTAACAATG<br>ATTATTACAGATCTTTACCAGGAGTTTTCTGTGGTGTA<br>GATGCTGTAAATTTACTTACTAATATGTTTACACCACT<br>AATTCAACCTATTGGTGCTTTGGACATATCAGCATCTA<br>TAGTAGCTGGTGGTATTGTAGCTATCGTAGTAACATGC<br>CTTGCCTACTATTTTATGAGGTTTAGAAGAGCTTTTGG<br>TGAATACAGTCATGTAGTTGCCTTTAATACTTTACTAT<br>TCCTTATGTCATTCACTGTACTCTGTTTAACACCAGTTT<br>ACTCATTCTTACCTGGTGTTTATTCTGTTATTTACTTGT<br>ACTTGACATTTTATCTTACTAATGATGTTTCTTTTTTAG<br>CACATATTCAGTGGATGGTTATGTTCACACCTTTAGTA<br>CCTTTCTGGATAACAATTGCTTATATCATTTGTATTTCC<br>ACAAAGCATTTCTATTGGTTCTTTAGTAATTACCTAAA<br>GAGACGTGTAGTCTTTAATGGTGTTTCCTTTAGTACTT<br>TTGAAGAAGCTGCGCTGTGCACCTTTTTGTTAAATAAA<br>GAAATGTATCTAAAGTTGCGTAGTGATGTGCTATTACC<br>TCTTACGCAATATAATAGATACTTAGCTCTTTATAATA<br>AGTACAAGTATTTTAGTGGAGCAATGGATACAACTAG<br>CTACAGAGAAGCTGCTTGTTGTCATCTCGCAAAGGCTC<br>TCAATGACTTCAGTAACTCAGGTTCTGATGTTCTTTAC<br>CAACCACCACAAACCTCTATCACCTCAGCTGTTTTGCA<br>GAGTGGTTTTAGAAAAATGGCATTCCCATCTGGTAAA<br>GTTGAGGGTTGTATGGTACAAGTAACTTGTGGTACAA<br>CTACACTTAACGGTCTTTGGCTTGATGACGTAGTTTAC<br>TGTCCAAGACATGTGATCTGCACCTCTGAAGACATGCT<br>TAACCCTAATTATGAAGATTTACTCATTCGTAAGTCTA<br>ATCATAATTTCTTGGTACAGGCTGGTAATGTTCAACTC<br>AGGGTTATTGGACATTCTATGCAAAATTGTGTACTTAA<br>GCTTAAGGTTGATACAGCCAATCCTAAGACACCTAAG<br>TATAAGTTTGTTCGCATTCAACCAGGACAGACTTTTTC<br>AGTGTTAGCTTGTTACAATGGTTCACCATCTGGTGTTT<br>ACCAATGTGCTATGAGGCCCAATTTCACTATTAAGGGT<br>TCATTCCTTAATGGTTCATGTGGTAGTGTTGGTTTTAA<br>CATAGATTATGACTGTGTCTCTTTTTGTTACATGCACC |

TABLE 5-continued

SARS-CoV2 gene sequences

| Gene | Start | End | Sequence |
|---|---|---|---|
| | | | ATATGGAATTACCAACTGGAGTTCATGCTGGCACAGA |
| | | | CTTAGAAGGTAACTTTTATGGACCTTTTGTTGACAGGC |
| | | | AAACAGCACAAGCAGCTGGTACGGACACAACTATTAC |
| | | | AGTTAATGTTTTAGCTTGGTTGTACGCTGCTGTTATAA |
| | | | ATGGAGACAGGTGGTTTCTCAATCGATTTACCACAACT |
| | | | CTTAATGACTTTAACCTTGTGGCTATGAAGTACAATTA |
| | | | TGAACCTCTAACACAAGACCATGTTGACATACTAGGA |
| | | | CCTCTTTCTGCTCAAACTGGAATTGCCGTTTTAGATAT |
| | | | GTGTGCTTCATTAAAAGAATTACTGCAAAATGGTATG |
| | | | AATGGACGTACCATATTGGGTAGTGCTTTATTAGAAG |
| | | | ATGAATTTACACCTTTTGATGTTGTTAGACAATGCTCA |
| | | | GGTGTTACTTTCCAAAGTGCAGTGAAAAGAACAATCA |
| | | | AGGGTACACACCACTGGTTGTTACTCACAATTTTGACT |
| | | | TCACTTTTAGTTTTAGTCCAGAGTACTCAATGGTCTTT |
| | | | GTTCTTTTTTTTGTATGAAAATGCCTTTTTACCTTTTGC |
| | | | TATGGGTATTATTGCTATGTCTGCTTTTGCAATGATGT |
| | | | TTGTCAAACATAAGCATGCATTTCTCTGTTTGTTTTTGT |
| | | | TACCTTCTCTTGCCACTGTAGCTTATTTTAATATGGTCT |
| | | | ATATGCCTGCTAGTTGGGTGATGCGTATTATGACATGG |
| | | | TTGGATATGGTTGATACTAGTTTGTCTGGTTTTAAGCT |
| | | | AAAAGACTGTGTTATGTATGCATCAGCTGTAGTGTTAC |
| | | | TAATCCTTATGACAGCAAGAACTGTGTATGATGATGG |
| | | | TGCTAGGAGAGTGTGGACACTTATGAATGTCTTGACA |
| | | | CTCGTTTATAAAGTTTATTATGGTAATGCTTTAGATCA |
| | | | AGCCATTTCCATGTGGGCTCTTATAATCTCTGTTACTT |
| | | | CTAACTACTCAGGTGTAGTTACAACTGTCATGTTTTTG |
| | | | GCCAGAGGTATTGTTTTTATGTGTGTTGAGTATTGCCC |
| | | | TATTTTCTTCATAACTGGTAATACACTTCAGTGTATAA |
| | | | TGCTAGTTTATTGTTTCTTAGGCTATTTTTGTACTTGTT |
| | | | ACTTTGGCCTCTTTTGTTTACTCAACCGCTACTTTAGAC |
| | | | TGACTCTTGGTGTTTATGATTACTTAGTTTCTACACAG |
| | | | GAGTTTAGATATATGAATTCACAGGGACTACTCCCAC |
| | | | CCAAGAATAGCATAGATGCCTTCAAACTCAACATTAA |
| | | | ATTGTTGGGTGTTGGTGGCAAACCTTGTATCAAAGTAG |
| | | | CCACTGTACAGTCTAAAATGTCAGATGTAAAGTGCAC |
| | | | ATCAGTAGTCTTACTCTCAGTTTTGCAACAACTCAGAG |
| | | | TAGAATCATCATCTAAATTGTGGGCTCAATGTGTCCAG |
| | | | TTACACAATGACATTCTCTTAGCTAAAGATACTACTGA |
| | | | AGCCTTTGAAAAAATGGTTTCACTACTTTCTGTTTTGC |
| | | | TTTCCATGCAGGGTGCTGTAGACATAAACAAGCTTTGT |
| | | | GAAGAAATGCTGGACAACAGGGCAACCTTACAAGCTA |
| | | | TAGCCTCAGAGTTTAGTTCCCTTCCATCATATGCAGCT |
| | | | TTTGCTACTGCTCAAGAAGCTTATGAGCAGGCTGTTGC |
| | | | TAATGGTGATTCTGAAGTTGTTCTTAAAAAGTTGAAGA |
| | | | AGTCTTTGAATGTGGCTAAATCTGAATTTGACCGTGAT |
| | | | GCAGCCATGCAACGTAAGTTGGAAAAGATGGCTGATC |
| | | | AAGCTATGACCCAAATGTATAAACAGGCTAGATCTGA |
| | | | GGACAAGAGGGCAAAAGTTACTAGTGCTATGCAGACA |
| | | | ATGCTTTTCACTATGCTTAGAAAGTTGGATAATGATGC |
| | | | ACTCAACAACATTATCAACAATGCAAGAGATGGTTGT |
| | | | GTTCCCTTGAACATAATACCTCTTACAACAGCAGCCAA |
| | | | ACTAATGGTTGTCATACCAGACTATAACACATATAAA |
| | | | AATACGTGTGATGGTACAACATTTACTTATGCATCAGC |
| | | | ATTGTGGGAAATCCAACAGGTTGTAGATGCAGATAGT |
| | | | AAAATTGTTCAACTTAGTGAAATTAGTATGGACAATTC |
| | | | ACCTAATTTAGCATGGCCTCTTATTGTAACAGCTTTAA |
| | | | GGGCCAATTCTGCTGTCAAATTACAGAATAATGAGCT |
| | | | TAGTCCTGTTGCACTACGACAGATGTCTTGTGCTGCCG |
| | | | GTACTACACAAACTGCTTGCACTGATGACAATGCGTT |
| | | | AGCTTACTACAACACAACAAAGGGAGGTAGGTTTGTA |
| | | | CTTGCACTGTTATCCGATTTACAGGATTTGAAATGGGC |
| | | | TAGATTCCCTAAGAGTGATGGAACTGGTACTATCTATA |
| | | | CAGAACTGGAACCACCTTGTAGGTTTGTTACAGACAC |
| | | | ACCTAAAGGTCCTAAAGTGAAGTATTTATACTTTATTA |
| | | | AAGGATTAAACAACCTAAATAGAGGTATGGTACTTGG |
| | | | TAGTTTAGCTGCCACAGTACGTCTACAAGCTGGTAATG |
| | | | CAACAGAAGTGCCTGCCAATTCAACTGTATTATCTTTC |
| | | | TGTGCTTTTGCTGTAGATGCTGCTAAAGCTTACAAAGA |
| | | | TTATCTAGCTAGTGGGGGACAACCAATCACTAATTGT |
| | | | GTTAAGATGTTGTGTACACACACTGGTACTGGTCAGG |
| | | | CAATAACAGTTACACCGGAAGCCAATATGGATCAAGA |
| | | | ATCCTTTGGTGGTGCATCGTGTTGTCTGTACTGCCGTT |
| | | | GCCACATAGATCATCCAAATCCTAAAGGATTTTGTGA |
| | | | CTTAAAAGGTAAGTATGTACAAATACCTACAACTTGT |
| | | | GCTAATGACCCTGTGGGTTTTACACTTAAAAACACAGT |
| | | | CTGTACCGTCTGCGGTATGTGGAAAGGTTATGGCTGTA |

TABLE 5-continued

SARS-CoV2 gene sequences

| Gene | Start | End | Sequence |
|---|---|---|---|
| | | | GTTGTGATCAACTCCGCGAACCCATGCTTCAGTCAGCT |
| | | | GATGCACAATCGTTTTTAAACGGGTTTGCGGTGTAAGT |
| | | | GCAGCCCGTCTTACACCGTGCGGCACAGGCACTAGTA |
| | | | CTGATGTCGTATACAGGGCTTTTGACATCTACAATGAT |
| | | | AAAGTAGCTGGTTTTGCTAAATTCCTAAAAACTAATTG |
| | | | TTGTCGCTTCCAAGAAAAGGACGAAGATGACAATTTA |
| | | | ATTGATTCTTACTTTGTAGTTAAGAGACACACTTTCTC |
| | | | TAACTACCAACATGAAGAAACAATTTATAATTTACTTA |
| | | | AGGATTGTCCAGCTGTTGCTAAACATGACTTCTTTAAG |
| | | | TTTAGAATAGACGGTGACATGGTACCACATATATCAC |
| | | | GTCAACGTCTTACTAAATACACAATGGCAGACCTCGT |
| | | | CTATGCTTTAAGGCATTTTGATGAAGGTAATTGTGACA |
| | | | CATTAAAAGAAATACTTGTCACATACAATTGTTGTGAT |
| | | | GATGATTATTTCAATAAAAAGGACTGGTATGATTTTGT |
| | | | AGAAAACCCAGATATATTACGCGTATACGCCAACTTA |
| | | | GGTGAACGTGTACGCCAAGCTTTGTTAAAAACAGTAC |
| | | | AATTCTGTGATGCCATGCGAAATGCTGGTATTGTTGGT |
| | | | GTACTGACATTAGATAATCAAGATCTCAATGGTAACT |
| | | | GGTATGATTTCGGTGATTTCATACAAACCACGCCAGGT |
| | | | AGTGGAGTTCCTGTTGTAGATTCTTATTATTCATTGTT |
| | | | AATGCCTATATTAACCTTGACCAGGGCTTTAACTGCAG |
| | | | AGTCACATGTTGACACTGACTTAACAAAGCCTTACATT |
| | | | AAGTGGGATTTGTTAAAATATGACTTCACGGAAGAGA |
| | | | GGTTAAAACTCTTTGACCGTTATTTTAAATATTGGGAT |
| | | | CAGACATACCACCCAAATTGTGTTAACTGTTTGGATGA |
| | | | CAGATGCATTCTGCATTGTGCAAACTTTAATGTTTTAT |
| | | | TCTCTACAGTGTTCCCACCTACAAGTTTTGGACCACTA |
| | | | GTGAGAAAAATATTTGTTGATGGTGTTCCATTTGTAGT |
| | | | TTCAACTGGATACCACTTCAGAGAGCTAGGTGTTGTAC |
| | | | ATAATCAGGATGTAAACTTACATAGCTCTAGACTTAGT |
| | | | TTTAAGGAATTACTTGTGTATGCTGCTGACCCTGCTAT |
| | | | GCACGCTGCTTCTGGTAATCTATTACTAGATAAACGCA |
| | | | CTACGTGCTTTTCAGTAGCTGCACTTACTAACAATGTT |
| | | | GCTTTTCAAACTGTCAAACCCGGTAATTTTAACAAAGA |
| | | | CTTCTATGACTTTGCTGTGTCTAAGGGTTTCTTTAAGG |
| | | | AAGGAAGTTCTGTTGAATTAAAACACTTCTTCTTTGCT |
| | | | CAGGATGGTAATGCTGCTATCAGCGATTATGACTACT |
| | | | ATCGTTATAATCTACCAACAATGTGTGATATCAGACA |
| | | | ACTACTATTTGTAGTTGAAGTTGTTGATAAGTACTTTG |
| | | | ATTGTTACGATGGTGGCTGTATTAATGCTAACCAAGTC |
| | | | ATCGTCAACAACCTAGACAAATCAGCTGGTTTTCCATT |
| | | | TAATAAATGGGGTAAGGCTAGACTTTATTATGATTCA |
| | | | ATGAGTTATGAGGATCAAGATGCACTTTTCGCATATAC |
| | | | AAAACGTAATGTCATCCCTACTATAACTCAAATGAAT |
| | | | CTTAAGTATGCCATTAGTGCAAAGAATAGAGCTCGCA |
| | | | CCGTAGCTGGTGTCTCTATCTGTAGTACTATGACCAAT |
| | | | AGACAGTTTCATCAAAAATTATTGAAATCAATAGCCG |
| | | | CCACTAGAGGAGCTACTGTAGTAATTGGAACAAGCAA |
| | | | ATTCTATGGTGGTTGGCACAACATGTTAAAAACTGTTT |
| | | | ATAGTGATGTAGAAAACCCTCACCTTATGGGTTGGGA |
| | | | TTATCCTAAATGTGATAGAGCCATGCCTAACATGCTTA |
| | | | GAATTATGGCCTCACTTGTTCTTGCTCGCAAACATACA |
| | | | ACGTGTTGTAGCTTGTCACACCGTTTCTATAGATTAGC |
| | | | TAATGAGTGTGCTCAAGTATTGAGTGAAATGGTCATG |
| | | | TGTGGCGGTTCACTATATGTTAAACCAGGTGGAACCTC |
| | | | ATCAGGAGATGCCACAACTGCTTATGCTAATAGTGTTT |
| | | | TTAACATTTGTCAAGCTGTCACGGCCAATGTTAATGCA |
| | | | CTTTTATCTACTGATGGTAACAAAATTGCCGATAAGTA |
| | | | TGTCCGCAATTTACAACACAGACTTTATGAGTGTCTCT |
| | | | ATAGAAATAGAGATGTTGACACAGACTTTGTGAATGA |
| | | | GTTTTACGCATATTTGCGTAAACATTTCTCAATGATGA |
| | | | TACTCTCTGACGATGCTGTTGTGTGTTTCAATAGCACT |
| | | | TATGCATCTCAAGGTCTAGTGGCTAGCATAAAGAACT |
| | | | TTAAGTCAGTTCTTTATTATCAAAACAATGTTTTTATG |
| | | | TCTGAAGCAAAATGTTGGACTGAGACTGACCTTACTA |
| | | | AAGGACCTCATGAATTTTGCTCTCAACATACAATGCTA |
| | | | GTTAAACAGGGTGATGATTATGTGTACCTTCCTTACCC |
| | | | AGATCCATCAAGAATCCTAGGGGCCGGCTGTTTTGTA |
| | | | GATGATATCGTAAAAACAGATGGTACACTTATGATTG |
| | | | AACGGTTCGTGTCTTTAGCTATAGATGCTTACCCACTT |
| | | | ACTAAACATCCTAATCAGGAGTATGCTGATGTCTTTCA |
| | | | TTTGTACTTACAATACATAAGAAAGCTACATGATGAG |
| | | | TTAACAGGACACATGTTAGACATGTATTCTGTTATGCT |
| | | | TACTAATGATAACACTTCAAGGTATTGGGAACCTGAG |
| | | | TTTTATGAGGCTATGTACACACCGCATACAGTCTTACA |
| | | | GGCTGTTGGGGCTTGTGTTCTTTGCAATTCACAGACTT |

TABLE 5-continued

SARS-CoV2 gene sequences

| Gene | Start | End | Sequence |
|---|---|---|---|
| | | | CATTAAGATGTGGTGCTTGCATACGTAGACCATTCTTA |
| | | | TGTTGTAAATGCTGTTACGACCATGTCATATCAACATC |
| | | | ACATAAATTAGTCTTGTCTGTTAATCCGTATGTTTGCA |
| | | | ATGCTCCAGGTTGTGATGTCACAGATGTGACTCAACTT |
| | | | TACTTAGGAGGTATGAGCTATTATTGTAAATCACATAA |
| | | | ACCACCCATTAGTTTTCCATTGTGTGCTAATGGACAAG |
| | | | TTTTTGGTTTATATAAAAATACATGTGTTGGTAGCGAT |
| | | | AATGTTACTGACTTTAATGCAATTGCAACATGTGACTG |
| | | | GACAAATGCTGGTGATTACATTTTAGCTAACACCTGTA |
| | | | CTGAAAGACTCAAGCTTTTTGCAGCAGAAACGCTCAA |
| | | | AGCTACTGAGGAGACATTTAAACTGTCTTATGGTATTG |
| | | | CTACTGTACGTGAAGTGCTGTCTGACAGAGAATTACA |
| | | | TCTTTCATGGGAAGTTGGTAAACCTAGACCACCACTTA |
| | | | ACCGAAATTATGTCTTTACTGGTTATCGTGTAACTAAA |
| | | | AACAGTAAAGTACAAATAGGAGAGTACACCTTTGAAA |
| | | | AAGGTGACTATGGTGATGCTGTTGTTTACCGAGGTAC |
| | | | AACAACTTACAAATTAAATGTTGGTGATTATTTTGTGC |
| | | | TGACATCACATACAGTAATGCCATTAAGTGCACCTAC |
| | | | ACTAGTGCCACAAGAGCACTATGTTAGAATTACTGGC |
| | | | TTATACCCAACACTCAATATCTCAGATGAGTTTTCTAG |
| | | | CAATGTTGCAAATTATCAAAAGGTTGGTATGCAAAAG |
| | | | TATTCTACACTCCAGGGACCACCTGGTACTGGTAAGA |
| | | | GTCATTTTGCTATTGGCCTAGCTCTCTACTACCCTTCTG |
| | | | CTCGCATAGTGTATACAGCTTGCTCTCATGCCGCTGTT |
| | | | GATGCACTATGTGAGAAGGCATTAAAATATTTGCCTA |
| | | | TAGATAAATGTAGTAGAATTATACCTGCACGTGCTCGT |
| | | | GTAGAGTGTTTTGATAAATTCAAAGTGAATTCAACATT |
| | | | AGAACAGTATGTCTTTTGTACTGTAAATGCATTGCCTG |
| | | | AGACGACAGCAGATATAGTTGTCTTTGATGAAATTTC |
| | | | AATGGCCACAAATTATGATTTGAGTGTTGTCAATGCCA |
| | | | GATTACGTGCTAAGCACTATGTGTACATTGGCGACCCT |
| | | | GCTCAATTACCTGCACCACGCACATTGCTAACTAAGG |
| | | | GCACACTAGAACCAGAATATTTCAATTCAGTGTGTAG |
| | | | ACTTATGAAAACTATAGGTCCAGACATGTTCCTCGGA |
| | | | ACTTGTCGGCGTTGTCCTGCTGAAATTGTTGACACTGT |
| | | | GAGTGCTTTGGTTTATGATAATAAGCTTAAAGCACATA |
| | | | AAGACAAATCAGCTCAATGCTTTAAAATGTTTTATAA |
| | | | GGGTGTTATCACGCATGATGTTTCATCTGCAATTAACA |
| | | | GGCCACAAATAGGCGTGGTAAGAGAATTCCTTACACG |
| | | | TAACCCTGCTTGGAGAAAAGCTGTCTTTATTTCACCTT |
| | | | ATAATTCACAGAATGCTGTAGCCTCAAAGATTTTGGG |
| | | | ACTACCAACTCAAACTGTTGATTCATCACAGGGCTCA |
| | | | GAATATGACTATGTCATATTCACTCAAACCACTGAAA |
| | | | CAGCTCACTCTTGTAATGTAAACAGATTTAATGTTGCT |
| | | | ATTACCAGAGCAAAAGTAGGCATACTTTGCATAATGT |
| | | | CTGATAGAGACCTTTATGACAAGTTGCAATTTACAAGT |
| | | | CTTGAAATTCCACGTAGGAATGTGGCAACTTTACAAG |
| | | | CTGAAAATGTAACAGGACTCTTTAAAGATTGTAGTAA |
| | | | GGTAATCACTGGGTTACATCCTACACAGGCACCTACA |
| | | | CACCTCAGTGTTGACACTAAATTCAAAACTGAAGGTTT |
| | | | ATGTGTTGACATACCTGGCATACCTAAGGACATGACC |
| | | | TATAGAAGACTCATCTCTATGATGGGTTTTAAAATGAA |
| | | | TTATCAAGTTAATGGTTACCCTAACATGTTTATCACCC |
| | | | GCGAAGAAGCTATAAGACATGTACGTGCATGGATTGG |
| | | | CTTCGATGTCGAGGGGTGTCATGCTACTAGAGAAGCT |
| | | | GTTGGTACCAATTTACCTTTACAGCTAGGTTTTTCTAC |
| | | | AGGTGTTAACCTAGTTGCTGTACCTACAGGTTATGTTG |
| | | | ATACACCTAATAATACAGATTTTTCCAGAGTTAGTGCT |
| | | | AAACCACCGCCTGGAGATCAATTTAAACACCTCATAC |
| | | | CACTTATGTACAAAGGACTTCCTTGGAATGTAGTGCGT |
| | | | ATAAAGATTGTACAAATGTTAAGTGACACACTTAAAA |
| | | | ATCTCTCTGACAGAGTCGTATTTGTCTTATGGGCACAT |
| | | | GGCTTTGAGTTGACATCTATGAAGTATTTTGTGAAAAT |
| | | | AGGACCTGAGCGCACCTGTTGTCTATGTGATAGACGT |
| | | | GCCACATGCTTTTCCACTGCTTCAGACACTTATGCCTG |
| | | | TTGGCATCATTCTATTGGATTTGATTACGTCTATAATC |
| | | | CGTTTATGATTGATGTTCAACAATGGGGTTTTACAGGT |
| | | | AACCTACAAAGCAACCATGATCTGTATTGTCAAGTCC |
| | | | ATGGTAATGCACATGTAGCTAGTTGTGATGCAATCAT |
| | | | GACTAGGTGTCTAGCTGTCCACGAGTGCTTTGTTAAGC |
| | | | GTGTTGACTGGACTATTGAATATCCTATAATTGGTGAT |
| | | | GAACTGAAGATTAATGCGGCTTGTAGAAAGGTTCAAC |
| | | | ACATGGTTGTTAAAGCTGCATTATTAGCAGACAAATTC |
| | | | CCAGTTCTTCACGACATTGGTAACCCTAAAGCTATTAA |
| | | | GTGTGTACCTCAAGCTGATGTAGAATGGAAGTTCTAT |
| | | | GATGCACAGCCTTGTAGTGACAAAGCTTATAAAATAG |

TABLE 5-continued

SARS-CoV2 gene sequences

| Gene | Start | End | Sequence |
|---|---|---|---|
| | | | AAGAATTATTCTATTCTTATGCCACACATTCTGACAAA<br>TTCACAGATGGTGTATGCCTATTTTGGAATTGCAATGT<br>CGATAGATATCCTGCTAATTCCATTGTTTGTAGATTTG<br>ACACTAGAGTGCTATCTAACCTTAACTTGCCTGGTTGT<br>GATGGTGGCAGTTTGTATGTAAATAAACATGCATTCC<br>ACACACCAGCTTTTGATAAAAGTGCTTTTGTTAATTTA<br>AAACAATTACCATTTTTCTATTACTCTGACAGTCCATG<br>TGAGTCTCATGGAAAACAAGTAGTGTCAGATATAGAT<br>TATGTACCACTAAAGTCTGCTACGTGTATAACACGTTG<br>CAATTTAGGTGGTGCTGTCTGTAGACATCATGCTAATG<br>AGTACAGATTGTATCTCGATGCTTATAACATGATGATC<br>TCAGCTGGCTTTAGCTTGTGGGTTTACAAACAATTTGA<br>TACTTATAACCTCTGGAACACTTTTACAAGACTTCAGA<br>GTTTAGAAAATGTGGCTTTTAATGTTGTAAATAAGGG<br>ACACTTTGATGGACAACAGGGTGAAGTACCAGTTTCT<br>ATCATTAATAACACTGTTTACACAAAAGTTGATGGTGT<br>TGATGTAGAATTGTTTGAAAATAAAACAACATTACCT<br>GTTAATGTAGCATTTGAGCTTTGGGCTAAGCGCAACAT<br>TAAACCAGTACCAGAGGTGAAAATACTCAATAATTTG<br>GGTGTGGACATTGCTGCTAATACTGTGATCTGGGACTA<br>CAAAAGAGATGCTCCAGCACATATATCTACTATTGGT<br>GTTTGTTCTATGACTGACATAGCCAAGAAACCAACTG<br>AAACGATTTGTGCACCACTCACTGTCTTTTTTGATGGT<br>AGAGTTGATGGTCAAGTAGACTTATTTAGAAATGCCC<br>GTAATGGTGTTCTTATTACAGAAGGTAGTGTTAAAGGT<br>TTACAACCATCTGTAGGTCCCAAACAAGCTAGTCTTAA<br>TGGAGTCACATTAATTGGAGAAGCCGTAAAAACACAG<br>TTCAATTATTATAAGAAAGTTGATGGTGTTGTCCAACA<br>ATTACCTGAAACTTACTTTACTCAGAGTAGAAATTTAC<br>AAGAATTTAAACCCAGGAGTCAAATGGAAATTGATTT<br>CTTAGAATTAGCTATGGATGAATTCATTGAACGGTATA<br>AATTAGAAGGCTATGCCTTCGAACATATCGTTTATGGA<br>GATTTTAGTCATAGTCAGTTAGGTGGTTTACATCTACT<br>GATTGGACTAGCTAAACGTTTTAAGGAATCACCTTTTG<br>AATTAGAAGATTTTATTCCTATGGACAGTACAGTTAAA<br>AACTATTTCATAACAGATGCGCAAACAGGTTCATCTA<br>AGTGTGTGTGTTCTGTTATTGATTTATTACTTGATGATT<br>TTGTTGAAATAATAAAATCCCAAGATTTATCTGTAGTT<br>TCTAAGGTTGTCAAAGTGACTATTGACTATACAGAAA<br>TTTCATTTATGCTTTGGTGTAAAGATGGCCATGTAGAA<br>ACATTTTACCCAAAATTACAATCTAGTCAAGCGTGGC<br>AACCGGGTGTTGCTATGCCTAATCTTTACAAAATGCAA<br>AGAATGCTATTAGAAAAGTGTGACCTTCAAAATTATG<br>GTGATAGTGCAACATTACCTAAAGGCATAATGATGAA<br>TGTCGCAAAATATACTCAACTGTGTCAATATTTAAACA<br>CATTAACATTAGCTGTACCCTATAATATGAGAGTTATA<br>CATTTTGGTGCTGGTTCTGATAAAGGAGTTGCACCAGG<br>TACAGCTGTTTTAAGACAGTGGTTGCCTACGGGTACGC<br>TGCTTGTCGATTCAGATCTTAATGACTTTGTCTCTGAT<br>GCAGATTCAACTTTGATTGGTGATTGTGCAACTGTACA<br>TACAGCTAATAAATGGGATCTCATTATTAGTGATATGT<br>ACGACCCTAAGACTAAAAATGTTACAAAAGAAAATGA<br>CTCTAAAGAGGGTTTTTTCACTTACATTTGTGGGTTTA<br>TACAACAAAAGCTAGCTCTTGGAGGTTCCGTGGCTAT<br>AAAGATAACAGAACATTCTTGGAATGCTGATCTTTAT<br>AAGCTCATGGGACACTTCGCATGGTGGACAGCCTTTG<br>TTACTAATGTGAATGCGTCATCATCTGAAGCATTTTTA<br>ATTGGATGTAATTATCTTGGCAAACCACGCGAACAAA<br>TAGATGGTTATGTCATGCATGCAAATTACATATTTTGG<br>AGGAATACAAATCCAATTCAGTTGTCTTCCTATTCTTT<br>ATTTGACATGAGTAAATTTCCCCTTAAATTAAGGGGTA<br>CTGCTGTTATGTCTTTAAAAGAAGGTCAAATCAATGAT<br>ATGATTTTATCTCTTCTTAGTAAAGGTAGACTTATAAT<br>TAGAGAAAACAACAGAGTTGTTATTTCTAGTGATGTTC<br>TTGTTAACAACTA |
| S (SEQ ID NO: 4) | 21563 | 25384 | ATGTTTGTTTTTCTTGTTTTATTGCCACTAGTCTCTAGT<br>CAGTGTGTTAATCTTACAACCAGAACTCAATTACCCCC<br>TGCATACACTAATTCTTTCACACGTGGTGTTTATTACC<br>CTGACAAAGTTTTCAGATCCTCAGTTTTACATTCAACT<br>CAGGACTTGTTCTTACCTTTCTTTTCCAATGTTACTTGG<br>TTCCATGCTATACATGTCTCTGGGACCAATGGTACTAA<br>GAGGTTTGATAACCCTGTCCTACCATTTAATGATGGTG<br>TTTATTTTGCTTCCACTGAGAAGTCTAACATAATAAGA<br>GGCTGGATTTTTGGTACTACTTTAGATTCGAAGACCCA<br>GTCCCTACTTATTGTTAATAACGCTACTAATGTTGTTA |

TABLE 5-continued

SARS-CoV2 gene sequences

| Gene | Start | End | Sequence |
|---|---|---|---|
| | | | TTAAAGTCTGTGAATTTCAATTTTGTAATGATCCATTT |
| | | | TTGGGTGTTTATTACCACAAAAACAACAAAAGTTGGA |
| | | | TGGAAAGTGAGTTCAGAGTTTATTCTAGTGCGAATAA |
| | | | TTGCACTTTTGAATATGTCTCTCAGCCTTTTCTTATGGA |
| | | | CCTTGAAGGAAAACAGGGTAATTTCAAAAATCTTAGG |
| | | | GAATTTGTGTTTAAGAATATTGATGGTTATTTTAAAAT |
| | | | ATATTCTAAGCACACGCCTATTAATTTAGTGCGTGATC |
| | | | TCCCTCAGGGTTTTTCGGCTTTAGAACCATTGGTAGAT |
| | | | TTGCCAATAGGTATTAACATCACTAGGTTTCAAACTTT |
| | | | ACTTGCTTTACATAGAAGTTATTTGACTCCTGGTGATT |
| | | | CTTCTTCAGGTTGGACAGCTGGTGCTGCAGCTTATTAT |
| | | | GTGGGTTATCTTCAACCTAGGACTTTTCTATTAAAATA |
| | | | TAATGAAAATGGAACCATTACAGATGCTGTAGACTGT |
| | | | GCACTTGACCCTCTCTCAGAAACAAAGTGTACGTTGA |
| | | | AATCCTTCACTGTAGAAAAAGGAATCTATCAAACTTCT |
| | | | AACTTTAGAGTCCAACCAACAGAATCTATTGTTAGATT |
| | | | TCCTAATATTACAAACTTGTGCCCTTTTGGTGAAGTTT |
| | | | TTAACGCCACCAGATTTGCATCTGTTTATGCTTGGAAC |
| | | | AGGAAGAGAATCAGCAACTGTGTTGCTGATTATTCTG |
| | | | TCCTATATAATTCCGCATCATTTTCCACTTTTAAGTGTT |
| | | | ATGGAGTGTCTCCTACTAAATTAAATGATCTCTGCTTT |
| | | | ACTAATGTCTATGCAGATTCATTTGTAATTAGAGGTGA |
| | | | TGAAGTCAGACAAATCGCTCCAGGGCAAACTGGAAAG |
| | | | ATTGCTGATTATAATTATAAATTACCAGATGATTTTAC |
| | | | AGGCTGCGTTATAGCTTGGAATTCTAACAATCTTGATT |
| | | | CTAAGGTTGGTGGTAATTATAATTACCTGTATAGATTG |
| | | | TTTAGGAAGTCTAATCTCAAACCTTTTGAGAGAGATAT |
| | | | TTCAACTGAAATCTATCAGGCCGGTAGCACACCTTGTA |
| | | | ATGGTGTTGAAGGTTTTAATTGTTACTTTCCTTTACAA |
| | | | TCATATGGTTTCCAACCCACTAATGGTGTTGGTTACCA |
| | | | ACCATACAGAGTAGTAGTACTTTCTTTTGAACTTCTAC |
| | | | ATGCACCAGCAACTGTTTGTGGACCTAAAAAGTCTAC |
| | | | TAATTTGGTTAAAAACAAATGTGTCAATTTCAACTTCA |
| | | | ATGGTTTAACAGGCACAGGTGTTCTTACTGAGTCTAAC |
| | | | AAAAAGTTTCTGCCTTTCCAACAATTTGGCAGAGACAT |
| | | | TGCTGACACTACTGATGCTGTCCGTGATCCACAGACAC |
| | | | TTGAGATTCTTGACATTACACCATGTTCTTTTGGTGGT |
| | | | GTCAGTGTTATAACACCAGGAACAAATACTTCTAACC |
| | | | AGGTTGCTGTTCTTTATCAGGATGTTAACTGCACAGAA |
| | | | GTCCCTGTTGCTATTCATGCAGATCAACTTACTCCTAC |
| | | | TTGGCGTGTTTATTCTACAGGTTCTAATGTTTTTCAAA |
| | | | CACGTGCAGGCTGTTTAATAGGGGCTGAACATGTCAA |
| | | | CAACTCATATGAGTGTGACATACCCATTGGTGCAGGT |
| | | | ATATGCGCTAGTTATCAGACTCAGACTAATTCTCCTCG |
| | | | GCGGGCACGTAGTGTAGCTAGTCAATCCATCATTGCCT |
| | | | ACACTATGTCACTTGGTGCAGAAAATTCAGTTGCTTAC |
| | | | TCTAATAACTCTATTGCCATACCCACAAATTTTACTAT |
| | | | TAGTGTTACCACAGAAATTCTACCAGTGTCTATGACCA |
| | | | AGACATCAGTAGATTGTACAATGTACATTTGTGGTGAT |
| | | | TCAACTGAATGCAGCAATCTTTTGTTGCAATATGGCAG |
| | | | TTTTTGTACACAATTAAACCGTGCTTTAACTGGAATAG |
| | | | CTGTTGAACAAGACAAAAACACCCAAGAAGTTTTTGC |
| | | | ACAAGTCAAACAAATTTACAAAACACCACCAATTAAA |
| | | | GATTTTGGTGGTTTTAATTTTTCACAAATATTACCAGA |
| | | | TCCATCAAAACCAAGCAAGAGGTCATTTATTGAAGAT |
| | | | CTACTTTTCAACAAAGTGACACTTGCAGATGCTGGCTT |
| | | | CATCAAACAATATGGTGATTGCCTTGGTGATATTGCTG |
| | | | CTAGAGACCTCATTTGTGCACAAAAGTTTAACGGCCTT |
| | | | ACTGTTTTGCCACCTTTGCTCACAGATGAAATGATTGC |
| | | | TCAATACACTTCTGCACTGTTAGCGGGTACAATCACTT |
| | | | CTGGTTGGACCTTTGGTGCAGGTGCTGCATTACAAATA |
| | | | CCATTTGCTATGCAAATGGCTTATAGGTTTAATGGTAT |
| | | | TGGAGTTACACAGAATGTTCTCTATGAGAACCAAAAA |
| | | | TTGATTGCCAACCAATTTAATAGTGCTATTGGCAAAAT |
| | | | TCAAGACTCACTTTCTTCCACAGCAAGTGCACTTGGAA |
| | | | AACTTCAAGATGTGGTCAACCAAAATGCACAAGCTTT |
| | | | AAACACGCTTGTTAAACAACTTAGCTCCAATTTTGGTG |
| | | | CAATTTCAAGTGTTTTAAATGATATCCTTTCACGTCTT |
| | | | GACAAAGTTGAGGCTGAAGTGCAAATTGATAGGTTGA |
| | | | TCACAGGCAGACTTCAAAGTTTGCAGACATATGTGAC |
| | | | TCAACAATTAATTAGAGCTGCAGAAATCAGAGCTTCT |
| | | | GCTAATCTTGCTGCTACTAAAATGTCAGAGTGTGTACT |
| | | | TGGACAATCAAAAAGAGTTGATTTTTGTGGAAAGGGC |
| | | | TATCATCTTATGTCCTTCCCTCAGTCAGCACCTCATGG |
| | | | TGTAGTCTTCTTGCATGTGACTTATGTCCCTGCACAAG |
| | | | AAAAGAACTTCACAACTGCTCCTGCCATTTGTCATGAT |

TABLE 5-continued

SARS-CoV2 gene sequences

| Gene | Start | End | Sequence |
|---|---|---|---|
| | | | GGAAAAGCACACTTTCCTCGTGAAGGTGTCTTTGTTTC AAATGGCACACACTGGTTTGTAACACAAAGGAATTTT TATGAACCACAAATCATTACTACAGACAACACATTTG TGTCTGGTAACTGTGATGTTGTAATAGGAATTGTCAAC AACACAGTTTATGATCCTTTGCAACCTGAATTAGACTC ATTCAAGGAGGAGTTAGATAAATATTTTAAGAATCAT ACATCACCAGATGTTGATTTAGGTGACATCTCTGGCAT TAATGCTTCAGTTGTAAACATTCAAAAAGAAATTGAC CGCCTCAATGAGGTTGCCAAGAATTTAAATGAATCTCT CATCGATCTCCAAGAACTTGGAAAGTATGAGCAGTAT ATAAAATGGCCATGGTACATTTGGCTAGGTTTTATAGC TGGCTTGATTGCCATAGTAATGGTGACAATTATGCTTT GCTGTATGACCAGTTGCTGTAGTTGTCTCAAGGGCTGT TGTTCTTGTGGATCCTGCTGCAAATTTGATGAAGACGA CTCTGAGCCAGTGCTCAAAGGAGTCAAATTACATTAC ACATA |
| 3a (SEQ ID NO: 5) | 25393 | 26220 | ATGGATTTGTTTATGAGAATCTTCACAATTGGAACTGT AACTTTGAAGCAAGGTGAAATCAAGGATGCTACTCCT TCAGATTTTGTTCGCGCTACTGCAACGATACCGATACA AGCCTCACTCCCTTTCGGATGGCTTATTGTTGGCGTTG CACTTCTTGCTGTTTTTCAGAGCGCTTCCAAAATCATA ACCCTCAAAAAGAGATGGCAACTAGCACTCTCCAAGG GTGTTCACTTTGTTTGCAACTTGCTGTTGTTGTTTGTAA CAGTTTACTCACACCTTTTGCTCGTTGCTGCTGGCCTT GAAGCCCCTTTTCTCTATCTTTATGCTTTAGTCTACTTC TTGCAGAGTATAAACTTTGTAAGAATAATAATGAGGC TTTGGCTTTGCTGGAAATGCCGTTCCAAAAACCCATTA CTTTATGATGCCAACTATTTTCTTTGCTGGCATACTAA TTGTTACGACTATTGTATACCTTACAATAGTGTAACTT CTTCAATTGTCATTACTTCAGGTGATGGCACAACAAGT CCTATTTCTGAACATGACTACCAGATTGGTGGTTATAC TGAAAAATGGGAATCTGGAGTAAAAGACTGTGTTGTA TTACACAGTTACTTCACTTCAGACTATTACCAGCTGTA CTCAACTCAATTGAGTACAGACACTGGTGTTGAACAT GTTACCTTCTTCATCTACAATAAAATTGTTGATGAGCC TGAAGAACATGTCCAAATTCACACAATCGACGGTTCA TCCGGAGTTGTTAATCCAGTAATGGAACCAATTTATGA TGAACCGACGACGACTACTAGCGTGCCTTTGTA |
| E (SEQ ID NO: 6) | 26245 | 26472 | ATGTACTCATTCGTTTCGGAAGAGACAGGTACGTTAAT AGTTAATAGCGTACTTCTTTTTCTTGCTTTCGTGGTATT CTTGCTAGTTACACTAGCCATCCTTACTGCGCTTCGAT TGTGTGCGTACTGCTGCAATATTGTTAACGTGAGTCTT GTAAAACCTTCTTTTTACGTTTACTCTCGTGTTAAAAA TCTGAATTCTTCTAGAGTTCCTGATCTTCTGGTCTA |
| M (SEQ ID NO: 7) | 26523 | 27191 | ATGGCAGATTCCAACGGTACTATTACCGTTGAAGAGC TTAAAAAGCTCCTTGAACAATGGAACCTAGTAATAGG TTTCCTATTCCTTACATGGATTTGTCTTCTACAATTTGC CTATGCCAACAGGAATAGGTTTTTGTATATAATTAAGT TAATTTTCCTCTGGCTGTTATGGCCAGTAACTTTAGCT TGTTTTGTGCTTGCTGCTGTTTACAGAATAAATTGGAT CACCGGTGGAATTGCTATCGCAATGGCTTGTCTTGTAG GCTTGATGTGGCTCAGCTACTTCATTGCTTCTTTCAGA CTGTTTGCGCGTACGCGTTCCATGTGGTCATTCAATCC AGAAACTAACATTCTTCTCAACGTGCCACTCCATGGCA CTATTCTGACCAGACCGCTTCTAGAAAGTGAACTCGTA ATCGGAGCTGTGATCCTTCGTGGACATCTTCGTATTGC TGGACACCATCTAGGACGCTGTGACATCAAGGACCTG CCTAAAGAAATCACTGTTGCTACATCACGAACGCTTTC TTATTACAAATTGGGAGCTTCGCAGCGTGTAGCAGGT GACTCAGGTTTTGCTGCATACAGTCGCTACAGGATTGG CAACTATAAATTAAACACAGACCATTCCAGTAGCAGT GACAATATTGCTTTGCTTGTACAGTA |
| 7a (SEQ ID NO: 8) | 27394 | 27759 | ATGAAAATTATTCTTTTCTTGGCACTGATAACACTCGC TACTTGTGAGCTTTATCACTACCAAGAGTGTGTTAGAG GTACAACAGTACTTTTAAAAGAACCTTGCTCTTCTGGA ACATACGAGGGCAATTCACCATTTCATCCTCTAGCTGA TAACAAATTTGCACTGACTTGCTTTAGCACTCAATTTG CTTTTGCTTGTCCTGACGGCGTAAAACACGTCTATCAG TTACGTGCCAGATCAGTTTCACCTAAACTGTTCATCAG ACAAGAGGAAGTTCAAGAACTTTACTCTCCAATTTTTC TTATTGTTGCGGCAATAGTGTTTATAACACTTTGCTTC ACACTCAAAAGAAAGACAGAATG |

TABLE 5-continued

SARS-CoV2 gene sequences

| Gene | Start | End | Sequence |
|---|---|---|---|
| 8a (SEQ ID NO: 9) | 27894 | 28259 | ATGAAATTTCTTGTTTTCTTAGGAATCATCACAACTGT AGCTGCATTTCACCAAGAATGTAGTTTACAGTCATGTA CTCAACATCAACCATATGTAGTTGATGACCCGTGTCCT ATTCACTTCTATTCTAAATGGTATATTAGAGTAGGAGC TAGAAAATCAGCACCTTTAATTGAATTGTGCGTGGAT GAGGCTGGTTCTAAATCACCCATTCAGTACATCGATAT CGGTAATTATACAGTTTCCTGTTTACCTTTTACAATTA ATTGCCAGGAACCTAAATTGGGTAGTCTTGTAGTGCGT TGTTCGTTCTATGAAGACTTTTTAGAGTATCATGACGT TCGTGTTGTTTTAGATTTCATCTA |
| N (SEQ ID NO: 10) | 28274 | 29533 | ATGTCTGATAATGGACCCCAAAATCAGCGAAATGCAC CCCGCATTACGTTTGGTGGACCCTCAGATTCAACTGGC AGTAACCAGAATGGAGAACGCAGTGGGGCGCGATCA AAACAACGTCGGCCCCAAGGTTTACCCAATAATACTG CGTCTTGGTTCACCGCTCTCACTCAACATGGCAAGGAA GACCTTAAATTCCCTCGAGGACAAGGCGTTCCAATTA ACACCAATAGCAGTCCAGATGACCAAATTGGCTACTA CCGAAGAGCTACCAGACGAATTCGTGGTGGTGACGGT AAAATGAAAGATCTCAGTCCAAGATGGTATTTCTACT ACCTAGGAACTGGGCCAGAAGCTGGACTTCCCTATGG TGCTAACAAAGACGGCATCATATGGGTTGCAACTGAG GGAGCCTTGAATACACCAAAAGATCACATTGGCACCC GCAATCCTGCTAACAATGCTGCAATCGTGCTACAACTT CCTCAAGGAACAACATTGCCAAAAGGCTTCTACGCAG AAGGGAGCAGAGGCGGCAGTCAAGCCTCTTCTCGTTC CTCATCACGTAGTCGCAACAGTTCAAGAAATTCAACT CCAGGCAGCAGTAGGGGAACTTCTCCTGCTAGAATGG CTGGCAATGGCGGTGATGCTGCTCTTGCTTTGCTGCTG CTTGACAGATTGAACCAGCTTGAGAGCAAAATGTCTG GTAAAGGCCAACAACAACAAGGCCAAACTGTCACTAA GAAATCTGCTGCTGAGGCTTCTAAGAAGCCTCGGCAA AAACGTACTGCCACTAAAGCATACAATGTAACACAAG CTTTCGGCAGACGTGGTCCAGAACAAACCCAAGGAAA TTTTGGGGACCAGGAACTAATCAGACAAGGAACTGAT TACAAACATTGGCCGCAAATTGCACAATTTGCCCCCA GCGCTTCAGCGTTCTTCGGAATGTCGCGCATTGGCATG GAAGTCACACCTTCGGGAACGTGGTTGACCTACACAG GTGCCATCAAATTGGATGACAAAGATCCAAATTTCAA AGATCAAGTCATTTTGCTGAATAAGCATATTGACGCAT ACAAAACATTCCCACCAACAGAGCCTAAAAAGGACAA AAAGAAGAAGGCTGATGAAACTCAAGCCTTACCGCAG AGACAGAAGAAACAGCAAACTGTGACTCTTCTTCCTG CTGCAGATTTGGATGATTTCTCCAAACAATTGCAACAA TCCATGAGCAGTGCTGACTCAACTCAGGCCTA |

The invention covers a combination of bioinformatic approaches to identify regions of conservation (based on 718 patient isolates) in combination with features essential for RISC entry and tolerance of chemical modifications. The method uses a scoring scheme to identify siRNAs that target regions of related viral genomes with low mutation rates. Since viral targets are known to mutate frequently, it was imperative to select siRNAs targeting regions that are predicted to remain constant. We identified these regions as those with high homology to the six most closely-related coronavirus genomes (Middle East respiratory syndrome-related coronavirus (MERS-CoV), Human coronavirus 229E, Human coronavirus NL63 (HCoV-NL63), Human coronavirus HKU1 (HCoV-HKU1), Human coronavirus OC43 (HCoV-OC43), and SARS coronavirus) indicating low rates of mutation within these regions.

The percent homology to the related coronavirus genomes was determined for every position for each of the SARS-CoV-2 target genes. siRNA sequence designs were then scored by the number of positions within the sequence having a percentage homology greater than 70% within position 2-8 and greater than 50% for at least 10 bases within the remaining positions of the 16-nucleotide targeting region of the 20-nucleotide siRNA. The design algorithm identified a 20-nucleotide siRNA sequences and scored them by their predicted efficiency to knockdown the target transcript. The 20-nucleotide siRNA target regions are summarized in Table 6A and Table 7. Top scoring siRNAs had the highest potential to knockdown the target transcript and targeted regions with the highest homology to other closely related coronaviruses (Middle East respiratory syndrome-related coronavirus (MERS-CoV), Human coronavirus 229E, Human coronavirus NL63 (HCoV-NL63), Human coronavirus HKU1 (HCoV-HKU1), Human coronavirus OC43 (HCoV-OC43), and SARS coronavirus) are summarized in Table 8 and were selected for synthesis. ASOs targeting SARS-CoV-2 genes are summarized in Table 9.

TABLE 6A

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| orf1ab_14080 | GGUAACUGG UAUGAUUUC GG | 11 | AATCAAGATCTCAATGGTAACTGGTAT GATTTCGGTGATTTCATA | 119 |
| orf1ab_14361 | UCUGCAUUG UGCAAACUU UA | 12 | GGATGACAGATGCATTCTGCATTGTGC AAACTTTAATGTTTTATT | 120 |
| orf1ab_14830 | UGUGAUAUC AGACAACUA CU | 13 | AATCTACCAACAATGTGTGATATCAGA CAACTACTATTTGTAGTT | 121 |
| orf1ab_15376 | UGUAGCUUG UCACACCGU UU | 14 | AAACATACAACGTGTTGTAGCTTGTCA CACCGTTTCTATAGATTA | 122 |
| orf1ab_15786 | UAAGUCAGU UCUUUAUUA UC | 15 | TAGCATAAAGAACTTTAAGTCAGTTCT TTATTATCAAAACAATGT | 123 |
| orf1ab_17107 | UUUGCUAUU GGCCUAGCU CU | 16 | ACTGGTAAGAGTCATTTTGCTATTGGC CTAGCTCTCTACTACCCT | 124 |
| orf1ab_17370 | GGCCACAAA UUAUGAUU UGA | 17 | TGATGAAATTTCAATGGCCACAAATTA TGATTTGAGTGTTGTCAA | 125 |
| orf1ab_18025 | GUGGCAACU UUACAAGCU GA | 18 | ATTCCACGTAGGAATGTGGCAACTTTA CAAGCTGAAAATGTAACA | 126 |
| orf1ab_18571 | UCUGACAGA GUCGUAUUU GU | 19 | ACACTTAAAAATCTCTCTGACAGAGTC GTATTTGTCTTATGGGCA | 127 |
| orf1ab_20497 | UCUGUUAUU GAUUUAUU ACU | 20 | TCTAAGTGTGTGTGTTCTGTTATTGATT TATTACTTGATGATTTT | 128 |
| orf1ab_20892 | UGCACCAGG UACAGCUGU UU | 21 | TTCTGATAAAGGAGTTGCACCAGGTAC AGCTGTTTTAAGACAGTG | 129 |
| orf1ab_21391 | UUUGACAUG AGUAAAUU UCC | 22 | TCTTCCTATTCTTTATTTGACATGAGTA AATTTCCCCTTAAATTA | 130 |
| orf1a_416 | UGUGGCUUA GUAGAAGU UGA | 23 | CTTAAAGATGGCACTTGTGGCTTAGTA GAAGTTGAAAAAGGCGTT | 131 |
| orf1a_2290 | UCAGACAUU CUUUAAGCU UG | 24 | AATTAAGGAGAGTGTTCAGACATTCTT TAAGCTTGTAAATAAATT | 132 |
| orf1a_6059 | UGUGAUAA UAUCAAAUU UGC | 25 | AATTTTAAGTTTGTATGTGATAATATC AAATTTGCTGATGATTTA | 133 |
| orf1a_6322 | UGAAACAUC AAAUUCGUU UG | 26 | GAGCACAAAACCAGTTGAAACATCAA ATTCGTTTGATGTACTGAA | 134 |
| orf1a_6499 | ACCAGCAAA UAAUAGUU UAA | 27 | AGACATTATACTTAAACCAGCAAATAA TAGTTTAAAAATTACAGA | 135 |
| orf1a_7643 | GCUGGUAGU ACAUUUAUU AG | 28 | TGTGATACATTCTGTGCTGGTAGTACA TTTATTAGTGATGAAGTT | 136 |

TABLE 6A-continued

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| orf1a_8200 | UGUAGAAACUAAAGAUGUUG | 29 | GTTTGTTGATTCAGATGTAGAAACTAAAGATGTTGTTGAATGTCT | 137 |
| orf1a_8201 | GUAGAAACUAAAGAUGUUGU | 30 | TTTGTTGATTCAGATGTAGAAACTAAAGATGTTGTTGAATGTCTT | 138 |
| orf1a_8744 | UUUGCUAACAAACAUGCUGA | 31 | TCTACAGATACTTGTTTTGCTAACAAACATGCTGATTTTGACACA | 139 |
| orf1a_9679 | CUGGAUAACAAUUGCUUAUA | 32 | ACCTTTAGTACCTTTCTGGATAACAATTGCTTATATCATTTGTAT | 140 |
| orf1a_11594 | CAGUGUAUAAUGCUAGUUUA | 33 | ACTGGTAATACACTTCAGTGTATAATGCTAGTTTATTGTTTCTTA | 141 |
| orf1a_12932 | CCUAAAGUGAAGUAUUUAUA | 34 | GACACACCTAAAGGTCCTAAAGTGAAGTATTTATACTTTATTAAA | 142 |
| S_21944 | AUUAAAGUCUGUGAAUUUCA | 35 | GCTACTAATGTTGTTATTAAAGTCTGTGAATTTCAATTTTGTAAT | 143 |
| S_22223 | UCGGCUUUAGAACCAUUGGU | 36 | CTCCCTCAGGGTTTTTCGGCTTTAGAACCATTGGTAGATTTGCCA | 144 |
| S_22550 | CCUAAUAUUACAAACUUGUG | 37 | TCTATTGTTAGATTTCCTAATATTACAAACTTGTGCCCTTTTGGT | 145 |
| S_22820 | GAUUAUAAUUAUAAAUUACC | 38 | ACTGGAAAGATTGCTGATTATAATTATAAATTACCAGATGATTTT | 146 |
| S_22898 | GGUGGUAAUUAUAAUUACCU | 39 | CTTGATTCTAAGGTTGGTGGTAATTATAATTACCTGTATAGATTG | 147 |
| S_23174 | UGUGUCAAUUUCAACUUCAA | 40 | TTGGTTAAAAACAAATGTGTCAATTTCAACTTCAATGGTTTAACA | 148 |
| S_23239 | UCUGCCUUUCCAACAAUUUG | 41 | GTCTAACAAAAAGTTTCTGCCTTTCCAACAATTTGGCAGAGACAT | 149 |
| S_23240 | CUGCCUUUCCAACAAUUUGG | 42 | TCTAACAAAAAGTTTCTGCCTTTCCAACAATTTGGCAGAGACATT | 150 |
| S_23774 | UGUACAAUGUACAUUUGUGG | 43 | AAGACATCAGTAGATTGTACAATGTACATTTGTGGTGATTCAACT | 151 |
| S_24056 | GGCUUCAUCAAACAAUAUGG | 44 | ACACTTGCAGATGCTGGCTTCATCAAACAATATGGTGATTGCCTT | 152 |
| S_24289 | UGGAGUUACACAGAAUGUUC | 45 | TAGGTTTAATGGTATTGGAGTTACACAGAATGTTCTCTATGAGAA | 153 |
| S_25375 | UUACACAUAAACGAACUUAU | 46 | AGGAGTCAAATTACATTACACATAAACGAACTTATGGATTTGTTT | 154 |

TABLE 6A-continued

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| 3a_25413 | CUUCACAAU UGGAACUGU AA | 47 | TTTGTTTATGAGAATCTTCACAATTGG AACTGTAACTTTGAAGCA | 155 |
| 3a_25630 | GUUUGCAAC UUGCUGUUG UU | 48 | AAGGGTGTTCACTTTGTTTGCAACTTG CTGTTGTTGTTTGTAACA | 156 |
| 3a_25717 | UAUGCUUUA GUCUACUUC UU | 49 | CCTTTTCTCTATCTTTATGCTTTAGTCT ACTTCTTGCAGAGTATA | 157 |
| 3a_25734 | CUUGCAGAG UAUAAACUU UG | 50 | TGCTTTAGTCTACTTCTTGCAGAGTAT AAACTTTGTAAGAATAAT | 158 |
| 3a_25736 | UGCAGAGUA UAAACUUUG UA | 51 | CTTTAGTCTACTTCTTGCAGAGTATAA ACTTTGTAAGAATAATAA | 159 |
| 3a_25745 | UAAACUUUG UAAGAAUA AUA | 52 | ACTTCTTGCAGAGTATAAACTTTGTAA GAATAATAATGAGGCTTT | 160 |
| 3a_25868 | CUUACAAUA GUGUAACUU CU | 53 | ACGACTATTGTATACCTTACAATAGTG TAACTTCTTCAATTGTCA | 161 |
| 3a_25870 | UACAAUAGU GUAACUUCU UC | 54 | GACTATTGTATACCTTACAATAGTGTA ACTTCTTCAATTGTCATT | 162 |
| 3a_25914 | CACAACAAG UCCUAUUUC UG | 55 | TACTTCAGGTGATGGCACAACAAGTCC TATTTCTGAACATGACTA | 163 |
| 3a_25992 | UGUUGUAU UACACAGUU ACU | 56 | TGGAGTAAAAGACTGTGTTGTATTACA CAGTTACTTCACTTCAGA | 164 |
| 3a_26018 | CAGACUAUU ACCAGCUGU AC | 57 | ACAGTTACTTCACTTCAGACTATTACC AGCTGTACTCAACTCAAT | 165 |
| 3a_26066 | UUGAACAUG UUACCUUCU UC | 58 | GTACAGACACTGGTGTTGAACATGTTA CCTTCTTCATCTACAATA | 166 |
| E_26258 | UUUCGGAAG AGACAGGUA CG | 59 | TTATGTACTCATTCGTTTCGGAAGAGA CAGGTACGTTAATAGTTA | 167 |
| E_26261 | CGGAAGAGA CAGGUACGU UA | 60 | TGTACTCATTCGTTTCGGAAGAGACAG GTACGTTAATAGTTAATA | 168 |
| E_26269 | ACAGGUACG UUAAUAGU UAA | 61 | TTCGTTTCGGAAGAGACAGGTACGTTA ATAGTTAATAGCGTACTT | 169 |
| E_26277 | GUUAAUAG UUAAUAGCG UAC | 62 | GGAAGAGACAGGTACGTTAATAGTTA ATAGCGTACTTCTTTTTCT | 170 |
| E_26305 | CUUGCUUUC GUGGUAUUC UU | 63 | AGCGTACTTCTTTTTCTTGCTTTCGTGG TATTCTTGCTAGTTACA | 171 |
| E_26313 | CGUGGUAUU CUUGCUAGU UA | 64 | TCTTTTTCTTGCTTTCGTGGTATTCTTG CTAGTTACACTAGCCAT | 172 |

TABLE 6A-continued

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| E_26369 | ACUGCUGCA AUAUUGUU AAC | 65 | TTCGATTGTGTGCGTACTGCTGCAATA TTGTTAACGTGAGTCTTG | 173 |
| E_26374 | UGCAAUAUU GUUAACGUG AG | 66 | TTGTGTGCGTACTGCTGCAATATTGTT AACGTGAGTCTTGTAAAA | 174 |
| E_26455 | CCUGAUCUU CUGGUCUAA AC | 67 | AATTCTTCTAGAGTTCCTGATCTTCTGG TCTAAACGAACTAAATA | 175 |
| E_26463 | UCUGGUCUA AACGAACUA AA | 68 | TAGAGTTCCTGATCTTCTGGTCTAAAC GAACTAAATATTATATTA | 176 |
| E_26467 | GUCUAAACG AACUAAAUA UU | 69 | GTTCCTGATCTTCTGGTCTAAACGAAC TAAATATTATATTAGTTT | 177 |
| E_26470 | UAAACGAAC UAAAUAUU AUA | 70 | CCTGATCTTCTGGTCTAAACGAACTAA ATATTATATTAGTTTTTC | 178 |
| M_26573 | UGAACAAUG GAACCUAGU AA | 71 | GCTTAAAAAGCTCCTTGAACAATGGAA CCTAGTAATAGGTTTCCT | 179 |
| M_26581 | GGAACCUAG UAAUAGGU UUC | 72 | AGCTCCTTGAACAATGGAACCTAGTAA TAGGTTTCCTATTCCTTA | 180 |
| M_26602 | UAUUCCUUA CAUGGAUUU GU | 73 | TAGTAATAGGTTTCCTATTCCTTACAT GGATTTGTCTTCTACAAT | 181 |
| M_26624 | UCUACAAUU UGCCUAUGC CA | 74 | TACATGGATTTGTCTTCTACAATTTGCC TATGCCAACAGGAATAG | 182 |
| M_26637 | UAUGCCAAC AGGAAUAG GUU | 75 | CTTCTACAATTTGCCTATGCCAACAGG AATAGGTTTTTGTATATA | 183 |
| M_26638 | AUGCCAACA GGAAUAGG UUU | 76 | TTCTACAATTTGCCTATGCCAACAGGA ATAGGTTTTTGTATATAA | 184 |
| M_26693 | AUGGCCAGU AACUUUAGC UU | 77 | TTTCCTCTGGCTGTTATGGCCAGTAAC TTTAGCTTGTTTTGTGCT | 185 |
| M_26717 | UGUGCUUGC UGCUGUUUA CA | 78 | AACTTTAGCTTGTTTTGTGCTTGCTGCT GTTTACAGAATAAATTG | 186 |
| M_27014 | GCCUAAAGA AAUCACUGU UG | 79 | TGACATCAAGGACCTGCCTAAAGAAA TCACTGTTGCTACATCACG | 187 |
| M_27032 | UGCUACAUC ACGAACGCU UU | 80 | TAAAGAAATCACTGTTGCTACATCACG AACGCTTTCTTATTACAA | 188 |
| M_27035 | UACAUCACG AACGCUUUC UU | 81 | AGAAATCACTGTTGCTACATCACGAAC GCTTTCTTATTACAAATT | 189 |
| M_27123 | AUUGGCAAC UAUAAAUU AAA | 82 | TACAGTCGCTACAGGATTGGCAACTAT AAATTAAACACAGACCAT | 190 |

TABLE 6A-continued

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| 7a_27455 | AAGAGUGU GUUAGAGG UACA | 83 | AGCTTTATCACTACCAAGAGTGTGTTA GAGGTACAACAGTACTTT | 191 |
| 7a_27522 | UUCACCAUU UCAUCCUCU AG | 84 | AACATACGAGGGCAATTCACCATTTCA TCCTCTAGCTGATAACAA | 192 |
| 7a_27537 | UCUAGCUGA UAACAAAUU UG | 85 | TTCACCATTTCATCCTCTAGCTGATAA CAAATTTGCACTGACTTG | 193 |
| 7a_27553 | UUUGCACUG ACUUGCUUU AG | 86 | CTAGCTGATAACAAATTTGCACTGACT TGCTTTAGCACTCAATTT | 194 |
| 7a_27565 | UGCUUUAGC ACUCAAUUU GC | 87 | AAATTTGCACTGACTTGCTTTAGCACT CAATTTGCTTTTGCTTGT | 195 |
| 7a_27633 | AUCAGUUUC ACCUAAACU GU | 88 | TCAGTTACGTGCCAGATCAGTTTCACC TAAACTGTTCATCAGACA | 196 |
| 7a_27656 | UCAGACAAG AGGAAGUUC AA | 89 | CACCTAAACTGTTCATCAGACAAGAGG AAGTTCAAGAACTTTACT | 197 |
| 7a_27671 | UUCAAGAAC UUUACUCUC CA | 90 | TCAGACAAGAGGAAGTTCAAGAACTT TACTCTCCAATTTTTCTTA | 198 |
| 7a_27705 | UGCGGCAAU AGUGUUUA UAA | 91 | AATTTTTCTTATTGTTGCGGCAATAGT GTTTATAACACTTTGCTT | 199 |
| 7a_27715 | GUGUUUAU AACACUUUG CUU | 92 | ATTGTTGCGGCAATAGTGTTTATAACA CTTTGCTTCACACTCAAA | 200 |
| 7a_27720 | UAUAACACU UUGCUUCAC AC | 93 | TGCGGCAATAGTGTTTATAACACTTTG CTTCACACTCAAAAGAAA | 201 |
| 7a_27751 | ACAGAAUGA UUGAACUUU CA | 94 | ACACTCAAAAGAAAGACAGAATGATT GAACTTTCATTAATTGACT | 202 |
| 8b_27932 | AGCUGCAUU UCACCAAGA AU | 95 | AATCATCACAACTGTAGCTGCATTTCA CCAAGAATGTAGTTTACA | 203 |
| 8b_27940 | UUCACCAAG AAUGUAGU UUA | 96 | CAACTGTAGCTGCATTTCACCAAGAAT GTAGTTTACAGTCATGTA | 204 |
| 8b_27986 | UGUAGUUG AUGACCCGU GUC | 97 | TCAACATCAACCATATGTAGTTGATGA CCCGTGTCCTATTCACTT | 205 |
| 8b_28002 | UGUCCUAUU CACUUCUAU UC | 98 | GTAGTTGATGACCCGTGTCCTATTCAC TTCTATTCTAAATGGTAT | 206 |
| 8b_28024 | AAUGGUAU AUUAGAGU AGGA | 99 | TTCACTTCTATTCTAAATGGTATATTAG AGTAGGAGCTAGAAAAT | 207 |
| 8b_28091 | UUCUAAAUC ACCCAUUCA GU | 100 | CGTGGATGAGGCTGGTTCTAAATCACC CATTCAGTACATCGATAT | 208 |

TABLE 6A-continued

SARS-CoV2 Screened-20 nucleotide target sequences and 45 nucleotide target gene regions

| Sequence ID | 20 nt Sequence | SEQ ID NO: | 45 nt Gene Region | SEQ ID NO: |
|---|---|---|---|---|
| 8b_28119 | AUCGGUAAU UAUACAGUU UC | 101 | ATTCAGTACATCGATATCGGTAATTAT ACAGTTTCCTGTTTACCT | 209 |
| 8b_28127 | UUAUACAGU UUCCUGUUU AC | 102 | CATCGATATCGGTAATTATACAGTTTC CTGTTTACCTTTTACAAT | 210 |
| 8b_28128 | UAUACAGUU UCCUGUUUA CC | 103 | ATCGATATCGGTAATTATACAGTTTCC TGTTTACCTTTTACAATT | 211 |
| 8b_28163 | CCAGGAACC UAAAUUGG GUA | 104 | TTTTACAATTAATTGCCAGGAACCTAA ATTGGGTAGTCTTGTAGT | 212 |
| 8b_28218 | UUAGAGUA UCAUGACGU UCG | 105 | TTCTATGAAGACTTTTTAGAGTATCAT GACGTTCGTGTTGTTTTA | 213 |
| 8b_28222 | AGUAUCAUG ACGUUCGUG UU | 106 | ATGAAGACTTTTTAGAGTATCATGACG TTCGTGTTGTTTTAGATT | 214 |
| N_28407 | UACCCAAUA AUACUGCGU CU | 107 | GTCGGCCCCAAGGTTTACCCAATAATA CTGCGTCTTGGTTCACCG | 215 |
| N_28655 | GACGGCAUC AUAUGGGU UGC | 108 | TATGGTGCTAACAAAGACGGCATCATA TGGGTTGCAACTGAGGGA | 216 |
| N_28945 | UGACAGAUU GAACCAGCU UG | 109 | TGCTTTGCTGCTGCTTGACAGATTGAA CCAGCTTGAGAGCAAAAT | 217 |
| N_28992 | AACAACAAG GCCAAACUG UC | 110 | CTGGTAAAGGCCAACAACAACAAGGC CAAACTGTCACTAAGAAAT | 218 |
| N_29141 | GAACUAAUC AGACAAGGA AC | 111 | AATTTTGGGGACCAGGAACTAATCAG ACAAGGAACTGATTACAAA | 219 |
| N_29276 | GGUGCCAUC AAAUUGGA UGA | 112 | TGGTTGACCTACACAGGTGCCATCAAA TTGGATGACAAAGATCCA | 220 |
| N_29292 | AUGACAAAG AUCCAAAUU UC | 113 | GTGCCATCAAATTGGATGACAAAGATC CAAATTTCAAAGATCAAG | 221 |
| N_29293 | UGACAAAGA UCCAAAUUU CA | 114 | TGCCATCAAATTGGATGACAAAGATCC AAATTTCAAAGATCAAGT | 222 |
| N_29303 | CCAAAUUUC AAAGAUCAA GU | 115 | TTGGATGACAAAGATCCAAATTTCAAA GATCAAGTCATTTTGCTG | 223 |
| N_29307 | AUUUCAAAG AUCAAGUCA UU | 116 | ATGACAAAGATCCAAATTTCAAAGATC AAGTCATTTTGCTGAATA | 224 |
| N_29328 | UGCUGAAUA AGCAUAUUG AC | 117 | AAGATCAAGTCATTTTGCTGAATAAGC ATATTGACGCATACAAAA | 225 |
| N_29464 | UGCAGAUUU GGAUGAUU UCU | 118 | GACTCTTCTTCCTGCTGCAGATTTGGA TGATTTCTCCAAACAATT | 226 |

TABLE 6B

Modified antisense strand (21 nucleotide length for screening)

| Sequence ID | Modified AS strand (21mer for screening) | SEQ ID NO: |
|---|---|---|
| orflab_14080 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_14361 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_14830 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_15376 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_15786 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_17107 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_17370 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_18025 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_18571 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_20497 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_20892 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orflab_21391 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_416 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_2290 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_6059 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_6322 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_6499 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_7643 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_8200 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_8201 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_8744 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_9679 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_11594 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| orfla_12932 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_21944 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_22223 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_22550 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_22820 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_22898 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_23174 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_23239 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_23240 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_23774 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_24056 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_24289 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| S_25375 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25413 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25630 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25717 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25734 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25736 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25745 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25868 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25870 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25914 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_25992 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_26018 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 3a_26066 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26258 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26261 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26269 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26277 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26305 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26313 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26369 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26374 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26455 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26463 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26467 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| E_26470 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26573 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26581 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26602 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26624 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26637 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26638 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26693 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_26717 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_27014 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_27032 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_27035 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| M_27123 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27455 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27522 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27537 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |

TABLE 6B-continued

Modified antisense strand (21 nucleotide length for screening)

| Sequence ID | Modified AS strand (21mer for screening) | SEQ ID NO: |
|---|---|---|
| 7a_27553 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a 27565 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27633 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27656 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27671 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27705 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27715 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27720 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 7a_27751 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_27932 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_27940 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_27986 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28002 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28024 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28091 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28119 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28127 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28128 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28163 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28218 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| 8b_28222 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_28407 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_28655 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_28945 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_28992 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29141 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29276 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29292 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29293 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29303 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29307 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29328 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |
| N_29464 | P(mU)#(fA)#(mA)(mC)(mA)(fU)(mG)(mA)(mA)(mU)(mA)(mC)(mU)(fU)#(mG)#(fG)#(mC)#(mU)#(mU)#(mU)#(mU) | 227 |

TABLE 6C

Modified sense strand - 16 nucleotides in length

| Sequence ID | Modified sense strand 16 nt | SEQ ID NO: |
|---|---|---|
| orflab_14080 | (mA)#(mU)#(mC)(mA)(fU)(fA)(fC)(mC)(fA)(mG)(mU)(mU)(mA)#(mC)#(mA)-TegChol | 228 |
| orflab_14361 | (mG)#(mU)#(mU)(mU)(mG)(fC)(fA)(fC)(mA)(fA)(mU)(mG)(mC)(mA)#(mG)#(mA)-TegChol | 229 |
| orflab_14830 | (mU)#(mU)#(mU)(mG)(fC)(fA)(fC)(mA)(fA)(mU)(mG)(mC)(mA)#(mG)#(mA)-TegChol | 230 |
| orflab_15376 | (mG)#(mU)#(mG)(mU)(fG)(fA)(fC)(mA)(fA)(mG)(mC)(mU)(mA)#(mC)#(mA)-TegChol | 231 |
| orflab_15786 | (mU)#(mA)#(mA)(mA)(fG)(fA)(fA)(mC)(fU)(mG)(mA)(mC)(mU)#(mU)#(mA)-TegChol | 232 |
| orflab_17107 | (mU)#(mA)#(mG)(mG)(fC)(fC)(fA)(mA)(fU)(mA)(mG)(mC)(mA)#(mA)#(mA)-TegChol | 233 |
| orflab_17370 | (mU)#(mC)#(mA)(mU)(fA)(fA)(fU)(mU)(fU)(mG)(mU)(mG)(mG)#(mC)#(mA)-TegChol | 234 |
| orflab_18025 | (mU)#(mU)#(mG)(mU)(fA)(fA)(fA)(mG)(fU)(mU)(mG)(mC)(mC)#(mA)#(mA)-TegChol | 235 |
| orflab_18571 | (mU)#(mA)#(mC)(mG)(fA)(fC)(fU)(mC)(fU)(mG)(mU)(mC)(mA)#(mG)#(mA)-TegChol | 236 |
| orflab_20497 | (mU)#(mA)#(mA)(mA)(fU)(fC)(fA)(mA)(fU)(mA)(mA)(mC)(mA)#(mG)#(mA)-TegChol | 237 |
| orflab_20892 | (mG)#(mC)#(mU)(mG)(fU)(fA)(fC)(mC)(fU)(mG)(mG)(mU)(mG)#(mC)#(mA)-TegChol | 238 |
| orflab_21391 | (mU)#(mU)#(mU)(mA)(fC)(fU)(fC)(mA)(fU)(mG)(mU)(mC)(mA)#(mA)#(mA)-TegChol | 239 |
| orfla_416 | (mU)#(mU)#(mC)(mU)(fA)(fC)(fU)(mA)(fA)(mG)(mC)(mC)(mA)#(mC)#(mA)-TegChol | 240 |
| orfla_2290 | (mU)#(mU)#(mA)(mA)(fA)(fG)(fA)(mA)(fU)(mG)(mU)(mC)(mU)#(mG)#(mA)-TegChol | 241 |
| orfla_6059 | (mU)#(mU)#(mU)(mG)(fA)(fU)(fA)(mU)(fU)(mA)(mU)(mC)(mA)#(mC)#(mA)-TegChol | 242 |
| orfla_6322 | (mG)#(mA)#(mA)(mU)(fU)(fU)(fG)(mA)(fU)(mG)(mU)(mU)(mU)#(mC)#(mA)-TegChol | 243 |
| orfla_6499 | (mC)#(mU)#(mA)(mU)(fU)(fA)(fU)(mU)(fU)(mG)(mC)(mU)(mG)#(mG)#(mA)-TegChol | 244 |
| orfla_7643 | (mA)#(mA)#(mA)(mU)(fG)(fU)(fA)(mC)(fU)(mA)(mC)(mC)(mA)#(mA)#(mA)-TegChol | 245 |
| orfla_8200 | (mU)#(mC)#(mU)(mU)(fU)(fA)(fG)(mU)(fU)(mU)(mC)(mU)(mA)#(mC)#(mA)-TegChol | 246 |
| orfla_8201 | (mA)#(mU)#(mC)(mU)(fU)(fU)(fA)(mG)(fU)(mU)(mU)(mC)(mU)#(mA)#(mA)-TegChol | 247 |
| orfla_8744 | (mA)#(mU)#(mG)(mU)(fU)(fU)(fG)(mU)(fU)(mA)(mG)(mC)(mA)#(mA)#(mA)-TegChol | 248 |
| orfla_9679 | (mG)#(mC)#(mA)(mA)(fU)(fU)(fG)(mU)(fU)(mA)(mU)(mC)(mC)#(mA)#(mA)-TegChol | 249 |
| orfla_11594 | (mU)#(mA)#(mG)(mC)(fA)(fU)(fU)(mA)(fU)(mA)(mC)(mA)(mC)#(mU)#(mA)-TegChol | 250 |
| orfla_12932 | (mA)#(mU)#(mA)(mC)(fU)(fU)(fC)(mA)(fC)(mU)(mU)(mU)(mA)#(mG)#(mA)-TegChol | 251 |
| S_21944 | (mU)#(mU)#(mC)(mA)(fC)(fA)(fG)(mA)(fC)(mU)(mU)(mU)(mA)#(mA)#(mA)-TegChol | 252 |
| S_22223 | (mU)#(mG)#(mG)(mU)(fU)(fC)(fU)(mA)(fA)(mA)(mG)(mC)(mC)#(mG)#(mA)-TegChol | 253 |
| S_22550 | (mG)#(mU)#(mU)(mU)(fG)(fU)(fA)(mA)(fU)(mA)(mU)(mU)(mA)#(mG)#(mA)-TegChol | 254 |
| S_22820 | (mU)#(mU)#(mU)(mA)(fU)(fA)(fA)(mU)(fU)(mA)(mU)(mA)(mA)#(mU)#(mA)-TegChol | 255 |
| S_22898 | (mA)#(mU)#(mU)(mA)(fU)(fA)(fA)(mU)(fU)(mA)(mC)(mC)(mA)#(mC)#(mA)-TegChol | 256 |
| S_23174 | (mG)#(mU)#(mU)(mG)(fA)(fA)(fA)(mU)(fU)(mG)(mA)(mC)(mA)#(mC)#(mA)-TegChol | 257 |

TABLE 6C-continued

Modified sense strand - 16 nucleotides in length

| Sequence ID | Modified sense strand 16 nt | SEQ ID NO: |
|---|---|---|
| S_23239 | (mU)#(mG)#(mU)(mU)(fG)(fG)(fA)(mA)(fA)(mG)(mG)(mC)(mA)#(mG)#(mA)-TegChol | 258 |
| S_23240 | (mU)#(mU)#(mG)(mU)(fU)(fG)(fG)(mA)(fA)(mA)(mG)(mG)(mC)#(mA)#(mA)-TegChol | 259 |
| S_23774 | (mA)#(mA)#(mU)(mG)(fU)(fA)(fC)(mA)(fU)(mU)(mG)(mU)(mA)#(mC)#(mA)-TegChol | 260 |
| S_24056 | (mU)#(mU)#(mG)(mU)(fU)(fU)(fG)(mA)(fU)(mG)(mA)(mA)(mG)#(mC)#(mA)-TegChol | 261 |
| S_24289 | (mU)#(mU)#(mC)(mU)(fG)(fU)(fG)(mU)(fA)(mA)(mC)(mU)(mC)#(mC)#(mA)-TegChol | 262 |
| S_25375 | (mU)#(mU)#(mC)(mG)(fU)(fU)(fU)(mA)(fU)(mG)(mU)(mG)(mU)#(mA)#(mA)-TegChol | 263 |
| 3a_25413 | (mG)#(mU)#(mU)(mC)(fC)(fA)(fA)(mU)(fU)(mG)(mU)(mG)(mA)#(mA)#(mA)-TegChol | 264 |
| 3a_25630 | (mC)#(mA)#(mG)(mC)(fA)(fA)(fG)(mU)(fU)(mG)(mC)(mA)(mA)#(mA)#(mA)-TegChol | 265 |
| 3a_25717 | (mG)#(mU)#(mA)(mG)(fA)(fC)(fU)(mA)(fA)(mA)(mG)(mC)(mA)#(mU)#(mA)-TegChol | 266 |
| 3a_25734 | (mU)#(mU)#(mU)(mA)(fU)(fA)(fC)(mU)(fC)(mU)(mG)(mC)(mA)#(mA)#(mA)-TegChol | 267 |
| 3a_25736 | (mA)#(mG)#(mU)(mU)(fU)(fA)(fU)(mA)(fC)(mU)(mC)(mU)(mG)#(mC)#(mA)-TegChol | 268 |
| 3a_25745 | (mU)#(mU)#(mC)(mU)(fU)(fA)(fC)(mA)(fA)(mA)(mG)(mU)(mU)#(mU)#(mA)-TegChol | 269 |
| 3a_25868 | (mU)#(mU)#(mA)(mC)(fA)(fC)(fU)(mA)(fU)(mU)(mG)(mU)(mA)#(mA)#(mA)-TegChol | 270 |
| 3a_25870 | (mA)#(mG)#(mU)(mU)(fA)(fC)(fA)(mC)(fU)(mA)(mU)(mU)(mG)#(mU)#(mA)-TegChol | 271 |
| 3a_25914 | (mA)#(mU)#(mA)(mG)(fG)(fA)(fC)(mU)(fU)(mG)(mU)(mU)(mG)#(mU)#(mA)-TegChol | 272 |
| 3a_25992 | (mC)#(mU)#(mG)(mU)(fG)(fU)(fA)(mA)(fU)(mA)(mC)(mA)(mA)#(mC)#(mA)-TegChol | 273 |
| 3a_26018 | (mG)#(mC)#(mU)(mG)(fG)(fU)(fA)(mA)(fU)(mA)(mG)(mU)(mC)#(mU)#(mA)-TegChol | 274 |
| 3a_26066 | (mA)#(mG)#(mG)(mU)(fA)(fA)(fC)(mA)(fU)(mG)(mU)(mU)(mC)#(mA)#(mA)-TegChol | 275 |
| E_26258 | (mC)#(mU)#(mG)(mU)(fC)(fU)(fC)(mU)(fU)(mC)(mC)(mG)(mA)#(mA)#(mA)-TegChol | 276 |
| E_26261 | (mU)#(mA)#(mC)(mC)(fU)(fG)(fU)(mC)(fU)(mC)(mU)(mU)(mC)#(mC)#(mA)-TegChol | 277 |
| E_26269 | (mU)#(mA)#(mU)(mU)(fA)(fA)(fC)(mG)(fU)(mA)(mC)(mC)(mU)#(mG)#(mA)-TegChol | 278 |
| E_26277 | (mC)#(mU)#(mA)(mU)(fU)(fA)(fA)(mC)(fU)(mA)(mU)(mU)(mA)#(mA)#(mA)-TegChol | 279 |
| E_26305 | (mU)#(mA)#(mC)(mC)(fA)(fC)(fG)(mA)(fA)(mA)(mG)(mC)(mA)#(mA)#(mA)-TegChol | 280 |
| E_26313 | (mA)#(mG)#(mC)(mA)(fA)(fG)(fA)(mA)(fU)(mA)(mC)(mC)(mA)#(mC)#(mA)-TegChol | 281 |
| E_26369 | (mC)#(mA)#(mA)(mU)(fA)(fU)(fU)(mG)(fC)(mA)(mG)(mC)(mA)#(mG)#(mA)-TegChol | 282 |
| E_26374 | (mG)#(mU)#(mU)(mA)(fA)(fC)(fA)(mA)(fU)(mA)(mU)(mU)(mG)#(mC)#(mA)-TegChol | 283 |
| E_26455 | (mG)#(mA)#(mC)(mC)(fA)(fG)(fA)(mA)(fG)(mA)(mU)(mC)(mA)#(mG)#(mA)-TegChol | 284 |
| E_26463 | (mU)#(mU)#(mC)(mG)(fU)(fU)(fU)(mA)(fG)(mA)(mC)(mC)(mA)#(mG)#(mA)-TegChol | 285 |
| E_26467 | (mU)#(mU)#(mA)(mG)(fU)(fU)(fC)(mG)(fU)(mU)(mU)(mA)(mG)#(mA)#(mA)-TegChol | 286 |
| E_26470 | (mU)#(mA)#(mU)(mU)(fU)(fA)(fG)(mU)(fU)(mC)(mG)(mU)(mU)#(mU)#(mA)-TegChol | 287 |
| M_26573 | (mA)#(mG)#(mG)(mU)(fU)(fC)(fC)(mA)(fU)(mU)(mG)(mU)(mU)#(mC)#(mA)-TegChol | 288 |
| M_26581 | (mC)#(mU)#(mA)(mU)(fU)(fA)(fC)(mU)(fA)(mG)(mG)(mU)(mU)#(mC)#(mA)-TegChol | 289 |
| M_26602 | (mU)#(mC)#(mC)(mA)(fU)(fG)(fU)(mA)(fA)(mG)(mG)(mA)(mA)#(mU)#(mA)-TegChol | 290 |
| M_26624 | (mU)#(mA)#(mG)(mG)(fC)(fA)(fA)(mA)(fU)(mU)(mG)(mU)(mA)#(mG)#(mA)-TegChol | 291 |
| M_26637 | (mA)#(mU)#(mU)(mC)(fC)(fU)(fG)(mU)(fU)(mG)(mG)(mC)(mA)#(mU)#(mA)-TegChol | 292 |
| M_26638 | (mU)#(mA)#(mU)(mU)(fC)(fC)(fU)(mG)(fU)(mU)(mG)(mG)(mC)#(mA)#(mA)-TegChol | 293 |
| M_26693 | (mA)#(mA)#(mA)(mG)(fU)(fU)(fA)(mC)(fU)(mG)(mG)(mC)(mC)#(mA)#(mA)-TegChol | 294 |
| M_26717 | (mA)#(mC)#(mA)(mG)(fC)(fA)(fG)(mC)(fA)(mA)(mG)(mC)(mA)#(mC)#(mA)-TegChol | 295 |
| M_27014 | (mG)#(mU)#(mG)(mA)(fU)(fU)(fU)(mC)(fU)(mU)(mU)(mA)(mG)#(mG)#(mA)-TegChol | 296 |
| M_27032 | (mG)#(mU)#(mU)(mC)(fG)(fU)(fG)(mA)(fU)(mG)(mU)(mA)(mG)#(mC)#(mA)-TegChol | 297 |
| M_27035 | (mA)#(mG)#(mC)(mG)(fU)(fU)(fC)(mG)(fU)(mG)(mA)(mU)(mG)#(mU)#(mA)-TegChol | 298 |
| M_27123 | (mU)#(mU)#(mU)(mA)(fU)(fA)(fG)(mU)(fU)(mG)(mC)(mC)(mA)#(mA)#(mA)-TegChol | 299 |
| 7a_27455 | (mC)#(mU)#(mC)(mU)(fA)(fA)(fC)(mA)(fC)(mA)(mC)(mU)(mC)#(mU)#(mA)-TegChol | 300 |
| 7a_27522 | (mG)#(mG)#(mA)(mU)(fG)(fA)(fA)(mA)(fU)(mG)(mG)(mU)(mG)#(mA)#(mA)-TegChol | 301 |
| 7a_27537 | (mU)#(mU)#(mG)(mU)(fU)(fA)(fU)(mC)(fA)(mG)(mC)(mU)(mA)#(mG)#(mA)-TegChol | 302 |
| 7a_27553 | (mG)#(mC)#(mA)(mA)(fG)(fU)(fC)(mA)(fG)(mU)(mG)(mC)(mA)#(mA)#(mA)-TegChol | 303 |
| 7a_27565 | (mU)#(mU)#(mG)(mA)(fG)(fU)(fG)(mC)(fU)(mA)(mA)(mA)(mG)#(mC)#(mA)-TegChol | 304 |
| 7a_27633 | (mU)#(mU)#(mA)(mG)(fG)(fU)(fG)(mA)(fA)(mA)(mC)(mU)(mG)#(mA)#(mA)-TegChol | 305 |
| 7a_27656 | (mC)#(mU)#(mU)(mC)(fC)(fU)(fC)(mU)(fU)(mG)(mU)(mC)(mU)#(mG)#(mA)-TegChol | 306 |
| 7a_27671 | (mA)#(mG)#(mU)(mA)(fA)(fA)(fG)(mU)(fU)(mC)(mU)(mU)(mG)#(mA)#(mA)-TegChol | 307 |
| 7a_27705 | (mA)#(mA)#(mC)(mA)(fC)(fU)(fA)(mU)(fU)(mG)(mC)(mC)(mG)#(mC)#(mA)-TegChol | 308 |
| 7a_27715 | (mA)#(mA)#(mG)(mU)(fG)(fU)(fU)(mA)(fU)(mA)(mA)(mA)(mC)#(mA)#(mA)-TegChol | 309 |
| 7a_27720 | (mA)#(mA)#(mG)(mC)(fA)(fA)(fA)(mG)(fU)(mG)(mU)(mU)(mA)#(mU)#(mA)-TegChol | 310 |
| 7a_27751 | (mG)#(mU)#(mU)(mC)(fA)(fA)(fU)(mC)(fA)(mU)(mU)(mC)(mU)#(mG)#(mA)-TegChol | 311 |
| 8b_27932 | (mU)#(mG)#(mG)(mU)(fG)(fA)(fA)(mA)(fU)(mG)(mC)(mA)(mG)#(mC)#(mA)-TegChol | 312 |
| 8b_27940 | (mU)#(mA)#(mC)(mA)(fU)(fU)(fC)(mU)(fU)(mG)(mG)(mU)(mG)#(mA)#(mA)-TegChol | 313 |
| 8b_27986 | (mG)#(mG)#(mG)(mU)(fC)(fA)(fU)(mC)(fA)(mA)(mC)(mU)(mA)#(mC)#(mA)-TegChol | 314 |
| 8b_28002 | (mG)#(mA)#(mA)(mG)(fU)(fG)(fA)(mA)(fU)(mA)(mG)(mG)(mA)#(mC)#(mA)-TegChol | 315 |
| 8b_28024 | (mC)#(mU)#(mC)(mU)(fA)(fA)(fU)(mA)(fU)(mA)(mC)(mC)(mA)#(mU)#(mA)-TegChol | 316 |
| 8b_28091 | (mA)#(mU)#(mG)(mG)(fG)(fU)(fG)(mA)(fU)(mU)(mU)(mA)(mG)#(mA)#(mA)-TegChol | 317 |
| 8b_28119 | (mU)#(mG)#(mU)(mA)(fU)(fA)(fA)(mU)(fU)(mA)(mC)(mC)(mG)#(mA)#(mA)-TegChol | 318 |
| 8b_28127 | (mC)#(mA)#(mG)(mG)(fA)(fA)(fA)(mC)(fU)(mG)(mU)(mA)(mU)#(mA)#(mA)-TegChol | 319 |
| 8b_28128 | (mA)#(mC)#(mA)(mG)(fG)(fA)(fA)(mA)(fC)(mU)(mG)(mU)(mA)#(mU)#(mA)-TegChol | 320 |
| 8b_28163 | (mA)#(mA)#(mU)(mU)(fU)(fA)(fG)(mG)(fU)(mU)(mC)(mC)(mU)#(mG)#(mA)-TegChol | 321 |
| 8b_28218 | (mG)#(mU)#(mC)(mA)(fU)(fG)(fA)(mU)(fA)(mC)(mU)(mC)(mU)#(mA)#(mA)-TegChol | 322 |
| 8b_28222 | (mG)#(mA)#(mA)(mC)(fG)(fU)(fC)(mA)(fU)(mG)(mA)(mU)(mA)#(mC)#(mA)-TegChol | 323 |
| N_28407 | (mC)#(mA)#(mG)(mU)(fA)(fU)(fU)(mA)(fU)(mU)(mG)(mG)(mG)#(mU)#(mA)-TegChol | 324 |
| N_28655 | (mC)#(mC)#(mA)(mU)(fA)(fU)(fG)(mA)(fU)(mG)(mC)(mC)(mG)#(mU)#(mA)-TegChol | 325 |
| N_28945 | (mU)#(mG)#(mG)(mU)(fU)(fC)(fA)(mA)(fU)(mC)(mU)(mG)(mU)#(mC)#(mA)-TegChol | 326 |
| N_28992 | (mU)#(mU)#(mU)(mG)(fG)(fC)(fC)(mU)(fU)(mG)(mU)(mU)(mG)#(mU)#(mA)-TegChol | 327 |
| N_29141 | (mU)#(mU)#(mG)(mU)(fC)(fU)(fG)(mA)(fU)(mU)(mA)(mG)(mU)#(mU)#(mA)-TegChol | 328 |
| N_29276 | (mC)#(mA)#(mA)(mU)(fU)(fU)(fG)(mA)(fU)(mG)(mG)(mC)(mA)#(mC)#(mA)-TegChol | 329 |
| N_29292 | (mU)#(mU)#(mG)(mG)(fA)(fU)(fC)(mU)(fU)(mU)(mG)(mU)(mC)#(mA)#(mA)-TegChol | 330 |
| N_29293 | (mU)#(mU)#(mU)(mG)(fG)(fA)(fU)(mC)(fU)(mU)(mU)(mG)(mU)#(mC)#(mA)-TegChol | 331 |

TABLE 6C-continued

| Sequence ID | Modified sense strand 16 nt | SEQ ID NO: |
|---|---|---|
| Modified sense strand - 16 nucleotides in length | | |
| N_29303 | (mA)#(mU)#(mC)(mU)(fU)(fU)(fG)(mA)(fA)(mA)(mU)(mU)(mU)#(mG)#(mA)-TegChol | 332 |
| N_29307 | (mC)#(mU)#(mU)(mG)(fA)(fU)(fC)(mU)(fU)(mU)(mG)(mA)(mA)#(mA)#(mA)-TegChol | 333 |
| N_29328 | (mU)#(mA)#(mU)(mG)(fC)(fU)(fU)(mA)(fU)(mU)(mC)(mA)(mG)#(mC)#(mA)-TegChol | 334 |
| N_29464 | (mU)#(mC)#(mA)(mU)(fC)(fC)(fA)(mA)(fA)(mU)(mC)(mU)(mG)#(mC)#(mA)-TegChol | 335 |

TABLE 6D

| Sequence ID | Modified sense strand 18 nt | SEQ ID NO: |
|---|---|---|
| Modified sense strand - 18 nucleotides in length | | |
| orf1ab_14080 | (mG)#(mA)#(mA)(mA)(mU)(mC)(mA)(mU)(mA)(mC)(mC)(mA)(mG)(mU)(mU)(mA)#(mC)#(mA) | 336 |
| orf1ab_14361 | (mA)#(mA)#(mG)(mU)(mU)(mU)(mG)(mC)(mA)(mC)(mA)(mA)(mU)(mG)(mC)(mA)#(mG)#(mA) | 337 |
| orf1ab_14830 | (mU)#(mA)#(mG)(mU)(mU)(mG)(mU)(mC)(mU)(mG)(mA)(mU)(mA)(mU)(mC)(mA)#(mC)#(mA) | 338 |
| orf1ab_15376 | (mA)#(mC)#(mG)(mG)(mU)(mG)(mU)(mG)(mA)(mC)(mA)(mA)(mG)(mC)(mU)(mA)#(mC)#(mA) | 339 |
| orf1ab_15786 | (mU)#(mA)#(mA)(mU)(mA)(mA)(mA)(mG)(mA)(mA)(mC)(mU)(mG)(mA)(mC)(mU)#(mU)#(mA) | 340 |
| orf1ab_17107 | (mA)#(mG)#(mC)(mU)(mA)(mG)(mG)(mC)(mC)(mA)(mA)(mU)(mA)(mG)(mC)(mA)#(mA)#(mA) | 341 |
| orf1ab_17370 | (mA)#(mA)#(mA)(mU)(mC)(mA)(mU)(mA)(mA)(mU)(mU)(mU)(mG)(mU)(mG)(mG)#(mC)#(mA) | 342 |
| orf1ab_18025 | (mA)#(mG)#(mC)(mU)(mU)(mG)(mU)(mA)(mA)(mA)(mG)(mU)(mU)(mG)(mC)(mC)#(mA)#(mA) | 343 |
| orf1ab_18571 | (mA)#(mA)#(mA)(mU)(mA)(mC)(mG)(mA)(mC)(mU)(mC)(mU)(mG)(mU)(mC)(mA)#(mG)#(mA) | 344 |
| orf1ab_20497 | (mU)#(mA)#(mA)(mU)(mA)(mA)(mA)(mU)(mC)(mA)(mA)(mU)(mA)(mA)(mC)(mA)#(mG)#(mA) | 345 |
| orf1ab_20892 | (mA)#(mC)#(mA)(mG)(mC)(mU)(mG)(mU)(mA)(mC)(mC)(mU)(mG)(mG)(mU)(mG)#(mC)#(mA) | 346 |
| orf1ab_21391 | (mA)#(mA)#(mA)(mU)(mU)(mU)(mA)(mC)(mU)(mC)(mA)(mU)(mG)(mU)(mC)(mA)#(mA)#(mA) | 347 |
| orf1a_416 | (mA)#(mA)#(mC)(mU)(mU)(mC)(mU)(mA)(mC)(mU)(mA)(mA)(mG)(mC)(mC)(mA)#(mC)#(mA) | 348 |
| orf1a_2290 | (mA)#(mG)#(mC)(mU)(mU)(mA)(mA)(mA)(mG)(mA)(mA)(mU)(mG)(mU)(mC)(mU)#(mG)#(mA) | 349 |
| orf1a_6059 | (mA)#(mA)#(mA)(mU)(mU)(mU)(mG)(mA)(mU)(mA)(mU)(mU)(mA)(mU)(mC)(mA)#(mC)#(mA) | 350 |
| orf1a_6322 | (mA)#(mA)#(mC)(mG)(mA)(mA)(mU)(mU)(mU)(mG)(mA)(mU)(mG)(mU)(mU)(mU)#(mC)#(mA) | 351 |
| orf1a_6499 | (mA)#(mA)#(mA)(mC)(mU)(mA)(mU)(mU)(mA)(mU)(mU)(mU)(mG)(mC)(mU)(mG)#(mG)#(mA) | 352 |
| orf1a_7643 | (mA)#(mA)#(mU)(mA)(mA)(mA)(mU)(mG)(mU)(mA)(mC)(mU)(mA)(mC)(mC)(mA)#(mG)#(mA) | 353 |
| orf1a_8200 | (mA)#(mC)#(mA)(mU)(mC)(mU)(mU)(mU)(mA)(mG)(mU)(mU)(mU)(mC)(mU)(mA)#(mC)#(mA) | 354 |
| orf1a_8201 | (mA)#(mA)#(mC)(mA)(mU)(mC)(mU)(mU)(mU)(mA)(mG)(mU)(mU)(mU)(mC)(mU)#(mA)#(mA) | 355 |
| orf1a_8744 | (mA)#(mG)#(mC)(mA)(mU)(mG)(mU)(mU)(mU)(mG)(mU)(mU)(mA)(mG)(mC)(mA)#(mA)#(mA) | 356 |
| orf1a_9679 | (mU)#(mA)#(mA)(mG)(mC)(mA)(mA)(mU)(mU)(mG)(mU)(mU)(mA)(mU)(mC)(mC)#(mA)#(mA) | 357 |
| orf1a_11594 | (mA)#(mA)#(mC)(mU)(mA)(mG)(mC)(mA)(mU)(mU)(mA)(mU)(mA)(mC)(mA)(mC)#(mU)#(mA) | 358 |
| orf1a_12932 | (mU)#(mA)#(mA)(mA)(mU)(mA)(mC)(mU)(mU)(mC)(mA)(mC)(mU)(mU)(mU)(mA)#(mG)#(mA) | 359 |
| S_21944 | (mA)#(mA)#(mA)(mU)(mU)(mC)(mA)(mC)(mA)(mG)(mA)(mC)(mU)(mU)(mU)(mA)#(mA)#(mA) | 360 |
| S_22223 | (mC)#(mA)#(mA)(mU)(mG)(mG)(mU)(mU)(mC)(mU)(mA)(mA)(mA)(mG)(mC)(mC)#(mG)#(mA) | 361 |
| S_22550 | (mC)#(mA)#(mA)(mG)(mU)(mU)(mU)(mG)(mU)(mA)(mA)(mU)(mA)(mU)(mU)(mA)#(mG)#(mA) | 362 |
| S_22820 | (mU)#(mA)#(mA)(mU)(mU)(mU)(mA)(mU)(mA)(mA)(mU)(mU)(mA)(mU)(mA)(mA)#(mU)#(mA) | 363 |
| S_22898 | (mG)#(mU)#(mA)(mA)(mU)(mU)(mA)(mU)(mA)(mA)(mU)(mU)(mA)(mC)(mC)(mA)#(mC)#(mA) | 364 |
| S_23174 | (mG)#(mA)#(mA)(mG)(mU)(mU)(mG)(mA)(mA)(mA)(mU)(mU)(mG)(mA)(mC)(mA)#(mC)#(mA) | 365 |
| S_23239 | (mA)#(mA)#(mU)(mU)(mG)(mU)(mU)(mG)(mG)(mA)(mA)(mA)(mG)(mG)(mC)(mA)#(mG)#(mA) | 366 |
| S_23240 | (mA)#(mA)#(mA)(mU)(mU)(mG)(mU)(mU)(mG)(mG)(mA)(mA)(mA)(mG)(mG)(mC)#(mA)#(mA) | 367 |
| S_23774 | (mA)#(mC)#(mA)(mA)(mA)(mU)(mG)(mU)(mA)(mC)(mA)(mU)(mU)(mG)(mU)(mA)#(mC)#(mA) | 368 |
| S_24056 | (mA)#(mU)#(mA)(mU)(mU)(mG)(mU)(mU)(mU)(mG)(mA)(mU)(mG)(mA)(mA)(mG)#(mC)#(mA) | 369 |
| S_24289 | (mA)#(mC)#(mA)(mU)(mU)(mC)(mU)(mG)(mU)(mG)(mU)(mA)(mA)(mC)(mU)(mC)#(mC)#(mA) | 370 |
| S_25375 | (mA)#(mA)#(mG)(mU)(mU)(mC)(mG)(mU)(mU)(mU)(mA)(mU)(mG)(mU)(mG)(mU)#(mA)#(mA) | 371 |
| 3a_25413 | (mA)#(mC)#(mA)(mG)(mU)(mU)(mC)(mC)(mA)(mA)(mU)(mU)(mG)(mU)(mG)(mA)#(mA)#(mA) | 372 |
| 3a_25630 | (mC)#(mA)#(mA)(mC)(mA)(mG)(mC)(mA)(mA)(mG)(mU)(mU)(mG)(mC)(mA)(mA)#(mA)#(mA) | 373 |
| 3a_25717 | (mG)#(mA)#(mA)(mG)(mU)(mA)(mG)(mA)(mC)(mU)(mA)(mA)(mA)(mG)(mC)(mA)#(mU)#(mA) | 374 |
| 3a_25734 | (mA)#(mA)#(mG)(mU)(mU)(mU)(mA)(mU)(mA)(mC)(mU)(mC)(mU)(mG)(mC)(mA)#(mA)#(mA) | 375 |
| 3a_25736 | (mC)#(mA)#(mA)(mA)(mG)(mU)(mU)(mU)(mA)(mU)(mA)(mC)(mU)(mC)(mU)(mG)#(mC)#(mA) | 376 |
| 3a_25745 | (mU)#(mU)#(mA)(mU)(mU)(mC)(mU)(mU)(mA)(mC)(mA)(mA)(mA)(mG)(mU)(mU)#(mU)#(mA) | 377 |
| 3a_25868 | (mA)#(mA)#(mG)(mU)(mU)(mA)(mC)(mA)(mC)(mU)(mA)(mU)(mU)(mG)(mU)(mA)#(mA)#(mA) | 378 |
| 3a_25870 | (mA)#(mG)#(mA)(mA)(mG)(mU)(mU)(mA)(mC)(mA)(mC)(mU)(mA)(mU)(mU)(mG)#(mU)#(mA) | 379 |
| 3a_25914 | (mG)#(mA)#(mA)(mA)(mU)(mA)(mG)(mG)(mA)(mC)(mU)(mU)(mG)(mU)(mU)(mG)#(mU)#(mA) | 380 |
| 3a_25992 | (mU)#(mA)#(mA)(mC)(mU)(mG)(mU)(mG)(mU)(mA)(mA)(mU)(mA)(mC)(mA)(mA)#(mC)#(mA) | 381 |
| 3a_26018 | (mA)#(mC)#(mA)(mG)(mC)(mU)(mG)(mG)(mU)(mA)(mA)(mU)(mA)(mG)(mU)(mC)#(mU)#(mA) | 382 |
| 3a_26066 | (mA)#(mG)#(mA)(mA)(mG)(mG)(mU)(mA)(mA)(mC)(mA)(mU)(mG)(mU)(mU)(mC)#(mA)#(mA) | 383 |
| E_26258 | (mU)#(mA)#(mC)(mC)(mU)(mG)(mU)(mC)(mU)(mC)(mU)(mU)(mC)(mC)(mG)(mA)#(mA)#(mA) | 384 |
| E_26261 | (mA)#(mC)#(mG)(mU)(mA)(mC)(mC)(mU)(mG)(mU)(mC)(mU)(mC)(mU)(mU)(mC)#(mC)#(mA) | 385 |
| E_26269 | (mA)#(mA)#(mC)(mU)(mA)(mU)(mU)(mA)(mA)(mC)(mG)(mU)(mA)(mC)(mC)(mU)#(mG)#(mA) | 386 |
| E_26277 | (mA)#(mC)#(mG)(mC)(mU)(mA)(mU)(mU)(mA)(mA)(mC)(mU)(mA)(mU)(mU)(mA)#(mA)#(mA) | 387 |
| E_26305 | (mG)#(mA)#(mA)(mU)(mA)(mC)(mC)(mA)(mC)(mG)(mA)(mA)(mA)(mG)(mC)(mA)#(mA)#(mA) | 388 |
| E_26313 | (mA)#(mC)#(mU)(mA)(mG)(mC)(mA)(mA)(mG)(mA)(mA)(mU)(mA)(mC)(mC)(mA)#(mC)#(mA) | 389 |
| E_26369 | (mU)#(mA)#(mA)(mC)(mA)(mA)(mU)(mA)(mU)(mU)(mG)(mC)(mA)(mG)(mC)(mA)#(mG)#(mA) | 390 |
| E_26374 | (mC)#(mA)#(mC)(mG)(mU)(mU)(mA)(mA)(mC)(mA)(mA)(mU)(mA)(mU)(mU)(mG)#(mC)#(mA) | 391 |
| E_26455 | (mU)#(mU)#(mA)(mG)(mA)(mC)(mC)(mA)(mG)(mA)(mA)(mG)(mA)(mU)(mC)(mA)#(mG)#(mA) | 392 |
| E_26463 | (mU)#(mA)#(mG)(mU)(mU)(mC)(mG)(mU)(mU)(mU)(mA)(mG)(mA)(mC)(mC)(mA)#(mG)#(mA) | 393 |
| E_26467 | (mU)#(mA)#(mU)(mU)(mU)(mA)(mG)(mU)(mU)(mC)(mG)(mU)(mU)(mU)(mA)(mG)#(mA)#(mA) | 394 |

TABLE 6D-continued

| Modified sense strand - 18 nucleotides in length | | |
|---|---|---|
| Sequence ID | Modified sense strand 18 nt | SEQ ID NO: |
| E_26470 | (mU)#(mA)#(mA)(mU)(mA)(mU)(mU)(mU)(mA)(mG)(mU)(mU)(mC)(mG)(mU)(mU)#(mU)#(mA) | 395 |
| M_26573 | (mA)#(mC)#(mU)(mA)(mG)(mG)(mU)(mU)(mC)(mC)(mA)(mU)(mU)(mG)(mU)(mU)#(mC)#(mA) | 396 |
| M_26581 | (mA)#(mA)#(mC)(mC)(mU)(mA)(mU)(mU)(mA)(mC)(mU)(mA)(mG)(mG)(mU)(mU)#(mC)#(mA) | 397 |
| M_26602 | (mA)#(mA)#(mA)(mU)(mC)(mC)(mA)(mU)(mG)(mU)(mA)(mA)(mG)(mG)(mA)(mA)#(mU)#(mA) | 398 |
| M_26624 | (mG)#(mC)#(mA)(mU)(mA)(mG)(mG)(mC)(mA)(mA)(mA)(mU)(mU)(mG)(mU)(mA)#(mG)#(mA) | 399 |
| M_26637 | (mC)#(mC)#(mU)(mA)(mU)(mU)(mC)(mC)(mU)(mG)(mU)(mU)(mG)(mG)(mC)(mA)#(mU)#(mA) | 400 |
| M_26638 | (mA)#(mC)#(mC)(mU)(mA)(mU)(mU)(mC)(mC)(mU)(mG)(mU)(mU)(mG)(mG)(mC)#(mA)#(mA) | 401 |
| M_26693 | (mG)#(mC)#(mU)(mA)(mA)(mA)(mG)(mU)(mU)(mA)(mC)(mU)(mG)(mG)(mC)(mC)#(mA)#(mA) | 402 |
| M_26717 | (mU)#(mA)#(mA)(mA)(mC)(mA)(mG)(mC)(mA)(mG)(mC)(mA)(mA)(mG)(mC)(mA)#(mC)#(mA) | 403 |
| M_27014 | (mA)#(mC)#(mA)(mG)(mU)(mG)(mA)(mU)(mU)(mU)(mC)(mU)(mU)(mU)(mA)(mG)#(mG)#(mA) | 404 |
| M_27032 | (mA)#(mG)#(mC)(mG)(mU)(mU)(mC)(mG)(mU)(mG)(mA)(mU)(mG)(mU)(mA)(mG)#(mC)#(mA) | 405 |
| M_27035 | (mG)#(mA)#(mA)(mA)(mG)(mC)(mG)(mU)(mU)(mC)(mG)(mU)(mG)(mA)(mU)(mG)#(mU)#(mA) | 406 |
| M_27123 | (mU)#(mA)#(mA)(mU)(mU)(mU)(mA)(mU)(mA)(mG)(mU)(mU)(mG)(mC)(mC)(mA)#(mA)#(mA) | 407 |
| 7a_27455 | (mU)#(mA)#(mC)(mC)(mU)(mC)(mU)(mA)(mA)(mC)(mA)(mC)(mA)(mC)(mU)(mC)#(mU)#(mA) | 408 |
| 7a_27522 | (mA)#(mG)#(mA)(mG)(mG)(mA)(mU)(mG)(mA)(mA)(mA)(mU)(mG)(mG)(mU)(mG)#(mA)#(mA) | 409 |
| 7a_27537 | (mA)#(mA)#(mU)(mU)(mU)(mG)(mU)(mU)(mA)(mU)(mC)(mA)(mG)(mC)(mU)(mA)#(mG)#(mA) | 410 |
| 7a_27553 | (mA)#(mA)#(mA)(mG)(mC)(mA)(mA)(mG)(mU)(mC)(mA)(mG)(mU)(mG)(mC)(mA)#(mA)#(mA) | 411 |
| 7a_27565 | (mA)#(mA)#(mA)(mU)(mU)(mG)(mA)(mG)(mU)(mG)(mC)(mU)(mA)(mA)(mA)(mG)#(mC)#(mA) | 412 |
| 7a_27633 | (mA)#(mG)#(mU)(mU)(mU)(mA)(mG)(mG)(mU)(mG)(mA)(mA)(mA)(mC)(mU)(mG)#(mA)#(mA) | 413 |
| 7a_27656 | (mG)#(mA)#(mA)(mC)(mU)(mU)(mC)(mC)(mU)(mC)(mU)(mU)(mG)(mU)(mC)(mU)#(mG)#(mA) | 414 |
| 7a_27671 | (mG)#(mA)#(mG)(mA)(mG)(mU)(mA)(mA)(mA)(mG)(mU)(mU)(mC)(mU)(mU)(mG)#(mA)#(mA) | 415 |
| 7a_27705 | (mA)#(mU)#(mA)(mA)(mC)(mA)(mC)(mU)(mA)(mU)(mU)(mG)(mC)(mC)(mG)#(mC)#(mA) | 416 |
| 7a_27715 | (mG)#(mC)#(mA)(mA)(mA)(mG)(mU)(mG)(mU)(mU)(mA)(mU)(mA)(mA)(mA)(mC)#(mA)#(mA) | 417 |
| 7a_27720 | (mG)#(mU)#(mG)(mA)(mA)(mG)(mC)(mA)(mA)(mA)(mG)(mU)(mG)(mU)(mU)(mA)#(mU)#(mA) | 418 |
| 7a_27751 | (mA)#(mA)#(mA)(mG)(mU)(mU)(mC)(mA)(mA)(mU)(mC)(mA)(mU)(mU)(mC)(mU)#(mG)#(mA) | 419 |
| 8b_27932 | (mU)#(mC)#(mU)(mU)(mG)(mG)(mU)(mG)(mA)(mA)(mA)(mU)(mG)(mC)(mA)(mG)#(mC)#(mA) | 420 |
| 8b_27940 | (mA)#(mA)#(mC)(mU)(mA)(mC)(mA)(mU)(mU)(mC)(mU)(mU)(mG)(mG)(mU)(mG)#(mA)#(mA) | 421 |
| 8b_27986 | (mC)#(mA)#(mC)(mG)(mG)(mG)(mU)(mC)(mA)(mU)(mC)(mA)(mA)(mC)(mU)(mA)#(mC)#(mA) | 422 |
| 8b_28002 | (mA)#(mU)#(mA)(mG)(mA)(mA)(mG)(mU)(mG)(mA)(mA)(mU)(mA)(mG)(mG)(mA)#(mC)#(mA) | 423 |
| 8b_28024 | (mC)#(mU)#(mA)(mC)(mU)(mC)(mU)(mA)(mA)(mU)(mA)(mU)(mA)(mC)(mC)(mA)#(mU)#(mA) | 424 |
| 8b_28091 | (mU)#(mG)#(mA)(mA)(mU)(mG)(mG)(mG)(mU)(mG)(mA)(mU)(mU)(mU)(mA)(mG)#(mA)#(mA) | 425 |
| 8b_28119 | (mA)#(mA)#(mC)(mU)(mG)(mU)(mA)(mU)(mA)(mA)(mU)(mU)(mA)(mC)(mC)(mG)#(mA)#(mA) | 426 |
| 8b_28127 | (mA)#(mA)#(mA)(mC)(mA)(mG)(mG)(mA)(mA)(mA)(mC)(mU)(mG)(mU)(mA)(mU)#(mA)#(mA) | 427 |
| 8b_28128 | (mU)#(mA)#(mA)(mA)(mC)(mA)(mG)(mG)(mA)(mA)(mA)(mC)(mU)(mG)(mU)(mA)#(mU)#(mA) | 428 |
| 8b_28163 | (mC)#(mC)#(mC)(mA)(mA)(mU)(mU)(mU)(mA)(mG)(mG)(mU)(mU)(mC)(mC)(mU)#(mG)#(mA) | 429 |
| 8b_28218 | (mA)#(mA)#(mC)(mG)(mU)(mC)(mA)(mU)(mG)(mA)(mU)(mA)(mC)(mU)(mC)(mU)#(mA)#(mA) | 430 |
| 8b_28222 | (mC)#(mA)#(mC)(mG)(mA)(mA)(mC)(mG)(mU)(mC)(mA)(mU)(mG)(mA)(mU)(mA)#(mC)#(mA) | 431 |
| N_28407 | (mA)#(mC)#(mG)(mC)(mA)(mG)(mU)(mA)(mU)(mU)(mA)(mU)(mU)(mG)(mG)(mG)#(mU)#(mA) | 432 |
| N_28655 | (mA)#(mA)#(mC)(mC)(mC)(mA)(mU)(mA)(mU)(mG)(mA)(mU)(mG)(mC)(mC)(mG)#(mU)#(mA) | 433 |
| N_28945 | (mA)#(mG)#(mC)(mU)(mG)(mG)(mU)(mU)(mC)(mA)(mA)(mU)(mC)(mU)(mG)(mU)#(mC)#(mA) | 434 |
| N_28992 | (mC)#(mA)#(mG)(mU)(mU)(mU)(mG)(mG)(mC)(mC)(mU)(mU)(mG)(mU)(mU)(mG)#(mU)#(mA) | 435 |
| N_29141 | (mU)#(mC)#(mC)(mU)(mU)(mG)(mU)(mC)(mU)(mG)(mA)(mU)(mU)(mA)(mG)(mU)#(mU)#(mA) | 436 |
| N_29276 | (mA)#(mU)#(mC)(mC)(mA)(mA)(mU)(mU)(mU)(mG)(mA)(mU)(mG)(mG)(mC)(mA)#(mC)#(mA) | 437 |
| N_29292 | (mA)#(mA)#(mU)(mU)(mU)(mG)(mG)(mA)(mU)(mC)(mU)(mU)(mU)(mG)(mU)(mC)#(mA)#(mA) | 438 |
| N_29293 | (mA)#(mA)#(mA)(mU)(mU)(mU)(mG)(mG)(mA)(mU)(mC)(mU)(mU)(mU)(mG)(mU)#(mC)#(mA) | 439 |
| N_29303 | (mU)#(mU)#(mG)(mA)(mU)(mC)(mU)(mU)(mU)(mG)(mA)(mA)(mA)(mU)(mU)(mU)#(mG)#(mA) | 440 |
| N_29307 | (mU)#(mG)#(mA)(mC)(mU)(mU)(mG)(mA)(mU)(mC)(mU)(mU)(mU)(mG)(mA)(mA)#(mA)#(mA) | 441 |
| N_29328 | (mC)#(mA)#(mA)(mU)(mA)(mU)(mG)(mC)(mU)(mU)(mA)(mU)(mU)(mC)(mA)(mG)#(mC)#(mA) | 442 |
| N_29464 | (mA)#(mA)#(mA)(mU)(mC)(mA)(mU)(mC)(mC)(mA)(mA)(mA)(mU)(mC)(mU)(mG)#(mC)#(mA) | 443 |

TABLE 7

| SARS-CoV2-Additional target sequences | | | | |
|---|---|---|---|---|
| Sequence ID | 20 nt Sequence | SEQ ID NO: | 45 nt Gene Region | SEQ ID NO: |
| 3a_25688 | CUGGCCUUGAAGCC CCUUUU | 444 | TTTTGCTCGTTGCTGCT GGCCTTGAAGCCCCTT TTCTCTATCTTT | 642 |
| 3a_25570 | UCCAAAAUCAUAAC CCUCAA | 445 | GTTTTTCAGAGCGCTTC CAAAATCATAACCCTC AAAAAGAGATGG | 643 |
| 3a_25852 | UACGACUAUUGUA UACCUUA | 446 | TGGCATACTAATTGTT ACGACTATTGTATACC TTACAATAGTGTA | 644 |

TABLE 7-continued

| SARS-CoV2-Additional target sequences | | | | |
|---|---|---|---|---|
| Sequence ID | 20 nt Sequence | SEQ ID NO: | 45 nt Gene Region | SEQ ID NO: |
| 3a_25518 | UUUCGGAUGGCUUAUUGUUG | 447 | ACAAGCCTCACTCCCTTTCGGATGGCTTATTGTTGGCGTTGCACT | 645 |
| 3a_25974 | AUCUGGAGUAAAAGACUGUG | 448 | TACTGAAAAATGGGAATCTGGAGTAAAAGACTGTGTTGTATTACA | 646 |
| 3a_25835 | GCUGGCAUACUAAUUGUUAC | 449 | CCAACTATTTTCTTTGCTGGCATACTAATTGTTACGACTATTGTA | 647 |
| 3a_25645 | UUGUUGUUUGUAACAGUUUA | 450 | GTTTGCAACTTGCTGTTGTTGTTTGTAACAGTTTACTCACACCTT | 648 |
| 3a_25773 | UUGGCUUUGCUGGAAAUGCC | 451 | AATAATAATGAGGCTTTGGCTTTGCTGGAAATGCCGTTCCAAAAA | 649 |
| 3a_25921 | AGUCCUAUUUCUGAACAUGA | 452 | GGTGATGGCACAACAAGTCCTATTTCTGAACATGACTACCAGATT | 650 |
| 3a_26114 | AAGAACAUGUCCAAAUUCAC | 453 | TTGTTGATGAGCCTGAAGAACATGTCCAAATTCACACAATCGACG | 651 |
| 3a_25750 | UUUGUAAGAAUAAUAAUGAG | 454 | TTGCAGAGTATAAACTTTGTAAGAATAATAATGAGGCTTTGGCTT | 652 |
| 3a_25862 | GUAUACCUUACAAUAGUGUA | 455 | ATTGTTACGACTATTGTATACCTTACAATAGTGTAACTTCTTCAA | 653 |
| 3a_25847 | AUUGUUACGACUAUUGUAUA | 456 | TTTGCTGGCATACTAATTGTTACGACTATTGTATACCTTACAATA | 654 |
| 3a_26105 | AUGAGCCUGAAGAACAUGUC | 457 | ACAATAAAATTGTTGATGAGCCTGAAGAACATGTCCAAATTCACA | 655 |
| 3a_25863 | UAUACCUUACAAUAGUGUAA | 458 | TTGTTACGACTATTGTATACCTTACAATAGTGTAACTTCTTCAAT | 656 |
| 3a_26164 | CCAGUAAUGGAACCAAUUUA | 459 | TCCGGAGTTGTTAATCCAGTAATGGAACCAATTTATGATGAACCG | 657 |
| 3a_25706 | UUCUCUAUCUUUAUGCUUUA | 460 | GCCTTGAAGCCCCTTTTCTCTATCTTTATGCTTTAGTCTACTTCT | 658 |
| 3a_25595 | GAUGGCAACUAGCACUCUCC | 461 | TAACCCTCAAAAAGAGATGGCAACTAGCACTCTCCAAGGGTGTTC | 659 |
| 3a_25611 | CUCCAAGGGUGUUCACUUUG | 462 | ATGGCAACTAGCACTCTCCAAGGGTGTTCACTTTGTTTGCAACTT | 660 |
| 3a_25405 | AUGAGAAUCUUCACAAUUGG | 463 | CTTATGGATTTGTTTATGAGAATCTTCACAATTGGAACTGTAACT | 661 |
| 3a_25535 | UUGGCGUUGCACUUCUUGCU | 464 | TCGGATGGCTTATTGTTGGCGTTGCACTTCTTGCTGTTTTTCAGA | 662 |

TABLE 7-continued

| SARS-CoV2-Additional target sequences | | | | |
|---|---|---|---|---|
| Sequence ID | 20 nt Sequence | SEQ ID NO: | 45 nt Gene Region | SEQ ID NO: |
| 3a_25653 | UGUAACAGUUUAC UCACACC | 465 | CTTGCTGTTGTTGTTTG TAACAGTTTACTCACA CCTTTTGCTCGT | 663 |
| 7a_27598 | GACGGCGUAAAAC ACGUCUA | 466 | GCTTTTGCTTGTCCTGA CGGCGTAAAACACGTC TATCAGTTACGT | 664 |
| 7a_27483 | UUUAAAAGAACCU UGCUCUU | 467 | AGGTACAACAGTACTT TTAAAAGAACCTTGCT CTTCTGGAACATA | 665 |
| 7a_27258 | GAGGACUUUUAAA GUUUCCA | 468 | ATTACTAATTATTATG AGGACTTTTAAAGTTT CCATTTGGAATCT | 666 |
| 7a_27264 | UUUUAAAGUUUCC AUUUGGA | 469 | AATTATTATGAGGACT TTTAAAGTTTCCATTTG GAATCTTGATTA | 667 |
| 7a_27257 | UGAGGACUUUUAA AGUUUCC | 470 | TATTACTAATTATTATG AGGACTTTTAAAGTTT CCATTTGGAATC | 668 |
| 7a_27334 | ACUGAGAAUAAAU AUUCUCA | 471 | TTATCTAAGTCACTAA CTGAGAATAAATATTC TCAATTAGATGAA | 669 |
| 7a_27595 | CCUGACGGCGUAAA ACACGU | 472 | TTTGCTTTTGCTTGTCC TGACGGCGTAAAACAC GTCTATCAGTTA | 670 |
| 7a_27466 | AGAGGUACAACAG UACUUUU | 473 | TACCAAGAGTGTGTTA GAGGTACAACAGTACT TTTAAAAGAACCT | 671 |
| 7a_27237 | AGAGAUAUUACUA AUUAUUA | 474 | TCAGGTTACTATAGCA GAGATATTACTAATTA TTATGAGGACTTT | 672 |
| 7a_27395 | UGAAAAUUAUUCU UUUCUUG | 475 | TTGATTAAACGAACAT GAAAATTATTCTTTTCT TGGCACTGATAA | 673 |
| 7a_27289 | GAUUACAUCAUAA ACCUCAU | 476 | TCCATTTGGAATCTTG ATTACATCATAAACCT CATAATTAAAAAT | 674 |
| 7a_27243 | AUUACUAAUUAUU AUGAGGA | 477 | TACTATAGCAGAGATA TTACTAATTATTATGA GGACTTTTAAAGT | 675 |
| 7a_27319 | UUAUCUAAGUCAC UAACUGA | 478 | CTCATAATTAAAAATT TATCTAAGTCACTAAC TGAGAATAAATAT | 676 |
| 7a_27226 | GUUACUAUAGCAG AGAUAUU | 479 | CTCGTTGACTTTCAGGT TACTATAGCAGAGATA TTACTAATTATT | 677 |
| 7a_27256 | AUGAGGACUUUUA AAGUUUC | 480 | ATATTACTAATTATTAT GAGGACTTTTAAAGTT TCCATTTGGAAT | 678 |
| 7a_27203 | UGUUUCAUCUCGU UGACUUU | 481 | GTAAGTGACAACAGAT GTTTCATCTCGTTGACT TTCAGGTTACTA | 679 |
| 7a_27292 | UACAUCAUAAACCU CAUAAU | 482 | ATTTGGAATCTTGATT ACATCATAAACCTCAT AATTAAAAATTTA | 680 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| 7a_27333 | AACUGAGAAUAAA UAUUCUC | 483 | TTTATCTAAGTCACTA ACTGAGAATAAATATT CTCAATTAGATGA | 681 |
| 7a_27255 | UAUGAGGACUUUU AAAGUUU | 484 | GATATTACTAATTATT ATGAGGACTTTTAAAG TTTCCATTTGGAA | 682 |
| 7a_27381 | UGAUUAAACGAAC AUGAAAA | 485 | GCAACCAATGGAGATT GATTAAACGAACATGA AAATTATTCTTTT | 683 |
| 7a_27750 | GACAGAAUGAUUG AACUUUC | 486 | CACACTCAAAAGAAAG ACAGAATGATTGAACT TTCATTAATTGAC | 684 |
| 7a_27445 | UAUCACUACCAAGA GUGUGU | 487 | GCTACTTGTGAGCTTT ATCACTACCAAGAGTG TGTTAGAGGTACA | 685 |
| 8b_27795 | UUAGCCUUUCUGCU AUUCCU | 488 | TTCTATTTGTGCTTTTT AGCCTTTCTGCTATTCC TTGTTTTAATT | 686 |
| 8b_27803 | UCUGCUAUUCCUUG UUUUAA | 489 | GTGCTTTTTAGCCTTTC TGCTATTCCTTGTTTTA ATTATGCTTAT | 687 |
| 8b_27888 | ACGAACAUGAAAU UUCUUGU | 490 | ACTTGTCACGCCTAAA CGAACATGAAATTTCT TGTTTTCTTAGGA | 688 |
| 8b_28236 | CGUGUUGUUUUAG AUUUCAU | 491 | GAGTATCATGACGTTC GTGTTGTTTTAGATTTC ATCTAAACGAAC | 689 |
| 8b_27895 | UGAAAUUUCUUGU UUUCUUA | 492 | ACGCCTAAACGAACAT GAAATTTCTTGTTTTCT TAGGAATCATCA | 690 |
| 8b_28142 | UUUACCUUUUACA AUUAAUU | 493 | TTATACAGTTTCCTGTT TACCTTTTACAATTAAT TGCCAGGAACC | 691 |
| 8b_27802 | UUCUGCUAUUCCUU GUUUUA | 494 | TGTGCTTTTTAGCCTTT CTGCTATTCCTTGTTTT AATTATGCTTA | 692 |
| 8b_27808 | UAUUCCUUGUUUU AAUUAUG | 495 | TTTTAGCCTTTCTGCTA TTCCTTGTTTTAATTAT GCTTATTATCT | 693 |
| 8b_27796 | UAGCCUUUCUGCUA UUCCUU | 496 | TCTATTTGTGCTTTTTA GCCTTTCTGCTATTCCT TGTTTTAATTA | 694 |
| 8b_27815 | UGUUUUAAUUAUG CUUAUUA | 497 | CTTTCTGCTATTCCTTG TTTTAATTATGCTTATT ATCTTTTGGTT | 695 |
| 8b_28044 | GCUAGAAAAUCAG CACCUUU | 498 | TATATTAGAGTAGGAG CTAGAAAATCAGCACC TTTAATTGAATTG | 696 |
| 8b_27794 | UUUAGCCUUUCUGC UAUUCC | 499 | CTTCTATTTGTGCTTTT TAGCCTTTCTGCTATTC CTTGTTTTAAT | 697 |
| 8b_28234 | UUCGUGUUGUUUU AGAUUUC | 500 | TAGAGTATCATGACGT TCGTGTTGTTTTAGATT TCATCTAAACGA | 698 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| 8b_27817 | UUUUAAUUAUGCU UAUUAUC | 501 | TTCTGCTATTCCTTGTT TTAATTATGCTTATTAT CTTTTGGTTCT | 699 |
| 8b_27970 | CUCAACAUCAACCA UAUGUA | 502 | GTTTACAGTCATGTAC TCAACATCAACCATAT GTAGTTGATGACC | 700 |
| 8b_28043 | AGCUAGAAAAUCA GCACCUU | 503 | GTATATTAGAGTAGGA GCTAGAAAATCAGCAC CTTTAATTGAATT | 701 |
| 8b_28219 | UAGAGUAUCAUGA CGUUCGU | 504 | TCTATGAAGACTTTTTA GAGTATCATGACGTTC GTGTTGTTTTAG | 702 |
| 8b_27764 | ACUUUCAUUAAUU GACUUCU | 505 | AGACAGAATGATTGAA CTTTCATTAATTGACTT CTATTTGTGCTT | 703 |
| 8b_27963 | UCAUGUACUCAACA UCAACC | 506 | GAATGTAGTTTACAGT CATGTACTCAACATCA ACCATATGTAGTT | 704 |
| 8b_28104 | AUUCAGUACAUCG AUAUCGG | 507 | GGTTCTAAATCACCCA TTCAGTACATCGATAT CGGTAATTATACA | 705 |
| 8b_28018 | AUUCUAAAUGGUA UAUUAGA | 503 | GTCCTATTCACTTCTAT TCTAAATGGTATATTA GAGTAGGAGCTA | 706 |
| 8b_27892 | ACAUGAAAUUUCU UGUUUUC | 509 | GTCACGCCTAAACGAA CATGAAATTTCTTGTTT TCTTAGGAATCA | 707 |
| E_26390 | UGAGUCUUGUAAA ACCUUCU | 510 | GCAATATTGTTAACGT GAGTCTTGTAAAACCT TCTTTTTACGTTT | 708 |
| E_26391 | GAGUCUUGUAAAA CCUUCUU | 511 | CAATATTGTTAACGTG AGTCTTGTAAAACCTT CTTTTTACGTTTA | 709 |
| E_26392 | AGUCUUGUAAAAC CUUCUUU | 512 | AATATTGTTAACGTGA GTCTTGTAAAACCTTCT TTTTACGTTTAC | 710 |
| E_26468 | UCUAAACGAACUA AAUAUUA | 513 | TTCCTGATCTTCTGGTC TAAACGAACTAAATAT TATATTAGTTTT | 711 |
| E_26321 | UCUUGCUAGUUAC ACUAGCC | 514 | TTGCTTTCGTGGTATTC TTGCTAGTTACACTAG CCATCCTTACTG | 712 |
| E_26259 | UUCGGAAGAGACA GGUACGU | 515 | TATGTACTCATTCGTTT CGGAAGAGACAGGTAC GTTAATAGTTAA | 713 |
| E_26460 | UCUUCUGGUCUAA ACGAACU | 516 | TTCTAGAGTTCCTGATC TTCTGGTCTAAACGAA CTAAATATTATA | 714 |
| E_26284 | GUUAAUAGCGUAC UUCUUUU | 517 | ACAGGTACGTTAATAG TTAATAGCGTACTTCTT TTTCTTGCTTTC | 715 |
| E_26314 | GUGGUAUUCUUGC UAGUUAC | 518 | CTTTTTCTTGCTTTCGT GGTATTCTTGCTAGTTA CACTAGCCATC | 716 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| E_26274 | UACGUUAAUAGUU AAUAGCG | 519 | TTCGGAAGAGACAGGT ACGTTAATAGTTAATA GCGTACTTCTTTT | 717 |
| E_26260 | UCGGAAGAGACAG GUACGUU | 520 | ATGTACTCATTCGTTTC GGAAGAGACAGGTAC GTTAATAGTTAAT | 718 |
| E_26308 | GCUUUCGUGGUAU UCUUGCU | 521 | GTACTTCTTTTTCTTGC TTTCGTGGTATTCTTGC TAGTTACACTA | 719 |
| E_26411 | UUUACGUUUACUC UCGUGUU | 522 | TTGTAAAACCTTCTTTT TACGTTTACTCTCGTGT TAAAAATCTGA | 720 |
| E_26265 | AGAGACAGGUACG UUAAUAG | 523 | CTCATTCGTTTCGGAA GAGACAGGTACGTTAA TAGTTAATAGCGT | 721 |
| E_26279 | UAAUAGUUAAUAG CGUACUU | 524 | AAGAGACAGGTACGTT AATAGTTAATAGCGTA CTTCTTTTTCTTG | 722 |
| E_26312 | UCGUGGUAUUCUU GCUAGUU | 525 | TTCTTTTTCTTGCTTTC GTGGTATTCTTGCTAGT TACACTAGCCA | 723 |
| E_26464 | CUGGUCUAAACGA ACUAAAU | 526 | AGAGTTCCTGATCTTCT GGTCTAAACGAACTAA ATATTATATTAG | 724 |
| E_26231 | AUGAGUACGAACU UAUGUAC | 527 | TGTAAGCACAAGCTGA TGAGTACGAACTTATG TACTCATTCGTTT | 725 |
| E_26469 | CUAAACGAACUAA AUAUUAU | 528 | TCCTGATCTTCTGGTCT AAACGAACTAAATATT ATATTAGTTTTT | 726 |
| E_26413 | UACGUUUACUCUCG UGUUAA | 529 | GTAAAACCTTCTTTTTA CGTTTACTCTCGTGTTA AAAATCTGAAT | 727 |
| E_26281 | AUAGUUAAUAGCG UACUUCU | 530 | GAGACAGGTACGTTAA TAGTTAATAGCGTACT TCTTTTTCTTGCT | 728 |
| E_26462 | UUCUGGUCUAAAC GAACUAA | 531 | CTAGAGTTCCTGATCTT CTGGTCTAAACGAACT AAATATTATATT | 729 |
| M_26517 | UUAGCCAUGGCAG AUUCCAA | 532 | TTTGGAACTTTAATTTT AGCCATGGCAGATTCC AACGGTACTATT | 730 |
| M_26522 | CAUGGCAGAUUCCA ACGGUA | 533 | AACTTTAATTTTAGCC ATGGCAGATTCCAACG GTACTATTACCGT | 731 |
| M_26656 | UUUUGUAUAUAAU UAAGUUA | 534 | CCAACAGGAATAGGTT TTTGTATATAATTAAGT TAATTTTCCTCT | 732 |
| M_26603 | AUUCCUUACAUGG AUUUGUC | 535 | AGTAATAGGTTTCCTA TTCCTTACATGGATTTG TCTTCTACAATT | 733 |
| M_26572 | UUGAACAAUGGAA CCUAGUA | 536 | AGCTTAAAAAGCTCCT TGAACAATGGAACCTA GTAATAGGTTTCC | 734 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| M_27101 | UGCUGCAUACAGUC GCUACA | 537 | AGGTGACTCAGGTTTT GCTGCATACAGTCGCT ACAGGATTGGCAA | 735 |
| M_27049 | UUUCUUAUUACAA AUUGGGA | 538 | CTACATCACGAACGCT TTCTTATTACAAATTGG GAGCTTCGCAGC | 736 |
| M_26580 | UGGAACCUAGUAA UAGGUUU | 539 | AAGCTCCTTGAACAAT GGAACCTAGTAATAGG TTTCCTATTCCTT | 737 |
| M_26733 | UACAGAAUAAAUU GGAUCAC | 540 | GTGCTTGCTGCTGTTTA CAGAATAAATTGGATC ACCGGTGGAATT | 738 |
| M_26495 | UUUUCUGUUUGGA ACUUUAA | 541 | AAATATTATATTAGTTT TTCTGTTTGGAACTTTA ATTTTAGCCAT | 739 |
| M_26608 | UUACAUGGAUUUG UCUUCUA | 542 | TAGGTTTCCTATTCCTT ACATGGATTTGTCTTCT ACAATTTGCCT | 740 |
| M_26590 | UAAUAGGUUUCCU AUUCCUU | 543 | AACAATGGAACCTAGT AATAGGTTTCCTATTCC TTACATGGATTT | 741 |
| M_26501 | GUUUGGAACUUUA AUUUUAG | 544 | TATATTAGTTTTTCTGT TTGGAACTTTAATTTTA GCCATGGCAGA | 742 |
| M_26796 | UGGCUCAGCUACUU CAUUGC | 545 | CTTGTAGGCTTGATGT GGCTCAGCTACTTCAT TGCTTCTTTCAGA | 743 |
| M_26570 | CCUUGAACAAUGG AACCUAG | 546 | AGAGCTTAAAAAGCTC CTTGAACAATGGAACC TAGTAATAGGTTT | 744 |
| M_27124 | UUGGCAACUAUAA AUUAAAC | 547 | ACAGTCGCTACAGGAT TGGCAACTATAAATTA AACACAGACCATT | 745 |
| M_26814 | GCUUCUUUCAGACU GUUUGC | 548 | CTCAGCTACTTCATTGC TTCTTTCAGACTGTTTG CGCGTACGCGT | 746 |
| M_26694 | UGGCCAGUAACUU UAGCUUG | 549 | TTCCTCTGGCTGTTATG GCCAGTAACTTTAGCT TGTTTTGTGCTT | 747 |
| M_27047 | GCUUUCUUAUUAC AAAUUGG | 550 | TGCTACATCACGAACG CTTTCTTATTACAAATT GGGAGCTTCGCA | 748 |
| M_27153 | UCCAGUAGCAGUG ACAAUAU | 551 | TTAAACACAGACCATT CCAGTAGCAGTGACAA TATTGCTTTGCTT | 749 |
| M_27163 | GUGACAAUAUUGC UUUGCUU | 552 | ACCATTCCAGTAGCAG TGACAATATTGCTTTG CTTGTACAGTAAG | 750 |
| M_26473 | ACGAACUAAAUAU UAUAUUA | 553 | GATCTTCTGGTCTAAA CGAACTAAATATTATA TTAGTTTTTCTGT | 751 |
| N_29327 | UUGCUGAAUAAGC AUAUUGA | 554 | AAAGATCAAGTCATTT TGCTGAATAAGCATAT TGACGCATACAAA | 752 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| N_29216 | UUCGGAAUGUCGC GCAUUGG | 555 | AGCGCTTCAGCGTTCT TCGGAATGTCGCGCAT TGGCATGGAAGTC | 753 |
| N_28486 | CGUUCCAAUUAACA CCAAUA | 556 | CCCTCGAGGACAAGGC GTTCCAATTAACACCA ATAGCAGTCCAGA | 754 |
| N_28755 | UUCCUCAAGGAACA ACAUUG | 557 | CAATCGTGCTACAACT TCCTCAAGGAACAACA TTGCCAAAAGGCT | 755 |
| N_28585 | CAGUCCAAGAUGG UAUUUCU | 558 | TAAAATGAAAGATCTC AGTCCAAGATGGTATT TCTACTACCTAGG | 756 |
| N_28565 | GACGGUAAAAUGA AAGAUCU | 559 | CGAATTCGTGGTGGTG ACGGTAAAATGAAAGA TCTCAGTCCAAGA | 757 |
| N_28961 | CUUGAGAGCAAAA UGUCUGG | 560 | GACAGATTGAACCAGC TTGAGAGCAAAATGTC TGGTAAAGGCCAA | 758 |
| N_29310 | UCAAAGAUCAAGU CAUUUUG | 561 | ACAAAGATCCAAATTT CAAAGATCAAGTCATT TTGCTGAATAAGC | 759 |
| N_29177 | CCGCAAAUUGCACA AUUUGC | 562 | GATTACAAACATTGGC CGCAAATTGCACAATT TGCCCCCAGCGCT | 760 |
| N_28261 | CGAACAAACUAAA AUGUCUG | 563 | TAGATTTCATCTAAAC GAACAAACTAAAATGT CTGATAATGGACC | 761 |
| N_28476 | GAGGACAAGGCGU UCCAAUU | 564 | ACCTTAAATTCCCTCG AGGACAAGGCGTTCCA ATTAACACCAATA | 762 |
| N_29130 | UUGGGGACCAGGA ACUAAUC | 565 | AAACCCAAGGAAATTT TGGGGACCAGGAACTA ATCAGACAAGGAA | 763 |
| N_29455 | UCUUCCUGCUGCAG AUUUGG | 566 | GCAAACTGTGACTCTT CTTCCTGCTGCAGATTT GGATGATTTCTC | 764 |
| N_29465 | GCAGAUUUGGAUG AUUUCUC | 567 | ACTCTTCTTCCTGCTGC AGATTTGGATGATTTC TCCAAACAATTG | 765 |
| N_29132 | GGGGACCAGGAAC UAAUCAG | 568 | ACCCAAGGAAATTTTG GGGACCAGGAACTAAT CAGACAAGGAACT | 766 |
| N_29148 | UCAGACAAGGAAC UGAUUAC | 569 | GGGACCAGGAACTAAT CAGACAAGGAACTGAT TACAAACATTGGC | 767 |
| N_29291 | GAUGACAAAGAUC CAAAUUU | 570 | GGTGCCATCAAATTGG ATGACAAAGATCCAAA TTTCAAAGATCAA | 768 |
| N_29342 | AUUGACGCAUACA AAACAUU | 571 | TTGCTGAATAAGCATA TTGACGCATACAAAAC ATTCCCACCAACA | 769 |
| N_28589 | CCAAGAUGGUAUU UCUACUA | 572 | ATGAAAGATCTCAGTC CAAGATGGTATTTCTA CTACCTAGGAACT | 770 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| N_29133 | GGGACCAGGAACU AAUCAGA | 573 | CCCAAGGAAATTTTGG GGACCAGGAACTAATC AGACAAGGAACTG | 771 |
| N_29057 | CGUACUGCCACUAA AGCAUA | 574 | AAGCCTCGGCAAAAAC GTACTGCCACTAAAGC ATACAATGTAACA | 772 |
| N_28682 | GGAGCCUUGAAUA CACCAAA | 575 | TGGGTTGCAACTGAGG GAGCCTTGAATACACC AAAAGATCACATT | 773 |
| orf1a_7249 | UUUGGCAUAUAUU CUUUUCA | 576 | AGTTGCAGAGTGGTTT TTGGCATATATTCTTTT CACTAGGTTTTT | 774 |
| orf1a_1066 | UGGGGAAUGUCCA AAUUUUG | 577 | ATTTGACACCTTCAAT GGGGAATGTCCAAATT TTGTATTTCCCTT | 775 |
| orf1a_11197 | UGCCACUGUAGCUU AUUUUA | 578 | TTTGTTACCTTCTCTTG CCACTGTAGCTTATTTT AATATGGTCTA | 776 |
| orf1a_13292 | UGUGACUUAAAAG GUAAGUA | 579 | AATCCTAAAGGATTTT GTGACTTAAAAGGTAA GTATGTACAAATA | 777 |
| orf1a_12931 | UCCUAAAGUGAAG UAUUUAU | 580 | AGACACACCTAAAGGT CCTAAAGTGAAGTATT TATACTTTATTAA | 778 |
| orf1a_4598 | CUUGUUACAAUGCC ACUUGG | 581 | GATCTAAATGAAACTC TTGTTACAATGCCACTT GGCTATGTAACA | 779 |
| orf1a_12515 | UGUGAUGGUACAA CAUUUAC | 582 | ACATATAAAAATACGT GTGATGGTACAACATT TACTTATGCATCA | 780 |
| orf1a_9060 | AUUGUUAUGAUAC CAAUGUA | 583 | GTAAGCCAGTACCATA TTGTTATGATACCAAT GTACTAGAAGGTT | 781 |
| orf1a_1286 | UGCGAAUUUUGUG GCACUGA | 584 | TTTGTTAAAGCCACTT GCGAATTTTGTGGCAC TGAGAATTTGACT | 782 |
| orf1a_9707 | AUUUCCACAAAGC AUUUCUA | 585 | GCTTATATCATTTGTAT TTCCACAAAGCATTTC TATTGGTTCTTT | 783 |
| orf1a_5110 | UAAAACAUUUUAU GUUUUAC | 586 | TAATTCACATGAAGGT AAAACATTTTATGTTTT ACCTAATGATGA | 784 |
| orf1a_9041 | UCUGGUAAGCCAG UACCAUA | 587 | ATTTTTAAAGATGCTTC TGGTAAGCCAGTACCA TATTGTTATGAT | 785 |
| orf1a_11687 | CUUGGUGUUUAUG AUUACUU | 588 | TACTTTAGACTGACTCT TGGTGTTTATGATTACT TAGTTTCTACA | 786 |
| orf1a_12215 | UUGAAUGUGGCUA AAUCUGA | 589 | AAGTTGAAGAAGTCTT TGAATGTGGCTAAATC TGAATTTGACCGT | 787 |
| orf1a_11254 | UAUGACAUGGUUG GAUAUGG | 590 | TTGGGTGATGCGTATT ATGACATGGTTGGATA TGGTTGATACTAG | 788 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| orf1a_6963 | UUUUACUAUUAAG UGUUUGC | 591 | ATATTATAATTTGGTTT TTACTATTAAGTGTTTG CCTAGGTTCTT | 789 |
| orf1a_2969 | AUGGCUACAUACU ACUUAUU | 592 | TTAGATGAGTGGAGTA TGGCTACATACTACTT ATTTGATGAGTCT | 790 |
| orf1a_5449 | UAGAGAAACAAUG AGUUACU | 593 | TGAGTTAGGTGATGTT AGAGAAACAATGAGTT ACTTGTTTCAACA | 791 |
| orf1a_5238 | ACCCACAAGUUAAU GGUUUA | 594 | CTAAAAAGTGGAAATA CCCACAAGTTAATGGT TTAACTTCTATTA | 792 |
| orf1a_8059 | UUCAUCAACUUUU AACGUAC | 595 | TTACGTTAATACGTTTT CATCAACTTTTAACGT ACCAATGGAAAA | 793 |
| orf1a_12276 | UGGCUGAUCAAGC UAUGACC | 596 | GTAAGTTGGAAAAGAT GGCTGATCAAGCTATG ACCCAAATGTATA | 794 |
| orf1a_4097 | UUCUUAAAGAAAG AUGCUCC | 597 | GACATTGACATCACTT TCTTAAAGAAAGATGC TCCATATATAGTG | 795 |
| orf1ab_19120 | UAUAAAAUAGAAG AAUUAUU | 598 | TGTAGTGACAAAGCTT ATAAAATAGAAGAATT ATTCTATTCTTAT | 796 |
| orf1ab_17193 | GAAGGCAUUAAAA UAUUUGC | 599 | TGATGCACTATGTGAG AAGGCATTAAAATATT TGCCTATAGATAA | 797 |
| orf1ab_17034 | UGCAAAUUAUCAA AAGGUUG | 600 | GTTTTCTAGCAATGTTG CAAATTATCAAAAGGT TGGTATGCAAAA | 798 |
| orf1ab_19748 | UUGAAAAUAAAAC AACAUUA | 601 | TTGATGTAGAATTGTTT GAAAATAAAACAACAT TACCTGTTAATG | 799 |
| orf1ab_17980 | UAUGACAAGUUGC AAUUUAC | 602 | TCTGATAGAGACCTTT ATGACAAGTTGCAATT TACAAGTCTTGAA | 800 |
| orf1ab_21482 | UUAGUAAAGGUAG ACUUAUA | 603 | TGATTTTATCTCTTCTT AGTAAAGGTAGACTTA TAATTAGAGAAA | 801 |
| orf1ab_13842 | UGAUGAAGGUAAU UGUGACA | 604 | TGCTTTAAGGCATTTTG ATGAAGGTAATTGTGA CACATTAAAAGA | 802 |
| orf1ab_19071 | UGAUGUAGAAUGG AAGUUCU | 605 | GTGTGTACCTCAAGCT GATGTAGAATGGAAGT TCTATGATGCACA | 803 |
| orf1ab_13878 | UGUCACAUACAAU UGUUGUG | 606 | ATTAAAAGAAATACTT GTCACATACAATTGTT GTGATGATGATTA | 804 |
| orf1ab_16555 | AAUGCAAUUGCAA CAUGUGA | 607 | AATGTTACTGACTTTA ATGCAATTGCAACATG TGACTGGACAAAT | 805 |
| orf1ab_17284 | UCAACAUUAGAAC AGUAUGU | 608 | AAATTCAAAGTGAATT CAACATTAGAACAGTA TGTCTTTTGTACT | 806 |

TABLE 7-continued

SARS-CoV2-Additional target sequences

| Sequence ID | 20 nt Sequence | SEQ ID NO: | 45 nt Gene Region | SEQ ID NO: |
|---|---|---|---|---|
| orf1ab_17852 | CAGAAUAUGACUA UGUCAUA | 609 | ATTCATCACAGGGCTC AGAATATGACTATGTC ATATTCACTCAAA | 807 |
| orf1ab_17671 | GUUAUCACGCAUG AUGUUUC | 610 | ATGTTTTATAAGGGTG TTATCACGCATGATGT TTCATCTGCAATT | 808 |
| orf1ab_21331 | CAUGCAAAUUACA UAUUUUG | 611 | GATGGTTATGTCATGC ATGCAAATTACATATT TTGGAGGAATACA | 809 |
| orf1ab_18612 | GUUGACAUCUAUG AAGUAUU | 612 | GGCACATGGCTTTGAG TTGACATCTATGAAGT ATTTTGTGAAAAT | 810 |
| orf1ab_19345 | UUUGUUAAUUUAA AACAAUU | 613 | TTTGATAAAAGTGCTT TTGTTAATTTAAAACA ATTACCATTTTTC | 811 |
| orf1ab_15409 | AAUGAGUGUGCUC AAGUAUU | 614 | TTCTATAGATTAGCTA ATGAGTGTGCTCAAGT ATTGAGTGAAATG | 812 |
| orf1ab_19617 | UCAGAGUUUAGAA AAUGUGG | 615 | CACTTTTACAAGACTT CAGAGTTTAGAAAATG TGGCTTTTAATGT | 813 |
| orf1ab_21444 | AAAAGAAGGUCAA AUCAAUG | 616 | TGCTGTTATGTCTTTA AAAGAAGGTCAAATCA ATGATATGATTTT | 814 |
| orf1ab_20511 | AUUACUUGAUGAU UUUGUUG | 617 | TTCTGTTATTGATTTA TTACTTGATGATTTTG TTGAAATAATAAA | 815 |
| orf1ab_21174 | AGAACAUUCUUGG AAUGCUG | 618 | GGCTATAAAGATAACA GAACATTCTTGGAATG CTGATCTTTATAA | 816 |
| orf1ab_19732 | GUUGAUGUAGAAU UGUUUGA | 619 | ACAAAAGTTGATGGTG TTGATGTAGAATTGTT TGAAAATAAAACA | 817 |
| S_24473 | GGUGCAAUUUCAA GUGUUUU | 620 | CTTAGCTCCAATTTTGG TGCAATTTCAAGTGTTT TAAATGATATC | 818 |
| S_22368 | AUCUUCAACCUAGG ACUUUU | 621 | CTTATTATGTGGGTTAT CTTCAACCTAGGACTT TTCTATTAAAAT | 819 |
| S_24635 | GCUGCUACUAAAA UGUCAGA | 622 | GCTTCTGCTAATCTTGC TGCTACTAAAATGTCA GAGTGTGTACTT | 820 |
| S_21952 | CUGUGAAUUUCAA UUUUGUA | 623 | TGTTGTTATTAAAGTCT GTGAATTTCAATTTTGT AATGATCCATT | 821 |
| S_23698 | UGCCAUACCCACAA AUUUUA | 624 | CTCTAATAACTCTATTG CCATACCCACAAATTT TACTATTAGTGT | 822 |
| S_23936 | CCACCAAUUAAAGA UUUUGG | 625 | CAAATTTACAAAACAC CACCAATTAAAGATTT TGGTGGTTTTAAT | 823 |
| S_22807 | UGGAAAGAUUGCU GAUUAUA | 626 | CGCTCCAGGGCAAACT GGAAAGATTGCTGATT ATAATTATAAATT | 824 |

TABLE 7-continued

| SARS-CoV2-Additional target sequences | | | | |
|---|---|---|---|---|
| Sequence ID | 20 nt Sequence | SEQ ID NO: | 45 nt Gene Region | SEQ ID NO: |
| S_21938 | GUUGUUAUUAAAG UCUGUGA | 627 | AATAACGCTACTAATG TTGTTATTAAAGTCTGT GAATTTCAATTT | 825 |
| S_22138 | UGUGUUUAAGAAU AUUGAUG | 628 | AAATCTTAGGGAATTT GTGTTTAAGAATATTG ATGGTTATTTTAA | 826 |
| S_24828 | UUCCUCGUGAAGG UGUCUUU | 629 | ATGGAAAAGCACACTT TCCTCGTGAAGGTGTC TTTGTTTCAAATG | 827 |
| S_23315 | CUUGACAUUACACC AUGUUC | 630 | CAGACACTTGAGATTC TTGACATTACACCATG TTCTTTTGGTGGT | 828 |
| S_25376 | UACACAUAAACGA ACUUAUG | 631 | GGAGTCAAATTACATT ACACATAAACGAACTT ATGGATTTGTTTA | 829 |
| S_22259 | AUUAACAUCACUA GGUUUCA | 632 | GATTTGCCAATAGGTA TTAACATCACTAGGTT TCAAACTTTACTT | 830 |
| S_22129 | UAGGGAAUUUGUG UUUAAGA | 633 | TAATTTCAAAAATCTT AGGGAATTTGTGTTTA AGAATATTGATGG | 831 |
| S_24254 | UUUGCUAUGCAAA UGGCUUA | 634 | GCATTACAAATACCAT TTGCTATGCAAATGGC TTATAGGTTTAAT | 832 |
| S_22276 | UCAAACUUUACUU GCUUUAC | 635 | TAACATCACTAGGTTT CAAACTTTACTTGCTTT ACATAGAAGTTA | 833 |
| S_23270 | GCUGACACUACUGA UGCUGU | 636 | TTTGGCAGAGACATTG CTGACACTACTGATGC TGTCCGTGATCCA | 834 |
| S_25235 | AUUGCCAUAGUAA UGGUGAC | 637 | TTTATAGCTGGCTTGAT TGCCATAGTAATGGTG ACAATTATGCTT | 835 |
| S_23842 | UACACAAUUAAACC GUGCUU | 638 | ATATGGCAGTTTTTGT ACACAATTAAACCGTG CTTTAACTGGAAT | 836 |
| S_23307 | UUGAGAUUCUUGA CAUUACA | 639 | GTGATCCACAGACACT TGAGATTCTTGACATT ACACCATGTTCTT | 837 |
| S_21808 | UGUCCUACCAUUUA AUGAUG | 640 | GAGGTTTGATAACCCT GTCCTACCATTTAATG ATGGTGTTTATTT | 838 |
| S_23935 | ACCACCAAUUAAAG AUUUUG | 641 | ACAAATTTACAAAACA CCACCAATTAAAGATT TTGGTGGTTTTAA | 839 |

TABLE 8

| Top SARS-CoV-2 based on homology. | | | | |
|---|---|---|---|---|
| Sequence ID | 20 nt Sequence | SEQ ID NO: | 45 nt Gene Region | SEQ ID NO: |
| E_26313 | CGUGGUAUUCU UGCUAGUUA | 64 | TCTTTTTCTTGCTTTCGTGGTATT CTTGCTAGTTACACTAGCCAT | 172 |

TABLE 8-continued

Top SARS-CoV-2 based on homology.

| Sequence ID | 20 nt Sequence | SEQ ID NO: | 45 nt Gene Region | SEQ ID NO: |
|---|---|---|---|---|
| 8b_27986 | UGUAGUUGAUG ACCCGUGUC | 97 | TCAACATCAACCATATGTAGTTG ATGACCCGTGTCCTATTCACTT | 205 |
| 7a27720 | UAUAACACUUU GCUUCACAC | 93 | TGCGGCAATAGTGTTTATAACAC TTTGCTTCACACTCAAAAGAAA | 201 |
| orf1ab_14080 | GGUAACUGGUA UGAUUUCGG | 11 | AATCAAGATCTCAATGGTAACTG GTATGATTTCGGTGATTTCATA | 119 |
| M_26581 | GGAACCUAGUA AUAGGUUUC | 72 | AGCTCCTTGAACAATGGAACCTA GTAATAGGTTTCCTATTCCTTA | 180 |
| 522820 | GAUUAUAAUUA UAAAUUACC | 38 | ACTGGAAAGATTGCTGATTATAA TTATAAATTACCAGATGATTTT | 146 |
| orf1ab_21391 | UUUGACAUGAG UAAAUUUCC | 22 | TCTTCCTATTCTTTATTTGACATG AGTAAATTTCCCCTTAAATTA | 130 |
| orf1ab_17107 | UUUGCUAUUGG CCUAGCUCU | 16 | ACTGGTAAGAGTCATTTTGCTAT TGGCCTAGCTCTCTACTACCCT | 124 |
| orf1ab_20892 | UGCACCAGGUA CAGCUGUUU | 21 | TTCTGATAAAGGAGTTGCACCAG GTACAGCTGTTTTAAGACAGTG | 129 |
| orf1ab_20497 | UCUGUUAUUGA UUUAUUACU | 20 | TCTAAGTGTGTGTGTTCTGTTATT GATTTATTACTTGATGATTTT | 128 |
| N_28655 | GACGGCAUCAU AUGGGUUGC | 108 | TATGGTGCTAACAAAGACGGCAT CATATGGGTTGCAACTGAGGGA | 216 |
| 524289 | UGGAGUUACAC AGAAUGUUC | 45 | TAGGTTTAATGGTATTGGAGTTA CACAGAATGTTCTCTATGAGAA | 153 |
| M_26624 | UCUACAAUUUG CCUAUGCCA | 74 | TACATGGATTTGTCTTCTACAATT TGCCTATGCCAACAGGAATAG | 182 |
| orf1a_7643 | GCUGGUAGUAC AUUUAUUAG | 28 | TGTGATACATTCTGTGCTGGTAG TACATTTATTAGTGATGAAGTT | 136 |
| orf1a_12932 | CCUAAAGUGAA GUAUUUAUA | 34 | GACACACCTAAAGGTCCTAAAGT GAAGTATTTATACTTTATTAAA | 142 |
| E_26305 | CUUGCUUUCGU GGUAUUCUU | 63 | AGCGTACTTCTTTTTCTTGCTTTC GTGGTATTCTTGCTAGTTACA | 171 |
| M_26602 | UAUUCCUUACA UGGAUUUGU | 73 | TAGTAATAGGTTTCCTATTCCTTA CATGGATTTGTCTTCTACAAT | 181 |
| 3a_25630 | GUUUGCAACUU GCUGUUGUU | 48 | AAGGGTGTTCACTTTGTTTGCAA CTTGCTGTTGTTGTTTGTAACA | 156 |
| E_26455 | CCUGAUCUUCU GGUCUAAAC | 67 | AATTCTTCTAGAGTTCCTGATCTT CTGGTCTAAACGAACTAAATA | 175 |
| E_26463 | UCUGGUCUAAA CGAACUAAA | 68 | TAGAGTTCCTGATCTTCTGGTCTA AACGAACTAAATATTATATTA | 176 |
| 522550 | CCUAAUAUUAC AAACUUGUG | 37 | TCTATTGTTAGATTTCCTAATATT ACAAACTTGTGCCCTTTTGGT | 145 |
| orf1a_8744 | UUUGCUAACAA ACAUGCUGA | 31 | TCTACAGATACTTGTTTTGCTAAC AAACATGCTGATTTTGACACA | 139 |
| orf1ab_17370 | GGCCACAAAUU AUGAUUUGA | 17 | TGATGAAATTTCAATGGCCACAA ATTATGATTTGAGTGTTGTCAA | 125 |
| 7a_27633 | AUCAGUUUCAC CUAAACUGU | 88 | TCAGTTACGTGCCAGATCAGTTT CACCTAAACTGTTCATCAGACA | 196 |
| M_27014 | GCCUAAAGAAA UCACUGUUG | 79 | TGACATCAAGGACCTGCCTAAAG AAATCACTGTTGCTACATCACG | 187 |

TABLE 8-continued

| Top SARS-CoV-2 based on homology. | | | | |
|---|---|---|---|---|
| Sequence ID | 20 nt Sequence | SEQ ID NO: | 45 nt Gene Region | SEQ ID NO: |
| S_25375 | UUACACAUAAA CGAACUUAU | 46 | AGGAGTCAAATTACATTACACAT AAACGAACTTATGGATTTGTTT | 154 |
| 7a_27715 | GUGUUUAUAAC ACUUUGCUU | 92 | ATTGTTGCGGCAATAGTGTTTAT AACACTTTGCTTCACACTCAAA | 200 |

TABLE 9

| Antisense oligonucleotides targeting viral factors | | |
|---|---|---|
| Oligo ID | Sequence | SEQ ID NO: |
| orf1a_416 | ACTTCTACTAAGCCAC | 840 |
| orf1a_2290 | AAGCTTAAAGAATGTC | 841 |
| orf1a_8744-1 | CAGCATGTTTGTTAGC | 842 |
| orf1a_8744-2 | GCATGTTTGTTAGCAA | 843 |
| orf1a_9679-1 | AAGCAATTGTTATCCA | 844 |
| orf1a_9679-2 | TAAGCAATTGTTATCC | 845 |
| orf1ab_14361 | GTTTGCACAATGCAGA | 846 |
| orf1ab_17107 | AGAGCTAGGCCAATAG | 847 |
| orf1ab_18025 | AGCTTGTAAAGTTGCC | 848 |
| orf1ab_20892-1 | CAGCTGTACCTGGTGC | 849 |
| orf1ab_20892-2 | ACAGCTGTACCTGGTG | 850 |
| orf1ab_20892-3 | AACAGCTGTACCTGGT | 851 |
| S_22223-1 | AATGGTTCTAAAGCCG | 852 |
| S_22223-2 | CAATGGTTCTAAAGCC | 853 |
| S_23174 | TGAAGTTGAAATTGAC | 854 |
| S_23774 | CCACAAATGTACATTG | 855 |
| S_23778 | CAATGTACATTTGTGG | 856 |
| S_25375-1 | AGTTCGTTTATGTGTA | 857 |
| S_25375-2 | TAAGTTCGTTTATGTG | 858 |
| 3a_25717 | GAAGTAGACTAAAGCA | 859 |
| 3a_25914 | AATAGGACTTGTTGTG | 860 |
| 3a_25992 | AACTGTGTAATACAAC | 861 |
| 3a_26018-1 | ACAGCTGGTAATAGTC | 862 |
| 3a_26018-2 | CAGCTGGTAATAGTCT | 863 |
| 3a_26018-3 | TACAGCTGGTAATAGT | 864 |
| E_26258 | TACCTGTCTCTTCCGA | 865 |
| E_26261 | TAACGTACCTGTCTCT | 866 |
| E_26369-1 | AACAATATTGCAGCAG | 867 |
| E_26369-2 | TAACAATATTGCAGCA | 868 |

TABLE 9-continued

| Antisense oligonucleotides targeting viral factors | | |
|---|---|---|
| Oligo ID | Sequence | SEQ ID NO: |
| E_26374-1 | CGTTAACAATATTGCA | 869 |
| E_26374-2 | CTCACGTTAACAATAT | 870 |
| M_26581-1 | ACCTATTACTAGGTTC | 871 |
| M_26581-2 | AAACCTATTACTAGGT | 872 |
| M_26602-1 | ACAAATCCATGTAAGG | 873 |
| M_26602-2 | CAAATCCATGTAAGGA | 874 |
| M_26624 | TGGCATAGGCAAATTG | 875 |
| M_26717 | GTAAACAGCAGCAAGC | 876 |
| 7a_27455 | GTACCTCTAACACACT | 877 |
| 7a_27553 | AGCAAGTCAGTGCAAA | 878 |
| 7a_27565-1 | ATTGAGTGCTAAAGCA | 879 |
| 7a_27565-2 | GCAAATTGAGTGCTAA | 880 |
| 7a_27705 | AAACACTATTGCCGCA | 881 |
| 7a_27720 | GTGTGAAGCAAAGTGT | 882 |
| 8b_27940 | AAACTACATTCTTGGT | 883 |
| 8b_28002 | AGAAGTGAATAGGACA | 884 |
| 8b_28091-1 | TGAATGGGTGATTTAG | 885 |
| 8b_28091-2 | GAATGGGTGATTTAGA | 886 |
| 8b_28119 | AAACTGTATAATTACC | 887 |
| 8b_28163 | CCCAATTTAGGTTCCT | 888 |
| N_28655 | ACCCATATGATGCCGT | 889 |
| N_28945-1 | CAAGCTGGTTCAATCT | 890 |
| N_28945-2 | GCTGGTTCAATCTGTC | 891 |
| N_29141-1 | CCTTGTCTGATTAGTT | 892 |
| N_29141-2 | CTTGTCTGATTAGTTC | 893 |
| N_29307 | AATGACTTGATCTTTG | 894 |

Figure 3A:
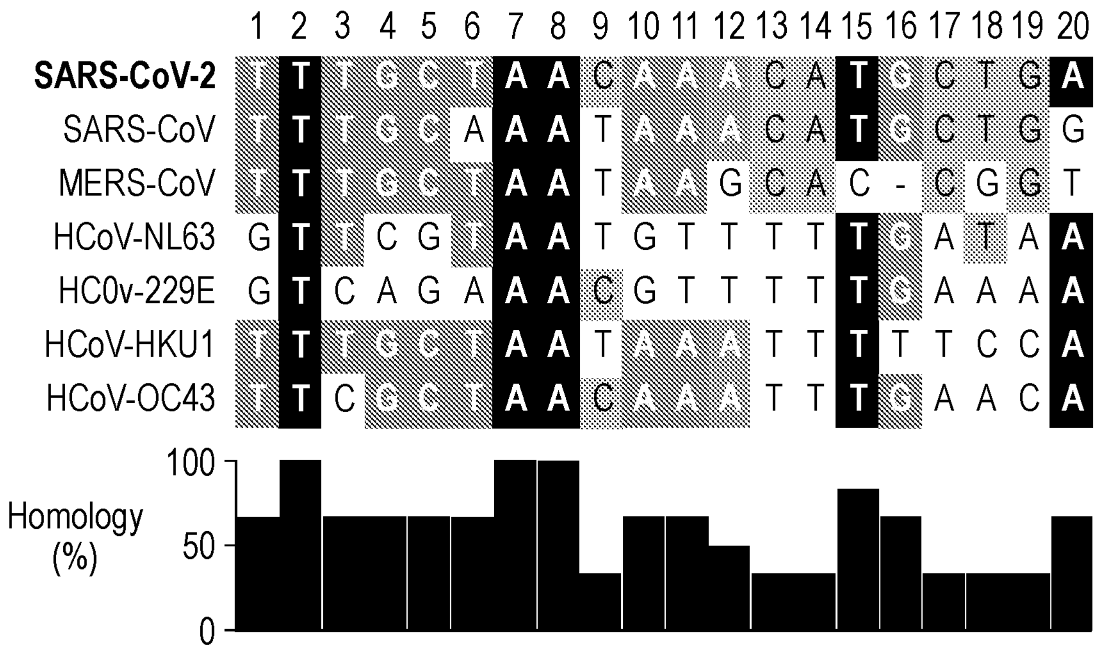
FIG. 3A-3B depict an alignment of siRNAs and ASOs selected for synthesis directed to six closely-related CoVs using a novel algorithm. Aligned genome regions of CoVs are shaded based on homology with darker coloring indicating higher homology with respect to SARS-CoV-2. The siRNA position is indicated on the top. Per position percent homology of SARS-CoV-2 to the six related CoVs is plotted on the bottom. SiRNA with low homology scores of 59 are shown in FIG. 3A (SEQ ID NOS 2583-2589, respectively, in order of appearance). SiRNA with a high homology score are shown in FIG. 3B (SEQ ID NOS 2590-2596, respectively, in order of appearance). Gaps in alignment are indicated with dashes (-).
Figure 3B:
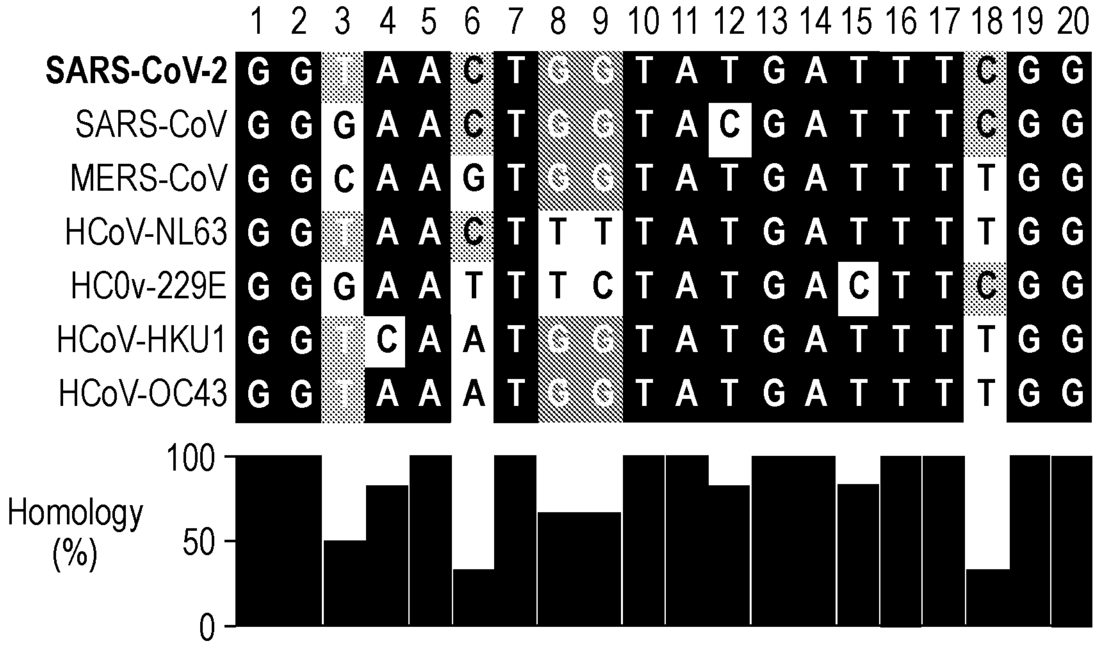

An alignment of siRNA and ASO selected for synthesis to six closely-related CoVs using the novel algorithm is shown in FIG. 3. Aligned genome regions of CoVs are shaded based on homology with darker coloring indicating higher homology with respect to SARS-CoV-2. The siRNA position is indicated on the top. Per position percent homology of SARS-CoV-2 to the six related CoVs is plotted on the bottom. SiRNA with low homology scores of 59 are shown in FIG. 3A. SiRNA with a high homology scores of score of 78 are shown in FIG. 3B. Gaps in alignment are indicated with dashes (-).

Figure 4A:
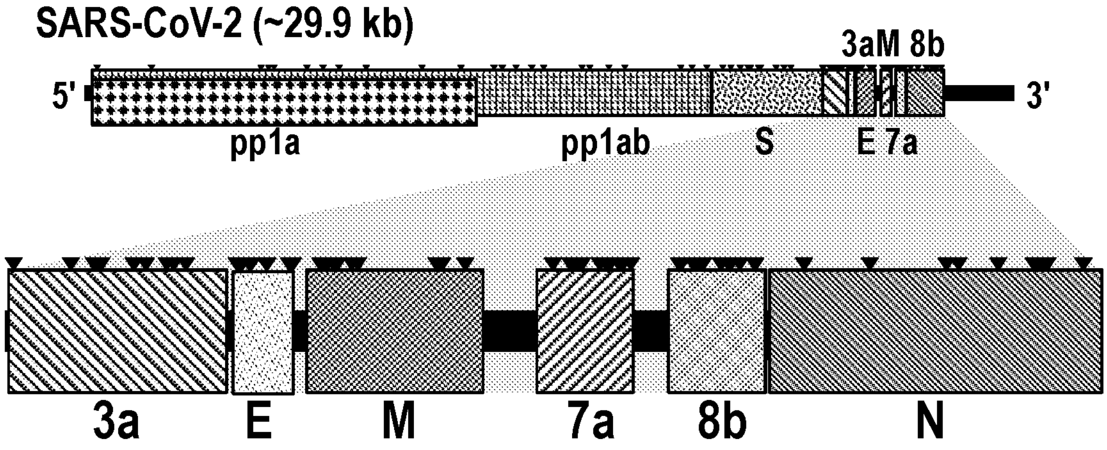
FIG. 4A-4B depict siRNA and ASO target selection based on the ability to target many SARS-CoV-2 genomes from patient isolates.
Figure 4B:
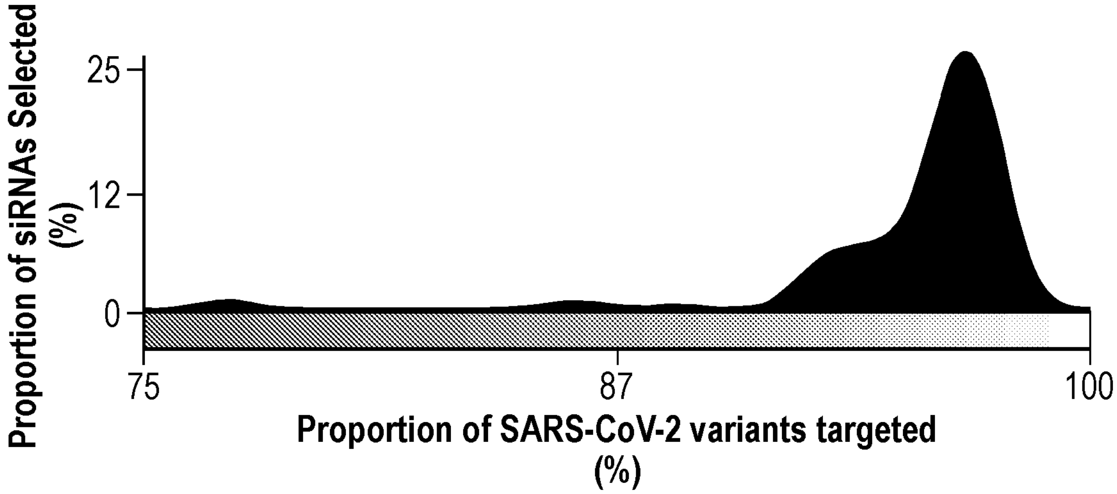
Figure 5A:
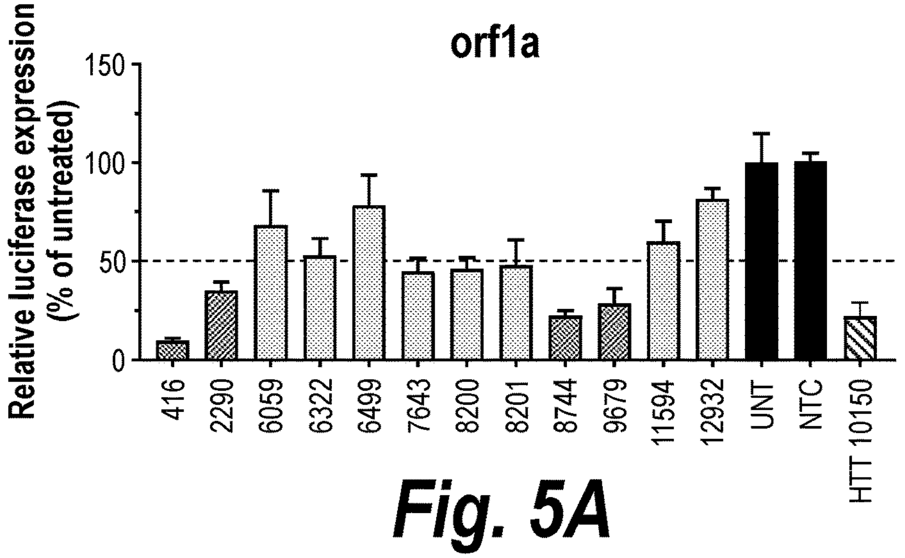
FIG. 5A-5I depicts the identification of siRNA hits for SARS-CoV-2. SiRNAs targeting different genes in the SARS-CoV-2 genome were tested for silencing efficacy.
Figure 5B:
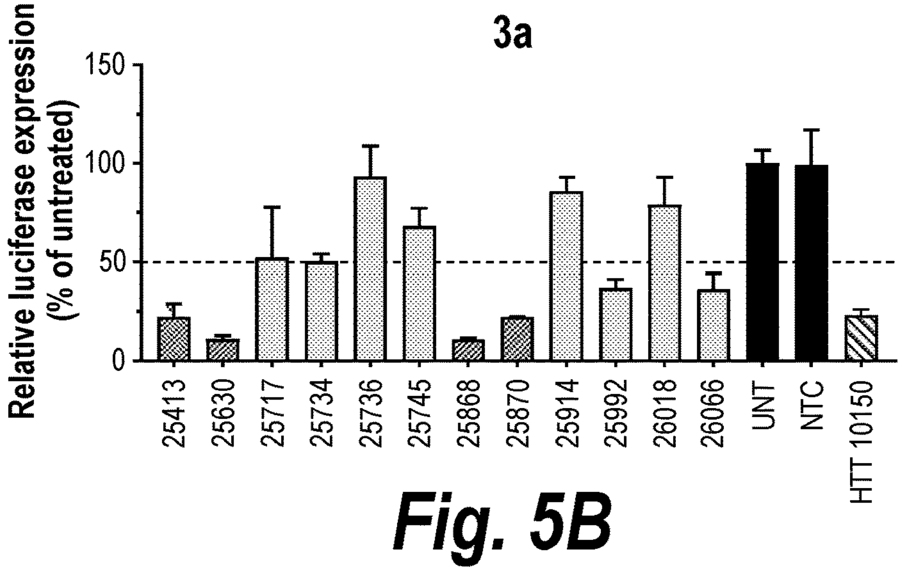
Figure 5C:
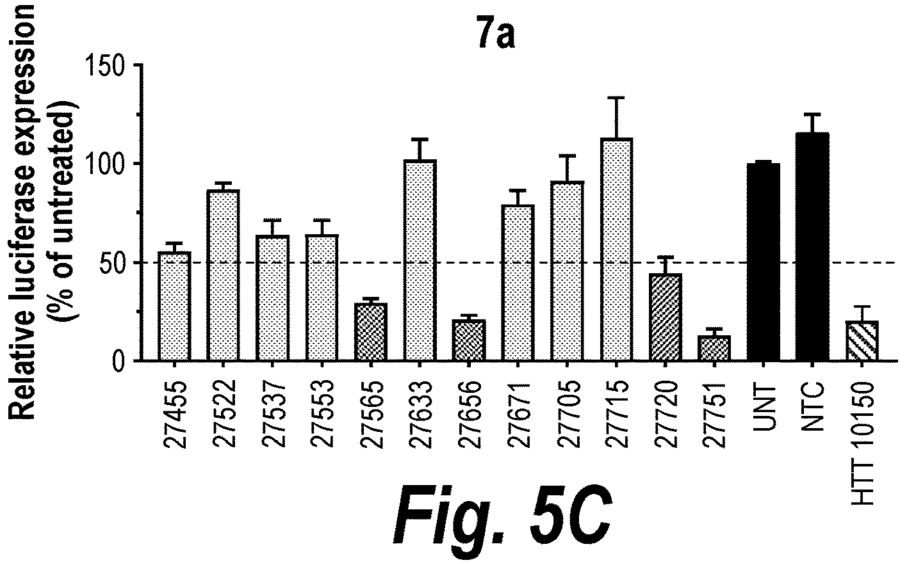
Figure 5D:
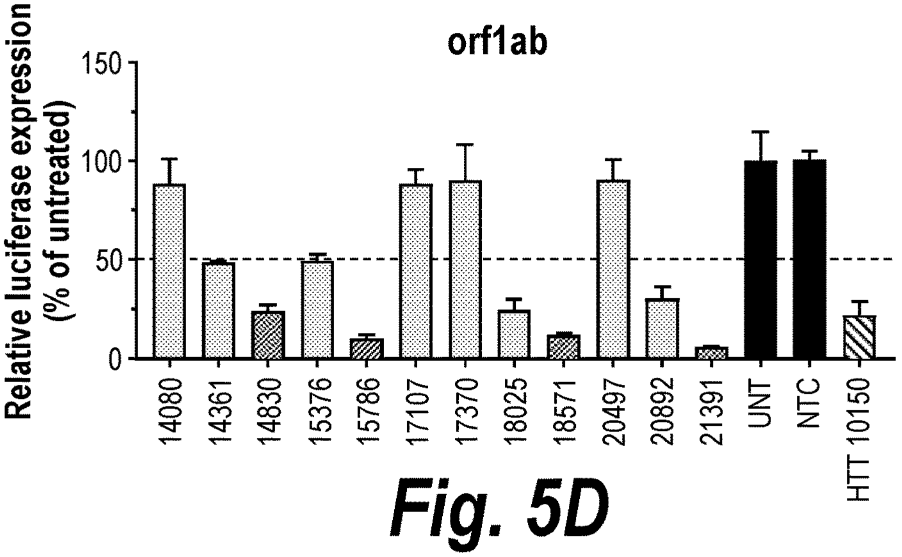
Figure 5E:
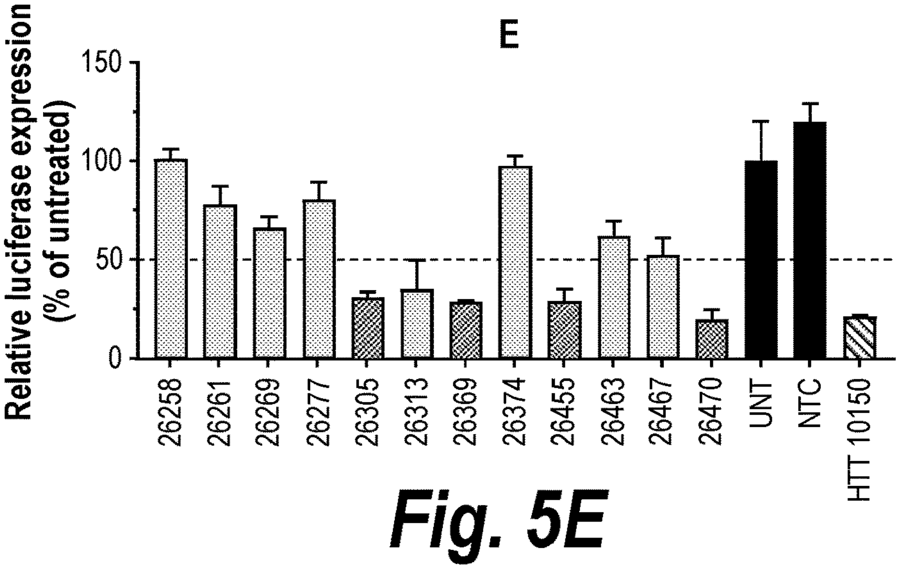
Figure 5F:
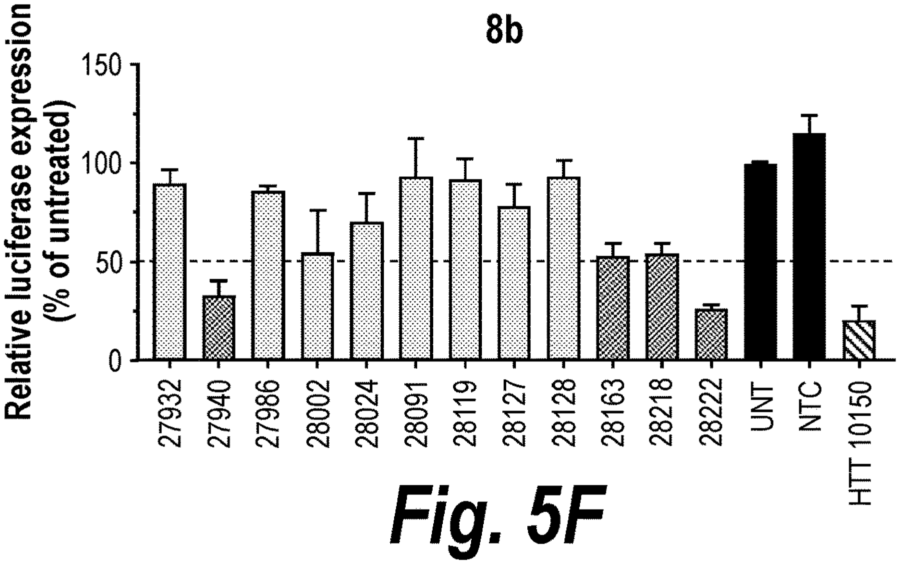
Figure 5G:
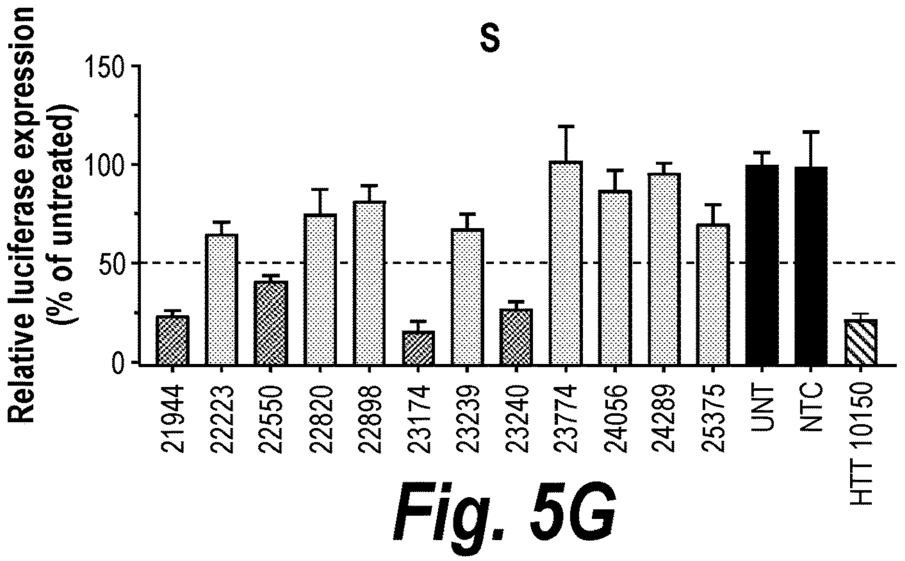
Figure 5H:
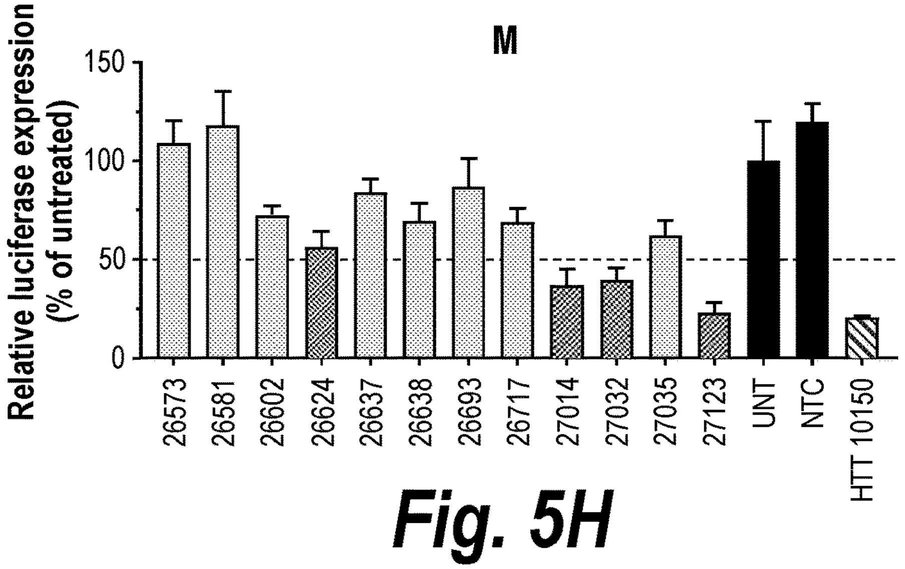
Figure 5I:
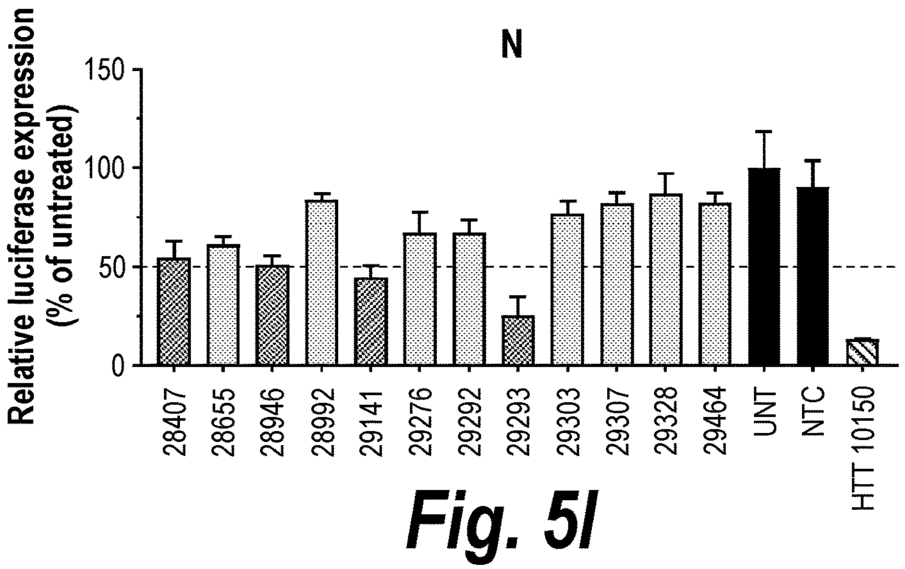
Figure 6A:
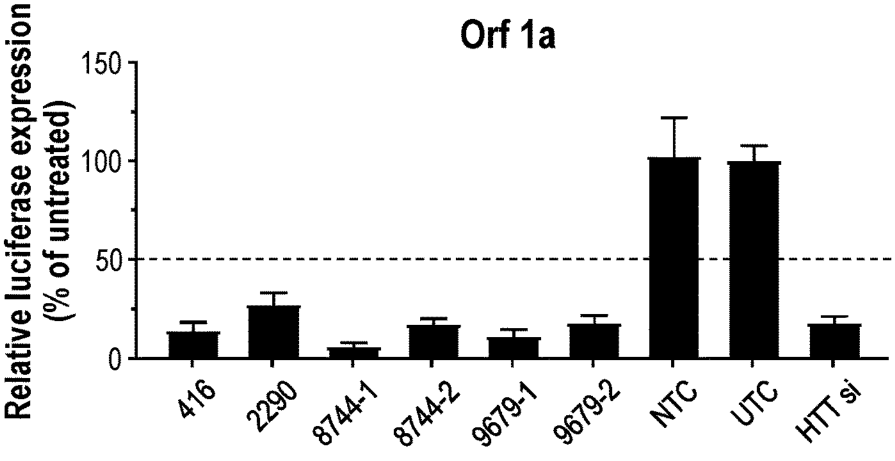
FIG. 6A-6I depict the identification of ASO hits for SARS-CoV-2. ASOs targeting different genes in the SARS-CoV2 genome were tested for silencing efficacy.
Figure 6B:
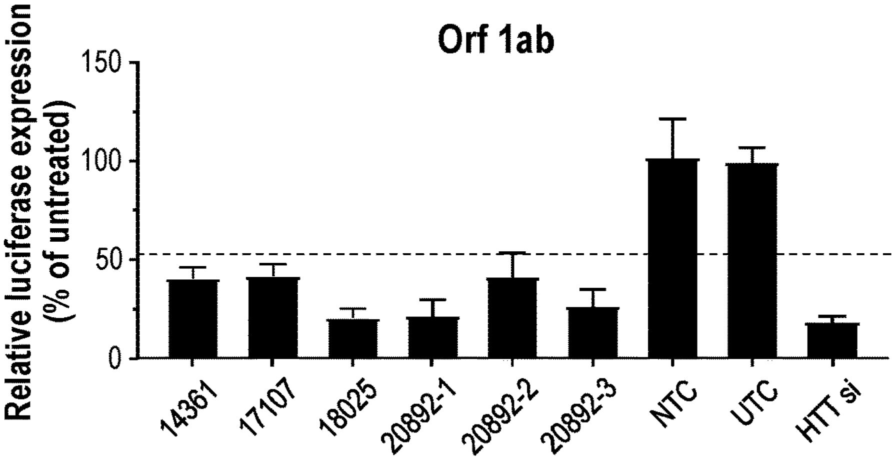
Figure 6C:
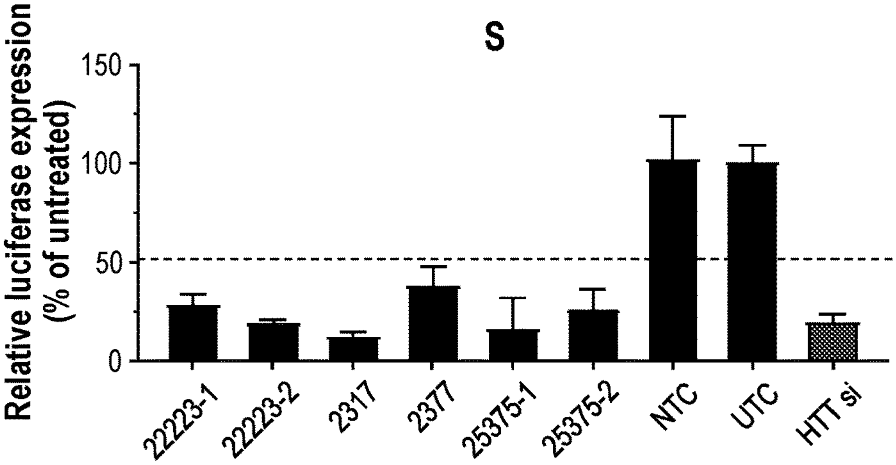
Figure 6D:
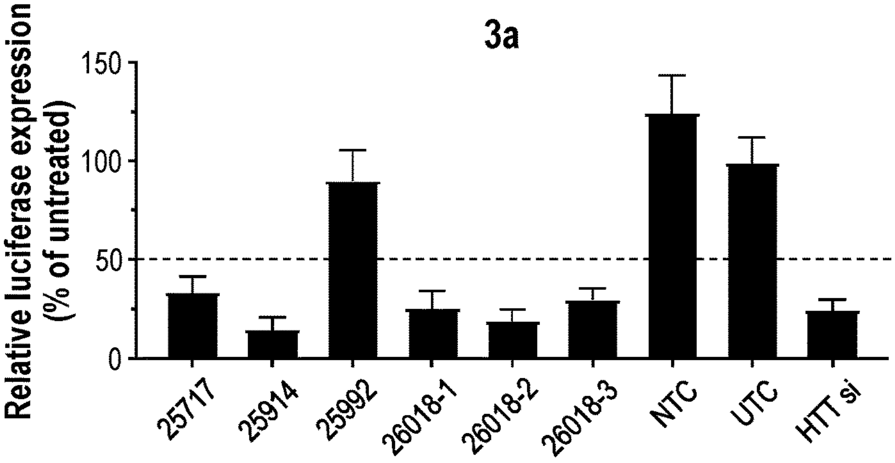
Figure 6E:
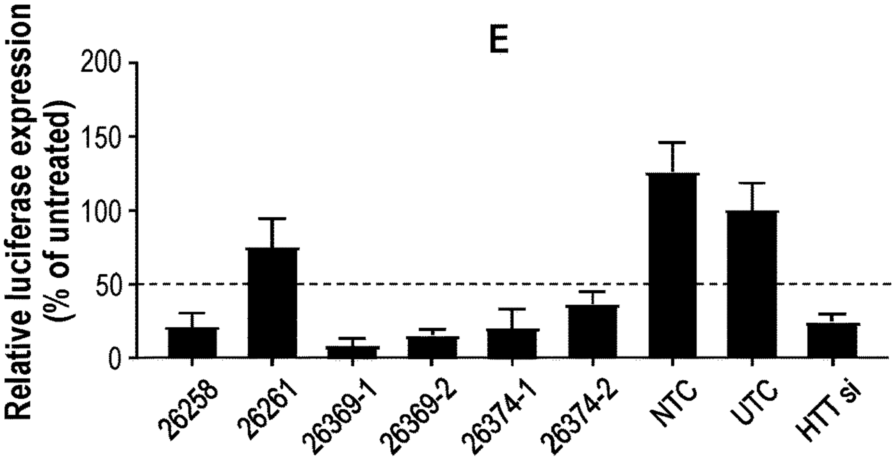
Figure 6F:
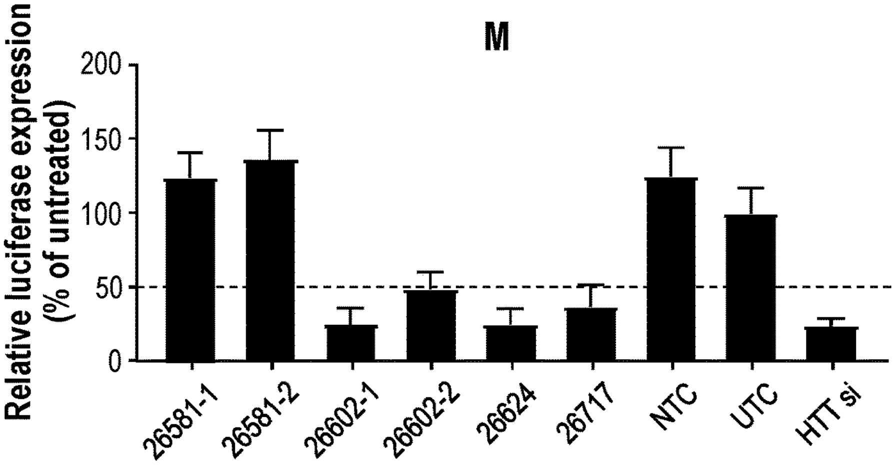
Figure 6G:
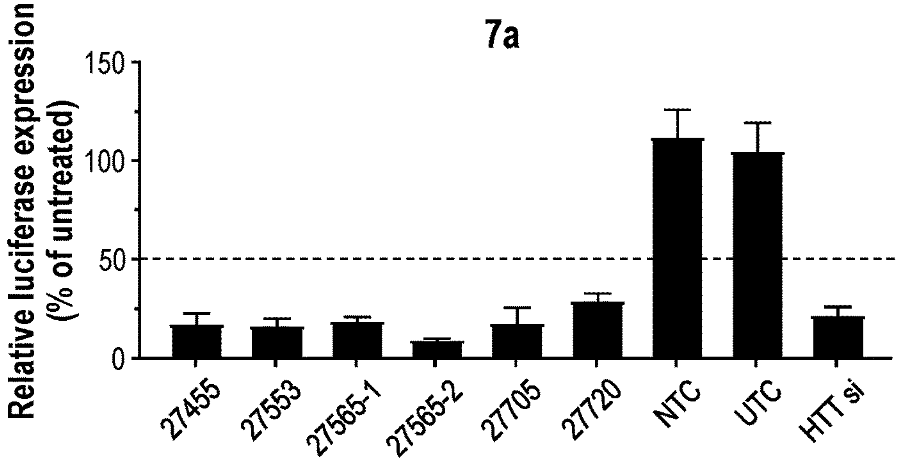
Figure 6H:
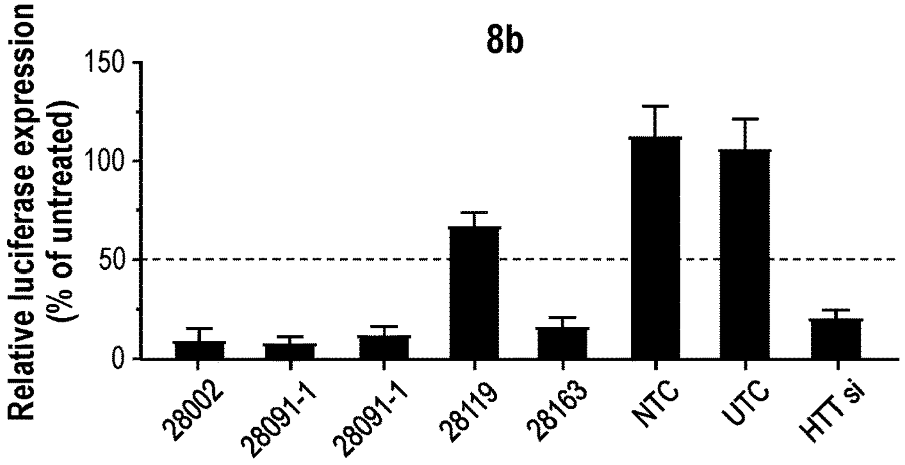
Figure 6I:
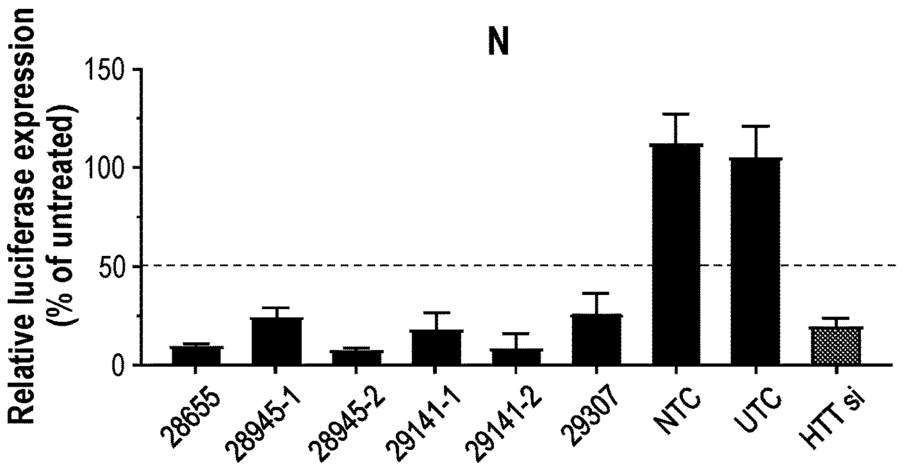

SiRNA and ASO target selections were based on the ability to target many SARS-CoV-2 genomes from patient isolates. siRNAs and ASOs were selected to target regions of the 9 selection genes with low mutation rates in other coronaviruses (FIG. 4A). The proportion of SARS-CoV-2 variants from patient isolates targeted by all selected siRNAs is plotted at the bottom. siRNAs and ASOs were selected to target regions of the 9 selection genes with low mutation rates in other coronaviruses (see previous figure), which resulted in selecting siRNAs that together target all isolates from SARS-CoV-infected patients, with >90% of siRNAs and ASOs selected targeting >95% of these genomes. The proportion of SARS-CoV-2 variants from patient isolates targeted by all selected siRNAs is plotted at the bottom. The coloured gradient indicates proportion of variant genomes targeted, with red indicating siRNAs that target fewer variants (with the lowest value being 77% of all variants targeted) and white indicating higher number of genomes targeted. Arrows in the gene diagram indicate siRNA and ASO target positions in the SARS-CoV2 genome and are coloured based on proportion of SARS-CoV-2 variants targeted and correlate with the colored gradient in the bottom plot. Dark red arrows indicate siRNAs that target <85% of genomes from patient isolates, while white and light pink arrows indicate siRNAs that target >90% of genomes SARS-CoV-2 isolates patients.

The scoring scheme methodology resulted in the selection of siRNAs that target all 708 SARS-CoV2 patient isolates available at the time of design with >95% of siRNAs (103 siRNAs) selected targeting more than 90% of the SARS-CoV2 genomes obtained from patient isolates. Furthermore, >60% of siRNAs (66 siRNAs) selected target more than 97% of these patient isolates.

Figure 7A:
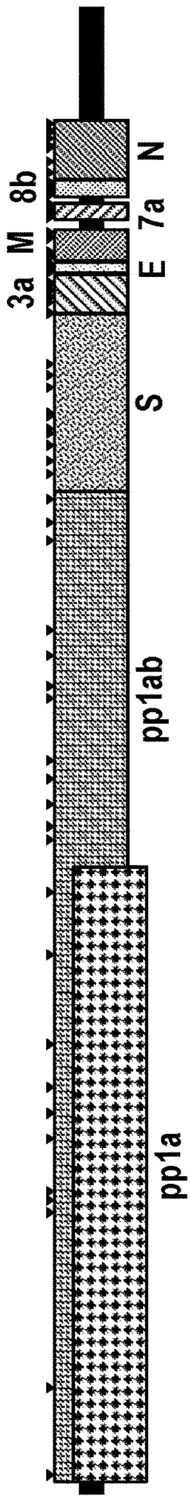
FIG. 7A-7B depict the identification of siRNA hits for SARS-CoV2 and mapping onto genes in the SARS-CoV-2 genome.
Figure 7B:
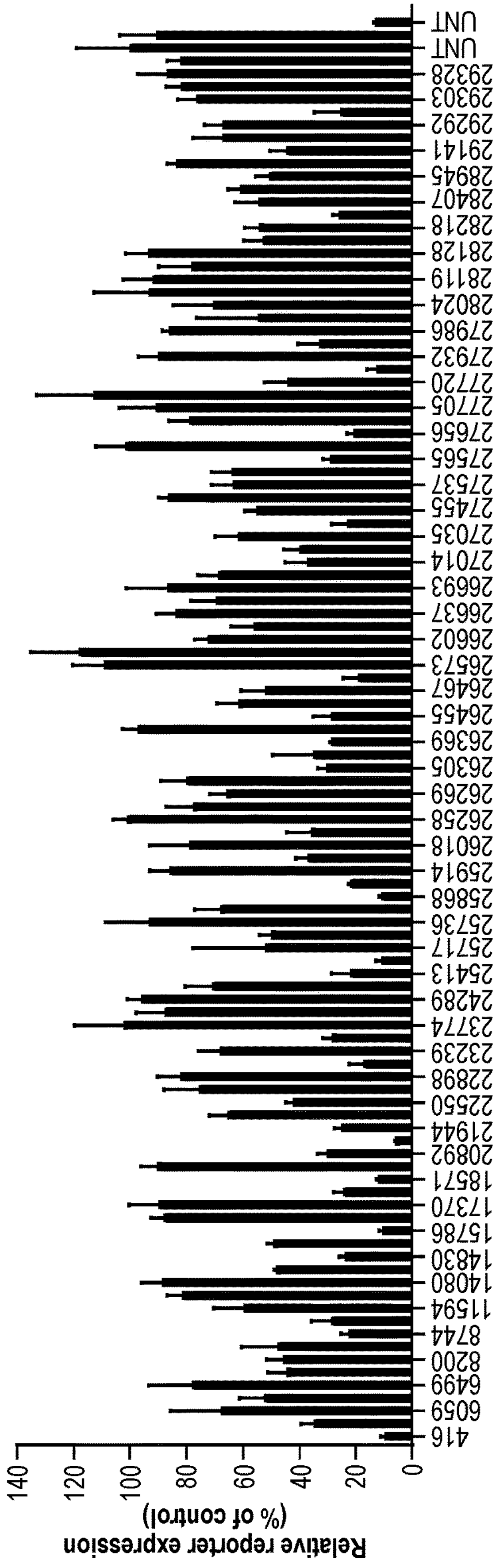
Figure 8A:
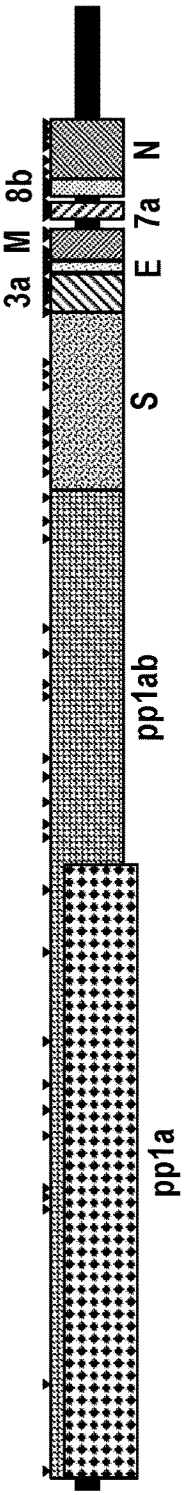
FIG. 8A-8B depicts the identification of ASO hits for SARS-CoV-2 and mapping onto genes in the SARS-CoV-2 genome.
Figure 8B:
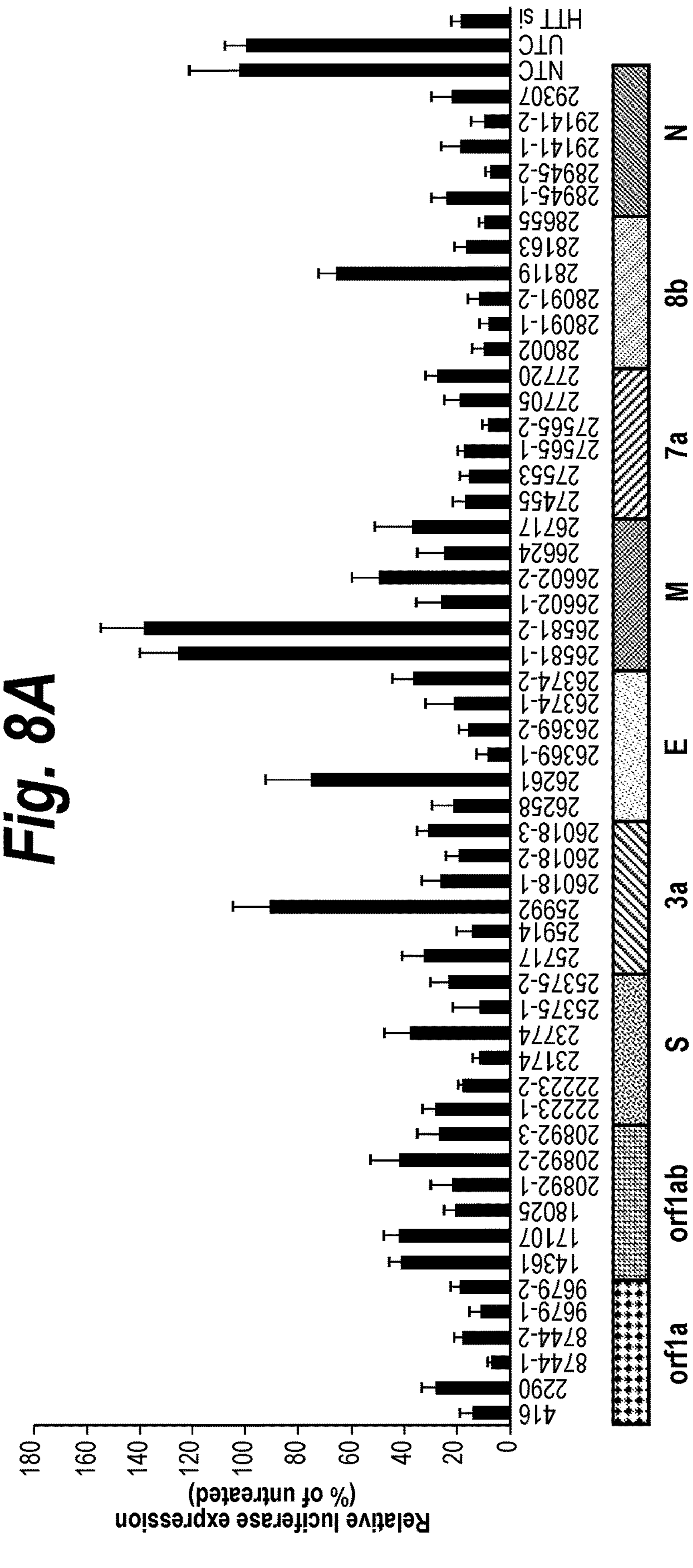
Figure 9A:
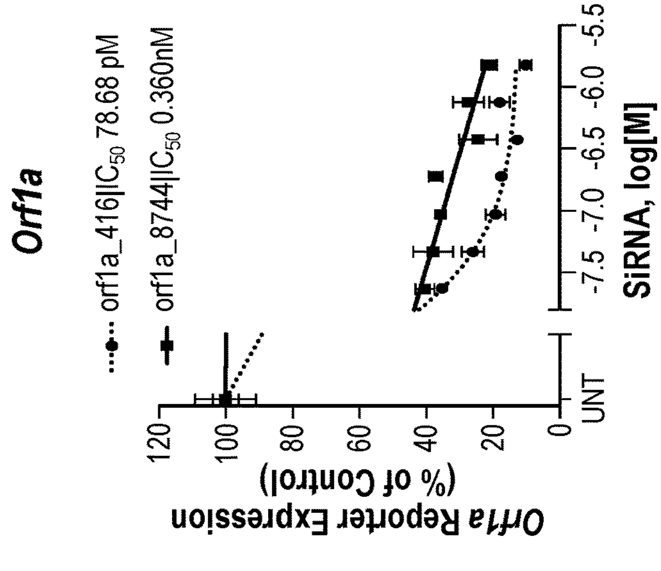
FIG. 9A-9I depict the validation and determination of $IC_{50}$ values. SiRNAs targeting different genes in the SARS-CoV-2 genome were tested for silencing efficacy in 8-point dose response studies.
Figure 9B:
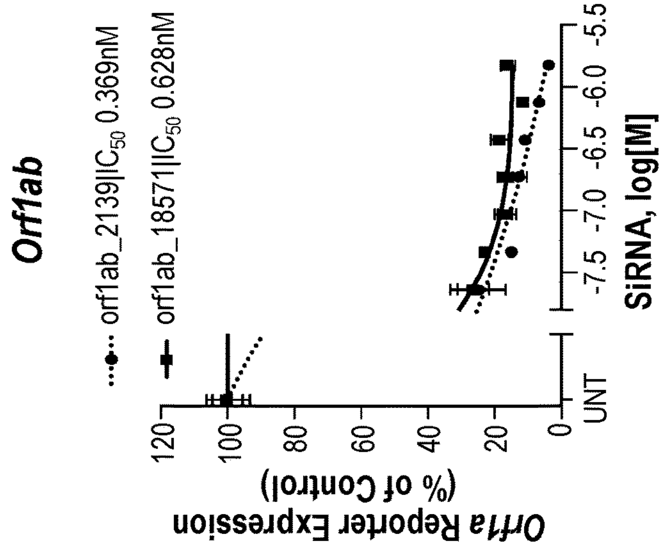
Figure 9C:
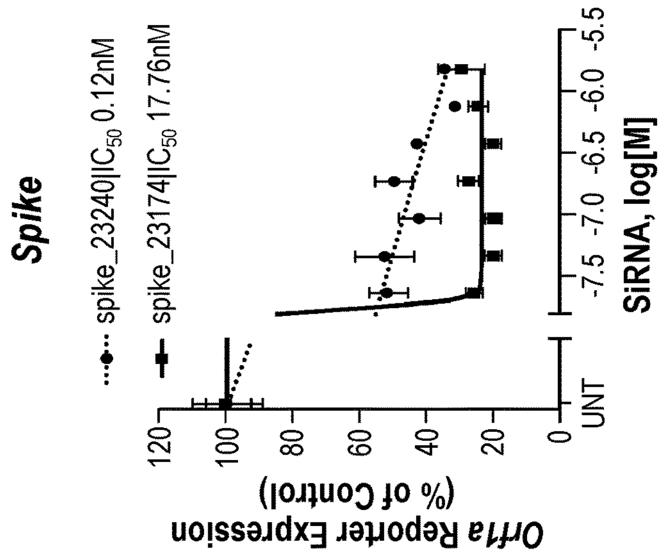
Figure 9D:
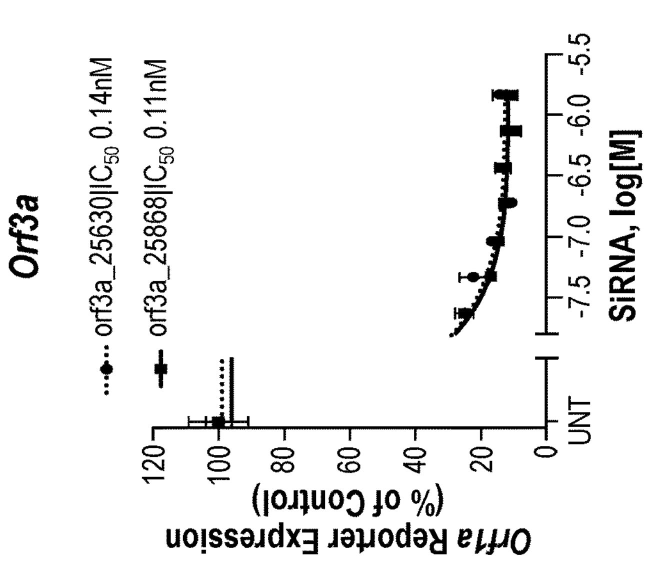
Figure 9E:
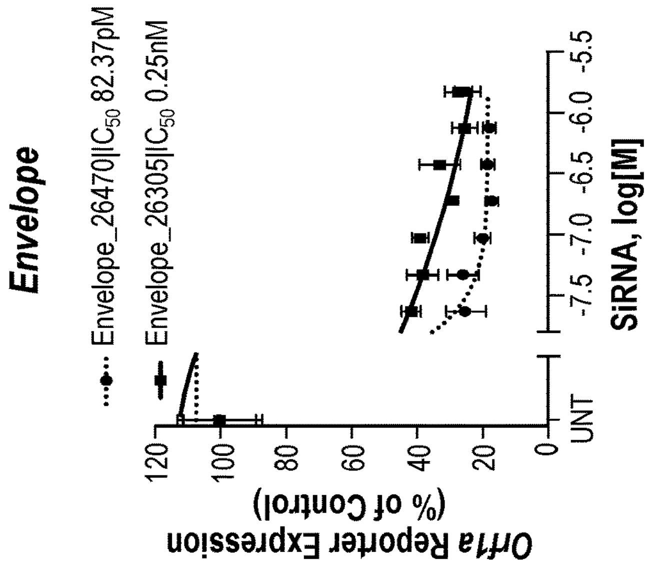
Figure 9F:
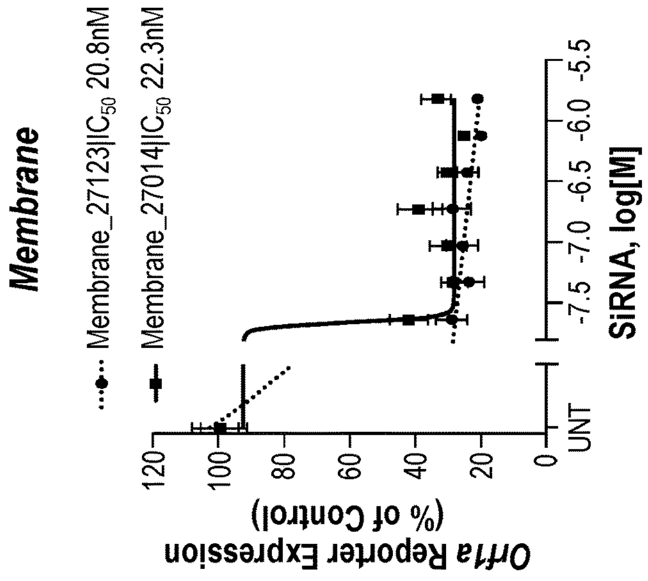
Figure 9G:
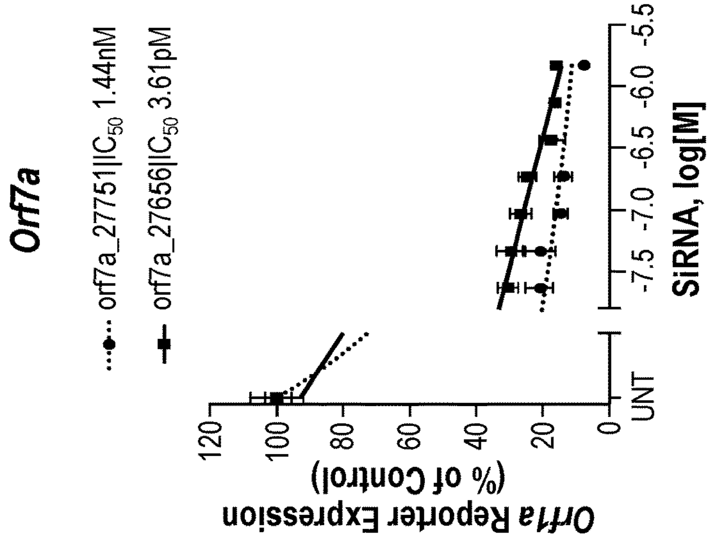
Figure 9H:
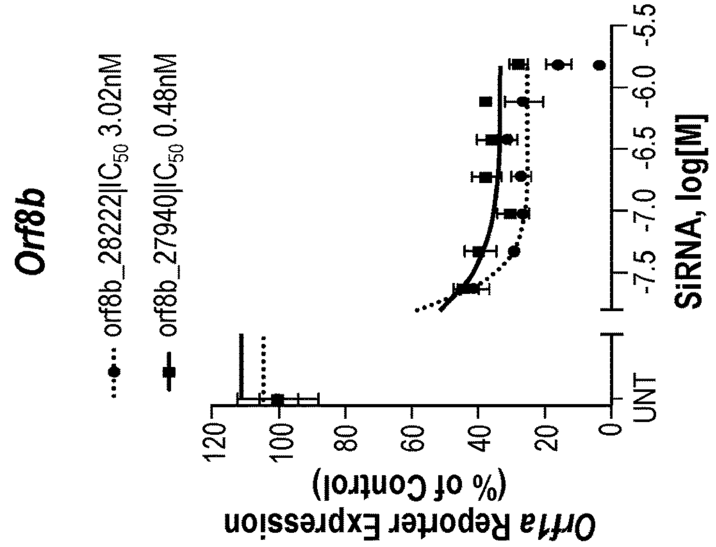
Figure 9I:
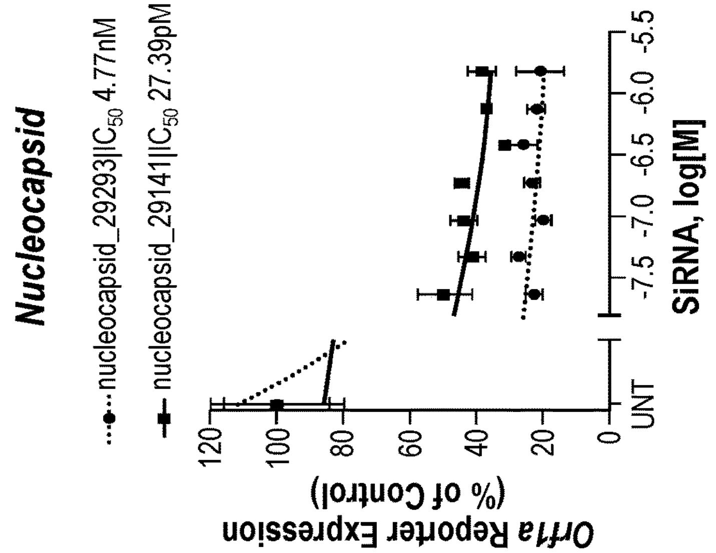

SiRNAs targeting different genes in the SARS-CoV2 genome were tested for silencing efficacy of the orf1a, 3a, 7a, orf1ab, E, gene 8b, S, M and N genes (FIG. 5, FIG. 7). For each target, at least 3 siRNAs were identified that that reduced target mRNA expression below 75% compared to untreated controls. siRNAs were tested in Hela cells and silencing was assessed using the psi-check reporter system, using an siRNA concentration of 1.5 uM and an assessment timepoint of 72 hours. Likewise, ASOs targeting the different genes in the SARS-CoV2 genome were tested for silencing efficacy, as depicted in FIG. 6 and FIG. 8. For each target, at least 3 ASOs were identified that reduced target mRNA expression below 75% compared to untreated controls. SiRNAs targeting the orf1a, 3a, 7a, orf1ab, E, gene 8b, S, M and N genes in the SARS-CoV2 genome were subsequently tested for silencing efficacy in 8-point dose response studies. Each siRNA showed potent and efficacious target silencing with $IC_{50}$ values in the low nanomolar range.

Figure 10:
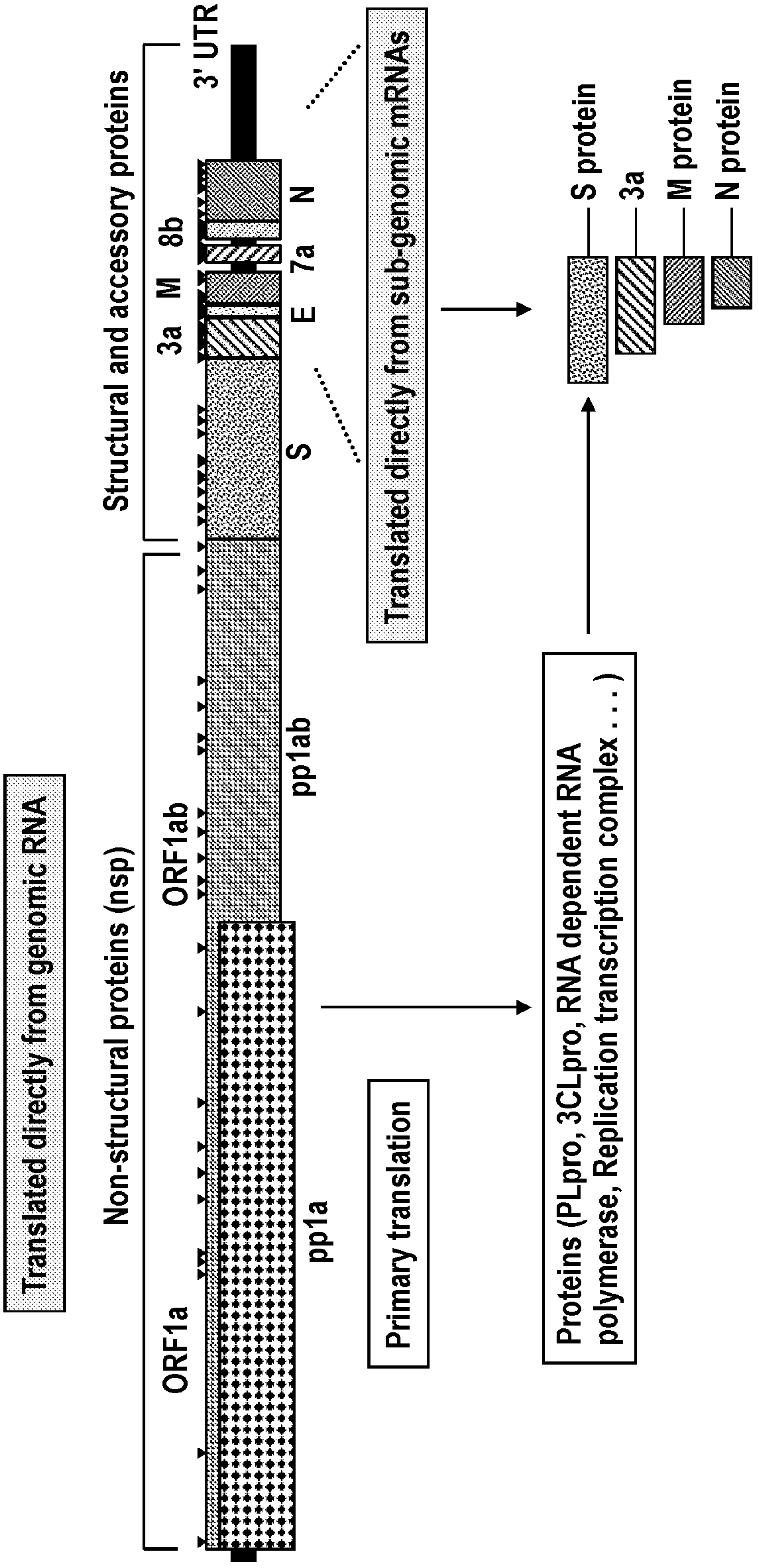
FIG. 10 depicts a schematic showing SARS-CoV-2 genes and their functions. Non-structural genes undergo primary translation while structural and accessory proteins are translated from sub-genomic mRNAs.
Figure 11A:
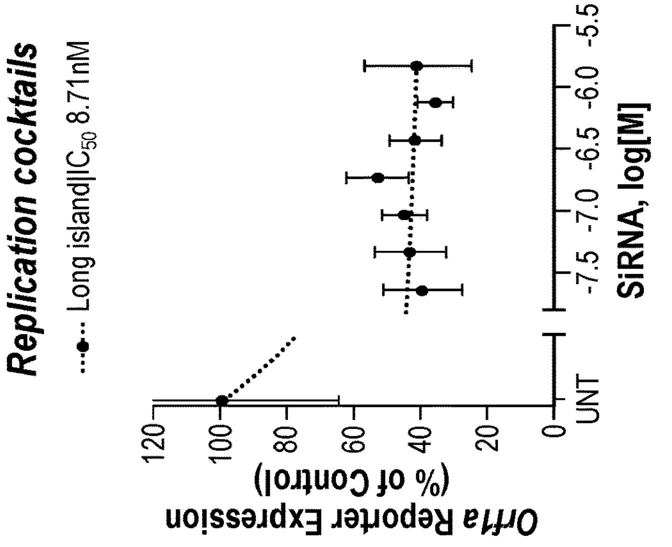
FIG. 11A-11E depict validation and determination of $IC_{50}$ values for siRNA cocktails targeting SARS-CoV-2 Genes.
Figure 11B:
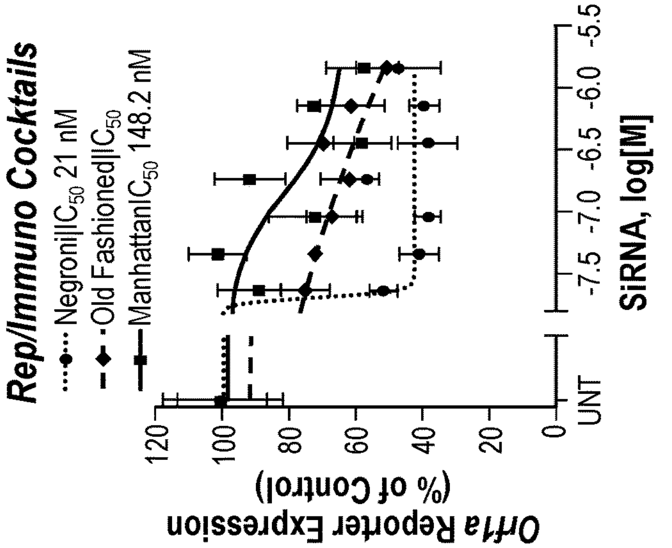
Figure 11C:
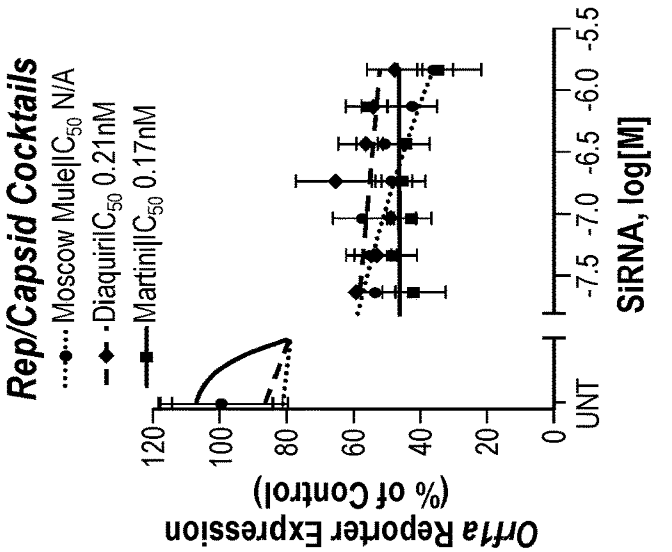
Figure 11E:
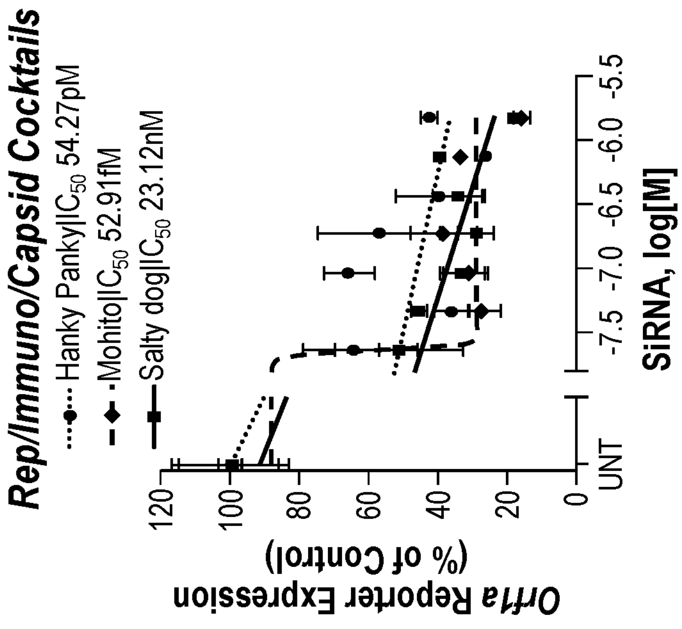
Figure 11D:
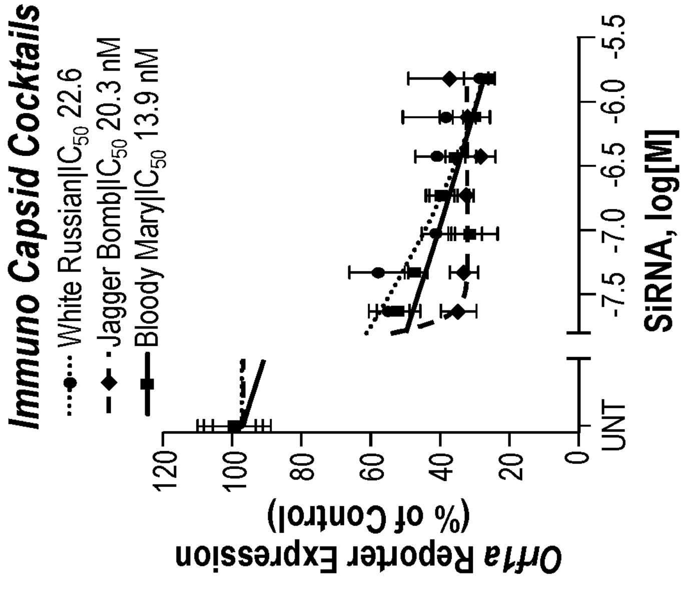

FIG. 10 depicts a schematic showing genes comprising genome and their functions. Comprised of structural and non-structural genes. Non-structural genes undergo primary translation while structural and accessory proteins are translated from sub-genomic mRNAs. The secondary structure of sub-genomic mRNAs may enhance targetability by siRNAs.

Development and optimization of siRNA cocktails targeting SARS-CoV2. Like other RNA viruses, SARS-CoV2 mutates. Therefore, multiple siRNAs in cocktails are necessary to minimize the chances of mutant development. Several siRNA cocktails were developed targeting g+ strand only, g+ strand and terminal 3'UTR (region shared by all secondary mRNA variants), as well as a variety of other combinations. The cocktails are screened in SARS-CoV-2 infected VERO6 cells to define optimal siRNA combinations against the live virus. The strategy of targeting the + strand (orf1a and orf1ab with S and N protein) is particularly novel and active in blocking SARS-CoV-2 infection. The cocktails are combinations of at least 3 siRNAs targeting different regions of the viral genome. Table 10 shows the compositions of the various cocktails tested.

TABLE 10

List of siRNA combinations for targeting SARS-COV-2

| Combo | Code name | Strategy | Compounds (Sequence IDs) | | |
|---|---|---|---|---|---|
| 1 | Cosmopolitan | Replication | 416 | 9679 | 21391 |
| 2 | Screwdriver | Replication | 416 | 8744 | 21391 |
| 3 | Long Island | Replication | 9679 | 8744 | 21391 |
| 4 | Negroni | Rep/Immun | 416 | 9679 | 27565 |
| 5 | Old Fashioned | Rep/Immun | 416 | 21391 | 27565 |
| 6 | Manhattan | Rep/Immun | 21391 | 27656 | 27751 |
| 7 | Moscow Mule | Rep/capsid | 416 | 23174 | 26305 |
| 8 | Daiquiri | Rep/capsid | 9679 | 23174 | 29293 |
| 9 | Martini | Rep/capsid | 21391 | 26305 | 29293 |
| 10 | Jaegger Bomb | Immun/capsid | 23174 | 26470 | 27565 |
| 11 | Bloody Mary | Immun/capsid | 23174 | 27123 | 27656 |
| 12 | White Russian | Immun/capsid | 23174 | 27032 | 27751 |
| 13 | Mojito | Rep/imm/cap | 416 | 26305 | 27565 |
| 14 | Salty Dog | Rep/imm/cap | 9679 | 26369 | 27656 |
| 15 | Hanky Panky | Rep/imm/cap | 21391 | 27032 | 27751 |

The validation and determination of $IC_{50}$ values for siRNA cocktails targeting SARS-CoV-2 genes are depicted in FIG. 11. SiRNA cocktails targeting different genes in the SARS-CoV2 genome were tested for silencing efficacy in 8-point dose response studies. Each siRNA showed potent and efficacious target silencing with $IC_{50}$ values in the low nanomolar range. Results for replication cocktails are shown in FIG. 11A, for Replication/Immuno cocktails in FIG. 11B, for Replication/Capsid cocktails in FIG. 11C, for Immuno/Capsid cocktails in FIG. 11D, and for Replication/Immuno/Capsid cocktails in FIG. 11E.

Example 2. Targeting of Human Genes

SiRNAs targeting of ACE2, FURIN, TMPRSS2, IL-6, and IL-6 Receptor (IL-6R) can be used alone or in combination with siRNAs targeting SARS-CoV2 for comprehensive treatment of SARS-CoV-2 treatment. Hyper functional, fully chemical stabilized siRNAs were identified targeting these a selection of these host cell genes involved in infection and spread.

Studies of ACE2 knock out mice show some toxicity in the heart and muscle, thus limiting the use of traditional small molecules and antibodies that do not differentiate between tissues. EPA-conjugates have no functional delivery to muscle and heart, and thus might be a better option for ACE2 modulation. In addition, local intratracheal delivery of di-valent compounds results in minimal heart and muscle delivery, representing a very powerful option for modulation of host genes, where lung-selective targeting with minimized overall exposure is required.

Host target 45 nucleotide gene regions and 20 nucleotide target regions are summarized in Table 11A-11D and Table 12A-12E.

TABLE 11A

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_924 | UCCCGCAU GGUGGUUU CUUU | 895 | AGTGACTCATGTTCAT CCCGCATGGTGGTTTC TTTGCGCTGTATA | 1095 | mouse |
| TMPRSS 2_903 | UACCACAG UGACUCAU GUUC | 896 | CTCTATAAAAAACTCT ACCACAGTGACTCATG TTCATCCCGCATG | 1096 | mouse |
| TMPRSS 2_868 | UGAGCUCA GGCAACGU UGAC | 897 | TTATGAAGCTGAATGT GAGCTCAGGCAACGT TGACCTCTATAAAA | 1097 | mouse |
| TMPRSS 2_866 | UCUUCAAA AGCAGUGG UUUC | 898 | CACAGTGATGCCTGTT CTTCAAAAGCAGTGGT TTCTTTACGCTGT | 1098 | human |
| TMPRSS 2_866 | UGUGAGCU CAGGCAAC GUUG | 899 | CTTTATGAAGCTGAAT GTGAGCTCAGGCAAC GTTGACCTCTATAA | 1099 | mouse |
| TMPRSS 2_849 | ACCACAGU GAUGCCUG UUCU | 900 | TCTATAAAAAACTGTA CCACAGTGATGCCTGT TCTTCAAAAGCAG | 1100 | human |
| TMPRSS 2_819 | CCGGCAAU GUCGAUAU CUAU | 901 | AACTGAACACAAGTG CCGGCAATGTCGATAT CTATAAAAAACTGT | 1101 | human |
| TMPRSS 2_815 | AGUGCCGG CAAUGUCG AUAU | 902 | ATGAAACTGAACACA AGTGCCGGCAATGTC GATATCTATAAAAAA | 1102 | human |
| TMPRSS 2_783 | AAAGACAU GGGAUACA AGAA | 903 | GGGAGAGCAGCATGT AAAGACATGGGATAC AAGAACAATTTTTAT | 1103 | mouse |
| TMPRSS 2_753 | UUUACUCU AGCCAAGG AAUA | 904 | GCTATAAGAATAATTT TTACTCTAGCCAAGGA ATAGTGGATGACA | 1104 | human |
| TMPRSS 2_691 | GCUUCAUC CUCCAGGU UUAC | 905 | GTCTCTACGGACAAA GCTTCATCCTCCAGGT TTACTCATCTCAGA | 1105 | mouse |
| TMPRSS 2_682 | ACGGACAA AGCUUCAU CCUC | 906 | GTTGTGTTCGTCTCTA CGGACAAAGCTTCATC CTCCAGGTTTACT | 1106 | mouse |
| TMPRSS 2_587 | UGGGUCUU CAGGCACA UGCA | 907 | GTCTGAGATGGAGTGT GGGTCTTCAGGCACAT GCATCAGCTCTTC | 1107 | mouse |
| TMPRSS 2_550 | UCUGGGAC AGCAACUG UUCU | 908 | TCTTGCTTTGGAGGTT CTGGGACAGCAACTG TTCTACGTCTGAGA | 1108 | mouse |
| TMPRSS 2_545 | ACCUGCAU CAACCCCU CUAA | 909 | TGCGACTCCTCAGGTA CCTGCATCAACCCCTC TAACTGGTGTGAT | 1109 | human |
| TMPRSS 2_536 | CUUGCUUU GGAGGUUC UGGG | 910 | TGCTGTGGCTGCTGTC TTGCTTTGGAGGTTCT GGGACAGCAACTG | 1110 | mouse |
| TMPRSS 2_497 | AUGGGCAG CAAGUGCU CCAA | 911 | CTACTCTGGAAGTTCA TGGGCAGCAAGTGCT CCAACTCTGGGATA | 1111 | human |
| TMPRSS 2_470 | UAAGAAAU CGCUGUGU UUAG | 912 | GTGCACCTCAAAGTCT AAGAAATCGCTGTGTT TAGCCCTCGCCCT | 1112 | mouse |
| TMPRSS 2_461 | CUCAAAGU CUAAGAAA UCGC | 913 | AGGAGCACTGTGCAC CTCAAAGTCTAAGAA ATCGCTGTGTTTAGC | 1113 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_415 | UAAGAAAG CACUGUGC AUCA | 914 | GTGCACCTCAAAGACT AAGAAAGCACTGTGC ATCACCTTGACCCT | 1114 | human |
| TMPRSS 2_410 | CUCAACAU CUGUCAUC CACA | 915 | GATTACAACGCAAGC CTCAACATCTGTCATC CACACACATCCCAA | 1115 | mouse |
| TMPRSS 2_3204 | AUCAUGCA AAUAAAUU AUGC | 916 | ATTGTGAAAATGAAT ATCATGCAAATAAATT ATGCAATTTTTTTT | 1116 | human |
| TMPRSS 2_3203 | UAUCAUGC AAAUAAAU UAUG | 917 | AATTGTGAAAATGAA TATCATGCAAATAAAT TATGCAATTTTTTT | 1117 | human |
| TMPRSS 2_3192 | GUGAAAAU GAAUAUCA UGCA | 918 | CTGTAAAGTTCAATTG TGAAAATGAATATCAT GCAAATAAATTAT | 1118 | human |
| TMPRSS 2_3190 | UUGUGAAA AUGAAUAU CAUG | 919 | AACTGTAAAGTTCAAT TGTGAAAATGAATATC ATGCAAATAAATT | 1119 | human |
| TMPRSS 2_3185 | UUCAAUUG UGAAAAUG AAUA | 920 | TTTTAAACTGTAAAGT TCAATTGTGAAAATGA ATATCATGCAAAT | 1120 | human |
| TMPRSS 2_3184 | GUUCAAUU GUGAAAAU GAAU | 921 | TTTTTAAACTGTAAAG TTCAATTGTGAAAATG AATATCATGCAAA | 1121 | human |
| TMPRSS 2_3178 | UGUAAAGU UCAAUUGU GAAA | 922 | GTATCTTTTTAAACT GTAAAGTTCAATTGTG AAAATGAATATCA | 1122 | human |
| TMPRSS 2_3175 | AACUGUAA AGUUCAAU UGUG | 923 | TTTGTATCTTTTTTAA ACTGTAAAGTTCAATT GTGAAAATGAATA | 1123 | human |
| TMPRSS 2_3172 | UUAAACUG UAAAGUUC AAUU | 924 | TTTTTTGTATCTTTTTT AAACTGTAAAGTTCA ATTGTGAAAATGA | 1124 | human |
| TMPRSS 2_3171 | UUUAAACU GUAAAGUU CAAU | 925 | TTTTTTTGTATCTTTTT TAAACTGTAAAGTTCA ATTGTGAAAATG | 1125 | human |
| TMPRSS 2_3139 | GUGAACAA CUGUUUGU CUUU | 926 | CCCCTTCTTATTTATG TGAACAACTGTTTGTC TTTTTTTGTATCT | 1126 | human |
| TMPRSS 2_3137 | AUGUGAAC AACUGUUU GUCU | 927 | TGCCCCTTCTTATTTA TGTGAACAACTGTTTG TCTTTTTTTGTAT | 1127 | human |
| TMPRSS 2_3136 | UAUGUGAA CAACUGUU UGUC | 928 | TTGCCCCTTCTTATTT ATGTGAACAACTGTTT GTCTTTTTTTGTA | 1128 | human |
| TMPRSS 2_3135 | UUAUGUGA ACAACUGU UUGU | 929 | ATTGCCCCTTCTTATT TATGTGAACAACTGTT TGTCTTTTTTTGT | 1129 | human |
| TMPRSS 2_3133 | AUUUAUGU GAACAACU GUUU | 930 | TTATTGCCCCTTCTTA TTTATGTGAACAACTG TTTGTCTTTTTTT | 1130 | human |
| TMPRSS 2_3130 | AAAUAUAU GAAUAAAG UAUA | 931 | TGAGATTCCACTGTGA AATATATGAATAAAG TATATAATTCTTTT | 1131 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_3129 | UCUUAUUU AUGUGAAC AACU | 932 | TTCTTTATTGCCCCTTC TTATTTATGTGAACAA CTGTTTGTCTTT | 1132 | human |
| TMPRSS 2_3120 | AUUGCCCC UUCUUAUU UAUG | 933 | ACGTCTTCCTTCTTTA TTGCCCCTTCTTATTT ATGTGAACAACTG | 1133 | human |
| TMPRSS 2_3118 | GAUUCCAC UGUGAAAU AUAU | 934 | TGTTCTGAGCTGTGAG ATTCCACTGTGAAATA TATGAATAAAGTA | 1134 | mouse |
| TMPRSS 2_3106 | UCUGAGCU GUGAGAUU CCAC | 935 | CTGCTTTGTGTCTGTT CTGAGCTGTGAGATTC CACTGTGAAATAT | 1135 | mouse |
| TMPRSS 2_3097 | UGUGUCUG UUCUGAGC UGUG | 936 | GGTTATTTCCTGCTTT GTGTCTGTTCTGAGCT GTGAGATTCCACT | 1136 | mouse |
| TMPRSS 2_3094 | UAAUGGUG AAAACGUC UUCC | 937 | TCCTAAAAGGTGTTGT AATGGTGAAAACGTC TTCCTTCTTTATTG | 1137 | human |
| TMPRSS 2_3093 | GUAAUGGU GAAAACGU CUUC | 938 | ATCCTAAAAGGTGTTG TAATGGTGAAAACGT CTTCCTTCTTTATT | 1138 | human |
| TMPRSS 2_3090 | CCUGCUUU GUGUCUGU UCUG | 939 | GTTGGTTGGTTATTTC CTGCTTTGTGTCTGTT CTGAGCTGTGAGA | 1139 | mouse |
| TMPRSS 2_3080 | UUGGUUAU UUCCUGCU UUGU | 940 | TGTCTTTGCTGTTGGT TGGTTATTTCCTGCTT TGTGTCTGTTCTG | 1140 | mouse |
| TMPRSS 2_3076 | ACAUCCUA AAAGGUGU UGUA | 941 | CTTGCTCCCCAAGACA CATCCTAAAAGGTGTT GTAATGGTGAAAA | 1141 | human |
| TMPRSS 2_2994 | CUGUGCAC AUGCCUCU GUAG | 942 | ATTTGCAGGATCTGTC TGTGCACATGCCTCTG TAGAGAGCAGCAT | 1142 | human |
| TMPRSS 2_2988 | GCUGUAAG GUACCUAC AUAC | 943 | GGGACCTTCTTAGATG CTGTAAGGTACCTACA TACAGACTAAATG | 1143 | mouse |
| TMPRSS 2_2980 | UUUGCAGG AUCUGUCU GUGC | 944 | AGTCATGCAATCCCAT TTGCAGGATCTGTCTG TGCACATGCCTCT | 1144 | human |
| TMPRSS 2_2973 | AAUCCCAU UUGCAGGA UCUG | 945 | AATGGAAAGTCATGC AATCCCATTTGCAGGA TCTGTCTGTGCACA | 1145 | human |
| TMPRSS 2_2973 | GGGACCUU CUUAGAUG CUGU | 946 | CCTCATGCGTCCTCTG GGACCTTCTTAGATGC TGTAAGGTACCTA | 1146 | mouse |
| TMPRSS 2_2972 | UGGGACCU UCUUAGAU GCUG | 947 | CCCTCATGCGTCCTCT GGGACCTTCTTAGATG CTGTAAGGTACCT | 1147 | mouse |
| TMPRSS 2_2960 | UGGAAAGU CAUGCAAU CCCA | 948 | GACTTAACCTTGAAAT GGAAAGTCATGCAAT CCCATTTGCAGGAT | 1148 | human |
| TMPRSS 2_2952 | CCUUGAAA UGGAAAGU CAUG | 949 | ACAGCTAGGACTTAA CCTTGAAATGGAAAG TCATGCAATCCCATT | 1149 | human |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_2936 | UACAGCUA GGACUUAA CCUU | 950 | TGAAATGAATGATTCT ACAGCTAGGACTTAA CCTTGAAATGGAAA | 1150 | human |
| TMPRSS 2_2933 | UUCUACAG CUAGGACU UAAC | 951 | GAATGAAATGAATGA TTCTACAGCTAGGACT TAACCTTGAAATGG | 1151 | human |
| TMPRSS 2_2926 | UGAAUGAU UCUACAGC UAGG | 952 | TTTGCAAGAATGAAAT GAATGATTCTACAGCT AGGACTTAACCTT | 1152 | human |
| TMPRSS 2_2910 | GUUUGCAA GAAUGAAA UGAA | 953 | TGGCCAAGCAGGCTG GTTTGCAAGAATGAA ATGAATGATTCTACA | 1153 | human |
| TMPRSS 2_2898 | CCAAGCAG GCUGGUUU GCAA | 954 | GGTTCTGCCTCCTGGC CAAGCAGGCTGGTTTG CAAGAATGAAATG | 1154 | human |
| TMPRSS 2_2877 | UGGGUCAU AACUGGGA CUCC | 955 | TCAGAAGGCAGTGAA TGGGTCATAACTGGG ACTCCATCTTTGCTG | 1155 | mouse |
| TMPRSS 2_2796 | ACCAAAUA UGAAGUAU GAAU | 956 | AGCCATGCCAGAATT ACCAAATATGAAGTA TGAATGTCTTACCCA | 1156 | mouse |
| TMPRSS 2_2793 | AUUACCAA AUAUGAAG UAUG | 957 | GAAAGCCATGCCAGA ATTACCAAATATGAA GTATGAATGTCTTAC | 1157 | mouse |
| TMPRSS 2_2792 | UGUGGUCC CUUCCAAU GCUG | 958 | TTGTTTTGGACTCTCT GTGGTCCCTTCCAATG CTGTGGGTTTCCA | 1158 | human |
| TMPRSS 2_2787 | GCCAGAAU UACCAAAU AUGA | 959 | TACCAGGAAAGCCAT GCCAGAATTACCAAA TATGAAGTATGAATG | 1159 | mouse |
| TMPRSS 2_2786 | UGCCAGAA UUACCAAA UAUG | 960 | ATACCAGGAAAGCCA TGCCAGAATTACCAA ATATGAAGTATGAAT | 1160 | mouse |
| TMPRSS 2_2784 | CAUGCCAG AAUUACCA AAUA | 961 | TTATACCAGGAAAGC CATGCCAGAATTACCA AATATGAAGTATGA | 1161 | mouse |
| TMPRSS 2_2779 | AAAGCCAU GCCAGAAU UACC | 962 | TGGGTTTATACCAGGA AAGCCATGCCAGAAT TACCAAATATGAAG | 1162 | mouse |
| TMPRSS 2_2770 | UAUACCAG GAAAGCCA UGCC | 963 | TTCTGGCCCTGGGTTT ATACCAGGAAAGCCA TGCCAGAATTACCA | 1163 | mouse |
| TMPRSS 2_2757 | GAAGAAGA GAAAGAUG UGUU | 964 | GCCCATGGTGGCGGC GAAGAAGAGAAAGAT GTGTTTTGTTTTGGA | 1164 | human |
| TMPRSS 2_2753 | CGGCGAAG AAGAGAAA GAUG | 965 | AAGTGCCCATGGTGG CGGCGAAGAAGAGAA AGATGTGTTTTGTTT | 1165 | human |
| TMPRSS 2_2727 | AGAGAGGA GAUCAUUG UCUU | 966 | TCAGATAAAGATGAA AGAGAGGAGATCATT GTCTTCTGTCTTCTT | 1166 | mouse |
| TMPRSS 2_2712 | UCAGAUAA AGAUGAAA GAGA | 967 | TAGAAGTTCCTAGCTT CAGATAAAGATGAAA GAGAGGAGATCATT | 1167 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_2705 | CCUAGCUU CAGAUAAA GAUG | 968 | ATGAGATTAGAAGTTC CTAGCTTCAGATAAAG ATGAAAGAGAGGA | 1168 | mouse |
| TMPRSS 2_2699 | CUCCUGAC UUAACGUU CUAU | 969 | TGACAAAATGACTGG CTCCTGACTTAACGTT CTATAAATGAATGT | 1169 | human |
| TMPRSS 2_2698 | GCUCCUGA CUUAACGU UCUA | 970 | TTGACAAAATGACTG GCTCCTGACTTAACGT TCTATAAATGAATG | 1170 | human |
| TMPRSS 2_2697 | GGCUCCUG ACUUAACG UUCU | 971 | TTTGACAAAATGACTG GCTCCTGACTTAACGT TCTATAAATGAAT | 1171 | human |
| TMPRSS 2_2695 | AUUAGAAG UUCCUAGC UUCA | 972 | TAGACTGGCAATGAG ATTAGAAGTTCCTAGC TTCAGATAAAGATG | 1172 | mouse |
| TMPRSS 2_2689 | AAUGAGAU UAGAAGUU CCUA | 973 | GTTCTGTAGACTGGCA ATGAGATTAGAAGTTC CTAGCTTCAGATA | 1173 | mouse |
| TMPRSS 2_2687 | GCAAUGAG AUUAGAAG UUCC | 974 | TTGTTCTGTAGACTGG CAATGAGATTAGAAG TTCCTAGCTTCAGA | 1174 | mouse |
| TMPRSS 2_2684 | UGACAAAA UGACUGGC UCCU | 975 | CTATTTCAGCTGCTTT GACAAAATGACTGGC TCCTGACTTAACGT | 1175 | human |
| TMPRSS 2_2682 | UUUGACAA AAUGACUG GCUC | 976 | GCCTATTTCAGCTGCT TTGACAAAATGACTG GCTCCTGACTTAAC | 1176 | human |
| TMPRSS 2_2668 | UAGGUUGU UCUGUAGA CUGG | 977 | CCTCTTCCAGATGGTT AGGTTGTTCTGTAGAC TGGCAATGAGATT | 1177 | mouse |
| TMPRSS 2_2667 | UUAGGUUG UUCUGUAG ACUG | 978 | ACCTCTTCCAGATGGT TAGGTTGTTCTGTAGA CTGGCAATGAGAT | 1178 | mouse |
| TMPRSS 2_2657 | UUCCAGAU GGUUAGGU UGUU | 979 | CAGACACTAGACCTCT TCCAGATGGTTAGGTT GTTCTGTAGACTG | 1179 | mouse |
| TMPRSS 2_2641 | AUCAUCUU UGCCAAGU AAGA | 980 | ACTCTTTGAAACTGTA TCATCTTTGCCAAGTA AGAGTGGTGGCCT | 1180 | human |
| TMPRSS 2_2641 | UCAGACAC UAGACCUC UUCC | 981 | CTGTGTGATTGTGCCT CAGACACTAGACCTCT TCCAGATGGTTAG | 1181 | mouse |
| TMPRSS 2_2632 | UGAAACUG UAUCAUCU UUGC | 982 | CTTCATTTAACTCTTT GAAACTGTATCATCTT TGCCAAGTAAGAG | 1182 | human |
| TMPRSS 2_2630 | UUUGAAAC UGUAUCAU CUUU | 983 | ACCTTCATTTAACTCT TTGAAACTGTATCATC TTTGCCAAGTAAG | 1183 | human |
| TMPRSS 2_2625 | AACUCUUU GAAACUGU AUCA | 984 | AGTCCACCTTCATTTA ACTCTTTGAAACTGTA TCATCTTTGCCAA | 1184 | human |
| TMPRSS 2_2621 | UUGGACUG UGUGAUUG UGCC | 985 | GGAGTTCACCTGCATT TGGACTGTGTGATTGT GCCTCAGACACTA | 1185 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_2613 | CCACCUUC AUUUAACU CUUU | 986 | ATGTCTCCAAGTAGTC CACCTTCATTTAACTC TTTGAAACTGTAT | 1186 | human |
| TMPRSS 2_2609 | UAGUCCAC CUUCAUUU AACU | 987 | TTTGATGTCTCCAAGT AGTCCACCTTCATTTA ACTCTTTGAAACT | 1187 | human |
| TMPRSS 2_2594 | UUUGAUGU CUCCAAGU AGUC | 988 | CCTGGAAACTTAGCTT TTGATGTCTCCAAGTA GTCCACCTTCATT | 1188 | human |
| TMPRSS 2_2588 | UUAGCUUU UGAUGUCU CCAA | 989 | AGTGCTCCTGGAAACT TAGCTTTTGATGTCTC CAAGTAGTCCACC | 1189 | human |
| TMPRSS 2_2579 | CCUGGAAA CUUAGCUU UUGA | 990 | TGCTACCTCAGTGCTC CTGGAAACTTAGCTTT TGATGTCTCCAAG | 1190 | human |
| TMPRSS 2_2564 | UACUACCU CACUGCAC CUGG | 991 | TTGTGTTTCTTCTCTTA CTACCTCACTGCACCT GGACACTAGAGT | 1191 | mouse |
| TMPRSS 2_2543 | UCUGGGUU GUGUUUCU UCUC | 992 | TTCAGTCACCTTGCTT CTGGGTTGTGTTTCTT CTCTTACTACCTC | 1192 | mouse |
| TMPRSS 2_2540 | UUUCCAUG UUAUGUUU CUAC | 993 | GTTTAAGGTACACTGT TTCCATGTTATGTTTC TACACATTGCTAC | 1193 | human |
| TMPRSS 2_2533 | UACACUGU UUCCAUGU UAUG | 994 | ATGCTCAGTTTAAGGT ACACTGTTTCCATGTT ATGTTTCTACACA | 1194 | human |
| TMPRSS 2_2525 | GUUUAAGG UACACUGU UUCC | 995 | AATCAAGGATGCTCA GTTTAAGGTACACTGT TTCCATGTTATGTT | 1195 | human |
| TMPRSS 2_2524 | AGUUUAAG GUACACUG UUUC | 996 | AAATCAAGGATGCTC AGTTTAAGGTACACTG TTTCCATGTTATGT | 1196 | human |
| TMPRSS 2_2506 | AUCAGAAU CAGGGACU UGUG | 997 | TGGAGGCTCAGGTCC ATCAGAATCAGGGAC TTGTGATTTCAGTCA | 1197 | mouse |
| TMPRSS 2_2505 | GGGGAAAU CAAGGAUG CUCA | 998 | AAATTGAGGTCCATG GGGGAAATCAAGGAT GCTCAGTTTAAGGTA | 1198 | human |
| TMPRSS 2_2500 | AGGUCCAU CAGAAUCA GGGA | 999 | ATCAAATGGAGGCTC AGGTCCATCAGAATC AGGGACTTGTGATTT | 1199 | mouse |
| TMPRSS 2_2498 | UCAGGUCC AUCAGAAU CAGG | 1000 | TAATCAAATGGAGGC TCAGGTCCATCAGAAT CAGGGACTTGTGAT | 1200 | mouse |
| TMPRSS 2_2463 | UGGAGCCU GUAUAGCU CAGC | 1001 | TGGCCTAGTACCTGAT GGAGCCTGTATAGCTC AGCTAATCAAATG | 1201 | mouse |
| TMPRSS 2_2441 | ACAGGCAU GGCCUAGU ACCU | 1002 | CTCTTAGCTTTGGCTA CAGGCATGGCCTAGT ACCTGATGGAGCCT | 1202 | mouse |
| TMPRSS 2_2414 | CCUGAAAC UUACCUCU UAGC | 1003 | CTCAGCCTCTCAGAGC CTGAAACTTACCTCTT AGCTTTGGCTACA | 1203 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_2406 | UCUCAGAG CCUGAAAC UUAC | 1004 | CTGTTTCTCTCAGCCT CTCAGAGCCTGAAACT TACCTCTTAGCTT | 1204 | mouse |
| TMPRSS 2_2341 | UGGGUGAG CUCUACAU GGUG | 1005 | TGCCGGCATGTCCCTT GGGTGAGCTCTACATG GTGTTATTCAGTC | 1205 | mouse |
| TMPRSS 2_2311 | AGAGCAAG AAGCUAAU GCCG | 1006 | CTAGGCAGATCTCTCA GAGCAAGAAGCTAAT GCCGGCATGTCCCT | 1206 | mouse |
| TMPRSS 2_2280 | UUCCCAAG CUAAGGGC CUAG | 1007 | AGGGTGATGGAGGCT TTCCCAAGCTAAGGGC CTAGGCAGATCTCT | 1207 | mouse |
| TMPRSS 2_2257 | AUAGACAG UGCCCUUG GUGC | 1008 | TTATGGGGTGAGAAT ATAGACAGTGCCCTTG GTGCGAGGGAAGCA | 1208 | human |
| TMPRSS 2_2196 | GGUGACGU GGUAGUCA CUUG | 1009 | CAGCCCTTCATGGGTG GTGACGTGGTAGTCAC TTGTAAGGGGAAC | 1209 | human |
| TMPRSS 2_2165 | UGGGCUGG UCAUACUG UCAU | 1010 | ATCTGCTGTGCAGGTT GGGCTGGTCATACTGT CATGATTTCATTA | 1210 | mouse |
| TMPRSS 2_2163 | GUUGGGCU GGUCAUAC UGUC | 1011 | AAATCTGCTGTGCAGG TTGGGCTGGTCATACT GTCATGATTTCAT | 1211 | mouse |
| TMPRSS 2_2047 | UGAGUAAC CUGAUGAC CUGA | 1012 | AAGGACTATGACCTCT GAGTAACCTGATGAC CTGAGAAAGAGTAA | 1212 | mouse |
| TMPRSS 2_2041 | GACCUCUG AGUAACCU GAUG | 1013 | ATCACTAAGGACTATG ACCTCTGAGTAACCTG ATGACCTGAGAAA | 1213 | mouse |
| TMPRSS 2_2023 | UGGAUCAC UAAGGACU AUGA | 1014 | TGCTCAGGCCTTTTTT GGATCACTAAGGACT ATGACCTCTGAGTA | 1214 | mouse |
| TMPRSS 2_2022 | UUGGAUCA CUAAGGAC UAUG | 1015 | ATGCTCAGGCCTTTTT TGGATCACTAAGGACT ATGACCTCTGAGT | 1215 | mouse |
| TMPRSS 2_1978 | ACUCUCAU GUUGGAAC UUCU | 1016 | GCAGAGGAGGGTGGC ACTCTCATGTTGGAAC TTCTTTTGGGCTCA | 1216 | mouse |
| TMPRSS 2_1952 | CUUUCCAG GGGCCAAU UUUG | 1017 | TCTTCCTGCTGAGTCC TTTCCAGGGGCCAATT TTGGATGAGCATG | 1217 | human |
| TMPRSS 2_193 | ACCACCAG CUAUUGGA CCUU | 1018 | TTTGAACTCAGGGTCA CCACCAGCTATTGGAC CTTACTATGAAAA | 1218 | human |
| TMPRSS 2_1924 | UGCCCCAU UGAGAUCU UCCU | 1019 | GAGAGGGGTGGAGGC TGCCCCATTGAGATCT TCCTGCTGAGTCCT | 1219 | human |
| TMPRSS 2_1922 | GAUGACCA GAUUCUGU UGGG | 1020 | GCTCCCACCAGAATG GATGACCAGATTCTGT TGGGTTTGGGCACA | 1220 | mouse |
| TMPRSS 2_1910 | CCCACCAG AAUGGAUG ACCA | 1021 | GCCACTTCTGCAGCTC CCACCAGAATGGATG ACCAGATTCTGTTG | 1221 | mouse |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_1821 | UUCACUUU UAUUAAAC AGUG | 1022 | TGATTCGAAGGGCCTT TCACTTTTATTAAACA GTGACTTGTTTGA | 1222 | mouse |
| TMPRSS 2_1820 | UUUCACUU UUAUUAAA CAGU | 1023 | ATGATTCGAAGGGCCT TTCACTTTTATTAAAC AGTGACTTGTTTG | 1223 | mouse |
| TMPRSS 2_1811 | CGAAGGGC CUUUCACU UUUA | 1024 | CCTTTTGAGATGATTC GAAGGGCCTTTCACTT TTATTAAACAGTG | 1224 | mouse |
| TMPRSS 2_1799 | UUUGAGAU GAUUCGAA GGGC | 1025 | GTGCACAATGTACCTT TTGAGATGATTCGAAG GGCCTTTCACTTT | 1225 | mouse |
| TMPRSS 2_1792 | UGUACCUU UUGAGAUG AUUC | 1026 | ACTTCCTGTGCACAAT GTACCTTTTGAGATGA TTCGAAGGGCCTT | 1226 | mouse |
| TMPRSS 2_1784 | GUGCACAA UGUACCUU UUGA | 1027 | GAATTTTAACTTCCTG TGCACAATGTACCTTT TGAGATGATTCGA | 1227 | mouse |
| TMPRSS 2_1782 | CUGUGCAC AAUGUACC UUUU | 1028 | CTGAATTTTAACTTCC TGTGCACAATGTACCT TTTGAGATGATTC | 1228 | mouse |
| TMPRSS 2_1766 | CCUGAAUU UUAACUUC CUGU | 1029 | CAAGAAAACCAAGGG CCTGAATTTTAACTTC CTGTGCACAATGTA | 1229 | mouse |
| TMPRSS 2_1764 | UAAACAGU GAACUUGU CUGG | 1030 | TCACTTCATTTTTATT AAACAGTGAACTTGTC TGGCTTTGGCACT | 1230 | human |
| TMPRSS 2_1763 | UUAAACAG UGAACUUG UCUG | 1031 | GTCACTTCATTTTTAT TAAACAGTGAACTTGT CTGGCTTTGGCAC | 1231 | human |
| TMPRSS 2_1762 | AGGGCCUG AAUUUUAA CUUC | 1032 | TCTGCAAGAAAACCA AGGGCCTGAATTTTAA CTTCCTGTGCACAA | 1232 | mouse |
| TMPRSS 2_1761 | AAGGGCCU GAAUUUUA ACUU | 1033 | TTCTGCAAGAAAACC AAGGGCCTGAATTTTA ACTTCCTGTGCACA | 1233 | mouse |
| TMPRSS 2_1751 | CAAGAAAA CCAAGGGC CUGA | 1034 | TTCAACAACCTTCTGC AAGAAAACCAAGGGC CTGAATTTTAACTT | 1234 | mouse |
| TMPRSS 2_1749 | UGCAAGAA AACCAAGG GCCU | 1035 | TCTTCAACAACCTTCT GCAAGAAAACCAAGG GCCTGAATTTTAAC | 1235 | mouse |
| TMPRSS 2_1748 | CUGCAAGA AAACCAAG GGCC | 1036 | GTCTTCAACAACCTTC TGCAAGAAAACCAAG GGCCTGAATTTTAA | 1236 | mouse |
| TMPRSS 2_1746 | UUCUGCAA GAAAACCA AGGG | 1037 | TTGTCTTCAACAACCT TCTGCAAGAAAACCA AGGGCCTGAATTTT | 1237 | mouse |
| TMPRSS 2_1740 | AUUCAGAG GUCACUUC AUUU | 1038 | TTACTCTTAGAGATGA TTCAGAGGTCACTTCA TTTTTATTAAACA | 1238 | human |
| TMPRSS 2_1738 | UGAUUCAG AGGUCACU UCAU | 1039 | ATTTACTCTTAGAGAT GATTCAGAGGTCACTT CATTTTTATTAAA | 1239 | human |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_1731 | UUAGAGAU GAUUCAGA GGUC | 1040 | GTGCATGATTTACTCT TAGAGATGATTCAGA GGTCACTTCATTTT | 1240 | human |
| TMPRSS 2_1724 | UUUACUCU UAGAGAUG AUUC | 1041 | CTTCCCCGTGCATGAT TTACTCTTAGAGATGA TTCAGAGGTCACT | 1241 | human |
| TMPRSS 2_1716 | UGUCCCAG ACUUCCUU UGUC | 1042 | TAATCCACGTGGCTTT GTCCCAGACTTCCTTT GTCTTCAACAACC | 1242 | mouse |
| TMPRSS 2_1714 | CCGUGCAU GAUUUACU CUUA | 1043 | GCTGGTTTTGCTTCCC CGTGCATGATTTACTC TTAGAGATGATTC | 1243 | human |
| TMPRSS 2_1711 | GGCUUUGU CCCAGACU UCCU | 1044 | ACAGCTAATCCACGTG GCTTTGTCCCAGACTT CCTTTGTCTTCAA | 1244 | mouse |
| TMPRSS 2_1710 | UUCCCCGU GCAUGAUU UACU | 1045 | TGGGGCTGGTTTTGCT TCCCCGTGCATGATTT ACTCTTAGAGATG | 1245 | human |
| TMPRSS 2_1681 | UUACAAGA AAACAAUG GGGC | 1046 | GTCCTTGACGTCGTTT TACAAGAAAACAATG GGGCTGGTTTTGCT | 1246 | human |
| TMPRSS 2_1680 | UUUACAAG AAAACAAU GGGG | 1047 | CGTCCTTGACGTCGTT TTACAAGAAAACAAT GGGGCTGGTTTTGC | 1247 | human |
| TMPRSS 2_1679 | UUUUACAA GAAAACAA UGGG | 1048 | TCGTCCTTGACGTCGT TTTACAAGAAAACAA TGGGGCTGGTTTTG | 1248 | human |
| TMPRSS 2_1663 | UUCGUCCU UGACGUCG UUUU | 1049 | CTAATCCACATGGTCT TCGTCCTTGACGTCGT TTTACAAGAAAAC | 1249 | human |
| TMPRSS 2_1656 | ACGGUAUU UACAGAUU GGAU | 1050 | GTATACGGGAACGTG ACGGTATTTACAGATT GGATCTACCAGCAA | 1250 | mouse |
| TMPRSS 2_1655 | GACGGUAU UUACAGAU UGGA | 1051 | AGTATACGGGAACGT GACGGTATTTACAGAT TGGATCTACCAGCA | 1251 | mouse |
| TMPRSS 2_1645 | ACGGGAAC GUGACGGU AUUU | 1052 | TCAGACCTGGAGTATA CGGGAACGTGACGGT ATTTACAGATTGGA | 1252 | mouse |
| TMPRSS 2_1604 | AUGGUAUU CACGGACU GGAU | 1053 | GTGTACGGGAATGTG ATGGTATTCACGGACT GGATTTATCGACAA | 1253 | human |
| TMPRSS 2_1603 | GAUGGUAU UCACGGAC UGGA | 1054 | AGTGTACGGGAATGT GATGGTATTCACGGAC TGGATTTATCGACA | 1254 | human |
| TMPRSS 2_1595 | GGGAAUGU GAUGGUAU UCAC | 1055 | AGACCAGGAGTGTAC GGGAATGTGATGGTA TTCACGGACTGGATT | 1255 | human |
| TMPRSS 2_1593 | ACGGGAAU GUGAUGGU AUUC | 1056 | ACAGACCAGGAGTGT ACGGGAATGTGATGG TATTCACGGACTGGA | 1256 | human |
| TMPRSS 2_158 | GUUGAUAA CAGCAAGA UGGC | 1057 | TCATTACTCGATGCTG TTGATAACAGCAAGA TGGCTTTGAACTCA | 1257 | human |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_156 | CUGUUGAU AACAGCAA GAUG | 1058 | TATCATTACTCGATGC TGTTGATAACAGCAA GATGGCTTTGAACT | 1258 | human |
| TMPRSS 2_1559 | UCUGGCUG UGCCAAAG CUUA | 1059 | GATACAAGCTGGGGT TCTGGCTGTGCCAAAG CTTACAGACCAGGA | 1259 | human |
| TMPRSS 2_1559 | GGUUACUU UGAAGAAU GGGA | 1060 | CAGTGGAGGGCCGCT GGTTACTTTGAAGAAT GGGATCTGGTGGCT | 1260 | mouse |
| TMPRSS 2_1452 | UGUAAUAG UAAAUACA UAUA | 1061 | ATCGAGCCCTCCAAAT GTAATAGTAAATACAT ATACAACAACCTA | 1261 | mouse |
| TMPRSS 2_1447 | CCAAAUGU AAUAGUAA AUAC | 1062 | CCTTGATCGAGCCCTC CAAATGTAATAGTAA ATACATATACAACA | 1262 | mouse |
| TMPRSS 2_1445 | CUCCAAAU GUAAUAGU AAAU | 1063 | ACCCTTGATCGAGCCC TCCAAATGTAATAGTA AATACATATACAA | 1263 | mouse |
| TMPRSS 2_1439 | CGAGCCCU CCAAAUGU AAUA | 1064 | CATGGTACCCTTGATC GAGCCCTCCAAATGTA ATAGTAAATACAT | 1264 | mouse |
| TMPRSS 2_1436 | GAUCGAGC CCUCCAAA UGUA | 1065 | TGCCATGGTACCCTTG ATCGAGCCCTCCAAAT GTAATAGTAAATA | 1265 | mouse |
| TMPRSS 2_1413 | AUGUCUAU GACAACCU GAUC | 1066 | GATGCAACAGCAGAT ATGTCTATGACAACCT GATCACACCAGCCA | 1266 | human |
| TMPRSS 2_1404 | UCGGACGU GUUGAAUG CUGC | 1067 | GAGAAAGGGAAGACC TCGGACGTGTTGAATG CTGCCATGGTACCC | 1267 | mouse |
| TMPRSS 2_1403 | AACAGCAG AUAUGUCU AUGA | 1068 | GAGACACAGAGATGC AACAGCAGATATGTCT ATGACAACCTGATC | 1268 | human |
| TMPRSS 2_1403 | CUCGGACG UGUUGAAU GCUG | 1069 | TGAGAAAGGGAAGAC CTCGGACGTGTTGAAT GCTGCCATGGTACC | 1269 | mouse |
| TMPRSS 2_1397 | AGAUGCAA CAGCAGAU AUGU | 1070 | CTCATTGAGACACAG AGATGCAACAGCAGA TATGTCTATGACAAC | 1270 | human |
| TMPRSS 2_1388 | UGAGAAAG GGAAGACC UCGG | 1071 | GTGGGGGGCCACCTA TGAGAAAGGGAAGAC CTCGGACGTGTTGAA | 1271 | mouse |
| TMPRSS 2_136 | AUACCUAU CAUUACUC GAUG | 1072 | TATTGAACATTCCAGA TACCTATCATTACTCG ATGCTGTTGATAA | 1272 | human |
| TMPRSS 2_1352 | UCAGAAGU GCUGAACG CUGC | 1073 | GAGAAAGGGAAGACC TCAGAAGTGCTGAAC GCTGCCAAGGTGCTT | 1273 | human |
| TMPRSS 2_1351 | CUCAGAAG UGCUGAAC GCUG | 1074 | GGAGAAAGGGAAGAC CTCAGAAGTGCTGAA CGCTGCCAAGGTGCT | 1274 | human |
| TMPRSS 2_132 | CCAGAUAC CUAUCAUU ACUC | 1075 | GTCATATTGAACATTC CAGATACCTATCATTA CTCGATGCTGTTG | 1275 | human |

TABLE 11A-continued

Host target TMPRSS-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| TMPRSS 2_131 | UCCAGAUA CCUAUCAU UACU | 1076 | GGTCATATTGAACATT CCAGATACCTATCATT ACTCGATGCTGTT | 1276 | human |
| TMPRSS 2_1287 | UUGGCUUU UAAUGAUC UAGU | 1077 | AAGCTGCAGACACCTT TGGCTTTTAATGATCT AGTGAAGCCAGTG | 1277 | mouse |
| TMPRSS 2_1270 | UGAAGCUG CAGACACC UUUG | 1078 | ACGACATTGCTCTCAT GAAGCTGCAGACACC TTTGGCTTTTAATG | 1278 | mouse |
| TMPRSS 2_1254 | AACGACAU UGCUCUCA UGAA | 1079 | TCTAAGACCAAGAAT AACGACATTGCTCTCA TGAAGCTGCAGACA | 1279 | mouse |
| TMPRSS 2_1225 | GCAGAAGC CUCUGACU UUCA | 1080 | TGCGCTGATGAAGCTG CAGAAGCCTCTGACTT TCAACGACCTAGT | 1280 | human |
| TMPRSS 2_1220 | UUCCCAUC CAAAUUAC GACU | 1081 | GGTAGAAAAAGTAAT TTCCCATCCAAATTAC GACTCTAAGACCAA | 1281 | mouse |
| TMPRSS 2_1191 | GGAAGUAG ACACCAGG UAGA | 1082 | TCTCTCATGTTCTATG GAAGTAGACACCAGG TAGAAAAAGTAATT | 1282 | mouse |
| TMPRSS 2_1190 | UGGAAGUA GACACCAG GUAG | 1083 | GTCTCTCATGTTCTAT GGAAGTAGACACCAG GTAGAAAAAGTAAT | 1283 | mouse |
| TMPRSS 2_1183 | UGUUCUAU GGAAGUAG ACAC | 1084 | TGAGACAGTCTCTCAT GTTCTATGGAAGTAGA CACCAGGTAGAAA | 1284 | mouse |
| TMPRSS 2_1181 | UAUGACUC CAAGACCA AGAA | 1085 | ATTTCTCATCCAAATT ATGACTCCAAGACCA AGAACAATGACATT | 1285 | human |
| TMPRSS 2_1168 | UUCUCAUC CAAAUUAU GACU | 1086 | AGTAGAAAAAGTGAT TTCTCATCCAAATTAT GACTCCAAGACCAA | 1286 | human |
| TMPRSS 2_1168 | UGAGACAG UCUCUCAU GUUC | 1087 | CATTTGCGGGAATTCT GAGACAGTCTCTCATG TTCTATGGAAGTA | 1287 | mouse |
| TMPRSS 2_1167 | CUGAGACA GUCUCUCA UGUU | 1088 | GCATTTGCGGGAATTC TGAGACAGTCTCTCAT GTTCTATGGAAGT | 1288 | mouse |
| TMPRSS 2_1157 | UGCGGGAA UUCUGAGA CAGU | 1089 | GTACTGGACGGCATTT GCGGGAATTCTGAGA CAGTCTCTCATGTT | 1289 | mouse |
| TMPRSS 2_114 | CAGGUCAU AUUGAACA UUCC | 1090 | CCGCCTGGAGCGCGG CAGGTCATATTGAACA TTCCAGATACCTAT | 1290 | human |
| TMPRSS 2_1117 | GAGACAAU CUUUCAUG UUCU | 1091 | ATTTGCGGGGATTTTG AGACAATCTTTCATGT TCTATGGAGCCGG | 1291 | human |
| TMPRSS 2_109 | CGCGGCAG GUCAUAUU GAAC | 1092 | GAGCGCCGCCTGGAG CGCGGCAGGTCATATT GAACATTCCAGATA | 1292 | human |
| TMPRSS 2_1087 | AUGGCAUU GGACGGCA UUUG | 1093 | ACCTCTTAACAATCCA TGGCATTGGACGGCAT TTGCGGGGATTTT | 1293 | human |

TABLE 11A-continued

| Host target TMPRSS-20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| TMPRSS 2_1086 | CAUGGCAU UGGACGGC AUUU | 1094 | AACCTCTTAACAATCC ATGGCATTGGACGGC ATTTGCGGGGATTT | 1294 | human |

TABLE 11B

| Host target IL-6 - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| IL6_999 | UUGUAUUU AUAUAAUG UAUA | 1295 | AAAGAAATATTTATATTG TATTTATATAATGTATAAA TGGTTTTT | 1495 | human |
| IL6_998 | AUUGUAUU UAUAUAAU GUAU | 1296 | TAAAGAAATATTTATATT GTATTTATATAATGTATAA ATGGTTTT | 1496 | human |
| IL6_995 | UAUAUUGU AUUUAUAU AAUG | 1297 | TTTTAAAGAAATATTTATA TTGTATTTATATAATGTAT AAATGGT | 1497 | human |
| IL6_994 | UUAUAUUG UAUUUAUA UAAU | 1298 | TTTTTAAAGAAATATTTAT ATTGTATTTATATAATGTA TAAATGG | 1498 | human |
| IL6_989 | AAUAUUUA UAUUGUAU UUAU | 1299 | ACATATTTTTAAAGAAAT ATTTATATTGTATTTATAT AATGTATA | 1499 | human |
| IL6_984 | AAAGAAAU AUUUAUAU UGUA | 1300 | CTTATACATATTTTTAAAG AAATATTTATATTGTATTT ATATAAT | 1500 | human |
| IL6_982 | UUAAAGAA AUAUUUAU AUUG | 1301 | AACTTATACATATTTTTAA AGAAATATTTATATTGTAT TTATATA | 1501 | human |
| IL6_980 | UUUUAAAG AAAUAUUU AUAU | 1302 | CTAACTTATACATATTTTT AAAGAAATATTTATATTG TATTTATA | 1502 | human |
| IL6_963 | GGCUAACUU AUACAUAUU UU | 1303 | TTACCTCAAATAAATGGC TAACTTATACATATTTTTA AAGAAATA | 1503 | human |
| IL6_962 | UGGCUAACU UAUACAUAU UU | 1304 | CTTACCTCAAATAAATGG CTAACTTATACATATTTTT AAAGAAAT | 1504 | human |
| IL6_955 | AAAUAAAU GGCUAACUU AUA | 1305 | GTGTAGGCTTACCTCAAA TAAATGGCTAACTTATAC ATATTTTTA | 1505 | human |
| IL6_951 | CCUCAAAUA AAUGGCUAA CU | 1306 | GAAAGTGTAGGCTTACCT CAAATAAATGGCTAACTT ATACATATT | 1506 | human |
| IL6_950 | ACCUCAAAU AAAUGGCUA AC | 1307 | GGAAAGTGTAGGCTTACC TCAAATAAATGGCTAACT TATACATAT | 1507 | human |
| IL6_949 | UACCUCAAA UAAAUGGCU AA | 1308 | TGGAAAGTGTAGGCTTAC CTCAAATAAATGGCTAAC TTATACATA | 1508 | human |

TABLE 11B-continued

| Host target IL-6 - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| IL6_948 | UUACCUCAA AUAAAUGGC UA | 1309 | TTGGAAAGTGTAGGCTTA CCTCAAATAAATGGCTAA CTTATACAT | 1509 | human |
| IL6_947 | CUUACCUCA AAUAAAUG GCU | 1310 | CTTGGAAAGTGTAGGCTT ACCTCAAATAAATGGCTA ACTTATACA | 1510 | human |
| IL6_943 | UAGGCUUAC CUCAAAUAA AU | 1311 | ATTTCTTGGAAAGTGTAG GCTTACCTCAAATAAATG GCTAACTTA | 1511 | human |
| IL6_934 | UGGAAAGU GUAGGCUUA CCU | 1312 | AGCCAGATCATTTCTTGG AAAGTGTAGGCTTACCTC AAATAAATG | 1512 | human |
| IL6_932 | CUUGGAAAG UGUAGGCUU AC | 1313 | AGAGCCAGATCATTTCTT GGAAAGTGTAGGCTTACC TCAAATAAA | 1513 | human |
| IL6_917 | AGAGCCAGA UCAUUUCUU GG | 1314 | AATATCCTTTGTTTCAGAG CCAGATCATTTCTTGGAA AGTGTAGG | 1514 | human |
| IL6_912 | GUUUCAGAG CCAGAUCAU UU | 1315 | GTTTGAATATCCTTTGTTT CAGAGCCAGATCATTTCTT GGAAAGT | 1515 | human |
| IL6_894 | GCAGUUUGA AUAUCCUUU GU | 1316 | ATGGAAAGTGGCTATGCA GTTTGAATATCCTTTGTTT CAGAGCCA | 1516 | human |
| IL6_878 | AAUGGAAA GUGGCUAUG CAG | 1317 | TAGTTTTGAAATAATAAT GGAAAGTGGCTATGCAGT TTGAATATC | 1517 | human |
| IL6_870 | GAAAUAAU AAUGGAAA GUGG | 1318 | TTATGTATTAGTTTTGAAA TAATAATGGAAAGTGGCT ATGCAGTT | 1518 | human |
| IL6_867 | UUUGAAAU AAUAAUGG AAAG | 1319 | ATTTTATGTATTAGTTTTG AAATAATAATGGAAAGTG GCTATGCA | 1519 | human |
| IL6_858 | UGUAUUAG UUUUGAAA UAAU | 1320 | ACTTGAAACATTTTATGTA TTAGTTTTGAAATAATAAT GGAAAGT | 1520 | human |
| IL6_856 | UAUGUAUU AGUUUUGA AAUA | 1321 | CCACTTGAAACATTTTATG TATTAGTTTTGAAATAATA ATGGAAA | 1521 | human |
| IL6_851 | CAUUUUAUG UAUUAGUU UUG | 1322 | AAGTACCACTTGAAACAT TTTATGTATTAGTTTTGAA ATAATAAT | 1522 | human |
| IL6_843 | ACUUGAAAC AUUUUAUG UAU | 1323 | TTTTTAAGAAGTACCACTT GAAACATTTTATGTATTAG TTTTGAA | 1523 | human |
| IL6_840 | ACCACUUGA AACAUUUUA UG | 1324 | ATATTTTTAAGAAGTACC ACTTGAAACATTTTATGTA TTAGTTTT | 1524 | human |
| IL6_839 | UACCACUUG AAACAUUUU AU | 1325 | TATATTTTTAAGAAGTACC ACTTGAAACATTTTATGTA TTAGTTT | 1525 | human |
| IL6_838 | GUACCACUU GAAACAUUU UA | 1326 | TTATATTTTTAAGAAGTAC CACTTGAAACATTTTATGT ATTAGTT | 1526 | human |

TABLE 11B-continued

| Host target IL-6 - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| IL6_831 | UUAAGAAG UACCACUUG AAA | 1327 | GTCATATTTATATTTTTAA GAAGTACCACTTGAAACA TTTTATGT | 1527 | human |
| IL6_830 | UUUAAGAA GUACCACUU GAA | 1328 | AGTCATATTTATATTTTTA AGAAGTACCACTTGAAAC ATTTTATG | 1528 | human |
| IL6_829 | UUUUAAGA AGUACCACU UGA | 1329 | AAGTCATATTTATATTTTT AAGAAGTACCACTTGAAA CATTTTAT | 1529 | human |
| IL6_809 | UAUGUAAG UCAUAUUUA UAU | 1330 | GAAGCTGAGTTAATTTAT GTAAGTCATATTTATATTT TTAAGAAG | 1530 | human |
| IL6_808 | UUAUGUAA GUCAUAUUU AUA | 1331 | TGAAGCTGAGTTAATTTAT GTAAGTCATATTTATATTT TTAAGAA | 1531 | human |
| IL6_805 | AAUUUAUG UAAGUCAUA UUU | 1332 | ATGTGAAGCTGAGTTAAT TTATGTAAGTCATATTTAT ATTTTTAA | 1532 | human |
| IL6_804 | UAAUUUAU GUAAGUCAU AUU | 1333 | TATGTGAAGCTGAGTTAA TTTATGTAAGTCATATTTA TATTTTTA | 1533 | human |
| IL6_803 | UUAAUUUA UGUAAGUCA UAU | 1334 | ATATGTGAAGCTGAGTTA ATTTATGTAAGTCATATTT ATATTTTT | 1534 | human |
| IL6_801 | AGUUAAUU UAUGUAAG UCAU | 1335 | AAATATGTGAAGCTGAGT TAATTTATGTAAGTCATAT TTATATTT | 1535 | human |
| IL6_800 | GAGUUAAU UUAUGUAA GUCA | 1336 | TAAATATGTGAAGCTGAG TTAATTTATGTAAGTCATA TTTATATT | 1536 | human |
| IL6_799 | UGAGUUAA UUUAUGUA AGUC | 1337 | TTAAATATGTGAAGCTGA GTTAATTTATGTAAGTCAT ATTTATAT | 1537 | human |
| IL6_798 | CUGAGUUAA UUUAUGUA AGU | 1338 | TTTAAATATGTGAAGCTG AGTTAATTTATGTAAGTCA TATTTATA | 1538 | human |
| IL6_794 | GAAGCUGAG UUAAUUUA UGU | 1339 | AATATTTAAATATGTGAA GCTGAGTTAATTTATGTAA GTCATATT | 1539 | human |
| IL6_793 | UGAAGCUGA GUUAAUUU AUG | 1340 | TAATATTTAAATATGTGA AGCTGAGTTAATTTATGTA AGTCATAT | 1540 | human |
| IL6_792 | GUGAAGCUG AGUUAAUU UAU | 1341 | TTAATATTTAAATATGTGA AGCTGAGTTAATTTATGTA AGTCATA | 1541 | human |
| IL6_790 | AUGUGAAGC UGAGUUAA UUU | 1342 | TATTAATATTTAAATATGT GAAGCTGAGTTAATTTAT GTAAGTCA | 1542 | human |
| IL6_788 | AUAUGUGA AGCUGAGUU AAU | 1343 | TTTATTAATATTTAAATAT GTGAAGCTGAGTTAATTT ATGTAAGT | 1543 | human |
| IL6_784 | UUAAAUAU GUGAAGCUG AGU | 1344 | TTAATTTATTAATATTTAA ATATGTGAAGCTGAGTTA ATTTATGT | 1544 | human |

TABLE 11B-continued

| Host target IL-6 - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| IL6_783 | UUUAAAUAUGUGAAGCUGAG | 1345 | TTTAATTTATTAATATTTAAATATGTGAAGCTGAGTTAATTTATG | 1545 | human |
| IL6_782 | AUUUAAAUAUGUGAAGCUGA | 1346 | TTTTAATTTATTAATATTTAAATATGTGAAGCTGAGTTAATTTAT | 1546 | human |
| IL6_778 | UAAUAUUUAAAUAUGUGAAG | 1347 | TTATTTTTAATTTATTAATATTTAAATATGTGAAGCTGAGTTAAT | 1547 | human |
| IL6_776 | AUUAAUAUUUAAAUAUGUGA | 1348 | AATTATTTTTAATTTATTAATATTTAAATATGTGAAGCTGAGTTA | 1548 | human |
| IL6_774 | UUAUUAAUAUUUAAAUAUGU | 1349 | TTAATTATTTTTAATTTATTAATATTTAAATATGTGAAGCTGAGT | 1549 | human |
| IL6_770 | UAAUUUAUUAAUAUUUAAAU | 1350 | TATTTTAATTATTTTTAATTTATTAATATTTAAATATGTGAAGCT | 1550 | human |
| IL6_768 | UUUAAUUUAUUAAUAUUUAA | 1351 | ACTATTTTAATTATTTTTAATTTATTAATATTTAAATATGTGAAG | 1551 | human |
| IL6_747 | UAGGACACUAUUUUAAUUAU | 1352 | TAAAAGTATGAGCGTTAGGACACTATTTTAATTATTTTAATTTA | 1552 | human |
| IL6_746 | UUAGGACACUAUUUUAAUUA | 1353 | CTAAAAGTATGAGCGTTAGGACACTATTTTAATTATTTTTAATTT | 1553 | human |
| IL6_745 | GUUAGGACACUAUUUUAAUU | 1354 | ACTAAAAGTATGAGCGTTAGGACACTATTTTAATTATTTTTAATT | 1554 | human |
| IL6_743 | GCGUUAGGACACUAUUUUAA | 1355 | GAACTAAAAGTATGAGCGTTAGGACACTATTTTAATTATTTTTAA | 1555 | human |
| IL6_742 | AGCGUUAGGACACUAUUUUA | 1356 | AGAACTAAAAGTATGAGCGTTAGGACACTATTTTAATTATTTTTA | 1556 | human |
| IL6_741 | GAGCGUUAGGACACUAUUUU | 1357 | GAGAACTAAAAGTATGAGCGTTAGGACACTATTTTAATTATTTTT | 1557 | human |
| IL6_740 | UGAGCGUUAGGACACUAUUU | 1358 | GGAGAACTAAAAGTATGAGCGTTAGGACACTATTTTAATTATTTT | 1558 | human |
| IL6_739 | AUGAGCGUUAGGACACUAUU | 1359 | TGGAGAACTAAAAGTATGAGCGTTAGGACACTATTTTAATTATTT | 1559 | human |
| IL6_731 | CUAAAAGUAUGAGCGUUAGG | 1360 | GTTCTCTATGGAGAACTAAAAGTATGAGCGTTAGGACACTATTTT | 1560 | human |
| IL6_723 | AUGGAGAACUAAAAGUAUGA | 1361 | CTTATGTTGTTCTCTATGGAGAACTAAAAGTATGAGCGTTAGGAC | 1561 | human |
| IL6_717 | UUCUCUAUGGAGAACUAAAA | 1362 | ACAGAACTTATGTTGTTCTCTATGGAGAACTAAAAGTATGAGCGT | 1562 | human |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_697 | UGGGCACAGAACUUAUGUUG | 1363 | CAGAAACCTGTCCACTGGGCACAGAACTTATGTTGTTCTCTATGG | 1563 | human |
| IL6_691 | GUCCACUGGGCACAGAACUU | 1364 | TCTGGTCAGAAACCTGTCCACTGGGCACAGAACTTATGTTGTTCT | 1564 | human |
| IL6_654 | GUUGUUAAUGGGCAUUCCUU | 1365 | GCACCTCAGATTGTTGTTGTTAATGGGCATTCCTTCTTCTGGTCA | 1565 | human |
| IL6_629 | UGUAGCAUGGGCACCUCAGA | 1366 | GGGCTCTTCGGCAAATGTAGCATGGGCACCTCAGATTGTTGTTGT | 1566 | human |
| IL6_580 | CGCAGCUUUAAGGAGUUCCU | 1367 | ACTCATCTCATTCTGCGCAGCTTTAAGGAGTTCCTGCAGTCCAGC | 1567 | human |
| IL6_58 | CCAGCUAUGAACUCCUUCUC | 1368 | CTCCCCTCCAGGAGCCCAGCTATGAACTCCTTCTCCACAATACCC | 1568 | human |
| IL6_561 | GACAACUCAUCUCAUUCUGC | 1369 | GTGGCTGCAGGACATGACAACTCATCTCATTCTGCGCAGCTTTAA | 1569 | human |
| IL6_54 | GAGCCCAGCUAUGAACUCCU | 1370 | CTATCTCCCCTCCAGGAGCCCAGCTATGAACTCCTTCTCCACAAT | 1570 | human |
| IL6_427 | AUGAGUACAAAAGUCCUGAU | 1371 | GCCAGAGCTGTGCAGATGAGTACAAAAGTCCTGATCCAGTTCCTG | 1571 | human |
| IL6_423 | GCAGAUGAGUACAAAAGUCC | 1372 | ACAAGCCAGAGCTGTGCAGATGAGTACAAAAGTCCTGATCCAGTT | 1572 | human |
| IL6_404 | AGGAACAAGCCAGAGCUGUG | 1373 | GATTTGAGAGTAGTGAGGAACAAGCCAGAGCTGTGCAGATGAGTA | 1573 | human |
| IL6_382 | CAGAACAGAUUUGAGAGUAG | 1374 | TACCTAGAGTACCTCCAGAACAGATTTGAGAGTAGTGAGGAACAA | 1574 | human |
| IL6_381 | CCAGAACAGAUUUGAGAGUA | 1375 | ATACCTAGAGTACCTCCAGAACAGATTTGAGAGTAGTGAGGAACA | 1575 | human |
| IL6_352 | UUGGAGUUUGAGGUAUACCU | 1376 | ATCATCACTGGTCTTTTGGAGTTTGAGGTATACCTAGAGTACCTC | 1576 | human |
| IL6_343 | ACUGGUCUUUUGGAGUUUGA | 1377 | CTGGTGAAAATCATCACTGGTCTTTTGGAGTTTGAGGTATACCTA | 1577 | human |
| IL6_339 | CAUCACUGGUCUUUUGGAGU | 1378 | TTGCCTGGTGAAAATCATCACTGGTCTTTTGGAGTTTGAGGTATA | 1578 | human |
| IL6_331 | GUGAAAAUCAUCACUGGUCU | 1379 | GAGGAGACTTGCCTGGTGAAAATCATCACTGGTCTTTTGGAGTTT | 1579 | human |
| IL6_325 | UGCCUGGUGAAAAUCAUCAC | 1380 | TTCAATGAGGAGACTTGCCTGGTGAAAATCATCACTGGTCTTTTG | 1580 | human |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_324 | UUGCCUGGUGAAAAUCAUCA | 1381 | ATTCAATGAGGAGACTTGCCTGGTGAAAATCATCACTGGTCTTTT | 1581 | human |
| IL6_311 | UCAAUGAGGAGACUUGCCUG | 1382 | GCTTCCAATCTGGATTCAATGAGGAGACTTGCCTGGTGAAAATCA | 1582 | human |
| IL6_309 | AUUCAAUGAGGAGACUUGCC | 1383 | ATGCTTCCAATCTGGATTCAATGAGGAGACTTGCCTGGTGAAAAT | 1583 | human |
| IL6_296 | GCUUCCAAUCUGGAUUCAAU | 1384 | CTGAAAAAGATGGATGCTTCCAATCTGGATTCAATGAGGAGACTT | 1584 | human |
| IL6_248 | UGGCAGAAAACAACCUGAAC | 1385 | GCAGCAAAGAGGCACTGGCAGAAAACAACCTGAACCTTCCAAAGA | 1585 | human |
| IL6_217 | AGUAACAUGUGUGAAAGCAG | 1386 | GAGACATGTAACAAGAGTAACATGTGTGAAAGCAGCAAAGAGGCA | 1586 | human |
| IL6_210 | UAACAAGAGUAACAUGUGUG | 1387 | GAGAAAGGAGACATGTAACAAGAGTAACATGTGTGAAAGCAGCAA | 1587 | human |
| IL6_209 | GUAACAAGAGUAACAUGUGU | 1388 | TGAGAAAGGAGACATGTAACAAGAGTAACATGTGTGAAAGCAGCA | 1588 | human |
| IL6_203 | AGACAUGUAACAAGAGUAAC | 1389 | CAGCCCTGAGAAAGGAGACATGTAACAAGAGTAACATGTGTGAAA | 1589 | human |
| IL6_201 | GGAGACAUGUAACAAGAGUA | 1390 | CTCAGCCCTGAGAAAGGAGACATGTAACAAGAGTAACATGTGTGA | 1590 | human |
| IL6_1008 | UAUAAUGUAUAAAUGGUUUU | 1391 | TTTATATTGTATTTATATAATGTATAAATGGTTTTTATACCAATA | 1591 | human |
| IL6_1007 | AUAUAAUGUAUAAAUGGUUU | 1392 | ATTTATATTGTATTTATATAATGTATAAATGGTTTTTATACCAAT | 1592 | human |
| IL6_1006 | UAUAUAAUGUAUAAAUGGUU | 1393 | TATTTATATTGTATTTATATAATGTATAAATGGTTTTTATACCAA | 1593 | human |
| IL6_1000 | UGUAUUUAUAUAAUGUAUAA | 1394 | AAGAAATATTTATATTGTATTTATATAATGTATAAATGGTTTTTA | 1594 | human |
| IL6_937 | UGUUAUAUGUUAUAGUUUUG | 1395 | AAGTGTCACTTGAAATGTTATATGTTATAGTTTTGAAATGATAAC | 1595 | mouse |
| IL6_402 | UUGCCUAUUGAAAAUUUCCU | 1396 | ATATAATCAGGAAATTTGCCTATTGAAAATTTCCTCTGGTCTTCT | 1596 | mouse |
| IL6_1044 | UUGCUAAUUUAAAUAUGUUU | 1397 | GTTTACCTCAATGAATTGCTAATTTAAATATGTTTTTAAAGAAAT | 1597 | mouse |
| IL6_891 | UAAUUUAUGAUUGAUAUUUA | 1398 | AAGTAAACTTTAAGTTAATTTATGATTGATATTTATTATTTTTAT | 1598 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_855 | UAAUUUAUUGAUAAUUUAAA | 1399 | TATTTTAATTATTTTTAATTTATTGATAATTTAAATAAGTAAACT | 1599 | mouse |
| IL6_1036 | UCAAUGAAUUGCUAAUUUAA | 1400 | ATGTATAAGTTTACCTCAATGAATTGCTAATTTAAATATGTTTTT | 1600 | mouse |
| IL6_886 | UAAGUUAAUUUAUGAUUGAU | 1401 | TAAATAAGTAAACTTTAAGTTAATTTATGATTGATATTTATTATT | 1601 | mouse |
| IL6_884 | UUUAAGUUAAUUUAUGAUUG | 1402 | TTTAAATAAGTAAACTTTAAGTTAATTTATGATTGATATTTATTA | 1602 | mouse |
| IL6_827 | AAUGUUGGGACACUAUUUUA | 1403 | AGAACTGACAATATGAATGTTGGGACACTATTTTAATTATTTTTA | 1603 | mouse |
| IL6_1029 | GUUUACCUCAAUGAAUUGCU | 1404 | TCTTGGAATGTATAAGTTTACCTCAATGAATTGCTAATTTAAATA | 1604 | mouse |
| IL6_1016 | UUGGAAUGUAUAAGUUUACC | 1405 | TAGCCAGATGGTTTCTTGGAATGTATAAGTTTACCTCAATGAATT | 1605 | mouse |
| IL6_779 | UGUCAGGUAUCUGACUUAUG | 1406 | GAAAATATATCCTGTTGTCAGGTATCTGACTTATGTTGTTCTCTA | 1606 | mouse |
| IL6_1066 | AAAGAAAUCUUUGUGAUGUA | 1407 | TTTAAATATGTTTTTAAAGAAATCTTTGTGATGTATTTTTATAAT | 1607 | mouse |
| IL6_854 | UUAAUUUAUUGAUAAUUUAA | 1408 | CTATTTTAATTATTTTTAATTTATTGATAATTTAAATAAGTAAAC | 1608 | mouse |
| IL6_830 | GUUGGGACACUAUUUUAAUU | 1409 | ACTGACAATATGAATGTTGGGACACTATTTTAATTATTTTTAATT | 1609 | mouse |
| IL6_1089 | UUAUAAUGUUUAGACUGUCU | 1410 | CTTTGTGATGTATTTTTATAATGTTTAGACTGTCTTCAAACAAAT | 1610 | mouse |
| IL6_931 | UUGAAAUGUUAUAUGUUAUA | 1411 | TTTATGAAGTGTCACTTGAAATGTTATATGTTATAGTTTTGAAAT | 1611 | mouse |
| IL6_538 | AACCAAGAGGUAAAAGAUUU | 1412 | CTAATTCATATCTTCAACCAAGAGGTAAAAGATTTACATAAAATA | 1612 | mouse |
| IL6_887 | AAGUUAAUUUAUGAUUGAUA | 1413 | AAATAAGTAAACTTTAAGTTAATTTATGATTGATATTTATTATTT | 1613 | mouse |
| IL6_408 | AUUGAAAAUUUCCUCUGGUC | 1414 | TCAGGAAATTTGCCTATTGAAAATTTCCTCTGGTCTTCTGGAGTA | 1614 | mouse |
| IL6_235 | GGCUUAAUUACACAUGUUCU | 1415 | ACTTCACAAGTCGGAGGCTTAATTACACATGTTCTCTGGGAAATC | 1615 | mouse |
| IL6_725 | CUAAGCAUAUCAGUUUGUGG | 1416 | CCTAGTGCGTTATGCCTAAGCATATCAGTTTGTGGACATTCCTCA | 1616 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_401 | UUUGCCUAUUGAAAAUUUCC | 1417 | GATATAATCAGGAAATTTGCCTATTGAAAATTTCCTCTGGTCTTC | 1617 | mouse |
| IL6_973 | AUCUAUUUGAUAUAAAUAUU | 1418 | AATGATAACCTAAAAATCTATTTGATATAAATATTCTGTTACCTA | 1618 | mouse |
| IL6_926 | GUCACUUGAAAUGUUAUAUG | 1419 | TTATTTTTATGAAGTGTCACTTGAAATGTTATATGTTATAGTTTT | 1619 | mouse |
| IL6_862 | UUGAUAAUUUAAAUAAGUAA | 1420 | ATTATTTTTAATTTATTGATAATTTAAATAAGTAAACTTTAAGTT | 1620 | mouse |
| IL6_868 | AUUUAAAUAAGUAAACUUUA | 1421 | TTTAATTTATTGATAATTTAAATAAGTAAACTTTAAGTTAATTTA | 1621 | mouse |
| IL6_869 | UUUAAAUAAGUAAACUUUAA | 1422 | TTAATTTATTGATAATTTAAATAAGTAAACTTTAAGTTAATTTAT | 1622 | mouse |
| IL6_885 | UUAAGUUAAUUUAUGAUUGA | 1423 | TTAAATAAGTAAACTTTAAGTTAATTTATGATTGATATTTATTAT | 1623 | mouse |
| IL6_871 | UAAAUAAGUAAACUUUAAGU | 1424 | AATTTATTGATAATTTAAATAAGTAAACTTTAAGTTAATTTATGA | 1624 | mouse |
| IL6_652 | UUCAUCUUGAAAUCACUUGA | 1425 | ACCAAGACCATCCAATTCATCTTGAAATCACTTGAAGAATTTCTA | 1625 | mouse |
| IL6_816 | CUGACAAUAUGAAUGUUGGG | 1426 | GTTCTCTACGAAGAACTGACAATATGAATGTTGGGACACTATTTT | 1626 | mouse |
| IL6_802 | UUCUCUACGAAGAACUGACA | 1427 | ATCTGACTTATGTTGTTCTCTACGAAGAACTGACAATATGAATGT | 1627 | mouse |
| IL6_761 | UCAGAAAAUAUAUCCUGUUG | 1428 | CATTCCTCACTGTGGTCAGAAAATATATCCTGTTGTCAGGTATCT | 1628 | mouse |
| IL6_1007 | GAUGGUUUCUUGGAAUGUAU | 1429 | TCTGTTACCTAGCCAGATGGTTTCTTGGAATGTATAAGTTTACCT | 1629 | mouse |
| IL6_923 | AGUGUCACUUGAAAUGUUAU | 1430 | TTATTATTTTTATGAAGTGTCACTTGAAATGTTATATGTTATAGT | 1630 | mouse |
| IL6_978 | UUUGAUAUAAAUAUUCUGUU | 1431 | TAACCTAAAAATCTATTTGATATAAATATTCTGTTACCTAGCCAG | 1631 | mouse |
| IL6_1063 | UUUAAAGAAAUCUUUGUGAU | 1432 | TAATTTAAATATGTTTTAAAGAAATCTTTGTGATGTATTTTTAT | 1632 | mouse |
| IL6_953 | UUUGAAAUGAUAACCUAAAA | 1433 | GTTATATGTTATAGTTTTGAAATGATAACCTAAAAATCTATTTGA | 1633 | mouse |
| IL6_389 | AUAAUCAGGAAAUUUGCCUA | 1434 | GCTACCAAACTGGATATAATCAGGAAATTTGCCTATTGAAAATTT | 1634 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_541 | CAAGAGGUA AAAGAUUU ACA | 1435 | ATTCATATCTTCAACCAAG AGGTAAAAGATTTACATA AAATAGTC | 1635 | mouse |
| IL6_268 | GAAAUGAG AAAAGAGU UGUG | 1436 | CTCTGGGAAATCGTGGAA ATGAGAAAAGAGTTGTGC AATGGCAAT | 1636 | mouse |
| IL6_880 | AAACUUUAA GUUAAUUU AUG | 1437 | ATAATTTAAATAAGTAAA CTTTAAGTTAATTTATGAT TGATATTT | 1637 | mouse |
| IL6_861 | AUUGAUAA UUUAAAUA AGUA | 1438 | AATTATTTTTAATTTATTG ATAATTTAAATAAGTAAA CTTTAAGT | 1638 | mouse |
| IL6_875 | UAAGUAAAC UUUAAGUU AAU | 1439 | TATTGATAATTTAAATAA GTAAACTTTAAGTTAATTT ATGATTGA | 1639 | mouse |
| IL6_256 | UGGGAAAUC GUGGAAAU GAG | 1440 | ATTACACATGTTCTCTGGG AAATCGTGGAAATGAGAA AAGAGTTG | 1640 | mouse |
| IL6_351 | AGAGAUACA AAGAAAUG AUG | 1441 | CAATCTGAAACTTCCAGA GATACAAAGAAATGATGG ATGCTACCA | 1641 | mouse |
| IL6_824 | AUGAAUGU UGGGACACU AUU | 1442 | CGAAGAACTGACAATATG AATGTTGGGACACTATTTT AATTATTT | 1642 | mouse |
| IL6_332 | AAAACAAUC UGAAACUUC CA | 1443 | ATGATGCACTTGCAGAAA ACAATCTGAAACTTCCAG AGATACAAA | 1643 | mouse |
| IL6_403 | UGCCUAUUG AAAAUUUCC UC | 1444 | TATAATCAGGAAATTTGC CTATTGAAAATTTCCTCTG GTCTTCTG | 1644 | mouse |
| IL6_762 | CAGAAAAUA UAUCCUGUU GU | 1445 | ATTCCTCACTGTGGTCAGA AAATATATCCTGTTGTCAG GTATCTG | 1645 | mouse |
| IL6_879 | UAAACUUUA AGUUAAUU UAU | 1446 | GATAATTTAAATAAGTAA ACTTTAAGTTAATTTATGA TTGATATT | 1646 | mouse |
| IL6_947 | UAUAGUUU UGAAAUGA UAAC | 1447 | TGAAATGTTATATGTTATA GTTTTGAAATGATAACCT AAAAATCT | 1647 | mouse |
| IL6_649 | CAAUUCAUC UUGAAAUCA CU | 1448 | AGGACCAAGACCATCCAA TTCATCTTGAAATCACTTG AAGAATTT | 1648 | mouse |
| IL6_897 | AUGAUUGA UAUUUAUU AUUU | 1449 | ACTTTAAGTTAATTTATGA TTGATATTTATTATTTTTA TGAAGTG | 1649 | mouse |
| IL6_1043 | AUUGCUAAU UUAAAUAU GUU | 1450 | AGTTTACCTCAATGAATTG CTAATTTAAATATGTTTTT AAAGAAA | 1650 | mouse |
| IL6_576 | UACCCCAAU UUCCAAUGC UC | 1451 | TAAAATAGTCCTTCCTACC CCAATTTCCAATGCTCTCC TAACAGA | 1651 | mouse |
| IL6_90 | CUCUGCAAG AGACUUCCA UC | 1452 | CGCTATGAAGTTCCTCTCT GCAAGAGACTTCCATCCA GTTGCCTT | 1652 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_378 | CCAAACUGG AUAUAAUCA GG | 1453 | AAATGATGGATGCTACCA AACTGGATATAATCAGGA AATTTGCCT | 1653 | mouse |
| IL6_853 | UUUAAUUU AUUGAUAA UUUA | 1454 | ACTATTTTAATTATTTTTA ATTTATTGATAATTTAAAT AAGTAAA | 1654 | mouse |
| IL6_367 | GAUGGAUGC UACCAAACU GG | 1455 | GAGATACAAAGAAATGAT GGATGCTACCAAACTGGA TATAATCAG | 1655 | mouse |
| IL6_992 | UCUGUUACC UAGCCAGAU GG | 1456 | ATTTGATATAAATATTCTG TTACCTAGCCAGATGGTTT CTTGGAA | 1656 | mouse |
| IL6_939 | UUAUAUGU UAUAGUUU UGAA | 1457 | GTGTCACTTGAAATGTTAT ATGTTATAGTTTTGAAATG ATAACCT | 1657 | mouse |
| IL6_1037 | CAAUGAAUU GCUAAUUUA AA | 1458 | TGTATAAGTTTACCTCAAT GAATTGCTAATTTAAATAT GTTTTTA | 1658 | mouse |
| IL6_661 | AAAUCACUU GAAGAAUU UCU | 1459 | ATCCAATTCATCTTGAAAT CACTTGAAGAATTTCTAA AAGTCACT | 1659 | mouse |
| IL6_1042 | AAUUGCUAA UUUAAAUA UGU | 1460 | AAGTTTACCTCAATGAATT GCTAATTTAAATATGTTTT TAAAGAA | 1660 | mouse |
| IL6_995 | GUUACCUAG CCAGAUGGU UU | 1461 | TGATATAAATATTCTGTTA CCTAGCCAGATGGTTTCTT GGAATGT | 1661 | mouse |
| IL6_1017 | UGGAAUGU AUAAGUUU ACCU | 1462 | AGCCAGATGGTTTCTTGG AATGTATAAGTTTACCTCA ATGAATTG | 1662 | mouse |
| IL6_929 | ACUUGAAAU GUUAUAUG UUA | 1463 | TTTTTATGAAGTGTCACTT GAAATGTTATATGTTATA GTTTTGAA | 1663 | mouse |
| IL6_878 | GUAAACUUU AAGUUAAU UUA | 1464 | TGATAATTTAAATAAGTA AACTTTAAGTTAATTTATG ATTGATAT | 1664 | mouse |
| IL6_945 | GUUAUAGU UUUGAAAU GAUA | 1465 | CTTGAAATGTTATATGTTA TAGTTTTGAAATGATAAC CTAAAAAT | 1665 | mouse |
| IL6_285 | GUGCAAUGG CAAUUCUGA UU | 1466 | AATGAGAAAAGAGTTGTG CAATGGCAATTCTGATTGT ATGAACAA | 1666 | mouse |
| IL6_662 | AAUCACUUG AAGAAUUUC UA | 1467 | TCCAATTCATCTTGAAATC ACTTGAAGAATTTCTAAA AGTCACTT | 1667 | mouse |
| IL6_852 | UUUUAAUU UAUUGAUA AUUU | 1468 | CACTATTTTAATTATTTTT AATTTATTGATAATTTAAA TAAGTAA | 1668 | mouse |
| IL6_348 | UCCAGAGAU ACAAAGAAA UG | 1469 | AAACAATCTGAAACTTCC AGAGATACAAAGAAATGA TGGATGCTA | 1669 | mouse |
| IL6_883 | CUUUAAGUU AAUUUAUG AUU | 1470 | ATTTAAATAAGTAAACTTT AAGTTAATTTATGATTGAT ATTTATT | 1670 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_1033 | ACCUCAAUG AAUUGCUAA UU | 1471 | GGAATGTATAAGTTTACC TCAATGAATTGCTAATTTA AATATGTT | 1671 | mouse |
| IL6_758 | UGGUCAGAA AAUAUAUCC UG | 1472 | GGACATTCCTCACTGTGGT CAGAAAATATATCCTGTT GTCAGGTA | 1672 | mouse |
| IL6_1090 | UAUAAUGU UUAGACUGU CUU | 1473 | TTTGTGATGTATTTTTATA ATGTTTAGACTGTCTTCAA ACAAATA | 1673 | mouse |
| IL6_979 | UUGAUAUA AAUAUUCUG UUA | 1474 | AACCTAAAAATCTATTTG ATATAAATATTCTGTTACC TAGCCAGA | 1674 | mouse |
| IL6_916 | UUUAUGAA GUGUCACUU GAA | 1475 | TTGATATTTATTATTTTTA TGAAGTGTCACTTGAAAT GTTATATG | 1675 | mouse |
| IL6_328 | GCAGAAAAC AAUCUGAAA CU | 1476 | AACGATGATGCACTTGCA GAAAACAATCTGAAACTT CCAGAGATA | 1676 | mouse |
| IL6_831 | UUGGGACAC UAUUUUAA UUA | 1477 | CTGACAATATGAATGTTG GGACACTATTTTAATTATT TTTAATTT | 1677 | mouse |
| IL6_385 | GGAUAUAA UCAGGAAAU UUG | 1478 | GGATGCTACCAAACTGGA TATAATCAGGAAATTTGC CTATTGAAA | 1678 | mouse |
| IL6_1087 | UUUUAUAA UGUUUAGAC UGU | 1479 | ATCTTTGTGATGTATTTTT ATAATGTTTAGACTGTCTT CAAACAA | 1679 | mouse |
| IL6_249 | UGUUCUCUG GGAAAUCGU GG | 1480 | AGGCTTAATTACACATGTT CTCTGGGAAATCGTGGAA ATGAGAAA | 1680 | mouse |
| IL6_670 | GAAGAAUU UCUAAAAGU CAC | 1481 | ATCTTGAAATCACTTGAA GAATTTCTAAAAGTCACTT TGAGATCT | 1681 | mouse |
| IL6_653 | UCAUCUUGA AAUCACUUG AA | 1482 | CCAAGACCATCCAATTCA TCTTGAAATCACTTGAAG AATTTCTAA | 1682 | mouse |
| IL6_283 | UUGUGCAAU GGCAAUUCU GA | 1483 | GAAATGAGAAAAGAGTTG TGCAATGGCAATTCTGATT GTATGAAC | 1683 | mouse |
| IL6_532 | AUCUUCAAC CAAGAGGUA AA | 1484 | GAAACTCTAATTCATATCT TCAACCAAGAGGTAAAAG ATTTACAT | 1684 | mouse |
| IL6_996 | UUACCUAGC CAGAUGGUU UC | 1485 | GATATAAATATTCTGTTAC CTAGCCAGATGGTTTCTTG GAATGTA | 1685 | mouse |
| IL6_1032 | UACCUCAAU GAAUUGCUA AU | 1486 | TGGAATGTATAAGTTTAC CTCAATGAATTGCTAATTT AAATATGT | 1686 | mouse |
| IL6_657 | CUUGAAAUC ACUUGAAGA AU | 1487 | GACCATCCAATTCATCTTG AAATCACTTGAAGAATTT CTAAAAGT | 1687 | mouse |
| IL6_895 | UUAUGAUU GAUAUUUA UUAU | 1488 | AAACTTTAAGTTAATTTAT GATTGATATTTATTATTTT TATGAAG | 1688 | mouse |

TABLE 11B-continued

Host target IL-6 - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| IL6_400 | AUUUGCCUA UUGAAAAU UUC | 1489 | GGATATAATCAGGAAATT TGCCTATTGAAAATTTCCT CTGGTCTT | 1689 | mouse |
| IL6_1014 | UCUUGGAAU GUAUAAGU UUA | 1490 | CCTAGCCAGATGGTTTCTT GGAATGTATAAGTTTACC TCAATGAA | 1690 | mouse |
| IL6_866 | UAAUUUAA AUAAGUAA ACUU | 1491 | TTTTTAATTTATTGATAAT TTAAATAAGTAAACTTTA AGTTAATT | 1691 | mouse |
| IL6_339 | UCUGAAACU UCCAGAGAU AC | 1492 | ACTTGCAGAAAACAATCT GAAACTTCCAGAGATACA AAGAAATGA | 1692 | mouse |
| IL6_233 | GAGGCUUAA UUACACAUG UU | 1493 | CCACTTCACAAGTCGGAG GCTTAATTACACATGTTCT CTGGGAAA | 1693 | mouse |
| IL6_877 | AGUAAACUU UAAGUUAA UUU | 1494 | TTGATAATTTAAATAAGT AAACTTTAAGTTAATTTAT GATTGATA | 1694 | mouse |

TABLE 11C

Host target FURIN - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| FURIN_4183 | AUGGACAUGAG AUAAUGUUA | 1695 | TGCTGGTTCTATTTAATGGACAT GAGATAATGTTAGAGGTTTTAA | 1795 | human |
| FURIN_3561 | UUUAGAUGCUG AUGAUUUGU | 1696 | TTGTGATTATTTCACTTTAGATG CTGATGATTTGTTTTTGTATTT | 1796 | human |
| FURIN_3555 | UUUCACUUUAG AUGCUGAUG | 1697 | TTCACTTTGTGATTATTTCACTTT AGATGCTGATGATTTGTTTTT | 1797 | human |
| FURIN_3563 | UAGAUGCUGAU GAUUUGUUU | 1698 | GTGATTATTTCACTTTAGATGCT GATGATTTGTTTTTGTATTTTT | 1798 | human |
| FURIN_3529 | GAGGAUAUAUU UUCACUUUG | 1699 | TCTCAGGGGCTGTTTGAGGATAT ATTTTCACTTTGTGATTATTTC | 1799 | human |
| FURIN_4161 | CCAGCAUUGCU GGUUCUAUU | 1700 | GTAATTTAAACAGGCCCAGCATT GCTGGTTCTATTTAATGGACAT | 1800 | human |
| FURIN_3537 | AUUUUCACUUU GUGAUUAUU | 1701 | GCTGTTTGAGGATATATTTTCAC TTTGTGATTATTTCACTTTAGA | 1801 | human |
| FURIN_1873 | GCCUUCAUGAC AACUCAUUC | 1702 | GGGTTTAATGACTGGGCCTTCAT GACAACTCATTCCTGGGATGAG | 1802 | human |
| FURIN_3545 | UUUGUGAUUAU UUCACUUUA | 1703 | AGGATATATTTTCACTTTGTGAT TATTTCACTTTAGATGCTGATG | 1803 | human |
| FURIN_3525 | GUUUGAGGAUA UAUUUUCAC | 1704 | GGGATCTCAGGGGCTGTTTGAGG ATATATTTTCACTTTGTGATTA | 1804 | human |
| FURIN_4184 | UGGACAUGAGA UAAUGUUAG | 1705 | GCTGGTTCTATTTAATGGACATG AGATAATGTTAGAGGTTTTAAA | 1805 | human |
| FURIN_3995 | UCUGGGAGUCC CCUUUUCUU | 1706 | ATCAGTCCCCTCCCATCTGGGAG TCCCCTTTTCTTTTCTACCCTA | 1806 | human |

TABLE 11C-continued

Host target FURIN - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| FURIN_4152 | UAAACAGGCCC AGCAUUGCU | 1707 | TTTTTTCTTGTAATTTAAACAGG CCCAGCATTGCTGGTTCTATTT | 1807 | human |
| FURIN_1878 | CAUGACAACUC AUUCCUGGG | 1708 | TAATGACTGGGCCTTCATGACAA CTCATTCCTGGGATGAGGATCC | 1808 | human |
| FURIN_4192 | AGAUAAUGUUA GAGGUUUUA | 1709 | TATTTAATGGACATGAGATAATG TTAGAGGTTTTAAAGTGATTAA | 1809 | human |
| FURIN_1969 | ACCAAGUUCAC CCUCGUACU | 1710 | AACTATGGGACGCTGACCAAGTT CACCCTCGTACTCTATGGCACC | 1810 | human |
| FURIN_312 | AGCAGCAACAG GAACCUUGG | 1711 | GTTGCTATGGGTGGTAGCAGCAA CAGGAACCTTGGTCCTGCTAGC | 1811 | human |
| FURIN_3538 | UUUUCACUUUG UGAUUAUUU | 1712 | CTGTTTGAGGATATATTTTCACT TTGTGATTATTTCACTTTAGAT | 1812 | human |
| FURIN_4193 | GAUAAUGUUAG AGGUUUUAA | 1713 | ATTTAATGGACATGAGATAATGT TAGAGGTTTTAAAGTGATTAAA | 1813 | human |
| FURIN_3957 | UUUGCACCCCU CCCAUUAGG | 1714 | TCTTCTGACGTGCCTTTTGCACC CCTCCCATTAGGACAATCAGTC | 1814 | human |
| FURIN_1925 | UAGAGAUUGAA AACACCAGC | 1715 | CTGGCGAGTGGGTCCTAGAGATT GAAAACACCAGCGAAGCCAACA | 1815 | human |
| FURIN_2894 | AAAGGAGUGAA ACCUUUAGG | 1716 | CCCTTCCATGTGGAGAAAGGAGT GAAACCTTTAGGGCAGCTTGCC | 1816 | human |
| FURIN_4117 | CUGGGUUGGUG CACAGUGAU | 1717 | TGGTTTTGTAAGATGCTGGGTTG GTGCACAGTGATTTTTTTCTTG | 1817 | human |
| FURIN_3534 | UAUAUUUUCAC UUUGUGAUU | 1718 | GGGGCTGTTTGAGGATATATTTT CACTTTGTGATTATTTCACTTT | 1818 | human |
| FURIN_4150 | UUUAAACAGGC CCAGCAUUG | 1719 | ATTTTTTTCTTGTAATTTAAACAG GCCCAGCATTGCTGGTTCTAT | 1819 | human |
| FURIN_3929 | CCCUCAAACCU CCUCUUCUG | 1720 | TGACCTGTCATGCCCCCCTCAAA CCTCCTCTTCTGACGTGCCTTT | 1820 | human |
| FURIN_3560 | CUUUAGAUGCU GAUGAUUUG | 1721 | TTTGTGATTATTTCACTTTAGATG CTGATGATTTGTTTTTGTATT | 1821 | human |
| FURIN_4100 | GCUGGUUUUGU AAGAUGCUG | 1722 | CTCGTGGCCAGCCCGGCTGGTTT TGTAAGATGCTGGGTTGGTGCA | 1822 | human |
| FURIN_712 | CACGGCAUUGU GGUCUCCAU | 1723 | CAGGGCTACACAGGGCACGGCA TTGTGGTCTCCATTCTGGACGAT | 1823 | human |
| FURIN_3541 | UCACUUUGUGA UUAUUUCAC | 1724 | TTTGAGGATATATTTTCACTTTGT GATTATTTCACTTTAGATGCT | 1824 | human |
| FURIN_4169 | GCUGGUUCUAU UUAAUGGAC | 1725 | AACAGGCCCAGCATTGCTGGTTC TATTTAATGGACATGAGATAAT | 1825 | human |
| FURIN_1303 | AGCAGUGGCAA CCAGAAUGA | 1726 | CTGGCCACGACCTACAGCAGTG GCAACCAGAATGAGAAGCAGATC | 1826 | human |
| FURIN_765 | CUUGGCAGGCA AUUAUGAUC | 1727 | GAAGAACCACCCGGACTTGGCA GGCAATTATGATCCTGGGGCCAG | 1827 | human |
| FURIN_1942 | AGCGAAGCCAA CAACUAUGG | 1728 | GAGATTGAAAACACCAGCGAAG CCAACAACTATGGGACGCTGACC | 1828 | human |
| FURIN_1945 | GAAGCCAACAA CUAUGGGAC | 1729 | ATTGAAAACACCAGCGAAGCCA ACAACTATGGGACGCTGACCAAG | 1829 | human |
| FURIN_2780 | GGAGACUGCUU CCCAUCCUA | 1730 | GGAGGCAAGAGGGGTGGAGACT GCTTCCCATCCTACCCTCGGGCC | 1830 | human |

TABLE 11C-continued

| Host target FURIN - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| FURIN_3827 | UCAUAGGUCAC UGGCUCUCC | 1731 | CGCCATGCCGGGGGTTCATAGGT CACTGGCTCTCCAAGTGCCAGA | 1831 | human |
| FURIN_3547 | UGUGAUUAUUU CACUUUAGA | 1732 | GATATATTTTCACTTTGTGATTAT TTCACTTTAGATGCTGATGAT | 1832 | human |
| FURIN_3559 | ACUUUAGAUGC UGAUGAUUU | 1733 | CTTTGTGATTATTTCACTTTAGAT GCTGATGATTTGTTTTTGTAT | 1833 | human |
| FURIN_4177 | UAUUUAAUGGA CAUGAGAUA | 1734 | CAGCATTGCTGGTTCTATTTAAT GGACATGAGATAATGTTAGAGG | 1834 | human |
| FURIN_2158 | UAUAGCACCGA GAAUGACGU | 1735 | GTCCTCGATACGCACTATAGCAC CGAGAATGACGTGGAGACCATC | 1835 | human |
| FURIN_4165 | CAUUGCUGGUU CUAUUUAAU | 1736 | TTTAAACAGGCCCAGCATTGCTG GTTCTATTTAATGGACATGAGA | 1836 | human |
| FURIN_4186 | GACAUGAGAUA AUGUUAGAG | 1737 | TGGTTCTATTTAATGGACATGAG ATAATGTTAGAGGTTTTAAAGT | 1837 | human |
| FURIN_779 | AUGAUCCUGGG GCCAGUUUU | 1738 | ACTTGGCAGGCAATTATGATCCT GGGGCCAGTTTTGATGTCAATG | 1838 | human |
| FURIN_1871 | GGGCCUUCAUG ACAACUCAU | 1739 | ATGGGTTTAATGACTGGGCCTTC ATGACAACTCATTCCTGGGATG | 1839 | human |
| FURIN_3552 | UUAUUUCACUU UAGAUGCUG | 1740 | ATTTTCACTTTGTGATTATTTCAC TTTAGATGCTGATGATTTGTT | 1840 | human |
| FURIN_4180 | UUAAUGGACAU GAGAUAAUG | 1741 | CATTGCTGGTTCTATTTAATGGA CATGAGATAATGTTAGAGGTTT | 1841 | human |
| FURIN_1429 | GCCAAUAAGAA CCUCACAUG | 1742 | GCTCTCACCCTGGAGGCCAATAA GAACCTCACATGGCGGGACATG | 1842 | human |
| FURIN_1654 | AAAGACAUCGG GAAACGGCU | 1743 | ATCCTCACCGAGCCCAAAGACAT CGGGAAACGGCTCGAGGTGCGG | 1843 | human |
| FURIN_3968 | CCCAUUAGGAC AAUCAGUCC | 1744 | GCCTTTTGCACCCCTCCCATTAG GACAATCAGTCCCCTCCCATCT | 1844 | human |
| FURIN_1855 | GAUGGGUUUAA UGACUGGGC | 1745 | CATGACTACTCCGCAGATGGGTT TAATGACTGGGCCTTCATGACA | 1845 | human |
| FURIN_3513 | AUCUCAGGGGC UGUUUGAGG | 1746 | CTTTCCCCTGTGGGGATCTCAGG GGCTGTTTGAGGATATATTTTC | 1846 | human |
| FURIN_4108 | UGUAAGAUGCU GGGUUGGUG | 1747 | CAGCCCGGCTGGTTTTGTAAGAT GCTGGGTTGGTGCACAGTGATT | 1847 | human |
| FURIN_4170 | CUGGUUCUAUU UAAUGGACA | 1748 | ACAGGCCCAGCATTGCTGGTTCT ATTTAATGGACATGAGATAATG | 1848 | human |
| FURIN_367 | UUCACCAACAC GUGGGCUGU | 1749 | CAGGGCCAGAAGGTCTTCACCA ACACGTGGGCTGTGCGCATCCCT | 1849 | human |
| FURIN_2492 | UGCGCUCUGGC UUUAGUUUU | 1750 | TCCTGGTCCTGCAGCTGCGCTCT GGCTTTAGTTTTCGGGGGGTGA | 1850 | human |
| FURIN_2882 | UUCCAUGUGGA GAAAGGAGU | 1751 | CACCCTCAGCACCCCTTCCATGT GGAGAAAGGAGTGAAACCTTTA | 1851 | human |
| FURIN_4175 | UCUAUUUAAUG GACAUGAGA | 1752 | CCCAGCATTGCTGGTTCTATTTA ATGGACATGAGATAATGTTAGA | 1852 | human |
| FURIN_4201 | UAGAGGUUUUA AAGUGAUUA | 1753 | GACATGAGATAATGTTAGAGGTT TTAAAGTGATTAAACGTGCAGA | 1853 | human |
| FURIN_749 | AGAAGAACCAC CCGGACUUG | 1754 | TGGACGATGGCATCGAGAAGAA CCACCCGGACTTGGCAGGCAATT | 1854 | human |

TABLE 11C-continued

Host target FURIN - 20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| FURIN_3523 | CUGUUUGAGGA UAUAUUUUC | 1755 | TGGGGATCTCAGGGGCTGTTTGA GGATATATTTTCACTTTGTGAT | 1855 | human |
| FURIN_1856 | AUGGGUUUAAU GACUGGGCC | 1756 | ATGACTACTCCGCAGATGGGTTT AATGACTGGGCCTTCATGACAA | 1856 | human |
| FURIN_1859 | GGUUUAAUGAC UGGGCCUUC | 1757 | ACTACTCCGCAGATGGGTTTAAT GACTGGGCCTTCATGACAACTC | 1857 | human |
| FURIN_2638 | UUUAUCAAAGA CCAGAGCGC | 1758 | GGCGAGAGGACCGCCTTTATCA AAGACCAGAGCGCCCTCTGATGA | 1858 | human |
| FURIN_3516 | UCAGGGGCUGU UUGAGGAUA | 1759 | TCCCCTGTGGGGATCTCAGGGGC TGTTTGAGGATATATTTTCACT | 1859 | human |
| FURIN_3554 | AUUUCACUUUA GAUGCUGAU | 1760 | TTTCACTTTGTGATTATTTCACTT TAGATGCTGATGATTTGTTTT | 1860 | human |
| FURIN_1936 | AACACCAGCGA AGCCAACAA | 1761 | GTCCTAGAGATTGAAAACACCA GCGAAGCCAACAACTATGGGACG | 1861 | human |
| FURIN_2458 | CUGGUCUUCGU CACUGUCUU | 1762 | TGCGCCTTCATCGTGCTGGTCTT CGTCACTGTCTTCCTGGTCCTG | 1862 | human |
| FURIN_313 | GCAGCAACAGG AACCUUGGU | 1763 | TTGCTATGGGTGGTAGCAGCAAC AGGAACCTTGGTCCTGCTAGCA | 1863 | human |
| FURIN_2520 | GAAGGUGUACA CCAUGGACC | 1764 | TAGTTTTCGGGGGGTGAAGGTGT ACACCATGGACCGTGGCCTCAT | 1864 | human |
| FURIN_1310 | GCAACCAGAAU GAGAAGCAG | 1765 | CGACCTACAGCAGTGGCAACCA GAATGAGAAGCAGATCGTGACGA | 1865 | human |
| FURIN_1752 | CACCCUGUCCU AUAAUCGCC | 1766 | CGCTCAGGCGCGGCTCACCCTGT CCTATAATCGCCGTGGCGACCT | 1866 | human |
| FURIN_4166 | AUUGCUGGUUC UAUUUAAUG | 1767 | TTAAACAGGCCCAGCATTGCTGG TTCTATTTAATGGACATGAGAT | 1867 | human |
| FURIN_834 | GUACACACAGA UGAAUGACA | 1768 | TGACCCCCAGCCTCGGTACACAC AGATGAATGACAACAGGCACGG | 1868 | human |
| FURIN_3517 | CAGGGGCUGUU UGAGGAUAU | 1769 | CCCCTGTGGGGATCTCAGGGGCT GTTTGAGGATATATTTTCACTT | 1869 | human |
| FURIN_3550 | GAUUAUUUCAC UUUAGAUGC | 1770 | ATATTTTCACTTTGTGATTATTTC ACTTTAGATGCTGATGATTTG | 1870 | human |
| FURIN_2694 | UCCCCUCCUUG GGCACUUUU | 1771 | ACCCCCTCAAGCCAATCCCCTCC TTGGGCACTTTTTAATTCACCA | 1871 | human |
| FURIN_578 | UGGCAAAGCGA CGGACUAAA | 1772 | GGCTGGAACAGCAGGTGGCAAA GCGACGGACTAAACGGGACGTGT | 1872 | human |
| FURIN_1246 | UUUGGCAACGU GCCGUGGUA | 1773 | AGCAGCGCCACGCAGTTTGGCA ACGTGCCGTGGTACAGCGAGGCC | 1873 | human |
| FURIN_1425 | GGAGGCCAAUA AGAACCUCA | 1774 | CATTGCTCTCACCCTGGAGGCCA ATAAGAACCTCACATGGCGGGA | 1874 | human |
| FURIN_1018 | AUCCACAUCUA CAGUGCCAG | 1775 | CTGAACCCCAACCACATCCACAT CTACAGTGCCAGCTGGGGCCCC | 1875 | human |
| FURIN_1858 | GGGUUUAAUGA CUGGGCCUU | 1776 | GACTACTCCGCAGATGGGTTTAA TGACTGGGCCTTCATGACAACT | 1876 | human |
| FURIN_1924 | CUAGAGAUUGA AAACACCAG | 1777 | TCTGGCGAGTGGGTCCTAGAGAT TGAAAACACCAGCGAAGCCAAC | 1877 | human |
| FURIN_293 | CCUGGUUGCUA UGGGUGGUA | 1778 | CCATGGAGCTGAGGCCCTGGTTG CTATGGGTGGTAGCAGCAACAG | 1878 | human |

TABLE 11C-continued

| Host target FURIN - 20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| FURIN_790 | GCCAGUUUUGA UGUCAAUGA | 1779 | AATTATGATCCTGGGGCCAGTTT TGATGTCAATGACCAGGACCCT | 1879 | human |
| FURIN_962 | AUGGCGAGGUG ACAGAUGCA | 1780 | GGGTGCGCATGCTGGATGGCGA GGTGACAGATGCAGTGGAGGCAC | 1880 | human |
| FURIN_1757 | UGUCCUAUAAU CGCCGUGGC | 1781 | AGGCGCGGCTCACCCTGTCCTAT AATCGCCGTGGCGACCTGGCCA | 1881 | human |
| FURIN_1848 | CUCCGCAGAUG GGUUUAAUG | 1782 | CAGGCCACATGACTACTCCGCAG ATGGGTTTAATGACTGGGCCTT | 1882 | human |
| FURIN_3020 | GUCCCUCUAAA GCAAUAAUG | 1783 | CTCTTGCCCTTCCCTGTCCCTCTA AAGCAATAATGGTCCCATCCA | 1883 | human |
| FURIN_3511 | GGAUCUCAGGG GCUGUUUGA | 1784 | TGCTTTCCCCTGTGGGGATCTCA GGGGCTGTTTGAGGATATATTT | 1884 | human |
| FURIN_760 | CCGGACUUGGC AGGCAAUUA | 1785 | ATCGAGAAGAACCACCCGGACT TGGCAGGCAATTATGATCCTGGG | 1885 | human |
| FURIN_770 | CAGGCAAUUAU GAUCCUGGG | 1786 | ACCACCCGGACTTGGCAGGCAA TTATGATCCTGGGGCCAGTTTTG | 1886 | human |
| FURIN_827 | AGCCUCGGUAC ACACAGAUG | 1787 | AGGACCCTGACCCCCAGCCTCGG TACACACAGATGAATGACAACA | 1887 | human |
| FURIN_1199 | GCUACACCAAC AGUAUCUAC | 1788 | GCTGCAACTGCGACGGCTACACC AACAGTATCTACACGCTGTCCA | 1888 | human |
| FURIN_2459 | UGGUCUUCGUC ACUGUCUUC | 1789 | GCGCCTTCATCGTGCTGGTCTTC GTCACTGTCTTCCTGGTCCTGC | 1889 | human |
| FURIN_4106 | UUUGUAAGAUG CUGGGUUGG | 1790 | GCCAGCCCGGCTGGTTTTGTAAG ATGCTGGGTTGGTGCACAGTGA | 1890 | human |
| FURIN_4173 | GUUCUAUUUAA UGGACAUGA | 1791 | GGCCCAGCATTGCTGGTTCTATT TAATGGACATGAGATAATGTTA | 1891 | human |
| FURIN_4199 | GUUAGAGGUUU UAAAGUGAU | 1792 | TGGACATGAGATAATGTTAGAG GTTTTAAAGTGATTAAACGTGCA | 1892 | human |
| FURIN_773 | GCAAUUAUGAU CCUGGGGCC | 1793 | ACCCGGACTTGGCAGGCAATTAT GATCCTGGGGCCAGTTTTGATG | 1893 | human |
| FURIN_786 | UGGGGCCAGUU UUGAUGUCA | 1794 | AGGCAATTATGATCCTGGGGCCA GTTTTGATGTCAATGACCAGGA | 1894 | human |

TABLE 11D

| Host target ACE2-20 nucleotide targets and 45 nucleotide gene target regions | | | | | |
|---|---|---|---|---|---|
| SEQUENCE ID | 20 nt Sequence | SEQ ID NO: | 45 nt Gene Region | SEQ ID NO: | Species |
| ACE2_ 52 | UUGGAUUUCAUAC CAUGUGG | 1895 | TGACATAGATACTCTTTGGATTT CATACCATGTGGAGGCTTTCTT | 2095 | human |
| ACE2_ 2730 | UGUCAAAACUAUG ACUCUGU | 1896 | AAAGATATCATTAAATGTCAAA ACTATGACTCTGTTCAGAAAAAA | 2096 | human |
| ACE2_ 1918 | CCUAGCAUUGGAA AAUGUUG | 1897 | ATCAGAACCCTGGACCCTAGCAT TGGAAAATGTTGTAGGAGCAAA | 2097 | human |
| ACE2_ 2674 | AUGUAAAUGUUAA UUUCAUG | 1898 | AGGTGATTTTGTTGTATGTAAAT GTTAATTTCATGGTATAGAAAA | 2098 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_2849 | UCUGUUUCUUAAUAAGGAUU | 1899 | GGATTTGACTTCTGTTCTGTTTCTTAATAAGGATTTTGTATTAGA | 2099 | human |
| ACE2_30 | CAGGAGUUGACAUAGAUACU | 1900 | ATGGCTACAGAGGATCAGGAGTTGACATAGATACTCTTTGGATTT | 2100 | human |
| ACE2_1739 | AAUGAUUACUCAUUCAUUCG | 1901 | CTGTTCCATGTTTCTAATGATTACTCATTCATTCGATATTACACA | 2101 | human |
| ACE2_2567 | AUCGAUAUUAGCAAAGGAGA | 1902 | AATCCTTATGCCTCCATCGATATTAGCAAAGGAGAAAATAATCCA | 2102 | human |
| ACE2_2690 | CAUGGUAUAGAAAAUAUAAG | 1903 | TGTAAATGTTAATTTCATGGTATAGAAAATATAAGATGATAAAGA | 2103 | human |
| ACE2_2239 | UUUGAAACCAAGAAUCUCCU | 1904 | TGTGCGAGTGGCTAATTTGAAACCAAGAATCTCCTTTAATTTCTT | 2104 | human |
| ACE2_2465 | AUGGGAGUGAUAGUGGUUGG | 1905 | GTTTTTGGAGTTGTGATGGGAGTGATAGTGGTTGGCATTGTCATC | 2105 | human |
| ACE2_906 | UUGAAGAGAUUAAACCAUUA | 1906 | ATGTGGAACATACCTTTGAAGAGATTAAACCATTATATGAACATC | 2106 | human |
| ACE2_2666 | UUUGUUGUAUGUAAAUGUUA | 1907 | TCCTCTTGAGGTGATTTTGTTGTATGTAAATGTTAATTTCATGGT | 2107 | human |
| ACE2_2688 | UUCAUGGUAUAGAAAAUAUA | 1908 | TATGTAAATGTTAATTTCATGGTATAGAAAATATAAGATGATAAA | 2108 | human |
| ACE2_2830 | CUCUGGAUUUGACUUCUGUU | 1909 | AGTATTTATTTCTGTCTCTGGATTTGACTTCTGTTCTGTTTCTTA | 2109 | human |
| ACE2_916 | UAAACCAUUAUAUGAACAUC | 1910 | TACCTTTGAAGAGATTAAACCATTATATGAACATCTTCATGCCTA | 2110 | human |
| ACE2_2650 | UUCCUCUUGAGGUGAUUUUG | 1911 | GAAAAATCTATGTTTTTCCTCTTGAGGTGATTTTGTTGTATGTAA | 2111 | human |
| ACE2_2723 | CAUUAAAUGUCAAAACUAUG | 1912 | AGATGATAAAGATATCATTAAATGTCAAAACTATGACTCTGTTCA | 2112 | human |
| ACE2_2582 | GGAGAAAAUAAUCCAGGAUU | 1913 | ATCGATATTAGCAAAGGAGAAAATAATCCAGGATTCCAAAACACT | 2113 | human |
| ACE2_2778 | UGGCCAAGGAGAGAGCAUCU | 1914 | TGTCCAAAGACAACATGGCCAAGGAGAGAGCATCTTCATTGACAT | 2114 | human |
| ACE2_2918 | UCAGGGAUAAUCUAAAUGUA | 1915 | GGTCTCACAGGCTGTTCAGGGATAATCTAAATGTAAATGTCTGTT | 2115 | human |
| ACE2_1500 | UUCAAGAAGACAAUGAAACA | 1916 | TTCTGTCACCCGATTTTCAAGAAGACAATGAAACAGAAATAAACT | 2116 | human |
| ACE2_1769 | AGGACCCUUUACCAAUUCCA | 1917 | ATTCGATATTACACAAGGACCCTTTACCAATTCCAGTTTCAAGAA | 2117 | human |
| ACE2_1936 | UGUAGGAGCAAAGAACAUGA | 1918 | AGCATTGGAAAATGTTGTAGGAGCAAAGAACATGAATGTAAGGCC | 2118 | human |
| ACE2_1939 | AGGAGCAAAGAACAUGAAUG | 1919 | ATTGGAAAATGTTGTAGGAGCAAAGAACATGAATGTAAGGCCACT | 2119 | human |
| ACE2_2545 | UGGAGAAAAUCCUUAUGCCU | 1920 | AAATAAAGCAAGAAGTGGAGAAAATCCTTATGCCTCCATCGATAT | 2120 | human |
| ACE2_2660 | GGUGAUUUUGUUGUAUGUAA | 1921 | TGTTTTTCCTCTTGAGGTGATTTTGTTGTATGTAAATGTTAATTT | 2121 | human |
| ACE2_1447 | UUCUGCAGCCACACCUAAGC | 1922 | GGAAATCATGTCACTTTCTGCAGCCACACCTAAGCATTTAAAATC | 2122 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_ 2734 | AAAACUAUGACUC UGUUCAG | 1923 | ATATCATTAAATGTCAAAACTAT GACTCTGTTCAGAAAAAAAATT | 2123 | human |
| ACE2_ 2927 | AUCUAAAUGUAAA UGUCUGU | 1924 | GGCTGTTCAGGGATAATCTAAAT GTAAATGTCTGTTGAATTTCTG | 2124 | human |
| ACE2_ 167 | UUAGUCUAGGGAA AGUCAUU | 1925 | TCTCATGAGGAGGTTTTAGTCTA GGGAAAGTCATTCAGTGGATGT | 2125 | human |
| ACE2_ 2982 | GGAGCAAGUGUUG GAUCUUG | 1926 | CAAGGATATATCATTGGAGCAA GTGTTGGATCTTGTATGGAATAT | 2126 | human |
| ACE2_ 2837 | UUUGACUUCUGUU CUGUUUC | 1927 | ATTTCTGTCTCTGGATTTGACTTC TGTTCTGTTTCTTAATAAGGA | 2127 | human |
| ACE2_ 2867 | UUUUGUAUUAGAG UAUAUUA | 1928 | GTTTCTTAATAAGGATTTTGTAT TAGAGTATATTAGGGAAAGTGT | 2128 | human |
| ACE2_ 745 | GAGGCCAUUAUAU GAAGAGU | 1929 | GGTCGGCAAGCAGCTGAGGCCA TTATATGAAGAGTATGTGGTCTT | 2129 | human |
| ACE2_ 2246 | CCAAGAAUCUCCU UUAAUUU | 1930 | GTGGCTAATTTGAAACCAAGAAT CTCCTTTAATTTCTTTGTCACT | 2130 | human |
| ACE2_ 2612 | GAUGAUGUUCAGA CCUCCUU | 1931 | GGATTCCAAAACACTGATGATGT TCAGACCTCCTTTTAGAAAAAT | 2131 | human |
| ACE2_ 2831 | UCUGGAUUUGACU UCUGUUC | 1932 | GTATTTATTTCTGTCTCTGGATTT GACTTCTGTTCTGTTTCTTAA | 2132 | human |
| ACE2_ 272 | UCCACCAUUGAGG AACAGGC | 1933 | GTAACTGCTGCTCAGTCCACCAT TGAGGAACAGGCCAAGACATTT | 2133 | human |
| ACE2_ 641 | UUAUUACUUGAAC CAGGUUU | 1934 | AATCCACAAGAATGCTTATTACT TGAACCAGGTTTGAATGAAATA | 2134 | human |
| ACE2_ 649 | UGAACCAGGUUUG AAUGAAA | 1935 | AGAATGCTTATTACTTGAACCAG GTTTGAATGAAATAATGGCAAA | 2135 | human |
| ACE2_ 2026 | UGUGGGAUGGAGU ACCGACU | 1936 | GAACAAGAATTCTTTTGTGGGAT GGAGTACCGACTGGAGTCCATA | 2136 | human |
| ACE2_ 2657 | UGAGGUGAUUUUG UUGUAUG | 1937 | CTATGTTTTTCCTCTTGAGGTGAT TTTGTTGTATGTAAATGTTAA | 2137 | human |
| ACE2_ 3435 | UGUAUUUGCUCAC AGUGUUU | 1938 | GTCTCTTAAATCTTTTGTATTTGC TCACAGTGTTTGAGCAGTGCT | 2138 | human |
| ACE2_ 643 | AUUACUUGAACCA GGUUUGA | 1939 | TCCACAAGAATGCTTATTACTTG AACCAGGTTTGAATGAAATAAT | 2139 | human |
| ACE2_ 785 | AUGGCAAGAGCAA AUCAUUA | 1940 | GTCTTGAAAAATGAGATGGCAA GAGCAAATCATTATGAGGACTAT | 2140 | human |
| ACE2_ 1072 | UGGACAGAAACCA AACAUAG | 1941 | TTTGACAGTTCCCTTTGGACAGA AACCAAACATAGATGTTACTGA | 2141 | human |
| ACE2_ 2870 | UGUAUUAGAGUAU AUUAGGG | 1942 | TCTTAATAAGGATTTTGTATTAG AGTATATTAGGGAAAGTGTGTA | 2142 | human |
| ACE2_ 2974 | AUAUCAUUGGAGC AAGUGUU | 1943 | GTTGAAAACAAGGATATATCATT GGAGCAAGTGTTGGATCTTGTA | 2143 | human |
| ACE2_ 2676 | GUAAAUGUUAAUU UCAUGGU | 1944 | GTGATTTTGTTGTATGTAAATGT TAATTTCATGGTATAGAAAATA | 2144 | human |
| ACE2_ 2856 | CUUAAUAAGGAUU UUGUAUU | 1945 | ACTTCTGTTCTGTTTCTTAATAAG GATTTTGTATTAGAGTATATT | 2145 | human |
| ACE2_ 122 | CCCAAGUUCAAAG GCUGAUA | 1946 | TTGAATAGCGCCCAACCCAAGTT CAAAGGCTGATAAGAGAGAAAA | 2146 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_1564 | UCUGCCAUUUACUUACAUGU | 1947 | CACGATTGTTGGGACTCTGCCATTTACTTACATGTTAGAGAAGTG | 2147 | human |
| ACE2_1960 | AAGGCCACUGCUCAACUACU | 1948 | AAAGAACATGAATGTAAGGCCACTGCTCAACTACTTTGAGCCCTT | 2148 | human |
| ACE2_212 | GGGACGAUGUCAAGCUCUUC | 1949 | GATCTTGGCTCACAGGGGACGATGTCAAGCTCTTCCTGGCTCCTT | 2149 | human |
| ACE2_317 | CACGAAGCCGAAGACCUGUU | 1950 | TTGGACAAGTTTAACCACGAAGCCGAAGACCTGTTCTATCAAAGT | 2150 | human |
| ACE2_472 | ACAAGAAAUUCAGAAUCUCA | 1951 | CCAAATGTATCCACTACAAGAAATTCAGAATCTCACAGTCAAGCT | 2151 | human |
| ACE2_2287 | UGUGUCUGAUAUCAUUCCUA | 1952 | CACTGCACCTAAAAATGTGTCTGATATCATTCCTAGAACTGAAGT | 2152 | human |
| ACE2_2919 | CAGGGAUAAUCUAAAUGUAA | 1953 | GTCTCACAGGCTGTTCAGGGATAATCTAAATGTAAATGTCTGTTG | 2153 | human |
| ACE2_3334 | CUGAUAGAAACUCAUUUCUA | 1954 | ACTCCCAGAGCATGCCTGATAGAAACTCATTTCTACTGTTCTCTA | 2154 | human |
| ACE2_1358 | UAUGAUAUGGCAUAUGCUGC | 1955 | ATGGGGCATATCCAGTATGATATGGCATATGCTGCACAACCTTTT | 2155 | human |
| ACE2_1549 | CACGAUUGUUGGGACUCUGC | 1956 | GCTCAAACAAGCACTCACGATTGTTGGGACTCTGCCATTTACTTA | 2156 | human |
| ACE2_2615 | GAUGUUCAGACCUCCUUUUA | 1957 | TTCCAAAACACTGATGATGTTCAGACCTCCTTTTAGAAAAATCTA | 2157 | human |
| ACE2_2705 | AUAAGAUGAUAAAGAUAUCA | 1958 | CATGGTATAGAAAATATAAGATGATAAAGATATCATTAAATGTCA | 2158 | human |
| ACE2_2711 | UGAUAAAGAUAUCAUUAAAU | 1959 | ATAGAAAATATAAGATGATAAAGATATCATTAAATGTCAAAACTA | 2159 | human |
| ACE2_2852 | GUUUCUUAAUAAGGAUUUUG | 1960 | TTTGACTTCTGTTCTGTTTCTTAATAAGGATTTTGTATTAGAGTA | 2160 | human |
| ACE2_2868 | UUUGUAUUAGAGUAUAUUAG | 1961 | TTTCTTAATAAGGATTTTGTATTAGAGTATATTAGGGAAAGTGTG | 2161 | human |
| ACE2_357 | CUUGGAAUUAUAACACCAAU | 1962 | AAAGTTCACTTGCTTCTTGGAATTATAACACCAATATTACTGAAG | 2162 | human |
| ACE2_2342 | AGCCGUAUCAAUGAUGCUUU | 1963 | ATCAGGATGTCCCGGAGCCGTATCAATGATGCTTTCCGTCTGAAT | 2163 | human |
| ACE2_2822 | AUUUCUGUCUCUGGAUUUGA | 1964 | TTGCTTTCAGTATTTATTTCTGTCTCTGGATTTGACTTCTGTTCT | 2164 | human |
| ACE2_3465 | GAGCACAAAGCAGACACUCA | 1965 | TGTTTGAGCAGTGCTGAGCACAAAGCAGACACTCAATAAATGCTA | 2165 | human |
| ACE2_2715 | AAAGAUAUCAUUAAAUGUCA | 1966 | AAAATATAAGATGATAAAGATATCATTAAATGTCAAAACTATGAC | 2166 | human |
| ACE2_90 | GUGACCUUGACUGAGUUUUG | 1967 | CTTTCTTACTTCCACGTGACCTTGACTGAGTTTTGAATAGCGCCC | 2167 | human |
| ACE2_892 | UGUGGAACAUACCUUUGAAG | 1968 | CCAGTTGATTGAAGATGTGGAACATACCTTTGAAGAGATTAAACC | 2168 | human |
| ACE2_2162 | UAUGCUAUGAGGCAGUACUU | 1969 | CGATCATCTGTTGCATATGCTATGAGGCAGTACTTTTTAAAAGTA | 2169 | human |
| ACE2_2434 | UUCCAUAUGGCUGAUUGUUU | 1970 | TAACCAGCCCCCTGTTTCCATATGGCTGATTGTTTTTGGAGTTGT | 2170 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_687 | ACUACAAUGAGAGGCUCUGG | 1971 | TGGCAAACAGTTTAGACTACAATGAGAGGCTCTGGGCTTGGGAAA | 2171 | human |
| ACE2_2238 | AUUUGAAACCAAGAAUCUCC | 1972 | ATGTGCGAGTGGCTAATTTGAAACCAAGAATCTCCTTTAATTTCT | 2172 | human |
| ACE2_2944 | UGUUGAAUUUCUGAAGUUGA | 1973 | CTAAATGTAAATGTCTGTTGAATTTCTGAAGTTGAAAACAAGGAT | 2173 | human |
| ACE2_3416 | CCCAGUCUCUUAAAUCUUUU | 1974 | CCTCTGAAGTGGGTACCCAGTCTCTTAAATCTTTTGTATTTGCTC | 2174 | human |
| ACE2_2464 | GAUGGGAGUGAUAGUGGUUG | 1975 | TGTTTTTGGAGTTGTGATGGGAGTGATAGTGGTTGGCATTGTCAT | 2175 | human |
| ACE2_2611 | UGAUGAUGUUCAGACCUCCU | 1976 | AGGATTCCAAAACACTGATGATGTTCAGACCTCCTTTTAGAAAAA | 2176 | human |
| ACE2_352 | UGCUUCUUGGAAUUAUAACA | 1977 | CTATCAAAGTTCACTTGCTTCTTGGAATTATAACACCAATATTAC | 2177 | human |
| ACE2_2929 | CUAAAUGUAAAUGUCUGUUG | 1978 | CTGTTCAGGGATAATCTAAATGTAAATGTCTGTTGAATTTCTGAA | 2178 | human |
| ACE2_407 | AAUGCUGGGGACAAAUGGUC | 1979 | GTCCAAAACATGAATAATGCTGGGGACAAATGGTCTGCCTTTTTA | 2179 | human |
| ACE2_1498 | UUUUCAAGAAGACAAUGAAA | 1980 | TCTTCTGTCACCCGATTTTCAAGAAGACAATGAAACAGAAATAAA | 2180 | human |
| ACE2_2098 | UCUUGGAGAUAAAGCAUAUG | 1981 | AAGCCTAAAATCAGCTCTTGGAGATAAAGCATATGAATGGAACGA | 2181 | human |
| ACE2_2129 | AAUGAAAUGUACCUGUUCCG | 1982 | TATGAATGGAACGACAATGAAATGTACCTGTTCCGATCATCTGTT | 2182 | human |
| ACE2_2702 | AAUAUAAGAUGAUAAAGAUA | 1983 | TTTCATGGTATAGAAAATATAAGATGATAAAGATATCATTAAATG | 2183 | human |
| ACE2_2846 | UGUUCUGUUUCUUAAUAAGG | 1984 | TCTGGATTTGACTTCTGTTCTGTTTCTTAATAAGGATTTTGTATT | 2184 | human |
| ACE2_3156 | UUUGCCUACAGUGAUGUUUG | 1985 | CAAGTACTATGGTGATTTGCCTACAGTGATGTTTGGAATCGATCA | 2185 | human |
| ACE2_150 | AAUCUCAUGAGGAGGUUUUA | 1986 | GCTGATAAGAGAGAAAATCTCATGAGGAGGTTTTAGTCTAGGGAA | 2186 | human |
| ACE2_2706 | UAAGAUGAUAAAGAUAUCAU | 1987 | ATGGTATAGAAAATATAAGATGATAAAGATATCATTAAATGTCAA | 2187 | human |
| ACE2_3168 | GAUGUUUGGAAUCGAUCAUG | 1988 | TGATTTGCCTACAGTGATGTTTGGAATCGATCATGCTTTCTTCAA | 2188 | human |
| ACE2_447 | CCACACUUGCCCAAAUGUAU | 1989 | TTTTAAAGGAACAGTCCACACTTGCCCAAATGTATCCACTACAAG | 2189 | human |
| ACE2_831 | GAGACUAUGAAGUAAAUGGG | 1990 | GGGATTATTGGAGAGGAGACTATGAAGTAAATGGGGTAGATGGCT | 2190 | human |
| ACE2_2796 | CUUCAUUGACAUUGCUUUCA | 1991 | CCAAGGAGAGAGCATCTTCATTGACATTGCTTTCAGTATTTATTT | 2191 | human |
| ACE2_2937 | AAAUGUCUGUUGAAUUUCUG | 1992 | GGATAATCTAAATGTAAATGTCTGTTGAATTTCTGAAGTTGAAAA | 2192 | human |
| ACE2_3049 | UGUAGCUGCAAGGAUUGAGA | 1993 | GTGCCTGGGAACTGGTGTAGCTGCAAGGATTGAGAATGGCATGCA | 2193 | human |
| ACE2_35 | GUUGACAUAGAUACUCUUUG | 1994 | TACAGAGGATCAGGAGTTGACATAGATACTCTTTGGATTTCATAC | 2194 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_391 | UGUCCAAAACAUGAAUAAUG | 1995 | TATTACTGAAGAGAATGTCCAAAACATGAATAATGCTGGGGACAA | 2195 | human |
| ACE2_2709 | GAUGAUAAAGAUAUCAUUAA | 1996 | GTATAGAAAATATAAGATGATAAAGATATCATTAAATGTCAAAAC | 2196 | human |
| ACE2_2869 | UUGUAUUAGAGUAUAUUAGG | 1997 | TTCTTAATAAGGATTTTGTATTAGAGTATATTAGGGAAAGTGTGT | 2197 | human |
| ACE2_3124 | UUCACAGUAACUCAGUUCAA | 1998 | GGATGACATGCTTTCTTCACAGTAACTCAGTTCAAGTACTATGGT | 2198 | human |
| ACE2_29 | UCAGGAGUUGACAUAGAUAC | 1999 | CATGGCTACAGAGGATCAGGAGTTGACATAGATACTCTTTGGATT | 2199 | human |
| ACE2_1050 | UGUACUCUUUGACAGUUCCC | 2000 | GATTTTGGACAAATCTGTACTCTTTGACAGTTCCCTTTGGACAGA | 2200 | human |
| ACE2_1400 | GGAGCUAAUGAAGGAUUCCA | 2001 | TTTCTGCTAAGAAATGGAGCTAATGAAGGATTCCATGAAGCTGTT | 2201 | human |
| ACE2_1981 | UGAGCCCUUAUUUACCUGGC | 2002 | ACTGCTCAACTACTTTGAGCCCTTATTTACCTGGCTGAAAGACCA | 2202 | human |
| ACE2_2164 | UGCUAUGAGGCAGUACUUUU | 2003 | ATCATCTGTTGCATATGCTATGAGGCAGTACTTTTTAAAAGTAAA | 2203 | human |
| ACE2_2672 | GUAUGUAAAUGUUAAUUUCA | 2004 | TGAGGTGATTTTGTTGTATGTAAATGTTAATTTCATGGTATAGAA | 2204 | human |
| ACE2_2795 | UCUUCAUUGACAUUGCUUUC | 2005 | GCCAAGGAGAGAGCATCTTCATTGACATTGCTTTCAGTATTTATT | 2205 | human |
| ACE2_2900 | UUUGGUCUCACAGGCUGUUC | 2006 | TAGGGAAAGTGTGTATTTGGTCTCACAGGCTGTTCAGGGATAATC | 2206 | human |
| ACE2_140 | UAAGAGAGAAAAUCUCAUGA | 2007 | AAGTTCAAAGGCTGATAAGAGAGAAAATCTCATGAGGAGGTTTTA | 2207 | human |
| ACE2_1337 | CAUGAGAUGGGGCAUAUCCA | 2008 | TTCCTGACAGCTCATCATGAGATGGGGCATATCCAGTATGATATG | 2208 | human |
| ACE2_1735 | UUCUAAUGAUUACUCAUUCA | 2009 | ATCTCTGTTCCATGTTTCTAATGATTACTCATTCATTCGATATTA | 2209 | human |
| ACE2_2346 | GUAUCAAUGAUGCUUUCCGU | 2010 | GGATGTCCCGGAGCCGTATCAATGATGCTTTCCGTCTGAATGACA | 2210 | human |
| ACE2_2959 | GUUGAAAACAAGGAUAUAUC | 2011 | TGTTGAATTTCTGAAGTTGAAAACAAGGATATATCATTGGAGCAA | 2211 | human |
| ACE2_887 | GAAGAUGUGGAACAUACCUU | 2012 | CGCGGCCAGTTGATTGAAGATGTGGAACATACCTTTGAAGAGATT | 2212 | human |
| ACE2_905 | UUUGAAGAGAUUAAACCAUU | 2013 | GATGTGGAACATACCTTTGAAGAGATTAAACCATTATATGAACAT | 2213 | human |
| ACE2_2010 | AGAACAAGAAUUCUUUUGUG | 2014 | CCTGGCTGAAAGACCAGAACAAGAATTCTTTTGTGGGATGGAGTA | 2214 | human |
| ACE2_2575 | UAGCAAAGGAGAAAUAAAUC | 2015 | TGCCTCCATCGATATTAGCAAAGGAGAAAATAATCCAGGATTCCA | 2215 | human |
| ACE2_2962 | GAAAACAAGGAUAUAUCAUU | 2016 | TGAATTTCTGAAGTTGAAAACAAGGATATATCATTGGAGCAAGTG | 2216 | human |
| ACE2_3184 | CAUGCUUUCUUCAAGGUGAC | 2017 | ATGTTTGGAATCGATCATGCTTTCTTCAAGGTGACAGGTCTAAAG | 2217 | human |
| ACE2_120 | AACCCAAGUUCAAAGGCUGA | 2018 | TTTTGAATAGCGCCCAACCCAAGTTCAAAGGCTGATAAGAGAGAA | 2218 | human |
| ACE2_927 | AUGAACAUCUUCAUGCCUAU | 2019 | AGATTAAACCATTATATGAACATCTTCATGCCTATGTGAGGGCAA | 2219 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_2504 | ACUGGGAUCAGAGAUCGGAA | 2020 | GTCATCCTGATCTTCACTGGGATCAGAGATCGGAAGAAGAAAAAT | 2220 | human |
| ACE2_3191 | UCUUCAAGGUGACAGGUCUA | 2021 | GAATCGATCATGCTTTCTTCAAGGTGACAGGTCTAAAGAGAGAAG | 2221 | human |
| ACE2_517 | UCAGCAAAAUGGGUCUUCAG | 2022 | TCAGCTGCAGGCTCTTCAGCAAAATGGGTCTTCAGTGCTCTCAGA | 2222 | human |
| ACE2_674 | GCAAACAGUUUAGACUACAA | 2023 | TTGAATGAAATAATGGCAAACAGTTTAGACTACAATGAGAGGCTC | 2223 | human |
| ACE2_917 | AAACCAUUAUAUGAACAUCU | 2024 | ACCTTTGAAGAGATTAAACCATTATATGAACATCTTCATGCCTAT | 2224 | human |
| ACE2_1048 | UCUGUACUCUUUGACAGUUC | 2025 | TAGATTTTGGACAAATCTGTACTCTTTGACAGTTCCCTTTGGACA | 2225 | human |
| ACE2_1057 | UUUGACAGUUCCCUUUGGAC | 2026 | GACAAATCTGTACTCTTTGACAGTTCCCTTTGGACAGAAACCAAA | 2226 | human |
| ACE2_1514 | GAAACAGAAAUAAACUUCCU | 2027 | TTTCAAGAAGACAATGAAACAGAAATAAACTTCCTGCTCAAACAA | 2227 | human |
| ACE2_2814 | CAGUAUUUAUUUCUGUCUCU | 2028 | CATTGACATTGCTTTCAGTATTTATTTCTGTCTCTGGATTTGACT | 2228 | human |
| ACE2_3136 | CAGUUCAAGUACUAUGGUGA | 2029 | TTCTTCACAGTAACTCAGTTCAAGTACTATGGTGATTTGCCTACA | 2229 | human |
| ACE2_392 | GUCCAAAACAUGAAUAAUGC | 2030 | ATTACTGAAGAGAATGTCCAAAACATGAATAATGCTGGGGACAAA | 2230 | human |
| ACE2_959 | UUGAUGAAUGCCUAUCCUUC | 2031 | TATGTGAGGGCAAAGTTGATGAATGCCTATCCTTCCTATATCAGT | 2231 | human |
| ACE2_2158 | UGCAUAUGCUAUGAGGCAGU | 2032 | GTTCCGATCATCTGTTGCATATGCTATGAGGCAGTACTTTTTAAA | 2232 | human |
| ACE2_2558 | UAUGCCUCCAUCGAUAUUAG | 2033 | AGTGGAGAAAATCCTTATGCCTCCATCGATATTAGCAAAGGAGAA | 2233 | human |
| ACE2_34 | AGUUGACAUAGAUACUCUUU | 2034 | CTACAGAGGATCAGGAGTTGACATAGATACTCTTTGGATTTCATA | 2234 | human |
| ACE2_166 | UUUAGUCUAGGAAAGUCAU | 2035 | ATCTCATGAGGAGGTTTTAGTCTAGGGAAAGTCATTCAGTGGATG | 2235 | human |
| ACE2_446 | UCCACACUUGCCCAAAUGUA | 2036 | TTTTTAAAGGAACAGTCCACACTTGCCCAAATGTATCCACTACAA | 2236 | human |
| ACE2_1483 | UCUUCUGUCACCCGAUUUUC | 2037 | TTTAAAATCCATTGGTCTTCTGTCACCCGATTTTCAAGAAGACAA | 2237 | human |
| ACE2_2696 | AUAGAAAAUAUAAGAUGAUA | 2038 | TGTTAATTTCATGGTATAGAAAATATAAGATGATAAAGATATCAT | 2238 | human |
| ACE2_1370 | UAUGCUGCACAACCUUUUCU | 2039 | CAGTATGATATGGCATATGCTGCACAACCTTTTCTGCTAAGAAAT | 2239 | human |
| ACE2_2833 | UGGAUUUGACUUCUGUUCUG | 2040 | ATTTATTTCTGTCTCTGGATTTGACTTCTGTTCTGTTTCTTAATA | 2240 | human |
| ACE2_2840 | GACUUCUGUUCUGUUUCUUA | 2041 | TCTGTCTCTGGATTTGACTTCTGTTCTGTTTCTTAATAAGGATTT | 2241 | human |
| ACE2_3087 | CUUUCAUUUAAUCCAUUGUC | 2042 | GCATGCATTAGCTCACTTTCATTTAATCCATTGTCAAGGATGACA | 2242 | human |
| ACE2_3107 | AAGGAUGACAUGCUUUCUUC | 2043 | ATTTAATCCATTGTCAAGGATGACATGCTTTCTTCACAGTAACTC | 2243 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_3233 | AGGUAGAGGACAUUGCUUUU | 2044 | AAGAATCCAGGGAACAGGTAGAGGACATTGCTTTTTCACTTCCAA | 2244 | human |
| ACE2_1160 | UUUGUAUCUGUUGGUCUUCC | 2045 | GAGGCCGAGAAGTTCTTTGTATCTGTTGGTCTTCCTAATATGACT | 2245 | human |
| ACE2_1619 | AUUCCCAAAGACCAGUGGAU | 2046 | GTCTTTAAAGGGGAAATTCCCAAAGACCAGTGGATGAAAAAGTGG | 2246 | human |
| ACE2_2004 | AAGACCAGAACAAGAAUUCU | 2047 | TATTTACCTGGCTGAAAGACCAGAACAAGAATTCTTTTGTGGGAT | 2247 | human |
| ACE2_2107 | UAAAGCAUAUGAAUGGAACG | 2048 | ATCAGCTCTTGGAGATAAAGCATATGAATGGAACGACAATGAAAT | 2248 | human |
| ACE2_2832 | CUGGAUUUGACUUCUGUUCU | 2049 | TATTTATTTCTGTCTCTGGATTTGACTTCTGTTCTGTTTCTTAAT | 2249 | human |
| ACE2_2885 | UAGGGAAAGUGUGUAUUUGG | 2050 | TGTATTAGAGTATATTAGGGAAAGTGTGTATTTGGTCTCACAGGC | 2250 | human |
| ACE2_3072 | GCAUGCAUUAGCUCACUUUC | 2051 | CAAGGATTGAGAATGGCATGCATTAGCTCACTTTCATTTAATCCA | 2251 | human |
| ACE2_1170 | UUGGUCUUCCUAAUAUGACU | 2052 | AGTTCTTTGTATCTGTTGGTCTTCCTAATATGACTCAAGGATTCT | 2252 | human |
| ACE2_1733 | GUUUCUAAUGAUUACUCAUU | 2053 | GCATCTCTGTTCCATGTTTCTAATGATTACTCATTCATTCGATAT | 2253 | human |
| ACE2_1762 | UUACACAAGGACCCUUUACC | 2054 | CTCATTCATTCGATATTACACAAGGACCCTTTACCAATTCCAGTT | 2254 | human |
| ACE2_2240 | UUGAAACCAAGAAUCUCCUU | 2055 | GTGCGAGTGGCTAATTTGAAACCAAGAATCTCCTTTAATTTCTTT | 2255 | human |
| ACE2_2291 | UCUGAUAUCAUUCCUAGAAC | 2056 | GCACCTAAAAATGTGTCTGATATCATTCCTAGAACTGAAGTTGAA | 2256 | human |
| ACE2_3033 | AGUGCCUGGGAACUGGUGUA | 2057 | ATCACTTGTAAGGACAGTGCCTGGGAACTGGTGTAGCTGCAAGGA | 2257 | human |
| ACE2_3064 | UGAGAAUGGCAUGCAUUAGC | 2058 | TGTAGCTGCAAGGATTGAGAATGGCATGCATTAGCTCACTTTCAT | 2258 | human |
| ACE2_3075 | UGCAUUAGCUCACUUUCAUU | 2059 | GGATTGAGAATGGCATGCATTAGCTCACTTTCATTTAATCCATTG | 2259 | human |
| ACE2_3397 | UCACCCUCUGAAGUGGGUAC | 2060 | ATTCCAACTGTATGTTCACCCTCTGAAGTGGGTACCCAGTCTCTT | 2260 | human |
| ACE2_157 | UGAGGAGGUUUUAGUCUAGG | 2061 | AGAGAGAAAATCTCATGAGGAGGTTTTAGTCTAGGGAAAGTCATT | 2261 | human |
| ACE2_1012 | UUUGCUUGGUGAUAUGUGGG | 2062 | ATGCCTCCCTGCTCATTTGCTTGGTGATATGTGGGGTAGATTTTG | 2262 | human |
| ACE2_1344 | UGGGGCAUAUCCAGUAUGAU | 2063 | CAGCTCATCATGAGATGGGGCATATCCAGTATGATATGGCATATG | 2263 | human |
| ACE2_2113 | AUAUGAAUGGAACGACAAUG | 2064 | TCTTGGAGATAAAGCATATGAATGGAACGACAATGAAATGTACCT | 2264 | human |
| ACE2_2687 | UUUCAUGGUAUAGAAAAUAU | 2065 | GTATGTAAATGTTAATTTCATGGTATAGAAAATATAAGATGATAA | 2265 | human |
| ACE2_379 | UACUGAAGAGAAUGUCCAAA | 2066 | TTATAACACCAATATTACTGAAGAGAATGTCCAAAACATGAATAA | 2266 | human |
| ACE2_787 | GGCAAGAGCAAAUCAUUAUG | 2067 | CTTGAAAAAATGAGATGGCAAGAGCAAATCATTATGAGGACTATGG | 2267 | human |
| ACE2_1372 | UGCUGCACAACCUUUUCUGC | 2068 | GTATGATATGGCATATGCTGCACAACCTTTTCTGCTAAGAAATGG | 2268 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_2003 | AAAGACCAGAACAAGAAUUC | 2069 | TTATTTACCTGGCTGAAAGACCAGAACAAGAATTCTTTTGTGGGA | 2269 | human |
| ACE2_2123 | AACGACAAUGAAAUGUACCU | 2070 | AAAGCATATGAATGGAACGACAATGAAATGTACCTGTTCCGATCA | 2270 | human |
| ACE2_2224 | UGUGCGAGUGGCUAAUUUGA | 2071 | TTTTGGGGAGGAGGATGTGCGAGTGGCTAATTTGAAACCAAGAAT | 2271 | human |
| ACE2_2574 | UUAGCAAAGGAGAAAAUAAU | 2072 | ATGCCTCCATCGATATTAGCAAAGGAGAAAATAATCCAGGATTCC | 2272 | human |
| ACE2_3228 | GGAACAGGUAGAGGACAUUG | 2073 | GAGAGAAGAATCCAGGGAACAGGTAGAGGACATTGCTTTTTCACT | 2273 | human |
| ACE2_3424 | CUUAAAUCUUUUGUAUUUGC | 2074 | GTGGGTACCCAGTCTCTTAAATCTTTTGTATTTGCTCACAGTGTT | 2274 | human |
| ACE2_464 | UAUCCACUACAAGAAAUUCA | 2075 | ACACTTGCCCAAATGTATCCACTACAAGAAATTCAGAATCTCACA | 2275 | human |
| ACE2_1079 | AAACCAAACAUAGAUGUUAC | 2076 | GTTCCCTTTGGACAGAAACCAAACATAGATGTTACTGATGCAATG | 2276 | human |
| ACE2_1190 | CAAGGAUUCUGGGAAAAUUC | 2077 | CTTCCTAATATGACTCAAGGATTCTGGGAAAATTCCATGCTAACG | 2277 | human |
| ACE2_2007 | ACCAGAACAAGAAUUCUUUU | 2078 | TTACCTGGCTGAAAGACCAGAACAAGAATTCTTTTGTGGGATGGA | 2278 | human |
| ACE2_2680 | AUGUUAAUUUCAUGGUAUAG | 2079 | TTTTGTTGTATGTAAATGTTAATTTCATGGTATAGAAAATATAAG | 2279 | human |
| ACE2_2718 | GAUAUCAUUAAAUGUCAAAA | 2080 | ATATAAGATGATAAAGATATCATTAAATGTCAAAACTATGACTCT | 2280 | human |
| ACE2_2725 | UUAAAUGUCAAAACUAUGAC | 2081 | ATGATAAAGATATCATTAAATGTCAAAACTATGACTCTGTTCAGA | 2281 | human |
| ACE2_2910 | CAGGCUGUUCAGGGAUAAUC | 2082 | GTGTATTTGGTCTCACAGGCTGTTCAGGGATAATCTAAATGTAAA | 2282 | human |
| ACE2_3103 | UGUCAAGGAUGACAUGCUUU | 2083 | TTTCATTTAATCCATTGTCAAGGATGACATGCTTTCTTCACAGTA | 2283 | human |
| ACE2_3149 | AUGGUGAUUUGCCUACAGUG | 2084 | CTCAGTTCAAGTACTATGGTGATTTGCCTACAGTGATGTTTGGAA | 2284 | human |
| ACE2_1039 | UUGGACAAAUCUGUACUCUU | 2085 | TATGTGGGGTAGATTTTGGACAAATCTGTACTCTTTGACAGTTCC | 2285 | human |
| ACE2_1792 | UCAAGAAGCACUUUGUCAAG | 2086 | TTACCAATTCCAGTTTCAAGAAGCACTTTGTCAAGCAGCTAAACA | 2286 | human |
| ACE2_2258 | UUUAAUUUCUUUGUCACUGC | 2087 | AAACCAAGAATCTCCTTTAATTTCTTTGTCACTGCACCTAAAAAT | 2287 | human |
| ACE2_3056 | GCAAGGAUUGAGAAUGGCAU | 2088 | GGAACTGGTGTAGCTGCAAGGATTGAGAATGGCATGCATTAGCTC | 2288 | human |
| ACE2_3173 | UUGGAAUCGAUCAUGCUUUC | 2089 | TGCCTACAGTGATGTTTGGAATCGATCATGCTTTCTTCAAGGTGA | 2289 | human |
| ACE2_152 | UCUCAUGAGGAGGUUUUAGU | 2090 | TGATAAGAGAGAAAATCTCATGAGGAGGTTTTAGTCTAGGGAAAG | 2290 | human |
| ACE2_750 | CAUUAUAUGAAGAGUAUGUG | 2091 | GCAAGCAGCTGAGGCCATTATATGAAGAGTATGTGGTCTTGAAAA | 2291 | human |
| ACE2_1197 | UCUGGGAAAAUUCCAUGCUA | 2092 | ATATGACTCAAGGATTCTGGGAAAATTCCATGCTAACGGACCCAG | 2292 | human |

TABLE 11D-continued

Host target ACE2-20 nucleotide targets and 45 nucleotide gene target regions

| SEQUENCE ID | 20 nt Sequence | SEQ ID NO: | 45 nt Gene Region | SEQ ID NO: | Species |
|---|---|---|---|---|---|
| ACE2_ 1283 | UUCAGGAUCCUUA UGUGCAC | 2093 | CTGGGGAAGGGCGACTTCAGGA TCCTTATGTGCACAAAGGTGACA | 2293 | human |
| ACE2_ 1825 | AGGCCCUCUGCAC AAAUGUG | 2094 | AGCAGCTAAACATGAAGGCCCT CTGCACAAATGTGACATCTCAAA | 2294 | human |

TABLE 12A

Host targets screened-TMPRSS-20 nucleotide targets and 45 nucleotide gene target regions

| Sequence ID | Sequence | SEQ ID NO: | Gene Region | SEQ ID NO: | Species |
|---|---|---|---|---|---|
| TMPRSS 2_3153 | UGUGAAAAUGA AUAUCAUGC | 2295 | ACTGTAAAGTTCAATTGTGAAAAT GAATATCATGCAAATAAATTA | 2331 | human |
| TMPRSS 2_2577 | ACCUUCAUUUA ACUCUUUGA | 2296 | GTCTCCAAGTAGTCCACCTTCATT TAACTCTTTGAAACTGTATCA | 2332 | human |
| TMPRSS 2_1626 | UCGUCCUUGACG UCGUUUUA | 2297 | TAATCCACATGGTCTTCGTCCTTG ACGTCGTTTTACAAGAAAACA | 2333 | human |
| TMPRSS 2_1101 | GGAGCCGGAUA CCAAGUAGA | 2298 | TCTTTCATGTTCTATGGAGCCGGA TACCAAGTAGAAAAAGTGATT | 2334 | human |
| TMPRSS 2_810 | UACCACAGUGA UGCCUGUUC | 2299 | ATCTATAAAAAACTGTACCACAGT GATGCCTGTTCTTCAAAAGCA | 2335 | human |
| TMPRSS 2_3167 | UCAUGCAAAUA AAUUAUGCA | 2300 | TTGTGAAAATGAATATCATGCAAA TAAATTATGCAATTTTTTTTT | 2336 | human |
| TMPRSS 2_593 | UUGAAACUGUA UCAUCUUUG | 2301 | CCTTCATTTAACTCTTTGAAACTGT ATCATCTTTGCCAAGTAAGA | 2337 | human |
| TMPRSS 2_780 | GCCGGCAAUGUC GAUAUCUA | 2302 | AAACTGAACACAAGTGCCGGCAA TGTCGATATCTATAAAAAACTG | 2338 | human |
| TMPRSS 2_3054 | UGUAAUGGUGA AAACGUCUU | 2303 | CATCCTAAAAGGTGTTGTAATGGT GAAAACGTCTTCCTTCTTTAT | 2339 | human |
| TMPRSS 2_2625 | GGUGGCCUAUU UCAGCUGCU | 2304 | TTGCCAAGTAAGAGTGGTGGCCTA TTTCAGCTGCTTTGACAAAAT | 2340 | human |
| TMPRSS 2_2899 | ACAGCUAGGAC UUAACCUUG | 2305 | GAAATGAATGATTCTACAGCTAGG ACTTAACCTTGAAATGGAAAG | 2341 | human |
| TMPRSS 2_2485 | CAGUUUAAGGU ACACUGUUU | 2306 | GAAATCAAGGATGCTCAGTTTAAG GTACACTGTTTCCATGTTATG | 2342 | human |
| TMPRSS 2_886 | GCCGCCAGAGCA GGAUUGUG | 2307 | TCAACTTGAACTCAAGCCGCCAGA GCAGGATTGTGGGCGGCGAGA | 2343 | human |
| TMPRSS 2_1398 | CCAGCCAUGAUC UGUGCCGG | 2308 | GACAACCTGATCACACCAGCCATG ATCTGTGCCGGCTTCCTGCAG | 2344 | human |
| TMPRSS 2_984 | UCCAUCAUCACC CCCGAGUG | 2309 | CACGTGTGCGGAGGCTCCATCATC ACCCCCGAGTGGATCGTGACA | 2345 | human |
| TMPRSS 2_1404 | AUGAUCUGUGC CGGCUUCCU | 2310 | CTGATCACACCAGCCATGATCTGT GCCGGCTTCCTGCAGGGGAAC | 2346 | human |
| TMPRSS 2_138 | GCUUUGAACUC AGGGUCACC | 2311 | GATAACAGCAAGATGGCTTTGAA CTCAGGGTCACCACCAGCTATT | 2347 | human |
| TMPRSS 2_1297 | AGGAGAAAGGG AAGACCUCA | 2312 | GGTGGGGGGCCACCGAGGAGAAA GGGAAGACCTCAGAAGTGCTGA | 2348 | human |
| TMPRSS 2_937 | CCUGGCAGGUCA GCCUGCAC | 2313 | TCCCGGGGGCCTGGCCCTGGCAGG TCAGCCTGCACGTCCAGAACG | 2349 | human |

TABLE 12A-continued

Host targets screened-TMPRSS-20 nucleotide targets and 45 nucleotide gene target regions

| Sequence ID | Sequence | SEQ ID NO: | Gene Region | SEQ ID NO: | Species |
|---|---|---|---|---|---|
| TMPRSS 2_1296 | GAGGAGAAAGG GAAGACCUC | 2314 | GGGTGGGGGGCCACCGAGGAGAA AGGGAAGACCTCAGAAGTGCTG | 2350 | human |
| TMPRSS 2_942 | CAGGUCAGCCUG CACGUCCA | 2315 | GGGGCCTGGCCCTGGCAGGTCAG CCTGCACGTCCAGAACGTCCAC | 2351 | human |
| TMPRSS 2_1053 | CAUUGGACGGC AUUUGCGGG | 2316 | CTTAACAATCCATGGCATTGGACG GCATTTGCGGGGATTTTGAGA | 2352 | human |
| TMPRSS 2_979 | GAGGCUCCAUCA UCACCCCC | 2317 | ACGTCCACGTGTGCGGAGGCTCCA TCATCACCCCCGAGTGGATCG | 2353 | human |
| TMPRSS 2_1403 | CAUGAUCUGUG CCGGCUUCC | 2318 | CCTGATCACACCAGCCATGATCTG TGCCGGCTTCCTGCAGGGGAA | 2354 | human |
| TMPRSS 2_1397 | ACCAGCCAUGAU CUGUGCCG | 2319 | TGACAACCTGATCACACCAGCCAT GATCTGTGCCGGCTTCCTGCA | 2355 | human |
| TMPRSS 2_2779 | AAAGCCAUGCCA GAAUUACC | 962 | TGGGTTTATACCAGGAAAGCCATG CCAGAATTACCAAATATGAAG | 1162 | mouse |
| TMPRSS 2_1730 | UUUGUCUUCAA CAACCUUCU | 2320 | TTGTCCCAGACTTCCTTTGTCTTCA ACAACCTTCTGCAAGAAAAC | 2356 | mouse |
| TMPRSS 2_1785 | UGCACAAUGUA CCUUUUGAG | 2321 | AATTTTAACTTCCTGTGCACAATG TACCTTTTGAGATGATTCGAA | 2357 | mouse |
| TMPRSS 2_552 | UGGGACAGCAA CUGUUCUAC | 2322 | TTGCTTTGGAGGTTCTGGGACAGC AACTGTTCTACGTCTGAGATG | 2358 | mouse |
| TMPRSS 2_3120 | UUCCACUGUGA AAUAUAUGA | 2323 | TTCTGAGCTGTGAGATTCCACTGT GAAATATATGAATAAAGTATA | 2359 | mouse |
| TMPRSS 2_873 | UCAGGCAACGU UGACCUCUA | 2324 | AAGCTGAATGTGAGCTCAGGCAA CGTTGACCTCTATAAAAAACTC | 2360 | mouse |
| TMPRSS 2_1647 | GGGAACGUGAC GGUAUUUAC | 2325 | AGACCTGGAGTATACGGGAACGT GACGGTATTTACAGATTGGATC | 2361 | mouse |
| TMPRSS 2_1747 | UCUGCAAGAAA ACCAAGGGC | 2326 | TGTCTTCAACAACCTTCTGCAAGA AAACCAAGGGCCTGAATTTTA | 2362 | mouse |
| TMPRSS 2_1286 | UUUGGCUUUUA AUGAUCUAG | 2327 | GAAGCTGCAGACACCTTTGGCTTT TAATGATCTAGTGAAGCCAGT | 2363 | mouse |
| TMPRSS 2_88 | UAAGCGAGAAC UGGAGUAGG | 2328 | CCGCCTCCGGAGATTTAAGCGAGA ACTGGAGTAGGTCGTGTACTT | 2364 | mouse |
| TMPRSS 2_2243 | GUUGACAUGAC GGCCCUUUC | 2329 | CTTGCTCTCCTGCATGTTGACATG ACGGCCCTTTCCAAGGGTGAT | 2365 | mouse |
| TMPRSS 2_2539 | UGCUUCUGGGU UGUGUUUCU | 2330 | TGATTTCAGTCACCTTGCTTCTGG GTTGTGTTTCTTCTCTTACTA | 2366 | mouse |

TABLE 12B

Host targets screened - IL-6-20 nucleotide targets and 45 nucleotide gene target regions

| Sequence ID | Sequence | SEQ ID NO: | Gene Region | SEQ ID NO: | Species |
|---|---|---|---|---|---|
| IL6_ 933 | UUGGAAAGUGUA GGCUUACC | 2367 | GAGCCAGATCATTTCTTGGAAAG TGTAGGCTTACCTCAAATAAAT | 2389 | human |
| IL6_ 930 | CUUGAAAUGUUA UAUGUUAU | 2368 | TTTTATGAAGTGTCACTTGAAAT GTTATATGTTATAGTTTTGAAA | 2390 | mouse |

TABLE 12B-continued

Host targets screened - IL-6-20 nucleotide targets and 45 nucleotide gene target regions

| Sequence ID | Sequence | SEQ ID NO: | Gene Region | SEQ ID NO: | Species |
|---|---|---|---|---|---|
| IL6_896 | UAUGAUUGAUAUUUAUUAUU | 2369 | AACTTTAAGTTAATTTATGATTGATATTTATTATTTTTATGAAGT | 2391 | mouse |
| IL6_870 | UUAAAUAAGUAAACUUUAAG | 2370 | TAATTTATTGATAATTTAAATAAGTAAACTTTAAGTTAATTTATG | 2392 | mouse |
| IL6_835 | GACACUAUUUUAAUUAUUUU | 2371 | CAATATGAATGTTGGGACACTATTTTAATTATTTTTAATTTATTG | 2393 | mouse |
| IL6_834 | GGACACUAUUUUAAUUAUUU | 2372 | ACAATATGAATGTTGGGACACTATTTTAATTATTTTTAATTTATT | 2394 | mouse |
| IL6_832 | UGGGACACUAUUUUAAUUAU | 2373 | TGACAATATGAATGTTGGGACACTATTTTAATTATTTTTAATTTA | 2395 | mouse |
| IL6_741 | GUGGACAUUCCUCACUGUGG | 2374 | TAAGCATATCAGTTTGTGGACATTCCTCACTGTGGTCAGAAAATA | 2396 | mouse |
| IL6_669 | UGAAGAAUUUCUAAAAGUCA | 2375 | CATCTTGAAATCACTTGAAGAATTTCTAAAAGTCACTTTGAGATC | 2397 | mouse |
| IL6_635 | AUGGGCACCUCAGAUUGUUG | 2376 | TTCGGCAAATGTAGCATGGGCACCTCAGATTGTTGTTGTTAATGG | 2398 | human |
| IL6_621 | UCGGCAAAUGUAGCAUGGGC | 2377 | CAGCCTGAGGGCTCTTCGGCAAATGTAGCATGGGCACCTCAGATT | 2399 | human |
| IL6_621 | UCGGCAAAUGUAGCAUGGGC | 2377 | CAGCCTGAGGGCTCTTCGGCAAATGTAGCATGGGCACCTCAGATT | 2399 | human |
| IL6_386 | GAUAUAAUCAGGAAAUUUGC | 2378 | GATGCTACCAAACTGGATATAATCAGGAAATTTGCCTATTGAAAA | 2400 | mouse |
| IL6_360 | UGAGGUAUACCUAGAGUACC | 2379 | TGGTCTTTTGGAGTTTGAGGTATACCTAGAGTACCTCCAGAACAG | 2401 | human |
| IL6_330 | GGUGAAAAUCAUCACUGGUC | 2380 | TGAGGAGACTTGCCTGGTGAAAATCATCACTGGTCTTTTGGAGTT | 2402 | human |
| IL6_330 | GGUGAAAAUCAUCACUGGUC | 2380 | TGAGGAGACTTGCCTGGTGAAAATCATCACTGGTCTTTTGGAGTT | 2402 | human |
| IL6_323 | CUUGCCUGGUGAAAAUCAUC | 2381 | GATTCAATGAGGAGACTTGCCTGGTGAAAATCATCACTGGTCTTT | 2403 | human |
| IL6_323 | CUUGCCUGGUGAAAAUCAUC | 2381 | GATTCAATGAGGAGACTTGCCTGGTGAAAATCATCACTGGTCTTT | 2403 | human |
| IL6_284 | UGUGCAAUGGCAAUUCUGAU | 2382 | AAATGAGAAAAGAGTTGTGCAATGGCAATTCTGATTGTATGAACA | 2404 | mouse |
| IL6_263 | UGAACCUUCCAAAGAUGGCU | 2383 | TGGCAGAAAACAACCTGAACCTTCCAAAGATGGCTGAAAAAGATG | 2405 | human |
| IL6_246 | ACUGGCAGAAAACAACCUGA | 2384 | AAGCAGCAAAGAGGCACTGGCAGAAAACAACCTGAACCTTCCAAA | 2406 | human |
| IL6_246 | ACUGGCAGAAAACAACCUGA | 2384 | AAGCAGCAAAGAGGCACTGGCAGAAAACAACCTGAACCTTCCAAA | 2406 | human |
| IL6_229 | GAAAGCAGCAAAGAGGCACU | 2385 | AAGAGTAACATGTGTGAAAGCAGCAAAGAGGCACTGGCAGAAAAC | 2407 | human |
| IL6_229 | GAAAGCAGCAAAGAGGCACU | 2385 | AAGAGTAACATGTGTGAAAGCAGCAAAGAGGCACTGGCAGAAAAC | 2407 | human |
| IL6_187 | UCAGCCCUGAGAAAGGAGAC | 2386 | ATCCTCGACGGCATCTCAGCCCTGAGAAAGGAGACATGTAACAAG | 2408 | human |
| IL6_1045 | UGCUAAUUUAAAUAUGUUUU | 2387 | TTTACCTCAATGAATTGCTAATTTAAATATGTTTTTAAAGAAATC | 2409 | mouse |

TABLE 12B-continued

Host targets screened - IL-6-20 nucleotide targets and 45 nucleotide gene target regions

| Sequence ID | Sequence | SEQ ID NO: | Gene Region | SEQ ID NO: | Species |
|---|---|---|---|---|---|
| IL6_1015 | CUUGGAAUGUAUAAGUUUAC | 2388 | CTAGCCAGATGGTTTCTTGGAATGTATAAGTTTACCTCAATGAAT | 2410 | mouse |

TABLE 12C

Host targets screened - ACE2_-20 nucleotide targets and 45 nucleotide gene target regions

| Sequence ID | Sequence | SEQ ID NO: | Gene Region | SEQ ID NO: | Species |
|---|---|---|---|---|---|
| ACE2_119 | CAACCCAAGUUCAAAGGCUG | 2411 | GTTTTGAATAGCGCCCAACCCAAGTTCAAAGGCTGATAAGAGAGA | 2435 | human |
| ACE2_336 | UCUAUCAAAGUUCACUUGCU | 2412 | AAGCCGAAGACCTGTTCTATCAAAGTTCACTTGCTTCTTGGAATT | 2436 | human |
| ACE2_349 | ACUUGCUUCUUGGAAUUAUA | 2413 | GTTCTATCAAAGTTCACTTGCTTCTTGGAATTATAACACCAATAT | 2437 | human |
| ACE2_358 | UUGGAAUUAUAACACCAAUA | 2414 | AAGTTCACTTGCTTCTTGGAATTATAACACCAATATTACTGAAGA | 2438 | human |
| ACE2_626 | AAUCCACAAGAAUGCUUAUU | 2415 | GTTTGTAACCCAGATAATCCACAAGAATGCTTATTACTTGAACCA | 2439 | human |
| ACE2_784 | GAUGGCAAGAGCAAAUCAUU | 2416 | GGTCTTGAAAAATGAGATGGCAAGAGCAAATCATTATGAGGACTA | 2440 | human |
| ACE2_908 | GAAGAGAUUAAACCAUUAUA | 2417 | GTGGAACATACCTTTGAAGAGATTAAACCATTATATGAACATCTT | 2441 | human |
| ACE2_1034 | AGAUUUUGGACAAAUCUGUA | 2418 | GGTGATATGTGGGGTAGATTTTGGACAAATCTGTACTCTTTGACA | 2442 | human |
| ACE2_1071 | UUGGACAGAAACCAAACAUA | 2419 | CTTTGACAGTTCCCTTTGGACAGAAACCAAACATAGATGTTACTG | 2443 | human |
| ACE2_1178 | CCUAAUAUGACUCAAGGAUU | 2420 | GTATCTGTTGGTCTTCCTAATATGACTCAAGGATTCTGGGAAAAT | 2444 | human |
| ACE2_1387 | UCUGCUAAGAAAUGGAGCUA | 2421 | TGCTGCACAACCTTTTCTGCTAAGAAATGGAGCTAATGAAGGATT | 2445 | human |
| ACE2_1430 | GGGGAAAUCAUGUCACUUUC | 2422 | TTCCATGAAGCTGTTGGGGAAATCATGTCACTTTCTGCAGCCACA | 2446 | human |
| ACE2_1513 | UGAAACAGAAAUAAACUUCC | 2423 | TTTTCAAGAAGACAATGAAACAGAAATAAACTTCCTGCTCAAACA | 2447 | human |
| ACE2_1548 | UCACGAUUGUUGGGACUCUG | 2424 | TGCTCAAACAAGCACTCACGATTGTTGGGACTCTGCCATTTACTT | 2448 | human |
| ACE2_1591 | GUGGAGGUGGAUGGUCUUUA | 2425 | TTACATGTTAGAGAAGTGGAGGTGGATGGTCTTTAAAGGGGAAAT | 2449 | human |
| ACE2_1737 | CUAAUGAUUACUCAUUCAUU | 2426 | CTCTGTTCCATGTTTCTAATGATTACTCATTCATTCGATATTACA | 2450 | human |
| ACE2_1755 | UUCGAUAUUACACAAGGACC | 2427 | ATGATTACTCATTCATTCGATATTACACAAGGACCCTTTACCAAT | 2451 | human |
| ACE2_1775 | CUUUACCAAUUCCAGUUUCA | 2428 | TATTACACAAGGACCCTTTACCAATTCCAGTTTCAAGAAGCACTT | 2452 | human |
| ACE2_1832 | CUGCACAAAUGUGACAUCUC | 2429 | AAACATGAAGGCCCTCTGCACAAATGTGACATCTCAAACTCTACA | 2453 | human |

TABLE 12C-continued

| Host targets screened - ACE2_-20 nucleotide targets and 45 nucleotide gene target regions | | | | | |
|---|---|---|---|---|---|
| Sequence ID | Sequence | SEQ ID NO: | Gene Region | SEQ ID NO: | Species |
| ACE2_ 2697 | UAGAAAAUAUAA GAUGAUAA | 2430 | GTTAATTTCATGGTATAGAAAATA TAAGATGATAAAGATATCATT | 2454 | human |
| ACE2_ 2777 | AUGGCCAAGGAG AGAGCAUC | 2431 | TTGTCCAAAGACAACATGGCCAAG GAGAGAGCATCTTCATTGACA | 2455 | human |
| ACE2_ 2800 | AUUGACAUUGCU UUCAGUAU | 2432 | GGAGAGAGCATCTTCATTGACATT GCTTTCAGTATTTATTTCTGT | 2456 | human |
| ACE2_ 2812 | UUCAGUAUUUAU UUCUGUCU | 2433 | TTCATTGACATTGCTTTCAGTATTT ATTTCTGTCTCTGGATTTGA | 2457 | human |
| ACE2_ 3172 | UUUGGAAUCGAU CAUGCUUU | 2434 | TTGCCTACAGTGATGTTTGGAATC GATCATGCTTTCTTCAAGGTG | 2458 | human |

TABLE 12D

| Host targets screened - FURIN-20 nucleotide targets and 45 nucleotide gene target regions | | | | | |
|---|---|---|---|---|---|
| Sequence ID | Sequence | SEQ ID NO: | Gene Region | SEQ ID NO: | Species |
| FURIN_ 443 | UCAACCUGGG CCAGAUCUUC | 2459 | GGAAGCATGGGTTCCTCAACCTGG GCCAGATCTTCGGGGACTATT | 2483 | human |
| FURIN_ 470 | AUUACCACUU CUGGCAUCGA | 2460 | AGATCTTCGGGGACTATTACCACTT CTGGCATCGAGGAGTGACGA | 2484 | human |
| FURIN_ 769 | GCAGGCAAUU AUGAUCCUGG | 2461 | AACCACCCGGACTTGGCAGGCAAT TATGATCCTGGGGCCAGTTTT | 2485 | human |
| FURIN_ 796 | UUUGAUGUCA AUGACCAGGA | 2462 | GATCCTGGGGCCAGTTTTGATGTCA ATGACCAGGACCCTGACCCC | 2486 | human |
| FURIN_ 1426 | GAGGCCAAUA AGAACCUCAC | 2463 | ATTGCTCTCACCCTGGAGGCCAAT AAGAACCTCACATGGCGGGAC | 2487 | human |
| FURIN_ 1876 | UUCAUGACAA CUCAUUCCUG | 2464 | TTTAATGACTGGGCCTTCATGACAA CTCATTCCTGGGATGAGGAT | 2488 | human |
| FURIN_ 1959 | UGGGACGCUG ACCAAGUUCA | 2465 | CGAAGCCAACAACTATGGGACGCT GACCAAGTTCACCCTCGTACT | 2489 | human |
| FURIN_ 1967 | UGACCAAGUU CACCCUCGUA | 2466 | ACAACTATGGGACGCTGACCAAGT TCACCCTCGTACTCTATGGCA | 2490 | human |
| FURIN_ 2711 | UUUUAAUUCA CCAAAGUAUU | 2467 | CCCTCCTTGGGCACTTTTTAATTCA CCAAAGTATTTTTTTATCTT | 2491 | human |
| FURIN_ 2712 | UUUAAUUCAC CAAAGUAUUU | 2468 | CCTCCTTGGGCACTTTTTAATTCAC CAAAGTATTTTTTTATCTTG | 2492 | human |
| FURIN_ 3524 | UGUUUGAGGA UAUAUUUUCA | 2469 | GGGGATCTCAGGGGCTGTTTGAGG ATATATTTTCACTTTGTGATT | 2493 | human |
| FURIN_ 3526 | UUUGAGGAUA UAUUUUCACU | 2470 | GGATCTCAGGGGCTGTTTGAGGAT ATATTTTCACTTTGTGATTAT | 2494 | human |
| FURIN_ 3528 | UGAGGAUAUA UUUUCACUUU | 2471 | ATCTCAGGGGCTGTTTGAGGATAT ATTTTCACTTTGTGATTATTT | 2495 | human |
| FURIN_ 3539 | UUUCACUUUG UGAUUAUUUC | 2472 | TGTTTGAGGATATATTTTCACTTTG TGATTATTTCACTTTAGATG | 2496 | human |
| FURIN_ 3553 | UAUUUCACUU UAGAUGCUGA | 2473 | TTTTCACTTTGTGATTATTTCACTTT AGATGCTGATGATTTGTTT | 2497 | human |

TABLE 12D-continued

Host targets screened - FURIN-20 nucleotide targets and 45 nucleotide gene target regions

| Sequence ID | Sequence | SEQ ID NO: | Gene Region | SEQ ID NO: | Species |
|---|---|---|---|---|---|
| FURIN_ 3562 | UUAGAUGCUG AUGAUUUGUU | 2474 | TGTGATTATTTCACTTTAGATGCTG ATGATTTGTTTTTGTATTTT | 2498 | human |
| FURIN_ 4101 | CUGGUUUUGU AAGAUGCUGG | 2475 | TCGTGGCCAGCCCGGCTGGTTTTGT AAGATGCTGGGTTGGTGCAC | 2499 | human |
| FURIN_ 4118 | UGGGUUGGUG CACAGUGAUU | 2476 | GGTTTTGTAAGATGCTGGGTTGGTG CACAGTGATTTTTTTCTTGT | 2500 | human |
| FURIN_ 4143 | CUUGUAAUUU AAACAGGCCC | 2477 | CACAGTGATTTTTTTCTTGTAATTT AAACAGGCCCAGCATTGCTG | 2501 | human |
| FURIN_ 4151 | UUAAACAGGC CCAGCAUUGC | 2478 | TTTTTTTCTTGTAATTTAAACAGGC CCAGCATTGCTGGTTCTATT | 2502 | human |
| FURIN_ 4160 | CCCAGCAUUG CUGGUUCUAU | 2479 | TGTAATTTAAACAGGCCCAGCATT GCTGGTTCTATTTAATGGACA | 2503 | human |
| FURIN_ 4190 | UGAGAUAAUG UUAGAGGUUU | 2480 | TCTATTTAATGGACATGAGATAAT GTTAGAGGTTTTAAAGTGATT | 2504 | human |
| FURIN_ 4191 | GAGAUAAUGU UAGAGGUUUU | 2481 | CTATTTAATGGACATGAGATAATG TTAGAGGTTTTAAAGTGATTA | 2505 | human |
| FURIN_ 4200 | UUAGAGGUUU UAAAGUGAUU | 2482 | GGACATGAGATAATGTTAGAGGTT TTAAAGTGATTAAACGTGCAG | 2506 | human |

TABLE 12E

Host targets screened - IL-6R-20 nucleotide targets and 45 nucleotide gene target regions

| Sequence ID | Sequence | SEQ ID NO: | Gene Region | SEQ ID NO: | Species |
|---|---|---|---|---|---|
| IL6R_ 38 | UGAGUCAUGUG CGAGUGGGA | 2507 | GACCGTCCGCCGCTCTGAGTCAT GTGCGAGTGGGAAGTCGCACTG | 2529 | human |
| IL6R_ 437 | AGAGCCGGAAG ACAAUGCCA | 2508 | GACCTGCCCGGGGGTAGAGCCG GAAGACAATGCCACTGTTCACTG | 2530 | human |
| IL6R_ 666 | CUCAGCAAUGU UGUUUGUGA | 2509 | TTCCGGAAGAGCCCCCTCAGCAA TGTTGTTTGTGAGTGGGGTCCT | 2531 | human |
| IL6R_ 728 | GCUCUUGGUGA GGAAGUUUC | 2510 | GACGACAAAGGCTGTGCTCTTGG TGAGGAAGTTTCAGAACAGTCC | 2532 | human |
| IL6R_ 876 | AGUGUCGGGAG CAAGUUCAG | 2511 | ATGTGCGTCGCCAGTAGTGTCGG GAGCAAGTTCAGCAAAACTCAA | 2533 | human |
| IL6R_ 891 | UUCAGCAAAAC UCAAACCUU | 2512 | AGTGTCGGGAGCAAGTTCAGCA AAACTCAAACCTTTCAGGGTTGT | 2534 | human |
| IL6R_ 902 | UCAAACCUUUCA GGGUUGUG | 2513 | CAAGTTCAGCAAAACTCAAACCT TTCAGGGTTGTGGAATCTTGCA | 2535 | human |
| IL6R_ 910 | UUCAGGGUUGU GGAAUCUUG | 2514 | GCAAAACTCAAACCTTTCAGGGT TGTGGAATCTTGCAGCCTGATC | 2536 | human |
| IL6R_ 1011 | CACUCCUGGAAC UCAUCUUU | 2515 | ACCTGGCAAGACCCCCACTCCTG GAACTCATCTTTCTACAGACTA | 2537 | human |
| IL6R_ 1012 | ACUCCUGGAACU CAUCUUUC | 2516 | CCTGGCAAGACCCCCACTCCTGG AACTCATCTTTCTACAGACTAC | 2538 | human |
| IL6R_ 1042 | GGUUUGAGCUC AGAUAUCGG | 2517 | CTTTCTACAGACTACGGTTTGAG CTCAGATATCGGGCTGAACGGT | 2539 | human |

TABLE 12E-continued

Host targets screened - IL-6R-20 nucleotide targets and 45 nucleotide gene target regions

| Sequence ID | Sequence | SEQ ID NO: | Gene Region | SEQ ID NO: | Species |
|---|---|---|---|---|---|
| IL6R_1051 | UCAGAUAUCGGGCUGAACGG | 2518 | GACTACGGTTTGAGCTCAGATATCGGGCTGAACGGTCAAAGACAT | 2540 | human |
| IL6R_1063 | CUGAACGGUCAAAGACAUUC | 2519 | AGCTCAGATATCGGGCTGAACGGTCAAAGACATTCACAACATGGA | 2541 | human |
| IL6R_1073 | AAAGACAUUCACAACAUGGA | 2520 | TCGGGCTGAACGGTCAAAGACATTCACAACATGGATGGTCAAGGA | 2542 | human |
| IL6R_1105 | UCCAGCAUCACUGUGUCAUC | 2521 | GGATGGTCAAGGACCTCCAGCATCACTGTGTCATCCACGACGCCT | 2543 | human |
| IL6R_1229 | UUGGACAGAAGGUCUCCUGA | 2522 | GGCCATGGGCACGCCTTGGACAGAAGGTCTCCTGAGAGGGTCACT | 2544 | human |
| IL6R_1244 | CCUGAGAGGGUCACUGCAAA | 2523 | TTGGACAGAAGGTCTCCTGAGAGGGTCACTGCAAAAGAGAATCTC | 2545 | human |
| IL6R_1255 | CACUGCAAAAGAGAAUCUCG | 2524 | GTCTCCTGAGAGGGTCACTGCAAAAGAGAATCTCGTTCCAACCTC | 2546 | human |
| IL6R_1258 | UGCAAAAGAGAAUCUCGUUC | 2525 | TCCTGAGAGGGTCACTGCAAAAGAGAATCTCGTTCCAACCTCCCT | 2547 | human |
| IL6R_1350 | GUGGACCACGCCUAAACUAA | 2526 | CCTGTCAATCTGAACGTGGACCACGCCTAAACTAATTTTTGACTG | 2548 | human |
| IL6R_1351 | UGGACCACGCCUAAACUAAU | 2527 | CTGTCAATCTGAACGTGGACCACGCCTAAACTAATTTTTGACTGC | 2549 | human |
| IL6R_1381 | UGUGCCAGCUGGAGUGAUGA | 2528 | CTAATTTTTGACTGCTGTGCCAGCTGGAGTGATGATAGGCTCACT | 2550 | human |

Figure 12A:
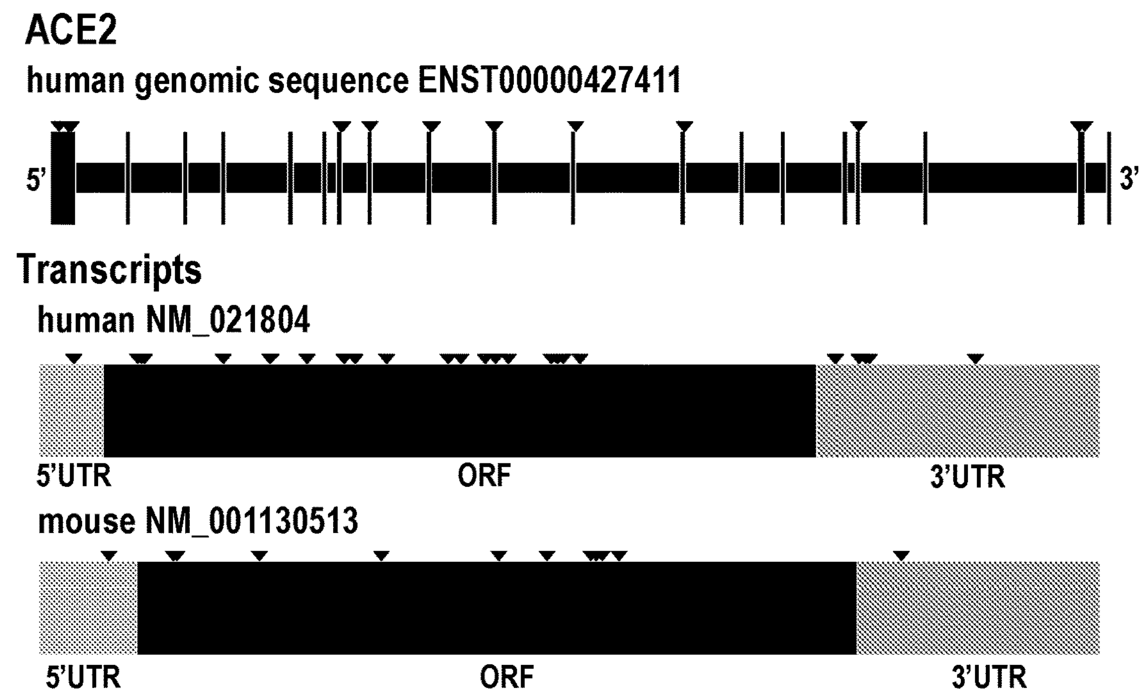
FIG. 12A-12B depict design of siRNAs targeting ACE2 (FIG. 12A) and FURIN (FIG. 12B).
Figure 12B:
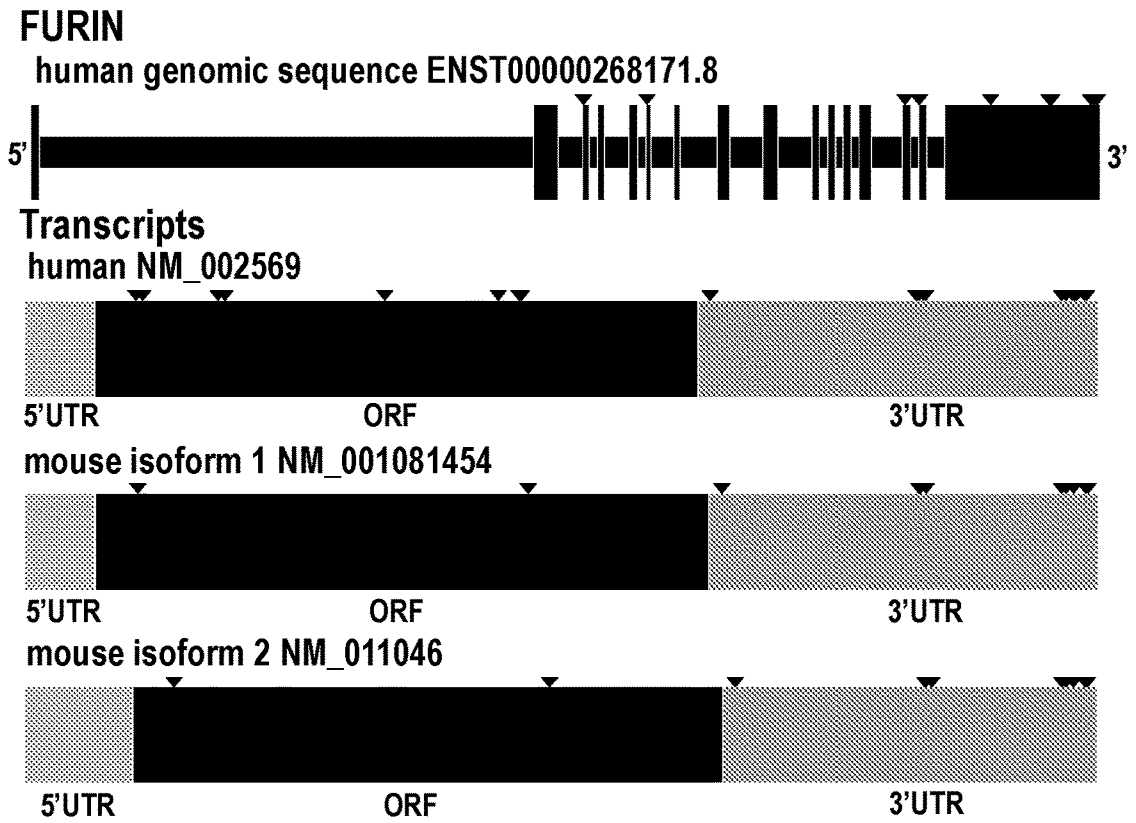

Using a novel algorithm, a panel of siRNAs targeting various regions of ACE2 and FURIN mRNA were designed (FIG. 12). For ASOs, a second step of selection involved testing the secondary structure (accessibility) of the target using the online algorithm lncASO. The sequences of ASOs targeting ACE2 and FURIN are summarized in Table 13A and Table 131B, respectively.

TABLE 13A

ASOs targeting host factors-ACE2 target

| Oligo ID | Sequence (anti sense) | SEQ ID NO: | homology Human | homology Mouse | homology Monkey |
|---|---|---|---|---|---|
| ACE2_171 | GCAAGTGAACTTTGAT | 2551 | Y | Y | Y |
| ACE2_250 | AAAGGCAGACCATTTG | 2552 | Y | Y | N |
| ACE2_567 | GGCCTCAGCTGCTTGC | 2553 | Y | Y | Y |
| ACE2_694 | GCCGCGGCTGTAGTCA | 2554 | Y | N | N |
| ACE2_702 | ATCAACTGGCCGCGGC | 2555 | Y | N | N |
| ACE2_851 | TACCCCACATATCACC | 2556 | Y | Y | Y |
| ACE2_938 | AGGCCTGGTCCACCAT | 2557 | Y | N | N |
| ACE2_1326 | TCTTCTTGAAAATCGG | 2558 | Y | Y | N |
| ACE2_1425 | AAGACCATCCACCTCC | 2559 | Y | Y | Y |
| ACE2_1533 | GGGTCACAGTATGTTT | 2560 | Y | Y | Y |
| ACE2_1666 | GATGTCACATTTGTGC | 2561 | Y | Y | Y |
| ACE2_2806 | GAGTTCACGGAGGCCC | 2562 | Y | N | N |

TABLE 13B

ASOs targeting host factors-FURIN target

| Oligo ID | Sequence (anti sense) | SEQ ID NO: | homology Human | homology Mouse | homology Monkey |
|---|---|---|---|---|---|
| FURIN_176 | CCGGGGCTGACTGGTG | 2563 | Y | Y | Y |
| FURIN_450 | AAGATCTGGCCCAGGT | 2564 | Y | Y | N |
| FURIN_963 | GTCACCTCGCCATCCA | 2565 | Y | Y | Y |
| FURIN_1044 | TCATCCTCGGGGCCCC | 2566 | Y | N | Y |
| FURIN_1184 | CGCAGTTGCAGCTGTC | 2567 | Y | N | Y |
| FURIN_1229 | TGGCGCTGCTGATGGA | 2568 | Y | Y | Y |
| FURIN_1400 | TGATGCCGGCTGCTAA | 2569 | Y | N | Y |
| FURIN_1610 | GCTGGGGGGCCACTGT | 2570 | Y | Y | N |
| FURIN_2213 | CACATGAGGCGTGGCA | 2571 | Y | Y | Y |
| FURIN_2217 | GTGGCACATGAGGCGT | 2572 | Y | Y | Y |
| FURIN_2649 | AGGGCGCTCTGGTCTT | 2573 | Y | Y | Y |
| FURIN_2653 | TCAGAGGGCGCTCTGG | 2574 | Y | N | Y |

Figure 13A:
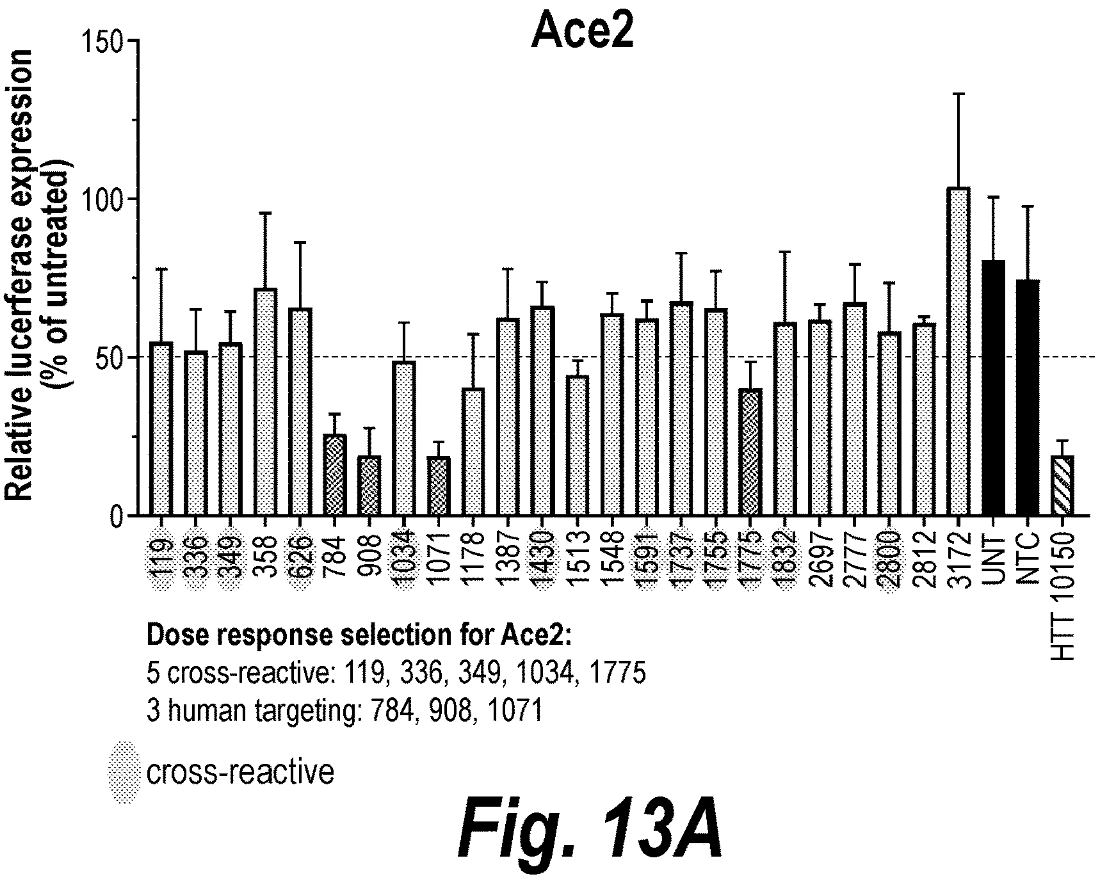
FIG. 13A-13B depict the identification of siRNA hits for ACE2 (FIG. 13A) and FURIN (FIG. 13B). siRNAs were tested in human Hacat cells and silencing was assessed using the QuantiGene assay and confirmed using psicheck reporter system. Concentration: 1.5 μM; Time point: 72 hours.
Figure 13B:
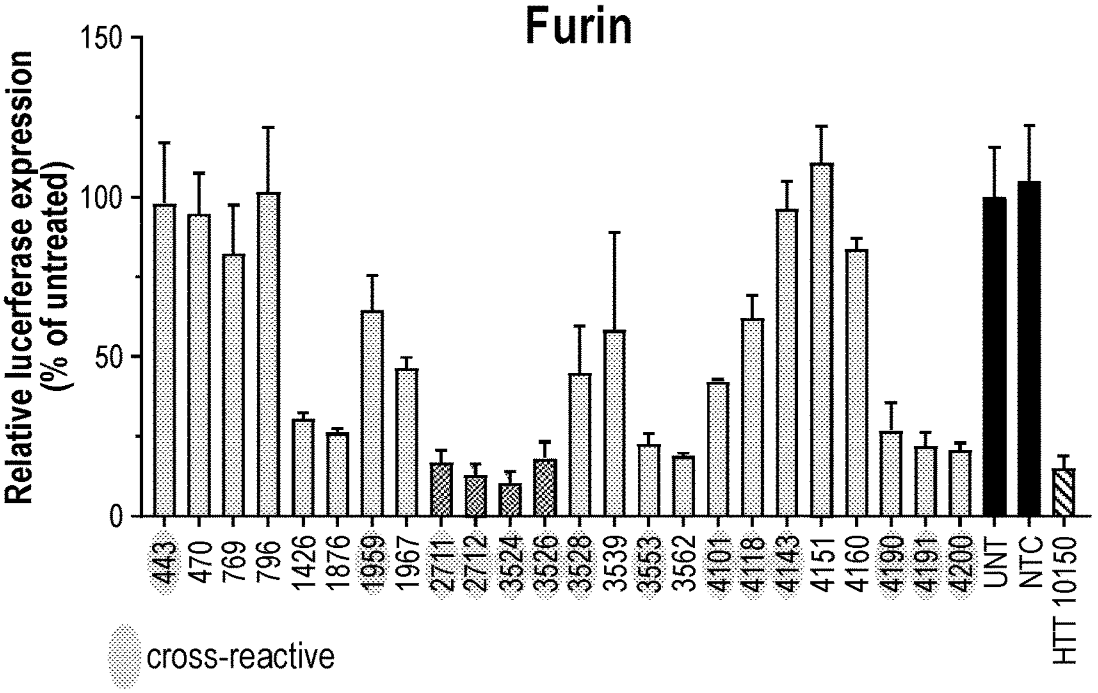
Figure 14A:
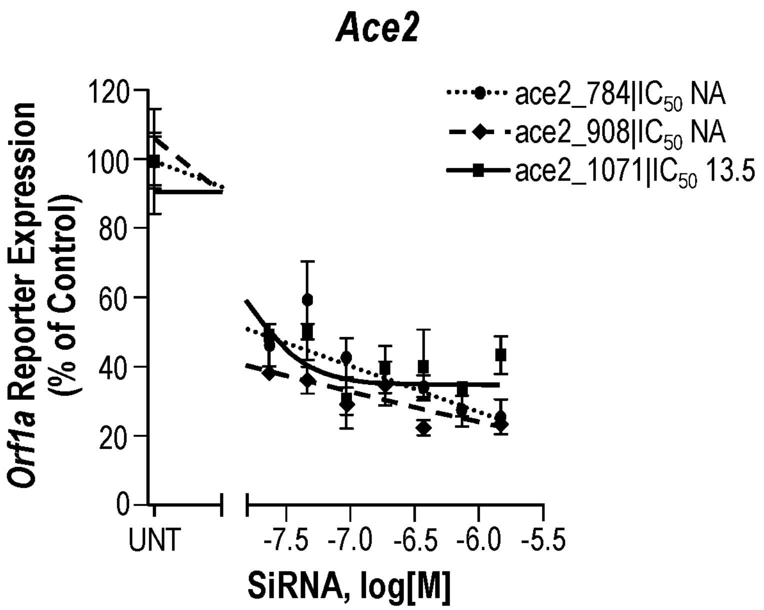
FIG. 14A-14B depict validation and determination of $IC_{50}$ values for siRNAs targeting ACE2 (FIG. 14A) and FURIN (FIG. 14B). siRNAs were tested in Hela cells and silencing was assessed using the psi-check reporter system. Concentration: Top=1.5 μM; Time point: 72 hours.
Figure 14B:
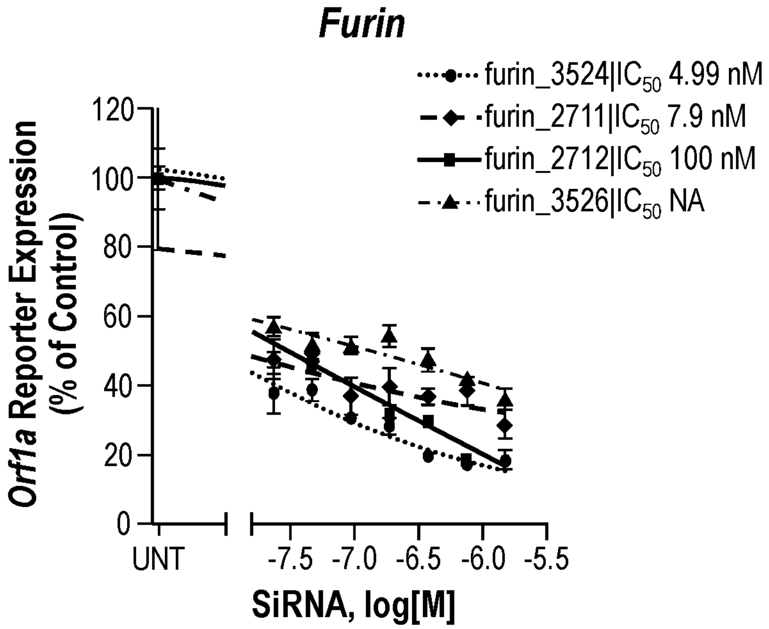
Figures 15A, 15B, 15C, 15D:
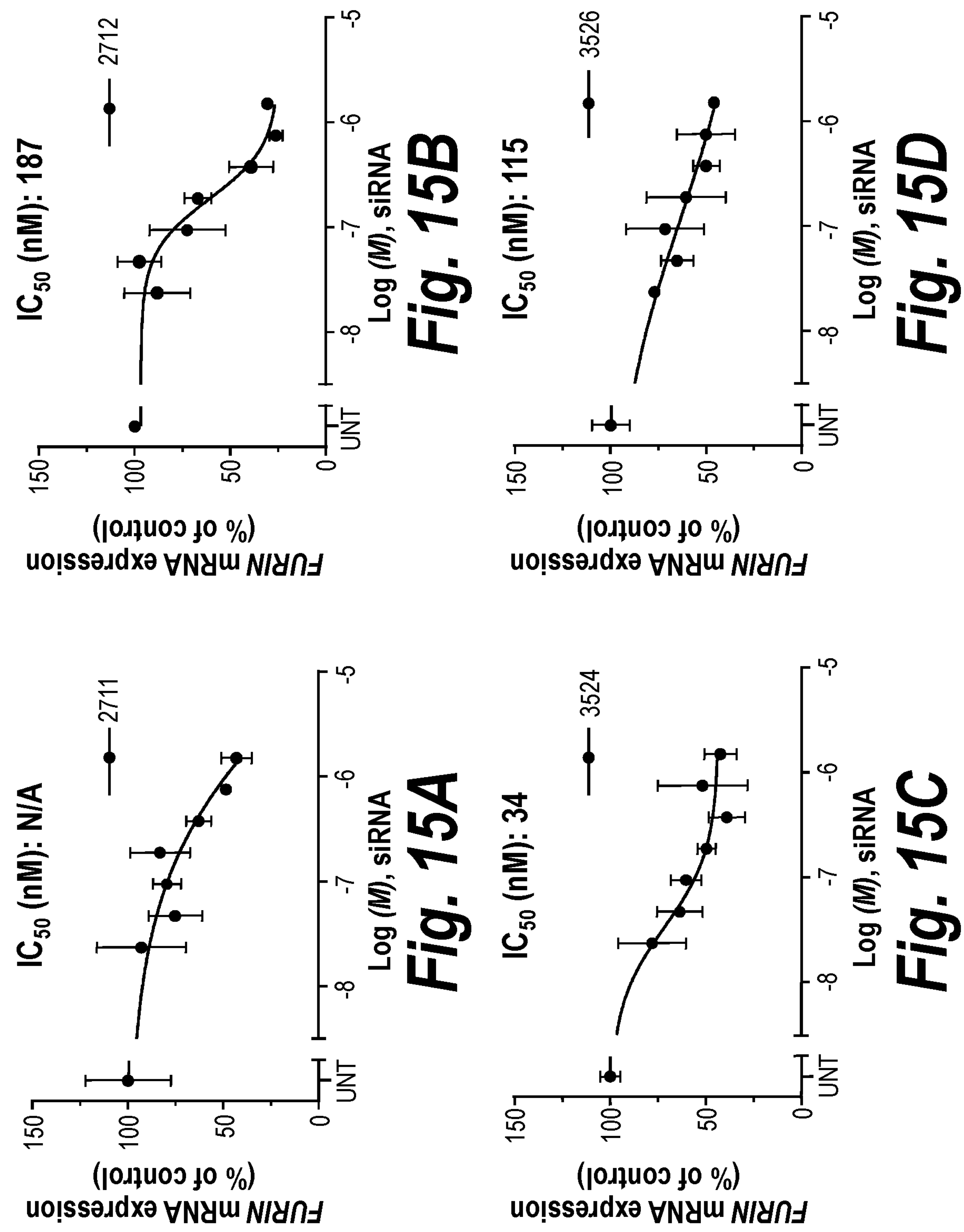
FIG. 15A-15D depict validation and determination of $IC_{50}$ values for siRNAs targeting FURIN.

SiRNAs targeting ACE2 and FURIN, two endogenous genes necessary for viral entry and spread were tested for silencing efficacy. FIG. 13A-13B depict the identification of siRNA hits for ACE2 and FURIN, respectively. For each target, at least 3 siRNAs were identified that reduced target mRNA expression below 75% compared to untreated controls. siRNAs were tested in human Hacat cells and silencing was assessed using the QuantiGene assay and confirmed using psicheck reporter system. FIG. 14A-14B depict validation and determination of $IC_{50}$ values for siRNAs targeting ACE2 (FIG. 14A) and FURIN (FIG. 14B). SiRNAs targeting ACE2 and FURIN were tested for silencing efficacy in 8-point dose response studies. Each siRNA showed potent and efficacious target silencing with $IC_{50}$ values in the low nanomolar range. FIG. 15A-15D depict validation and determination of $IC_{50}$ values for four selected siRNAs, tested for silencing efficacy in 8-point dose response studies. Each siRNA showed potent and efficacious target silencing with $IC_{50}$ values in the low nanomolar range. siRNAs were tested in HaCat cells and silencing was assessed using QuantiGene.

Figure 16A:
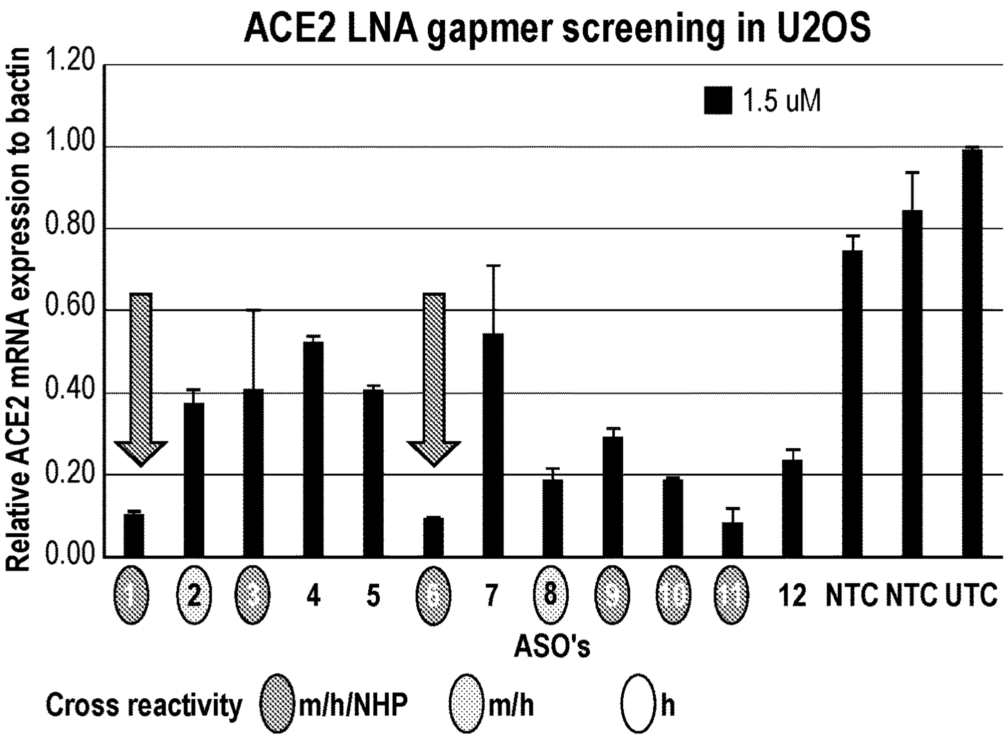
FIG. 16A-16B depict the identification of ASO hits for ACE2 and FURIN. Twelve LNA gapmers targeting ACE2 (FIG. 16A) and FURIN (FIG. 16B) were tested for silencing efficacy. ASOs were tested in human U2OS cells and silencing was assessed using QRT-PCR assay. Concentration: 1.5 μM; Time point: 72 hours.
Figure 16B:
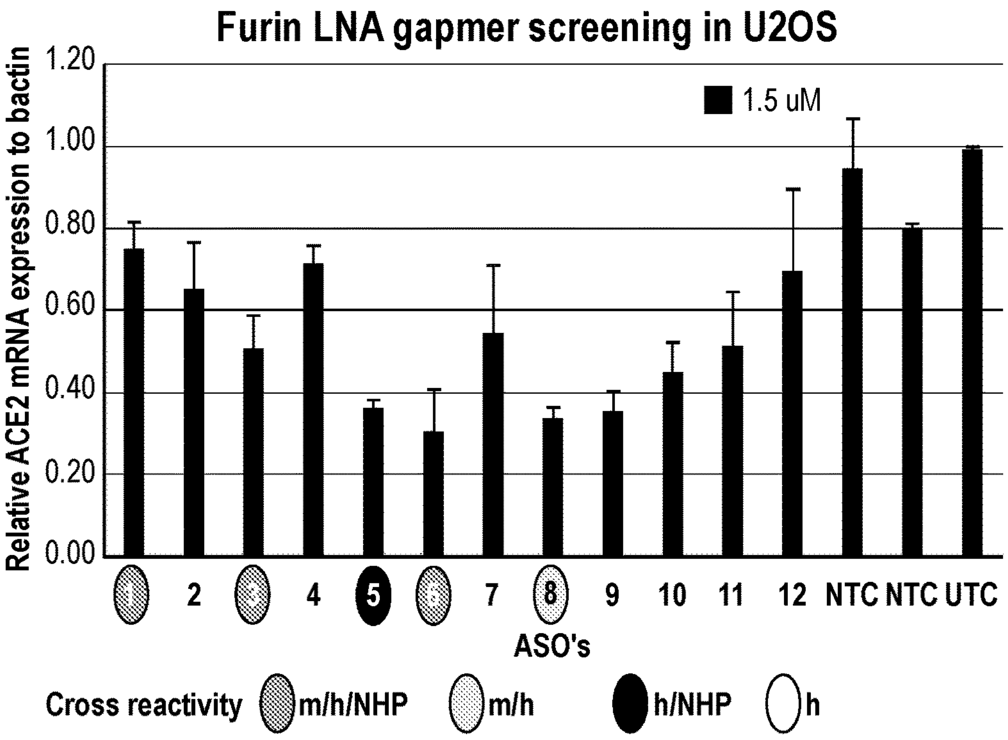
Figure 17A:
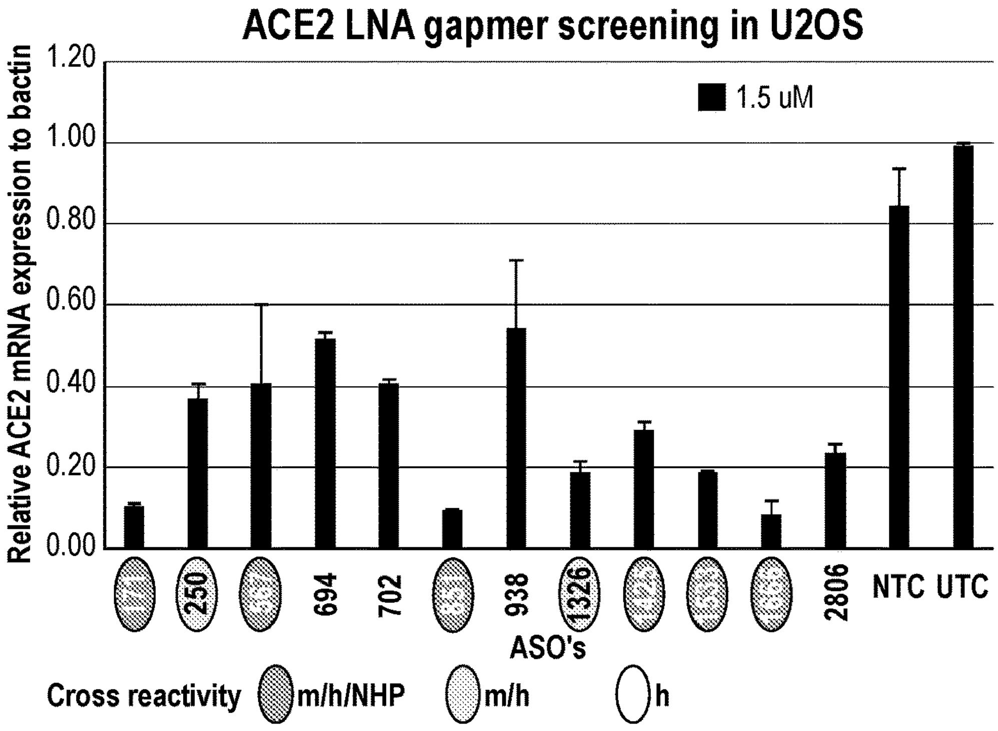
FIG. 17A-17B depict the identification of ASO hits for ACE2 and FURIN. Twelve LNA gapmers targeting ACE2 (FIG. 17A) and FURIN (FIG. 17B), were tested for silencing efficacy. ASOs were tested in human U2OS cells and silencing was assessed using QRT-PCR assay. Concentration: 1.5 μM; Time point: 72 hours.
Figure 17B:
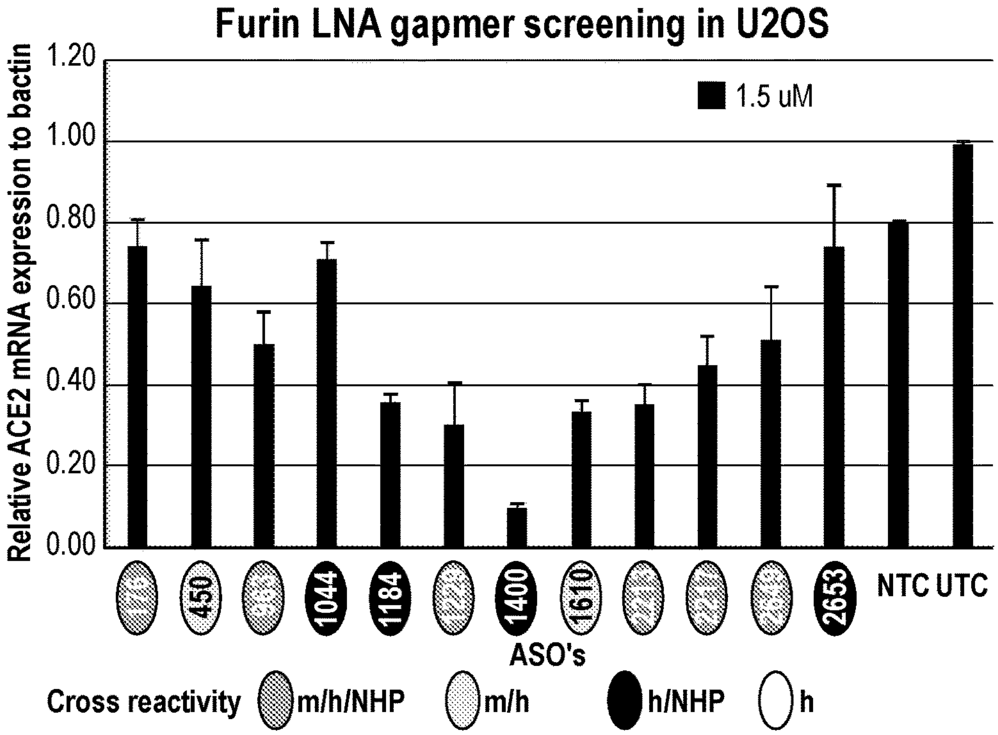
Figure 18A:
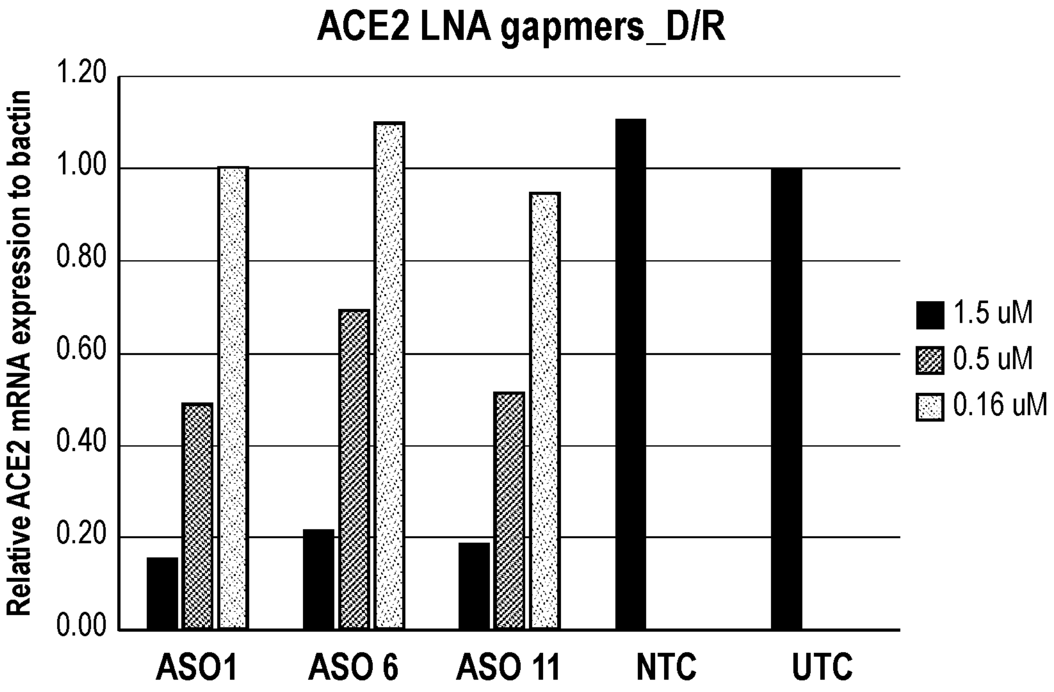
FIG. 18A-18B depict validation and determination of $IC_{50}$ values for ASOs targeting ACE2 (FIG. 18A) and FURIN (FIG. 18B). Concentration: Top=1.5 μM; Time point: 5 days.
Figure 18B:
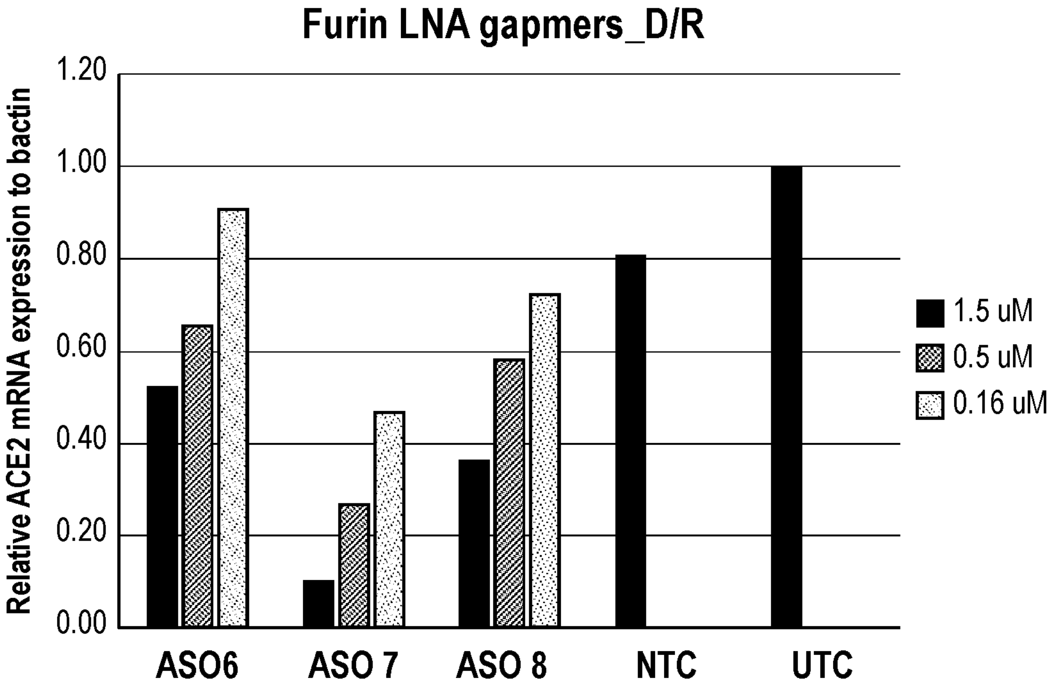
Figure 19A:
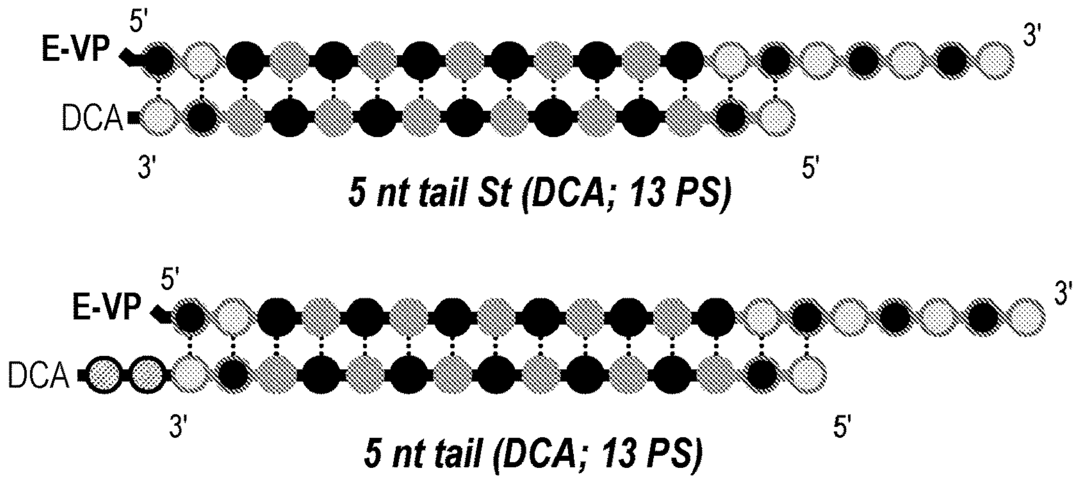
FIG. 19A-19F show that the presence of a two-thymidine linker between the conjugate and the siRNA does not impact siRNA tissue distribution profile. The siRNA structural configurations studied to evaluate the impact of the nature of the linker on distribution is shown in FIG. 19A, FIG. 19C, and FIG. 19E. The corresponding bar graphs for siRNA accumulation in the various tissues are shown in FIG. 19B, FIG. 19D, and FIG. 19F, respectively. Shown are siRNA strand accumulation of DCA-conjugated siRNA in liver, kidney, spleen, lung, heart, muscle and fat 1-week after a single SC injection with 20 mg/kg (n=5-6 mice per group±SD), measured by PNA hybridization assay.
Figure 19B:
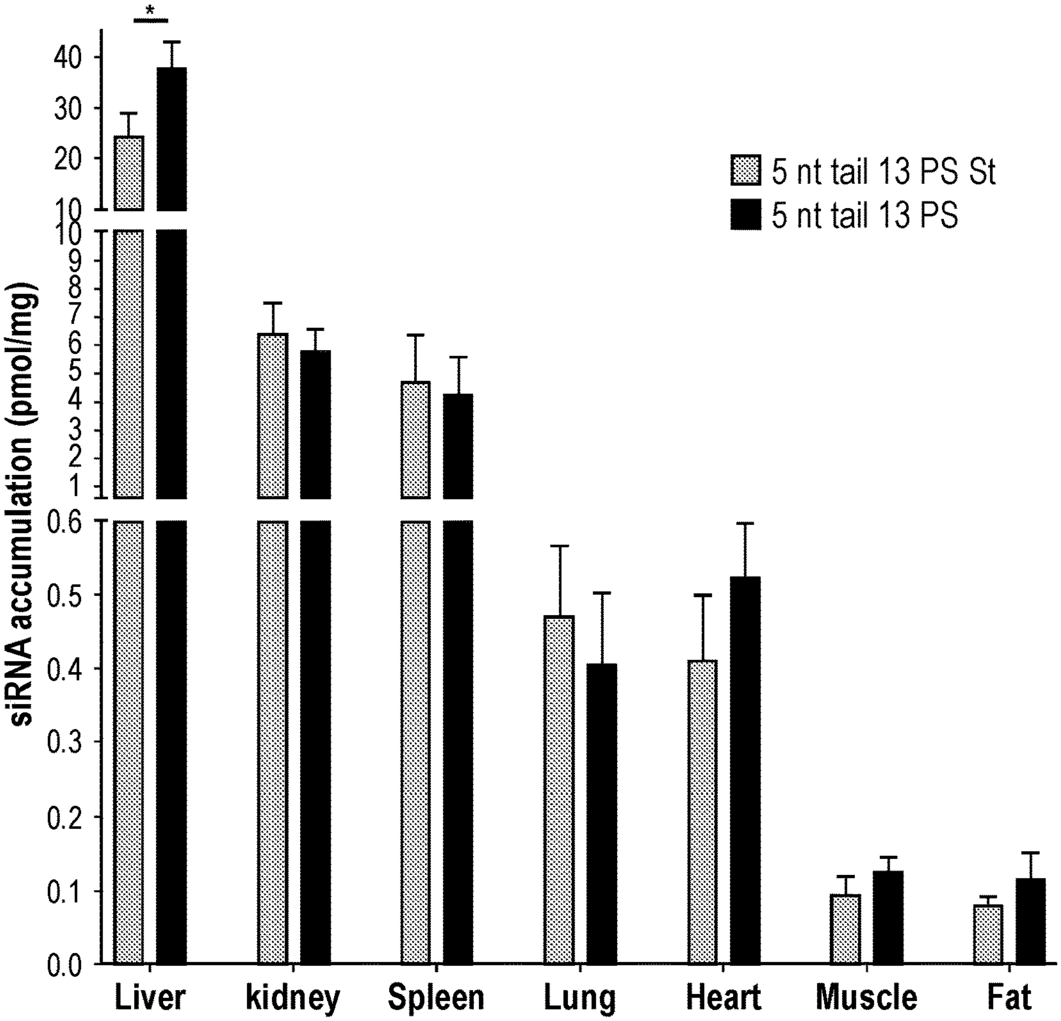
Figure 19C:
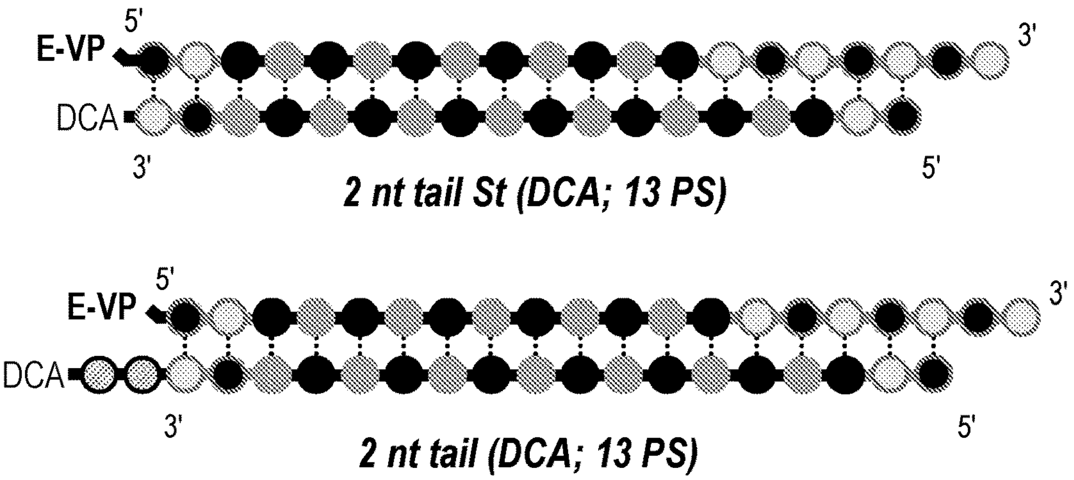
Figure 19D:
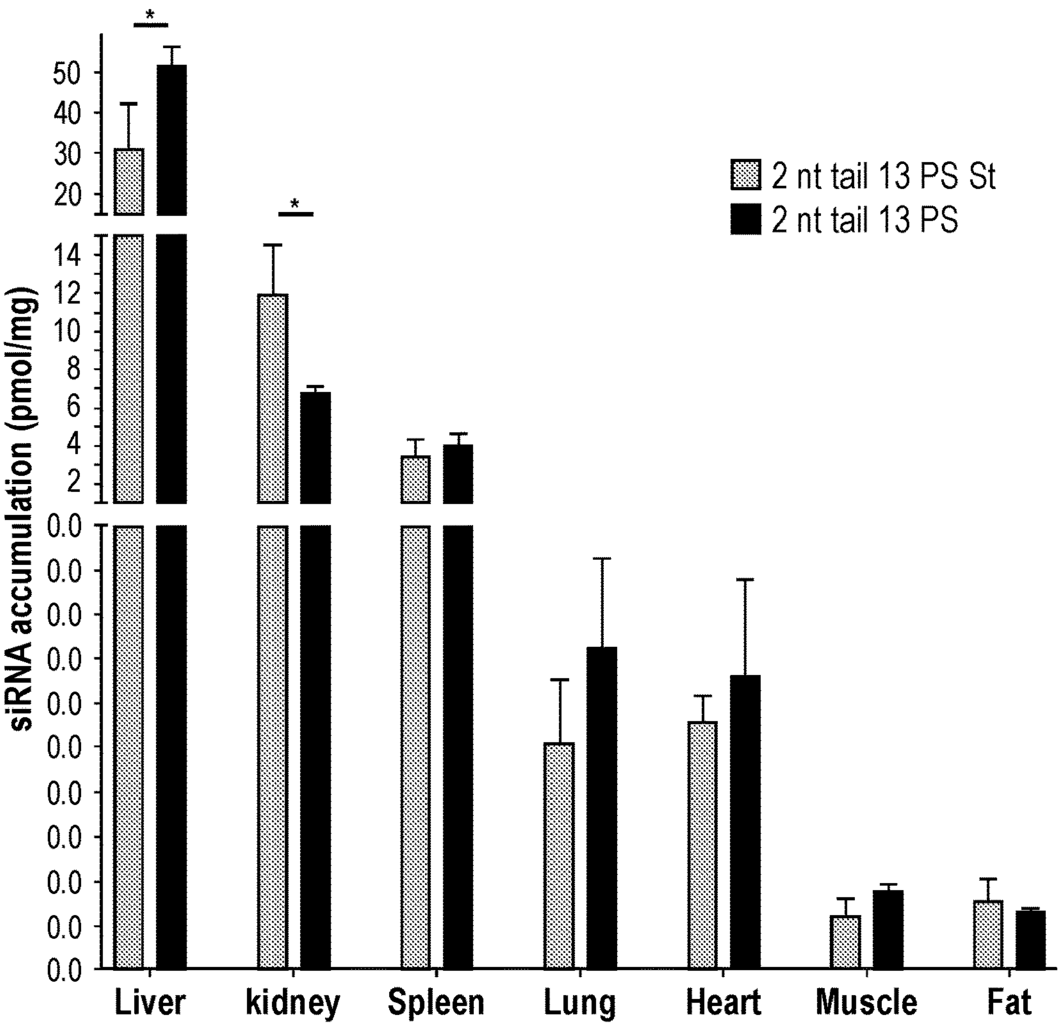
Figure 19E:
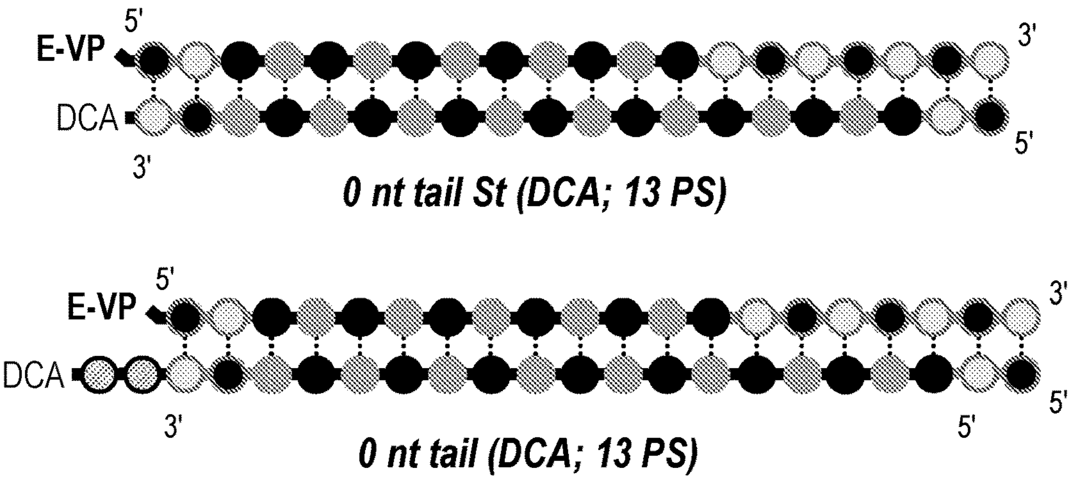
Figure 19F:
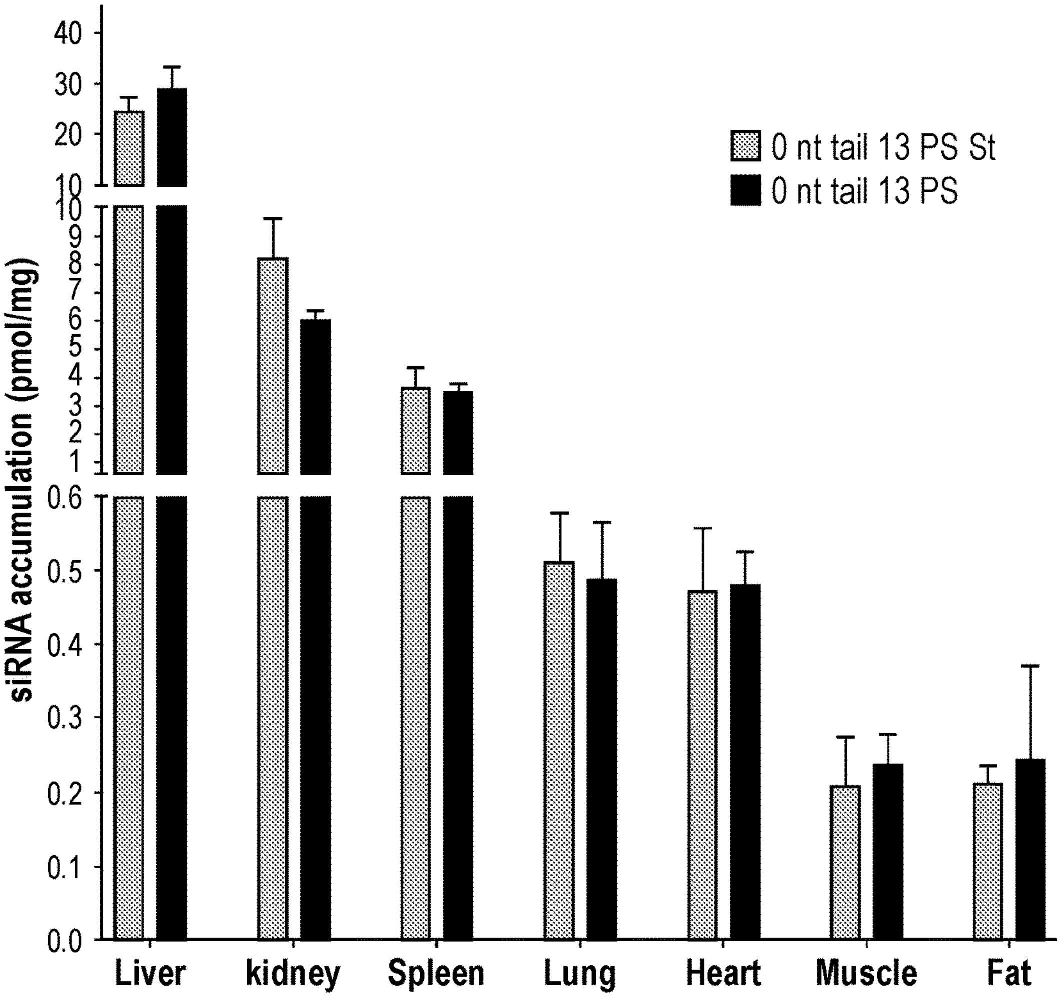

The identification of ASO hits for ACE2 and FURIN are shown in FIG. 16. Twelve LNA gapmers targeting ACE2 (FIG. 16A) and FURIN (FIG. 16B), two endogenous genes necessary for viral entry and spread, were tested for silencing efficacy. For each target, at least 3 ASOs were identified that reduced target mRNA expression below 75% compared to untreated controls. ASOs were tested in human U2OS cells and silencing was assessed using QRT-PCR assay. FIG. 17A-17B depict the identification of ASO hits for ACE2 and FURIN. Twelve LNA gapmers targeting ACE2 (FIG. 17A) and FURIN (FIG. 17B), two endogenous genes necessary for viral entry and spread for silencing efficacy. For each target, we identified at least 3 ASOs that reduced target mRNA expression below 75% compared to untreated controls. ASOs were tested in human U2OS cells and silencing was assessed using QRT-PCR assay. Concentration: 1.5 μM; Time point: 72 hours. FIG. 18 depict validation and determination of $IC_{50}$ values for ASOs targeting ACE2 (FIG. 18A) and FURIN (FIG. 18B). ASOs targeting ACE2 and FURIN were tested for silencing efficacy in 3-point dose response and gene expression was measured using QRT-PCR. Concentration: Top=1.5 μM; Time point: 5 days.

Example 3. Delivery to the Lungs

In the present invention, methodologies are disclosed for a uniform and efficient delivery of fully stabilized siRNAs to the lung. Lung delivery was achieved after intratracheal administration (IT). This route might have significant advantages when using siRNA cocktails for prophylaxis and in the field as it is minimally invasive. Efficient delivery is observed to several cell types, including endothelial, epithelial, fibroblasts and immune cells in the lungs. Hydrophobically modified siRNAs often induce strong immune responses after local delivery and thus can't be widely used. Surprisingly therapeutic distribution of Phosphorothioate enriched, fully modified siRNAs was observed after intratracheal administration. Delivery to relevant cell types was observed after administration of both monovalent and divalent compounds, with increased delivery after administration of divalent versus monovalent entities.

The presence of a two-thymidine linker between the conjugate and the siRNA does not impact siRNA tissue distribution profile (FIG. 19). Three different siRNA structural configurations were studied to evaluate the impact of the nature of the linker on distribution of DCA-conjugated siRNA in liver, kidney, spleen, lung, heart, muscle and fat 1-week after a single SC injection with 20 mg/kg (n=5-6 mice per group ±SD), as measured by a PNA hybridization assay. Data show efficient delivery of all three siRNA configurations to the lung.

Figure 20A:
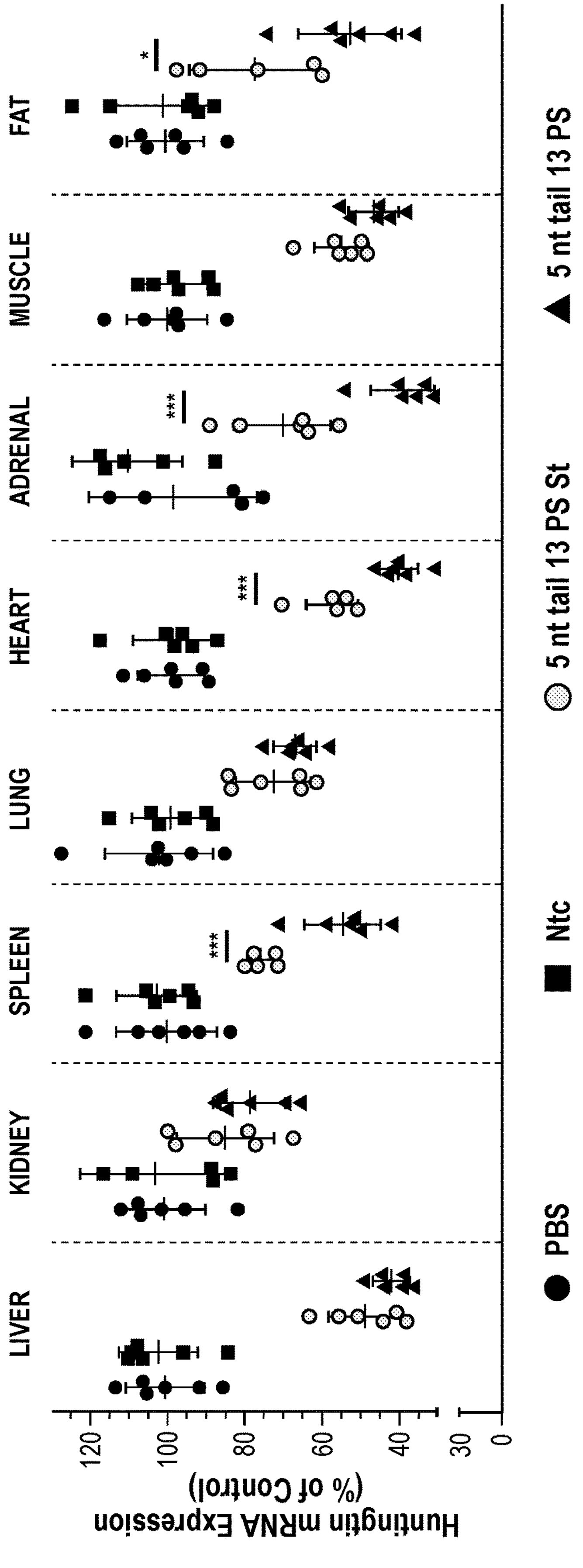
FIG. 20A-20B show that the presence of a two-thymidine linker increases DCA-conjugated siRNA silencing in multiple tissues.
Figure 20B:
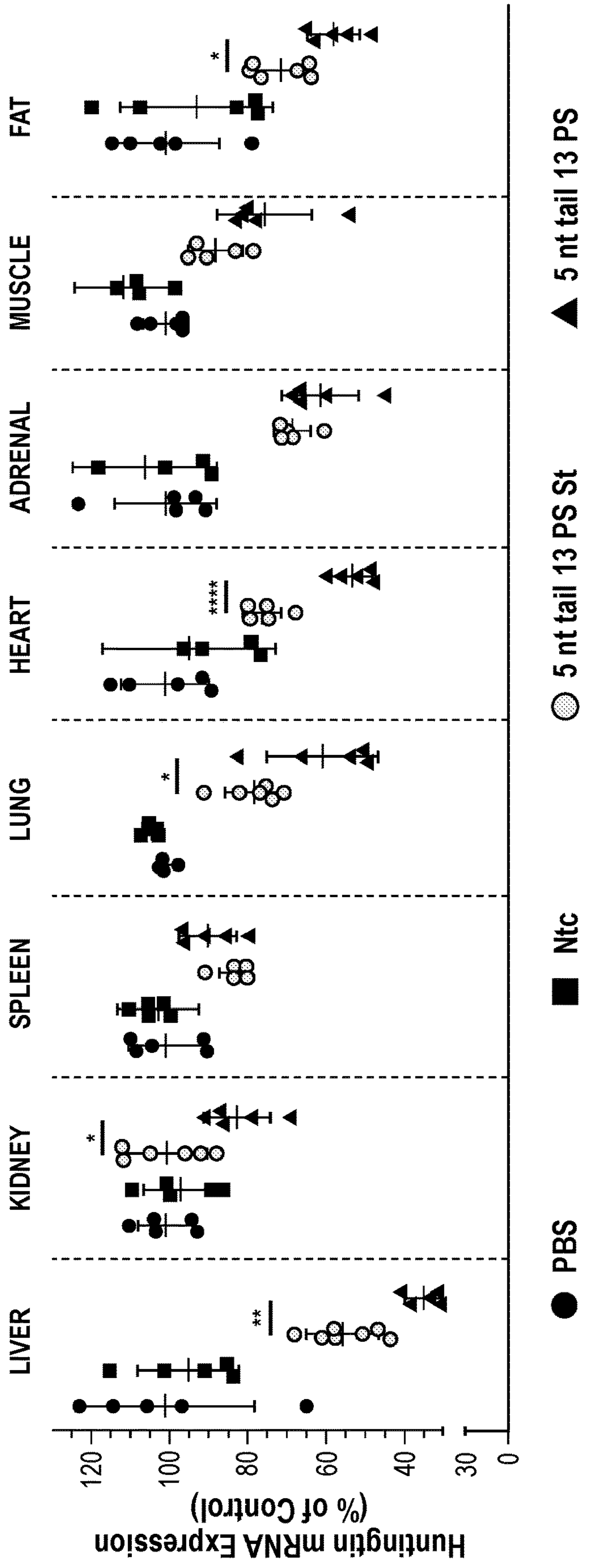

The presence of a two-thymidine linker was found to increase DCA-conjugated siRNA silencing in multiple tissues, as measured by huntingtin and cyclophilin B mRNA expression (FIG. 20). Six mice per group were injected with siRNA by SC injection (FVB/N mice); 20 mg/kg; and tissues were collected one week after injection. The mRNA levels were measured using QuantiGene® (Affymetrix), and normalized to a housekeeping gene, Hprt (Hypoxanthine-guanine phosphoribosyl transferase), and presented as percent of PBS (Phosphate buffered saline) control (mean±SD).

Figure 21:
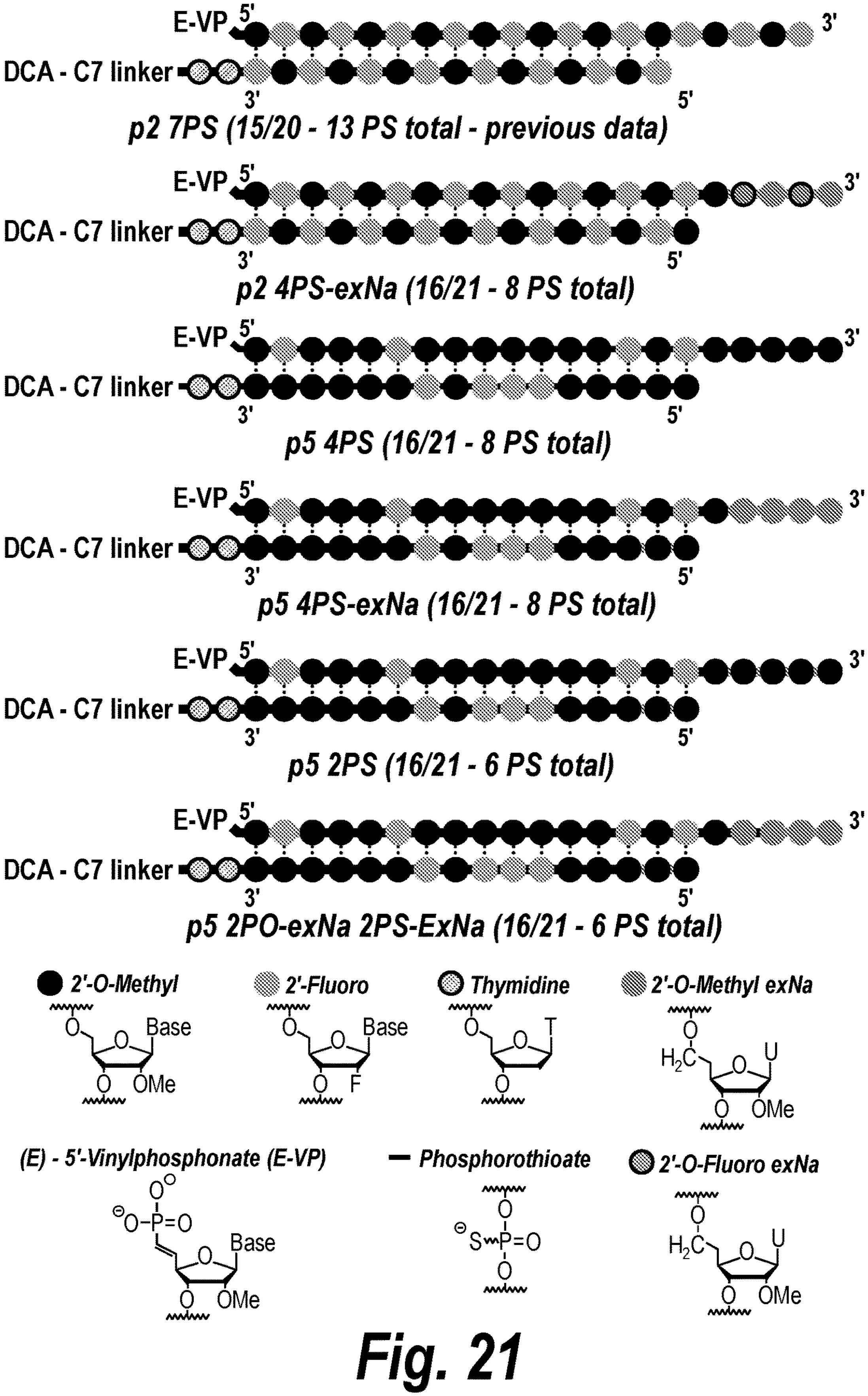
FIG. 21 depicts designs and structural configurations of siRNAs for lung delivery via systemic (SC). Schematic of siRNA structural configuration studied to evaluate the impact of the chemical composition on siRNA distribution and efficacy.
Figure 22:
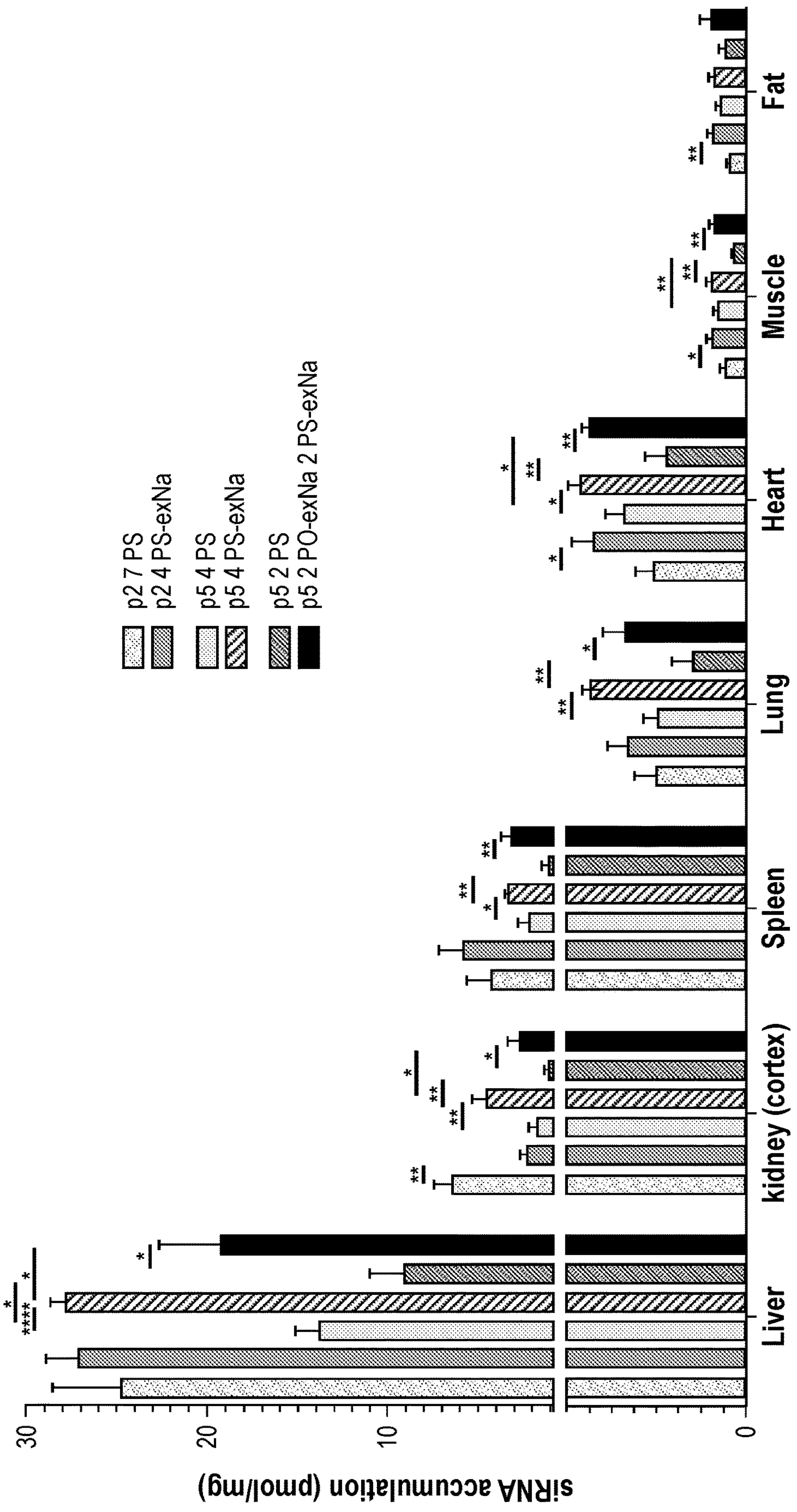
FIG. 22 depicts distribution and accumulation of siRNAs conjugated to DCA and containing different numbers of 3' exNA modifications and phosphorothioates. These data show increased accumulation of DCA-conjugated siRNAs with exNA modifications compared to those without exNAs in all tissues including the lungs. SC, 20 mg/kg, n=3, 1 week, PNA hybridization assay. p2 scaffold: 4PS-exNa≈7PS in liver, spleen, lung; 4PS-exNa>7 PS in heart, muscle, fat; 7PS>4PS-exNa in kidney. p5 scaffold: 4PS-exNa>2PO-exNa 2PS-exNa≥4 PS>2PS.

Six siRNAs were then designed containing different numbers of 3' exNA modifications and phosphorothioates. (FIG. 21) for lung delivery via systemic (SC) delivery. In FIG. 22 the impact of the chemical composition on siRNA distribution and efficacy is evaluated. The data show increased accumulation of DCA-conjugated siRNAs with exNA modifications compared to those without exNAs in all tissues including the lungs. Injections were done SC, 20 mg/kg, in three mice, for 1 week, and distributions were assessed in the PNA hybridization assay. Results show for the p2 scaffold show that 4PS-exNa accumulation was comparable to 7PS in liver, spleen, and lung; 4PS-exNa>7 PS in heart, muscle, fat; 7PS>4PS-exNa in kidney. p5 scaffold: 4PS-exNa>2PO-exNa 2PS-exNa≥4 PS>2 PS.

Figures 23A, 23B, 23C, 23D:
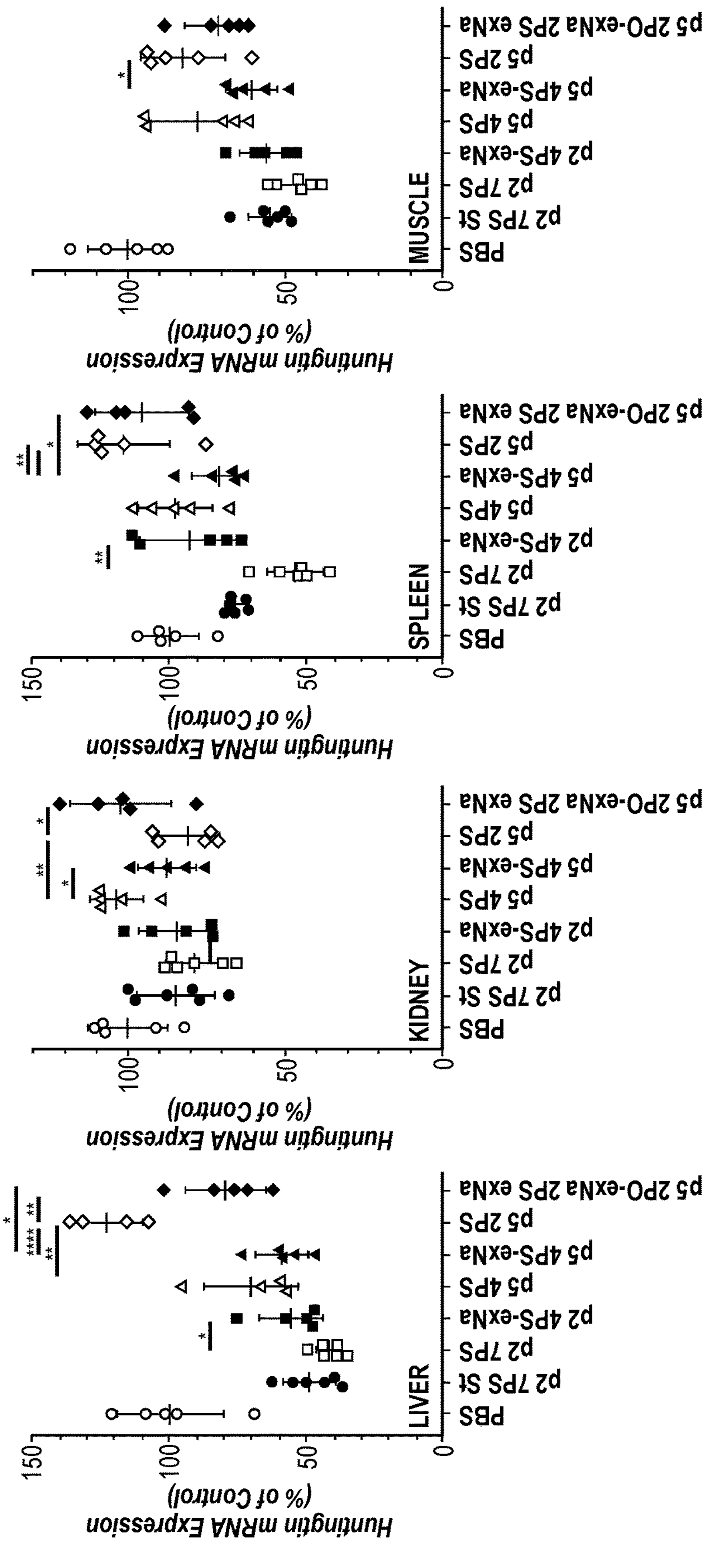
FIG. 23A-23H depict target mRNA silencing (Htt) after systemic administration of siRNAs conjugated to DCA and containing different numbers of 3' exNA modifications and phosphorothioates in various organ tissues.
Figures 23E, 23F, 23G, 23H:
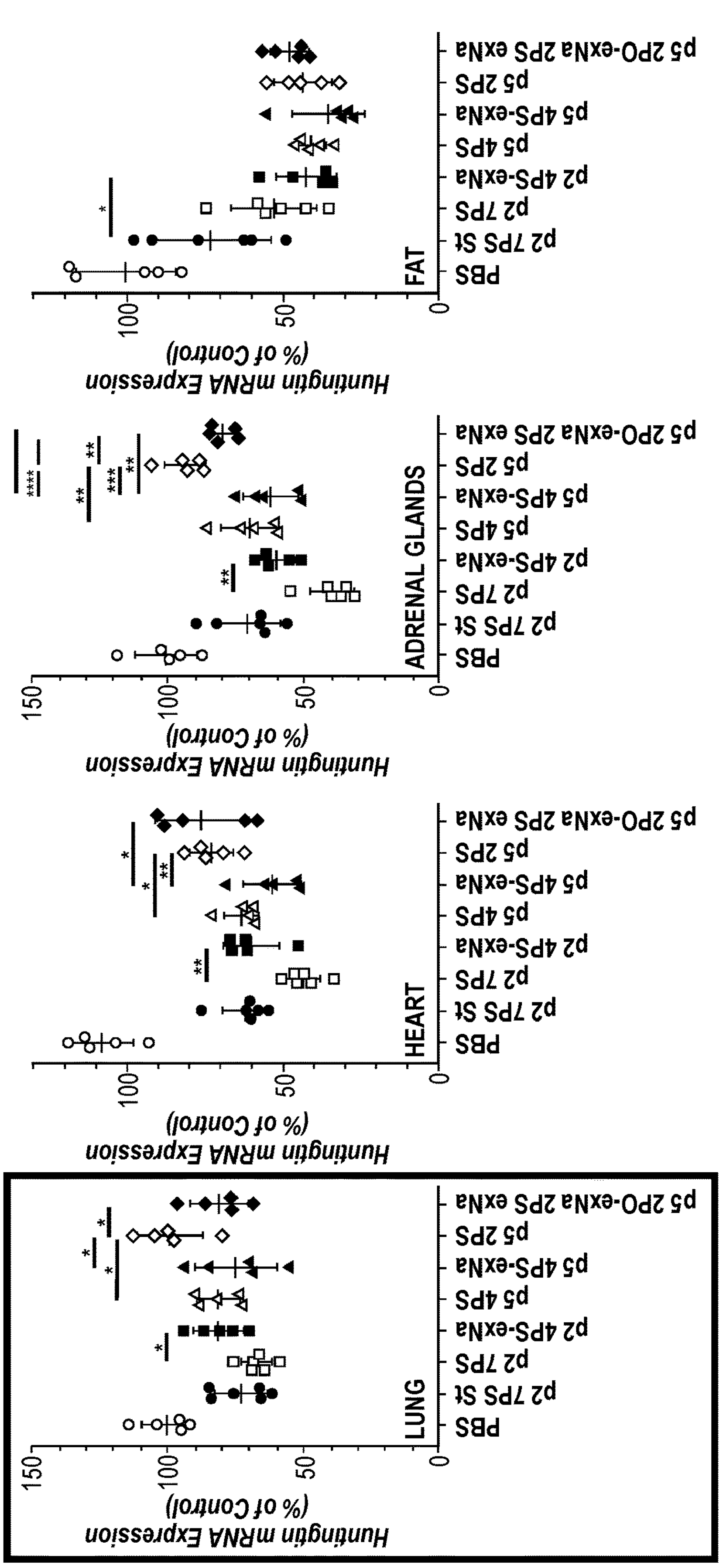

Increased silencing of DCA-conjugated siRNAs was achieved with exNA modifications compared to those without exNAs in all tissues including the lungs (FIG. 23). Target mRNA silencing (Htt) after systemic administration of siRNAs conjugated to DCA and containing different numbers of 3' exNA modifications and phosphorothioates was assessed in various organ tissues including the liver, kidney, spleen, muscle, lung, heart, adrenal glands, and fat. The delivery was done by SC injection, 20 mg/kg, in five mice per group for one week, and quantification was done with the bDNA QuantiGene assay.

Figure 24:
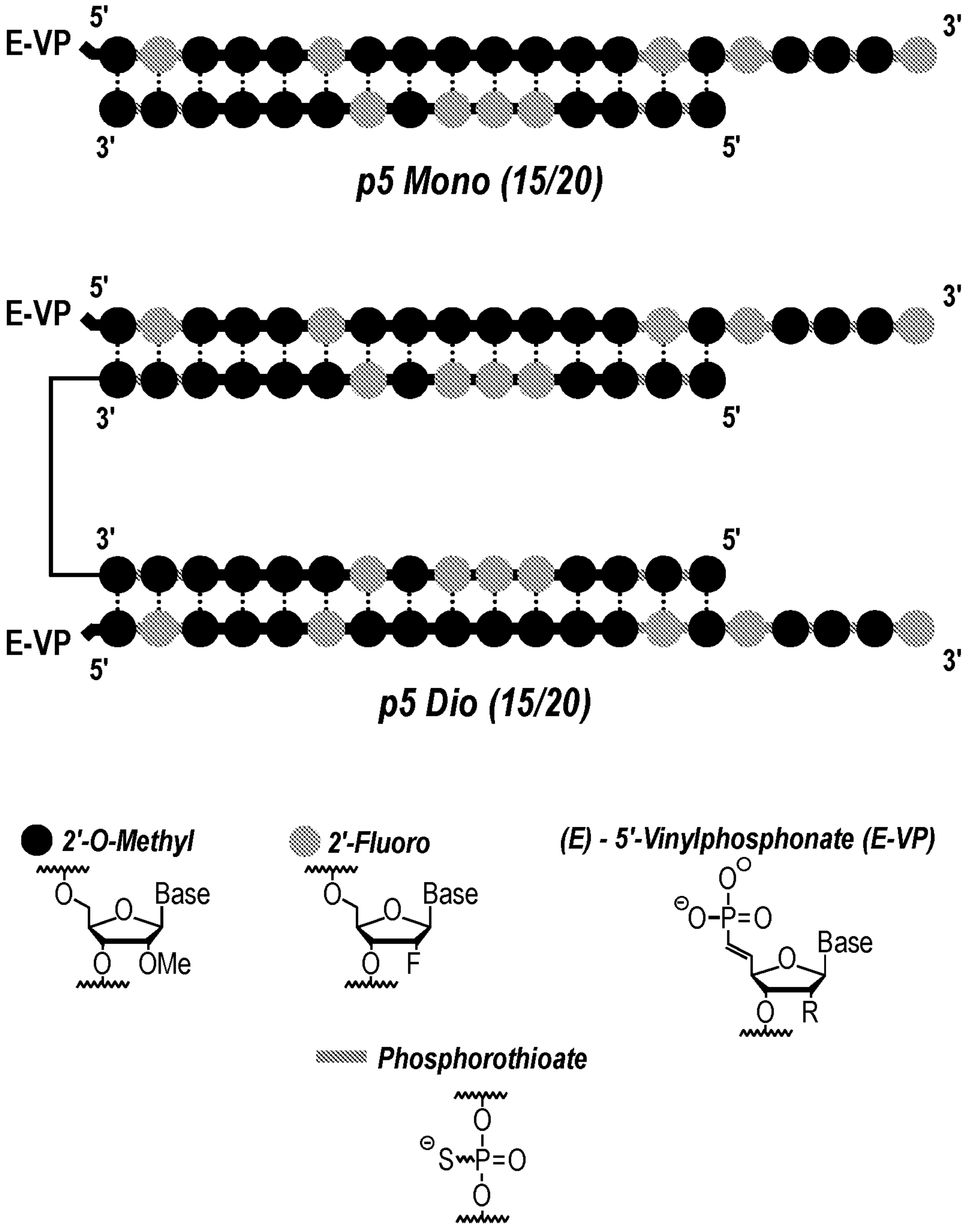
FIG. 24 depicts designs of siRNAs for lung delivery via intratracheal administration. Schematic of siRNA structural configuration studied to evaluate the impact of the chemical composition on siRNA distribution and efficacy.
Figure 25A:
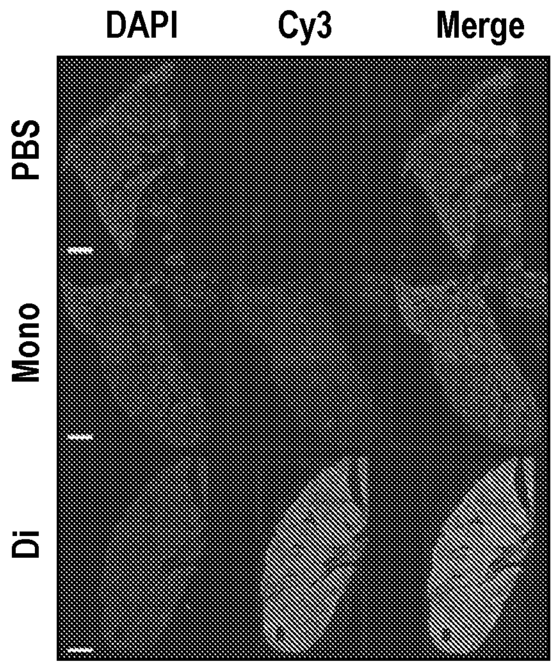
FIG. 25A-25B depict siRNA accumulation after intratracheal administration.
Figure 25B:
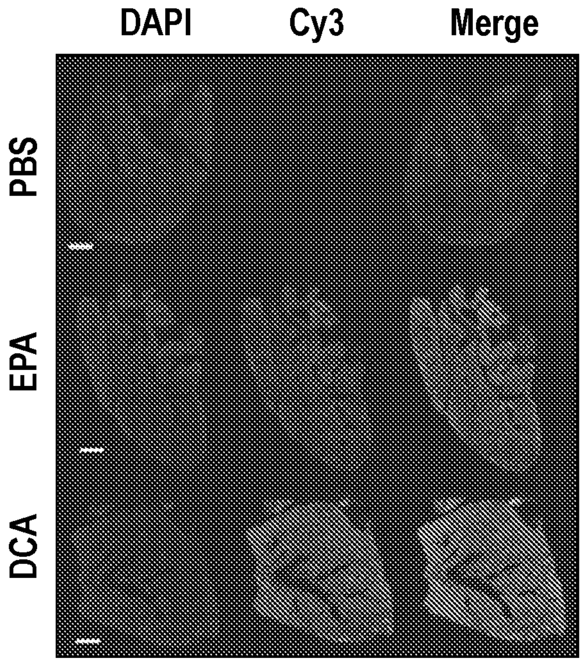

SiRNAs were then designed for lung delivery, to evaluate the impact of the chemical composition on siRNA distribution and efficacy (FIG. 24). The distribution and delivery throughout the lung of mono- and divalent siRNAs (Cy-3) is shown in FIG. 25A, and of DCA and EPA conjugated siRNAs (Cy-3) in FIG. 25B. Delivery via intratracheal injection (mono and divalent conjugates) were at 20 nmol for monovalent, and 40 nmol for divalent siRNAs, in two mice per group, and tissues were harvested after 24 h. Subcutaneous delivery (EPA and DCA conjugates) was at 40 nmol per construct in three mice per group and tissues were harvested after 48 h. Magnification is 5×, and the scale=1 mm.

Figure 26A:
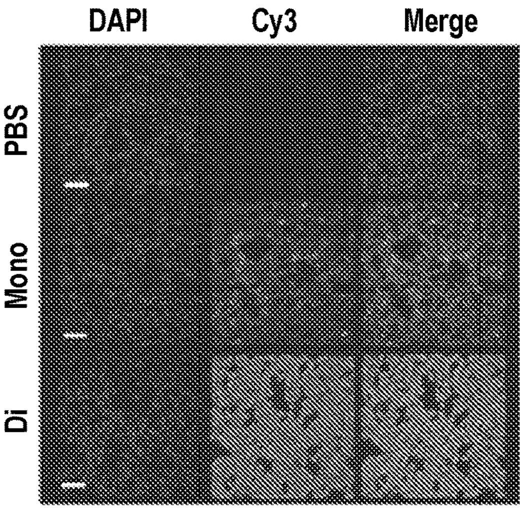
FIG. 26A-26C depict mono and di-valent siRNA accumulation after intratracheal administration.
Figure 26B:
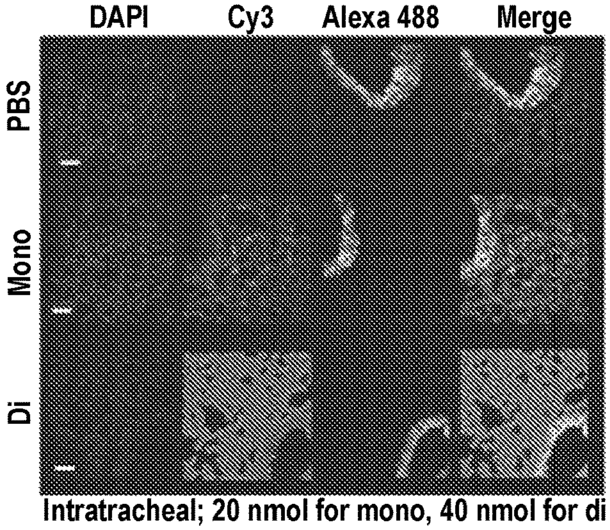
Figure 26C:
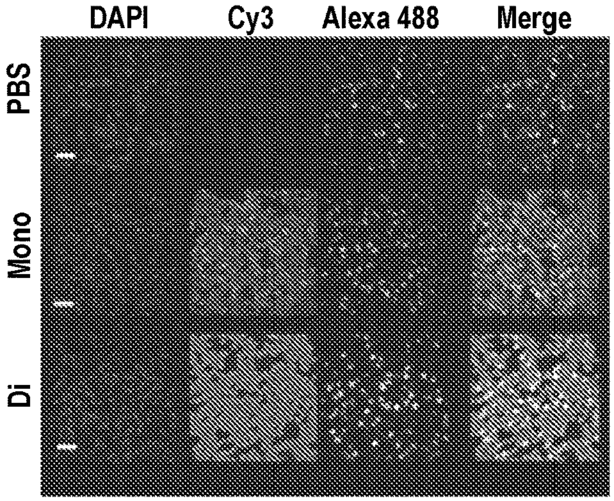
Figure 27A:
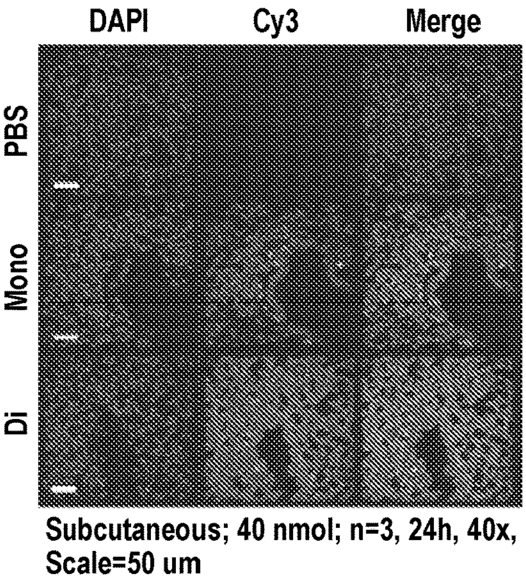
FIG. 27A-27C depict EPA and DCA conjugated siRNA distribution throughout the lungs after subcutaneous (SC) administration).
Figure 27B:
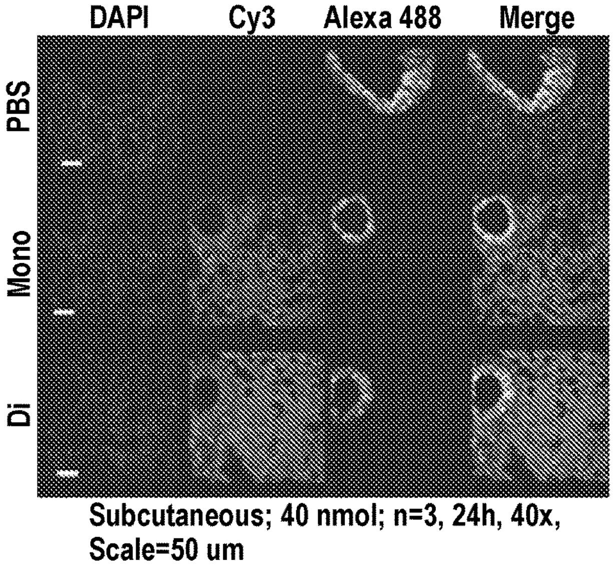
Figure 27C:
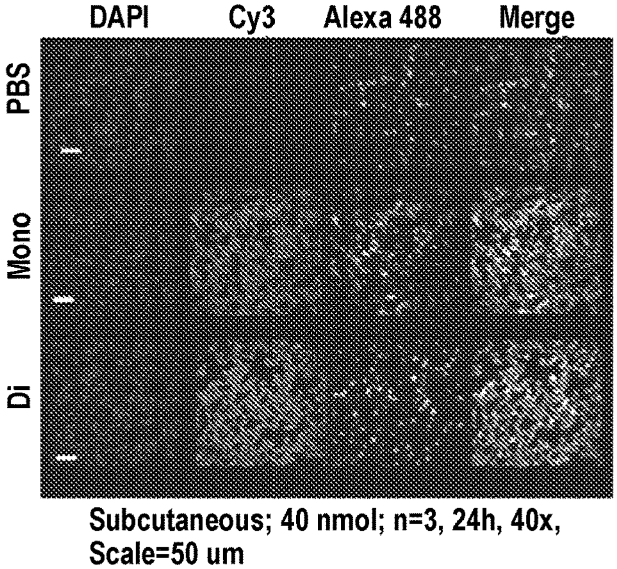

Divalent siRNAs distribute to all cells of the lungs and saturate both alveolar and epithelial (club) cells 24 hours after intratracheal administration. Accumulation of mono and di-valent siRNA (Cy-3, red) after intratracheal administration is shown in FIG. 26. Distribution is shown throughout the lung (FIG. 26A), in club cells (FIG. 26B; green), and in alveoli type II cells (FIG. 26C; green) as compared to PBS controls. FIG. 27 depict results obtained with EPA and DCA conjugates delivered by subcutaneous (SC) administration as assessed after 48 h.

Figures 28A, 28B:
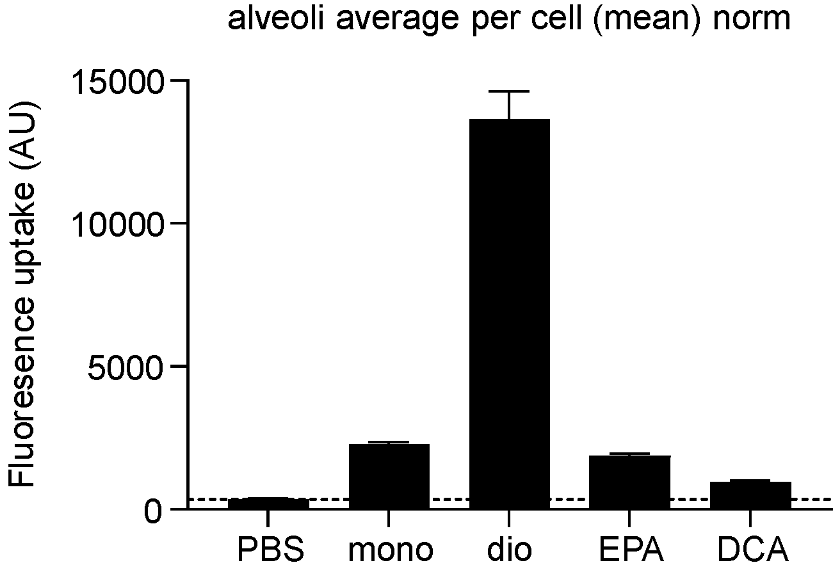
FIG. 28A-28D depict quantification of siRNA accumulation after systemic and intratracheal administration.
Figures 28C, 28D:
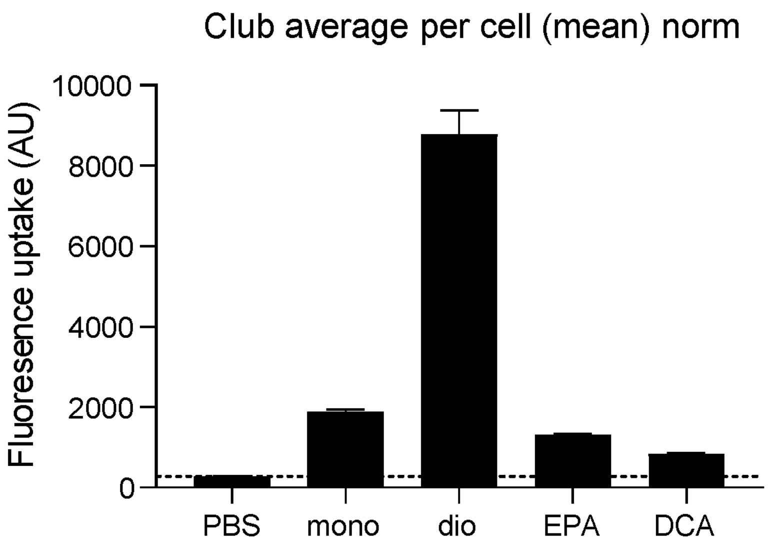

Divalent siRNAs showed the highest amount of uptake among mon-divalent, EPA-conjugated and DCA-conjugated siRNA's, both in alveolar cells as well as in club cells (FIG. 28A and FIG. 28C, respectively, as quantitated in FIG. 28B. and FIG. 28D, respectively). Quantitation was performed using cy3 fluorescence signal intensity and colocalization with markers of different cell types, siRNA accumulation was quantified after systemic (SC) administration of EPA and DCA conjugated siRNAs, and intratracheal administration of mono and di-valent siRNAs. All siRNAs delivered to cells throughout the lung but to different extents.

Figure 29A:
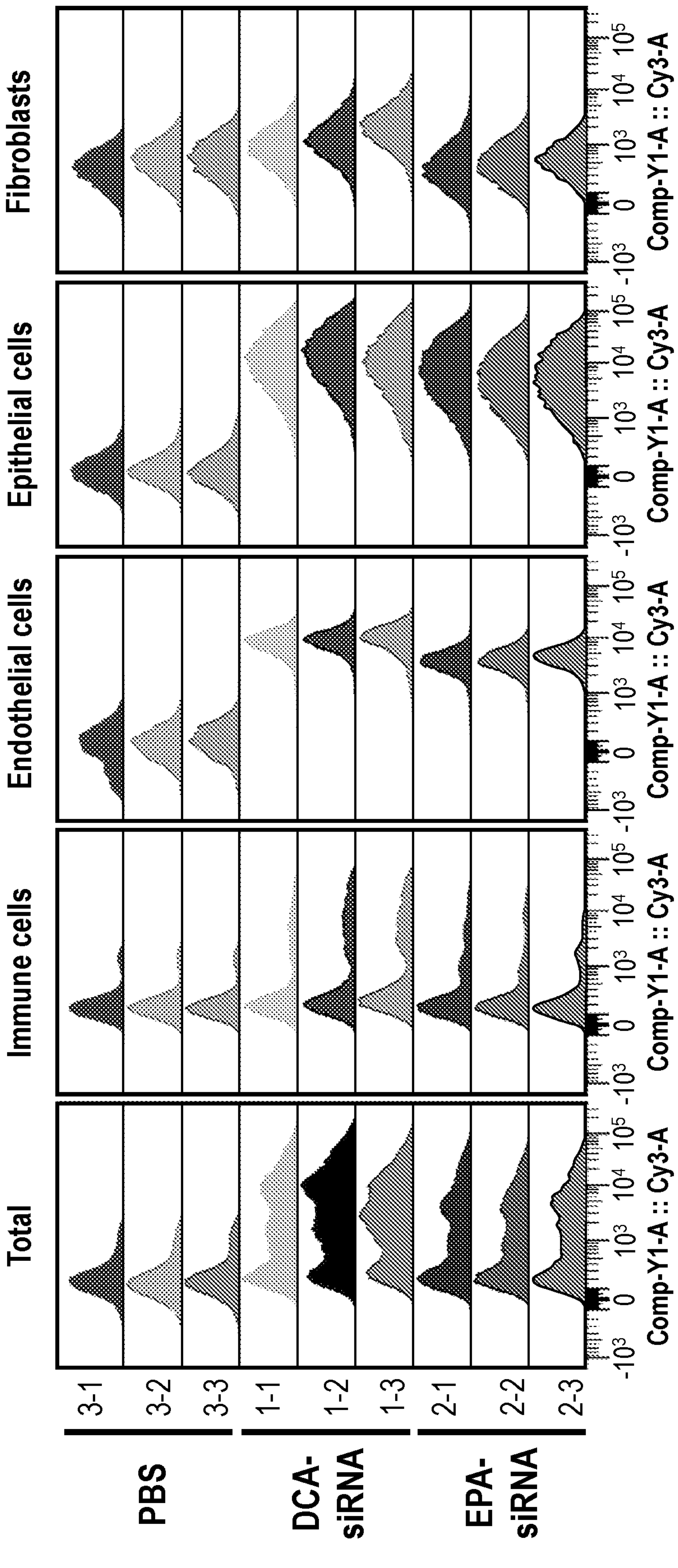
FIG. 29A-29G depict quantification of EPA and DCA conjugated siRNA accumulation after systemic administration.
Figures 29B, 29C, 29D, 29E, 29F, 29G:
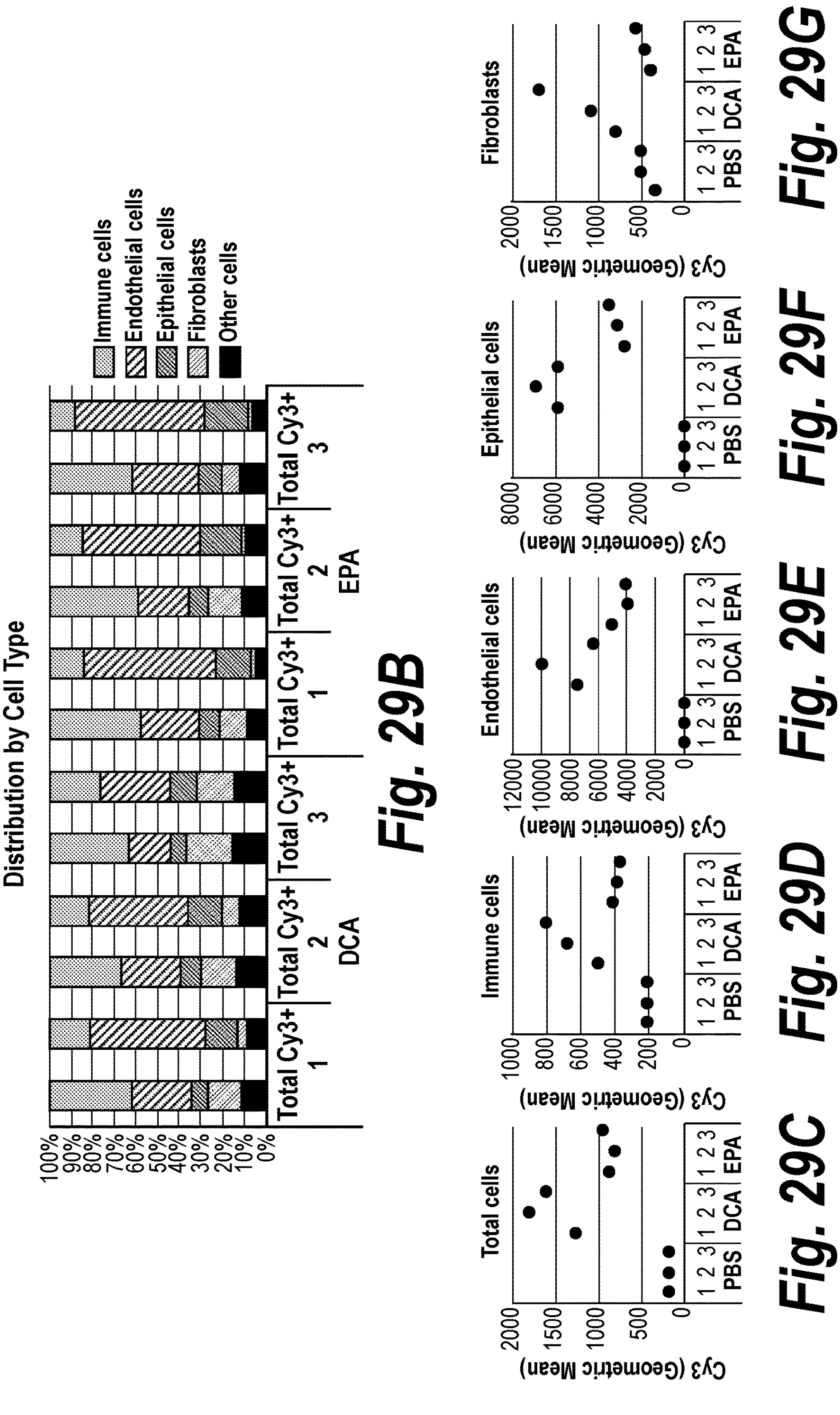
Figure 30A:
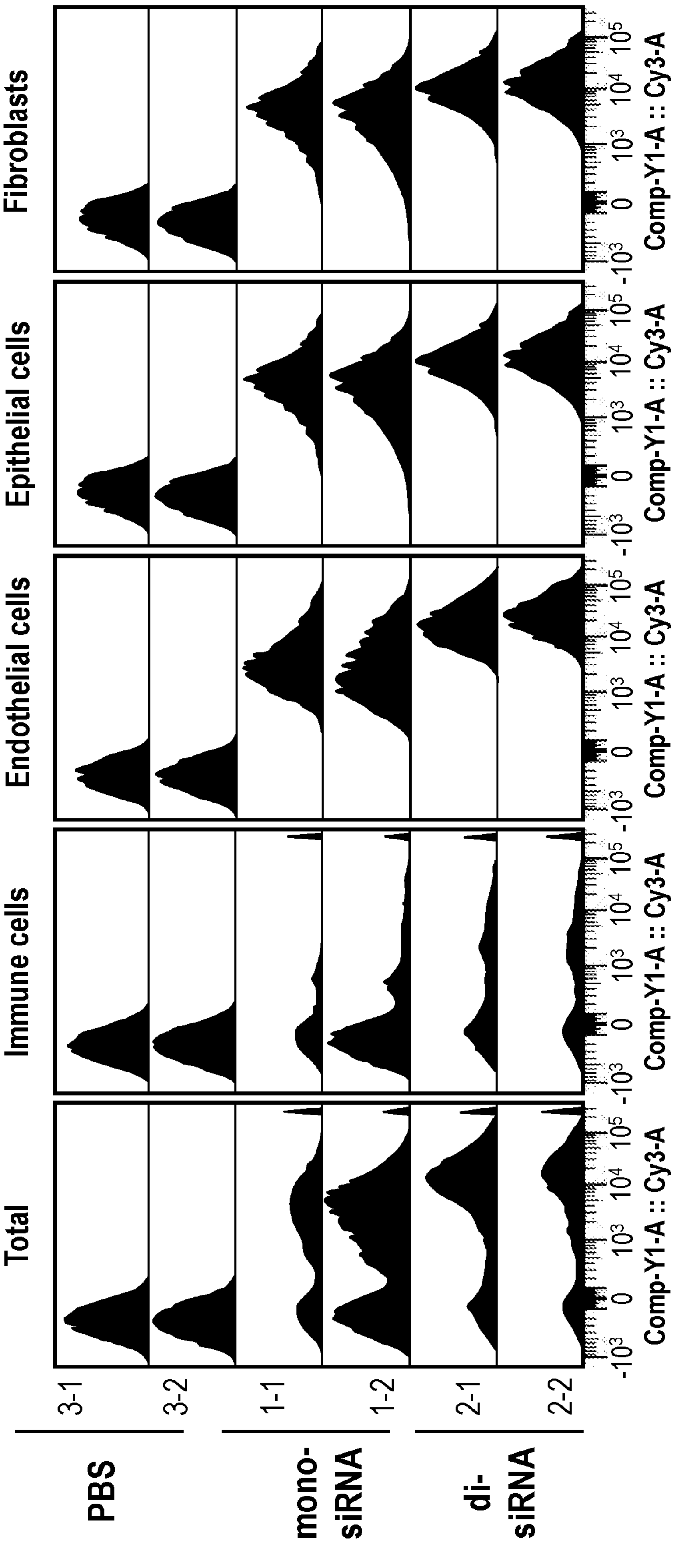
FIG. 30A-30G depict quantification of siRNA accumulation after intratracheal administration. Using flow cytometry, siRNA accumulation was quantified after intratracheal administration of mono and di-valent siRNAs.
Figure 30B:
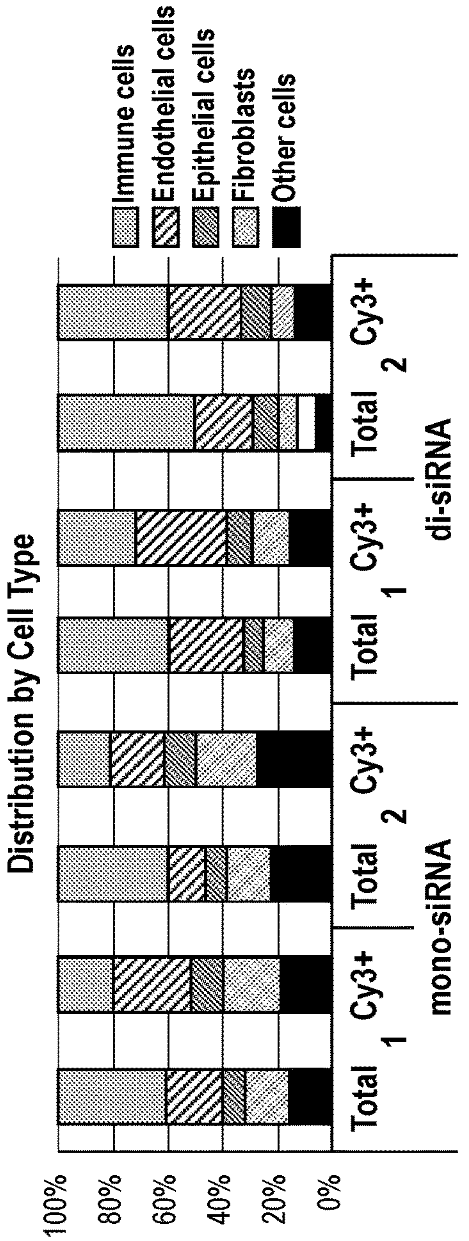
Figure 30C:
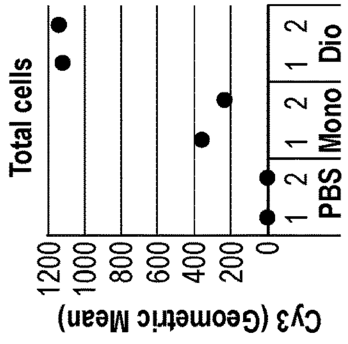
Figure 30D:
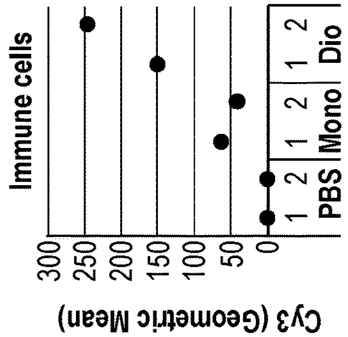
Figure 30E:
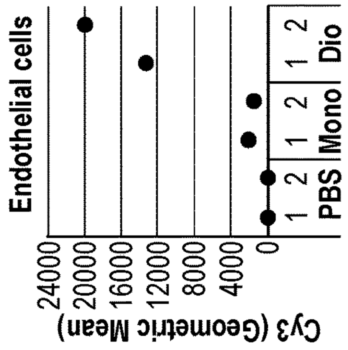
Figure 30F:
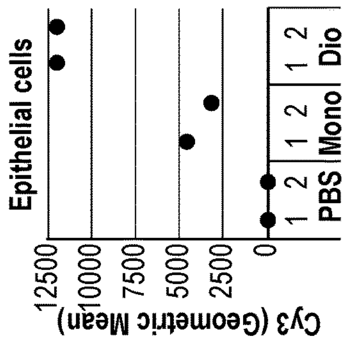
Figure 30G:
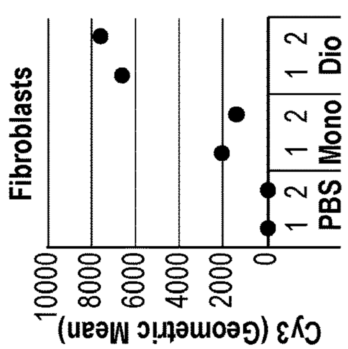

Monovalent, divalent, EPA-conjugated and DCA-conjugated siRNA 1 siRNAs delivered to cells throughout the lung, but to a different extent. Cy-3 signals were quantitated in total cells, immune cells, endothelial cells, epithelial cells and fibroblasts, after systemic (SC) administration of EPA and DCA conjugated siRNAs (FIG. 29A-29C) and after intratracheal (IT) administration of mono- and divalent siRNAs (FIG. 30A-30C).

Figure 31A:
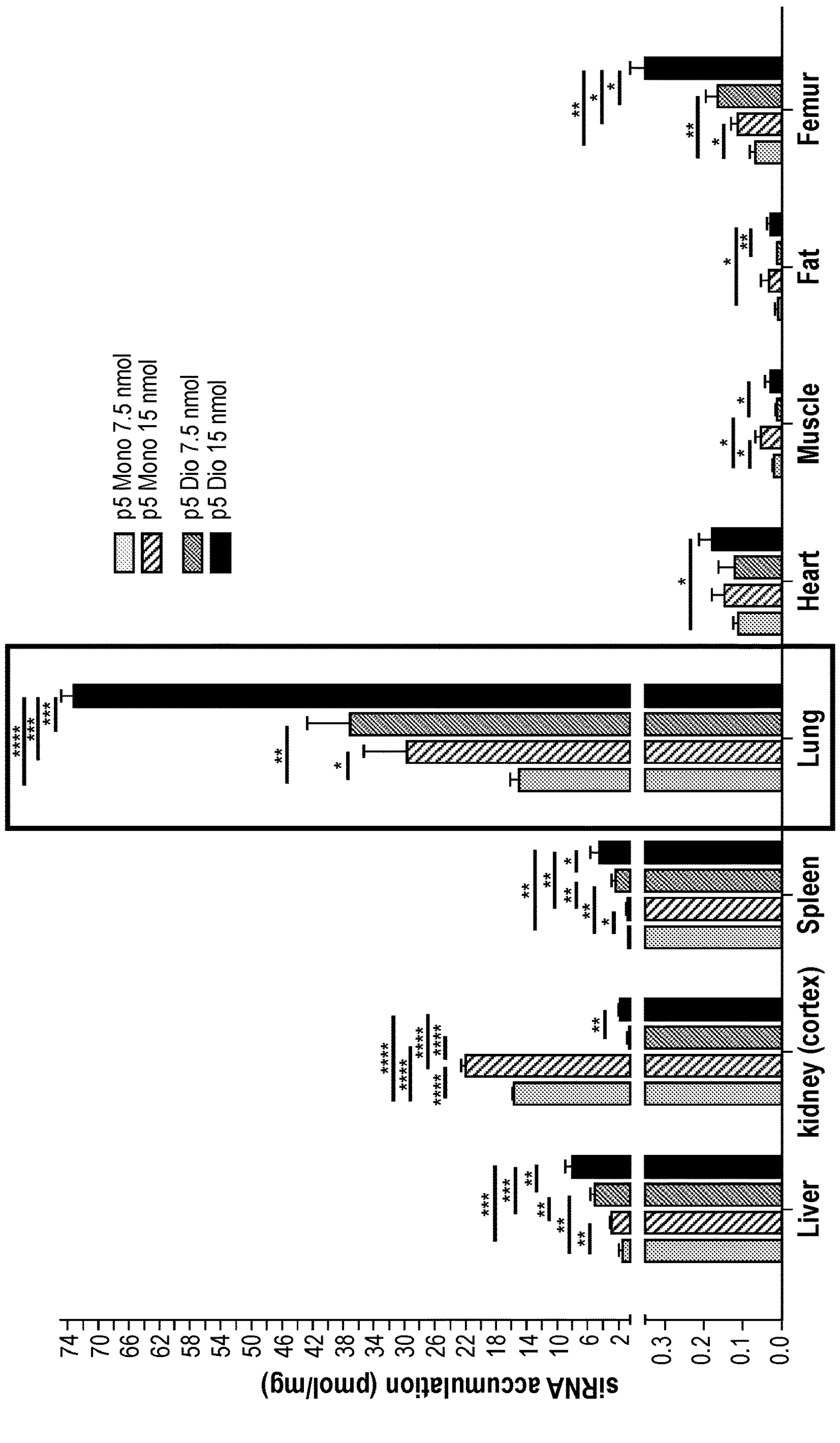
FIG. 31A-31B depict distribution and accumulation of mono and di-siRNAs.
Figure 31B:
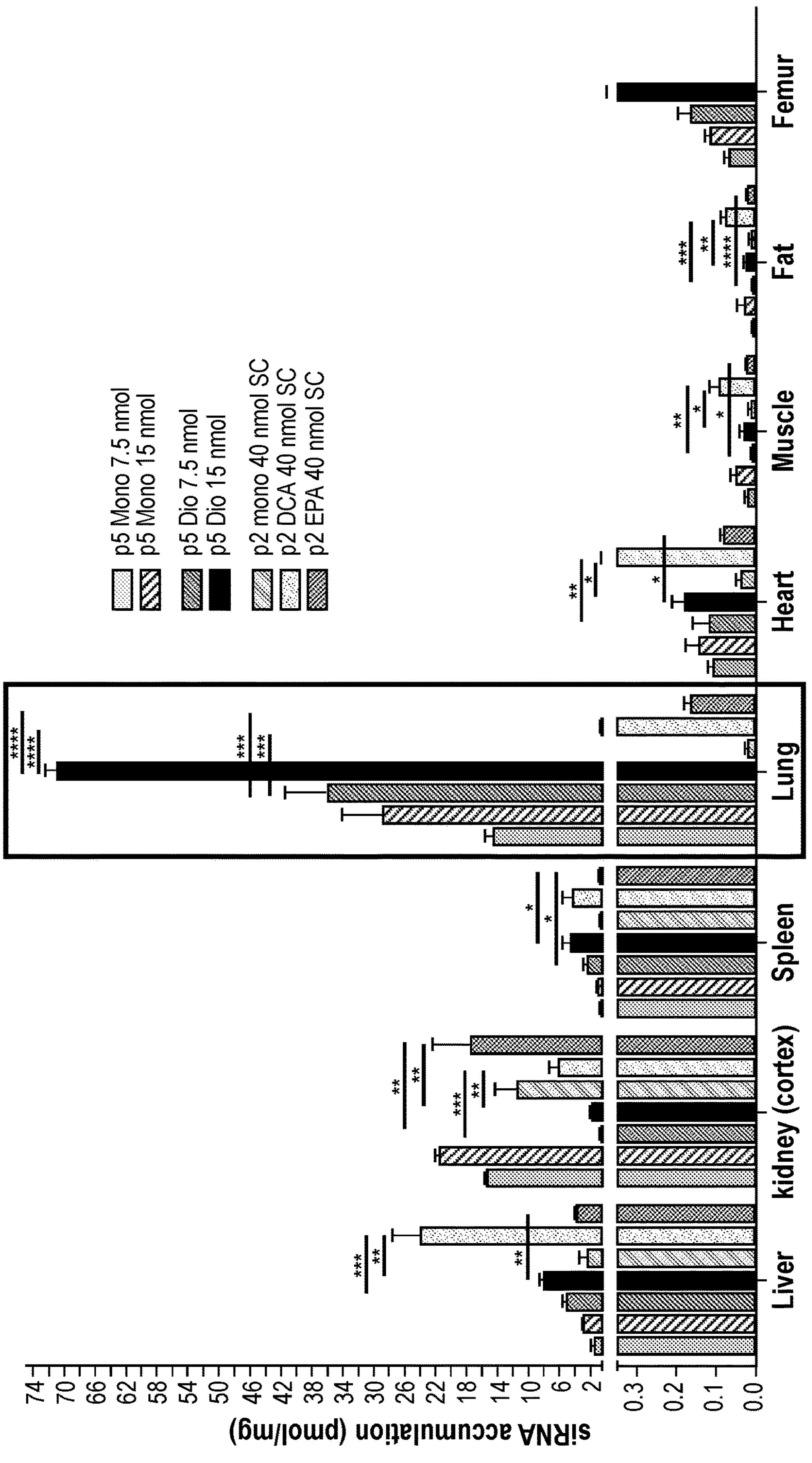
Figure 32A:
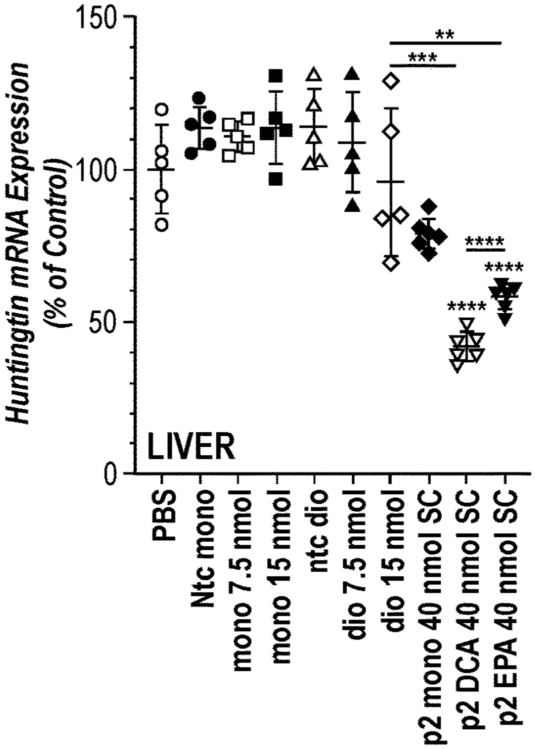
FIG. 32A-32H show target mRNA silencing (Htt) after intratracheal administration of mono and di-siRNAs in various tissues.
Figure 32B:
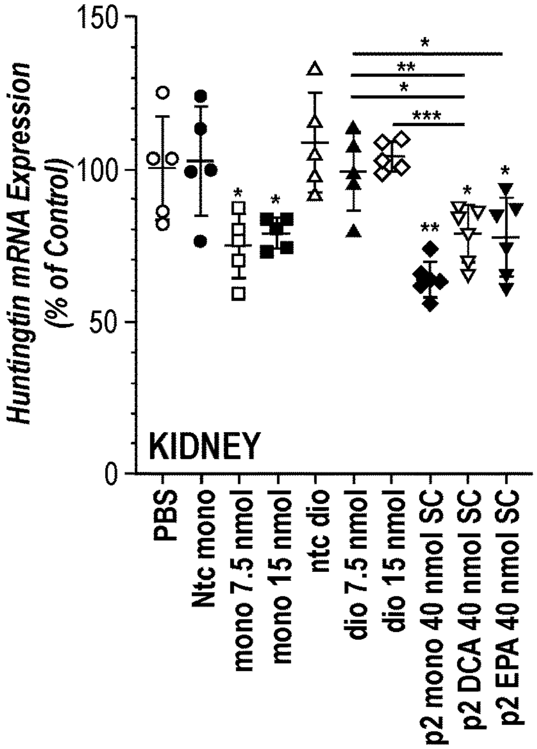
Figure 32C:
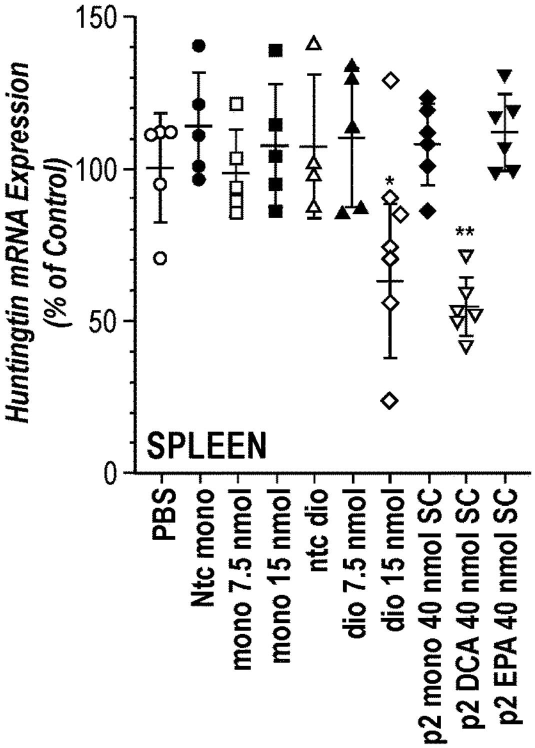
Figure 32D:
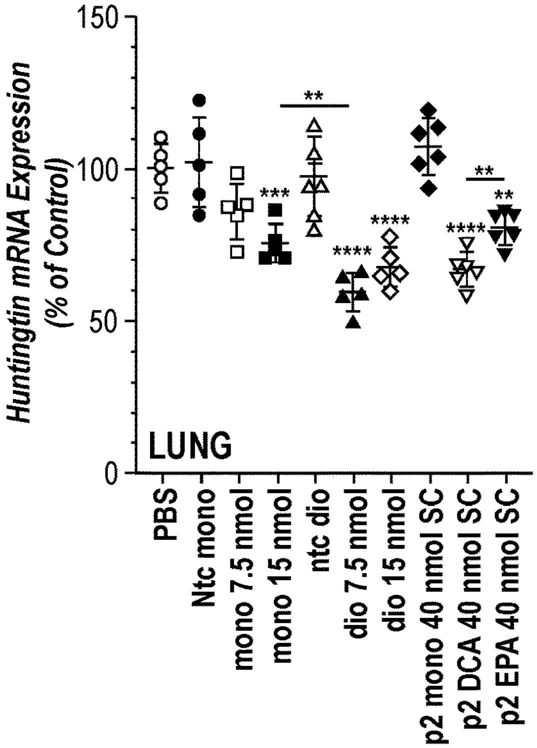
Figure 32E:
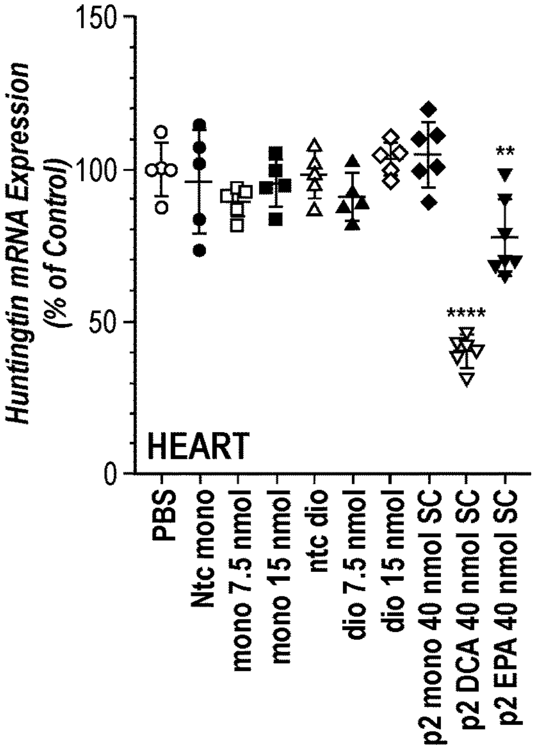
Figure 32F:
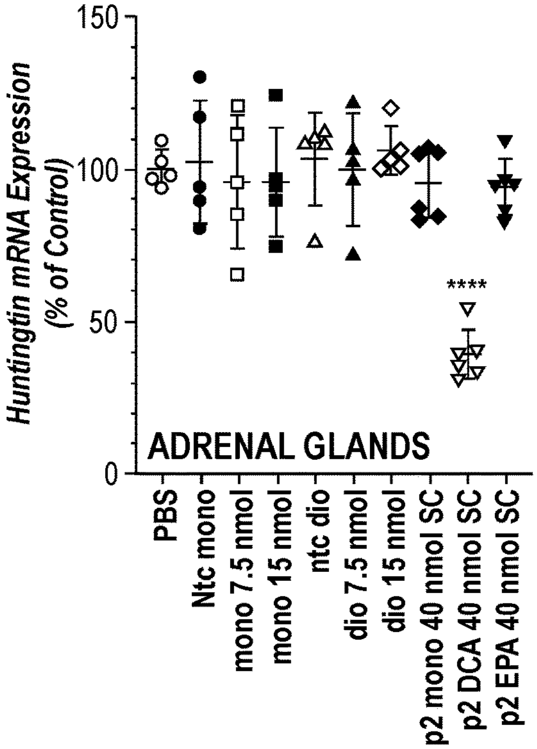
Figure 32G:
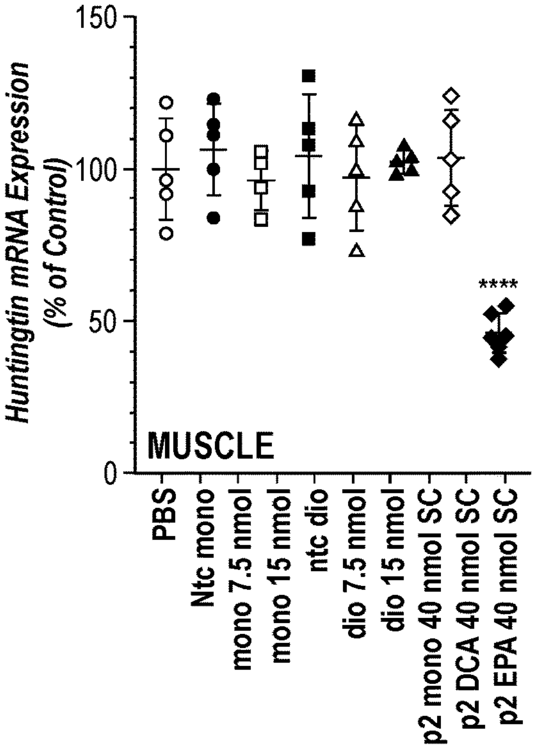
Figure 32H:
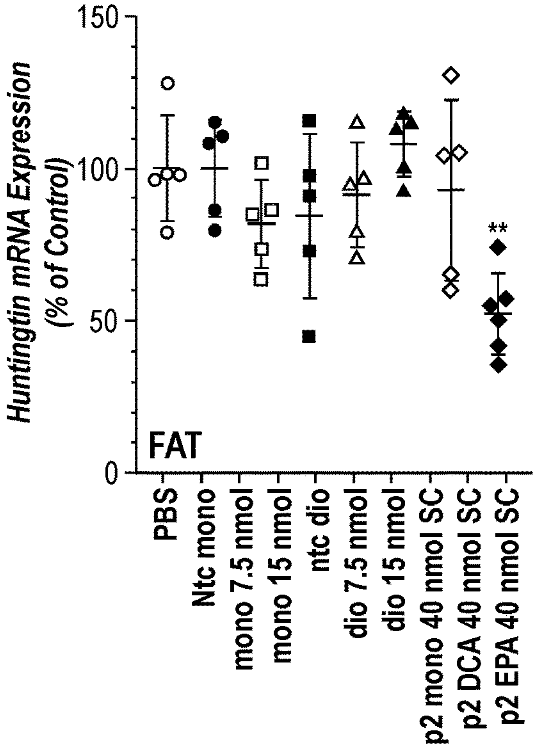
Figure 33:
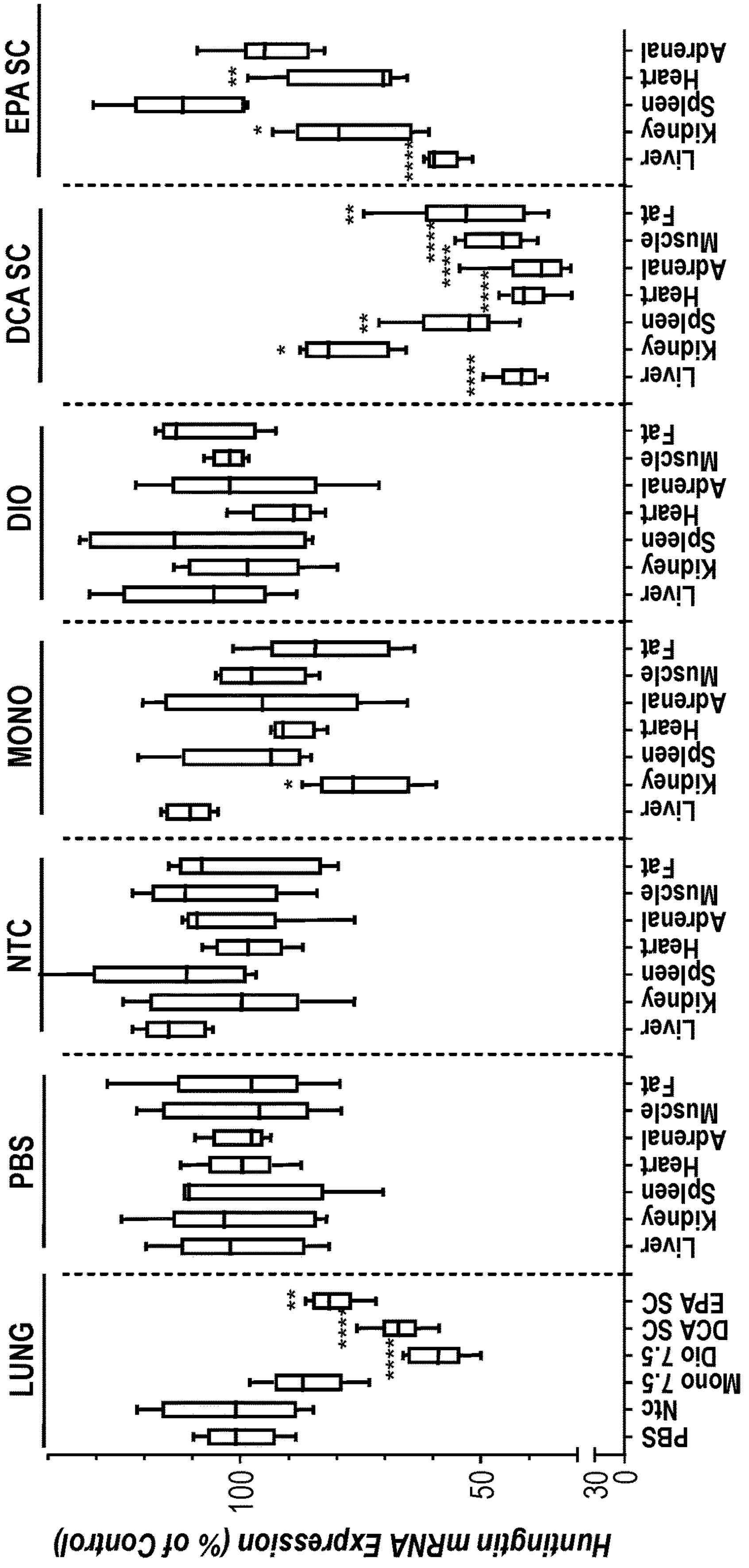
FIG. 33 depicts target mRNA silencing (Htt) after intratracheal administration of mono and di-siRNAs. Intratracheal, 7.5 or 15 nmol, n=5, 1 week, bDNA QuantiGene assay.

There is a clear increased accumulation of di-siRNA compared mono siRNA or DCA- or EPA-conjugated siRNA in the lungs. The distribution and accumulation of mono and di-siRNAs in various tissues were assessed after intratracheal injection, and for DCA- and EPA-conjugated siRNA after SC injection, as shown in FIG. 31. Amounts injected by intratracheal administration were 7.5 and 15 nmol, for mono- and divalent siRNA, respectively, and 40 nmol for EPA/DCA conjugated siRNA, in groups of three mice each, followed by quantitation of siRNA accumulation after a week using the PNA hybridization assay.

A low dose of di-siRNA achieved the best silencing in lungs without silencing the gene in other tissues. FIG. 32A-32H and FIG. 33 show target mRNA silencing (Htt) after intratracheal administration of mono and di-siRNAs (7.5 or 15 nmol, respectively) in liver, kidney, spleen, lung, heart, adrenal glands; muscle and fat tissues, showing that divalent siRNA selectively silences the Htt mRNA in the lung.

Example 4. Additional SARS-CoV-2 Target Sites

Materials and Methods for Example 4 siRNA Treatment and Infection Assay siRNAs were complexed with Lipofectamine RNAiMAX (Invitrogen) according to the manufacturer's protocol and added to the wells of a 96-well plate at the desired final concentration (10 nM for screening, concentration range for dose response assays). To each of these wells was added A549 cells expressing the human ACE2 receptor at a final concentration of 15,000 cells/well. The plate was incubated for 36 hours at 37° C., 5% $CO_2$. After 36 hours of siRNA treatment, SARS CoV-2 virus was added to each well at a final MOI of 0.1 (unless otherwise specified) and incubated for 1 hour. One hour after virus addition, wells were washed with PBS and incubated for a further 48 hours followed by processing for molecular biology analysis.

Viral RNA Abundance

Viral RNA abundance was measured from the supernatants of cells 48 hours post virus infection. Briefly, 100 μL of cell culture supernatant from cells was treated with Trizol-LS according to the manufacturer's recommendations. RNA was then isolated using standard protocols using chloroform and ethanol. The abundance of SARS-CoV-2 Nucleocapsid RNA was measured by real-time quantitative PCR using the QuantiFast Pathogen RT-PCR kit (Qiagen) with the 2019-nCoV CDC qPCR Probe (IDT).

Viral Protein Abundance

Viral protein abundance was measured using immunofluorescence staining with anti-SARS-CoV-2 spike antibody to detect viral spike protein. Briefly, cells were fixed using 4% paraformaldehyde and serial ethanol dehydration followed by standard immunofixation procedures to detect proteins. Cells staining positive for the viral spike protein were counted using a fluorescence microscope.

Figure 34:
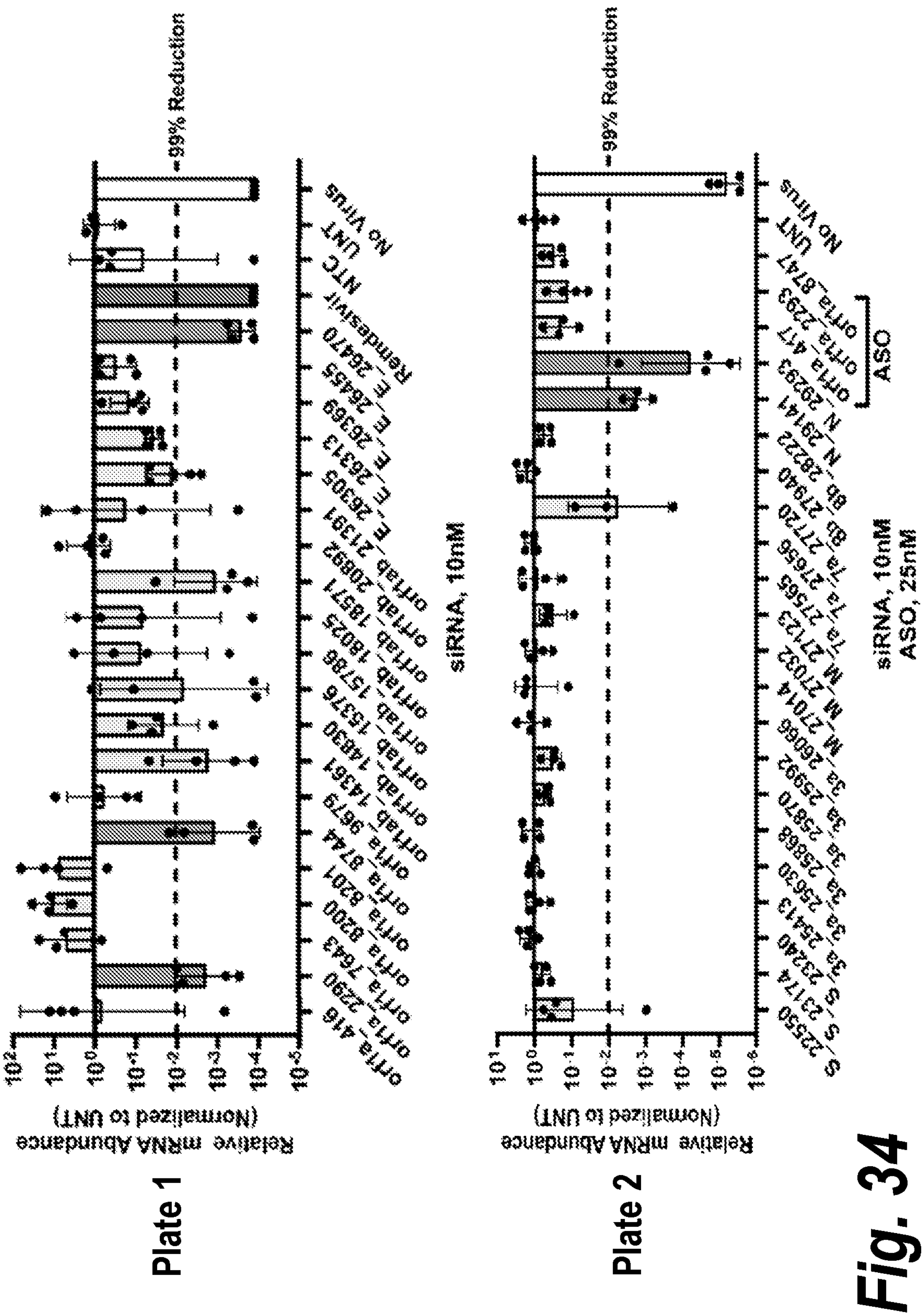
FIG. 34 depicts a screen of siRNAs and ASOs targeting various SARS-CoV2 genes and tested for silencing efficacy. siRNAs and ASOs were tested in in A549-ACE2 cells and silencing was assessed using the psi-check reporter system. siRNA concentration: 10 nM; ASO concentration: 25 nM; Time point: 72 hours.
Figure 34:
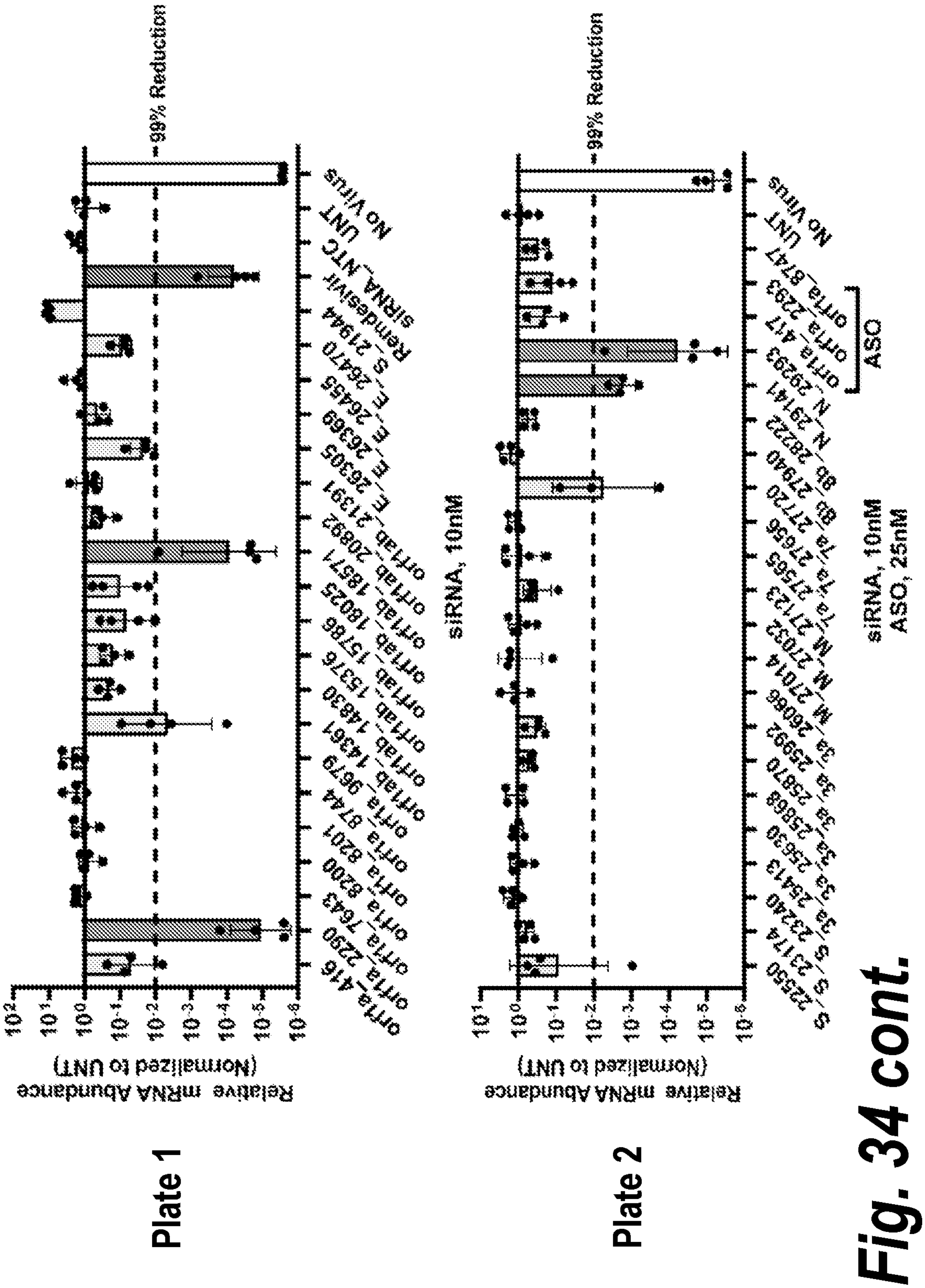

Additional siRNAs and ASOs were tested against various SARS-CoV2 genes. siRNAs and ASOs were tested in A549-ACE2 cells and silencing was assessed using the psi-check reporter system. siRNA concentration: 10 nM; ASO concentration: 25 nM; Time point: 72 hours. As shown in FIG. 34, numerous siRNAs and ASOs were capable of reducing SARS-CoV-2 mRNA levels by 99%, including several that reduce levels to a similar level as remdesivir, an approved therapy for COVID-19.

Figure 35:
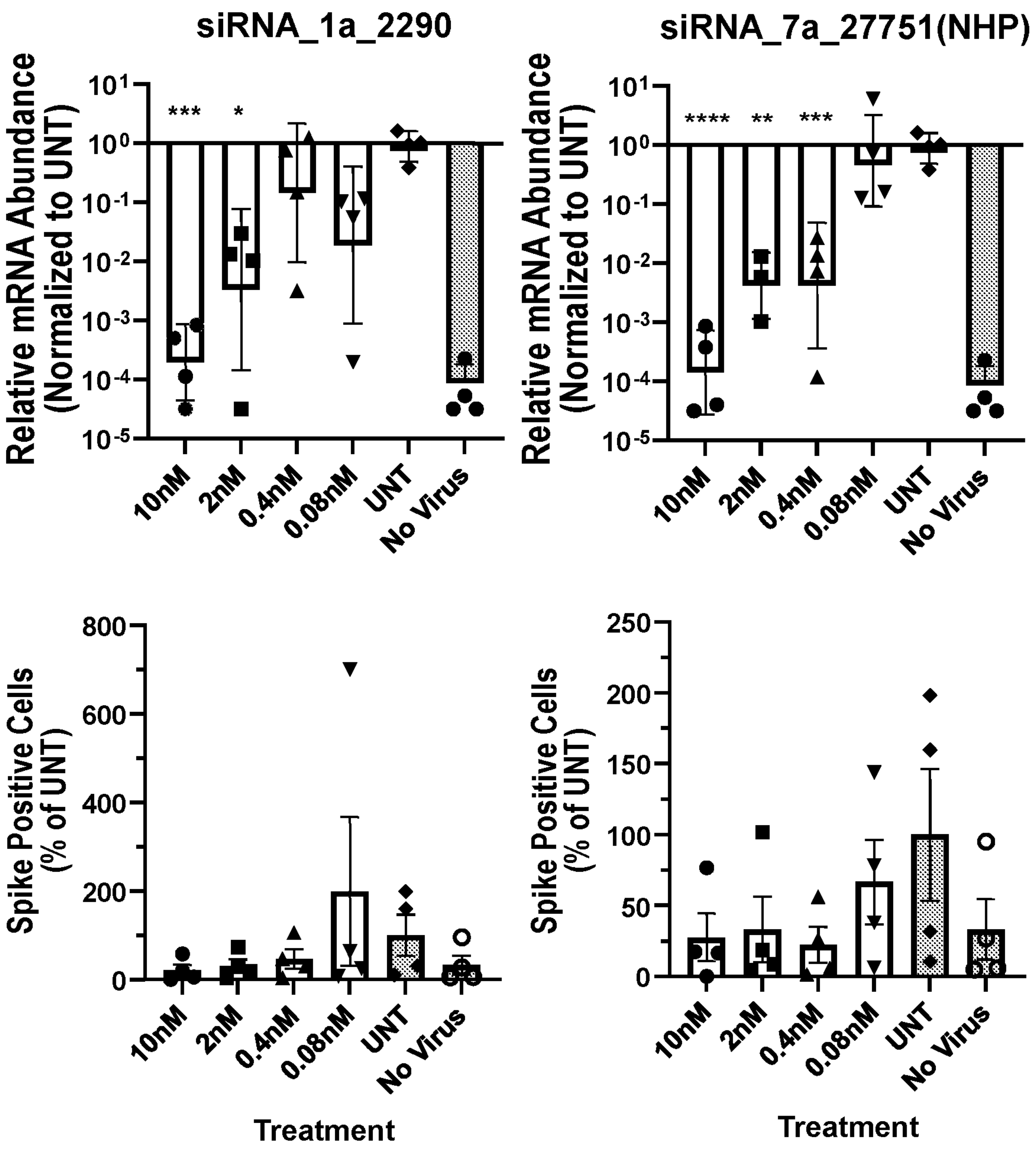
FIG. 35 depicts dose response data of select siRNAs targeting various SARS-CoV2 genes. The data reports relative mRNA abundance of the targeted SARS-CoV2 genes and the percent of cells that are positive for the SARS-CoV2 spike protein. siRNAs were tested in in A549-ACE2 cells and silencing was assessed using the psi-check reporter system.
Figure 35:
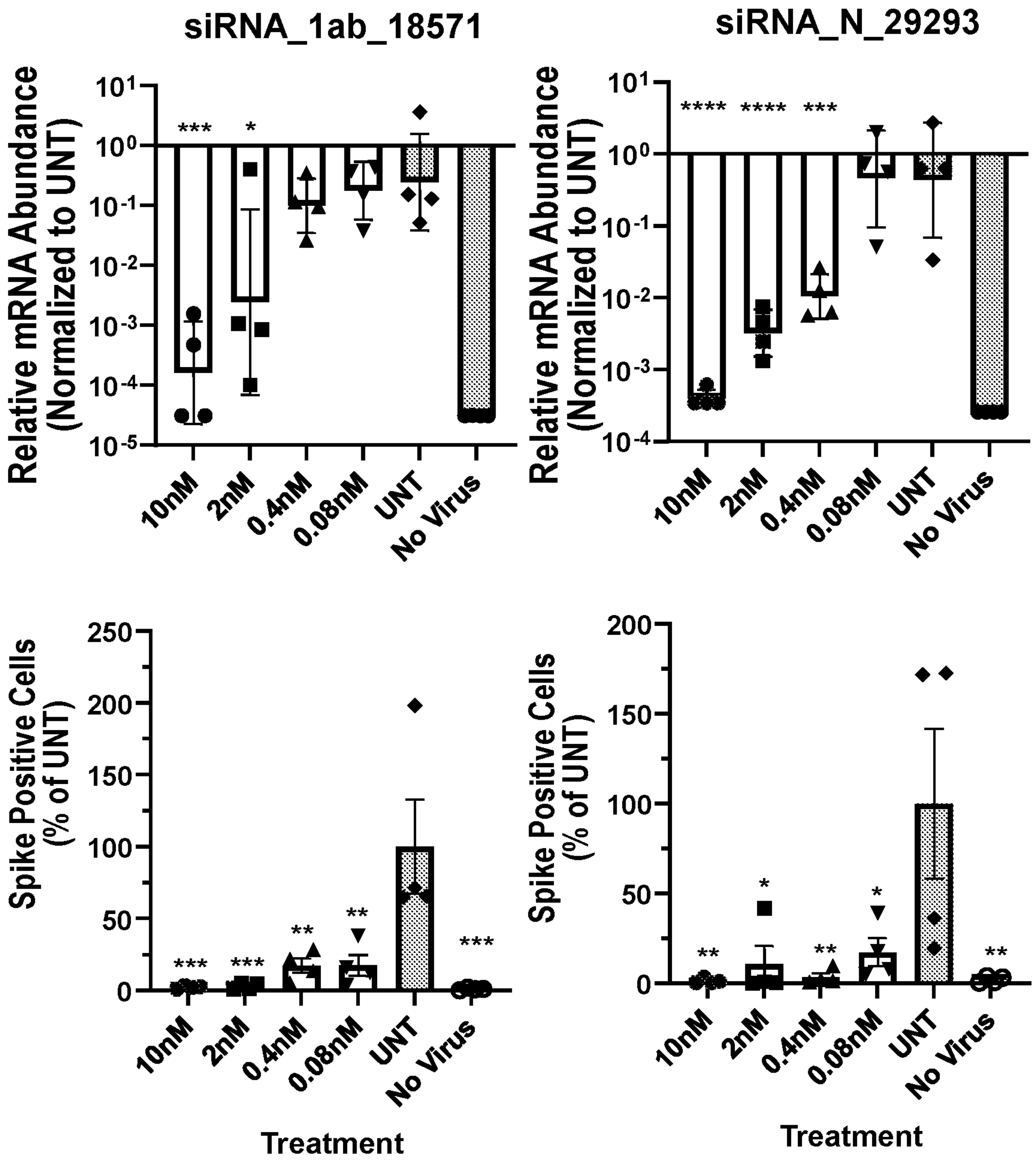

Based on the results of the screen performed in FIG. 34, several top hits were tested in dose response experiments. siRNAs 1a_2290, 7a_27751, 1ab_18571, and N_29293 were each tested at concentrations of 10 nM, 2 nM, 0.4 nM, and 0.08 nM. As shown in FIG. 35, each of the tested siRNAs were able to effectly silence SARS-CoV-2 mRNA at several doses. Moreover, the tested siRNAs led to reduction of SARS-CoV-2 spike protein positive cells.

Figure 36:
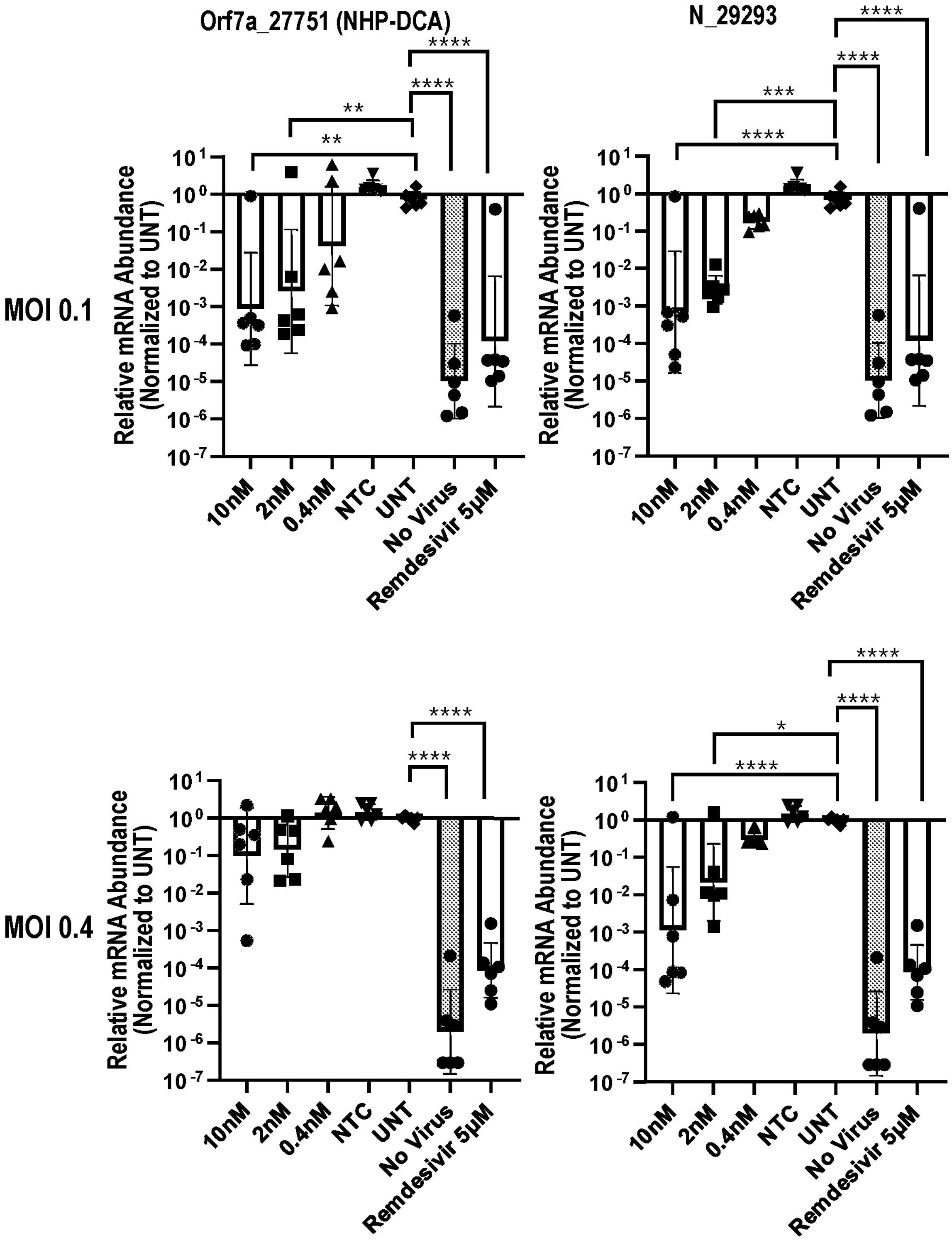
FIG. 36 depicts dose response data of select siRNAs targeting various SARS-CoV2 genes. The A549-ACE2 cells were infected with SARS-CoV-2 at a MOI of 0.1 and 0.4. The data reports relative mRNA abundance of the targeted SARS-CoV2 genes.
Figure 36:
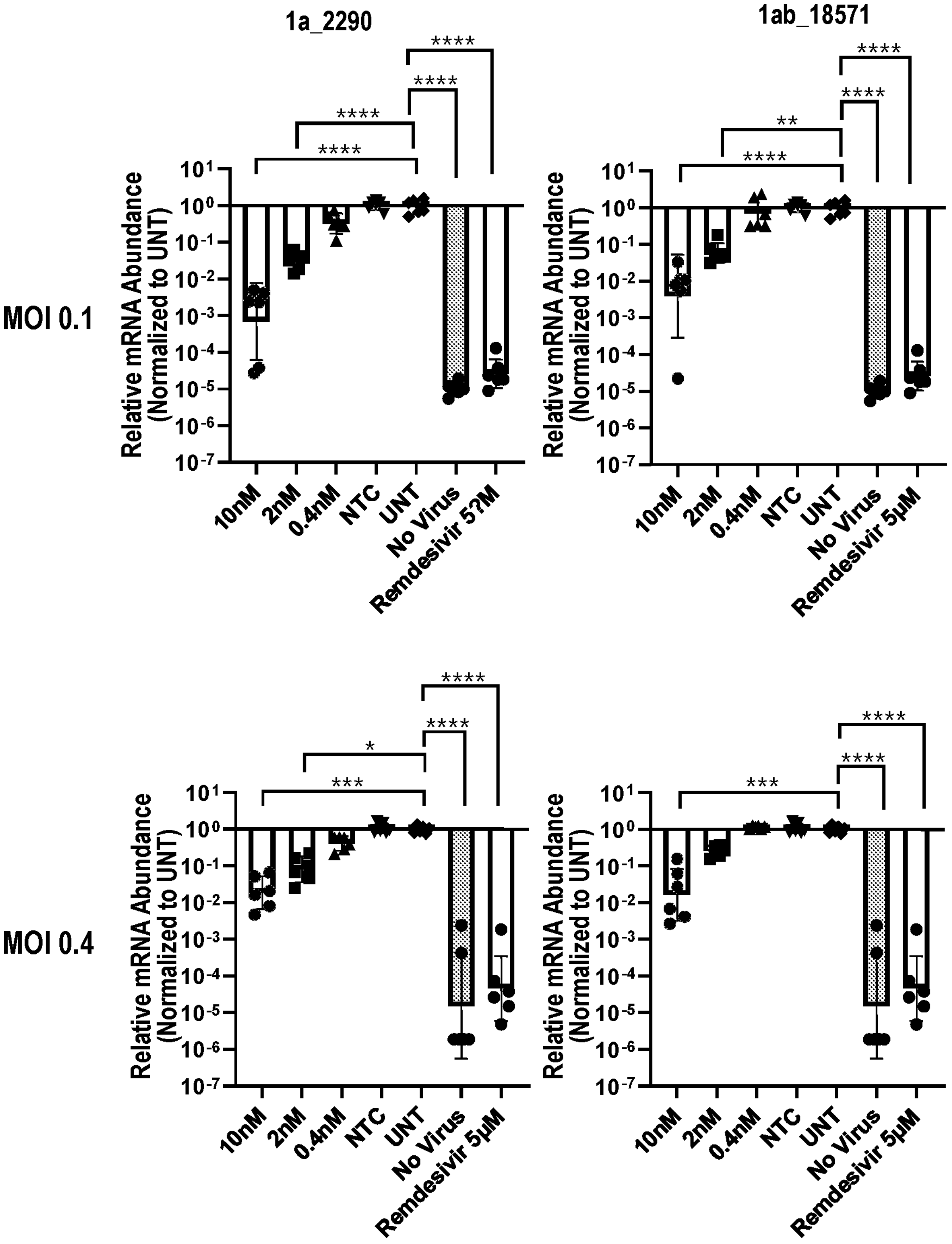

An additional dose response experiment was performed as described above for FIG. 35. In this experiment, cells were infected with SARS-CoV-2 at a multiplicity of infection (MOI) of 0.1 and 0.4. As shown in FIG. 36, the tested siRNAs were able to effectly silence SARS-CoV-2 mRNA at several doses and at both MOIs tested.

Figure 37:
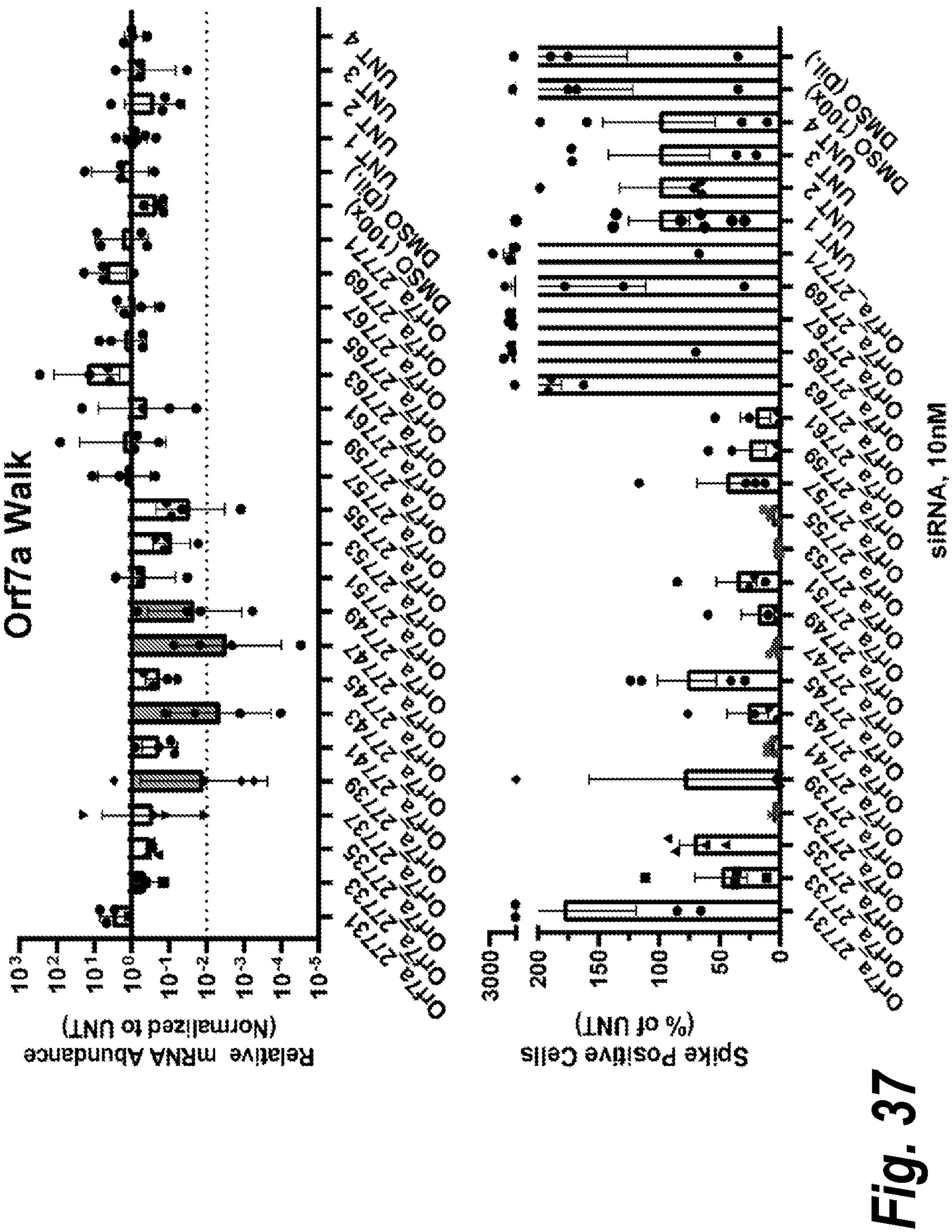
FIG. 37 depicts a screen of siRNAs targeting the orf7a SARS-CoV2 gene. siRNAs were tested in in A549-ACE2 cells and the data reports relative mRNA abundance of the targeted orf7a SARS-CoV2 gene and the percent of cells that are positive for the SARS-CoV2 spike protein. siRNA concentration: 10 nM; Time point: 72 hours.

An additional screen of siRNAs was performed targeting the orf7a SARS-CoV2 gene. siRNAs were tested in in A549-ACE2 cells and the data reported was relative mRNA abundance of the targeted orf7a SARS-CoV2 gene and the percent of cells that are positive for the SARS-CoV2 spike protein. siRNA concentration: 10 nM; Time point: 72 hours. As shown in FIG. 37, numerous siRNAs were identified that effectively target orf7a.

The antisense and sense strands of the siRNAs tested in FIGS. 35 and 36 are shown below in Table 14.

TABLE 14

Antisense and Sense sequences of select siRNAs.

| | Orf7a_27751 | SEQ ID NO: |
|---|---|---|
| Antisense | 5' UGAAAGUUCAAUCAUUCUUUU 3' | 2575 |
| Sense | 5' AAUGAUUGAACUUUCA 3' | 2576 |
| | N_29293 | |
| Antisense | 5' UGAAAUUUGGAUCUUUGUUUU 3' | 2577 |
| Sense | 5' AAAGAUCCAAAUUUCA 3' | 2578 |
| | Orf1a_2290 | |
| Antisense | 5' UAAGCUUAAAGAAUGUCUUUU 3' | 2579 |
| Sense | 5' ACAUUCUUUAAGCUUA 3' | 2580 |
| | Orf1ab_18571 | |
| Antisense | 5' UCAAAUACGACUCUGUCUUUU 3' | 2581 |
| Sense | 5' ACAGAGUCGUAUUUGA 3' | 2582 |

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), Current Protocols in Molecular Biology, John Wiley &Sons, NY (1993);

Ausubel, F. M. et al. eds., Short Protocols in Molecular Biology (4th Ed. 1999) John Wiley & Sons, NY. (ISBN 0-471-32938-X);

Controlled Drug Bioavailability, Drug Product Design and Performance, Smolen and Ball (eds.), Wiley, New York (1984);

Giege, R. and Ducruix, A. Barrett, Crystallization of Nucleic Acids and Proteins, a Practical Approach, 2nd ea., pp. 20 1-16, Oxford University Press, New York, New York, (1999);
Goodson, in Medical Applications of Controlled Release, vol. 2, pp. 115-138 (1984);
Hammerling, et al., in: Monoclonal Antibodies and T-Cell Hybridomas 563-681 (Elsevier, N.Y., 1981;
Harlow et al., Antibodies: a Laboratory Manual, (Cold Spring Harbor Laboratory Press, 2nd ed. 1988);
Kabat et al., Sequences of Proteins of Immunological Interest (National Institutes of Health, Bethesda, Md. (1987) and (1991);
Kabat, E. A., et al. (1991) Sequences of Proteins of Immunological Interest, Fifth Edition, U.S. Department of Health and Human Services, NIH Publication No. 91-3242;
Kontermann and Dubel eds., Antibody Engineering (2001) Springer-Verlag. New York. 790 pp. (ISBN 3-540-41354-5).
Kriegler, Gene Transfer and Expression, A Laboratory Manual, Stockton Press, NY (1990);
Lu and Weiner eds., Cloning and Expression Vectors for Gene Function Analysis (2001) BioTechniques Press. Westborough, MA 298 pp. (ISBN 1-881299-21-X).
Medical Applications of Controlled Release, Langer and Wise (eds.), CRC Pres., Boca Raton, Fla. (1974);
Old, R. W. & S. B. Primrose, Principles of Gene Manipulation: an Introduction to Genetic Engineering (3d Ed. 1985) Blackwell Scientific Publications, Boston. Studies in Microbiology; V.2:409 pp. (ISBN 0-632-01318-4).
Sambrook, J. et al. eds., Molecular Cloning: a Laboratory Manual (2d Ed. 1989) Cold Spring Harbor Laboratory Press, NY. Vols. 1-3. (ISBN 0-87969-309-6).
Sustained and Controlled Release Drug Delivery Systems, J. R. Robinson, ed., Marcel Dekker, Inc., New York, 1978
Winnacker, E. L. From Genes to Clones: Introduction to Gene Technology (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A double-stranded RNA oligonucleotide compound complementary to a SARS-CoV-2 nucleic acid sequence of SEQ ID NO:1, the compound comprising a sense strand and an antisense strand, the antisense strand consisting of a sequence selected from the group consisting of SEQ ID NO: 2575, SEQ ID NO: 2577, SEQ ID NO: 2579, and SEQ ID NO: 2581.

2. The oligonucleotide compound of claim 1, wherein the compound is selected from the group consisting of:

(a) a dsRNA comprising an antisense strand consisting of a sequence of SEQ ID NO: 2575 and a sense strand consisting of a sequence of SEQ ID NO: 2576, (b) a dsRNA comprising an antisense strand consisting of a sequence of SEQ ID NO: 2577 and a sense strand consisting of a sequence of SEQ ID NO: 2578, (c) a dsRNA comprising an antisense strand consisting of a sequence selected of SEQ ID NO: 2575 and a sense strand consisting of a sequence of SEQ ID NO: 2579, and (d) a dsRNA comprising an antisense strand consisting of a sequence selected of SEQ ID NO: 2580 and a sense strand consisting of a sequence of SEQ ID NO: 2581.

3. The oligonucleotide compound of claim 1, wherein the oligonucleotide compound comprises one or more modified nucleotide.

4. The oligonucleotide compound of claim 1, wherein the oligonucleotide compound comprises at least one modified internucleotide linkage of Formula I:

(I)

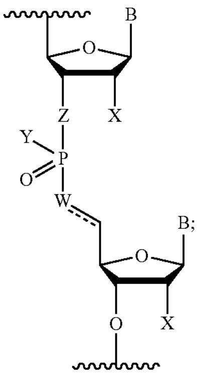

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and

=== is an optional double bond.

5. The oligonucleotide compound of claim 1, wherein a functional moiety is linked to one or both of the 5' end and 3' end of the sense strand.

6. A combination comprising two or more oligonucleotide compounds of claim 1.

7. A vector comprising a regulatory sequence operably linked to a nucleotide sequence that encodes an oligonucleotide compound of claim 1.

8. An isolated cell comprising the vector of claim 7.

9. A recombinant adeno-associated virus (rAAV) comprising the vector of claim 7 and an AAV capsid.

10. A branched oligonucleotide compound comprising two or more of the oligonucleotide compounds of claim 1 covalently bound to one another.

11. A branched RNA oligonucleotide compound comprising:

two or more RNA molecules each comprising 15 to 35 nucleotides in length, and wherein at least two of the RNA molecules each comprise a sequence that is perfectly complementary to at least 10 contiguous nucleotides of a 45 nucleotides target region sequence of SARS-CoV-2 selected from the group consisting of SEQ ID NOs: 127, 132, 202, and 222;

wherein the two or more RNA molecules are connected to one another by one or more moieties independently selected from a linker, a spacer, a branching point, and a combination thereof.

12. The oligonucleotide compound of claim 3, wherein the oligonucleotide compound comprises at least 80% chemically modified nucleotides or 100% chemically modified nucleotides.

13. The oligonucleotide compound of claim 3, wherein the one or more modified nucleotides each independently comprise a modification of a ribose group, a phosphate group, a nucleobase, or a combination thereof.

14. The oligonucleotide compound of claim 13, wherein each modification of the ribose group is independently selected from the group consisting of 2'-O-methyl, 2'-fluoro, 2'-deoxy, 2'-O-(2-methoxyethyl) (MOE), 2'-O-alkyl, 2'-O-alkoxy, 2'-O-alkylamino, 2'-$NH_2$, and a constrained nucleotide.

15. The oligonucleotide compound of claim 14, wherein the constrained nucleotide is selected from the group consisting of a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid (2',4'-$BNA^{NC}$), an alpha-L-locked nucleic acid, a tricyclo-DNA, and any combination thereof.

16. The oligonucleotide compound of claim 13, wherein each modification of the nucleobase group is independently selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, and halogenated aromatic groups.

17. The oligonucleotide compound of claim 13, wherein each modification of the phosphate group is independently selected from the group consisting of a phosphorothioate, phosphonoacetate (PACE), thiophosphonoacetate (thioPACE), amide, triazole, phosphonate, and phosphotriester modification.

18. The oligonucleotide compound of claim 17, comprising 4-16 phosphorothioate modifications or 6-13 phosphorothioate modifications.

* * * * *

SEQUENCE LISTING

```
<160> NUMBER OF SEQ ID NOS: 2596

<210> SEQ ID NO 1
<211> LENGTH: 29903
<212> TYPE: DNA
<213> ORGANISM: Severe acute respiratory syndrome coronavirus 2

<400> SEQUENCE: 1

attaaaggtt tataccttcc caggtaacaa accaaccaac tttcgatctc ttgtagatct     60

gttctctaaa cgaactttaa aatctgtgtg gctgtcactc ggctgcatgc ttagtgcact    120

cacgcagtat aattaataac taattactgt cgttgacagg acacgagtaa ctcgtctatc    180

ttctgcaggc tgcttacggt ttcgtccgtg ttgcagccga tcatcagcac atctaggttt    240

cgtccgggtg tgaccgaaag gtaagatgga gagccttgtc cctggtttca acgagaaaac    300

acacgtccaa ctcagtttgc ctgttttaca ggttcgcgac gtgctcgtac gtggctttgg    360

agactccgtg gaggaggtct tatcagaggc acgtcaacat cttaaagatg gcacttgtgg    420

cttagtagaa gttgaaaaag gcgttttgcc tcaacttgaa cagccctatg tgttcatcaa    480

acgttcggat gctcgaactg cacctcatgg tcatgttatg gttgagctgg tagcagaact    540

cgaaggcatt cagtacggtc gtagtggtga gacacttggt gtccttgtcc ctcatgtggg    600

cgaaatacca gtggcttacc gcaaggttct tcttcgtaag aacggtaata aaggagctgg    660

tggccatagt tacggcgccg atctaaagtc atttgactta ggcgacgagc ttggcactga    720

tccttatgaa gattttcaag aaaactggaa cactaaacat agcagtggtg ttacccgtga    780

actcatgcgt gagcttaacg gaggggcata cactcgctat gtcgataaca acttctgtgg    840

ccctgatggc taccctcttg agtgcattaa agaccttcta gcacgtgctg gtaaagcttc    900

atgcactttg tccgaacaac tggactttat tgacactaag aggggtgtat actgctgccg    960

tgaacatgag catgaaattg cttggtacac ggaacgttct gaaaagagct atgaattgca   1020

gacacctttt gaaattaaat tggcaaagaa atttgacacc ttcaatgggg aatgtccaaa   1080

ttttgtattt cccttaaatt ccataatcaa gactattcaa ccaagggttg aaaagaaaaa   1140
```

-continued

```
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
```

aggagcctta aataaggcta ctaacaatgc catgcaagtt gaatctgatg attacatagc 3540
tactaatgga ccacttaaag tgggtggtag ttgtgtttta agcggacaca atcttgctaa 3600
acactgtctt catgttgtcg gcccaaatgt taacaaaggt gaagacattc aacttcttaa 3660
gagtgcttat gaaaatttta atcagcacga agttctactt gcaccattat tatcagctgg 3720
tatttttggt gctgacccta tacattcttt aagagtttgt gtagatactg ttcgcacaaa 3780
tgtctactta gctgtctttg ataaaaatct ctatgacaaa cttgtttcaa gctttttgga 3840
aatgaagagt gaaaagcaag ttgaacaaaa gatcgctgag attcctaaag aggaagttaa 3900
gccatttata actgaaagta aaccttcagt tgaacagaga aaacaagatg ataagaaaat 3960
caaagcttgt gttgaagaag ttacaacaac tctggaagaa actaagttcc tcacagaaaa 4020
cttgttactt tatattgaca ttaatggcaa tcttcatcca gattctgcca ctcttgttag 4080
tgacattgac atcactttct taaagaaaga tgctccatat atagtgggtg atgttgttca 4140
agagggtgtt ttaactgctg tggttatacc tactaaaaag gctggtggca ctactgaaat 4200
gctagcgaaa gctttgagaa aagtgccaac agacaattat ataaccactt acccgggtca 4260
gggtttaaat ggttacactg tagaggaggc aaagacagtg cttaaaaagt gtaaaagtgc 4320
cttttacatt ctaccatcta ttatctctaa tgagaagcaa gaaattcttg gaactgtttc 4380
ttggaatttg cgagaaatgc ttgcacatgc agaagaaaca cgcaaattaa tgcctgtctg 4440
tgtggaaact aaagccatag tttcaactat acagcgtaaa tataagggta ttaaaataca 4500
agagggtgtg gttgattatg gtgctagatt ttacttttac accagtaaaa caactgtagc 4560
gtcacttatc aacacactta acgatctaaa tgaaactctt gttacaatgc cacttggcta 4620
tgtaacacat ggcttaaatt tggaagaagc tgctcggtat atgagatctc tcaaagtgcc 4680
agctacagtt tctgtttctt cacctgatgc tgttacagcg tataatggtt atcttacttc 4740
ttcttctaaa acacctgaag aacattttat tgaaaccatc tcacttgctg gttcctataa 4800
agattggtcc tattctggac aatctacaca actaggtata gaatttctta agagaggtga 4860
taaaagtgta tattacacta gtaatcctac cacattccac ctagatggtg aagttatcac 4920
ctttgacaat cttaagacac ttctttcttt gagagaagtg aggactatta aggtgtttac 4980
aacagtagac aacattaacc tccacacgca agttgtggac atgtcaatga catatggaca 5040
acagtttggt ccaacttatt tggatggagc tgatgttact aaaataaaac ctcataattc 5100
acatgaaggt aaaacatttt atgttttacc taatgatgac actctacgtg ttgaggcttt 5160
tgagtactac cacacaactg atcctagttt tctgggtagg tacatgtcag cattaaatca 5220
cactaaaaag tggaaatacc cacaagttaa tggtttaact tctattaaat gggcagataa 5280
caactgttat cttgccactg cattgttaac actccaacaa atagagttga agtttaatcc 5340
acctgctcta caagatgctt attacagagc aagggctggt gaagctgcta acttttgtgc 5400
acttatctta gcctactgta ataagacagt aggtgagtta ggtgatgtta gagaaacaat 5460
gagttacttg tttcaacatg ccaatttaga ttcttgcaaa agagtcttga acgtggtgtg 5520
taaaacttgt ggacaacagc agacaaccct taagggtgta gaagctgtta tgtacatggg 5580
cacactttct tatgaacaat ttaagaaagg tgttcagata ccttgtacgt gtggtaaaca 5640
agctacaaaa tatctagtac aacaggagtc accttttgtt atgatgtcag caccacctgc 5700
tcagtatgaa cttaagcatg gtacatttac ttgtgctagt gagtacactg gtaattacca 5760
gtgtggtcac tataaacata taacttctaa agaaactttg tattgcatag acggtgcttt 5820
acttacaaag tcctcagaat acaaaggtcc tattacggat gttttctaca aagaaaacag 5880

-continued

```
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
```

-continued

```
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggacctttg ttgacaggca  10620
```

aacagcacaa gcagctggta cggacacaac tattacagtt aatgttttag cttggttgta 10680
cgctgctgtt ataaatggag acaggtggtt tctcaatcga tttaccacaa ctcttaatga 10740
ctttaacctt gtggctatga agtacaatta tgaacctcta acacaagacc atgttgacat 10800
actaggacct ctttctgctc aaactggaat tgccgtttta gatatgtgtg cttcattaaa 10860
agaattactg caaaatggta tgaatggacg taccatattg ggtagtgctt tattagaaga 10920
tgaatttaca ccttttgatg ttgttagaca atgctcaggt gttactttcc aaagtgcagt 10980
gaaaagaaca atcaagggta cacaccactg gttgttactc acaattttga cttcactttt 11040
agttttagtc cagagtactc aatggtcttt gttctttttt ttgtatgaaa atgccttttt 11100
accttttgct atgggtatta ttgctatgtc tgcttttgca atgatgtttg tcaaacataa 11160
gcatgcattt ctctgtttgt ttttgttacc ttctcttgcc actgtagctt attttaatat 11220
ggtctatatg cctgctagtt gggtgatgcg tattatgaca tggttggata tggttgatac 11280
tagtttgtct ggttttaagc taaaagactg tgttatgtat gcatcagctg tagtgttact 11340
aatccttatg acagcaagaa ctgtgtatga tgatggtgct aggagagtgt ggacacttat 11400
gaatgtcttg acactcgttt ataaagttta ttatggtaat gctttagatc aagccatttc 11460
catgtgggct cttataatct ctgttacttc taactactca ggtgtagtta caactgtcat 11520
gtttttggcc agaggtattg tttttatgtg tgttgagtat tgccctattt tcttcataac 11580
tggtaataca cttcagtgta taatgctagt ttattgtttc ttaggctatt tttgtacttg 11640
ttactttggc ctcttttgtt tactcaaccg ctactttaga ctgactcttg gtgtttatga 11700
ttacttagtt tctacacagg agtttagata tatgaattca cagggactac tcccacccaa 11760
gaatagcata gatgccttca aactcaacat taaattgttg ggtgttggtg gcaaaccttg 11820
tatcaaagta gccactgtac agtctaaaat gtcagatgta aagtgcacat cagtagtctt 11880
actctcagtt ttgcaacaac tcagagtaga atcatcatct aaattgtggg ctcaatgtgt 11940
ccagttacac aatgacattc tcttagctaa agatactact gaagcctttg aaaaaatggt 12000
ttcactactt tctgttttgc tttccatgca gggtgctgta gacataaaca agctttgtga 12060
agaaatgctg gacaacaggg caaccttaca agctatagcc tcagagttta gttcccttcc 12120
atcatatgca gcttttgcta ctgctcaaga agcttatgag caggctgttg ctaatggtga 12180
ttctgaagtt gttcttaaaa agttgaagaa gtctttgaat gtggctaaat ctgaatttga 12240
ccgtgatgca gccatgcaac gtaagttgga aaagatggct gatcaagcta tgacccaaat 12300
gtataaacag gctagatctg aggacaagag ggcaaaagtt actagtgcta tgcagacaat 12360
gcttttcact atgcttagaa agttggataa tgatgcactc aacaacatta tcaacaatgc 12420
aagagatggt tgtgttccct tgaacataat acctcttaca acagcagcca aactaatggt 12480
tgtcatacca gactataaca catataaaaa tacgtgtgat ggtacaacat ttacttatgc 12540
atcagcattg tgggaaatcc aacaggttgt agatgcagat agtaaaattg ttcaacttag 12600
tgaaattagt atggacaatt cacctaattt agcatggcct cttattgtaa cagctttaag 12660
ggccaattct gctgtcaaat tacagaataa tgagcttagt cctgttgcac tacgacagat 12720
gtcttgtgct gccggtacta cacaaactgc ttgcactgat gacaatgcgt tagcttacta 12780
caacacaaca aagggaggta ggtttgtact tgcactgtta tccgatttac aggatttgaa 12840
atgggctaga ttccctaaga gtgatggaac tggtactatc tatacagaac tggaaccacc 12900
ttgtaggttt gttacagaca cacctaaagg tcctaaagtg aagtatttat actttattaa 12960

```
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
```

aaacatacaa cgtgttgtag cttgtcacac cgtttctata gattagctaa tgagtgtgct 15420
caagtattga gtgaaatggt catgtgtggc ggttcactat atgttaaacc aggtggaacc 15480
tcatcaggag atgccacaac tgcttatgct aatagtgttt ttaacatttg tcaagctgtc 15540
acggccaatg ttaatgcact tttatctact gatggtaaca aaattgccga taagtatgtc 15600
cgcaatttac aacacagact ttatgagtgt ctctatagaa atagagatgt tgacacagac 15660
tttgtgaatg agttttacgc atatttgcgt aaacatttct caatgatgat actctctgac 15720
gatgctgttg tgtgtttcaa tagcacttat gcatctcaag gtctagtggc tagcataaag 15780
aactttaagt cagttcttta ttatcaaaac aatgttttta tgtctgaagc aaaatgttgg 15840
actgagactg accttactaa aggacctcat gaattttgct ctcaacatac aatgctagtt 15900
aaacagggtg atgattatgt gtaccttcct tacccagatc catcaagaat cctaggggcc 15960
ggctgttttg tagatgatat cgtaaaaaca gatggtacac ttatgattga acggttcgtg 16020
tctttagcta tagatgctta cccacttact aaacatccta atcaggagta tgctgatgtc 16080
tttcatttgt acttacaata cataagaaag ctacatgatg agttaacagg acacatgtta 16140
gacatgtatt ctgttatgct tactaatgat aacacttcaa ggtattggga acctgagttt 16200
tatgaggcta tgtacacacc gcatacagtc ttacaggctg ttggggcttg tgttctttgc 16260
aattcacaga cttcattaag atgtggtgct tgcatacgta gaccattctt atgttgtaaa 16320
tgctgttacg accatgtcat atcaacatca cataaattag tcttgtctgt taatccgtat 16380
gtttgcaatg ctccaggttg tgatgtcaca gatgtgactc aactttactt aggaggtatg 16440
agctattatt gtaaatcaca taaaccaccc attagttttc cattgtgtgc taatggacaa 16500
gtttttggtt tatataaaaa tacatgtgtt ggtagcgata atgttactga ctttaatgca 16560
attgcaacat gtgactggac aaatgctggt gattacattt tagctaacac ctgtactgaa 16620
agactcaagc tttttgcagc agaaacgctc aaagctactg aggagacatt taaactgtct 16680
tatggtattg ctactgtacg tgaagtgctg tctgacagag aattacatct ttcatgggaa 16740
gttggtaaac ctagaccacc acttaaccga aattatgtct ttactggtta tcgtgtaact 16800
aaaaacagta aagtacaaat aggagagtac acctttgaaa aaggtgacta tggtgatgct 16860
gttgtttacc gaggtacaac aacttacaaa ttaaatgttg gtgattattt tgtgctgaca 16920
tcacatacag taatgccatt aagtgcacct acactagtgc cacaagagca ctatgttaga 16980
attactggct tatacccaac actcaatatc tcagatgagt tttctagcaa tgttgcaaat 17040
tatcaaaagg ttggtatgca aaagtattct acactccagg gaccacctgg tactggtaag 17100
agtcattttg ctattggcct agctctctac taccctctg ctcgcatagt gtatacagct 17160
tgctctcatg ccgctgttga tgcactatgt gagaaggcat taaaatattt gcctatagat 17220
aaatgtagta gaattatacc tgcacgtgct cgtgtagagt gttttgataa attcaaagtg 17280
aattcaacat tagaacagta tgtcttttgt actgtaaatg cattgcctga gacgacagca 17340
gatatagttg tctttgatga aatttcaatg gccacaaatt atgatttgag tgttgtcaat 17400
gccagattac gtgctaagca ctatgtgtac attggcgacc ctgctcaatt acctgcacca 17460
cgcacattgc taactaaggg cacactagaa ccagaatatt tcaattcagt gtgtagactt 17520
atgaaaacta taggtccaga catgttcctc ggaacttgtc ggcgttgtcc tgctgaaatt 17580
gttgacactg tgagtgcttt ggtttatgat aataagctta aagcacataa agacaaatca 17640
gctcaatgct ttaaaatgtt ttataagggt gttatcacgc atgatgtttc atctgcaatt 17700

-continued

```
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtctttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
```

```
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attaccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
```

tgaccctctc tcagaaacaa agtgtacgtt gaaatccttc actgtagaaa aaggaatcta 22500
tcaaacttct aactttagag tccaaccaac agaatctatt gttagatttc ctaatattac 22560
aaacttgtgc ccttttggtg aagtttttaa cgccaccaga tttgcatctg tttatgcttg 22620
gaacaggaag agaatcagca actgtgttgc tgattattct gtcctatata attccgcatc 22680
attttccact tttaagtgtt atggagtgtc tcctactaaa ttaaatgatc tctgctttac 22740
taatgtctat gcagattcat ttgtaattag aggtgatgaa gtcagacaaa tcgctccagg 22800
gcaaactgga aagattgctg attataatta taaattacca gatgatttta caggctgcgt 22860
tatagcttgg aattctaaca atcttgattc taaggttggt ggtaattata attacctgta 22920
tagattgttt aggaagtcta atctcaaacc ttttgagaga gatatttcaa ctgaaatcta 22980
tcaggccggt agcacacctt gtaatggtgt tgaaggtttt aattgttact ttcctttaca 23040
atcatatggt ttccaaccca ctaatggtgt tggttaccaa ccatacagag tagtagtact 23100
ttcttttgaa cttctacatg caccagcaac tgtttgtgga cctaaaaagt ctactaattt 23160
ggttaaaaac aaatgtgtca atttcaactt caatggttta acaggcacag gtgttcttac 23220
tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400
ggatgttaac tgcacagaag tccctgttgc tattcatgca gatcaactta ctcctacttg 23460
gcgtgtttat tctacaggtt ctaatgtttt tcaaacacgt gcaggctgtt taataggggc 23520
tgaacatgtc aacaactcat atgagtgtga catacccatt ggtgcaggta tatgcgctag 23580
ttatcagact cagactaatt ctcctcggcg ggcacgtagt gtagctagtc aatccatcat 23640
tgcctacact atgtcacttg gtgcagaaaa ttcagttgct tactctaata actctattgc 23700
catacccaca aattttacta ttagtgttac cacagaaatt ctaccagtgt ctatgaccaa 23760
gacatcagta gattgtacaa tgtacatttg tggtgattca actgaatgca gcaatctttt 23820
gttgcaatat ggcagttttt gtacacaatt aaaccgtgct ttaactggaa tagctgttga 23880
acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360
aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560
cagagcgctt ccaaaatcat aaccctcaaa aagagatggc aactagcact ctccaagggt 25620
gttcactttg tttgcaactt gctgttgttg tttgtaacag tttactcaca ccttttgctc 25680
gttgctgctg gccttgaagc cccttttctc tatctttatg ctttagtcta cttcttgcag 25740
agtataaact tgtaagaat aataatgagg ctttggcttt gctggaaatg ccgttccaaa 25800
aacccattac tttatgatgc caactatttt ctttgctggc atactaattg ttacgactat 25860
tgtatacctt acaatagtgt aacttcttca attgtcatta cttcaggtga tggcacaaca 25920
agtcctattt ctgaacatga ctaccagatt ggtggttata ctgaaaaatg ggaatctgga 25980
gtaaaagact gtgttgtatt acacagttac ttcacttcag actattacca gctgtactca 26040
actcaattga gtacagacac tggtgttgaa catgttacct tcttcatcta caataaaatt 26100
gttgatgagc ctgaagaaca tgtccaaatt cacacaatcg acggttcatc cggagttgtt 26160
aatccagtaa tggaaccaat ttatgatgaa ccgacgacga ctactagcgt gcctttgtaa 26220
gcacaagctg atgagtacga acttatgtac tcattcgttt cggaagagac aggtacgtta 26280
atagttaata gcgtacttct ttttcttgct ttcgtggtat tcttgctagt tacactagcc 26340
atccttactg cgcttcgatt gtgtgcgtac tgctgcaata ttgttaacgt gagtcttgta 26400
aaaccttctt tttacgttta ctctcgtgtt aaaaatctga attcttctag agttcctgat 26460
cttctggtct aaacgaacta aatattatat tagtttttct gtttggaact ttaattttag 26520
ccatggcaga ttccaacggt actattaccg ttgaagagct taaaaagctc cttgaacaat 26580
ggaacctagt aataggtttc ctattcctta catggatttg tcttctacaa tttgcctatg 26640
ccaacaggaa taggtttttg tatataatta agttaatttt cctctggctg ttatggccag 26700
taactttagc ttgttttgtg cttgctgctg tttacagaat aaattggatc accggtggaa 26760
ttgctatcgc aatggcttgt cttgtaggct tgatgtggct cagctacttc attgcttctt 26820
tcagactgtt tgcgcgtacg cgttccatgt ggtcattcaa tccagaaact aacattcttc 26880
tcaacgtgcc actccatggc actattctga ccagaccgct tctagaaagt gaactcgtaa 26940
tcggagctgt gatccttcgt ggacatcttc gtattgctgg acaccatcta ggacgctgtg 27000
acatcaagga cctgcctaaa gaaatcactg ttgctacatc acgaacgctt tcttattaca 27060
aattgggagc ttcgcagcgt gtagcaggtg actcaggttt tgctgcatac agtcgctaca 27120
ggattggcaa ctataaatta aacacagacc attccagtag cagtgacaat attgctttgc 27180

```
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
```

```
ttttccgttt acgatatata gtctactctt gtgcagaatg aattctcgta actacatagc  29640

acaagtagat gtagttaact ttaatctcac atagcaatct ttaatcagtg tgtaacatta  29700

gggaggactt gaaagagcca ccacattttc accgaggcca cgcggagtac gatcgagtgt  29760

acagtgaaca atgctaggga gagctgccta tatggaagag ccctaatgtg taaaattaat  29820

tttagtagtg ctatccccat gtgattttaa tagcttctta ggagaatgac aaaaaaaaaa  29880

aaaaaaaaaa aaaaaaaaaa aaa                                          29903


<210> SEQ ID NO 2
<211> LENGTH: 13217
<212> TYPE: DNA
<213> ORGANISM: Severe acute respiratory syndrome coronavirus 2

<400> SEQUENCE: 2

atggagagcc ttgtccctgg tttcaacgag aaaacacacg tccaactcag tttgcctgtt     60

ttacaggttc gcgacgtgct cgtacgtggc tttggagact ccgtggagga ggtcttatca    120

gaggcacgtc aacatcttaa agatggcact tgtggcttag tagaagttga aaaaggcgtt    180

ttgcctcaac ttgaacagcc ctatgtgttc atcaaacgtt cggatgctcg aactgcacct    240

catggtcatg ttatggttga gctggtagca gaactcgaag gcattcagta cggtcgtagt    300

ggtgagacac ttggtgtcct tgtccctcat gtgggcgaaa taccagtggc ttaccgcaag    360

gttcttcttc gtaagaacgg taataaagga gctggtggcc atagttacgg cgccgatcta    420

aagtcatttg acttaggcga cgagcttggc actgatcctt atgaagattt tcaagaaaac    480

tggaacacta aacatagcag tggtgttacc cgtgaactca tgcgtgagct taacggaggg    540

gcatacactc gctatgtcga taacaacttc tgtggccctg atggctaccc tcttgagtgc    600

attaaagacc ttctagcacg tgctggtaaa gcttcatgca ctttgtccga acaactggac    660

tttattgaca ctaagagggg tgtatactgc tgccgtgaac atgagcatga aattgcttgg    720

tacacggaac gttctgaaaa gagctatgaa ttgcagacac cttttgaaat taaattggca    780

aagaaatttg acaccttcaa tggggaatgt ccaaattttg tatttccctt aaattccata    840

atcaagacta ttcaaccaag ggttgaaaag aaaaagcttg atggctttat gggtagaatt    900

cgatctgtct atccagttgc gtcaccaaat gaatgcaacc aaatgtgcct ttcaactctc    960

atgaagtgtg atcattgtgg tgaaacttca tggcagacgg gcgattttgt taaagccact   1020

tgcgaatttt gtggcactga gaatttgact aaagaaggtg ccactacttg tggttactta   1080

ccccaaaatg ctgttgttaa aatttattgt ccagcatgtc acaattcaga agtaggacct   1140

gagcatagtc ttgccgaata ccataatgaa tctggcttga aaaccattct tcgtaagggt   1200

ggtcgcacta ttgcctttgg aggctgtgtg ttctcttatg ttggttgcca taacaagtgt   1260

gcctattggg ttccacgtgc tagcgctaac ataggttgta accatacagg tgttgttgga   1320

gaaggttccg aaggtcttaa tgacaacctt cttgaaatac tccaaaaaga gaaagtcaac   1380

atcaatattg ttggtgactt taaacttaat gaagagatcg ccattatttt ggcatctttt   1440

tctgcttcca caagtgcttt tgtggaaact gtgaaaggtt tggattataa agcattcaaa   1500

caaattgttg aatcctgtgg taattttaaa gttacaaaag gaaaagctaa aaaaggtgcc   1560

tggaatattg gtgaacagaa atcaatactg agtcctcttt atgcatttgc atcagaggct   1620

gctcgtgttg tacgatcaat ttctcccgc actcttgaaa ctgctcaaaa ttctgtgcgt   1680

gttttacaga aggccgctat aacaatacta gatggaattt cacagtattc actgagactc   1740
```

-continued

```
attgatgcta tgatgttcac atctgatttg gctactaaca atctagttgt aatggcctac   1800
attacaggtg gtgttgttca gttgacttcg cagtggctaa ctaacatctt tggcactgtt   1860
tatgaaaaac tcaaacccgt ccttgattgg cttgaagaga agtttaagga aggtgtagag   1920
tttcttagag acggttggga aattgttaaa tttatctcaa cctgtgcttg tgaaattgtc   1980
ggtggacaaa ttgtcacctg tgcaaaggaa attaaggaga gtgttcagac attctttaag   2040
cttgtaaata aatttttggc tttgtgtgct gactctatca ttattggtgg agctaaactt   2100
aaagccttga atttaggtga aacatttgtc acgcactcaa agggattgta cagaaagtgt   2160
gttaaatcca gagaagaaac tggcctactc atgcctctaa aagccccaaa agaaattatc   2220
ttcttagagg gagaaacact tcccacagaa gtgttaacag aggaagttgt cttgaaaact   2280
ggtgatttac aaccattaga acaacctact agtgaagctg ttgaagctcc attggttggt   2340
acaccagttt gtattaacgg gcttatgttg ctcgaaatca aagacacaga aaagtactgt   2400
gcccttgcac ctaatatgat ggtaacaaac aataccttca cactcaaagg cggtgcacca   2460
acaaaggtta cttttggtga tgacactgtg atagaagtgc aaggttacaa gagtgtgaat   2520
atcacttttg aacttgatga aaggattgat aaagtactta atgagaagtg ctctgcctat   2580
acagttgaac tcggtacaga agtaaatgag ttcgcctgtg ttgtggcaga tgctgtcata   2640
aaaactttgc aaccagtatc tgaattactt acaccactgg gcattgattt agatgagtgg   2700
agtatggcta catactactt atttgatgag tctggtgagt ttaaattggc ttcacatatg   2760
tattgttctt tctaccctcc agatgaggat gaagaagaag gtgattgtga agaagaagag   2820
tttgagccat caactcaata tgagtatggt actgaagatg attaccaagg taaacctttg   2880
gaatttggtg ccacttctgc tgctcttcaa cctgaagaag agcaagaaga agattggtta   2940
gatgatgata gtcaacaaac tgttggtcaa caagacggca gtgaggacaa tcagacaact   3000
actattcaaa caattgttga ggttcaacct caattagaga tggaacttac accagttgtt   3060
cagactattg aagtgaatag ttttagtggt tatttaaaac ttactgacaa tgtatacatt   3120
aaaaatgcag acattgtgga agaagctaaa aaggtaaaac caacagtggt tgttaatgca   3180
gccaatgttt accttaaaca tggaggaggt gttgcaggag ccttaaataa ggctactaac   3240
aatgccatgc aagttgaatc tgatgattac atagctacta atggaccact taaagtgggt   3300
ggtagttgtg ttttaagcgg acacaatctt gctaaacact gtcttcatgt tgtcggccca   3360
aatgttaaca aaggtgaaga cattcaactt cttaagagtg cttatgaaaa ttttaatcag   3420
cacgaagttc tacttgcacc attattatca gctggtattt ttggtgctga ccctatacat   3480
tctttaagag tttgtgtaga tactgttcgc acaaatgtct acttagctgt ctttgataaa   3540
aatctctatg acaaacttgt ttcaagcttt ttggaaatga agagtgaaaa gcaagttgaa   3600
caaaagatcg ctgagattcc taaagaggaa gttaagccat ttataactga aagtaaacct   3660
tcagttgaac agagaaaaca agatgataag aaaatcaaag cttgtgttga agaagttaca   3720
acaactctgg aagaaactaa gttcctcaca gaaaacttgt tactttatat tgacattaat   3780
ggcaatcttc atccagattc tgccactctt gttagtgaca ttgacatcac tttcttaaag   3840
aaagatgctc catatatagt gggtgatgtt gttcaagagg gtgttttaac tgctgtggtt   3900
atacctacta aaaaggctgg tggcactact gaaatgctag cgaaagcttt gagaaaagtg   3960
ccaacagaca attatataac cacttacccg ggtcagggtt taaatggtta cactgtagag   4020
gaggcaaaga cagtgcttaa aaagtgtaaa agtgcctttt acattctacc atctattatc   4080
tctaatgaga agcaagaaat tcttggaact gtttcttgga atttgcgaga aatgcttgca   4140
```

-continued

```
catgcagaag aaacacgcaa attaatgcct gtctgtgtgg aaactaaagc catagtttca   4200
actatacagc gtaaatataa gggtattaaa atacaagagg gtgtggttga ttatggtgct   4260
agattttact tttacaccag taaaacaact gtagcgtcac ttatcaacac acttaacgat   4320
ctaaatgaaa ctcttgttac aatgccactt ggctatgtaa cacatggctt aaatttggaa   4380
gaagctgctc ggtatatgag atctctcaaa gtgccagcta cagtttctgt ttcttcacct   4440
gatgctgtta cagcgtataa tggttatctt acttcttctt ctaaaacacc tgaagaacat   4500
tttattgaaa ccatctcact tgctggttcc tataaagatt ggtcctattc tggacaatct   4560
acacaactag gtatagaatt tcttaagaga ggtgataaaa gtgtatatta cactagtaat   4620
cctaccacat tccacctaga tggtgaagtt atcacctttg acaatcttaa gacacttctt   4680
tctttgagag aagtgaggac tattaaggtg tttacaacag tagacaacat taacctccac   4740
acgcaagttg tggacatgtc aatgacatat ggacaacagt ttggtccaac ttatttggat   4800
ggagctgatg ttactaaaat aaaacctcat aattcacatg aaggtaaaac attttatgtt   4860
ttacctaatg atgacactct acgtgttgag gcttttgagt actaccacac aactgatcct   4920
agttttctgg gtaggtacat gtcagcatta aatcacacta aaaagtggaa atacccacaa   4980
gttaatggtt taacttctat taaatgggca gataacaact gttatcttgc cactgcattg   5040
ttaacactcc aacaaataga gttgaagttt aatccacctg ctctacaaga tgcttattac   5100
agagcaaggg ctggtgaagc tgctaacttt tgtgcactta tcttagccta ctgtaataag   5160
acagtaggtg agttaggtga tgttagagaa acaatgagtt acttgtttca acatgccaat   5220
ttagattctt gcaaaagagt cttgaacgtg gtgtgtaaaa cttgtggaca acagcagaca   5280
acccttaagg gtgtagaagc tgttatgtac atgggcacac tttcttatga acaatttaag   5340
aaaggtgttc agataccttg tacgtgtggt aaacaagcta caaaatatct agtacaacag   5400
gagtcacctt ttgttatgat gtcagcacca cctgctcagt atgaacttaa gcatggtaca   5460
tttacttgtg ctagtgagta cactggtaat taccagtgtg gtcactataa acatataact   5520
tctaaagaaa ctttgtattg catagacggt gctttactta caaagtcctc agaatacaaa   5580
ggtcctatta cggatgtttt ctacaaagaa aacagttaca caacaaccat aaaaccagtt   5640
acttataaat tggatggtgt tgtttgtaca gaaattgacc ctaagttgga caattattat   5700
aagaaagaca attcttattt cacagagcaa ccaattgatc ttgtaccaaa ccaaccatat   5760
ccaaacgcaa gcttcgataa ttttaagttt gtatgtgata atatcaaatt tgctgatgat   5820
ttaaaccagt taactggtta taagaaacct gcttcaagag agcttaaagt tacatttttc   5880
cctgacttaa atggtgatgt ggtggctatt gattataaac actacacacc ctcttttaag   5940
aaaggagcta aattgttaca taaacctatt gtttggcatg ttaacaatgc aactaataaa   6000
gccacgtata aaccaaatac ctggtgtata cgttgtcttt ggagcacaaa accagttgaa   6060
acatcaaatt cgtttgatgt actgaagtca gaggacgcgc agggaatgga taatcttgcc   6120
tgcgaagatc taaaaccagt ctctgaagaa gtagtggaaa atcctaccat acagaaagac   6180
gttcttgagt gtaatgtgaa aactaccgaa gttgtaggag acattatact taaaccagca   6240
aataatagtt taaaaattac agaagaggtt ggccacacag atctaatggc tgcttatgta   6300
gacaattcta gtcttactat taagaaacct aatgaattat ctagagtatt aggtttgaaa   6360
acccttgcta ctcatggttt agctgctgtt aatagtgtcc cttgggatac tatagctaat   6420
tatgctaagc cttttcttaa caaagttgtt agtacaacta ctaacatagt tacacggtgt   6480
```

-continued

```
ttaaaccgtg tttgtactaa ttatatgcct tatttcttta ctttattgct acaattgtgt   6540
acttttacta gaagtacaaa ttctagaatt aaagcatcta tgccgactac tatagcaaag   6600
aatactgtta agagtgtcgg taaattttgt ctagaggctt catttaatta tttgaagtca   6660
cctaattttt ctaaactgat aaatattata atttggtttt tactattaag tgtttgccta   6720
ggttctttaa tctactcaac cgctgcttta ggtgttttaa tgtctaattt aggcatgcct   6780
tcttactgta ctggttacag agaaggctat ttgaactcta ctaatgtcac tattgcaacc   6840
tactgtactg gttctatacc ttgtagtgtt tgtcttagtg gtttagattc tttagacacc   6900
tatccttctt tagaaactat acaaattacc atttcatctt ttaaatggga tttaactgct   6960
tttggcttag ttgcagagtg gtttttggca tatattcttt tcactaggtt tttctatgta   7020
cttggattgg ctgcaatcat gcaattgttt ttcagctatt ttgcagtaca ttttattagt   7080
aattcttggc ttatgtggtt aataattaat cttgtacaaa tggccccgat ttcagctatg   7140
gttagaatgt acatcttctt tgcatcattt tattatgtat ggaaaagtta tgtgcatgtt   7200
gtagacggtt gtaattcatc aacttgtatg atgtgttaca aacgtaatag agcaacaaga   7260
gtcgaatgta caactattgt taatggtgtt agaaggtcct tttatgtcta tgctaatgga   7320
ggtaaaggct tttgcaaact acacaattgg aattgtgtta attgtgatac attctgtgct   7380
ggtagtacat ttattagtga tgaagttgcg agagacttgt cactacagtt taaaagacca   7440
ataaatccta ctgaccagtc ttcttacatc gttgatagtg ttacagtgaa gaatggttcc   7500
atccatcttt actttgataa agctggtcaa aagacttatg aaagacattc tctctctcat   7560
tttgttaact tagacaacct gagagctaat aacactaaag gttcattgcc tattaatgtt   7620
atagtttttg atggtaaatc aaaatgtgaa gaatcatctg caaaatcagc gtctgtttac   7680
tacagtcagc ttatgtgtca acctatactg ttactagatc aggcattagt gtctgatgtt   7740
ggtgatagtg cggaagttgc agttaaaatg tttgatgctt acgttaatac gttttcatca   7800
acttttaacg taccaatgga aaaactcaaa acactagttg caactgcaga agctgaactt   7860
gcaaagaatg tgtccttaga caatgtctta tctactttta tttcagcagc tcggcaaggg   7920
tttgttgatt cagatgtaga aactaaagat gttgttgaat gtcttaaatt gtcacatcaa   7980
tctgacatag aagttactgg cgatagttgt aataactata tgctcaccta taacaaagtt   8040
gaaaacatga caccccgtga ccttggtgct tgtattgact gtagtgcgcg tcatattaat   8100
gcgcaggtag caaaaagtca caacattgct ttgatatgga acgttaaaga tttcatgtca   8160
ttgtctgaac aactacgaaa acaaatacgt agtgctgcta aaaagaataa cttacctttt   8220
aagttgacat gtgcaactac tagacaagtt gttaatgttg taacaacaaa gatagcactt   8280
aagggtggta aaattgttaa taattggttg aagcagttaa ttaaagttac acttgtgttc   8340
ctttttgttg ctgctatttt ctatttaata acacctgttc atgtcatgtc taaacatact   8400
gacttttcaa gtgaaatcat aggatacaag gctattgatg gtggtgtcac tcgtgacata   8460
gcatctacag atacttgttt tgctaacaaa catgctgatt ttgacacatg gtttagccag   8520
cgtggtggta gttatactaa tgacaaagct tgcccattga ttgctgcagt cataacaaga   8580
gaagtgggtt ttgtcgtgcc tggtttgcct ggcacgatat tacgcacaac taatggtgac   8640
tttttgcatt tcttacctag agtttttagt gcagttggta acatctgtta cacaccatca   8700
aaacttatag agtacactga ctttgcaaca tcagcttgtg ttttggctgc tgaatgtaca   8760
atttttaaag atgcttctgg taagccagta ccatattgtt atgataccaa tgtactagaa   8820
ggttctgttg cttatgaaag tttacgccct gacacacgtt atgtgctcat ggatggctct   8880
```

```
attattcaat ttcctaacac ctaccttgaa ggttctgtta gagtggtaac aacttttgat   8940
tctgagtact gtaggcacgg cacttgtgaa agatcagaag ctggtgtttg tgtatctact   9000
agtggtagat gggtacttaa caatgattat tacagatctt taccaggagt tttctgtggt   9060
gtagatgctg taaatttact tactaatatg tttacaccac taattcaacc tattggtgct   9120
ttggacatat cagcatctat agtagctggt ggtattgtag ctatcgtagt aacatgcctt   9180
gcctactatt ttatgaggtt tagaagagct tttggtgaat acagtcatgt agttgccttt   9240
aatactttac tattccttat gtcattcact gtactctgtt taacaccagt ttactcattc   9300
ttacctggtg tttattctgt tatttacttg tacttgacat tttatcttac taatgatgtt   9360
tctttttag cacatattca gtggatggtt atgttcacac ctttagtacc tttctggata   9420
acaattgctt atatcatttg tatttccaca aagcatttct attggttctt tagtaattac   9480
ctaaagagac gtgtagtctt taatggtgtt tcctttagta cttttgaaga agctgcgctg   9540
tgcacctttt tgttaaataa agaaatgtat ctaaagttgc gtagtgatgt gctattacct   9600
cttacgcaat ataatagata cttagctctt tataataagt acaagtattt tagtggagca   9660
atggatacaa ctagctacag agaagctgct tgttgtcatc tcgcaaaggc tctcaatgac   9720
ttcagtaact caggttctga tgttctttac caaccaccac aaacctctat cacctcagct   9780
gttttgcaga gtggttttag aaaaatggca ttcccatctg gtaaagttga gggttgtatg   9840
gtacaagtaa cttgtggtac aactacactt aacggtcttt ggcttgatga cgtagtttac   9900
tgtccaagac atgtgatctg cacctctgaa gacatgctta accctaatta tgaagattta   9960
ctcattcgta agtctaatca taatttcttg gtacaggctg gtaatgttca actcagggtt  10020
attggacatt ctatgcaaaa ttgtgtactt aagcttaagg ttgatacagc caatcctaag  10080
acacctaagt ataagtttgt tcgcattcaa ccaggacaga ctttttcagt gttagcttgt  10140
tacaatggtt caccatctgg tgtttaccaa tgtgctatga ggcccaattt cactattaag  10200
ggttcattcc ttaatggttc atgtggtagt gttggtttta acatagatta tgactgtgtc  10260
tctttttgtt acatgcacca tatggaatta ccaactggag ttcatgctgg cacagactta  10320
gaaggtaact tttatggacc ttttgttgac aggcaaacag cacaagcagc tggtacggac  10380
acaactatta cagttaatgt tttagcttgg ttgtacgctg ctgttataaa tggagacagg  10440
tggtttctca atcgatttac cacaactctt aatgacttta accttgtggc tatgaagtac  10500
aattatgaac ctctaacaca agaccatgtt gacatactag gacctctttc tgctcaaact  10560
ggaattgccg ttttagatat gtgtgcttca ttaaaagaat tactgcaaaa tggtatgaat  10620
ggacgtacca tattgggtag tgctttatta gaagatgaat ttacaccttt tgatgttgtt  10680
agacaatgct caggtgttac tttccaaagt gcagtgaaaa gaacaatcaa gggtacacac  10740
cactggttgt tactcacaat tttgacttca cttttagttt tagtccagag tactcaatgg  10800
tctttgttct ttttttgta tgaaaatgcc tttttacctt ttgctatggg tattattgct  10860
atgtctgctt ttgcaatgat gtttgtcaaa cataagcatg catttctctg tttgtttttg  10920
ttaccttctc ttgccactgt agcttatttt aatatggtct atatgcctgc tagttgggtg  10980
atgcgtatta tgacatggtt ggatatggtt gatactagtt tgtctggttt taagctaaaa  11040
gactgtgtta tgtatgcatc agctgtagtg ttactaatcc ttatgacagc aagaactgtg  11100
tatgatgatg gtgctaggag agtgtggaca cttatgaatg tcttgacact cgtttataaa  11160
gtttattatg gtaatgcttt agatcaagcc atttccatgt gggctcttat aatctctgtt  11220
```

-continued acttctaact actcaggtgt agttacaact gtcatgtttt tggccagagg tattgttttt 11280
atgtgtgttg agtattgccc tattttcttc ataactggta atacacttca gtgtataatg 11340
ctagtttatt gtttcttagg ctatttttgt acttgttact ttggcctctt ttgtttactc 11400
aaccgctact ttagactgac tcttggtgtt tatgattact tagtttctac acaggagttt 11460
agatatatga attcacaggg actactccca cccaagaata gcatagatgc cttcaaactc 11520
aacattaaat tgttgggtgt tggtggcaaa ccttgtatca aagtagccac tgtacagtct 11580
aaaatgtcag atgtaaagtg cacatcagta gtcttactct cagttttgca acaactcaga 11640
gtagaatcat catctaaatt gtgggctcaa tgtgtccagt tacacaatga cattctctta 11700
gctaaagata ctactgaagc ctttgaaaaa atggtttcac tactttctgt tttgctttcc 11760
atgcagggtg ctgtagacat aaacaagctt tgtgaagaaa tgctggacaa cagggcaacc 11820
ttacaagcta tagcctcaga gtttagttcc cttccatcat atgcagcttt tgctactgct 11880
caagaagctt atgagcaggc tgttgctaat ggtgattctg aagttgttct taaaaagttg 11940
aagaagtctt tgaatgtggc taaatctgaa tttgaccgtg atgcagccat gcaacgtaag 12000
ttggaaaaga tggctgatca agctatgacc caaatgtata aacaggctag atctgaggac 12060
aagagggcaa aagttactag tgctatgcag acaatgcttt tcactatgct tagaaagttg 12120
gataatgatg cactcaacaa cattatcaac aatgcaagag atggttgtgt tcccttgaac 12180
ataatacctc ttacaacagc agccaaacta atggttgtca taccagacta taacacatat 12240
aaaaatacgt gtgatggtac aacatttact tatgcatcag cattgtggga aatccaacag 12300
gttgtagatg cagatagtaa aattgttcaa cttagtgaaa ttagtatgga caattcacct 12360
aatttagcat ggcctcttat tgtaacagct ttaagggcca attctgctgt caaattacag 12420
aataatgagc ttagtcctgt tgcactacga cagatgtctt gtgctgccgg tactacacaa 12480
actgcttgca ctgatgacaa tgcgttagct tactacaaca caacaaaggg aggtaggttt 12540
gtacttgcac tgttatccga tttacaggat ttgaaatggg ctagattccc taagagtgat 12600
ggaactggta ctatctatac agaactggaa ccaccttgta ggtttgttac agacacacct 12660
aaaggtccta aagtgaagta tttatacttt attaaaggat taaacaacct aaatagaggt 12720
atggtacttg gtagtttagc tgccacagta cgtctacaag ctggtaatgc aacagaagtg 12780
cctgccaatt caactgtatt atctttctgt gcttttgctg tagatgctgc taaagcttac 12840
aaagattatc tagctagtgg gggacaacca atcactaatt gtgttaagat gttgtgtaca 12900
cacactggta ctggtcaggc aataacagtt acaccggaag ccaatatgga tcaagaatcc 12960
tttggtggtg catcgtgttg tctgtactgc cgttgccaca tagatcatcc aaatcctaaa 13020
ggattttgtg acttaaaagg taagtatgta caaataccta caacttgtgc taatgaccct 13080
gtgggtttta cacttaaaaa cacagtctgt accgtctgcg gtatgtggaa aggttatggc 13140
tgtagttgtg atcaactccg cgaacccatg cttcagtcag ctgatgcaca atcgttttta 13200
aacgggtttg cggtgta 13217

<210> SEQ ID NO 3
<211> LENGTH: 21289
<212> TYPE: DNA
<213> ORGANISM: Severe acute respiratory syndrome coronavirus 2

<400> SEQUENCE: 3
atggagagcc ttgtccctgg tttcaacgag aaaacacacg tccaactcag tttgcctgtt 60
ttacaggttc gcgacgtgct cgtacgtggc tttggagact ccgtggagga ggtcttatca 120

```
gaggcacgtc aacatcttaa agatggcact tgtggcttag tagaagttga aaaaggcgtt    180
ttgcctcaac ttgaacagcc ctatgtgttc atcaaacgtt cggatgctcg aactgcacct    240
catggtcatg ttatggttga gctggtagca gaactcgaag gcattcagta cggtcgtagt    300
ggtgagacac ttggtgtcct tgtccctcat gtgggcgaaa taccagtggc ttaccgcaag    360
gttcttcttc gtaagaacgg taataaagga gctggtggcc atagttacgg cgccgatcta    420
aagtcatttg acttaggcga cgagcttggc actgatcctt atgaagattt tcaagaaaac    480
tggaacacta aacatagcag tggtgttacc cgtgaactca tgcgtgagct taacggaggg    540
gcatacactc gctatgtcga taacaacttc tgtggccctg atggctaccc tcttgagtgc    600
attaaagacc ttctagcacg tgctggtaaa gcttcatgca ctttgtccga acaactggac    660
tttattgaca ctaagagggg tgtatactgc tgccgtgaac atgagcatga aattgcttgg    720
tacacggaac gttctgaaaa gagctatgaa ttgcagacac cttttgaaat taaattggca    780
aagaaatttg acaccttcaa tggggaatgt ccaaattttg tatttccctt aaattccata    840
atcaagacta ttcaaccaag ggttgaaaag aaaaagcttg atggctttat gggtagaatt    900
cgatctgtct atccagttgc gtcaccaaat gaatgcaacc aaatgtgcct ttcaactctc    960
atgaagtgtg atcattgtgg tgaaacttca tggcagacgg gcgattttgt taaagccact   1020
tgcgaatttt gtggcactga gaatttgact aaagaaggtg ccactacttg tggttactta   1080
ccccaaaatg ctgttgttaa aatttattgt ccagcatgtc acaattcaga agtaggacct   1140
gagcatagtc ttgccgaata ccataatgaa tctggcttga aaaccattct tcgtaagggt   1200
ggtcgcacta ttgcctttgg aggctgtgtg ttctcttatg ttggttgcca taacaagtgt   1260
gcctattggg ttccacgtgc tagcgctaac ataggttgta accatacagg tgttgttgga   1320
gaaggttccg aaggtcttaa tgacaacctt cttgaaatac tccaaaaaga gaaagtcaac   1380
atcaatattg ttggtgactt taaacttaat gaagagatcg ccattatttt ggcatctttt   1440
tctgcttcca caagtgcttt tgtggaaact gtgaaaggtt tggattataa agcattcaaa   1500
caaattgttg aatcctgtgg taattttaaa gttacaaaag gaaaagctaa aaaaggtgcc   1560
tggaatattg gtgaacagaa atcaatactg agtcctcttt atgcatttgc atcagaggct   1620
gctcgtgttg tacgatcaat ttttctcccgc actcttgaaa ctgctcaaaa ttctgtgcgt   1680
gttttacaga aggccgctat aacaatacta gatggaattt cacagtattc actgagactc   1740
attgatgcta tgatgttcac atctgatttg gctactaaca atctagttgt aatggcctac   1800
attacaggtg gtgttgttca gttgacttcg cagtggctaa ctaacatctt tggcactgtt   1860
tatgaaaaac tcaaacccgt ccttgattgg cttgaagaga agtttaagga aggtgtagag   1920
tttcttagag acggttggga aattgttaaa tttatctcaa cctgtgcttg tgaaattgtc   1980
ggtggacaaa ttgtcacctg tgcaaaggaa attaaggaga gtgttcagac attctttaag   2040
cttgtaaata aatttttggc tttgtgtgct gactctatca ttattggtgg agctaaactt   2100
aaagccttga atttaggtga aacatttgtc acgcactcaa agggattgta cagaaagtgt   2160
gttaaatcca gagaagaaac tggcctactc atgcctctaa aagccccaaa agaaattatc   2220
ttcttagagg gagaaacact tcccacagaa gtgttaacag aggaagttgt cttgaaaact   2280
ggtgatttac aaccattaga acaacctact agtgaagctg ttgaagctcc attggttggt   2340
acaccagttt gtattaacgg gcttatgttg ctcgaaatca aagacacaga aaagtactgt   2400
gcccttgcac ctaatatgat ggtaacaaac aataccttca cactcaaagg cggtgcacca   2460
```

```
acaaaggtta cttttggtga tgacactgtg atagaagtgc aaggttacaa gagtgtgaat   2520
atcacttttg aacttgatga aaggattgat aaagtactta atgagaagtg ctctgcctat   2580
acagttgaac tcggtacaga agtaaatgag ttcgcctgtg ttgtggcaga tgctgtcata   2640
aaaactttgc aaccagtatc tgaattactt acaccactgg gcattgattt agatgagtgg   2700
agtatggcta catactactt atttgatgag tctggtgagt ttaaattggc ttcacatatg   2760
tattgttctt tctaccctcc agatgaggat gaagaagaag gtgattgtga agaagaagag   2820
tttgagccat caactcaata tgagtatggt actgaagatg attaccaagg taaacctttg   2880
gaatttggtg ccacttctgc tgctcttcaa cctgaagaag agcaagaaga agattggtta   2940
gatgatgata gtcaacaaac tgttggtcaa caagacggca gtgaggacaa tcagacaact   3000
actattcaaa caattgttga ggttcaacct caattagaga tggaacttac accagttgtt   3060
cagactattg aagtgaatag ttttagtggt tatttaaaac ttactgacaa tgtatacatt   3120
aaaaatgcag acattgtgga agaagctaaa aaggtaaaac caacagtggt tgttaatgca   3180
gccaatgttt accttaaaca tggaggaggt gttgcaggag ccttaaataa ggctactaac   3240
aatgccatgc aagttgaatc tgatgattac atagctacta atggaccact taaagtgggt   3300
ggtagttgtg ttttaagcgg acacaatctt gctaaacact gtcttcatgt tgtcggccca   3360
aatgttaaca aaggtgaaga cattcaactt cttaagagtg cttatgaaaa ttttaatcag   3420
cacgaagttc tacttgcacc attattatca gctggtattt ttggtgctga ccctatacat   3480
tctttaagag tttgtgtaga tactgttcgc acaaatgtct acttagctgt ctttgataaa   3540
aatctctatg acaaacttgt ttcaagcttt ttggaaatga agagtgaaaa gcaagttgaa   3600
caaaagatcg ctgagattcc taaagaggaa gttaagccat ttataactga aagtaaacct   3660
tcagttgaac agagaaaaca agatgataag aaaatcaaag cttgtgttga agaagttaca   3720
acaactctgg aagaaactaa gttcctcaca gaaaacttgt tactttatat tgacattaat   3780
ggcaatcttc atccagattc tgccactctt gttagtgaca ttgacatcac tttcttaaag   3840
aaagatgctc catatatagt gggtgatgtt gttcaagagg gtgttttaac tgctgtggtt   3900
atacctacta aaaaggctgg tggcactact gaaatgctag cgaaagcttt gagaaaagtg   3960
ccaacagaca attatataac cacttacccg ggtcagggtt taaatggtta cactgtagag   4020
gaggcaaaga cagtgcttaa aaagtgtaaa agtgcctttt acattctacc atctattatc   4080
tctaatgaga agcaagaaat tcttggaact gtttcttgga atttgcgaga aatgcttgca   4140
catgcagaag aaacacgcaa attaatgcct gtctgtgtgg aaactaaagc catagtttca   4200
actatacagc gtaaatataa gggtattaaa atacaagagg gtgtggttga ttatggtgct   4260
agattttact tttacaccag taaaacaact gtagcgtcac ttatcaacac acttaacgat   4320
ctaaatgaaa ctcttgttac aatgccactt ggctatgtaa cacatggctt aaatttggaa   4380
gaagctgctc ggtatatgag atctctcaaa gtgccagcta cagtttctgt ttcttcacct   4440
gatgctgtta cagcgtataa tggttatctt acttcttctt ctaaaacacc tgaagaacat   4500
tttattgaaa ccatctcact tgctggttcc tataaagatt ggtcctattc tggacaatct   4560
acacaactag gtatagaatt tcttaagaga ggtgataaaa gtgtatatta cactagtaat   4620
cctaccacat tccacctaga tggtgaagtt atcacctttg acaatcttaa gacacttctt   4680
tctttgagag aagtgaggac tattaaggtg tttacaacag tagacaacat taacctccac   4740
acgcaagttg tggacatgtc aatgacatat ggacaacagt ttggtccaac ttatttggat   4800
ggagctgatg ttactaaaat aaaacctcat aattcacatg aaggtaaaac attttatgtt   4860
```

-continued

```
ttacctaatg atgacactct acgtgttgag gcttttgagt actaccacac aactgatcct   4920
agttttctgg gtaggtacat gtcagcatta aatcacacta aaaagtggaa atacccacaa   4980
gttaatggtt taacttctat taaatgggca gataacaact gttatcttgc cactgcattg   5040
ttaacactcc aacaaataga gttgaagttt aatccacctg ctctacaaga tgcttattac   5100
agagcaaggg ctggtgaagc tgctaacttt tgtgcactta tcttagccta ctgtaataag   5160
acagtaggtg agttaggtga tgttagagaa acaatgagtt acttgtttca acatgccaat   5220
ttagattctt gcaaaagagt cttgaacgtg gtgtgtaaaa cttgtggaca acagcagaca   5280
acccttaagg gtgtagaagc tgttatgtac atgggcacac tttcttatga acaatttaag   5340
aaaggtgttc agataccttg tacgtgtggt aaacaagcta caaaatatct agtacaacag   5400
gagtcacctt ttgttatgat gtcagcacca cctgctcagt atgaacttaa gcatggtaca   5460
tttacttgtg ctagtgagta cactggtaat taccagtgtg gtcactataa acatataact   5520
tctaaagaaa ctttgtattg catagacggt gctttactta caaagtcctc agaatacaaa   5580
ggtcctatta cggatgtttt ctacaaagaa aacagttaca caacaaccat aaaaccagtt   5640
acttataaat tggatggtgt tgtttgtaca gaaattgacc ctaagttgga caattattat   5700
aagaaagaca attcttattt cacagagcaa ccaattgatc ttgtaccaaa ccaaccatat   5760
ccaaacgcaa gcttcgataa ttttaagttt gtatgtgata atatcaaatt tgctgatgat   5820
ttaaaccagt taactggtta taagaaacct gcttcaagag agcttaaagt tacatttttc   5880
cctgacttaa atggtgatgt ggtggctatt gattataaac actacacacc ctcttttaag   5940
aaaggagcta aattgttaca taaacctatt gtttggcatg ttaacaatgc aactaataaa   6000
gccacgtata aaccaaatac ctggtgtata cgttgtcttt ggagcacaaa accagttgaa   6060
acatcaaatt cgtttgatgt actgaagtca gaggacgcgc agggaatgga taatcttgcc   6120
tgcgaagatc taaaaccagt ctctgaagaa gtagtggaaa atcctaccat acagaaagac   6180
gttcttgagt gtaatgtgaa aactaccgaa gttgtaggag acattatact taaaccagca   6240
aataatagtt taaaaattac agaagaggtt ggccacacag atctaatggc tgcttatgta   6300
gacaattcta gtcttactat taagaaacct aatgaattat ctagagtatt aggtttgaaa   6360
acccttgcta ctcatggttt agctgctgtt aatagtgtcc cttgggatac tatagctaat   6420
tatgctaagc cttttcttaa caaagttgtt agtacaacta ctaacatagt tacacggtgt   6480
ttaaaccgtg tttgtactaa ttatatgcct tatttcttta ctttattgct acaattgtgt   6540
acttttacta gaagtacaaa ttctagaatt aaagcatcta tgccgactac tatagcaaag   6600
aatactgtta agagtgtcgg taaattttgt ctagaggctt catttaatta tttgaagtca   6660
cctaattttt ctaaactgat aaatattata atttggtttt tactattaag tgtttgccta   6720
ggttctttaa tctactcaac cgctgcttta ggtgttttaa tgtctaattt aggcatgcct   6780
tcttactgta ctggttacag agaaggctat ttgaactcta ctaatgtcac tattgcaacc   6840
tactgtactg gttctatacc ttgtagtgtt tgtcttagtg gtttagattc tttagacacc   6900
tatccttctt tagaaactat acaaattacc atttcatctt ttaaatggga tttaactgct   6960
tttggcttag ttgcagagtg gtttttggca tatattcttt tcactaggtt tttctatgta   7020
cttggattgg ctgcaatcat gcaattgttt ttcagctatt ttgcagtaca ttttattagt   7080
aattcttggc ttatgtggtt aataattaat cttgtacaaa tggccccgat ttcagctatg   7140
gttagaatgt acatcttctt tgcatcattt tattatgtat ggaaaagtta tgtgcatgtt   7200
```

gtagacggtt gtaattcatc aacttgtatg atgtgttaca aacgtaatag agcaacaaga 7260
gtcgaatgta caactattgt taatggtgtt agaaggtcct tttatgtcta tgctaatgga 7320
ggtaaaggct tttgcaaact acacaattgg aattgtgtta attgtgatac attctgtgct 7380
ggtagtacat ttattagtga tgaagttgcg agagacttgt cactacagtt taaaagacca 7440
ataaatccta ctgaccagtc ttcttacatc gttgatagtg ttacagtgaa gaatggttcc 7500
atccatcttt actttgataa agctggtcaa aagacttatg aaagacattc tctctctcat 7560
tttgttaact tagacaacct gagagctaat aacactaaag gttcattgcc tattaatgtt 7620
atagtttttg atggtaaatc aaaatgtgaa gaatcatctg caaaatcagc gtctgtttac 7680
tacagtcagc ttatgtgtca acctatactg ttactagatc aggcattagt gtctgatgtt 7740
ggtgatagtg cggaagttgc agttaaaatg tttgatgctt acgttaatac gttttcatca 7800
acttttaacg taccaatgga aaaactcaaa acactagttg caactgcaga agctgaactt 7860
gcaaagaatg tgtccttaga caatgtctta tctactttta tttcagcagc tcggcaaggg 7920
tttgttgatt cagatgtaga aactaaagat gttgttgaat gtcttaaatt gtcacatcaa 7980
tctgacatag aagttactgg cgatagttgt aataactata tgctcaccta taacaaagtt 8040
gaaaacatga caccccgtga ccttggtgct tgtattgact gtagtgcgcg tcatattaat 8100
gcgcaggtag caaaaagtca caacattgct ttgatatgga acgttaaaga tttcatgtca 8160
ttgtctgaac aactacgaaa acaaatacgt agtgctgcta aaaagaataa cttacctttt 8220
aagttgacat gtgcaactac tagacaagtt gttaatgttg taacaacaaa gatagcactt 8280
aagggtggta aaattgttaa taattggttg aagcagttaa ttaaagttac acttgtgttc 8340
ctttttgttg ctgctatttt ctatttaata acacctgttc atgtcatgtc taaacatact 8400
gacttttcaa gtgaaatcat aggatacaag gctattgatg gtggtgtcac tcgtgacata 8460
gcatctacag atacttgttt tgctaacaaa catgctgatt ttgacacatg gtttagccag 8520
cgtggtggta gttatactaa tgacaaagct tgcccattga ttgctgcagt cataacaaga 8580
gaagtgggtt ttgtcgtgcc tggtttgcct ggcacgatat tacgcacaac taatggtgac 8640
tttttgcatt tcttacctag agtttttagt gcagttggta acatctgtta cacaccatca 8700
aaacttatag agtacactga ctttgcaaca tcagcttgtg ttttggctgc tgaatgtaca 8760
atttttaaag atgcttctgg taagccagta ccatattgtt atgataccaa tgtactagaa 8820
ggttctgttg cttatgaaag tttacgccct gacacacgtt atgtgctcat ggatggctct 8880
attattcaat ttcctaacac ctaccttgaa ggttctgtta gagtggtaac aacttttgat 8940
tctgagtact gtaggcacgg cacttgtgaa agatcagaag ctggtgtttg tgtatctact 9000
agtggtagat gggtacttaa caatgattat tacagatctt taccaggagt tttctgtggt 9060
gtagatgctg taaatttact tactaatatg tttacaccac taattcaacc tattggtgct 9120
ttggacatat cagcatctat agtagctggt ggtattgtag ctatcgtagt aacatgcctt 9180
gcctactatt ttatgaggtt tagaagagct tttggtgaat acagtcatgt agttgccttt 9240
aatactttac tattccttat gtcattcact gtactctgtt taacaccagt ttactcattc 9300
ttacctggtg tttattctgt tatttacttg tacttgacat tttatcttac taatgatgtt 9360
tctttttag cacatattca gtggatggtt atgttcacac ctttagtacc tttctggata 9420
acaattgctt atatcatttg tatttccaca aagcatttct attggttctt tagtaattac 9480
ctaaagagac gtgtagtctt taatggtgtt tcctttagta cttttgaaga agctgcgctg 9540
tgcacctttt tgttaaataa agaaatgtat ctaaagttgc gtagtgatgt gctattacct 9600

```
cttacgcaat ataatagata cttagctctt tataataagt acaagtattt tagtggagca   9660
atggatacaa ctagctacag agaagctgct tgttgtcatc tcgcaaaggc tctcaatgac   9720
ttcagtaact caggttctga tgttctttac caaccaccac aaacctctat cacctcagct   9780
gttttgcaga gtggttttag aaaaatggca ttcccatctg gtaaagttga gggttgtatg   9840
gtacaagtaa cttgtggtac aactacactt aacggtcttt ggcttgatga cgtagtttac   9900
tgtccaagac atgtgatctg cacctctgaa gacatgctta accctaatta tgaagattta   9960
ctcattcgta agtctaatca taatttcttg gtacaggctg gtaatgttca actcagggtt  10020
attggacatt ctatgcaaaa ttgtgtactt aagcttaagg ttgatacagc caatcctaag  10080
acacctaagt ataagtttgt tcgcattcaa ccaggacaga ctttttcagt gttagcttgt  10140
tacaatggtt caccatctgg tgtttaccaa tgtgctatga ggcccaattt cactattaag  10200
ggttcattcc ttaatggttc atgtggtagt gttggtttta acatagatta tgactgtgtc  10260
tctttttgtt acatgcacca tatggaatta ccaactggag ttcatgctgg cacagactta  10320
gaaggtaact tttatggacc ttttgttgac aggcaaacag cacaagcagc tggtacggac  10380
acaactatta cagttaatgt tttagcttgg ttgtacgctg ctgttataaa tggagacagg  10440
tggtttctca atcgatttac cacaactctt aatgacttta accttgtggc tatgaagtac  10500
aattatgaac ctctaacaca agaccatgtt gacatactag gacctctttc tgctcaaact  10560
ggaattgccg ttttagatat gtgtgcttca ttaaaagaat tactgcaaaa tggtatgaat  10620
ggacgtacca tattgggtag tgctttatta gaagatgaat ttacaccttt tgatgttgtt  10680
agacaatgct caggtgttac tttccaaagt gcagtgaaaa gaacaatcaa gggtacacac  10740
cactggttgt tactcacaat tttgacttca cttttagttt tagtccagag tactcaatgg  10800
tctttgttct ttttttgta tgaaaatgcc tttttacctt ttgctatggg tattattgct  10860
atgtctgctt ttgcaatgat gtttgtcaaa cataagcatg catttctctg tttgtttttg  10920
ttaccttctc ttgccactgt agcttatttt aatatggtct atatgcctgc tagttgggtg  10980
atgcgtatta tgacatggtt ggatatggtt gatactagtt tgtctggttt taagctaaaa  11040
gactgtgtta tgtatgcatc agctgtagtg ttactaatcc ttatgacagc aagaactgtg  11100
tatgatgatg gtgctaggag agtgtggaca cttatgaatg tcttgacact cgtttataaa  11160
gtttattatg gtaatgcttt agatcaagcc atttccatgt gggctcttat aatctctgtt  11220
acttctaact actcaggtgt agttacaact gtcatgtttt tggccagagg tattgttttt  11280
atgtgtgttg agtattgccc tattttcttc ataactggta atacacttca gtgtataatg  11340
ctagtttatt gtttcttagg ctatttttgt acttgttact ttggcctctt ttgtttactc  11400
aaccgctact ttagactgac tcttggtgtt tatgattact tagtttctac acaggagttt  11460
agatatatga attcacaggg actactccca cccaagaata gcatagatgc cttcaaactc  11520
aacattaaat tgttgggtgt tggtggcaaa ccttgtatca aagtagccac tgtacagtct  11580
aaaatgtcag atgtaaagtg cacatcagta gtcttactct cagttttgca acaactcaga  11640
gtagaatcat catctaaatt gtgggctcaa tgtgtccagt tacacaatga cattctctta  11700
gctaaagata ctactgaagc ctttgaaaaa atggtttcac tactttctgt tttgctttcc  11760
atgcagggtg ctgtagacat aaacaagctt tgtgaagaaa tgctggacaa cagggcaacc  11820
ttacaagcta tagcctcaga gtttagttcc cttccatcat atgcagcttt tgctactgct  11880
caagaagctt atgagcaggc tgttgctaat ggtgattctg aagttgttct taaaaagttg  11940
```

-continued

```
aagaagtctt tgaatgtggc taaatctgaa tttgaccgtg atgcagccat gcaacgtaag  12000
ttggaaaaga tggctgatca agctatgacc caaatgtata aacaggctag atctgaggac  12060
aagagggcaa aagttactag tgctatgcag acaatgcttt tcactatgct tagaaagttg  12120
gataatgatg cactcaacaa cattatcaac aatgcaagag atggttgtgt tcccttgaac  12180
ataatacctc ttacaacagc agccaaacta atggttgtca taccagacta taacacatat  12240
aaaaatacgt gtgatggtac aacatttact tatgcatcag cattgtggga aatccaacag  12300
gttgtagatg cagatagtaa aattgttcaa cttagtgaaa ttagtatgga caattcacct  12360
aatttagcat ggcctcttat tgtaacagct ttaagggcca attctgctgt caaattacag  12420
aataatgagc ttagtcctgt tgcactacga cagatgtctt gtgctgccgg tactacacaa  12480
actgcttgca ctgatgacaa tgcgttagct tactacaaca caacaaaggg aggtaggttt  12540
gtacttgcac tgttatccga tttacaggat ttgaaatggg ctagattccc taagagtgat  12600
ggaactggta ctatctatac agaactggaa ccaccttgta ggtttgttac agacacacct  12660
aaaggtccta aagtgaagta tttatacttt attaaaggat taaacaacct aaatagaggt  12720
atggtacttg gtagtttagc tgccacagta cgtctacaag ctggtaatgc aacagaagtg  12780
cctgccaatt caactgtatt atctttctgt gcttttgctg tagatgctgc taaagcttac  12840
aaagattatc tagctagtgg gggacaacca atcactaatt gtgttaagat gttgtgtaca  12900
cacactggta ctggtcaggc aataacagtt acaccggaag ccaatatgga tcaagaatcc  12960
tttggtggtg catcgtgttg tctgtactgc cgttgccaca tagatcatcc aaatcctaaa  13020
ggattttgtg acttaaaagg taagtatgta caaataccta caacttgtgc taatgaccct  13080
gtgggtttta cacttaaaaa cacagtctgt accgtctgcg gtatgtggaa aggttatggc  13140
tgtagttgtg atcaactccg cgaacccatg cttcagtcag ctgatgcaca atcgttttta  13200
aacgggtttg cggtgtaagt gcagcccgtc ttacaccgtg cggcacaggc actagtactg  13260
atgtcgtata cagggctttt gacatctaca atgataaagt agctggtttt gctaaattcc  13320
taaaaactaa ttgttgtcgc ttccaagaaa aggacgaaga tgacaattta attgattctt  13380
actttgtagt taagagacac actttctcta actaccaaca tgaagaaaca atttataatt  13440
tacttaagga ttgtccagct gttgctaaac atgacttctt taagtttaga atagacggtg  13500
acatggtacc acatatatca cgtcaacgtc ttactaaata cacaatggca gacctcgtct  13560
atgctttaag gcattttgat gaaggtaatt gtgacacatt aaaagaaata cttgtcacat  13620
acaattgttg tgatgatgat tatttcaata aaaaggactg gtatgatttt gtagaaaacc  13680
cagatatatt acgcgtatac gccaacttag gtgaacgtgt acgccaagct ttgttaaaaa  13740
cagtacaatt ctgtgatgcc atgcgaaatg ctggtattgt tggtgtactg acattagata  13800
atcaagatct caatggtaac tggtatgatt tcggtgattt catacaaacc acgccaggta  13860
gtggagttcc tgttgtagat tcttattatt cattgttaat gcctatatta accttgacca  13920
gggctttaac tgcagagtca catgttgaca ctgacttaac aaagccttac attaagtggg  13980
atttgttaaa atatgacttc acggaagaga ggttaaaact ctttgaccgt tattttaaat  14040
attgggatca gacataccac ccaaattgtg ttaactgttt ggatgacaga tgcattctgc  14100
attgtgcaaa ctttaatgtt ttattctcta cagtgttccc acctacaagt tttggaccac  14160
tagtgagaaa aatatttgtt gatggtgttc catttgtagt ttcaactgga taccacttca  14220
gagagctagg tgttgtacat aatcaggatg taaacttaca tagctctaga cttagtttta  14280
aggaattact tgtgtatgct gctgaccctg ctatgcacgc tgcttctggt aatctattac  14340
```

```
tagataaacg cactacgtgc ttttcagtag ctgcacttac taacaatgtt gcttttcaaa  14400
ctgtcaaacc cggtaatttt aacaaagact tctatgactt tgctgtgtct aagggtttct  14460
ttaaggaagg aagttctgtt gaattaaaac acttcttctt tgctcaggat ggtaatgctg  14520
ctatcagcga ttatgactac tatcgttata atctaccaac aatgtgtgat atcagacaac  14580
tactatttgt agttgaagtt gttgataagt actttgattg ttacgatggt ggctgtatta  14640
atgctaacca agtcatcgtc aacaacctag acaaatcagc tggttttcca tttaataaat  14700
ggggtaaggc tagactttat tatgattcaa tgagttatga ggatcaagat gcacttttcg  14760
catatacaaa acgtaatgtc atccctacta taactcaaat gaatcttaag tatgccatta  14820
gtgcaaagaa tagagctcgc accgtagctg gtgtctctat ctgtagtact atgaccaata  14880
gacagtttca tcaaaaatta ttgaaatcaa tagccgccac tagaggagct actgtagtaa  14940
ttggaacaag caaattctat ggtggttggc acaacatgtt aaaaactgtt tatagtgatg  15000
tagaaaaccc tcaccttatg ggttgggatt atcctaaatg tgatagagcc atgcctaaca  15060
tgcttagaat tatggcctca cttgttcttg ctcgcaaaca tacaacgtgt tgtagcttgt  15120
cacaccgttt ctatagatta gctaatgagt gtgctcaagt attgagtgaa atggtcatgt  15180
gtggcggttc actatatgtt aaaccaggtg gaacctcatc aggagatgcc acaactgctt  15240
atgctaatag tgtttttaac atttgtcaag ctgtcacggc caatgttaat gcacttttat  15300
ctactgatgg taacaaaatt gccgataagt atgtccgcaa tttacaacac agactttatg  15360
agtgtctcta tagaaataga gatgttgaca cagactttgt gaatgagttt tacgcatatt  15420
tgcgtaaaca tttctcaatg atgatactct ctgacgatgc tgttgtgtgt ttcaatagca  15480
cttatgcatc tcaaggtcta gtggctagca taaagaactt taagtcagtt ctttattatc  15540
aaaacaatgt ttttatgtct gaagcaaaat gttggactga gactgacctt actaaaggac  15600
ctcatgaatt ttgctctcaa catacaatgc tagttaaaca gggtgatgat tatgtgtacc  15660
ttccttaccc agatccatca agaatcctag gggccggctg ttttgtagat gatatcgtaa  15720
aaacagatgg tacacttatg attgaacggt tcgtgtcttt agctatagat gcttacccac  15780
ttactaaaca tcctaatcag gagtatgctg atgtctttca tttgtactta caatacataa  15840
gaaagctaca tgatgagtta acaggacaca tgttagacat gtattctgtt atgcttacta  15900
atgataacac ttcaaggtat tgggaacctg agttttatga ggctatgtac acaccgcata  15960
cagtcttaca ggctgttggg gcttgtgttc tttgcaattc acagacttca ttaagatgtg  16020
gtgcttgcat acgtagacca ttcttatgtt gtaaatgctg ttacgaccat gtcatatcaa  16080
catcacataa attagtcttg tctgttaatc cgtatgtttg caatgctcca ggttgtgatg  16140
tcacagatgt gactcaactt tacttaggag gtatgagcta ttattgtaaa tcacataaac  16200
cacccattag ttttccattg tgtgctaatg gacaagtttt tggtttatat aaaaatacat  16260
gtgttggtag cgataatgtt actgacttta atgcaattgc aacatgtgac tggacaaatg  16320
ctggtgatta cattttagct aacacctgta ctgaaagact caagcttttt gcagcagaaa  16380
cgctcaaagc tactgaggag acatttaaac tgtcttatgg tattgctact gtacgtgaag  16440
tgctgtctga cagagaatta catctttcat gggaagttgg taaacctaga ccaccactta  16500
accgaaatta tgtctttact ggttatcgtg taactaaaaa cagtaaagta caaataggag  16560
agtacacctt tgaaaaaggt gactatggtg atgctgttgt ttaccgaggt acaacaactt  16620
acaaattaaa tgttggtgat tattttgtgc tgacatcaca tacagtaatg ccattaagtg  16680
```

-continued

```
cacctacact agtgccacaa gagcactatg ttagaattac tggcttatac ccaacactca  16740
atatctcaga tgagttttct agcaatgttg caaattatca aaaggttggt atgcaaaagt  16800
attctacact ccagggacca cctggtactg gtaagagtca ttttgctatt ggcctagctc  16860
tctactaccc ttctgctcgc atagtgtata cagcttgctc tcatgccgct gttgatgcac  16920
tatgtgagaa ggcattaaaa tatttgccta tagataaatg tagtagaatt atacctgcac  16980
gtgctcgtgt agagtgtttt gataaattca aagtgaattc aacattagaa cagtatgtct  17040
tttgtactgt aaatgcattg cctgagacga cagcagatat agttgtcttt gatgaaattt  17100
caatggccac aaattatgat ttgagtgttg tcaatgccag attacgtgct aagcactatg  17160
tgtacattgg cgaccctgct caattacctg caccacgcac attgctaact aagggcacac  17220
tagaaccaga atatttcaat tcagtgtgta gacttatgaa aactataggt ccagacatgt  17280
tcctcggaac ttgtcggcgt tgtcctgctg aaattgttga cactgtgagt gctttggttt  17340
atgataataa gcttaaagca cataaagaca aatcagctca atgctttaaa atgttttata  17400
agggtgttat cacgcatgat gtttcatctg caattaacag gccacaaata ggcgtggtaa  17460
gagaattcct tacacgtaac cctgcttgga gaaaagctgt ctttatttca ccttataatt  17520
cacagaatgc tgtagcctca aagattttgg gactaccaac tcaaactgtt gattcatcac  17580
agggctcaga atatgactat gtcatattca ctcaaaccac tgaaacagct cactcttgta  17640
atgtaaacag atttaatgtt gctattacca gagcaaaagt aggcatactt tgcataatgt  17700
ctgatagaga cctttatgac aagttgcaat ttacaagtct tgaaattcca cgtaggaatg  17760
tggcaacttt acaagctgaa aatgtaacag gactctttaa agattgtagt aaggtaatca  17820
ctgggttaca tcctacacag gcacctacac acctcagtgt tgacactaaa ttcaaaactg  17880
aaggtttatg tgttgacata cctggcatac ctaaggacat gacctataga agactcatct  17940
ctatgatggg ttttaaaatg aattatcaag ttaatggtta ccctaacatg tttatcaccc  18000
gcgaagaagc tataagacat gtacgtgcat ggattggctt cgatgtcgag ggtgtcatg   18060
ctactagaga agctgttggt accaatttac ctttacagct aggtttttct acaggtgtta  18120
acctagttgc tgtacctaca ggttatgttg atacacctaa taatacagat tttccagag   18180
ttagtgctaa accaccgcct ggagatcaat ttaaacacct cataccactt atgtacaaag  18240
gacttccttg gaatgtagtg cgtataaaga ttgtacaaat gttaagtgac acacttaaaa  18300
atctctctga cagagtcgta tttgtcttat gggcacatgg ctttgagttg acatctatga  18360
agtattttgt gaaaatagga cctgagcgca cctgttgtct atgtgataga cgtgccacat  18420
gcttttccac tgcttcagac acttatgcct gttggcatca ttctattgga tttgattacg  18480
tctataatcc gtttatgatt gatgttcaac aatggggttt tacaggtaac ctacaaagca  18540
accatgatct gtattgtcaa gtccatggta atgcacatgt agctagttgt gatgcaatca  18600
tgactaggtg tctagctgtc cacgagtgct ttgttaagcg tgttgactgg actattgaat  18660
atcctataat tggtgatgaa ctgaagatta atgcggcttg tagaaaggtt caacacatgg  18720
ttgttaaagc tgcattatta gcagacaaat tcccagttct tcacgacatt ggtaacccta  18780
aagctattaa gtgtgtacct caagctgatg tagaatggaa gttctatgat gcacagcctt  18840
gtagtgacaa agcttataaa atagaagaat tattctattc ttatgccaca cattctgaca  18900
aattcacaga tggtgtatgc ctattttgga attgcaatgt cgatagatat cctgctaatt  18960
ccattgtttg tagatttgac actagagtgc tatctaacct taacttgcct ggttgtgatg  19020
gtggcagttt gtatgtaaat aaacatgcat tccacacacc agcttttgat aaaagtgctt  19080
```

ttgttaattt aaaacaatta ccatttttct attactctga cagtccatgt gagtctcatg 19140
gaaaacaagt agtgtcagat atagattatg taccactaaa gtctgctacg tgtataacac 19200
gttgcaattt aggtggtgct gtctgtagac atcatgctaa tgagtacaga ttgtatctcg 19260
atgcttataa catgatgatc tcagctggct ttagcttgtg ggtttacaaa caatttgata 19320
cttataacct ctggaacact tttacaagac ttcagagttt agaaaatgtg gcttttaatg 19380
ttgtaaataa gggacacttt gatggacaac agggtgaagt accagtttct atcattaata 19440
acactgttta cacaaaagtt gatggtgttg atgtagaatt gtttgaaaat aaaacaacat 19500
tacctgttaa tgtagcattt gagctttggg ctaagcgcaa cattaaacca gtaccagagg 19560
tgaaaatact caataatttg ggtgtggaca ttgctgctaa tactgtgatc tgggactaca 19620
aaagagatgc tccagcacat atatctacta ttggtgtttg ttctatgact gacatagcca 19680
agaaaccaac tgaaacgatt tgtgcaccac tcactgtctt ttttgatggt agagttgatg 19740
gtcaagtaga cttatttaga aatgcccgta atggtgttct tattacagaa ggtagtgtta 19800
aaggtttaca accatctgta ggtcccaaac aagctagtct taatggagtc acattaattg 19860
gagaagccgt aaaaacacag ttcaattatt ataagaaagt tgatggtgtt gtccaacaat 19920
tacctgaaac ttactttact cagagtagaa atttacaaga atttaaaccc aggagtcaaa 19980
tggaaattga tttcttagaa ttagctatgg atgaattcat tgaacggtat aaattagaag 20040
gctatgcctt cgaacatatc gtttatggag attttagtca tagtcagtta ggtggtttac 20100
atctactgat tggactagct aaacgtttta aggaatcacc ttttgaatta gaagatttta 20160
ttcctatgga cagtacagtt aaaaactatt tcataacaga tgcgcaaaca ggttcatcta 20220
agtgtgtgtg ttctgttatt gatttattac ttgatgattt tgttgaaata ataaaatccc 20280
aagatttatc tgtagtttct aaggttgtca aagtgactat tgactataca gaaatttcat 20340
ttatgctttg gtgtaaagat ggccatgtag aaacatttta cccaaaatta caatctagtc 20400
aagcgtggca accgggtgtt gctatgccta atctttacaa aatgcaaaga atgctattag 20460
aaaagtgtga ccttcaaaat tatggtgata gtgcaacatt acctaaaggc ataatgatga 20520
atgtcgcaaa atatactcaa ctgtgtcaat atttaaacac attaacatta gctgtaccct 20580
ataatatgag agttatacat tttggtgctg gttctgataa aggagttgca ccaggtacag 20640
ctgttttaag acagtggttg cctacgggta cgctgcttgt cgattcagat cttaatgact 20700
ttgtctctga tgcagattca actttgattg gtgattgtgc aactgtacat acagctaata 20760
aatgggatct cattattagt gatatgtacg accctaagac taaaaatgtt acaaaagaaa 20820
atgactctaa agagggtttt ttcacttaca tttgtgggtt tatacaacaa aagctagctc 20880
ttggaggttc cgtggctata aagataacag aacattcttg gaatgctgat ctttataagc 20940
tcatgggaca cttcgcatgg tggacagcct ttgttactaa tgtgaatgcg tcatcatctg 21000
aagcattttt aattggatgt aattatcttg gcaaaccacg cgaacaaata gatggttatg 21060
tcatgcatgc aaattacata ttttggagga atacaaatcc aattcagttg tcttcctatt 21120
ctttatttga catgagtaaa tttcccctta aattaagggg tactgctgtt atgtctttaa 21180
aagaaggtca aatcaatgat atgattttat ctcttcttag taaaggtaga cttataatta 21240
gagaaaacaa cagagttgtt atttctagtg atgttcttgt taacaacta 21289

<210> SEQ ID NO 4
<211> LENGTH: 3821
<212> TYPE: DNA

<213> ORGANISM: Severe acute respiratory syndrome coronavirus 2

<400> SEQUENCE: 4
atgtttgttt ttcttgtttt attgccacta gtctctagtc agtgtgttaa tcttacaacc 60
agaactcaat tacccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg atgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
cctcggcggg cacgtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280

```
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gattttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
tctgagccag tgctcaaagg agtcaaatta cattacacat a                       3821
```

<210> SEQ ID NO 5
<211> LENGTH: 827
<212> TYPE: DNA
<213> ORGANISM: Severe acute respiratory syndrome coronavirus 2

<400> SEQUENCE: 5

```
atggatttgt ttatgagaat cttcacaatt ggaactgtaa ctttgaagca aggtgaaatc     60
aaggatgcta ctccttcaga ttttgttcgc gctactgcaa cgataccgat acaagcctca    120
ctccctttcg gatggcttat tgttggcgtt gcacttcttg ctgtttttca gagcgcttcc    180
aaaatcataa ccctcaaaaa gagatggcaa ctagcactct ccaagggtgt tcactttgtt    240
tgcaacttgc tgttgttgtt tgtaacagtt tactcacacc ttttgctcgt tgctgctggc    300
cttgaagccc cttttctcta tctttatgct ttagtctact tcttgcagag tataaacttt    360
gtaagaataa taatgaggct ttggctttgc tggaaatgcc gttccaaaaa cccattactt    420
tatgatgcca actattttct ttgctggcat actaattgtt acgactattg tataccttac    480
aatagtgtaa cttcttcaat tgtcattact tcaggtgatg gcacaacaag tcctatttct    540
```

gaacatgact accagattgg tggttatact gaaaaatggg aatctggagt aaaagactgt 600
gttgtattac acagttactt cacttcagac tattaccagc tgtactcaac tcaattgagt 660
acagacactg gtgttgaaca tgttaccttc ttcatctaca ataaaattgt tgatgagcct 720
gaagaacatg tccaaattca cacaatcgac ggttcatccg gagttgttaa tccagtaatg 780
gaaccaattt atgatgaacc gacgacgact actagcgtgc ctttgta 827

<210> SEQ ID NO 6
<211> LENGTH: 227
<212> TYPE: DNA
<213> ORGANISM: Severe acute respiratory syndrome coronavirus 2

<400> SEQUENCE: 6
atgtactcat tcgtttcgga agagacaggt acgttaatag ttaatagcgt acttcttttt 60
cttgctttcg tggtattctt gctagttaca ctagccatcc ttactgcgct tcgattgtgt 120
gcgtactgct gcaatattgt taacgtgagt cttgtaaaac cttcttttta cgtttactct 180
cgtgttaaaa atctgaattc ttctagagtt cctgatcttc tggtcta 227

<210> SEQ ID NO 7
<211> LENGTH: 668
<212> TYPE: DNA
<213> ORGANISM: Severe acute respiratory syndrome coronavirus 2

<400> SEQUENCE: 7
atggcagatt ccaacggtac tattaccgtt gaagagctta aaaagctcct tgaacaatgg 60
aacctagtaa taggtttcct attccttaca tggatttgtc ttctacaatt tgcctatgcc 120
aacaggaata ggtttttgta tataattaag ttaatttttc tctggctgtt atggccagta 180
actttagctt gttttgtgct tgctgctgtt tacagaataa attggatcac cggtggaatt 240
gctatcgcaa tggcttgtct tgtaggcttg atgtggctca gctacttcat tgcttctttc 300
agactgtttg cgcgtacgcg ttccatgtgg tcattcaatc cagaaactaa cattcttctc 360
aacgtgccac tccatggcac tattctgacc agaccgcttc tagaaagtga actcgtaatc 420
ggagctgtga tccttcgtgg acatcttcgt attgctggac accatctagg acgctgtgac 480
atcaaggacc tgcctaaaga aatcactgtt gctacatcac gaacgctttc ttattacaaa 540
ttgggagctt cgcagcgtgt agcaggtgac tcaggttttg ctgcatacag tcgctacagg 600
attggcaact ataaattaaa cacagaccat tccagtagca gtgacaatat tgctttgctt 660
gtacagta 668

<210> SEQ ID NO 8
<211> LENGTH: 365
<212> TYPE: DNA
<213> ORGANISM: Severe acute respiratory syndrome coronavirus 2

<400> SEQUENCE: 8
atgaaaatta ttcttttctt ggcactgata acactcgcta cttgtgagct ttatcactac 60
caagagtgtg ttagaggtac aacagtactt ttaaaagaac cttgctcttc tggaacatac 120
gagggcaatt caccatttca tcctctagct gataacaaat ttgcactgac ttgctttagc 180
actcaatttg cttttgcttg tcctgacggc gtaaaacacg tctatcagtt acgtgccaga 240
tcagtttcac ctaaactgtt catcagacaa gaggaagttc aagaacttta ctctccaatt 300
tttcttattg ttgcggcaat agtgtttata acactttgct tcacactcaa aagaaagaca 360
gaatg 365

<210> SEQ ID NO 9
<211> LENGTH: 365
<212> TYPE: DNA
<213> ORGANISM: Severe acute respiratory syndrome coronavirus 2

<400> SEQUENCE: 9
atgaaatttc ttgttttctt aggaatcatc acaactgtag ctgcatttca ccaagaatgt 60
agtttacagt catgtactca acatcaacca tatgtagttg atgacccgtg tcctattcac 120
ttctattcta aatggtatat tagagtagga gctagaaaat cagcaccttt aattgaattg 180
tgcgtggatg aggctggttc taaatcaccc attcagtaca tcgatatcgg taattataca 240
gtttcctgtt taccttttac aattaattgc caggaaccta aattgggtag tcttgtagtg 300
cgttgttcgt tctatgaaga ctttttagag tatcatgacg ttcgtgttgt tttagatttc 360
atcta 365

<210> SEQ ID NO 10
<211> LENGTH: 1259
<212> TYPE: DNA
<213> ORGANISM: Severe acute respiratory syndrome coronavirus 2

<400> SEQUENCE: 10
atgtctgata atggacccca aaatcagcga aatgcacccc gcattacgtt tggtggaccc 60
tcagattcaa ctggcagtaa ccagaatgga gaacgcagtg gggcgcgatc aaaacaacgt 120
cggccccaag gtttacccaa taatactgcg tcttggttca ccgctctcac tcaacatggc 180
aaggaagacc ttaaattccc tcgaggacaa ggcgttccaa ttaacaccaa tagcagtcca 240
gatgaccaaa ttggctacta ccgaagagct accagacgaa ttcgtggtgg tgacggtaaa 300
atgaaagatc tcagtccaag atggtatttc tactacctag gaactgggcc agaagctgga 360
cttccctatg gtgctaacaa agacggcatc atatgggttg caactgaggg agccttgaat 420
acaccaaaag atcacattgg cacccgcaat cctgctaaca atgctgcaat cgtgctacaa 480
cttcctcaag gaacaacatt gccaaaaggc ttctacgcag aagggagcag aggcggcagt 540
caagcctctt ctcgttcctc atcacgtagt cgcaacagtt caagaaattc aactccaggc 600
agcagtaggg gaacttctcc tgctagaatg gctggcaatg gcggtgatgc tgctcttgct 660
ttgctgctgc ttgacagatt gaaccagctt gagagcaaaa tgtctggtaa aggccaacaa 720
caacaaggcc aaactgtcac taagaaatct gctgctgagg cttctaagaa gcctcggcaa 780
aaacgtactg ccactaaagc atacaatgta acacaagctt tcggcagacg tggtccagaa 840
caaacccaag gaaattttgg ggaccaggaa ctaatcagac aaggaactga ttacaaacat 900
tggccgcaaa ttgcacaatt tgcccccagc gcttcagcgt tcttcggaat gtcgcgcatt 960
ggcatggaag tcacaccttc gggaacgtgg ttgacctaca caggtgccat caaattggat 1020
gacaaagatc caaatttcaa agatcaagtc attttgctga ataagcatat tgacgcatac 1080
aaaacattcc caccaacaga gcctaaaaag gacaaaaaga agaaggctga tgaaactcaa 1140
gccttaccgc agagacagaa gaaacagcaa actgtgactc ttcttcctgc tgcagatttg 1200
gatgatttct ccaaacaatt gcaacaatcc atgagcagtg ctgactcaac tcaggccta 1259

<210> SEQ ID NO 11
<211> LENGTH: 20
<212> TYPE: RNA
<213> ORGANISM: Severe acute respiratory syndrome coronavirus 2

<400> SEQUENCE: 11
gguaacuggu augauuucgg 20

<210> SEQ ID NO 12
<211> LENGTH: 20
<212> TYPE: RNA
<213> ORGANISM: Severe acute respiratory syndrome coronavirus 2

<400> SEQUENCE: 12
ucugcauugu gcaaacuuua 20

<210> SEQ ID NO 13
<211> LENGTH: 20
<212> TYPE: RNA
<213> ORGANISM: Severe acute respiratory syndrome coronavirus 2

<400> SEQUENCE: 13
ugugauauca gacaacuacu 20

<210> SEQ ID NO 14
<211> LENGTH: 20
<212> TYPE: RNA
<213> ORGANISM: Severe acute respiratory syndrome coronavirus 2

<400> SEQUENCE: 14
uguagcuugu cacaccguuu 20

<210> SEQ ID NO 15
<211> LENGTH: 20
<212> TYPE: RNA
<213> ORGANISM: Severe acute respiratory syndrome coronavirus 2

<400> SEQUENCE: 15
uaagucaguu cuuuauuauc 20

<210> SEQ ID NO 16
<211> LENGTH: 20
<212> TYPE: RNA
<213> ORGANISM: Severe acute respiratory syndrome coronavirus 2

<400> SEQUENCE: 16
uuugcuauug gccuagcucu 20

<210> SEQ ID NO 17
<211> LENGTH: 20
<212> TYPE: RNA
<213> ORGANISM: Severe acute respiratory syndrome coronavirus 2

<400> SEQUENCE: 17
ggccacaaau uaugauuuga 20

<210> SEQ ID NO 18
<211> LENGTH: 20
<212> TYPE: RNA
<213> ORGANISM: Severe acute respiratory syndrome coronavirus 2

<400> SEQUENCE: 18
guggcaacuu uacaagcuga 20

<210> SEQ ID NO 19
<211> LENGTH: 20
<212> TYPE: RNA
<213> ORGANISM: Severe acute respiratory syndrome coronavirus 2

<400> SEQUENCE: 19
ucugacagag ucguauuugu 20

<210> SEQ ID NO 20
<211> LENGTH: 20
<212> TYPE: RNA
<213> ORGANISM: Severe acute respiratory syndrome coronavirus 2

<400> SEQUENCE: 20
ucuguuauug auuuauuacu 20

<210> SEQ ID NO 21
<211> LENGTH: 20
<212> TYPE: RNA
<213> ORGANISM: Severe acute respiratory syndrome coronavirus 2

<400> SEQUENCE: 21
ugcaccaggu acagcuguuu 20

<210> SEQ ID NO 22
<211> LENGTH: 20
<212> TYPE: RNA
<213> ORGANISM: Severe acute respiratory syndrome coronavirus 2

<400> SEQUENCE: 22
uuugacauga guaaauuucc 20

<210> SEQ ID NO 23
<211> LENGTH: 20
<212> TYPE: RNA
<213> ORGANISM: Severe acute respiratory syndrome coronavirus 2

<400> SEQUENCE: 23
uguggcuuag uagaaguuga 20

<210> SEQ ID NO 24
<211> LENGTH: 20
<212> TYPE: RNA
<213> ORGANISM: Severe acute respiratory syndrome coronavirus 2

<400> SEQUENCE: 24
ucagacauuc uuuaagcuug 20

<210> SEQ ID NO 25
<211> LENGTH: 20
<212> TYPE: RNA
<213> ORGANISM: Severe acute respiratory syndrome coronavirus 2

<400> SEQUENCE: 25
ugugauaaua ucaaauuugc 20

<210> SEQ ID NO 26
<211> LENGTH: 20
<212> TYPE: RNA
<213> ORGANISM: Severe acute respiratory syndrome coronavirus 2

<400> SEQUENCE: 26
ugaaacauca aauucguuug 20

<210> SEQ ID NO 27
<211> LENGTH: 20
<212> TYPE: RNA

<213> ORGANISM: Severe acute respiratory syndrome coronavirus 2

<400> SEQUENCE: 27
accagcaaau aauaguuuaa 20

<210> SEQ ID NO 28
<211> LENGTH: 20
<212> TYPE: RNA
<213> ORGANISM: Severe acute respiratory syndrome coronavirus 2

<400> SEQUENCE: 28
gcugguagua cauuuauuag 20

<210> SEQ ID NO 29
<211> LENGTH: 20
<212> TYPE: RNA
<213> ORGANISM: Severe acute respiratory syndrome coronavirus 2

<400> SEQUENCE: 29
uguagaaacu aaagauguug 20

<210> SEQ ID NO 30
<211> LENGTH: 20
<212> TYPE: RNA
<213> ORGANISM: Severe acute respiratory syndrome coronavirus 2

<400> SEQUENCE: 30
guagaaacua aagauguugu 20

<210> SEQ ID NO 31
<211> LENGTH: 20
<212> TYPE: RNA
<213> ORGANISM: Severe acute respiratory syndrome coronavirus 2

<400> SEQUENCE: 31
uuugcuaaca aacaugcuga 20

<210> SEQ ID NO 32
<211> LENGTH: 20
<212> TYPE: RNA
<213> ORGANISM: Severe acute respiratory syndrome coronavirus 2

<400> SEQUENCE: 32
cuggauaaca auugcuuaua 20

<210> SEQ ID NO 33
<211> LENGTH: 20
<212> TYPE: RNA
<213> ORGANISM: Severe acute respiratory syndrome coronavirus 2

<400> SEQUENCE: 33
caguguauaa ugcuaguuua 20

<210> SEQ ID NO 34
<211> LENGTH: 20
<212> TYPE: RNA
<213> ORGANISM: Severe acute respiratory syndrome coronavirus 2

<400> SEQUENCE: 34
ccuaaaguga aguauuuaua 20

<210> SEQ ID NO 35
<211> LENGTH: 20

<212> TYPE: RNA
<213> ORGANISM: Severe acute respiratory syndrome coronavirus 2

<400> SEQUENCE: 35
auuaaagucu gugaauuuca 20

<210> SEQ ID NO 36
<211> LENGTH: 20
<212> TYPE: RNA
<213> ORGANISM: Severe acute respiratory syndrome coronavirus 2

<400> SEQUENCE: 36
ucggcuuuag aaccauuggu 20

<210> SEQ ID NO 37
<211> LENGTH: 20
<212> TYPE: RNA
<213> ORGANISM: Severe acute respiratory syndrome coronavirus 2

<400> SEQUENCE: 37
ccuaauauua caaacuugug 20

<210> SEQ ID NO 38
<211> LENGTH: 20
<212> TYPE: RNA
<213> ORGANISM: Severe acute respiratory syndrome coronavirus 2

<400> SEQUENCE: 38
gauuauaauu auaaauuacc 20

<210> SEQ ID NO 39
<211> LENGTH: 20
<212> TYPE: RNA
<213> ORGANISM: Severe acute respiratory syndrome coronavirus 2

<400> SEQUENCE: 39
ggugguaauu auaauuaccu 20

<210> SEQ ID NO 40
<211> LENGTH: 20
<212> TYPE: RNA
<213> ORGANISM: Severe acute respiratory syndrome coronavirus 2

<400> SEQUENCE: 40
ugugucaauu ucaacuucaa 20

<210> SEQ ID NO 41
<211> LENGTH: 20
<212> TYPE: RNA
<213> ORGANISM: Severe acute respiratory syndrome coronavirus 2

<400> SEQUENCE: 41
ucugccuuuc caacaauuug 20

<210> SEQ ID NO 42
<211> LENGTH: 20
<212> TYPE: RNA
<213> ORGANISM: Severe acute respiratory syndrome coronavirus 2

<400> SEQUENCE: 42
cugccuuucc aacaauuugg 20

<210> SEQ ID NO 43

<211> LENGTH: 20
<212> TYPE: RNA
<213> ORGANISM: Severe acute respiratory syndrome coronavirus 2

<400> SEQUENCE: 43
uguacaaugu acauuugugg 20

<210> SEQ ID NO 44
<211> LENGTH: 20
<212> TYPE: RNA
<213> ORGANISM: Severe acute respiratory syndrome coronavirus 2

<400> SEQUENCE: 44
ggcuucauca aacaauaugg 20

<210> SEQ ID NO 45
<211> LENGTH: 20
<212> TYPE: RNA
<213> ORGANISM: Severe acute respiratory syndrome coronavirus 2

<400> SEQUENCE: 45
uggaguuaca cagaauguuc 20

<210> SEQ ID NO 46
<211> LENGTH: 20
<212> TYPE: RNA
<213> ORGANISM: Severe acute respiratory syndrome coronavirus 2

<400> SEQUENCE: 46
uuacacauaa acgaacuuau 20

<210> SEQ ID NO 47
<211> LENGTH: 20
<212> TYPE: RNA
<213> ORGANISM: Severe acute respiratory syndrome coronavirus 2

<400> SEQUENCE: 47
cuucacaauu ggaacuguaa 20

<210> SEQ ID NO 48
<211> LENGTH: 20
<212> TYPE: RNA
<213> ORGANISM: Severe acute respiratory syndrome coronavirus 2

<400> SEQUENCE: 48
guuugcaacu ugcuguuguu 20

<210> SEQ ID NO 49
<211> LENGTH: 20
<212> TYPE: RNA
<213> ORGANISM: Severe acute respiratory syndrome coronavirus 2

<400> SEQUENCE: 49
uaugcuuuag ucuacuucuu 20

<210> SEQ ID NO 50
<211> LENGTH: 20
<212> TYPE: RNA
<213> ORGANISM: Severe acute respiratory syndrome coronavirus 2

<400> SEQUENCE: 50
cuugcagagu auaaacuuug 20

<210> SEQ ID NO 51
<211> LENGTH: 20
<212> TYPE: RNA
<213> ORGANISM: Severe acute respiratory syndrome coronavirus 2

<400> SEQUENCE: 51
ugcagaguau aaacuuugua 20

<210> SEQ ID NO 52
<211> LENGTH: 20
<212> TYPE: RNA
<213> ORGANISM: Severe acute respiratory syndrome coronavirus 2

<400> SEQUENCE: 52
uaaacuuugu aagaauaaua 20

<210> SEQ ID NO 53
<211> LENGTH: 20
<212> TYPE: RNA
<213> ORGANISM: Severe acute respiratory syndrome coronavirus 2

<400> SEQUENCE: 53
cuuacaauag uguaacuucu 20

<210> SEQ ID NO 54
<211> LENGTH: 20
<212> TYPE: RNA
<213> ORGANISM: Severe acute respiratory syndrome coronavirus 2

<400> SEQUENCE: 54
uacaauagug uaacuucuuc 20

<210> SEQ ID NO 55
<211> LENGTH: 20
<212> TYPE: RNA
<213> ORGANISM: Severe acute respiratory syndrome coronavirus 2

<400> SEQUENCE: 55
cacaacaagu ccuauuucug 20

<210> SEQ ID NO 56
<211> LENGTH: 20
<212> TYPE: RNA
<213> ORGANISM: Severe acute respiratory syndrome coronavirus 2

<400> SEQUENCE: 56
uguuguauua cacaguuacu 20

<210> SEQ ID NO 57
<211> LENGTH: 20
<212> TYPE: RNA
<213> ORGANISM: Severe acute respiratory syndrome coronavirus 2

<400> SEQUENCE: 57
cagacuauua ccagcuguac 20

<210> SEQ ID NO 58
<211> LENGTH: 20
<212> TYPE: RNA
<213> ORGANISM: Severe acute respiratory syndrome coronavirus 2

<400> SEQUENCE: 58
uugaacaugu uaccuucuuc 20

<210> SEQ ID NO 59
<211> LENGTH: 20
<212> TYPE: RNA
<213> ORGANISM: Severe acute respiratory syndrome coronavirus 2

<400> SEQUENCE: 59
uuucggaaga gacagguacg 20

<210> SEQ ID NO 60
<211> LENGTH: 20
<212> TYPE: RNA
<213> ORGANISM: Severe acute respiratory syndrome coronavirus 2

<400> SEQUENCE: 60
cggaagagac agguacguua 20

<210> SEQ ID NO 61
<211> LENGTH: 20
<212> TYPE: RNA
<213> ORGANISM: Severe acute respiratory syndrome coronavirus 2

<400> SEQUENCE: 61
acagguacgu uaauaguuaa 20

<210> SEQ ID NO 62
<211> LENGTH: 20
<212> TYPE: RNA
<213> ORGANISM: Severe acute respiratory syndrome coronavirus 2

<400> SEQUENCE: 62
guuaauaguu aauagcguac 20

<210> SEQ ID NO 63
<211> LENGTH: 20
<212> TYPE: RNA
<213> ORGANISM: Severe acute respiratory syndrome coronavirus 2

<400> SEQUENCE: 63
cuugcuuucg ugguauucuu 20

<210> SEQ ID NO 64
<211> LENGTH: 20
<212> TYPE: RNA
<213> ORGANISM: Severe acute respiratory syndrome coronavirus 2

<400> SEQUENCE: 64
cgugguauuc uugcuaguua 20

<210> SEQ ID NO 65
<211> LENGTH: 20
<212> TYPE: RNA
<213> ORGANISM: Severe acute respiratory syndrome coronavirus 2

<400> SEQUENCE: 65
acugcugcaa uauuguuaac 20

<210> SEQ ID NO 66
<211> LENGTH: 20
<212> TYPE: RNA
<213> ORGANISM: Severe acute respiratory syndrome coronavirus 2

<400> SEQUENCE: 66
ugcaauauug uuaacgugag 20

<210> SEQ ID NO 67
<211> LENGTH: 20
<212> TYPE: RNA
<213> ORGANISM: Severe acute respiratory syndrome coronavirus 2

<400> SEQUENCE: 67
ccugaucuuc uggucuaaac 20

<210> SEQ ID NO 68
<211> LENGTH: 20
<212> TYPE: RNA
<213> ORGANISM: Severe acute respiratory syndrome coronavirus 2

<400> SEQUENCE: 68
ucuggucuaa acgaacuaaa 20

<210> SEQ ID NO 69
<211> LENGTH: 20
<212> TYPE: RNA
<213> ORGANISM: Severe acute respiratory syndrome coronavirus 2

<400> SEQUENCE: 69
gucuaaacga acuaaauauu 20

<210> SEQ ID NO 70
<211> LENGTH: 20
<212> TYPE: RNA
<213> ORGANISM: Severe acute respiratory syndrome coronavirus 2

<400> SEQUENCE: 70
uaaacgaacu aaauauuaua 20

<210> SEQ ID NO 71
<211> LENGTH: 20
<212> TYPE: RNA
<213> ORGANISM: Severe acute respiratory syndrome coronavirus 2

<400> SEQUENCE: 71
ugaacaaugg aaccuaguaa 20

<210> SEQ ID NO 72
<211> LENGTH: 20
<212> TYPE: RNA
<213> ORGANISM: Severe acute respiratory syndrome coronavirus 2

<400> SEQUENCE: 72
ggaaccuagu aauagguuuc 20

<210> SEQ ID NO 73
<211> LENGTH: 20
<212> TYPE: RNA
<213> ORGANISM: Severe acute respiratory syndrome coronavirus 2

<400> SEQUENCE: 73
uauuccuuac auggauuugu 20

<210> SEQ ID NO 74
<211> LENGTH: 20
<212> TYPE: RNA
<213> ORGANISM: Severe acute respiratory syndrome coronavirus 2

<400> SEQUENCE: 74
ucuacaauuu gccuaugcca 20

<210> SEQ ID NO 75
<211> LENGTH: 20
<212> TYPE: RNA
<213> ORGANISM: Severe acute respiratory syndrome coronavirus 2

<400> SEQUENCE: 75
uaugccaaca ggaauagguu 20

<210> SEQ ID NO 76
<211> LENGTH: 20
<212> TYPE: RNA
<213> ORGANISM: Severe acute respiratory syndrome coronavirus 2

<400> SEQUENCE: 76
augccaacag gaauagguuu 20

<210> SEQ ID NO 77
<211> LENGTH: 20
<212> TYPE: RNA
<213> ORGANISM: Severe acute respiratory syndrome coronavirus 2

<400> SEQUENCE: 77
auggccagua acuuuagcuu 20

<210> SEQ ID NO 78
<211> LENGTH: 20
<212> TYPE: RNA
<213> ORGANISM: Severe acute respiratory syndrome coronavirus 2

<400> SEQUENCE: 78
ugugcuugcu gcuguuuaca 20

<210> SEQ ID NO 79
<211> LENGTH: 20
<212> TYPE: RNA
<213> ORGANISM: Severe acute respiratory syndrome coronavirus 2

<400> SEQUENCE: 79
gccuaaagaa aucacuguug 20

<210> SEQ ID NO 80
<211> LENGTH: 20
<212> TYPE: RNA
<213> ORGANISM: Severe acute respiratory syndrome coronavirus 2

<400> SEQUENCE: 80
ugcuacauca cgaacgcuuu 20

<210> SEQ ID NO 81
<211> LENGTH: 20
<212> TYPE: RNA
<213> ORGANISM: Severe acute respiratory syndrome coronavirus 2

<400> SEQUENCE: 81
uacaucacga acgcuuucuu 20

<210> SEQ ID NO 82
<211> LENGTH: 20
<212> TYPE: RNA
<213> ORGANISM: Severe acute respiratory syndrome coronavirus 2

<400> SEQUENCE: 82
auuggcaacu auaaauuaaa                                          20

<210> SEQ ID NO 83
<211> LENGTH: 20
<212> TYPE: RNA
<213> ORGANISM: Severe acute respiratory syndrome coronavirus 2

<400> SEQUENCE: 83
aagagugugu uagagguaca                                          20

<210> SEQ ID NO 84
<211> LENGTH: 20
<212> TYPE: RNA
<213> ORGANISM: Severe acute respiratory syndrome coronavirus 2

<400> SEQUENCE: 84
uucaccauuu cauccucuag                                          20

<210> SEQ ID NO 85
<211> LENGTH: 20
<212> TYPE: RNA
<213> ORGANISM: Severe acute respiratory syndrome coronavirus 2

<400> SEQUENCE: 85
ucuagcugau aacaaauuug                                          20

<210> SEQ ID NO 86
<211> LENGTH: 20
<212> TYPE: RNA
<213> ORGANISM: Severe acute respiratory syndrome coronavirus 2

<400> SEQUENCE: 86
uuugcacuga cuugcuuuag                                          20

<210> SEQ ID NO 87
<211> LENGTH: 20
<212> TYPE: RNA
<213> ORGANISM: Severe acute respiratory syndrome coronavirus 2

<400> SEQUENCE: 87
ugcuuuagca cucaauuugc                                          20

<210> SEQ ID NO 88
<211> LENGTH: 20
<212> TYPE: RNA
<213> ORGANISM: Severe acute respiratory syndrome coronavirus 2

<400> SEQUENCE: 88
aucaguuuca ccuaaacugu                                          20

<210> SEQ ID NO 89
<211> LENGTH: 20
<212> TYPE: RNA
<213> ORGANISM: Severe acute respiratory syndrome coronavirus 2

<400> SEQUENCE: 89
ucagacaaga ggaaguucaa                                          20

<210> SEQ ID NO 90
<211> LENGTH: 20
<212> TYPE: RNA
<213> ORGANISM: Severe acute respiratory syndrome coronavirus 2

<400> SEQUENCE: 90
uucaagaacu uuacucucca 20

<210> SEQ ID NO 91
<211> LENGTH: 20
<212> TYPE: RNA
<213> ORGANISM: Severe acute respiratory syndrome coronavirus 2

<400> SEQUENCE: 91
ugcggcaaua guguuuauaa 20

<210> SEQ ID NO 92
<211> LENGTH: 20
<212> TYPE: RNA
<213> ORGANISM: Severe acute respiratory syndrome coronavirus 2

<400> SEQUENCE: 92
guguuuauaa cacuuugcuu 20

<210> SEQ ID NO 93
<211> LENGTH: 20
<212> TYPE: RNA
<213> ORGANISM: Severe acute respiratory syndrome coronavirus 2

<400> SEQUENCE: 93
uauaacacuu ugcuucacac 20

<210> SEQ ID NO 94
<211> LENGTH: 20
<212> TYPE: RNA
<213> ORGANISM: Severe acute respiratory syndrome coronavirus 2

<400> SEQUENCE: 94
acagaaugau ugaacuuuca 20

<210> SEQ ID NO 95
<211> LENGTH: 20
<212> TYPE: RNA
<213> ORGANISM: Severe acute respiratory syndrome coronavirus 2

<400> SEQUENCE: 95
agcugcauuu caccaagaau 20

<210> SEQ ID NO 96
<211> LENGTH: 20
<212> TYPE: RNA
<213> ORGANISM: Severe acute respiratory syndrome coronavirus 2

<400> SEQUENCE: 96
uucaccaaga auguaguuua 20

<210> SEQ ID NO 97
<211> LENGTH: 20
<212> TYPE: RNA
<213> ORGANISM: Severe acute respiratory syndrome coronavirus 2

<400> SEQUENCE: 97
uguaguugau gacccguguc 20

<210> SEQ ID NO 98
<211> LENGTH: 20
<212> TYPE: RNA
<213> ORGANISM: Severe acute respiratory syndrome coronavirus 2

<400> SEQUENCE: 98
uguccuauuc acuucuauuc 20

<210> SEQ ID NO 99
<211> LENGTH: 20
<212> TYPE: RNA
<213> ORGANISM: Severe acute respiratory syndrome coronavirus 2

<400> SEQUENCE: 99
aaugguauau uagaguagga 20

<210> SEQ ID NO 100
<211> LENGTH: 20
<212> TYPE: RNA
<213> ORGANISM: Severe acute respiratory syndrome coronavirus 2

<400> SEQUENCE: 100
uucuaaauca cccauucagu 20

<210> SEQ ID NO 101
<211> LENGTH: 20
<212> TYPE: RNA
<213> ORGANISM: Severe acute respiratory syndrome coronavirus 2

<400> SEQUENCE: 101
aucgguaauu auacaguuuc 20

<210> SEQ ID NO 102
<211> LENGTH: 20
<212> TYPE: RNA
<213> ORGANISM: Severe acute respiratory syndrome coronavirus 2

<400> SEQUENCE: 102
uuauacaguu uccuguuuac 20

<210> SEQ ID NO 103
<211> LENGTH: 20
<212> TYPE: RNA
<213> ORGANISM: Severe acute respiratory syndrome coronavirus 2

<400> SEQUENCE: 103
uauacaguuu ccuguuuacc 20

<210> SEQ ID NO 104
<211> LENGTH: 20
<212> TYPE: RNA
<213> ORGANISM: Severe acute respiratory syndrome coronavirus 2

<400> SEQUENCE: 104
ccaggaaccu aaauugggua 20

<210> SEQ ID NO 105
<211> LENGTH: 20
<212> TYPE: RNA
<213> ORGANISM: Severe acute respiratory syndrome coronavirus 2

<400> SEQUENCE: 105
uuagaguauc augacguucg 20

<210> SEQ ID NO 106
<211> LENGTH: 20
<212> TYPE: RNA

<213> ORGANISM: Severe acute respiratory syndrome coronavirus 2

<400> SEQUENCE: 106
aguaucauga cguucguguu 20

<210> SEQ ID NO 107
<211> LENGTH: 20
<212> TYPE: RNA
<213> ORGANISM: Severe acute respiratory syndrome coronavirus 2

<400> SEQUENCE: 107
uacccaauaa uacugcgucu 20

<210> SEQ ID NO 108
<211> LENGTH: 20
<212> TYPE: RNA
<213> ORGANISM: Severe acute respiratory syndrome coronavirus 2

<400> SEQUENCE: 108
gacggcauca uaugggguugc 20

<210> SEQ ID NO 109
<211> LENGTH: 20
<212> TYPE: RNA
<213> ORGANISM: Severe acute respiratory syndrome coronavirus 2

<400> SEQUENCE: 109
ugacagauug aaccagcuug 20

<210> SEQ ID NO 110
<211> LENGTH: 20
<212> TYPE: RNA
<213> ORGANISM: Severe acute respiratory syndrome coronavirus 2

<400> SEQUENCE: 110
aacaacaagg ccaaacuguc 20

<210> SEQ ID NO 111
<211> LENGTH: 20
<212> TYPE: RNA
<213> ORGANISM: Severe acute respiratory syndrome coronavirus 2

<400> SEQUENCE: 111
gaacuaauca gacaaggaac 20

<210> SEQ ID NO 112
<211> LENGTH: 20
<212> TYPE: RNA
<213> ORGANISM: Severe acute respiratory syndrome coronavirus 2

<400> SEQUENCE: 112
ggugccauca aauuggauga 20

<210> SEQ ID NO 113
<211> LENGTH: 20
<212> TYPE: RNA
<213> ORGANISM: Severe acute respiratory syndrome coronavirus 2

<400> SEQUENCE: 113
augacaaaga uccaaauuuc 20

<210> SEQ ID NO 114
<211> LENGTH: 20

<212> TYPE: RNA
<213> ORGANISM: Severe acute respiratory syndrome coronavirus 2

<400> SEQUENCE: 114
ugacaaagau ccaaauuuca 20

<210> SEQ ID NO 115
<211> LENGTH: 20
<212> TYPE: RNA
<213> ORGANISM: Severe acute respiratory syndrome coronavirus 2

<400> SEQUENCE: 115
ccaaauuuca aagaucaagu 20

<210> SEQ ID NO 116
<211> LENGTH: 20
<212> TYPE: RNA
<213> ORGANISM: Severe acute respiratory syndrome coronavirus 2

<400> SEQUENCE: 116
auuucaaaga ucaagucauu 20

<210> SEQ ID NO 117
<211> LENGTH: 20
<212> TYPE: RNA
<213> ORGANISM: Severe acute respiratory syndrome coronavirus 2

<400> SEQUENCE: 117
ugcugaauaa gcauauugac 20

<210> SEQ ID NO 118
<211> LENGTH: 20
<212> TYPE: RNA
<213> ORGANISM: Severe acute respiratory syndrome coronavirus 2

<400> SEQUENCE: 118
ugcagauuug gaugauuucu 20

<210> SEQ ID NO 119
<211> LENGTH: 45
<212> TYPE: DNA
<213> ORGANISM: Severe acute respiratory syndrome coronavirus 2

<400> SEQUENCE: 119
aatcaagatc tcaatggtaa ctggtatgat ttcggtgatt tcata 45

<210> SEQ ID NO 120
<211> LENGTH: 45
<212> TYPE: DNA
<213> ORGANISM: Severe acute respiratory syndrome coronavirus 2

<400> SEQUENCE: 120
ggatgacaga tgcattctgc attgtgcaaa ctttaatgtt ttatt 45

<210> SEQ ID NO 121
<211> LENGTH: 45
<212> TYPE: DNA
<213> ORGANISM: Severe acute respiratory syndrome coronavirus 2

<400> SEQUENCE: 121
aatctaccaa caatgtgtga tatcagacaa ctactatttg tagtt 45

<210> SEQ ID NO 122

<211> LENGTH: 45
<212> TYPE: DNA
<213> ORGANISM: Severe acute respiratory syndrome coronavirus 2

<400> SEQUENCE: 122
aaacatacaa cgtgttgtag cttgtcacac cgtttctata gatta 45

<210> SEQ ID NO 123
<211> LENGTH: 45
<212> TYPE: DNA
<213> ORGANISM: Severe acute respiratory syndrome coronavirus 2

<400> SEQUENCE: 123
tagcataaag aactttaagt cagttcttta ttatcaaaac aatgt 45

<210> SEQ ID NO 124
<211> LENGTH: 45
<212> TYPE: DNA
<213> ORGANISM: Severe acute respiratory syndrome coronavirus 2

<400> SEQUENCE: 124
actggtaaga gtcattttgc tattggccta gctctctact accct 45

<210> SEQ ID NO 125
<211> LENGTH: 45
<212> TYPE: DNA
<213> ORGANISM: Severe acute respiratory syndrome coronavirus 2

<400> SEQUENCE: 125
tgatgaaatt tcaatggcca caaattatga tttgagtgtt gtcaa 45

<210> SEQ ID NO 126
<211> LENGTH: 45
<212> TYPE: DNA
<213> ORGANISM: Severe acute respiratory syndrome coronavirus 2

<400> SEQUENCE: 126
attccacgta ggaatgtggc aactttacaa gctgaaaatg taaca 45

<210> SEQ ID NO 127
<211> LENGTH: 45
<212> TYPE: DNA
<213> ORGANISM: Severe acute respiratory syndrome coronavirus 2

<400> SEQUENCE: 127
acacttaaaa atctctctga cagagtcgta tttgtcttat gggca 45

<210> SEQ ID NO 128
<211> LENGTH: 45
<212> TYPE: DNA
<213> ORGANISM: Severe acute respiratory syndrome coronavirus 2

<400> SEQUENCE: 128
tctaagtgtg tgtgttctgt tattgattta ttacttgatg atttt 45

<210> SEQ ID NO 129
<211> LENGTH: 45
<212> TYPE: DNA
<213> ORGANISM: Severe acute respiratory syndrome coronavirus 2

<400> SEQUENCE: 129
ttctgataaa ggagttgcac caggtacagc tgttttaaga cagtg 45

<210> SEQ ID NO 130
<211> LENGTH: 45
<212> TYPE: DNA
<213> ORGANISM: Severe acute respiratory syndrome coronavirus 2

<400> SEQUENCE: 130
tcttcctatt ctttatttga catgagtaaa tttcccctta aatta 45

<210> SEQ ID NO 131
<211> LENGTH: 45
<212> TYPE: DNA
<213> ORGANISM: Severe acute respiratory syndrome coronavirus 2

<400> SEQUENCE: 131
cttaaagatg gcacttgtgg cttagtagaa gttgaaaaag gcgtt 45

<210> SEQ ID NO 132
<211> LENGTH: 45
<212> TYPE: DNA
<213> ORGANISM: Severe acute respiratory syndrome coronavirus 2

<400> SEQUENCE: 132
aattaaggag agtgttcaga cattctttaa gcttgtaaat aaatt 45

<210> SEQ ID NO 133
<211> LENGTH: 45
<212> TYPE: DNA
<213> ORGANISM: Severe acute respiratory syndrome coronavirus 2

<400> SEQUENCE: 133
aattttaagt ttgtatgtga taatatcaaa tttgctgatg attta 45

<210> SEQ ID NO 134
<211> LENGTH: 45
<212> TYPE: DNA
<213> ORGANISM: Severe acute respiratory syndrome coronavirus 2

<400> SEQUENCE: 134
gagcacaaaa ccagttgaaa catcaaattc gtttgatgta ctgaa 45

<210> SEQ ID NO 135
<211> LENGTH: 45
<212> TYPE: DNA
<213> ORGANISM: Severe acute respiratory syndrome coronavirus 2

<400> SEQUENCE: 135
agacattata cttaaaccag caaataatag tttaaaaatt acaga 45

<210> SEQ ID NO 136
<211> LENGTH: 45
<212> TYPE: DNA
<213> ORGANISM: Severe acute respiratory syndrome coronavirus 2

<400> SEQUENCE: 136
tgtgatacat tctgtgctgg tagtacattt attagtgatg aagtt 45

<210> SEQ ID NO 137
<211> LENGTH: 45
<212> TYPE: DNA
<213> ORGANISM: Severe acute respiratory syndrome coronavirus 2

<400> SEQUENCE: 137
gtttgttgat tcagatgtag aaactaaaga tgttgttgaa tgtct 45

<210> SEQ ID NO 138
<211> LENGTH: 45
<212> TYPE: DNA
<213> ORGANISM: Severe acute respiratory syndrome coronavirus 2

<400> SEQUENCE: 138
tttgttgatt cagatgtaga aactaaagat gttgttgaat gtctt 45

<210> SEQ ID NO 139
<211> LENGTH: 45
<212> TYPE: DNA
<213> ORGANISM: Severe acute respiratory syndrome coronavirus 2

<400> SEQUENCE: 139
tctacagata cttgttttgc taacaaacat gctgattttg acaca 45

<210> SEQ ID NO 140
<211> LENGTH: 45
<212> TYPE: DNA
<213> ORGANISM: Severe acute respiratory syndrome coronavirus 2

<400> SEQUENCE: 140
acctttagta cctttctgga taacaattgc ttatatcatt tgtat 45

<210> SEQ ID NO 141
<211> LENGTH: 45
<212> TYPE: DNA
<213> ORGANISM: Severe acute respiratory syndrome coronavirus 2

<400> SEQUENCE: 141
actggtaata cacttcagtg tataatgcta gtttattgtt tctta 45

<210> SEQ ID NO 142
<211> LENGTH: 45
<212> TYPE: DNA
<213> ORGANISM: Severe acute respiratory syndrome coronavirus 2

<400> SEQUENCE: 142
gacacaccta aaggtcctaa agtgaagtat ttatacttta ttaaa 45

<210> SEQ ID NO 143
<211> LENGTH: 45
<212> TYPE: DNA
<213> ORGANISM: Severe acute respiratory syndrome coronavirus 2

<400> SEQUENCE: 143
gctactaatg ttgttattaa agtctgtgaa tttcaatttt gtaat 45

<210> SEQ ID NO 144
<211> LENGTH: 45
<212> TYPE: DNA
<213> ORGANISM: Severe acute respiratory syndrome coronavirus 2

<400> SEQUENCE: 144
ctccctcagg gtttttcggc tttagaacca ttggtagatt tgcca 45

<210> SEQ ID NO 145
<211> LENGTH: 45
<212> TYPE: DNA
<213> ORGANISM: Severe acute respiratory syndrome coronavirus 2

<400> SEQUENCE: 145
tctattgtta gatttcctaa tattacaaac ttgtgccctt ttggt 45

<210> SEQ ID NO 146
<211> LENGTH: 45
<212> TYPE: DNA
<213> ORGANISM: Severe acute respiratory syndrome coronavirus 2

<400> SEQUENCE: 146
actggaaaga ttgctgatta taattataaa ttaccagatg atttt 45

<210> SEQ ID NO 147
<211> LENGTH: 45
<212> TYPE: DNA
<213> ORGANISM: Severe acute respiratory syndrome coronavirus 2

<400> SEQUENCE: 147
cttgattcta aggttggtgg taattataat tacctgtata gattg 45

<210> SEQ ID NO 148
<211> LENGTH: 45
<212> TYPE: DNA
<213> ORGANISM: Severe acute respiratory syndrome coronavirus 2

<400> SEQUENCE: 148
ttggttaaaa acaaatgtgt caatttcaac ttcaatggtt taaca 45

<210> SEQ ID NO 149
<211> LENGTH: 45
<212> TYPE: DNA
<213> ORGANISM: Severe acute respiratory syndrome coronavirus 2

<400> SEQUENCE: 149
gtctaacaaa aagtttctgc ctttccaaca atttggcaga gacat 45

<210> SEQ ID NO 150
<211> LENGTH: 45
<212> TYPE: DNA
<213> ORGANISM: Severe acute respiratory syndrome coronavirus 2

<400> SEQUENCE: 150
tctaacaaaa agtttctgcc tttccaacaa tttggcagag acatt 45

<210> SEQ ID NO 151
<211> LENGTH: 45
<212> TYPE: DNA
<213> ORGANISM: Severe acute respiratory syndrome coronavirus 2

<400> SEQUENCE: 151
aagacatcag tagattgtac aatgtacatt tgtggtgatt caact 45

<210> SEQ ID NO 152
<211> LENGTH: 45
<212> TYPE: DNA
<213> ORGANISM: Severe acute respiratory syndrome coronavirus 2

<400> SEQUENCE: 152
acacttgcag atgctggctt catcaaacaa tatggtgatt gcctt 45

<210> SEQ ID NO 153
<211> LENGTH: 45
<212> TYPE: DNA
<213> ORGANISM: Severe acute respiratory syndrome coronavirus 2

<400> SEQUENCE: 153
taggtttaat ggtattggag ttacacagaa tgttctctat gagaa 45

<210> SEQ ID NO 154
<211> LENGTH: 45
<212> TYPE: DNA
<213> ORGANISM: Severe acute respiratory syndrome coronavirus 2

<400> SEQUENCE: 154
aggagtcaaa ttacattaca cataaacgaa cttatggatt tgttt 45

<210> SEQ ID NO 155
<211> LENGTH: 45
<212> TYPE: DNA
<213> ORGANISM: Severe acute respiratory syndrome coronavirus 2

<400> SEQUENCE: 155
tttgtttatg agaatcttca caattggaac tgtaactttg aagca 45

<210> SEQ ID NO 156
<211> LENGTH: 45
<212> TYPE: DNA
<213> ORGANISM: Severe acute respiratory syndrome coronavirus 2

<400> SEQUENCE: 156
aagggtgttc actttgtttg caacttgctg ttgttgtttg taaca 45

<210> SEQ ID NO 157
<211> LENGTH: 45
<212> TYPE: DNA
<213> ORGANISM: Severe acute respiratory syndrome coronavirus 2

<400> SEQUENCE: 157
ccttttctct atctttatgc tttagtctac ttcttgcaga gtata 45

<210> SEQ ID NO 158
<211> LENGTH: 45
<212> TYPE: DNA
<213> ORGANISM: Severe acute respiratory syndrome coronavirus 2

<400> SEQUENCE: 158
tgctttagtc tacttcttgc agagtataaa ctttgtaaga ataat 45

<210> SEQ ID NO 159
<211> LENGTH: 45
<212> TYPE: DNA
<213> ORGANISM: Severe acute respiratory syndrome coronavirus 2

<400> SEQUENCE: 159
ctttagtcta cttcttgcag agtataaact ttgtaagaat aataa 45

<210> SEQ ID NO 160
<211> LENGTH: 45
<212> TYPE: DNA
<213> ORGANISM: Severe acute respiratory syndrome coronavirus 2

<400> SEQUENCE: 160
acttcttgca gagtataaac tttgtaagaa taataatgag gcttt 45

<210> SEQ ID NO 161
<211> LENGTH: 45
<212> TYPE: DNA
<213> ORGANISM: Severe acute respiratory syndrome coronavirus 2

<400> SEQUENCE: 161
acgactattg tataccttac aatagtgtaa cttcttcaat tgtca 45

<210> SEQ ID NO 162
<211> LENGTH: 45
<212> TYPE: DNA
<213> ORGANISM: Severe acute respiratory syndrome coronavirus 2

<400> SEQUENCE: 162
gactattgta taccttacaa tagtgtaact tcttcaattg tcatt 45

<210> SEQ ID NO 163
<211> LENGTH: 45
<212> TYPE: DNA
<213> ORGANISM: Severe acute respiratory syndrome coronavirus 2

<400> SEQUENCE: 163
tacttcaggt gatggcacaa caagtcctat ttctgaacat gacta 45

<210> SEQ ID NO 164
<211> LENGTH: 45
<212> TYPE: DNA
<213> ORGANISM: Severe acute respiratory syndrome coronavirus 2

<400> SEQUENCE: 164
tggagtaaaa gactgtgttg tattacacag ttacttcact tcaga 45

<210> SEQ ID NO 165
<211> LENGTH: 45
<212> TYPE: DNA
<213> ORGANISM: Severe acute respiratory syndrome coronavirus 2

<400> SEQUENCE: 165
acagttactt cacttcagac tattaccagc tgtactcaac tcaat 45

<210> SEQ ID NO 166
<211> LENGTH: 45
<212> TYPE: DNA
<213> ORGANISM: Severe acute respiratory syndrome coronavirus 2

<400> SEQUENCE: 166
gtacagacac tggtgttgaa catgttacct tcttcatcta caata 45

<210> SEQ ID NO 167
<211> LENGTH: 45
<212> TYPE: DNA
<213> ORGANISM: Severe acute respiratory syndrome coronavirus 2

<400> SEQUENCE: 167
ttatgtactc attcgtttcg gaagagacag gtacgttaat agtta 45

<210> SEQ ID NO 168
<211> LENGTH: 45
<212> TYPE: DNA
<213> ORGANISM: Severe acute respiratory syndrome coronavirus 2

<400> SEQUENCE: 168
tgtactcatt cgtttcggaa gagacaggta cgttaatagt taata 45

<210> SEQ ID NO 169
<211> LENGTH: 45
<212> TYPE: DNA
<213> ORGANISM: Severe acute respiratory syndrome coronavirus 2

<400> SEQUENCE: 169
ttcgtttcgg aagagacagg tacgttaata gttaatagcg tactt 45

<210> SEQ ID NO 170
<211> LENGTH: 45
<212> TYPE: DNA
<213> ORGANISM: Severe acute respiratory syndrome coronavirus 2

<400> SEQUENCE: 170
ggaagagaca ggtacgttaa tagttaatag cgtacttctt tttct 45

<210> SEQ ID NO 171
<211> LENGTH: 45
<212> TYPE: DNA
<213> ORGANISM: Severe acute respiratory syndrome coronavirus 2

<400> SEQUENCE: 171
agcgtacttc tttttcttgc tttcgtggta ttcttgctag ttaca 45

<210> SEQ ID NO 172
<211> LENGTH: 45
<212> TYPE: DNA
<213> ORGANISM: Severe acute respiratory syndrome coronavirus 2

<400> SEQUENCE: 172
tctttttctt gctttcgtgg tattcttgct agttacacta gccat 45

<210> SEQ ID NO 173
<211> LENGTH: 45
<212> TYPE: DNA
<213> ORGANISM: Severe acute respiratory syndrome coronavirus 2

<400> SEQUENCE: 173
ttcgattgtg tgcgtactgc tgcaatattg ttaacgtgag tcttg 45

<210> SEQ ID NO 174
<211> LENGTH: 45
<212> TYPE: DNA
<213> ORGANISM: Severe acute respiratory syndrome coronavirus 2

<400> SEQUENCE: 174
ttgtgtgcgt actgctgcaa tattgttaac gtgagtcttg taaaa 45

<210> SEQ ID NO 175
<211> LENGTH: 45
<212> TYPE: DNA
<213> ORGANISM: Severe acute respiratory syndrome coronavirus 2

<400> SEQUENCE: 175
aattcttcta gagttcctga tcttctggtc taaacgaact aaata 45

<210> SEQ ID NO 176
<211> LENGTH: 45
<212> TYPE: DNA
<213> ORGANISM: Severe acute respiratory syndrome coronavirus 2

<400> SEQUENCE: 176
tagagttcct gatcttctgg tctaaacgaa ctaaatatta tatta 45

<210> SEQ ID NO 177
<211> LENGTH: 45
<212> TYPE: DNA
<213> ORGANISM: Severe acute respiratory syndrome coronavirus 2

<400> SEQUENCE: 177
gttcctgatc ttctggtcta aacgaactaa atattatatt agttt 45

<210> SEQ ID NO 178
<211> LENGTH: 45
<212> TYPE: DNA
<213> ORGANISM: Severe acute respiratory syndrome coronavirus 2

<400> SEQUENCE: 178
cctgatcttc tggtctaaac gaactaaata ttatattagt ttttc 45

<210> SEQ ID NO 179
<211> LENGTH: 45
<212> TYPE: DNA
<213> ORGANISM: Severe acute respiratory syndrome coronavirus 2

<400> SEQUENCE: 179
gcttaaaaag ctccttgaac aatggaacct agtaataggt ttcct 45

<210> SEQ ID NO 180
<211> LENGTH: 45
<212> TYPE: DNA
<213> ORGANISM: Severe acute respiratory syndrome coronavirus 2

<400> SEQUENCE: 180
agctccttga acaatggaac ctagtaatag gtttcctatt cctta 45

<210> SEQ ID NO 181
<211> LENGTH: 45
<212> TYPE: DNA
<213> ORGANISM: Severe acute respiratory syndrome coronavirus 2

<400> SEQUENCE: 181
tagtaatagg tttcctattc cttacatgga tttgtcttct acaat 45

<210> SEQ ID NO 182
<211> LENGTH: 45
<212> TYPE: DNA
<213> ORGANISM: Severe acute respiratory syndrome coronavirus 2

<400> SEQUENCE: 182
tacatggatt tgtcttctac aatttgccta tgccaacagg aatag 45

<210> SEQ ID NO 183
<211> LENGTH: 45
<212> TYPE: DNA
<213> ORGANISM: Severe acute respiratory syndrome coronavirus 2

<400> SEQUENCE: 183
cttctacaat ttgcctatgc caacaggaat aggtttttgt atata 45

<210> SEQ ID NO 184
<211> LENGTH: 45
<212> TYPE: DNA
<213> ORGANISM: Severe acute respiratory syndrome coronavirus 2

<400> SEQUENCE: 184
ttctacaatt tgcctatgcc aacaggaata ggtttttgta tataa 45

<210> SEQ ID NO 185
<211> LENGTH: 45
<212> TYPE: DNA

<213> ORGANISM: Severe acute respiratory syndrome coronavirus 2

<400> SEQUENCE: 185
tttcctctgg ctgttatggc cagtaacttt agcttgtttt gtgct 45

<210> SEQ ID NO 186
<211> LENGTH: 45
<212> TYPE: DNA
<213> ORGANISM: Severe acute respiratory syndrome coronavirus 2

<400> SEQUENCE: 186
aactttagct tgttttgtgc ttgctgctgt ttacagaata aattg 45

<210> SEQ ID NO 187
<211> LENGTH: 45
<212> TYPE: DNA
<213> ORGANISM: Severe acute respiratory syndrome coronavirus 2

<400> SEQUENCE: 187
tgacatcaag gacctgccta aagaaatcac tgttgctaca tcacg 45

<210> SEQ ID NO 188
<211> LENGTH: 45
<212> TYPE: DNA
<213> ORGANISM: Severe acute respiratory syndrome coronavirus 2

<400> SEQUENCE: 188
taaagaaatc actgttgcta catcacgaac gctttcttat tacaa 45

<210> SEQ ID NO 189
<211> LENGTH: 45
<212> TYPE: DNA
<213> ORGANISM: Severe acute respiratory syndrome coronavirus 2

<400> SEQUENCE: 189
agaaatcact gttgctacat cacgaacgct ttcttattac aaatt 45

<210> SEQ ID NO 190
<211> LENGTH: 45
<212> TYPE: DNA
<213> ORGANISM: Severe acute respiratory syndrome coronavirus 2

<400> SEQUENCE: 190
tacagtcgct acaggattgg caactataaa ttaaacacag accat 45

<210> SEQ ID NO 191
<211> LENGTH: 45
<212> TYPE: DNA
<213> ORGANISM: Severe acute respiratory syndrome coronavirus 2

<400> SEQUENCE: 191
agctttatca ctaccaagag tgtgttagag gtacaacagt acttt 45

<210> SEQ ID NO 192
<211> LENGTH: 45
<212> TYPE: DNA
<213> ORGANISM: Severe acute respiratory syndrome coronavirus 2

<400> SEQUENCE: 192
aacatacgag ggcaattcac catttcatcc tctagctgat aacaa 45

<210> SEQ ID NO 193
<211> LENGTH: 45

<212> TYPE: DNA
<213> ORGANISM: Severe acute respiratory syndrome coronavirus 2

<400> SEQUENCE: 193
ttcaccattt catcctctag ctgataacaa atttgcactg acttg 45

<210> SEQ ID NO 194
<211> LENGTH: 45
<212> TYPE: DNA
<213> ORGANISM: Severe acute respiratory syndrome coronavirus 2

<400> SEQUENCE: 194
ctagctgata acaaatttgc actgacttgc tttagcactc aattt 45

<210> SEQ ID NO 195
<211> LENGTH: 45
<212> TYPE: DNA
<213> ORGANISM: Severe acute respiratory syndrome coronavirus 2

<400> SEQUENCE: 195
aaatttgcac tgacttgctt tagcactcaa tttgcttttg cttgt 45

<210> SEQ ID NO 196
<211> LENGTH: 45
<212> TYPE: DNA
<213> ORGANISM: Severe acute respiratory syndrome coronavirus 2

<400> SEQUENCE: 196
tcagttacgt gccagatcag tttcacctaa actgttcatc agaca 45

<210> SEQ ID NO 197
<211> LENGTH: 45
<212> TYPE: DNA
<213> ORGANISM: Severe acute respiratory syndrome coronavirus 2

<400> SEQUENCE: 197
cacctaaact gttcatcaga caagaggaag ttcaagaact ttact 45

<210> SEQ ID NO 198
<211> LENGTH: 45
<212> TYPE: DNA
<213> ORGANISM: Severe acute respiratory syndrome coronavirus 2

<400> SEQUENCE: 198
tcagacaaga ggaagttcaa gaactttact ctccaatttt tctta 45

<210> SEQ ID NO 199
<211> LENGTH: 45
<212> TYPE: DNA
<213> ORGANISM: Severe acute respiratory syndrome coronavirus 2

<400> SEQUENCE: 199
aatttttctt attgttgcgg caatagtgtt tataacactt tgctt 45

<210> SEQ ID NO 200
<211> LENGTH: 45
<212> TYPE: DNA
<213> ORGANISM: Severe acute respiratory syndrome coronavirus 2

<400> SEQUENCE: 200
attgttgcgg caatagtgtt tataacactt tgcttcacac tcaaa 45

<210> SEQ ID NO 201

<211> LENGTH: 45
<212> TYPE: DNA
<213> ORGANISM: Severe acute respiratory syndrome coronavirus 2

<400> SEQUENCE: 201
tgcggcaata gtgtttataa cactttgctt cacactcaaa agaaa 45

<210> SEQ ID NO 202
<211> LENGTH: 45
<212> TYPE: DNA
<213> ORGANISM: Severe acute respiratory syndrome coronavirus 2

<400> SEQUENCE: 202
acactcaaaa gaaagacaga atgattgaac tttcattaat tgact 45

<210> SEQ ID NO 203
<211> LENGTH: 45
<212> TYPE: DNA
<213> ORGANISM: Severe acute respiratory syndrome coronavirus 2

<400> SEQUENCE: 203
aatcatcaca actgtagctg catttcacca agaatgtagt ttaca 45

<210> SEQ ID NO 204
<211> LENGTH: 45
<212> TYPE: DNA
<213> ORGANISM: Severe acute respiratory syndrome coronavirus 2

<400> SEQUENCE: 204
caactgtagc tgcatttcac caagaatgta gtttacagtc atgta 45

<210> SEQ ID NO 205
<211> LENGTH: 45
<212> TYPE: DNA
<213> ORGANISM: Severe acute respiratory syndrome coronavirus 2

<400> SEQUENCE: 205
tcaacatcaa ccatatgtag ttgatgaccc gtgtcctatt cactt 45

<210> SEQ ID NO 206
<211> LENGTH: 45
<212> TYPE: DNA
<213> ORGANISM: Severe acute respiratory syndrome coronavirus 2

<400> SEQUENCE: 206
gtagttgatg acccgtgtcc tattcacttc tattctaaat ggtat 45

<210> SEQ ID NO 207
<211> LENGTH: 45
<212> TYPE: DNA
<213> ORGANISM: Severe acute respiratory syndrome coronavirus 2

<400> SEQUENCE: 207
ttcacttcta ttctaaatgg tatattagag taggagctag aaaat 45

<210> SEQ ID NO 208
<211> LENGTH: 45
<212> TYPE: DNA
<213> ORGANISM: Severe acute respiratory syndrome coronavirus 2

<400> SEQUENCE: 208
cgtggatgag gctggttcta aatcacccat tcagtacatc gatat 45

<210> SEQ ID NO 209
<211> LENGTH: 45
<212> TYPE: DNA
<213> ORGANISM: Severe acute respiratory syndrome coronavirus 2

<400> SEQUENCE: 209
attcagtaca tcgatatcgg taattataca gtttcctgtt tacct 45

<210> SEQ ID NO 210
<211> LENGTH: 45
<212> TYPE: DNA
<213> ORGANISM: Severe acute respiratory syndrome coronavirus 2

<400> SEQUENCE: 210
catcgatatc ggtaattata cagtttcctg tttacctttt acaat 45

<210> SEQ ID NO 211
<211> LENGTH: 45
<212> TYPE: DNA
<213> ORGANISM: Severe acute respiratory syndrome coronavirus 2

<400> SEQUENCE: 211
atcgatatcg gtaattatac agtttcctgt ttacctttta caatt 45

<210> SEQ ID NO 212
<211> LENGTH: 45
<212> TYPE: DNA
<213> ORGANISM: Severe acute respiratory syndrome coronavirus 2

<400> SEQUENCE: 212
ttttacaatt aattgccagg aacctaaatt gggtagtctt gtagt 45

<210> SEQ ID NO 213
<211> LENGTH: 45
<212> TYPE: DNA
<213> ORGANISM: Severe acute respiratory syndrome coronavirus 2

<400> SEQUENCE: 213
ttctatgaag actttttaga gtatcatgac gttcgtgttg tttta 45

<210> SEQ ID NO 214
<211> LENGTH: 45
<212> TYPE: DNA
<213> ORGANISM: Severe acute respiratory syndrome coronavirus 2

<400> SEQUENCE: 214
atgaagactt tttagagtat catgacgttc gtgttgtttt agatt 45

<210> SEQ ID NO 215
<211> LENGTH: 45
<212> TYPE: DNA
<213> ORGANISM: Severe acute respiratory syndrome coronavirus 2

<400> SEQUENCE: 215
gtcggcccca aggtttaccc aataatactg cgtcttggtt caccg 45

<210> SEQ ID NO 216
<211> LENGTH: 45
<212> TYPE: DNA
<213> ORGANISM: Severe acute respiratory syndrome coronavirus 2

<400> SEQUENCE: 216
tatggtgcta acaaagacgg catcatatgg gttgcaactg aggga 45

<210> SEQ ID NO 217
<211> LENGTH: 45
<212> TYPE: DNA
<213> ORGANISM: Severe acute respiratory syndrome coronavirus 2

<400> SEQUENCE: 217
tgctttgctg ctgcttgaca gattgaacca gcttgagagc aaaat 45

<210> SEQ ID NO 218
<211> LENGTH: 45
<212> TYPE: DNA
<213> ORGANISM: Severe acute respiratory syndrome coronavirus 2

<400> SEQUENCE: 218
ctggtaaagg ccaacaacaa caaggccaaa ctgtcactaa gaaat 45

<210> SEQ ID NO 219
<211> LENGTH: 45
<212> TYPE: DNA
<213> ORGANISM: Severe acute respiratory syndrome coronavirus 2

<400> SEQUENCE: 219
aattttgggg accaggaact aatcagacaa ggaactgatt acaaa 45

<210> SEQ ID NO 220
<211> LENGTH: 45
<212> TYPE: DNA
<213> ORGANISM: Severe acute respiratory syndrome coronavirus 2

<400> SEQUENCE: 220
tggttgacct acacaggtgc catcaaattg gatgacaaag atcca 45

<210> SEQ ID NO 221
<211> LENGTH: 45
<212> TYPE: DNA
<213> ORGANISM: Severe acute respiratory syndrome coronavirus 2

<400> SEQUENCE: 221
gtgccatcaa attggatgac aaagatccaa atttcaaaga tcaag 45

<210> SEQ ID NO 222
<211> LENGTH: 45
<212> TYPE: DNA
<213> ORGANISM: Severe acute respiratory syndrome coronavirus 2

<400> SEQUENCE: 222
tgccatcaaa ttggatgaca aagatccaaa tttcaaagat caagt 45

<210> SEQ ID NO 223
<211> LENGTH: 45
<212> TYPE: DNA
<213> ORGANISM: Severe acute respiratory syndrome coronavirus 2

<400> SEQUENCE: 223
ttggatgaca aagatccaaa tttcaaagat caagtcattt tgctg 45

<210> SEQ ID NO 224
<211> LENGTH: 45
<212> TYPE: DNA
<213> ORGANISM: Severe acute respiratory syndrome coronavirus 2

<400> SEQUENCE: 224
atgacaaaga tccaaatttc aaagatcaag tcattttgct gaata 45

<210> SEQ ID NO 225
<211> LENGTH: 45
<212> TYPE: DNA
<213> ORGANISM: Severe acute respiratory syndrome coronavirus 2

<400> SEQUENCE: 225
aagatcaagt cattttgctg aataagcata ttgacgcata caaaa 45

<210> SEQ ID NO 226
<211> LENGTH: 45
<212> TYPE: DNA
<213> ORGANISM: Severe acute respiratory syndrome coronavirus 2

<400> SEQUENCE: 226
gactcttctt cctgctgcag atttggatga tttctccaaa caatt 45

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 227
uaacaugaau acuuggcuuu u 21

<210> SEQ ID NO 228
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 228
aucauaccag uuaca 15

<210> SEQ ID NO 229
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 229
guuugcacaa ugcaga 16

<210> SEQ ID NO 230
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 230
uuugcacaau gcaga 15

<210> SEQ ID NO 231
<211> LENGTH: 15
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 231
gugugacaag cuaca 15

<210> SEQ ID NO 232
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
uaaagaacug acuua 15

<210> SEQ ID NO 233
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 233
uaggccaaua gcaaa 15

<210> SEQ ID NO 234
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 234
ucauaauuug uggca 15

<210> SEQ ID NO 235
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 235
uuguaaaguu gccaa 15

<210> SEQ ID NO 236
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 236
uacgacucug ucaga 15

<210> SEQ ID NO 237
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 237
uaaaucaaua acaga 15

<210> SEQ ID NO 238
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 238
gcuguaccug gugca 15

<210> SEQ ID NO 239
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 239
uuuacucaug ucaaa 15

<210> SEQ ID NO 240
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 240
uucuacuaag ccaca 15

<210> SEQ ID NO 241
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 241
uuaaagaaug ucuga 15

<210> SEQ ID NO 242
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 242
uuugauauua ucaca 15

<210> SEQ ID NO 243
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 243
gaauuugaug uuuca 15

<210> SEQ ID NO 244
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 244
cuauuauuug cugga 15

<210> SEQ ID NO 245
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 245
aaauguacua ccaga 15

<210> SEQ ID NO 246
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 246
ucuuuaguuu cuaca 15

<210> SEQ ID NO 247
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 247
aucuuuaguu ucuaa 15

<210> SEQ ID NO 248
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 248
auguuuguua gcaaa 15

<210> SEQ ID NO 249
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 249
gcaauuguua uccaa 15

<210> SEQ ID NO 250
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 250
uagcauuaua cacua 15

<210> SEQ ID NO 251
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 251
auacuucacu uuaga 15

<210> SEQ ID NO 252
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 252
uucacagacu uuaaa 15

<210> SEQ ID NO 253
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 253
ugguucuaaa gccga 15

<210> SEQ ID NO 254
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 254
guuuguaaua uuaga 15

<210> SEQ ID NO 255
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 255
uuuauaauua uaaua 15

<210> SEQ ID NO 256
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 256
auuauaauua ccaca 15

<210> SEQ ID NO 257
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 257
guugaaauug acaca 15

<210> SEQ ID NO 258
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 258
uguuggaaag gcaga 15

<210> SEQ ID NO 259
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 259
uuguuggaaa ggcaa 15

<210> SEQ ID NO 260
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 260
aauguacauu guaca 15

<210> SEQ ID NO 261
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 261
uuguuugaug aagca 15

<210> SEQ ID NO 262
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 262
uucuguguaa cucca 15

<210> SEQ ID NO 263
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 263
uucguuuaug uguaa 15

<210> SEQ ID NO 264
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 264
guuccaauug ugaaa 15

<210> SEQ ID NO 265
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 265
cagcaaguug caaaa 15

<210> SEQ ID NO 266
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 266
guagacuaaa gcaua 15

<210> SEQ ID NO 267
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 267
uuuauacucu gcaaa 15

<210> SEQ ID NO 268
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 268
aguuuauacu cugca 15

<210> SEQ ID NO 269
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 269
uucuuacaaa guuua 15

<210> SEQ ID NO 270
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 270
uuacacuauu guaaa 15

<210> SEQ ID NO 271
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 271
aguuacacua uugua 15

<210> SEQ ID NO 272
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
auaggacuug uugua 15

<210> SEQ ID NO 273
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 273
cuguguaaua caaca 15

<210> SEQ ID NO 274
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 274
gcugguaaua gucua 15

<210> SEQ ID NO 275
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 275
agguaacaug uucaa 15

<210> SEQ ID NO 276
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 276
cugucucuuc cgaaa 15

<210> SEQ ID NO 277
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 277
uaccugucuc uucca 15

<210> SEQ ID NO 278
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 278
uauuaacgua ccuga 15

<210> SEQ ID NO 279
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 279
cuauuaacua uuaaa 15

<210> SEQ ID NO 280
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 280
uaccacgaaa gcaaa 15

<210> SEQ ID NO 281
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 281
agcaagaaua ccaca 15

<210> SEQ ID NO 282
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 282
caauauugca gcaga 15

<210> SEQ ID NO 283
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 283
guuaacaaua uugca 15

<210> SEQ ID NO 284
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 284
gaccagaaga ucaga 15

<210> SEQ ID NO 285
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 285
uucguuuaga ccaga 15

<210> SEQ ID NO 286

<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 286
uuaguucguu uagaa 15

<210> SEQ ID NO 287
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 287
uauuuaguuc guuua 15

<210> SEQ ID NO 288
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
agguuccauu guuca 15

<210> SEQ ID NO 289
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 289
cuauuacuag guuca 15

<210> SEQ ID NO 290
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 290
uccauguaag gaaua 15

<210> SEQ ID NO 291
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 291
uaggcaaauu guaga 15

<210> SEQ ID NO 292
<211> LENGTH: 15

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 292
auuccuguug gcaua 15

<210> SEQ ID NO 293
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 293
uauuccuguu ggcaa 15

<210> SEQ ID NO 294
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 294
aaaguuacug gccaa 15

<210> SEQ ID NO 295
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 295
acagcagcaa gcaca 15

<210> SEQ ID NO 296
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 296
gugauuucuu uagga 15

<210> SEQ ID NO 297
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 297
guucgugaug uagca 15

<210> SEQ ID NO 298
<211> LENGTH: 15
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 298
agcguucgug augua 15

<210> SEQ ID NO 299
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 299
uuuauaguug ccaaa 15

<210> SEQ ID NO 300
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 300
cucuaacaca cucua 15

<210> SEQ ID NO 301
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301
ggaugaaaug gugaa 15

<210> SEQ ID NO 302
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302
uuguuaucag cuaga 15

<210> SEQ ID NO 303
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303
gcaagucagu gcaaa 15

<210> SEQ ID NO 304
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304
uugagugcua aagca 15

<210> SEQ ID NO 305
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305
uuaggugaaa cugaa 15

<210> SEQ ID NO 306
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
cuuccucuug ucuga 15

<210> SEQ ID NO 307
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 307
aguaaaguuc uugaa 15

<210> SEQ ID NO 308
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308
aacacuauug ccgca 15

<210> SEQ ID NO 309
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309
aaguguuaua aacaa 15

<210> SEQ ID NO 310
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 310
aagcaaagug uuaua 15

<210> SEQ ID NO 311
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
guucaaucau ucuga 15

<210> SEQ ID NO 312
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uggugaaaug cagca 15

<210> SEQ ID NO 313
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uacauucuug gugaa 15

<210> SEQ ID NO 314
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
gggucaucaa cuaca 15

<210> SEQ ID NO 315
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
gaagugaaua ggaca 15

<210> SEQ ID NO 316
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
cucuaauaua ccaua 15

<210> SEQ ID NO 317
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
augggugauu uagaa 15

<210> SEQ ID NO 318
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
uguauaauua ccgaa 15

<210> SEQ ID NO 319
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
caggaaacug uauaa 15

<210> SEQ ID NO 320
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
acaggaaacu guaua 15

<210> SEQ ID NO 321
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
aauuuagguu ccuga 15

<210> SEQ ID NO 322
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
gucaugauac ucuaa 15

<210> SEQ ID NO 323
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323
gaacgucaug auaca 15

<210> SEQ ID NO 324
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 324
caguauuauu gggua 15

<210> SEQ ID NO 325
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
ccauaugaug ccgua 15

<210> SEQ ID NO 326
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
ugguucaauc uguca 15

<210> SEQ ID NO 327
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
uuuggccuug uugua 15

<210> SEQ ID NO 328
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
uugucugauu aguua 15

<210> SEQ ID NO 329
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 329
caauuugaug gcaca 15

<210> SEQ ID NO 330
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 330
uuggaucuuu gucaa 15

<210> SEQ ID NO 331
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 331
uuuggaucuu uguca 15

<210> SEQ ID NO 332
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 332
aucuuugaaa uuuga 15

<210> SEQ ID NO 333
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 333
cuugaucuuu gaaaa 15

<210> SEQ ID NO 334
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 334
uaugcuuauu cagca 15

<210> SEQ ID NO 335
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 335
ucauccaaau cugca 15

<210> SEQ ID NO 336
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 336
gaaaucauac caguuaca 18

<210> SEQ ID NO 337
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 337
aaguuugcac aaugcaga 18

<210> SEQ ID NO 338
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 338
uaguugucug auaucaca 18

<210> SEQ ID NO 339
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 339
acggugugac aagcuaca 18

<210> SEQ ID NO 340
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 340
uaauaaagaa cugacuua 18

<210> SEQ ID NO 341
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 341
agcuaggcca auagcaaa 18

<210> SEQ ID NO 342
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 342
aaaucauaau uuguggca 18

<210> SEQ ID NO 343
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 343
agcuuguaaa guugccaa 18

<210> SEQ ID NO 344
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 344
aaauacgacu cugucaga 18

<210> SEQ ID NO 345
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 345
uaauaaauca auaacaga 18

<210> SEQ ID NO 346
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
acagcuguac cuggugca 18

<210> SEQ ID NO 347
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
aaauuuacuc augucaaa 18

<210> SEQ ID NO 348
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
aacuucuacu aagccaca 18

<210> SEQ ID NO 349
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
agcuuaaaga augucuga 18

<210> SEQ ID NO 350
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aaauuugaua uuaucaca 18

<210> SEQ ID NO 351
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
aacgaauuug auguuuca 18

<210> SEQ ID NO 352
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaacuauuau uugcugga 18

<210> SEQ ID NO 353
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 353
aauaaaugua cuaccaga 18

<210> SEQ ID NO 354
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 354
acaucuuuag uuucuaca 18

<210> SEQ ID NO 355
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 355
aacaucuuua guuucuaa 18

<210> SEQ ID NO 356
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 356
agcauguuug uuagcaaa 18

<210> SEQ ID NO 357
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 357
uaagcaauug uuauccaa 18

<210> SEQ ID NO 358
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 358
aacuagcauu auacacua 18

-continued

<210> SEQ ID NO 359
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 359
uaaauacuuc acuuuaga 18

<210> SEQ ID NO 360
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 360
aaauucacag acuuuaaa 18

<210> SEQ ID NO 361
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 361
caaugguucu aaagccga 18

<210> SEQ ID NO 362
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 362
caaguuugua auauuaga 18

<210> SEQ ID NO 363
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363
uaauuuauaa uuauaaua 18

<210> SEQ ID NO 364
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364
guaauuauaa uuaccaca 18

<210> SEQ ID NO 365

-continued

<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365
gaaguugaaa uugacaca 18

<210> SEQ ID NO 366
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366
aauuguugga aaggcaga 18

<210> SEQ ID NO 367
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367
aaauuguugg aaaggcaa 18

<210> SEQ ID NO 368
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
acaaauguac auuguaca 18

<210> SEQ ID NO 369
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
auauuguuug augaagca 18

<210> SEQ ID NO 370
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
acauucugug uaacucca 18

<210> SEQ ID NO 371
<211> LENGTH: 18

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
aaguucguuu auguguaa 18

<210> SEQ ID NO 372
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372
acaguuccaa uugugaaa 18

<210> SEQ ID NO 373
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 373
caacagcaag uugcaaaa 18

<210> SEQ ID NO 374
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 374
gaaguagacu aaagcaua 18

<210> SEQ ID NO 375
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 375
aaguuuauac ucugcaaa 18

<210> SEQ ID NO 376
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 376
caaaguuuau acucugca 18

<210> SEQ ID NO 377
<211> LENGTH: 18
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 377
uuauucuuac aaaguuua 18

<210> SEQ ID NO 378
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 378
aaguuacacu auuguaaa 18

<210> SEQ ID NO 379
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 379
agaaguuaca cuauugua 18

<210> SEQ ID NO 380
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
gaaauaggac uuguugua 18

<210> SEQ ID NO 381
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381
uaacugugua auacaaca 18

<210> SEQ ID NO 382
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
acagcuggua auagucua 18

<210> SEQ ID NO 383
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
agaagguaac auguucaa 18

<210> SEQ ID NO 384
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
uaccugucuc uuccgaaa 18

<210> SEQ ID NO 385
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
acguaccugu cucuucca 18

<210> SEQ ID NO 386
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
aacuauuaac guaccuga 18

<210> SEQ ID NO 387
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
acgcuauuaa cuauuaaa 18

<210> SEQ ID NO 388
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
gaauaccacg aaagcaaa 18

<210> SEQ ID NO 389
<211> LENGTH: 18
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 389
acuagcaaga auaccaca 18

<210> SEQ ID NO 390
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uaacaauauu gcagcaga 18

<210> SEQ ID NO 391
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
cacguuaaca auauugca 18

<210> SEQ ID NO 392
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
uuagaccaga agaucaga 18

<210> SEQ ID NO 393
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
uaguucguuu agaccaga 18

<210> SEQ ID NO 394
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uauuuaguuc guuuagaa 18

<210> SEQ ID NO 395
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 395
uaauauuuag uucguuua 18

<210> SEQ ID NO 396
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 396
acuagguucc auuguuca 18

<210> SEQ ID NO 397
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 397
aaccuauuac uagguuca 18

<210> SEQ ID NO 398
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 398
aaauccaugu aaggaaua 18

<210> SEQ ID NO 399
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 399
gcauaggcaa auuguaga 18

<210> SEQ ID NO 400
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
ccuauuccug uuggcaua 18

<210> SEQ ID NO 401
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
accuauuccu guuggcaa 18

<210> SEQ ID NO 402
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 402
gcuaaaguua cuggccaa 18

<210> SEQ ID NO 403
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 403
uaaacagcag caagcaca 18

<210> SEQ ID NO 404
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404
acagugauuu cuuuagga 18

<210> SEQ ID NO 405
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405
agcguucgug auguagca 18

<210> SEQ ID NO 406
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
gaaagcguuc gugaugua 18

<210> SEQ ID NO 407
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
uaauuuauag uugccaaa 18

<210> SEQ ID NO 408
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
uaccucuaac acacucua 18

<210> SEQ ID NO 409
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
agaggaugaa auggugaa 18

<210> SEQ ID NO 410
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
aauuuguuau cagcuaga 18

<210> SEQ ID NO 411
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411
aaagcaaguc agugcaaa 18

<210> SEQ ID NO 412
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
aaauugagug cuaaagca 18

<210> SEQ ID NO 413
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 413
aguuuaggug aaacugaa 18

<210> SEQ ID NO 414
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 414
gaacuuccuc uugucuga 18

<210> SEQ ID NO 415
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 415
gagaguaaag uucuugaa 18

<210> SEQ ID NO 416
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416
auaaacacua uugccgca 18

<210> SEQ ID NO 417
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417
gcaaaguguu auaaacaa 18

<210> SEQ ID NO 418
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
gugaagcaaa guguuaua 18

<210> SEQ ID NO 419
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419
aaaguucaau cauucuga 18

<210> SEQ ID NO 420
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 420
ucuuggugaa augcagca 18

<210> SEQ ID NO 421
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421
aacuacauuc uuggugaa 18

<210> SEQ ID NO 422
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 422
cacgggucau caacuaca 18

<210> SEQ ID NO 423
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 423
auagaaguga auaggaca 18

<210> SEQ ID NO 424
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 424
cuacucuaau auaccaua 18

<210> SEQ ID NO 425
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 425
ugaaugggug auuuagaa 18

<210> SEQ ID NO 426
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426
aacuguauaa uuaccgaa 18

<210> SEQ ID NO 427
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427
aaacaggaaa cuguauaa 18

<210> SEQ ID NO 428
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428
uaaacaggaa acuguaua 18

<210> SEQ ID NO 429
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 429
cccaauuuag guuccuga 18

<210> SEQ ID NO 430
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
aacgucauga uacucuaa 18

<210> SEQ ID NO 431
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431
cacgaacguc augauaca 18

<210> SEQ ID NO 432
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 432
acgcaguauu auugggua 18

<210> SEQ ID NO 433
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 433
aacccauaug augccgua 18

<210> SEQ ID NO 434
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 434
agcugguuca aucuguca 18

<210> SEQ ID NO 435
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435
caguuuggcc uuguugua 18

<210> SEQ ID NO 436
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436
uccuugucug auuaguua 18

<210> SEQ ID NO 437
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 437
auccaauuug auggcaca 18

<210> SEQ ID NO 438
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438
aauuuggauc uuugucaa 18

<210> SEQ ID NO 439
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
aaauuuggau cuuuguca 18

<210> SEQ ID NO 440
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
uugaucuuug aaauuuga 18

<210> SEQ ID NO 441
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441
ugacuugauc uuugaaaa 18

<210> SEQ ID NO 442
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442
caauaugcuu auucagca 18

<210> SEQ ID NO 443
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443
aaaucaucca aaucugca 18

<210> SEQ ID NO 444

<211> LENGTH: 20
<212> TYPE: RNA
<213> ORGANISM: Severe acute respiratory syndrome coronavirus 2

<400> SEQUENCE: 444
cuggccuuga agccccuuuu 20

<210> SEQ ID NO 445
<211> LENGTH: 20
<212> TYPE: RNA
<213> ORGANISM: Severe acute respiratory syndrome coronavirus 2

<400> SEQUENCE: 445
uccaaaauca uaacccucaa 20

<210> SEQ ID NO 446
<211> LENGTH: 20
<212> TYPE: RNA
<213> ORGANISM: Severe acute respiratory syndrome coronavirus 2

<400> SEQUENCE: 446
uacgacuauu guauaccuua 20

<210> SEQ ID NO 447
<211> LENGTH: 20
<212> TYPE: RNA
<213> ORGANISM: Severe acute respiratory syndrome coronavirus 2

<400> SEQUENCE: 447
uuucggaugg cuuauuguug 20

<210> SEQ ID NO 448
<211> LENGTH: 20
<212> TYPE: RNA
<213> ORGANISM: Severe acute respiratory syndrome coronavirus 2

<400> SEQUENCE: 448
aucuggagua aaagacugug 20

<210> SEQ ID NO 449
<211> LENGTH: 20
<212> TYPE: RNA
<213> ORGANISM: Severe acute respiratory syndrome coronavirus 2

<400> SEQUENCE: 449
gcuggcauac uaauuguuac 20

<210> SEQ ID NO 450
<211> LENGTH: 20
<212> TYPE: RNA
<213> ORGANISM: Severe acute respiratory syndrome coronavirus 2

<400> SEQUENCE: 450
uuguuguuug uaacaguuua 20

<210> SEQ ID NO 451
<211> LENGTH: 20
<212> TYPE: RNA
<213> ORGANISM: Severe acute respiratory syndrome coronavirus 2

<400> SEQUENCE: 451
uuggcuuugc uggaaaugcc 20

<210> SEQ ID NO 452
<211> LENGTH: 20
<212> TYPE: RNA
<213> ORGANISM: Severe acute respiratory syndrome coronavirus 2

<400> SEQUENCE: 452
aguccuauuu cugaacauga 20

<210> SEQ ID NO 453
<211> LENGTH: 20
<212> TYPE: RNA
<213> ORGANISM: Severe acute respiratory syndrome coronavirus 2

<400> SEQUENCE: 453
aagaacaugu ccaaauucac 20

<210> SEQ ID NO 454
<211> LENGTH: 20
<212> TYPE: RNA
<213> ORGANISM: Severe acute respiratory syndrome coronavirus 2

<400> SEQUENCE: 454
uuuguaagaa uaauaaugag 20

<210> SEQ ID NO 455
<211> LENGTH: 20
<212> TYPE: RNA
<213> ORGANISM: Severe acute respiratory syndrome coronavirus 2

<400> SEQUENCE: 455
guauaccuua caauagugua 20

<210> SEQ ID NO 456
<211> LENGTH: 20
<212> TYPE: RNA
<213> ORGANISM: Severe acute respiratory syndrome coronavirus 2

<400> SEQUENCE: 456
auuguuacga cuauuguaua 20

<210> SEQ ID NO 457
<211> LENGTH: 20
<212> TYPE: RNA
<213> ORGANISM: Severe acute respiratory syndrome coronavirus 2

<400> SEQUENCE: 457
augagccuga agaacauguc 20

<210> SEQ ID NO 458
<211> LENGTH: 20
<212> TYPE: RNA
<213> ORGANISM: Severe acute respiratory syndrome coronavirus 2

<400> SEQUENCE: 458
uauaccuuac aauaguguaa 20

<210> SEQ ID NO 459
<211> LENGTH: 20
<212> TYPE: RNA
<213> ORGANISM: Severe acute respiratory syndrome coronavirus 2

<400> SEQUENCE: 459
ccaguaaugg aaccaauuua 20

<210> SEQ ID NO 460
<211> LENGTH: 20
<212> TYPE: RNA
<213> ORGANISM: Severe acute respiratory syndrome coronavirus 2

<400> SEQUENCE: 460
uucucuaucu uuaugcuuua 20

<210> SEQ ID NO 461
<211> LENGTH: 20
<212> TYPE: RNA
<213> ORGANISM: Severe acute respiratory syndrome coronavirus 2

<400> SEQUENCE: 461
gauggcaacu agcacucucc 20

<210> SEQ ID NO 462
<211> LENGTH: 20
<212> TYPE: RNA
<213> ORGANISM: Severe acute respiratory syndrome coronavirus 2

<400> SEQUENCE: 462
cuccaagggu guucacuuug 20

<210> SEQ ID NO 463
<211> LENGTH: 20
<212> TYPE: RNA
<213> ORGANISM: Severe acute respiratory syndrome coronavirus 2

<400> SEQUENCE: 463
augagaaucu ucacaauugg 20

<210> SEQ ID NO 464
<211> LENGTH: 20
<212> TYPE: RNA
<213> ORGANISM: Severe acute respiratory syndrome coronavirus 2

<400> SEQUENCE: 464
uuggcguugc acuucuugcu 20

<210> SEQ ID NO 465
<211> LENGTH: 20
<212> TYPE: RNA
<213> ORGANISM: Severe acute respiratory syndrome coronavirus 2

<400> SEQUENCE: 465
uguaacaguu uacucacacc 20

<210> SEQ ID NO 466
<211> LENGTH: 20
<212> TYPE: RNA
<213> ORGANISM: Severe acute respiratory syndrome coronavirus 2

<400> SEQUENCE: 466
gacggcguaa aacacgucua 20

<210> SEQ ID NO 467
<211> LENGTH: 20
<212> TYPE: RNA
<213> ORGANISM: Severe acute respiratory syndrome coronavirus 2

<400> SEQUENCE: 467
uuuaaaagaa ccuugcucuu 20

<210> SEQ ID NO 468
<211> LENGTH: 20
<212> TYPE: RNA
<213> ORGANISM: Severe acute respiratory syndrome coronavirus 2

<400> SEQUENCE: 468
gaggacuuuu aaaguuucca 20

<210> SEQ ID NO 469
<211> LENGTH: 20
<212> TYPE: RNA
<213> ORGANISM: Severe acute respiratory syndrome coronavirus 2

<400> SEQUENCE: 469
uuuuaaaguu uccauuugga 20

<210> SEQ ID NO 470
<211> LENGTH: 20
<212> TYPE: RNA
<213> ORGANISM: Severe acute respiratory syndrome coronavirus 2

<400> SEQUENCE: 470
ugaggacuuu uaaaguuucc 20

<210> SEQ ID NO 471
<211> LENGTH: 20
<212> TYPE: RNA
<213> ORGANISM: Severe acute respiratory syndrome coronavirus 2

<400> SEQUENCE: 471
acugagaaua aauauucuca 20

<210> SEQ ID NO 472
<211> LENGTH: 20
<212> TYPE: RNA
<213> ORGANISM: Severe acute respiratory syndrome coronavirus 2

<400> SEQUENCE: 472
ccugacggcg uaaaacacgu 20

<210> SEQ ID NO 473
<211> LENGTH: 20
<212> TYPE: RNA
<213> ORGANISM: Severe acute respiratory syndrome coronavirus 2

<400> SEQUENCE: 473
agagguacaa caguacuuuu 20

<210> SEQ ID NO 474
<211> LENGTH: 20
<212> TYPE: RNA
<213> ORGANISM: Severe acute respiratory syndrome coronavirus 2

<400> SEQUENCE: 474
agagauauua cuaauuauua 20

<210> SEQ ID NO 475
<211> LENGTH: 20
<212> TYPE: RNA
<213> ORGANISM: Severe acute respiratory syndrome coronavirus 2

<400> SEQUENCE: 475
ugaaaauuau ucuuuucuug 20

<210> SEQ ID NO 476
<211> LENGTH: 20
<212> TYPE: RNA
<213> ORGANISM: Severe acute respiratory syndrome coronavirus 2

<400> SEQUENCE: 476
gauuacauca uaaaccucau 20

<210> SEQ ID NO 477
<211> LENGTH: 20
<212> TYPE: RNA
<213> ORGANISM: Severe acute respiratory syndrome coronavirus 2

<400> SEQUENCE: 477
auuacuaauu auuaugagga 20

<210> SEQ ID NO 478
<211> LENGTH: 20
<212> TYPE: RNA
<213> ORGANISM: Severe acute respiratory syndrome coronavirus 2

<400> SEQUENCE: 478
uuaucuaagu cacuaacuga 20

<210> SEQ ID NO 479
<211> LENGTH: 20
<212> TYPE: RNA
<213> ORGANISM: Severe acute respiratory syndrome coronavirus 2

<400> SEQUENCE: 479
guuacuauag cagagauauu 20

<210> SEQ ID NO 480
<211> LENGTH: 20
<212> TYPE: RNA
<213> ORGANISM: Severe acute respiratory syndrome coronavirus 2

<400> SEQUENCE: 480
augaggacuu uuaaaguuuc 20

<210> SEQ ID NO 481
<211> LENGTH: 20
<212> TYPE: RNA
<213> ORGANISM: Severe acute respiratory syndrome coronavirus 2

<400> SEQUENCE: 481
uguuucaucu cguugacuuu 20

<210> SEQ ID NO 482
<211> LENGTH: 20
<212> TYPE: RNA
<213> ORGANISM: Severe acute respiratory syndrome coronavirus 2

<400> SEQUENCE: 482
uacaucauaa accucauaau 20

<210> SEQ ID NO 483
<211> LENGTH: 20
<212> TYPE: RNA
<213> ORGANISM: Severe acute respiratory syndrome coronavirus 2

<400> SEQUENCE: 483
aacugagaau aaauauucuc 20

<210> SEQ ID NO 484
<211> LENGTH: 20
<212> TYPE: RNA
<213> ORGANISM: Severe acute respiratory syndrome coronavirus 2

<400> SEQUENCE: 484
uaugaggacu uuuaaaguuu 20

<210> SEQ ID NO 485
<211> LENGTH: 20
<212> TYPE: RNA
<213> ORGANISM: Severe acute respiratory syndrome coronavirus 2

<400> SEQUENCE: 485
ugauuaaacg aacaugaaaa 20

<210> SEQ ID NO 486
<211> LENGTH: 20
<212> TYPE: RNA
<213> ORGANISM: Severe acute respiratory syndrome coronavirus 2

<400> SEQUENCE: 486
gacagaauga uugaacuuuc 20

<210> SEQ ID NO 487
<211> LENGTH: 20
<212> TYPE: RNA
<213> ORGANISM: Severe acute respiratory syndrome coronavirus 2

<400> SEQUENCE: 487
uaucacuacc aagagugugu 20

<210> SEQ ID NO 488
<211> LENGTH: 20
<212> TYPE: RNA
<213> ORGANISM: Severe acute respiratory syndrome coronavirus 2

<400> SEQUENCE: 488
uuagccuuuc ugcuauuccu 20

<210> SEQ ID NO 489
<211> LENGTH: 20
<212> TYPE: RNA
<213> ORGANISM: Severe acute respiratory syndrome coronavirus 2

<400> SEQUENCE: 489
ucugcuauuc cuuguuuuaa 20

<210> SEQ ID NO 490
<211> LENGTH: 20
<212> TYPE: RNA
<213> ORGANISM: Severe acute respiratory syndrome coronavirus 2

<400> SEQUENCE: 490
acgaacauga aauuucuugu 20

<210> SEQ ID NO 491
<211> LENGTH: 20
<212> TYPE: RNA
<213> ORGANISM: Severe acute respiratory syndrome coronavirus 2

<400> SEQUENCE: 491
cguguuguuu uagauuucau 20

<210> SEQ ID NO 492
<211> LENGTH: 20
<212> TYPE: RNA
<213> ORGANISM: Severe acute respiratory syndrome coronavirus 2

<400> SEQUENCE: 492
ugaaauuucu uguuuucuua 20

<210> SEQ ID NO 493
<211> LENGTH: 20
<212> TYPE: RNA
<213> ORGANISM: Severe acute respiratory syndrome coronavirus 2

<400> SEQUENCE: 493
uuuaccuuuu acaauuaauu 20

<210> SEQ ID NO 494
<211> LENGTH: 20
<212> TYPE: RNA
<213> ORGANISM: Severe acute respiratory syndrome coronavirus 2

<400> SEQUENCE: 494
uucugcuauu ccuuguuuua 20

<210> SEQ ID NO 495
<211> LENGTH: 20
<212> TYPE: RNA
<213> ORGANISM: Severe acute respiratory syndrome coronavirus 2

<400> SEQUENCE: 495
uauuccuugu uuuaauuaug 20

<210> SEQ ID NO 496
<211> LENGTH: 20
<212> TYPE: RNA
<213> ORGANISM: Severe acute respiratory syndrome coronavirus 2

<400> SEQUENCE: 496
uagccuuucu gcuauuccuu 20

<210> SEQ ID NO 497
<211> LENGTH: 20
<212> TYPE: RNA
<213> ORGANISM: Severe acute respiratory syndrome coronavirus 2

<400> SEQUENCE: 497
uguuuuaauu augcuuauua 20

<210> SEQ ID NO 498
<211> LENGTH: 20
<212> TYPE: RNA
<213> ORGANISM: Severe acute respiratory syndrome coronavirus 2

<400> SEQUENCE: 498
gcuagaaaau cagcaccuuu 20

<210> SEQ ID NO 499
<211> LENGTH: 20
<212> TYPE: RNA
<213> ORGANISM: Severe acute respiratory syndrome coronavirus 2

<400> SEQUENCE: 499
uuuagccuuu cugcuauucc 20

<210> SEQ ID NO 500
<211> LENGTH: 20
<212> TYPE: RNA
<213> ORGANISM: Severe acute respiratory syndrome coronavirus 2

<400> SEQUENCE: 500
uucguguugu uuuagauuuc 20

<210> SEQ ID NO 501
<211> LENGTH: 20
<212> TYPE: RNA
<213> ORGANISM: Severe acute respiratory syndrome coronavirus 2

<400> SEQUENCE: 501
uuuuaauuau gcuuauuauc 20

<210> SEQ ID NO 502
<211> LENGTH: 20
<212> TYPE: RNA
<213> ORGANISM: Severe acute respiratory syndrome coronavirus 2

<400> SEQUENCE: 502
cucaacauca accauaugua 20

<210> SEQ ID NO 503
<211> LENGTH: 20
<212> TYPE: RNA
<213> ORGANISM: Severe acute respiratory syndrome coronavirus 2

<400> SEQUENCE: 503
agcuagaaaa ucagcaccuu 20

<210> SEQ ID NO 504
<211> LENGTH: 20
<212> TYPE: RNA
<213> ORGANISM: Severe acute respiratory syndrome coronavirus 2

<400> SEQUENCE: 504
uagaguauca ugacguucgu 20

<210> SEQ ID NO 505
<211> LENGTH: 20
<212> TYPE: RNA
<213> ORGANISM: Severe acute respiratory syndrome coronavirus 2

<400> SEQUENCE: 505
acuuucauua auugacuucu 20

<210> SEQ ID NO 506
<211> LENGTH: 20
<212> TYPE: RNA
<213> ORGANISM: Severe acute respiratory syndrome coronavirus 2

<400> SEQUENCE: 506
ucauguacuc aacaucaacc 20

<210> SEQ ID NO 507
<211> LENGTH: 20
<212> TYPE: RNA

<213> ORGANISM: Severe acute respiratory syndrome coronavirus 2

<400> SEQUENCE: 507
auucaguaca ucgauaucgg 20

<210> SEQ ID NO 508
<211> LENGTH: 20
<212> TYPE: RNA
<213> ORGANISM: Severe acute respiratory syndrome coronavirus 2

<400> SEQUENCE: 508
auucuaaaug guauauuaga 20

<210> SEQ ID NO 509
<211> LENGTH: 20
<212> TYPE: RNA
<213> ORGANISM: Severe acute respiratory syndrome coronavirus 2

<400> SEQUENCE: 509
acaugaaauu ucuuguuuuc 20

<210> SEQ ID NO 510
<211> LENGTH: 20
<212> TYPE: RNA
<213> ORGANISM: Severe acute respiratory syndrome coronavirus 2

<400> SEQUENCE: 510
ugagucuugu aaaaccuucu 20

<210> SEQ ID NO 511
<211> LENGTH: 20
<212> TYPE: RNA
<213> ORGANISM: Severe acute respiratory syndrome coronavirus 2

<400> SEQUENCE: 511
gagucuugua aaaccuucuu 20

<210> SEQ ID NO 512
<211> LENGTH: 20
<212> TYPE: RNA
<213> ORGANISM: Severe acute respiratory syndrome coronavirus 2

<400> SEQUENCE: 512
agucuuguaa aaccuucuuu 20

<210> SEQ ID NO 513
<211> LENGTH: 20
<212> TYPE: RNA
<213> ORGANISM: Severe acute respiratory syndrome coronavirus 2

<400> SEQUENCE: 513
ucuaaacgaa cuaaauauua 20

<210> SEQ ID NO 514
<211> LENGTH: 20
<212> TYPE: RNA
<213> ORGANISM: Severe acute respiratory syndrome coronavirus 2

<400> SEQUENCE: 514
ucuugcuagu uacacuagcc 20

<210> SEQ ID NO 515
<211> LENGTH: 20

<212> TYPE: RNA
<213> ORGANISM: Severe acute respiratory syndrome coronavirus 2

<400> SEQUENCE: 515
uucggaagag acagguacgu 20

<210> SEQ ID NO 516
<211> LENGTH: 20
<212> TYPE: RNA
<213> ORGANISM: Severe acute respiratory syndrome coronavirus 2

<400> SEQUENCE: 516
ucuucugguc uaaacgaacu 20

<210> SEQ ID NO 517
<211> LENGTH: 20
<212> TYPE: RNA
<213> ORGANISM: Severe acute respiratory syndrome coronavirus 2

<400> SEQUENCE: 517
guuaauagcg uacuucuuuu 20

<210> SEQ ID NO 518
<211> LENGTH: 20
<212> TYPE: RNA
<213> ORGANISM: Severe acute respiratory syndrome coronavirus 2

<400> SEQUENCE: 518
gugguauucu ugcuaguuac 20

<210> SEQ ID NO 519
<211> LENGTH: 20
<212> TYPE: RNA
<213> ORGANISM: Severe acute respiratory syndrome coronavirus 2

<400> SEQUENCE: 519
uacguuaaua guuaauagcg 20

<210> SEQ ID NO 520
<211> LENGTH: 20
<212> TYPE: RNA
<213> ORGANISM: Severe acute respiratory syndrome coronavirus 2

<400> SEQUENCE: 520
ucggaagaga cagguacguu 20

<210> SEQ ID NO 521
<211> LENGTH: 20
<212> TYPE: RNA
<213> ORGANISM: Severe acute respiratory syndrome coronavirus 2

<400> SEQUENCE: 521
gcuuucgugg uauucuugcu 20

<210> SEQ ID NO 522
<211> LENGTH: 20
<212> TYPE: RNA
<213> ORGANISM: Severe acute respiratory syndrome coronavirus 2

<400> SEQUENCE: 522
uuuacguuua cucucguguu 20

<210> SEQ ID NO 523

<211> LENGTH: 20
<212> TYPE: RNA
<213> ORGANISM: Severe acute respiratory syndrome coronavirus 2

<400> SEQUENCE: 523
agagacaggu acguuaauag 20

<210> SEQ ID NO 524
<211> LENGTH: 20
<212> TYPE: RNA
<213> ORGANISM: Severe acute respiratory syndrome coronavirus 2

<400> SEQUENCE: 524
uaauaguuaa uagcguacuu 20

<210> SEQ ID NO 525
<211> LENGTH: 20
<212> TYPE: RNA
<213> ORGANISM: Severe acute respiratory syndrome coronavirus 2

<400> SEQUENCE: 525
ucgugguauu cuugcuaguu 20

<210> SEQ ID NO 526
<211> LENGTH: 20
<212> TYPE: RNA
<213> ORGANISM: Severe acute respiratory syndrome coronavirus 2

<400> SEQUENCE: 526
cuggucuaaa cgaacuaaau 20

<210> SEQ ID NO 527
<211> LENGTH: 20
<212> TYPE: RNA
<213> ORGANISM: Severe acute respiratory syndrome coronavirus 2

<400> SEQUENCE: 527
augaguacga acuuauguac 20

<210> SEQ ID NO 528
<211> LENGTH: 20
<212> TYPE: RNA
<213> ORGANISM: Severe acute respiratory syndrome coronavirus 2

<400> SEQUENCE: 528
cuaaacgaac uaaauauuau 20

<210> SEQ ID NO 529
<211> LENGTH: 20
<212> TYPE: RNA
<213> ORGANISM: Severe acute respiratory syndrome coronavirus 2

<400> SEQUENCE: 529
uacguuuacu cucguguuaa 20

<210> SEQ ID NO 530
<211> LENGTH: 20
<212> TYPE: RNA
<213> ORGANISM: Severe acute respiratory syndrome coronavirus 2

<400> SEQUENCE: 530
auaguuaaua gcguacuucu 20

<210> SEQ ID NO 531
<211> LENGTH: 20
<212> TYPE: RNA
<213> ORGANISM: Severe acute respiratory syndrome coronavirus 2

<400> SEQUENCE: 531
uucuggucua aacgaacuaa 20

<210> SEQ ID NO 532
<211> LENGTH: 20
<212> TYPE: RNA
<213> ORGANISM: Severe acute respiratory syndrome coronavirus 2

<400> SEQUENCE: 532
uuagccaugg cagauuccaa 20

<210> SEQ ID NO 533
<211> LENGTH: 20
<212> TYPE: RNA
<213> ORGANISM: Severe acute respiratory syndrome coronavirus 2

<400> SEQUENCE: 533
cauggcagau uccaacggua 20

<210> SEQ ID NO 534
<211> LENGTH: 20
<212> TYPE: RNA
<213> ORGANISM: Severe acute respiratory syndrome coronavirus 2

<400> SEQUENCE: 534
uuuuguauau aauuaaguua 20

<210> SEQ ID NO 535
<211> LENGTH: 20
<212> TYPE: RNA
<213> ORGANISM: Severe acute respiratory syndrome coronavirus 2

<400> SEQUENCE: 535
auuccuuaca uggauuuguc 20

<210> SEQ ID NO 536
<211> LENGTH: 20
<212> TYPE: RNA
<213> ORGANISM: Severe acute respiratory syndrome coronavirus 2

<400> SEQUENCE: 536
uugaacaaug gaaccuagua 20

<210> SEQ ID NO 537
<211> LENGTH: 20
<212> TYPE: RNA
<213> ORGANISM: Severe acute respiratory syndrome coronavirus 2

<400> SEQUENCE: 537
ugcugcauac agucgcuaca 20

<210> SEQ ID NO 538
<211> LENGTH: 20
<212> TYPE: RNA
<213> ORGANISM: Severe acute respiratory syndrome coronavirus 2

<400> SEQUENCE: 538
uuucuuauua caaauuggga 20

<210> SEQ ID NO 539
<211> LENGTH: 20
<212> TYPE: RNA
<213> ORGANISM: Severe acute respiratory syndrome coronavirus 2

<400> SEQUENCE: 539
uggaaccuag uaauagguuu 20

<210> SEQ ID NO 540
<211> LENGTH: 20
<212> TYPE: RNA
<213> ORGANISM: Severe acute respiratory syndrome coronavirus 2

<400> SEQUENCE: 540
uacagaauaa auuggaucac 20

<210> SEQ ID NO 541
<211> LENGTH: 20
<212> TYPE: RNA
<213> ORGANISM: Severe acute respiratory syndrome coronavirus 2

<400> SEQUENCE: 541
uuuucuguuu ggaacuuuaa 20

<210> SEQ ID NO 542
<211> LENGTH: 20
<212> TYPE: RNA
<213> ORGANISM: Severe acute respiratory syndrome coronavirus 2

<400> SEQUENCE: 542
uuacauggau uugucuucua 20

<210> SEQ ID NO 543
<211> LENGTH: 20
<212> TYPE: RNA
<213> ORGANISM: Severe acute respiratory syndrome coronavirus 2

<400> SEQUENCE: 543
uaauagguuu ccuauuccuu 20

<210> SEQ ID NO 544
<211> LENGTH: 20
<212> TYPE: RNA
<213> ORGANISM: Severe acute respiratory syndrome coronavirus 2

<400> SEQUENCE: 544
guuuggaacu uuaauuuuag 20

<210> SEQ ID NO 545
<211> LENGTH: 20
<212> TYPE: RNA
<213> ORGANISM: Severe acute respiratory syndrome coronavirus 2

<400> SEQUENCE: 545
uggcucagcu acuucauugc 20

<210> SEQ ID NO 546
<211> LENGTH: 20
<212> TYPE: RNA
<213> ORGANISM: Severe acute respiratory syndrome coronavirus 2

<400> SEQUENCE: 546
ccuugaacaa uggaaccuag 20

<210> SEQ ID NO 547
<211> LENGTH: 20
<212> TYPE: RNA
<213> ORGANISM: Severe acute respiratory syndrome coronavirus 2

<400> SEQUENCE: 547
uuggcaacua uaaauuaaac 20

<210> SEQ ID NO 548
<211> LENGTH: 20
<212> TYPE: RNA
<213> ORGANISM: Severe acute respiratory syndrome coronavirus 2

<400> SEQUENCE: 548
gcuucuuuca gacuguuugc 20

<210> SEQ ID NO 549
<211> LENGTH: 20
<212> TYPE: RNA
<213> ORGANISM: Severe acute respiratory syndrome coronavirus 2

<400> SEQUENCE: 549
uggccaguaa cuuuagcuug 20

<210> SEQ ID NO 550
<211> LENGTH: 20
<212> TYPE: RNA
<213> ORGANISM: Severe acute respiratory syndrome coronavirus 2

<400> SEQUENCE: 550
gcuuucuuau uacaaauugg 20

<210> SEQ ID NO 551
<211> LENGTH: 20
<212> TYPE: RNA
<213> ORGANISM: Severe acute respiratory syndrome coronavirus 2

<400> SEQUENCE: 551
uccaguagca gugacaauau 20

<210> SEQ ID NO 552
<211> LENGTH: 20
<212> TYPE: RNA
<213> ORGANISM: Severe acute respiratory syndrome coronavirus 2

<400> SEQUENCE: 552
gugacaauau ugcuuugcuu 20

<210> SEQ ID NO 553
<211> LENGTH: 20
<212> TYPE: RNA
<213> ORGANISM: Severe acute respiratory syndrome coronavirus 2

<400> SEQUENCE: 553
acgaacuaaa uauuauauua 20

<210> SEQ ID NO 554
<211> LENGTH: 20
<212> TYPE: RNA
<213> ORGANISM: Severe acute respiratory syndrome coronavirus 2

<400> SEQUENCE: 554
uugcugaaua agcauauuga 20

<210> SEQ ID NO 555
<211> LENGTH: 20
<212> TYPE: RNA
<213> ORGANISM: Severe acute respiratory syndrome coronavirus 2

<400> SEQUENCE: 555
uucggaaugu cgcgcauugg 20

<210> SEQ ID NO 556
<211> LENGTH: 20
<212> TYPE: RNA
<213> ORGANISM: Severe acute respiratory syndrome coronavirus 2

<400> SEQUENCE: 556
cguuccaauu aacaccaaua 20

<210> SEQ ID NO 557
<211> LENGTH: 20
<212> TYPE: RNA
<213> ORGANISM: Severe acute respiratory syndrome coronavirus 2

<400> SEQUENCE: 557
uuccucaagg aacaacauug 20

<210> SEQ ID NO 558
<211> LENGTH: 20
<212> TYPE: RNA
<213> ORGANISM: Severe acute respiratory syndrome coronavirus 2

<400> SEQUENCE: 558
caguccaaga ugguauuucu 20

<210> SEQ ID NO 559
<211> LENGTH: 20
<212> TYPE: RNA
<213> ORGANISM: Severe acute respiratory syndrome coronavirus 2

<400> SEQUENCE: 559
gacgguaaaa ugaaagaucu 20

<210> SEQ ID NO 560
<211> LENGTH: 20
<212> TYPE: RNA
<213> ORGANISM: Severe acute respiratory syndrome coronavirus 2

<400> SEQUENCE: 560
cuugagagca aaaugucugg 20

<210> SEQ ID NO 561
<211> LENGTH: 20
<212> TYPE: RNA
<213> ORGANISM: Severe acute respiratory syndrome coronavirus 2

<400> SEQUENCE: 561
ucaaagauca agucauuuug 20

<210> SEQ ID NO 562
<211> LENGTH: 20
<212> TYPE: RNA
<213> ORGANISM: Severe acute respiratory syndrome coronavirus 2

<400> SEQUENCE: 562
ccgcaaauug cacaauuugc 20

<210> SEQ ID NO 563
<211> LENGTH: 20
<212> TYPE: RNA
<213> ORGANISM: Severe acute respiratory syndrome coronavirus 2

<400> SEQUENCE: 563
cgaacaaacu aaaaugucug 20

<210> SEQ ID NO 564
<211> LENGTH: 20
<212> TYPE: RNA
<213> ORGANISM: Severe acute respiratory syndrome coronavirus 2

<400> SEQUENCE: 564
gaggacaagg cguuccaauu 20

<210> SEQ ID NO 565
<211> LENGTH: 20
<212> TYPE: RNA
<213> ORGANISM: Severe acute respiratory syndrome coronavirus 2

<400> SEQUENCE: 565
uuggggacca ggaacuaauc 20

<210> SEQ ID NO 566
<211> LENGTH: 20
<212> TYPE: RNA
<213> ORGANISM: Severe acute respiratory syndrome coronavirus 2

<400> SEQUENCE: 566
ucuuccugcu gcagauuugg 20

<210> SEQ ID NO 567
<211> LENGTH: 20
<212> TYPE: RNA
<213> ORGANISM: Severe acute respiratory syndrome coronavirus 2

<400> SEQUENCE: 567
gcagauuugg augauuucuc 20

<210> SEQ ID NO 568
<211> LENGTH: 20
<212> TYPE: RNA
<213> ORGANISM: Severe acute respiratory syndrome coronavirus 2

<400> SEQUENCE: 568
ggggaccagg aacuaaucag 20

<210> SEQ ID NO 569
<211> LENGTH: 20
<212> TYPE: RNA
<213> ORGANISM: Severe acute respiratory syndrome coronavirus 2

<400> SEQUENCE: 569
ucagacaagg aacugauuac 20

<210> SEQ ID NO 570
<211> LENGTH: 20
<212> TYPE: RNA
<213> ORGANISM: Severe acute respiratory syndrome coronavirus 2

<400> SEQUENCE: 570
gaugacaaag auccaaauuu 20

<210> SEQ ID NO 571
<211> LENGTH: 20
<212> TYPE: RNA
<213> ORGANISM: Severe acute respiratory syndrome coronavirus 2

<400> SEQUENCE: 571
auugacgcau acaaaacauu 20

<210> SEQ ID NO 572
<211> LENGTH: 20
<212> TYPE: RNA
<213> ORGANISM: Severe acute respiratory syndrome coronavirus 2

<400> SEQUENCE: 572
ccaagauggu auuucuacua 20

<210> SEQ ID NO 573
<211> LENGTH: 20
<212> TYPE: RNA
<213> ORGANISM: Severe acute respiratory syndrome coronavirus 2

<400> SEQUENCE: 573
gggaccagga acuaaucaga 20

<210> SEQ ID NO 574
<211> LENGTH: 20
<212> TYPE: RNA
<213> ORGANISM: Severe acute respiratory syndrome coronavirus 2

<400> SEQUENCE: 574
cguacugcca cuaaagcaua 20

<210> SEQ ID NO 575
<211> LENGTH: 20
<212> TYPE: RNA
<213> ORGANISM: Severe acute respiratory syndrome coronavirus 2

<400> SEQUENCE: 575
ggagccuuga auacaccaaa 20

<210> SEQ ID NO 576
<211> LENGTH: 20
<212> TYPE: RNA
<213> ORGANISM: Severe acute respiratory syndrome coronavirus 2

<400> SEQUENCE: 576
uuuggcauau auucuuuuca 20

<210> SEQ ID NO 577
<211> LENGTH: 20
<212> TYPE: RNA
<213> ORGANISM: Severe acute respiratory syndrome coronavirus 2

<400> SEQUENCE: 577
uggggaaugu ccaaauuuug 20

<210> SEQ ID NO 578
<211> LENGTH: 20
<212> TYPE: RNA
<213> ORGANISM: Severe acute respiratory syndrome coronavirus 2

<400> SEQUENCE: 578
ugccacugua gcuuauuuua 20

<210> SEQ ID NO 579
<211> LENGTH: 20
<212> TYPE: RNA
<213> ORGANISM: Severe acute respiratory syndrome coronavirus 2

<400> SEQUENCE: 579
ugugacuuaa aagguaagua 20

<210> SEQ ID NO 580
<211> LENGTH: 20
<212> TYPE: RNA
<213> ORGANISM: Severe acute respiratory syndrome coronavirus 2

<400> SEQUENCE: 580
uccuaaagug aaguauuuau 20

<210> SEQ ID NO 581
<211> LENGTH: 20
<212> TYPE: RNA
<213> ORGANISM: Severe acute respiratory syndrome coronavirus 2

<400> SEQUENCE: 581
cuuguuacaa ugccacuugg 20

<210> SEQ ID NO 582
<211> LENGTH: 20
<212> TYPE: RNA
<213> ORGANISM: Severe acute respiratory syndrome coronavirus 2

<400> SEQUENCE: 582
ugugauggua caacauuuac 20

<210> SEQ ID NO 583
<211> LENGTH: 20
<212> TYPE: RNA
<213> ORGANISM: Severe acute respiratory syndrome coronavirus 2

<400> SEQUENCE: 583
auuguuauga uaccaaugua 20

<210> SEQ ID NO 584
<211> LENGTH: 20
<212> TYPE: RNA
<213> ORGANISM: Severe acute respiratory syndrome coronavirus 2

<400> SEQUENCE: 584
ugcgaauuuu guggcacuga 20

<210> SEQ ID NO 585
<211> LENGTH: 20
<212> TYPE: RNA
<213> ORGANISM: Severe acute respiratory syndrome coronavirus 2

<400> SEQUENCE: 585
auuuccacaa agcauuucua 20

<210> SEQ ID NO 586
<211> LENGTH: 20
<212> TYPE: RNA

<213> ORGANISM: Severe acute respiratory syndrome coronavirus 2

<400> SEQUENCE: 586
uaaaacauuu uauguuuuac 20

<210> SEQ ID NO 587
<211> LENGTH: 20
<212> TYPE: RNA
<213> ORGANISM: Severe acute respiratory syndrome coronavirus 2

<400> SEQUENCE: 587
ucugguaagc caguaccaua 20

<210> SEQ ID NO 588
<211> LENGTH: 20
<212> TYPE: RNA
<213> ORGANISM: Severe acute respiratory syndrome coronavirus 2

<400> SEQUENCE: 588
cuugguguuu augauuacuu 20

<210> SEQ ID NO 589
<211> LENGTH: 20
<212> TYPE: RNA
<213> ORGANISM: Severe acute respiratory syndrome coronavirus 2

<400> SEQUENCE: 589
uugaaugugg cuaaaucuga 20

<210> SEQ ID NO 590
<211> LENGTH: 20
<212> TYPE: RNA
<213> ORGANISM: Severe acute respiratory syndrome coronavirus 2

<400> SEQUENCE: 590
uaugacaugg uuggauaugg 20

<210> SEQ ID NO 591
<211> LENGTH: 20
<212> TYPE: RNA
<213> ORGANISM: Severe acute respiratory syndrome coronavirus 2

<400> SEQUENCE: 591
uuuuacuauu aaguguuugc 20

<210> SEQ ID NO 592
<211> LENGTH: 20
<212> TYPE: RNA
<213> ORGANISM: Severe acute respiratory syndrome coronavirus 2

<400> SEQUENCE: 592
auggcuacau acuacuuauu 20

<210> SEQ ID NO 593
<211> LENGTH: 20
<212> TYPE: RNA
<213> ORGANISM: Severe acute respiratory syndrome coronavirus 2

<400> SEQUENCE: 593
uagagaaaca augaguuacu 20

<210> SEQ ID NO 594
<211> LENGTH: 20

<212> TYPE: RNA
<213> ORGANISM: Severe acute respiratory syndrome coronavirus 2

<400> SEQUENCE: 594
acccacaagu uaaugguuua 20

<210> SEQ ID NO 595
<211> LENGTH: 20
<212> TYPE: RNA
<213> ORGANISM: Severe acute respiratory syndrome coronavirus 2

<400> SEQUENCE: 595
uucaucaacu uuuaacguac 20

<210> SEQ ID NO 596
<211> LENGTH: 20
<212> TYPE: RNA
<213> ORGANISM: Severe acute respiratory syndrome coronavirus 2

<400> SEQUENCE: 596
uggcugauca agcuaugacc 20

<210> SEQ ID NO 597
<211> LENGTH: 20
<212> TYPE: RNA
<213> ORGANISM: Severe acute respiratory syndrome coronavirus 2

<400> SEQUENCE: 597
uucuuaaaga aagaugcucc 20

<210> SEQ ID NO 598
<211> LENGTH: 20
<212> TYPE: RNA
<213> ORGANISM: Severe acute respiratory syndrome coronavirus 2

<400> SEQUENCE: 598
uauaaaauag aagaauuauu 20

<210> SEQ ID NO 599
<211> LENGTH: 20
<212> TYPE: RNA
<213> ORGANISM: Severe acute respiratory syndrome coronavirus 2

<400> SEQUENCE: 599
gaaggcauua aaauauuugc 20

<210> SEQ ID NO 600
<211> LENGTH: 20
<212> TYPE: RNA
<213> ORGANISM: Severe acute respiratory syndrome coronavirus 2

<400> SEQUENCE: 600
ugcaaauuau caaaagguug 20

<210> SEQ ID NO 601
<211> LENGTH: 20
<212> TYPE: RNA
<213> ORGANISM: Severe acute respiratory syndrome coronavirus 2

<400> SEQUENCE: 601
uugaaaauaa aacaacauua 20

<210> SEQ ID NO 602

<211> LENGTH: 20
<212> TYPE: RNA
<213> ORGANISM: Severe acute respiratory syndrome coronavirus 2

<400> SEQUENCE: 602
uaugacaagu ugcaauuuac 20

<210> SEQ ID NO 603
<211> LENGTH: 20
<212> TYPE: RNA
<213> ORGANISM: Severe acute respiratory syndrome coronavirus 2

<400> SEQUENCE: 603
uuaguaaagg uagacuuaua 20

<210> SEQ ID NO 604
<211> LENGTH: 20
<212> TYPE: RNA
<213> ORGANISM: Severe acute respiratory syndrome coronavirus 2

<400> SEQUENCE: 604
ugaugaaggu aauugugaca 20

<210> SEQ ID NO 605
<211> LENGTH: 20
<212> TYPE: RNA
<213> ORGANISM: Severe acute respiratory syndrome coronavirus 2

<400> SEQUENCE: 605
ugauguagaa uggaaguucu 20

<210> SEQ ID NO 606
<211> LENGTH: 20
<212> TYPE: RNA
<213> ORGANISM: Severe acute respiratory syndrome coronavirus 2

<400> SEQUENCE: 606
ugucacauac aauuguugug 20

<210> SEQ ID NO 607
<211> LENGTH: 20
<212> TYPE: RNA
<213> ORGANISM: Severe acute respiratory syndrome coronavirus 2

<400> SEQUENCE: 607
aaugcaauug caacauguga 20

<210> SEQ ID NO 608
<211> LENGTH: 20
<212> TYPE: RNA
<213> ORGANISM: Severe acute respiratory syndrome coronavirus 2

<400> SEQUENCE: 608
ucaacauuag aacaguaugu 20

<210> SEQ ID NO 609
<211> LENGTH: 20
<212> TYPE: RNA
<213> ORGANISM: Severe acute respiratory syndrome coronavirus 2

<400> SEQUENCE: 609
cagaauauga cuaugucaua 20

<210> SEQ ID NO 610
<211> LENGTH: 20
<212> TYPE: RNA
<213> ORGANISM: Severe acute respiratory syndrome coronavirus 2

<400> SEQUENCE: 610
guuaucacgc augauguuuc 20

<210> SEQ ID NO 611
<211> LENGTH: 20
<212> TYPE: RNA
<213> ORGANISM: Severe acute respiratory syndrome coronavirus 2

<400> SEQUENCE: 611
caugcaaauu acauauuuug 20

<210> SEQ ID NO 612
<211> LENGTH: 20
<212> TYPE: RNA
<213> ORGANISM: Severe acute respiratory syndrome coronavirus 2

<400> SEQUENCE: 612
guugacaucu augaaguauu 20

<210> SEQ ID NO 613
<211> LENGTH: 20
<212> TYPE: RNA
<213> ORGANISM: Severe acute respiratory syndrome coronavirus 2

<400> SEQUENCE: 613
uuuguuaauu uaaaacaauu 20

<210> SEQ ID NO 614
<211> LENGTH: 20
<212> TYPE: RNA
<213> ORGANISM: Severe acute respiratory syndrome coronavirus 2

<400> SEQUENCE: 614
aaugagugug cucaaguauu 20

<210> SEQ ID NO 615
<211> LENGTH: 20
<212> TYPE: RNA
<213> ORGANISM: Severe acute respiratory syndrome coronavirus 2

<400> SEQUENCE: 615
ucagaguuua gaaaaugugg 20

<210> SEQ ID NO 616
<211> LENGTH: 20
<212> TYPE: RNA
<213> ORGANISM: Severe acute respiratory syndrome coronavirus 2

<400> SEQUENCE: 616
aaaagaaggu caaaucaaug 20

<210> SEQ ID NO 617
<211> LENGTH: 20
<212> TYPE: RNA
<213> ORGANISM: Severe acute respiratory syndrome coronavirus 2

<400> SEQUENCE: 617
auuacuugau gauuuuguug 20

<210> SEQ ID NO 618
<211> LENGTH: 20
<212> TYPE: RNA
<213> ORGANISM: Severe acute respiratory syndrome coronavirus 2

<400> SEQUENCE: 618
agaacauucu uggaaugcug 20

<210> SEQ ID NO 619
<211> LENGTH: 20
<212> TYPE: RNA
<213> ORGANISM: Severe acute respiratory syndrome coronavirus 2

<400> SEQUENCE: 619
guugauguag aauuguuuga 20

<210> SEQ ID NO 620
<211> LENGTH: 20
<212> TYPE: RNA
<213> ORGANISM: Severe acute respiratory syndrome coronavirus 2

<400> SEQUENCE: 620
ggugcaauuu caaguguuuu 20

<210> SEQ ID NO 621
<211> LENGTH: 20
<212> TYPE: RNA
<213> ORGANISM: Severe acute respiratory syndrome coronavirus 2

<400> SEQUENCE: 621
aucuucaacc uaggacuuuu 20

<210> SEQ ID NO 622
<211> LENGTH: 20
<212> TYPE: RNA
<213> ORGANISM: Severe acute respiratory syndrome coronavirus 2

<400> SEQUENCE: 622
gcugcuacua aaaugucaga 20

<210> SEQ ID NO 623
<211> LENGTH: 20
<212> TYPE: RNA
<213> ORGANISM: Severe acute respiratory syndrome coronavirus 2

<400> SEQUENCE: 623
cugugaauuu caauuuugua 20

<210> SEQ ID NO 624
<211> LENGTH: 20
<212> TYPE: RNA
<213> ORGANISM: Severe acute respiratory syndrome coronavirus 2

<400> SEQUENCE: 624
ugccauaccc acaaauuuua 20

<210> SEQ ID NO 625
<211> LENGTH: 20
<212> TYPE: RNA
<213> ORGANISM: Severe acute respiratory syndrome coronavirus 2

<400> SEQUENCE: 625
ccaccaauua aagauuuugg 20

<210> SEQ ID NO 626
<211> LENGTH: 20
<212> TYPE: RNA
<213> ORGANISM: Severe acute respiratory syndrome coronavirus 2

<400> SEQUENCE: 626
uggaaagauu gcugauuaua 20

<210> SEQ ID NO 627
<211> LENGTH: 20
<212> TYPE: RNA
<213> ORGANISM: Severe acute respiratory syndrome coronavirus 2

<400> SEQUENCE: 627
guuguuauua aagucuguga 20

<210> SEQ ID NO 628
<211> LENGTH: 20
<212> TYPE: RNA
<213> ORGANISM: Severe acute respiratory syndrome coronavirus 2

<400> SEQUENCE: 628
uguguuuaag aauauugaug 20

<210> SEQ ID NO 629
<211> LENGTH: 20
<212> TYPE: RNA
<213> ORGANISM: Severe acute respiratory syndrome coronavirus 2

<400> SEQUENCE: 629
uuccucguga aggugucuuu 20

<210> SEQ ID NO 630
<211> LENGTH: 20
<212> TYPE: RNA
<213> ORGANISM: Severe acute respiratory syndrome coronavirus 2

<400> SEQUENCE: 630
cuugacauua caccauguuc 20

<210> SEQ ID NO 631
<211> LENGTH: 20
<212> TYPE: RNA
<213> ORGANISM: Severe acute respiratory syndrome coronavirus 2

<400> SEQUENCE: 631
uacacauaaa cgaacuuaug 20

<210> SEQ ID NO 632
<211> LENGTH: 20
<212> TYPE: RNA
<213> ORGANISM: Severe acute respiratory syndrome coronavirus 2

<400> SEQUENCE: 632
auuaacauca cuagguuuca 20

<210> SEQ ID NO 633
<211> LENGTH: 20
<212> TYPE: RNA
<213> ORGANISM: Severe acute respiratory syndrome coronavirus 2

<400> SEQUENCE: 633
uagggaauuu guguuuaaga 20

<210> SEQ ID NO 634
<211> LENGTH: 20
<212> TYPE: RNA
<213> ORGANISM: Severe acute respiratory syndrome coronavirus 2

<400> SEQUENCE: 634
uuugcuaugc aaauggcuua 20

<210> SEQ ID NO 635
<211> LENGTH: 20
<212> TYPE: RNA
<213> ORGANISM: Severe acute respiratory syndrome coronavirus 2

<400> SEQUENCE: 635
ucaaacuuua cuugcuuuac 20

<210> SEQ ID NO 636
<211> LENGTH: 20
<212> TYPE: RNA
<213> ORGANISM: Severe acute respiratory syndrome coronavirus 2

<400> SEQUENCE: 636
gcugacacua cugaugcugu 20

<210> SEQ ID NO 637
<211> LENGTH: 20
<212> TYPE: RNA
<213> ORGANISM: Severe acute respiratory syndrome coronavirus 2

<400> SEQUENCE: 637
auugccauag uaauggugac 20

<210> SEQ ID NO 638
<211> LENGTH: 20
<212> TYPE: RNA
<213> ORGANISM: Severe acute respiratory syndrome coronavirus 2

<400> SEQUENCE: 638
uacacaauua aaccgugcuu 20

<210> SEQ ID NO 639
<211> LENGTH: 20
<212> TYPE: RNA
<213> ORGANISM: Severe acute respiratory syndrome coronavirus 2

<400> SEQUENCE: 639
uugagauucu ugacauuaca 20

<210> SEQ ID NO 640
<211> LENGTH: 20
<212> TYPE: RNA
<213> ORGANISM: Severe acute respiratory syndrome coronavirus 2

<400> SEQUENCE: 640
uguccuacca uuuaaugaug 20

<210> SEQ ID NO 641
<211> LENGTH: 20
<212> TYPE: RNA
<213> ORGANISM: Severe acute respiratory syndrome coronavirus 2

<400> SEQUENCE: 641
accaccaauu aaagauuuug 20

<210> SEQ ID NO 642
<211> LENGTH: 45
<212> TYPE: DNA
<213> ORGANISM: Severe acute respiratory syndrome coronavirus 2

<400> SEQUENCE: 642
ttttgctcgt tgctgctggc cttgaagccc cttttctcta tcttt 45

<210> SEQ ID NO 643
<211> LENGTH: 45
<212> TYPE: DNA
<213> ORGANISM: Severe acute respiratory syndrome coronavirus 2

<400> SEQUENCE: 643
gtttttcaga gcgcttccaa aatcataacc ctcaaaaaga gatgg 45

<210> SEQ ID NO 644
<211> LENGTH: 45
<212> TYPE: DNA
<213> ORGANISM: Severe acute respiratory syndrome coronavirus 2

<400> SEQUENCE: 644
tggcatacta attgttacga ctattgtata ccttacaata gtgta 45

<210> SEQ ID NO 645
<211> LENGTH: 45
<212> TYPE: DNA
<213> ORGANISM: Severe acute respiratory syndrome coronavirus 2

<400> SEQUENCE: 645
acaagcctca ctccctttcg gatggcttat tgttggcgtt gcact 45

<210> SEQ ID NO 646
<211> LENGTH: 45
<212> TYPE: DNA
<213> ORGANISM: Severe acute respiratory syndrome coronavirus 2

<400> SEQUENCE: 646
tactgaaaaa tgggaatctg gagtaaaaga ctgtgttgta ttaca 45

<210> SEQ ID NO 647
<211> LENGTH: 45
<212> TYPE: DNA
<213> ORGANISM: Severe acute respiratory syndrome coronavirus 2

<400> SEQUENCE: 647
ccaactattt tctttgctgg catactaatt gttacgacta ttgta 45

<210> SEQ ID NO 648
<211> LENGTH: 45
<212> TYPE: DNA
<213> ORGANISM: Severe acute respiratory syndrome coronavirus 2

<400> SEQUENCE: 648
gtttgcaact tgctgttgtt gtttgtaaca gtttactcac acctt 45

<210> SEQ ID NO 649
<211> LENGTH: 45
<212> TYPE: DNA
<213> ORGANISM: Severe acute respiratory syndrome coronavirus 2

<400> SEQUENCE: 649
aataataatg aggctttggc tttgctggaa atgccgttcc aaaaa 45

<210> SEQ ID NO 650
<211> LENGTH: 45
<212> TYPE: DNA
<213> ORGANISM: Severe acute respiratory syndrome coronavirus 2

<400> SEQUENCE: 650
ggtgatggca caacaagtcc tatttctgaa catgactacc agatt 45

<210> SEQ ID NO 651
<211> LENGTH: 45
<212> TYPE: DNA
<213> ORGANISM: Severe acute respiratory syndrome coronavirus 2

<400> SEQUENCE: 651
ttgttgatga gcctgaagaa catgtccaaa ttcacacaat cgacg 45

<210> SEQ ID NO 652
<211> LENGTH: 45
<212> TYPE: DNA
<213> ORGANISM: Severe acute respiratory syndrome coronavirus 2

<400> SEQUENCE: 652
ttgcagagta taaactttgt aagaataata atgaggcttt ggctt 45

<210> SEQ ID NO 653
<211> LENGTH: 45
<212> TYPE: DNA
<213> ORGANISM: Severe acute respiratory syndrome coronavirus 2

<400> SEQUENCE: 653
attgttacga ctattgtata ccttacaata gtgtaacttc ttcaa 45

<210> SEQ ID NO 654
<211> LENGTH: 45
<212> TYPE: DNA
<213> ORGANISM: Severe acute respiratory syndrome coronavirus 2

<400> SEQUENCE: 654
tttgctggca tactaattgt tacgactatt gtatacctta caata 45

<210> SEQ ID NO 655
<211> LENGTH: 45
<212> TYPE: DNA
<213> ORGANISM: Severe acute respiratory syndrome coronavirus 2

<400> SEQUENCE: 655
acaataaaat tgttgatgag cctgaagaac atgtccaaat tcaca 45

<210> SEQ ID NO 656
<211> LENGTH: 45
<212> TYPE: DNA
<213> ORGANISM: Severe acute respiratory syndrome coronavirus 2

<400> SEQUENCE: 656
ttgttacgac tattgtatac cttacaatag tgtaacttct tcaat 45

<210> SEQ ID NO 657
<211> LENGTH: 45
<212> TYPE: DNA
<213> ORGANISM: Severe acute respiratory syndrome coronavirus 2

<400> SEQUENCE: 657
tccggagttg ttaatccagt aatggaacca atttatgatg aaccg 45

<210> SEQ ID NO 658
<211> LENGTH: 45
<212> TYPE: DNA
<213> ORGANISM: Severe acute respiratory syndrome coronavirus 2

<400> SEQUENCE: 658
gccttgaagc cccttttctc tatctttatg ctttagtcta cttct 45

<210> SEQ ID NO 659
<211> LENGTH: 45
<212> TYPE: DNA
<213> ORGANISM: Severe acute respiratory syndrome coronavirus 2

<400> SEQUENCE: 659
taaccctcaa aaagagatgg caactagcac tctccaaggg tgttc 45

<210> SEQ ID NO 660
<211> LENGTH: 45
<212> TYPE: DNA
<213> ORGANISM: Severe acute respiratory syndrome coronavirus 2

<400> SEQUENCE: 660
atggcaacta gcactctcca agggtgttca ctttgtttgc aactt 45

<210> SEQ ID NO 661
<211> LENGTH: 45
<212> TYPE: DNA
<213> ORGANISM: Severe acute respiratory syndrome coronavirus 2

<400> SEQUENCE: 661
cttatggatt tgtttatgag aatcttcaca attggaactg taact 45

<210> SEQ ID NO 662
<211> LENGTH: 45
<212> TYPE: DNA
<213> ORGANISM: Severe acute respiratory syndrome coronavirus 2

<400> SEQUENCE: 662
tcggatggct tattgttggc gttgcacttc ttgctgtttt tcaga 45

<210> SEQ ID NO 663
<211> LENGTH: 45
<212> TYPE: DNA
<213> ORGANISM: Severe acute respiratory syndrome coronavirus 2

<400> SEQUENCE: 663
cttgctgttg ttgtttgtaa cagtttactc acaccttttg ctcgt 45

<210> SEQ ID NO 664
<211> LENGTH: 45
<212> TYPE: DNA
<213> ORGANISM: Severe acute respiratory syndrome coronavirus 2

<400> SEQUENCE: 664
gcttttgctt gtcctgacgg cgtaaaacac gtctatcagt tacgt 45

<210> SEQ ID NO 665
<211> LENGTH: 45
<212> TYPE: DNA

<213> ORGANISM: Severe acute respiratory syndrome coronavirus 2

<400> SEQUENCE: 665
aggtacaaca gtacttttaa aagaaccttg ctcttctgga acata 45

<210> SEQ ID NO 666
<211> LENGTH: 45
<212> TYPE: DNA
<213> ORGANISM: Severe acute respiratory syndrome coronavirus 2

<400> SEQUENCE: 666
attactaatt attatgagga cttttaaagt ttccatttgg aatct 45

<210> SEQ ID NO 667
<211> LENGTH: 45
<212> TYPE: DNA
<213> ORGANISM: Severe acute respiratory syndrome coronavirus 2

<400> SEQUENCE: 667
aattattatg aggactttta aagtttccat ttggaatctt gatta 45

<210> SEQ ID NO 668
<211> LENGTH: 45
<212> TYPE: DNA
<213> ORGANISM: Severe acute respiratory syndrome coronavirus 2

<400> SEQUENCE: 668
tattactaat tattatgagg acttttaaag tttccatttg gaatc 45

<210> SEQ ID NO 669
<211> LENGTH: 45
<212> TYPE: DNA
<213> ORGANISM: Severe acute respiratory syndrome coronavirus 2

<400> SEQUENCE: 669
ttatctaagt cactaactga gaataaatat tctcaattag atgaa 45

<210> SEQ ID NO 670
<211> LENGTH: 45
<212> TYPE: DNA
<213> ORGANISM: Severe acute respiratory syndrome coronavirus 2

<400> SEQUENCE: 670
tttgcttttg cttgtcctga cggcgtaaaa cacgtctatc agtta 45

<210> SEQ ID NO 671
<211> LENGTH: 45
<212> TYPE: DNA
<213> ORGANISM: Severe acute respiratory syndrome coronavirus 2

<400> SEQUENCE: 671
taccaagagt gtgttagagg tacaacagta cttttaaaag aacct 45

<210> SEQ ID NO 672
<211> LENGTH: 45
<212> TYPE: DNA
<213> ORGANISM: Severe acute respiratory syndrome coronavirus 2

<400> SEQUENCE: 672
tcaggttact atagcagaga tattactaat tattatgagg acttt 45

<210> SEQ ID NO 673
<211> LENGTH: 45

<212> TYPE: DNA
<213> ORGANISM: Severe acute respiratory syndrome coronavirus 2

<400> SEQUENCE: 673
ttgattaaac gaacatgaaa attattcttt tcttggcact gataa 45

<210> SEQ ID NO 674
<211> LENGTH: 45
<212> TYPE: DNA
<213> ORGANISM: Severe acute respiratory syndrome coronavirus 2

<400> SEQUENCE: 674
tccatttgga atcttgatta catcataaac ctcataatta aaaat 45

<210> SEQ ID NO 675
<211> LENGTH: 45
<212> TYPE: DNA
<213> ORGANISM: Severe acute respiratory syndrome coronavirus 2

<400> SEQUENCE: 675
tactatagca gagatattac taattattat gaggactttt aaagt 45

<210> SEQ ID NO 676
<211> LENGTH: 45
<212> TYPE: DNA
<213> ORGANISM: Severe acute respiratory syndrome coronavirus 2

<400> SEQUENCE: 676
ctcataatta aaaatttatc taagtcacta actgagaata aatat 45

<210> SEQ ID NO 677
<211> LENGTH: 45
<212> TYPE: DNA
<213> ORGANISM: Severe acute respiratory syndrome coronavirus 2

<400> SEQUENCE: 677
ctcgttgact ttcaggttac tatagcagag atattactaa ttatt 45

<210> SEQ ID NO 678
<211> LENGTH: 45
<212> TYPE: DNA
<213> ORGANISM: Severe acute respiratory syndrome coronavirus 2

<400> SEQUENCE: 678
atattactaa ttattatgag gacttttaaa gtttccattt ggaat 45

<210> SEQ ID NO 679
<211> LENGTH: 45
<212> TYPE: DNA
<213> ORGANISM: Severe acute respiratory syndrome coronavirus 2

<400> SEQUENCE: 679
gtaagtgaca acagatgttt catctcgttg actttcaggt tacta 45

<210> SEQ ID NO 680
<211> LENGTH: 45
<212> TYPE: DNA
<213> ORGANISM: Severe acute respiratory syndrome coronavirus 2

<400> SEQUENCE: 680
atttggaatc ttgattacat cataaacctc ataattaaaa attta 45

<210> SEQ ID NO 681

<211> LENGTH: 45
<212> TYPE: DNA
<213> ORGANISM: Severe acute respiratory syndrome coronavirus 2

<400> SEQUENCE: 681
tttatctaag tcactaactg agaataaata ttctcaatta gatga 45

<210> SEQ ID NO 682
<211> LENGTH: 45
<212> TYPE: DNA
<213> ORGANISM: Severe acute respiratory syndrome coronavirus 2

<400> SEQUENCE: 682
gatattacta attattatga ggacttttaa agtttccatt tggaa 45

<210> SEQ ID NO 683
<211> LENGTH: 45
<212> TYPE: DNA
<213> ORGANISM: Severe acute respiratory syndrome coronavirus 2

<400> SEQUENCE: 683
gcaaccaatg gagattgatt aaacgaacat gaaaattatt ctttt 45

<210> SEQ ID NO 684
<211> LENGTH: 45
<212> TYPE: DNA
<213> ORGANISM: Severe acute respiratory syndrome coronavirus 2

<400> SEQUENCE: 684
cacactcaaa agaaagacag aatgattgaa ctttcattaa ttgac 45

<210> SEQ ID NO 685
<211> LENGTH: 45
<212> TYPE: DNA
<213> ORGANISM: Severe acute respiratory syndrome coronavirus 2

<400> SEQUENCE: 685
gctacttgtg agctttatca ctaccaagag tgtgttagag gtaca 45

<210> SEQ ID NO 686
<211> LENGTH: 45
<212> TYPE: DNA
<213> ORGANISM: Severe acute respiratory syndrome coronavirus 2

<400> SEQUENCE: 686
ttctatttgt gctttttagc ctttctgcta ttccttgttt taatt 45

<210> SEQ ID NO 687
<211> LENGTH: 45
<212> TYPE: DNA
<213> ORGANISM: Severe acute respiratory syndrome coronavirus 2

<400> SEQUENCE: 687
gtgcttttta gcctttctgc tattccttgt tttaattatg cttat 45

<210> SEQ ID NO 688
<211> LENGTH: 45
<212> TYPE: DNA
<213> ORGANISM: Severe acute respiratory syndrome coronavirus 2

<400> SEQUENCE: 688
acttgtcacg cctaaacgaa catgaaattt cttgttttct tagga 45

<210> SEQ ID NO 689
<211> LENGTH: 45
<212> TYPE: DNA
<213> ORGANISM: Severe acute respiratory syndrome coronavirus 2

<400> SEQUENCE: 689
gagtatcatg acgttcgtgt tgttttagat ttcatctaaa cgaac 45

<210> SEQ ID NO 690
<211> LENGTH: 45
<212> TYPE: DNA
<213> ORGANISM: Severe acute respiratory syndrome coronavirus 2

<400> SEQUENCE: 690
acgcctaaac gaacatgaaa tttcttgttt tcttaggaat catca 45

<210> SEQ ID NO 691
<211> LENGTH: 45
<212> TYPE: DNA
<213> ORGANISM: Severe acute respiratory syndrome coronavirus 2

<400> SEQUENCE: 691
ttatacagtt tcctgtttac cttttacaat taattgccag gaacc 45

<210> SEQ ID NO 692
<211> LENGTH: 45
<212> TYPE: DNA
<213> ORGANISM: Severe acute respiratory syndrome coronavirus 2

<400> SEQUENCE: 692
tgtgcttttt agcctttctg ctattccttg ttttaattat gctta 45

<210> SEQ ID NO 693
<211> LENGTH: 45
<212> TYPE: DNA
<213> ORGANISM: Severe acute respiratory syndrome coronavirus 2

<400> SEQUENCE: 693
ttttagcctt tctgctattc cttgttttaa ttatgcttat tatct 45

<210> SEQ ID NO 694
<211> LENGTH: 45
<212> TYPE: DNA
<213> ORGANISM: Severe acute respiratory syndrome coronavirus 2

<400> SEQUENCE: 694
tctatttgtg ctttttagcc tttctgctat tccttgtttt aatta 45

<210> SEQ ID NO 695
<211> LENGTH: 45
<212> TYPE: DNA
<213> ORGANISM: Severe acute respiratory syndrome coronavirus 2

<400> SEQUENCE: 695
ctttctgcta ttccttgttt taattatgct tattatcttt tggtt 45

<210> SEQ ID NO 696
<211> LENGTH: 45
<212> TYPE: DNA
<213> ORGANISM: Severe acute respiratory syndrome coronavirus 2

<400> SEQUENCE: 696
tatattagag taggagctag aaaatcagca cctttaattg aattg 45

<210> SEQ ID NO 697
<211> LENGTH: 45
<212> TYPE: DNA
<213> ORGANISM: Severe acute respiratory syndrome coronavirus 2

<400> SEQUENCE: 697
cttctatttg tgctttttag cctttctgct attccttgtt ttaat 45

<210> SEQ ID NO 698
<211> LENGTH: 45
<212> TYPE: DNA
<213> ORGANISM: Severe acute respiratory syndrome coronavirus 2

<400> SEQUENCE: 698
tagagtatca tgacgttcgt gttgttttag atttcatcta aacga 45

<210> SEQ ID NO 699
<211> LENGTH: 45
<212> TYPE: DNA
<213> ORGANISM: Severe acute respiratory syndrome coronavirus 2

<400> SEQUENCE: 699
ttctgctatt ccttgtttta attatgctta ttatcttttg gttct 45

<210> SEQ ID NO 700
<211> LENGTH: 45
<212> TYPE: DNA
<213> ORGANISM: Severe acute respiratory syndrome coronavirus 2

<400> SEQUENCE: 700
gtttacagtc atgtactcaa catcaaccat atgtagttga tgacc 45

<210> SEQ ID NO 701
<211> LENGTH: 45
<212> TYPE: DNA
<213> ORGANISM: Severe acute respiratory syndrome coronavirus 2

<400> SEQUENCE: 701
gtatattaga gtaggagcta gaaaatcagc acctttaatt gaatt 45

<210> SEQ ID NO 702
<211> LENGTH: 45
<212> TYPE: DNA
<213> ORGANISM: Severe acute respiratory syndrome coronavirus 2

<400> SEQUENCE: 702
tctatgaaga ctttttagag tatcatgacg ttcgtgttgt tttag 45

<210> SEQ ID NO 703
<211> LENGTH: 45
<212> TYPE: DNA
<213> ORGANISM: Severe acute respiratory syndrome coronavirus 2

<400> SEQUENCE: 703
agacagaatg attgaacttt cattaattga cttctatttg tgctt 45

<210> SEQ ID NO 704
<211> LENGTH: 45
<212> TYPE: DNA
<213> ORGANISM: Severe acute respiratory syndrome coronavirus 2

<400> SEQUENCE: 704
gaatgtagtt tacagtcatg tactcaacat caaccatatg tagtt 45

<210> SEQ ID NO 705
<211> LENGTH: 45
<212> TYPE: DNA
<213> ORGANISM: Severe acute respiratory syndrome coronavirus 2

<400> SEQUENCE: 705
ggttctaaat cacccattca gtacatcgat atcggtaatt ataca 45

<210> SEQ ID NO 706
<211> LENGTH: 45
<212> TYPE: DNA
<213> ORGANISM: Severe acute respiratory syndrome coronavirus 2

<400> SEQUENCE: 706
gtcctattca cttctattct aaatggtata ttagagtagg agcta 45

<210> SEQ ID NO 707
<211> LENGTH: 45
<212> TYPE: DNA
<213> ORGANISM: Severe acute respiratory syndrome coronavirus 2

<400> SEQUENCE: 707
gtcacgccta aacgaacatg aaatttcttg ttttcttagg aatca 45

<210> SEQ ID NO 708
<211> LENGTH: 45
<212> TYPE: DNA
<213> ORGANISM: Severe acute respiratory syndrome coronavirus 2

<400> SEQUENCE: 708
gcaatattgt taacgtgagt cttgtaaaac cttcttttta cgttt 45

<210> SEQ ID NO 709
<211> LENGTH: 45
<212> TYPE: DNA
<213> ORGANISM: Severe acute respiratory syndrome coronavirus 2

<400> SEQUENCE: 709
caatattgtt aacgtgagtc ttgtaaaacc ttctttttac gttta 45

<210> SEQ ID NO 710
<211> LENGTH: 45
<212> TYPE: DNA
<213> ORGANISM: Severe acute respiratory syndrome coronavirus 2

<400> SEQUENCE: 710
aatattgtta acgtgagtct tgtaaaacct tctttttacg tttac 45

<210> SEQ ID NO 711
<211> LENGTH: 45
<212> TYPE: DNA
<213> ORGANISM: Severe acute respiratory syndrome coronavirus 2

<400> SEQUENCE: 711
ttcctgatct tctggtctaa acgaactaaa tattatatta gtttt 45

<210> SEQ ID NO 712
<211> LENGTH: 45
<212> TYPE: DNA
<213> ORGANISM: Severe acute respiratory syndrome coronavirus 2

<400> SEQUENCE: 712
ttgctttcgt ggtattcttg ctagttacac tagccatcct tactg 45

<210> SEQ ID NO 713
<211> LENGTH: 45
<212> TYPE: DNA
<213> ORGANISM: Severe acute respiratory syndrome coronavirus 2

<400> SEQUENCE: 713
tatgtactca ttcgtttcgg aagagacagg tacgttaata gttaa 45

<210> SEQ ID NO 714
<211> LENGTH: 45
<212> TYPE: DNA
<213> ORGANISM: Severe acute respiratory syndrome coronavirus 2

<400> SEQUENCE: 714
ttctagagtt cctgatcttc tggtctaaac gaactaaata ttata 45

<210> SEQ ID NO 715
<211> LENGTH: 45
<212> TYPE: DNA
<213> ORGANISM: Severe acute respiratory syndrome coronavirus 2

<400> SEQUENCE: 715
acaggtacgt taatagttaa tagcgtactt ctttttcttg ctttc 45

<210> SEQ ID NO 716
<211> LENGTH: 45
<212> TYPE: DNA
<213> ORGANISM: Severe acute respiratory syndrome coronavirus 2

<400> SEQUENCE: 716
ctttttcttg ctttcgtggt attcttgcta gttacactag ccatc 45

<210> SEQ ID NO 717
<211> LENGTH: 45
<212> TYPE: DNA
<213> ORGANISM: Severe acute respiratory syndrome coronavirus 2

<400> SEQUENCE: 717
ttcggaagag acaggtacgt taatagttaa tagcgtactt ctttt 45

<210> SEQ ID NO 718
<211> LENGTH: 45
<212> TYPE: DNA
<213> ORGANISM: Severe acute respiratory syndrome coronavirus 2

<400> SEQUENCE: 718
atgtactcat tcgtttcgga agagacaggt acgttaatag ttaat 45

<210> SEQ ID NO 719
<211> LENGTH: 45
<212> TYPE: DNA
<213> ORGANISM: Severe acute respiratory syndrome coronavirus 2

<400> SEQUENCE: 719
gtacttcttt ttcttgcttt cgtggtattc ttgctagtta cacta 45

<210> SEQ ID NO 720
<211> LENGTH: 45
<212> TYPE: DNA
<213> ORGANISM: Severe acute respiratory syndrome coronavirus 2

<400> SEQUENCE: 720
ttgtaaaacc ttctttttac gtttactctc gtgttaaaaa tctga 45

<210> SEQ ID NO 721
<211> LENGTH: 45
<212> TYPE: DNA
<213> ORGANISM: Severe acute respiratory syndrome coronavirus 2

<400> SEQUENCE: 721
ctcattcgtt tcggaagaga caggtacgtt aatagttaat agcgt 45

<210> SEQ ID NO 722
<211> LENGTH: 45
<212> TYPE: DNA
<213> ORGANISM: Severe acute respiratory syndrome coronavirus 2

<400> SEQUENCE: 722
aagagacagg tacgttaata gttaatagcg tacttctttt tcttg 45

<210> SEQ ID NO 723
<211> LENGTH: 45
<212> TYPE: DNA
<213> ORGANISM: Severe acute respiratory syndrome coronavirus 2

<400> SEQUENCE: 723
ttctttttct tgctttcgtg gtattcttgc tagttacact agcca 45

<210> SEQ ID NO 724
<211> LENGTH: 45
<212> TYPE: DNA
<213> ORGANISM: Severe acute respiratory syndrome coronavirus 2

<400> SEQUENCE: 724
agagttcctg atcttctggt ctaaacgaac taaatattat attag 45

<210> SEQ ID NO 725
<211> LENGTH: 45
<212> TYPE: DNA
<213> ORGANISM: Severe acute respiratory syndrome coronavirus 2

<400> SEQUENCE: 725
tgtaagcaca agctgatgag tacgaactta tgtactcatt cgttt 45

<210> SEQ ID NO 726
<211> LENGTH: 45
<212> TYPE: DNA
<213> ORGANISM: Severe acute respiratory syndrome coronavirus 2

<400> SEQUENCE: 726
tcctgatctt ctggtctaaa cgaactaaat attatattag ttttt 45

<210> SEQ ID NO 727
<211> LENGTH: 45
<212> TYPE: DNA
<213> ORGANISM: Severe acute respiratory syndrome coronavirus 2

<400> SEQUENCE: 727
gtaaaacctt ctttttacgt ttactctcgt gttaaaaatc tgaat 45

<210> SEQ ID NO 728
<211> LENGTH: 45
<212> TYPE: DNA
<213> ORGANISM: Severe acute respiratory syndrome coronavirus 2

<400> SEQUENCE: 728
gagacaggta cgttaatagt taatagcgta cttctttttc ttgct 45

<210> SEQ ID NO 729
<211> LENGTH: 45
<212> TYPE: DNA
<213> ORGANISM: Severe acute respiratory syndrome coronavirus 2

<400> SEQUENCE: 729
ctagagttcc tgatcttctg gtctaaacga actaaatatt atatt 45

<210> SEQ ID NO 730
<211> LENGTH: 45
<212> TYPE: DNA
<213> ORGANISM: Severe acute respiratory syndrome coronavirus 2

<400> SEQUENCE: 730
tttggaactt taattttagc catggcagat tccaacggta ctatt 45

<210> SEQ ID NO 731
<211> LENGTH: 45
<212> TYPE: DNA
<213> ORGANISM: Severe acute respiratory syndrome coronavirus 2

<400> SEQUENCE: 731
aactttaatt ttagccatgg cagattccaa cggtactatt accgt 45

<210> SEQ ID NO 732
<211> LENGTH: 45
<212> TYPE: DNA
<213> ORGANISM: Severe acute respiratory syndrome coronavirus 2

<400> SEQUENCE: 732
ccaacaggaa taggtttttg tatataatta agttaatttt cctct 45

<210> SEQ ID NO 733
<211> LENGTH: 45
<212> TYPE: DNA
<213> ORGANISM: Severe acute respiratory syndrome coronavirus 2

<400> SEQUENCE: 733
agtaataggt ttcctattcc ttacatggat ttgtcttcta caatt 45

<210> SEQ ID NO 734
<211> LENGTH: 45
<212> TYPE: DNA
<213> ORGANISM: Severe acute respiratory syndrome coronavirus 2

<400> SEQUENCE: 734
agcttaaaaa gctccttgaa caatggaacc tagtaatagg tttcc 45

<210> SEQ ID NO 735
<211> LENGTH: 45
<212> TYPE: DNA
<213> ORGANISM: Severe acute respiratory syndrome coronavirus 2

<400> SEQUENCE: 735
aggtgactca ggttttgctg catacagtcg ctacaggatt ggcaa 45

<210> SEQ ID NO 736
<211> LENGTH: 45
<212> TYPE: DNA
<213> ORGANISM: Severe acute respiratory syndrome coronavirus 2

<400> SEQUENCE: 736
ctacatcacg aacgctttct tattacaaat tgggagcttc gcagc 45

<210> SEQ ID NO 737
<211> LENGTH: 45
<212> TYPE: DNA
<213> ORGANISM: Severe acute respiratory syndrome coronavirus 2

<400> SEQUENCE: 737
aagctccttg aacaatggaa cctagtaata ggtttcctat tcctt 45

<210> SEQ ID NO 738
<211> LENGTH: 45
<212> TYPE: DNA
<213> ORGANISM: Severe acute respiratory syndrome coronavirus 2

<400> SEQUENCE: 738
gtgcttgctg ctgtttacag aataaattgg atcaccggtg gaatt 45

<210> SEQ ID NO 739
<211> LENGTH: 45
<212> TYPE: DNA
<213> ORGANISM: Severe acute respiratory syndrome coronavirus 2

<400> SEQUENCE: 739
aaatattata ttagtttttc tgtttggaac tttaatttta gccat 45

<210> SEQ ID NO 740
<211> LENGTH: 45
<212> TYPE: DNA
<213> ORGANISM: Severe acute respiratory syndrome coronavirus 2

<400> SEQUENCE: 740
taggtttcct attccttaca tggatttgtc ttctacaatt tgcct 45

<210> SEQ ID NO 741
<211> LENGTH: 45
<212> TYPE: DNA
<213> ORGANISM: Severe acute respiratory syndrome coronavirus 2

<400> SEQUENCE: 741
aacaatggaa cctagtaata ggtttcctat tccttacatg gattt 45

<210> SEQ ID NO 742
<211> LENGTH: 45
<212> TYPE: DNA
<213> ORGANISM: Severe acute respiratory syndrome coronavirus 2

<400> SEQUENCE: 742
tatattagtt tttctgtttg gaactttaat tttagccatg gcaga 45

<210> SEQ ID NO 743
<211> LENGTH: 45
<212> TYPE: DNA
<213> ORGANISM: Severe acute respiratory syndrome coronavirus 2

<400> SEQUENCE: 743
cttgtaggct tgatgtggct cagctacttc attgcttctt tcaga 45

<210> SEQ ID NO 744
<211> LENGTH: 45
<212> TYPE: DNA

<213> ORGANISM: Severe acute respiratory syndrome coronavirus 2

<400> SEQUENCE: 744
agagcttaaa aagctccttg aacaatggaa cctagtaata ggttt 45

<210> SEQ ID NO 745
<211> LENGTH: 45
<212> TYPE: DNA
<213> ORGANISM: Severe acute respiratory syndrome coronavirus 2

<400> SEQUENCE: 745
acagtcgcta caggattggc aactataaat taaacacaga ccatt 45

<210> SEQ ID NO 746
<211> LENGTH: 45
<212> TYPE: DNA
<213> ORGANISM: Severe acute respiratory syndrome coronavirus 2

<400> SEQUENCE: 746
ctcagctact tcattgcttc tttcagactg tttgcgcgta cgcgt 45

<210> SEQ ID NO 747
<211> LENGTH: 45
<212> TYPE: DNA
<213> ORGANISM: Severe acute respiratory syndrome coronavirus 2

<400> SEQUENCE: 747
ttcctctggc tgttatggcc agtaacttta gcttgttttg tgctt 45

<210> SEQ ID NO 748
<211> LENGTH: 45
<212> TYPE: DNA
<213> ORGANISM: Severe acute respiratory syndrome coronavirus 2

<400> SEQUENCE: 748
tgctacatca cgaacgcttt cttattacaa attgggagct tcgca 45

<210> SEQ ID NO 749
<211> LENGTH: 45
<212> TYPE: DNA
<213> ORGANISM: Severe acute respiratory syndrome coronavirus 2

<400> SEQUENCE: 749
ttaaacacag accattccag tagcagtgac aatattgctt tgctt 45

<210> SEQ ID NO 750
<211> LENGTH: 45
<212> TYPE: DNA
<213> ORGANISM: Severe acute respiratory syndrome coronavirus 2

<400> SEQUENCE: 750
accattccag tagcagtgac aatattgctt tgcttgtaca gtaag 45

<210> SEQ ID NO 751
<211> LENGTH: 45
<212> TYPE: DNA
<213> ORGANISM: Severe acute respiratory syndrome coronavirus 2

<400> SEQUENCE: 751
gatcttctgg tctaaacgaa ctaaatatta tattagtttt tctgt 45

<210> SEQ ID NO 752
<211> LENGTH: 45

<212> TYPE: DNA
<213> ORGANISM: Severe acute respiratory syndrome coronavirus 2

<400> SEQUENCE: 752
aaagatcaag tcattttgct gaataagcat attgacgcat acaaa 45

<210> SEQ ID NO 753
<211> LENGTH: 45
<212> TYPE: DNA
<213> ORGANISM: Severe acute respiratory syndrome coronavirus 2

<400> SEQUENCE: 753
agcgcttcag cgttcttcgg aatgtcgcgc attggcatgg aagtc 45

<210> SEQ ID NO 754
<211> LENGTH: 45
<212> TYPE: DNA
<213> ORGANISM: Severe acute respiratory syndrome coronavirus 2

<400> SEQUENCE: 754
ccctcgagga caaggcgttc caattaacac caatagcagt ccaga 45

<210> SEQ ID NO 755
<211> LENGTH: 45
<212> TYPE: DNA
<213> ORGANISM: Severe acute respiratory syndrome coronavirus 2

<400> SEQUENCE: 755
caatcgtgct acaacttcct caaggaacaa cattgccaaa aggct 45

<210> SEQ ID NO 756
<211> LENGTH: 45
<212> TYPE: DNA
<213> ORGANISM: Severe acute respiratory syndrome coronavirus 2

<400> SEQUENCE: 756
taaaatgaaa gatctcagtc caagatggta tttctactac ctagg 45

<210> SEQ ID NO 757
<211> LENGTH: 45
<212> TYPE: DNA
<213> ORGANISM: Severe acute respiratory syndrome coronavirus 2

<400> SEQUENCE: 757
cgaattcgtg gtggtgacgg taaaatgaaa gatctcagtc caaga 45

<210> SEQ ID NO 758
<211> LENGTH: 45
<212> TYPE: DNA
<213> ORGANISM: Severe acute respiratory syndrome coronavirus 2

<400> SEQUENCE: 758
gacagattga accagcttga gagcaaaatg tctggtaaag gccaa 45

<210> SEQ ID NO 759
<211> LENGTH: 45
<212> TYPE: DNA
<213> ORGANISM: Severe acute respiratory syndrome coronavirus 2

<400> SEQUENCE: 759
acaaagatcc aaatttcaaa gatcaagtca ttttgctgaa taagc 45

<210> SEQ ID NO 760

<211> LENGTH: 45
<212> TYPE: DNA
<213> ORGANISM: Severe acute respiratory syndrome coronavirus 2

<400> SEQUENCE: 760
gattacaaac attggccgca aattgcacaa tttgccccca gcgct 45

<210> SEQ ID NO 761
<211> LENGTH: 45
<212> TYPE: DNA
<213> ORGANISM: Severe acute respiratory syndrome coronavirus 2

<400> SEQUENCE: 761
tagatttcat ctaaacgaac aaactaaaat gtctgataat ggacc 45

<210> SEQ ID NO 762
<211> LENGTH: 45
<212> TYPE: DNA
<213> ORGANISM: Severe acute respiratory syndrome coronavirus 2

<400> SEQUENCE: 762
accttaaatt ccctcgagga caaggcgttc caattaacac caata 45

<210> SEQ ID NO 763
<211> LENGTH: 45
<212> TYPE: DNA
<213> ORGANISM: Severe acute respiratory syndrome coronavirus 2

<400> SEQUENCE: 763
aaacccaagg aaattttggg gaccaggaac taatcagaca aggaa 45

<210> SEQ ID NO 764
<211> LENGTH: 45
<212> TYPE: DNA
<213> ORGANISM: Severe acute respiratory syndrome coronavirus 2

<400> SEQUENCE: 764
gcaaactgtg actcttcttc ctgctgcaga tttggatgat ttctc 45

<210> SEQ ID NO 765
<211> LENGTH: 45
<212> TYPE: DNA
<213> ORGANISM: Severe acute respiratory syndrome coronavirus 2

<400> SEQUENCE: 765
actcttcttc ctgctgcaga tttggatgat ttctccaaac aattg 45

<210> SEQ ID NO 766
<211> LENGTH: 45
<212> TYPE: DNA
<213> ORGANISM: Severe acute respiratory syndrome coronavirus 2

<400> SEQUENCE: 766
acccaaggaa attttgggga ccaggaacta atcagacaag gaact 45

<210> SEQ ID NO 767
<211> LENGTH: 45
<212> TYPE: DNA
<213> ORGANISM: Severe acute respiratory syndrome coronavirus 2

<400> SEQUENCE: 767
gggaccagga actaatcaga caaggaactg attacaaaca ttggc 45

<210> SEQ ID NO 768
<211> LENGTH: 45
<212> TYPE: DNA
<213> ORGANISM: Severe acute respiratory syndrome coronavirus 2

<400> SEQUENCE: 768
ggtgccatca aattggatga caaagatcca aatttcaaag atcaa 45

<210> SEQ ID NO 769
<211> LENGTH: 45
<212> TYPE: DNA
<213> ORGANISM: Severe acute respiratory syndrome coronavirus 2

<400> SEQUENCE: 769
ttgctgaata agcatattga cgcatacaaa acattcccac caaca 45

<210> SEQ ID NO 770
<211> LENGTH: 45
<212> TYPE: DNA
<213> ORGANISM: Severe acute respiratory syndrome coronavirus 2

<400> SEQUENCE: 770
atgaaagatc tcagtccaag atggtatttc tactacctag gaact 45

<210> SEQ ID NO 771
<211> LENGTH: 45
<212> TYPE: DNA
<213> ORGANISM: Severe acute respiratory syndrome coronavirus 2

<400> SEQUENCE: 771
cccaaggaaa ttttggggac caggaactaa tcagacaagg aactg 45

<210> SEQ ID NO 772
<211> LENGTH: 45
<212> TYPE: DNA
<213> ORGANISM: Severe acute respiratory syndrome coronavirus 2

<400> SEQUENCE: 772
aagcctcggc aaaaacgtac tgccactaaa gcatacaatg taaca 45

<210> SEQ ID NO 773
<211> LENGTH: 45
<212> TYPE: DNA
<213> ORGANISM: Severe acute respiratory syndrome coronavirus 2

<400> SEQUENCE: 773
tgggttgcaa ctgagggagc cttgaataca ccaaaagatc acatt 45

<210> SEQ ID NO 774
<211> LENGTH: 45
<212> TYPE: DNA
<213> ORGANISM: Severe acute respiratory syndrome coronavirus 2

<400> SEQUENCE: 774
agttgcagag tggtttttgg catatattct tttcactagg ttttt 45

<210> SEQ ID NO 775
<211> LENGTH: 45
<212> TYPE: DNA
<213> ORGANISM: Severe acute respiratory syndrome coronavirus 2

<400> SEQUENCE: 775
atttgacacc ttcaatgggg aatgtccaaa ttttgtattt ccctt 45

<210> SEQ ID NO 776
<211> LENGTH: 45
<212> TYPE: DNA
<213> ORGANISM: Severe acute respiratory syndrome coronavirus 2

<400> SEQUENCE: 776
tttgttacct tctcttgcca ctgtagctta ttttaatatg gtcta 45

<210> SEQ ID NO 777
<211> LENGTH: 45
<212> TYPE: DNA
<213> ORGANISM: Severe acute respiratory syndrome coronavirus 2

<400> SEQUENCE: 777
aatcctaaag gattttgtga cttaaaaggt aagtatgtac aaata 45

<210> SEQ ID NO 778
<211> LENGTH: 45
<212> TYPE: DNA
<213> ORGANISM: Severe acute respiratory syndrome coronavirus 2

<400> SEQUENCE: 778
agacacacct aaaggtccta aagtgaagta tttatacttt attaa 45

<210> SEQ ID NO 779
<211> LENGTH: 45
<212> TYPE: DNA
<213> ORGANISM: Severe acute respiratory syndrome coronavirus 2

<400> SEQUENCE: 779
gatctaaatg aaactcttgt tacaatgcca cttggctatg taaca 45

<210> SEQ ID NO 780
<211> LENGTH: 45
<212> TYPE: DNA
<213> ORGANISM: Severe acute respiratory syndrome coronavirus 2

<400> SEQUENCE: 780
acatataaaa atacgtgtga tggtacaaca tttacttatg catca 45

<210> SEQ ID NO 781
<211> LENGTH: 45
<212> TYPE: DNA
<213> ORGANISM: Severe acute respiratory syndrome coronavirus 2

<400> SEQUENCE: 781
gtaagccagt accatattgt tatgatacca atgtactaga aggtt 45

<210> SEQ ID NO 782
<211> LENGTH: 45
<212> TYPE: DNA
<213> ORGANISM: Severe acute respiratory syndrome coronavirus 2

<400> SEQUENCE: 782
tttgttaaag ccacttgcga attttgtggc actgagaatt tgact 45

<210> SEQ ID NO 783
<211> LENGTH: 45
<212> TYPE: DNA
<213> ORGANISM: Severe acute respiratory syndrome coronavirus 2

<400> SEQUENCE: 783
gcttatatca tttgtatttc cacaaagcat ttctattggt tcttt 45

<210> SEQ ID NO 784
<211> LENGTH: 45
<212> TYPE: DNA
<213> ORGANISM: Severe acute respiratory syndrome coronavirus 2

<400> SEQUENCE: 784
taattcacat gaaggtaaaa cattttatgt tttacctaat gatga 45

<210> SEQ ID NO 785
<211> LENGTH: 45
<212> TYPE: DNA
<213> ORGANISM: Severe acute respiratory syndrome coronavirus 2

<400> SEQUENCE: 785
atttttaaag atgcttctgg taagccagta ccatattgtt atgat 45

<210> SEQ ID NO 786
<211> LENGTH: 45
<212> TYPE: DNA
<213> ORGANISM: Severe acute respiratory syndrome coronavirus 2

<400> SEQUENCE: 786
tactttagac tgactcttgg tgtttatgat tacttagttt ctaca 45

<210> SEQ ID NO 787
<211> LENGTH: 45
<212> TYPE: DNA
<213> ORGANISM: Severe acute respiratory syndrome coronavirus 2

<400> SEQUENCE: 787
aagttgaaga agtctttgaa tgtggctaaa tctgaatttg accgt 45

<210> SEQ ID NO 788
<211> LENGTH: 45
<212> TYPE: DNA
<213> ORGANISM: Severe acute respiratory syndrome coronavirus 2

<400> SEQUENCE: 788
ttgggtgatg cgtattatga catggttgga tatggttgat actag 45

<210> SEQ ID NO 789
<211> LENGTH: 45
<212> TYPE: DNA
<213> ORGANISM: Severe acute respiratory syndrome coronavirus 2

<400> SEQUENCE: 789
atattataat ttggttttta ctattaagtg tttgcctagg ttctt 45

<210> SEQ ID NO 790
<211> LENGTH: 45
<212> TYPE: DNA
<213> ORGANISM: Severe acute respiratory syndrome coronavirus 2

<400> SEQUENCE: 790
ttagatgagt ggagtatggc tacatactac ttatttgatg agtct 45

<210> SEQ ID NO 791
<211> LENGTH: 45
<212> TYPE: DNA
<213> ORGANISM: Severe acute respiratory syndrome coronavirus 2

<400> SEQUENCE: 791
tgagttaggt gatgttagag aaacaatgag ttacttgttt caaca 45

<210> SEQ ID NO 792
<211> LENGTH: 45
<212> TYPE: DNA
<213> ORGANISM: Severe acute respiratory syndrome coronavirus 2

<400> SEQUENCE: 792
ctaaaaagtg gaaataccca caagttaatg gtttaacttc tatta 45

<210> SEQ ID NO 793
<211> LENGTH: 45
<212> TYPE: DNA
<213> ORGANISM: Severe acute respiratory syndrome coronavirus 2

<400> SEQUENCE: 793
ttacgttaat acgttttcat caacttttaa cgtaccaatg gaaaa 45

<210> SEQ ID NO 794
<211> LENGTH: 45
<212> TYPE: DNA
<213> ORGANISM: Severe acute respiratory syndrome coronavirus 2

<400> SEQUENCE: 794
gtaagttgga aaagatggct gatcaagcta tgacccaaat gtata 45

<210> SEQ ID NO 795
<211> LENGTH: 45
<212> TYPE: DNA
<213> ORGANISM: Severe acute respiratory syndrome coronavirus 2

<400> SEQUENCE: 795
gacattgaca tcactttctt aaagaaagat gctccatata tagtg 45

<210> SEQ ID NO 796
<211> LENGTH: 45
<212> TYPE: DNA
<213> ORGANISM: Severe acute respiratory syndrome coronavirus 2

<400> SEQUENCE: 796
tgtagtgaca aagcttataa aatagaagaa ttattctatt cttat 45

<210> SEQ ID NO 797
<211> LENGTH: 45
<212> TYPE: DNA
<213> ORGANISM: Severe acute respiratory syndrome coronavirus 2

<400> SEQUENCE: 797
tgatgcacta tgtgagaagg cattaaaata tttgcctata gataa 45

<210> SEQ ID NO 798
<211> LENGTH: 45
<212> TYPE: DNA
<213> ORGANISM: Severe acute respiratory syndrome coronavirus 2

<400> SEQUENCE: 798
gttttctagc aatgttgcaa attatcaaaa ggttggtatg caaaa 45

<210> SEQ ID NO 799
<211> LENGTH: 45
<212> TYPE: DNA
<213> ORGANISM: Severe acute respiratory syndrome coronavirus 2

<400> SEQUENCE: 799
ttgatgtaga attgtttgaa aataaaacaa cattacctgt taatg 45

<210> SEQ ID NO 800
<211> LENGTH: 45
<212> TYPE: DNA
<213> ORGANISM: Severe acute respiratory syndrome coronavirus 2

<400> SEQUENCE: 800
tctgatagag acctttatga caagttgcaa tttacaagtc ttgaa 45

<210> SEQ ID NO 801
<211> LENGTH: 45
<212> TYPE: DNA
<213> ORGANISM: Severe acute respiratory syndrome coronavirus 2

<400> SEQUENCE: 801
tgattttatc tcttcttagt aaaggtagac ttataattag agaaa 45

<210> SEQ ID NO 802
<211> LENGTH: 45
<212> TYPE: DNA
<213> ORGANISM: Severe acute respiratory syndrome coronavirus 2

<400> SEQUENCE: 802
tgctttaagg cattttgatg aaggtaattg tgacacatta aaaga 45

<210> SEQ ID NO 803
<211> LENGTH: 45
<212> TYPE: DNA
<213> ORGANISM: Severe acute respiratory syndrome coronavirus 2

<400> SEQUENCE: 803
gtgtgtacct caagctgatg tagaatggaa gttctatgat gcaca 45

<210> SEQ ID NO 804
<211> LENGTH: 45
<212> TYPE: DNA
<213> ORGANISM: Severe acute respiratory syndrome coronavirus 2

<400> SEQUENCE: 804
attaaaagaa atacttgtca catacaattg ttgtgatgat gatta 45

<210> SEQ ID NO 805
<211> LENGTH: 45
<212> TYPE: DNA
<213> ORGANISM: Severe acute respiratory syndrome coronavirus 2

<400> SEQUENCE: 805
aatgttactg actttaatgc aattgcaaca tgtgactgga caaat 45

<210> SEQ ID NO 806
<211> LENGTH: 45
<212> TYPE: DNA
<213> ORGANISM: Severe acute respiratory syndrome coronavirus 2

<400> SEQUENCE: 806
aaattcaaag tgaattcaac attagaacag tatgtctttt gtact 45

<210> SEQ ID NO 807
<211> LENGTH: 45
<212> TYPE: DNA
<213> ORGANISM: Severe acute respiratory syndrome coronavirus 2

<400> SEQUENCE: 807
attcatcaca gggctcagaa tatgactatg tcatattcac tcaaa 45

<210> SEQ ID NO 808
<211> LENGTH: 45
<212> TYPE: DNA
<213> ORGANISM: Severe acute respiratory syndrome coronavirus 2

<400> SEQUENCE: 808
atgttttata agggtgttat cacgcatgat gtttcatctg caatt 45

<210> SEQ ID NO 809
<211> LENGTH: 45
<212> TYPE: DNA
<213> ORGANISM: Severe acute respiratory syndrome coronavirus 2

<400> SEQUENCE: 809
gatggttatg tcatgcatgc aaattacata ttttggagga ataca 45

<210> SEQ ID NO 810
<211> LENGTH: 45
<212> TYPE: DNA
<213> ORGANISM: Severe acute respiratory syndrome coronavirus 2

<400> SEQUENCE: 810
ggcacatggc tttgagttga catctatgaa gtattttgtg aaaat 45

<210> SEQ ID NO 811
<211> LENGTH: 45
<212> TYPE: DNA
<213> ORGANISM: Severe acute respiratory syndrome coronavirus 2

<400> SEQUENCE: 811
tttgataaaa gtgcttttgt taatttaaaa caattaccat ttttc 45

<210> SEQ ID NO 812
<211> LENGTH: 45
<212> TYPE: DNA
<213> ORGANISM: Severe acute respiratory syndrome coronavirus 2

<400> SEQUENCE: 812
ttctatagat tagctaatga gtgtgctcaa gtattgagtg aaatg 45

<210> SEQ ID NO 813
<211> LENGTH: 45
<212> TYPE: DNA
<213> ORGANISM: Severe acute respiratory syndrome coronavirus 2

<400> SEQUENCE: 813
cacttttaca agacttcaga gtttagaaaa tgtggctttt aatgt 45

<210> SEQ ID NO 814
<211> LENGTH: 45
<212> TYPE: DNA
<213> ORGANISM: Severe acute respiratory syndrome coronavirus 2

<400> SEQUENCE: 814
tgctgttatg tctttaaaag aaggtcaaat caatgatatg atttt 45

<210> SEQ ID NO 815
<211> LENGTH: 45
<212> TYPE: DNA
<213> ORGANISM: Severe acute respiratory syndrome coronavirus 2

<400> SEQUENCE: 815
ttctgttatt gatttattac ttgatgattt tgttgaaata ataaa 45

<210> SEQ ID NO 816
<211> LENGTH: 45
<212> TYPE: DNA
<213> ORGANISM: Severe acute respiratory syndrome coronavirus 2

<400> SEQUENCE: 816
ggctataaag ataacagaac attcttggaa tgctgatctt tataa 45

<210> SEQ ID NO 817
<211> LENGTH: 45
<212> TYPE: DNA
<213> ORGANISM: Severe acute respiratory syndrome coronavirus 2

<400> SEQUENCE: 817
acaaaagttg atggtgttga tgtagaattg tttgaaaata aaaca 45

<210> SEQ ID NO 818
<211> LENGTH: 45
<212> TYPE: DNA
<213> ORGANISM: Severe acute respiratory syndrome coronavirus 2

<400> SEQUENCE: 818
cttagctcca attttggtgc aatttcaagt gttttaaatg atatc 45

<210> SEQ ID NO 819
<211> LENGTH: 45
<212> TYPE: DNA
<213> ORGANISM: Severe acute respiratory syndrome coronavirus 2

<400> SEQUENCE: 819
cttattatgt gggttatctt caacctagga cttttctatt aaaat 45

<210> SEQ ID NO 820
<211> LENGTH: 45
<212> TYPE: DNA
<213> ORGANISM: Severe acute respiratory syndrome coronavirus 2

<400> SEQUENCE: 820
gcttctgcta atcttgctgc tactaaaatg tcagagtgtg tactt 45

<210> SEQ ID NO 821
<211> LENGTH: 45
<212> TYPE: DNA
<213> ORGANISM: Severe acute respiratory syndrome coronavirus 2

<400> SEQUENCE: 821
tgttgttatt aaagtctgtg aatttcaatt ttgtaatgat ccatt 45

<210> SEQ ID NO 822
<211> LENGTH: 45
<212> TYPE: DNA
<213> ORGANISM: Severe acute respiratory syndrome coronavirus 2

<400> SEQUENCE: 822
ctctaataac tctattgcca tacccacaaa ttttactatt agtgt 45

<210> SEQ ID NO 823
<211> LENGTH: 45
<212> TYPE: DNA

<213> ORGANISM: Severe acute respiratory syndrome coronavirus 2

<400> SEQUENCE: 823
caaatttaca aaacaccacc aattaaagat tttggtggtt ttaat 45

<210> SEQ ID NO 824
<211> LENGTH: 45
<212> TYPE: DNA
<213> ORGANISM: Severe acute respiratory syndrome coronavirus 2

<400> SEQUENCE: 824
cgctccaggg caaactggaa agattgctga ttataattat aaatt 45

<210> SEQ ID NO 825
<211> LENGTH: 45
<212> TYPE: DNA
<213> ORGANISM: Severe acute respiratory syndrome coronavirus 2

<400> SEQUENCE: 825
aataacgcta ctaatgttgt tattaaagtc tgtgaatttc aattt 45

<210> SEQ ID NO 826
<211> LENGTH: 45
<212> TYPE: DNA
<213> ORGANISM: Severe acute respiratory syndrome coronavirus 2

<400> SEQUENCE: 826
aaatcttagg gaatttgtgt ttaagaatat tgatggttat tttaa 45

<210> SEQ ID NO 827
<211> LENGTH: 45
<212> TYPE: DNA
<213> ORGANISM: Severe acute respiratory syndrome coronavirus 2

<400> SEQUENCE: 827
atggaaaagc acactttcct cgtgaaggtg tctttgtttc aaatg 45

<210> SEQ ID NO 828
<211> LENGTH: 45
<212> TYPE: DNA
<213> ORGANISM: Severe acute respiratory syndrome coronavirus 2

<400> SEQUENCE: 828
cagacacttg agattcttga cattacacca tgttcttttg gtggt 45

<210> SEQ ID NO 829
<211> LENGTH: 45
<212> TYPE: DNA
<213> ORGANISM: Severe acute respiratory syndrome coronavirus 2

<400> SEQUENCE: 829
ggagtcaaat tacattacac ataaacgaac ttatggattt gttta 45

<210> SEQ ID NO 830
<211> LENGTH: 45
<212> TYPE: DNA
<213> ORGANISM: Severe acute respiratory syndrome coronavirus 2

<400> SEQUENCE: 830
gatttgccaa taggtattaa catcactagg tttcaaactt tactt 45

<210> SEQ ID NO 831
<211> LENGTH: 45

<212> TYPE: DNA
<213> ORGANISM: Severe acute respiratory syndrome coronavirus 2

<400> SEQUENCE: 831
taatttcaaa aatcttaggg aatttgtgtt taagaatatt gatgg 45

<210> SEQ ID NO 832
<211> LENGTH: 45
<212> TYPE: DNA
<213> ORGANISM: Severe acute respiratory syndrome coronavirus 2

<400> SEQUENCE: 832
gcattacaaa taccatttgc tatgcaaatg gcttataggt ttaat 45

<210> SEQ ID NO 833
<211> LENGTH: 45
<212> TYPE: DNA
<213> ORGANISM: Severe acute respiratory syndrome coronavirus 2

<400> SEQUENCE: 833
taacatcact aggtttcaaa ctttacttgc tttacataga agtta 45

<210> SEQ ID NO 834
<211> LENGTH: 45
<212> TYPE: DNA
<213> ORGANISM: Severe acute respiratory syndrome coronavirus 2

<400> SEQUENCE: 834
tttggcagag acattgctga cactactgat gctgtccgtg atcca 45

<210> SEQ ID NO 835
<211> LENGTH: 45
<212> TYPE: DNA
<213> ORGANISM: Severe acute respiratory syndrome coronavirus 2

<400> SEQUENCE: 835
tttatagctg gcttgattgc catagtaatg gtgacaatta tgctt 45

<210> SEQ ID NO 836
<211> LENGTH: 45
<212> TYPE: DNA
<213> ORGANISM: Severe acute respiratory syndrome coronavirus 2

<400> SEQUENCE: 836
atatggcagt ttttgtacac aattaaaccg tgctttaact ggaat 45

<210> SEQ ID NO 837
<211> LENGTH: 45
<212> TYPE: DNA
<213> ORGANISM: Severe acute respiratory syndrome coronavirus 2

<400> SEQUENCE: 837
gtgatccaca gacacttgag attcttgaca ttacaccatg ttctt 45

<210> SEQ ID NO 838
<211> LENGTH: 45
<212> TYPE: DNA
<213> ORGANISM: Severe acute respiratory syndrome coronavirus 2

<400> SEQUENCE: 838
gaggtttgat aaccctgtcc taccatttaa tgatggtgtt tattt 45

<210> SEQ ID NO 839

<211> LENGTH: 45
<212> TYPE: DNA
<213> ORGANISM: Severe acute respiratory syndrome coronavirus 2

<400> SEQUENCE: 839
acaaatttac aaaacaccac caattaaaga ttttggtggt tttaa 45

<210> SEQ ID NO 840
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 840
acttctacta agccac 16

<210> SEQ ID NO 841
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 841
aagcttaaag aatgtc 16

<210> SEQ ID NO 842
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 842
cagcatgttt gttagc 16

<210> SEQ ID NO 843
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 843
gcatgtttgt tagcaa 16

<210> SEQ ID NO 844
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 844
aagcaattgt tatcca 16

<210> SEQ ID NO 845
<211> LENGTH: 16
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 845
taagcaattg ttatcc 16

<210> SEQ ID NO 846
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 846
gtttgcacaa tgcaga 16

<210> SEQ ID NO 847
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 847
agagctaggc caatag 16

<210> SEQ ID NO 848
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 848
agcttgtaaa gttgcc 16

<210> SEQ ID NO 849
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 849
cagctgtacc tggtgc 16

<210> SEQ ID NO 850
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 850
acagctgtac ctggtg 16

<210> SEQ ID NO 851
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 851
aacagctgta cctggt 16

<210> SEQ ID NO 852
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 852
aatggttcta aagccg 16

<210> SEQ ID NO 853
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 853
caatggttct aaagcc 16

<210> SEQ ID NO 854
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 854
tgaagttgaa attgac 16

<210> SEQ ID NO 855
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 855
ccacaaatgt acattg 16

<210> SEQ ID NO 856
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 856
caatgtacat ttgtgg 16

<210> SEQ ID NO 857
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 857
agttcgttta tgtgta 16

<210> SEQ ID NO 858
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 858
taagttcgtt tatgtg 16

<210> SEQ ID NO 859
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 859
gaagtagact aaagca 16

<210> SEQ ID NO 860
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 860
aataggactt gttgtg 16

<210> SEQ ID NO 861
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 861
aactgtgtaa tacaac 16

<210> SEQ ID NO 862
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 862
acagctggta atagtc 16

<210> SEQ ID NO 863
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 863
cagctggtaa tagtct 16

<210> SEQ ID NO 864
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 864
tacagctggt aatagt 16

<210> SEQ ID NO 865
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 865
tacctgtctc ttccga 16

<210> SEQ ID NO 866
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 866
taacgtacct gtctct 16

<210> SEQ ID NO 867
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 867
aacaatattg cagcag 16

<210> SEQ ID NO 868
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 868
taacaatatt gcagca 16

<210> SEQ ID NO 869
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 869
cgttaacaat attgca 16

<210> SEQ ID NO 870
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 870
ctcacgttaa caatat 16

<210> SEQ ID NO 871
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 871
acctattact aggttc 16

<210> SEQ ID NO 872
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 872
aaacctatta ctaggt 16

<210> SEQ ID NO 873
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 873
acaaatccat gtaagg 16

<210> SEQ ID NO 874
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 874
caaatccatg taagga 16

<210> SEQ ID NO 875
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 875
tggcataggc aaattg 16

<210> SEQ ID NO 876
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 876
gtaaacagca gcaagc 16

<210> SEQ ID NO 877
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 877
gtacctctaa cacact 16

<210> SEQ ID NO 878
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 878
agcaagtcag tgcaaa 16

<210> SEQ ID NO 879
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 879
attgagtgct aaagca 16

<210> SEQ ID NO 880
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 880
gcaaattgag tgctaa 16

<210> SEQ ID NO 881
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 881
aaacactatt gccgca 16

<210> SEQ ID NO 882
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 882
gtgtgaagca aagtgt 16

<210> SEQ ID NO 883
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 883
aaactacatt cttggt 16

<210> SEQ ID NO 884
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 884
agaagtgaat aggaca 16

<210> SEQ ID NO 885
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 885
tgaatgggtg atttag 16

<210> SEQ ID NO 886
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 886
gaatgggtga tttaga 16

<210> SEQ ID NO 887
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 887
aaactgtata attacc 16

<210> SEQ ID NO 888
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 888
cccaatttag gttcct 16

<210> SEQ ID NO 889
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 889
acccatatga tgccgt 16

<210> SEQ ID NO 890
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 890
caagctggtt caatct 16

<210> SEQ ID NO 891
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 891
gctggttcaa tctgtc 16

<210> SEQ ID NO 892
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 892
ccttgtctga ttagtt 16

<210> SEQ ID NO 893
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 893
cttgtctgat tagttc 16

<210> SEQ ID NO 894
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 894
aatgacttga tctttg 16

<210> SEQ ID NO 895
<211> LENGTH: 20
<212> TYPE: RNA
<213> ORGANISM: Mus sp.

<400> SEQUENCE: 895
ucccgcaugg ugguuucuuu 20

<210> SEQ ID NO 896
<211> LENGTH: 20
<212> TYPE: RNA
<213> ORGANISM: Mus sp.

<400> SEQUENCE: 896
uaccacagug acucauguuc 20

<210> SEQ ID NO 897
<211> LENGTH: 20
<212> TYPE: RNA
<213> ORGANISM: Mus sp.

<400> SEQUENCE: 897
ugagcucagg caacguugac 20

<210> SEQ ID NO 898
<211> LENGTH: 20
<212> TYPE: RNA
<213> ORGANISM: Homo sapiens

<400> SEQUENCE: 898
ucuucaaaag cagugguuuc 20

<210> SEQ ID NO 899
<211> LENGTH: 20
<212> TYPE: RNA
<213> ORGANISM: Mus sp.

<400> SEQUENCE: 899
ugugagcuca ggcaacguug 20

<210> SEQ ID NO 900
<211> LENGTH: 20
<212> TYPE: RNA
<213> ORGANISM: Homo sapiens

<400> SEQUENCE: 900
accacaguga ugccuguucu 20

<210> SEQ ID NO 901
<211> LENGTH: 20
<212> TYPE: RNA
<213> ORGANISM: Homo sapiens

<400> SEQUENCE: 901
ccggcaaugu cgauaucuau 20

<210> SEQ ID NO 902
<211> LENGTH: 20
<212> TYPE: RNA
<213> ORGANISM: Homo sapiens

<400> SEQUENCE: 902
agugccggca augucgauau 20

<210> SEQ ID NO 903
<211> LENGTH: 20
<212> TYPE: RNA
<213> ORGANISM: Mus sp.

<400> SEQUENCE: 903
aaagacaugg gauacaagaa 20

<210> SEQ ID NO 904
<211> LENGTH: 20
<212> TYPE: RNA
<213> ORGANISM: Homo sapiens

<400> SEQUENCE: 904
uuuacucuag ccaaggaaua 20

<210> SEQ ID NO 905
<211> LENGTH: 20
<212> TYPE: RNA
<213> ORGANISM: Mus sp.

<400> SEQUENCE: 905
gcuucauccu ccagguuuac 20

<210> SEQ ID NO 906
<211> LENGTH: 20
<212> TYPE: RNA
<213> ORGANISM: Mus sp.

<400> SEQUENCE: 906
acggacaaag cuucauccuc 20

<210> SEQ ID NO 907
<211> LENGTH: 20
<212> TYPE: RNA
<213> ORGANISM: Mus sp.

<400> SEQUENCE: 907
ugggucuuca ggcacaugca 20

<210> SEQ ID NO 908
<211> LENGTH: 20
<212> TYPE: RNA
<213> ORGANISM: Mus sp.

<400> SEQUENCE: 908
ucugggacag caacuguucu 20

<210> SEQ ID NO 909
<211> LENGTH: 20
<212> TYPE: RNA
<213> ORGANISM: Homo sapiens

<400> SEQUENCE: 909
accugcauca accccucuaa 20

<210> SEQ ID NO 910
<211> LENGTH: 20
<212> TYPE: RNA
<213> ORGANISM: Mus sp.

<400> SEQUENCE: 910
cuugcuuugg agguucuggg 20

<210> SEQ ID NO 911
<211> LENGTH: 20
<212> TYPE: RNA
<213> ORGANISM: Homo sapiens

<400> SEQUENCE: 911
augggcagca agugcuccaa 20

<210> SEQ ID NO 912
<211> LENGTH: 20
<212> TYPE: RNA
<213> ORGANISM: Mus sp.

<400> SEQUENCE: 912
uaagaaaucg cuguguuuag 20

<210> SEQ ID NO 913
<211> LENGTH: 20
<212> TYPE: RNA
<213> ORGANISM: Mus sp.

<400> SEQUENCE: 913
cucaaagucu aagaaaucgc 20

<210> SEQ ID NO 914
<211> LENGTH: 20
<212> TYPE: RNA
<213> ORGANISM: Homo sapiens

<400> SEQUENCE: 914
uaagaaagca cugugcauca 20

<210> SEQ ID NO 915
<211> LENGTH: 20
<212> TYPE: RNA
<213> ORGANISM: Mus sp.

<400> SEQUENCE: 915
cucaacaucu gucauccaca 20

<210> SEQ ID NO 916
<211> LENGTH: 20
<212> TYPE: RNA
<213> ORGANISM: Homo sapiens

<400> SEQUENCE: 916
aucaugcaaa uaaauuaugc 20

<210> SEQ ID NO 917
<211> LENGTH: 20
<212> TYPE: RNA
<213> ORGANISM: Homo sapiens

```
<400> SEQUENCE: 917

uaucaugcaa auaaauuaug                                              20

<210> SEQ ID NO 918
<211> LENGTH: 20
<212> TYPE: RNA
<213> ORGANISM: Homo sapiens

<400> SEQUENCE: 918

gugaaaauga auaucaugca                                              20

<210> SEQ ID NO 919
<211> LENGTH: 20
<212> TYPE: RNA
<213> ORGANISM: Homo sapiens

<400> SEQUENCE: 919

uugugaaaau gaauaucaug                                              20

<210> SEQ ID NO 920
<211> LENGTH: 20
<212> TYPE: RNA
<213> ORGANISM: Homo sapiens

<400> SEQUENCE: 920

uucaauugug aaaaugaaua                                              20

<210> SEQ ID NO 921
<211> LENGTH: 20
<212> TYPE: RNA
<213> ORGANISM: Homo sapiens

<400> SEQUENCE: 921

guucaauugu gaaaaugaau                                              20

<210> SEQ ID NO 922
<211> LENGTH: 20
<212> TYPE: RNA
<213> ORGANISM: Homo sapiens

<400> SEQUENCE: 922

uguaaaguuc aauugugaaa                                              20

<210> SEQ ID NO 923
<211> LENGTH: 20
<212> TYPE: RNA
<213> ORGANISM: Homo sapiens

<400> SEQUENCE: 923

aacuguaaag uucaauugug                                              20

<210> SEQ ID NO 924
<211> LENGTH: 20
<212> TYPE: RNA
<213> ORGANISM: Homo sapiens

<400> SEQUENCE: 924

uuaaacugua aaguucaauu                                              20

<210> SEQ ID NO 925
<211> LENGTH: 20
<212> TYPE: RNA
```

<213> ORGANISM: Homo sapiens

<400> SEQUENCE: 925
uuuaaacugu aaaguucaau 20

<210> SEQ ID NO 926
<211> LENGTH: 20
<212> TYPE: RNA
<213> ORGANISM: Homo sapiens

<400> SEQUENCE: 926
gugaacaacu guuugucuuu 20

<210> SEQ ID NO 927
<211> LENGTH: 20
<212> TYPE: RNA
<213> ORGANISM: Homo sapiens

<400> SEQUENCE: 927
augugaacaa cuguuugucu 20

<210> SEQ ID NO 928
<211> LENGTH: 20
<212> TYPE: RNA
<213> ORGANISM: Homo sapiens

<400> SEQUENCE: 928
uaugugaaca acuguuuguc 20

<210> SEQ ID NO 929
<211> LENGTH: 20
<212> TYPE: RNA
<213> ORGANISM: Homo sapiens

<400> SEQUENCE: 929
uuaugugaac aacuguuugu 20

<210> SEQ ID NO 930
<211> LENGTH: 20
<212> TYPE: RNA
<213> ORGANISM: Homo sapiens

<400> SEQUENCE: 930
auuuauguga acaacuguuu 20

<210> SEQ ID NO 931
<211> LENGTH: 20
<212> TYPE: RNA
<213> ORGANISM: Mus sp.

<400> SEQUENCE: 931
aaauauauga auaaaguaua 20

<210> SEQ ID NO 932
<211> LENGTH: 20
<212> TYPE: RNA
<213> ORGANISM: Homo sapiens

<400> SEQUENCE: 932
ucuuauuuau gugaacaacu 20

<210> SEQ ID NO 933
<211> LENGTH: 20

<212> TYPE: RNA
<213> ORGANISM: Homo sapiens

<400> SEQUENCE: 933
auugccccuu cuuauuuaug 20

<210> SEQ ID NO 934
<211> LENGTH: 20
<212> TYPE: RNA
<213> ORGANISM: Mus sp.

<400> SEQUENCE: 934
gauuccacug ugaaauauau 20

<210> SEQ ID NO 935
<211> LENGTH: 20
<212> TYPE: RNA
<213> ORGANISM: Mus sp.

<400> SEQUENCE: 935
ucugagcugu gagauuccac 20

<210> SEQ ID NO 936
<211> LENGTH: 20
<212> TYPE: RNA
<213> ORGANISM: Mus sp.

<400> SEQUENCE: 936
ugugucuguu cugagcugug 20

<210> SEQ ID NO 937
<211> LENGTH: 20
<212> TYPE: RNA
<213> ORGANISM: Homo sapiens

<400> SEQUENCE: 937
uaauggugaa aacgucuucc 20

<210> SEQ ID NO 938
<211> LENGTH: 20
<212> TYPE: RNA
<213> ORGANISM: Homo sapiens

<400> SEQUENCE: 938
guaaugguga aaacgucuuc 20

<210> SEQ ID NO 939
<211> LENGTH: 20
<212> TYPE: RNA
<213> ORGANISM: Mus sp.

<400> SEQUENCE: 939
ccugcuuugu gucuguucug 20

<210> SEQ ID NO 940
<211> LENGTH: 20
<212> TYPE: RNA
<213> ORGANISM: Mus sp.

<400> SEQUENCE: 940
uugguuauuu ccugcuuugu 20

<210> SEQ ID NO 941

<211> LENGTH: 20
<212> TYPE: RNA
<213> ORGANISM: Homo sapiens

<400> SEQUENCE: 941
acauccuaaa agguguugua 20

<210> SEQ ID NO 942
<211> LENGTH: 20
<212> TYPE: RNA
<213> ORGANISM: Homo sapiens

<400> SEQUENCE: 942
cugugcacau gccucuguag 20

<210> SEQ ID NO 943
<211> LENGTH: 20
<212> TYPE: RNA
<213> ORGANISM: Mus sp.

<400> SEQUENCE: 943
gcuguaaggu accuacauac 20

<210> SEQ ID NO 944
<211> LENGTH: 20
<212> TYPE: RNA
<213> ORGANISM: Homo sapiens

<400> SEQUENCE: 944
uuugcaggau cugucugugc 20

<210> SEQ ID NO 945
<211> LENGTH: 20
<212> TYPE: RNA
<213> ORGANISM: Homo sapiens

<400> SEQUENCE: 945
aaucccauuu gcaggaucug 20

<210> SEQ ID NO 946
<211> LENGTH: 20
<212> TYPE: RNA
<213> ORGANISM: Mus sp.

<400> SEQUENCE: 946
gggaccuucu uagaugcugu 20

<210> SEQ ID NO 947
<211> LENGTH: 20
<212> TYPE: RNA
<213> ORGANISM: Mus sp.

<400> SEQUENCE: 947
ugggaccuuc uuagaugcug 20

<210> SEQ ID NO 948
<211> LENGTH: 20
<212> TYPE: RNA
<213> ORGANISM: Homo sapiens

<400> SEQUENCE: 948
uggaaaguca ugcaauccca 20

<210> SEQ ID NO 949
<211> LENGTH: 20
<212> TYPE: RNA
<213> ORGANISM: Homo sapiens

<400> SEQUENCE: 949
ccuugaaaug gaaagucaug 20

<210> SEQ ID NO 950
<211> LENGTH: 20
<212> TYPE: RNA
<213> ORGANISM: Homo sapiens

<400> SEQUENCE: 950
uacagcuagg acuuaaccuu 20

<210> SEQ ID NO 951
<211> LENGTH: 20
<212> TYPE: RNA
<213> ORGANISM: Homo sapiens

<400> SEQUENCE: 951
uucuacagcu aggacuuaac 20

<210> SEQ ID NO 952
<211> LENGTH: 20
<212> TYPE: RNA
<213> ORGANISM: Homo sapiens

<400> SEQUENCE: 952
ugaaugauuc uacagcuagg 20

<210> SEQ ID NO 953
<211> LENGTH: 20
<212> TYPE: RNA
<213> ORGANISM: Homo sapiens

<400> SEQUENCE: 953
guuugcaaga augaaaugaa 20

<210> SEQ ID NO 954
<211> LENGTH: 20
<212> TYPE: RNA
<213> ORGANISM: Homo sapiens

<400> SEQUENCE: 954
ccaagcaggc ugguuugcaa 20

<210> SEQ ID NO 955
<211> LENGTH: 20
<212> TYPE: RNA
<213> ORGANISM: Mus sp.

<400> SEQUENCE: 955
ugggucauaa cugggacucc 20

<210> SEQ ID NO 956
<211> LENGTH: 20
<212> TYPE: RNA
<213> ORGANISM: Mus sp.

<400> SEQUENCE: 956
accaaauaug aaguaugaau 20

<210> SEQ ID NO 957
<211> LENGTH: 20
<212> TYPE: RNA
<213> ORGANISM: Mus sp.

<400> SEQUENCE: 957
auuaccaaau augaaguaug                                               20

<210> SEQ ID NO 958
<211> LENGTH: 20
<212> TYPE: RNA
<213> ORGANISM: Homo sapiens

<400> SEQUENCE: 958
uguggucccu uccaaugcug                                               20

<210> SEQ ID NO 959
<211> LENGTH: 20
<212> TYPE: RNA
<213> ORGANISM: Mus sp.

<400> SEQUENCE: 959
gccagaauua ccaaauauga                                               20

<210> SEQ ID NO 960
<211> LENGTH: 20
<212> TYPE: RNA
<213> ORGANISM: Mus sp.

<400> SEQUENCE: 960
ugccagaauu accaaauaug                                               20

<210> SEQ ID NO 961
<211> LENGTH: 20
<212> TYPE: RNA
<213> ORGANISM: Mus sp.

<400> SEQUENCE: 961
caugccagaa uuaccaaaua                                               20

<210> SEQ ID NO 962
<211> LENGTH: 20
<212> TYPE: RNA
<213> ORGANISM: Mus sp.

<400> SEQUENCE: 962
aaagccaugc cagaauuacc                                               20

<210> SEQ ID NO 963
<211> LENGTH: 20
<212> TYPE: RNA
<213> ORGANISM: Mus sp.

<400> SEQUENCE: 963
uauaccagga aagccaugcc                                               20

<210> SEQ ID NO 964
<211> LENGTH: 20
<212> TYPE: RNA
<213> ORGANISM: Homo sapiens

<400> SEQUENCE: 964
gaagaagaga aagauguguu                                               20

<210> SEQ ID NO 965
<211> LENGTH: 20
<212> TYPE: RNA
<213> ORGANISM: Homo sapiens

<400> SEQUENCE: 965
cggcgaagaa gagaaagaug 20

<210> SEQ ID NO 966
<211> LENGTH: 20
<212> TYPE: RNA
<213> ORGANISM: Mus sp.

<400> SEQUENCE: 966
agagaggaga ucauugucuu 20

<210> SEQ ID NO 967
<211> LENGTH: 20
<212> TYPE: RNA
<213> ORGANISM: Mus sp.

<400> SEQUENCE: 967
ucagauaaag augaaagaga 20

<210> SEQ ID NO 968
<211> LENGTH: 20
<212> TYPE: RNA
<213> ORGANISM: Mus sp.

<400> SEQUENCE: 968
ccuagcuuca gauaaagaug 20

<210> SEQ ID NO 969
<211> LENGTH: 20
<212> TYPE: RNA
<213> ORGANISM: Homo sapiens

<400> SEQUENCE: 969
cuccugacuu aacguucuau 20

<210> SEQ ID NO 970
<211> LENGTH: 20
<212> TYPE: RNA
<213> ORGANISM: Homo sapiens

<400> SEQUENCE: 970
gcuccugacu uaacguucua 20

<210> SEQ ID NO 971
<211> LENGTH: 20
<212> TYPE: RNA
<213> ORGANISM: Homo sapiens

<400> SEQUENCE: 971
ggcuccugac uuaacguucu 20

<210> SEQ ID NO 972
<211> LENGTH: 20
<212> TYPE: RNA
<213> ORGANISM: Mus sp.

<400> SEQUENCE: 972
auuagaaguu ccuagcuuca 20

<210> SEQ ID NO 973
<211> LENGTH: 20
<212> TYPE: RNA
<213> ORGANISM: Mus sp.

<400> SEQUENCE: 973
aaugagauua gaaguuccua 20

<210> SEQ ID NO 974
<211> LENGTH: 20
<212> TYPE: RNA
<213> ORGANISM: Mus sp.

<400> SEQUENCE: 974
gcaaugagau uagaaguucc 20

<210> SEQ ID NO 975
<211> LENGTH: 20
<212> TYPE: RNA
<213> ORGANISM: Homo sapiens

<400> SEQUENCE: 975
ugacaaaaug acuggcuccu 20

<210> SEQ ID NO 976
<211> LENGTH: 20
<212> TYPE: RNA
<213> ORGANISM: Homo sapiens

<400> SEQUENCE: 976
uuugacaaaa ugacuggcuc 20

<210> SEQ ID NO 977
<211> LENGTH: 20
<212> TYPE: RNA
<213> ORGANISM: Mus sp.

<400> SEQUENCE: 977
uagguuguuc uguagacugg 20

<210> SEQ ID NO 978
<211> LENGTH: 20
<212> TYPE: RNA
<213> ORGANISM: Mus sp.

<400> SEQUENCE: 978
uuagguuguu cuguagacug 20

<210> SEQ ID NO 979
<211> LENGTH: 20
<212> TYPE: RNA
<213> ORGANISM: Mus sp.

<400> SEQUENCE: 979
uuccagaugg uuagguuguu 20

<210> SEQ ID NO 980
<211> LENGTH: 20
<212> TYPE: RNA
<213> ORGANISM: Homo sapiens

<400> SEQUENCE: 980
aucaucuuug ccaaguaaga 20

<210> SEQ ID NO 981
<211> LENGTH: 20
<212> TYPE: RNA
<213> ORGANISM: Mus sp.

<400> SEQUENCE: 981
ucagacacua gaccucuucc 20

<210> SEQ ID NO 982
<211> LENGTH: 20
<212> TYPE: RNA
<213> ORGANISM: Homo sapiens

<400> SEQUENCE: 982
ugaaacugua ucaucuuugc 20

<210> SEQ ID NO 983
<211> LENGTH: 20
<212> TYPE: RNA
<213> ORGANISM: Homo sapiens

<400> SEQUENCE: 983
uuugaaacug uaucaucuuu 20

<210> SEQ ID NO 984
<211> LENGTH: 20
<212> TYPE: RNA
<213> ORGANISM: Homo sapiens

<400> SEQUENCE: 984
aacucuuuga aacuguauca 20

<210> SEQ ID NO 985
<211> LENGTH: 20
<212> TYPE: RNA
<213> ORGANISM: Mus sp.

<400> SEQUENCE: 985
uuggacugug ugauugugcc 20

<210> SEQ ID NO 986
<211> LENGTH: 20
<212> TYPE: RNA
<213> ORGANISM: Homo sapiens

<400> SEQUENCE: 986
ccaccuucau uuaacucuuu 20

<210> SEQ ID NO 987
<211> LENGTH: 20
<212> TYPE: RNA
<213> ORGANISM: Homo sapiens

<400> SEQUENCE: 987
uaguccaccu ucauuuaacu 20

<210> SEQ ID NO 988
<211> LENGTH: 20
<212> TYPE: RNA
<213> ORGANISM: Homo sapiens

<400> SEQUENCE: 988
uuugaugucu ccaaguaguc 20

<210> SEQ ID NO 989
<211> LENGTH: 20
<212> TYPE: RNA
<213> ORGANISM: Homo sapiens

<400> SEQUENCE: 989
uuagcuuuug augucuccaa 20

<210> SEQ ID NO 990
<211> LENGTH: 20
<212> TYPE: RNA
<213> ORGANISM: Homo sapiens

<400> SEQUENCE: 990
ccuggaaacu uagcuuuuga 20

<210> SEQ ID NO 991
<211> LENGTH: 20
<212> TYPE: RNA
<213> ORGANISM: Mus sp.

<400> SEQUENCE: 991
uacuaccuca cugcaccugg 20

<210> SEQ ID NO 992
<211> LENGTH: 20
<212> TYPE: RNA
<213> ORGANISM: Mus sp.

<400> SEQUENCE: 992
ucuggguugu guuucuucuc 20

<210> SEQ ID NO 993
<211> LENGTH: 20
<212> TYPE: RNA
<213> ORGANISM: Homo sapiens

<400> SEQUENCE: 993
uuuccauguu auguuucuac 20

<210> SEQ ID NO 994
<211> LENGTH: 20
<212> TYPE: RNA
<213> ORGANISM: Homo sapiens

<400> SEQUENCE: 994
uacacuguuu ccauguuaug 20

<210> SEQ ID NO 995
<211> LENGTH: 20
<212> TYPE: RNA
<213> ORGANISM: Homo sapiens

<400> SEQUENCE: 995
guuuaaggua cacuguuucc 20

<210> SEQ ID NO 996
<211> LENGTH: 20
<212> TYPE: RNA
<213> ORGANISM: Homo sapiens

<400> SEQUENCE: 996
aguuuaaggu acacuguuuc 20

<210> SEQ ID NO 997
<211> LENGTH: 20
<212> TYPE: RNA
<213> ORGANISM: Mus sp.

<400> SEQUENCE: 997
aucagaauca gggacuugug 20

<210> SEQ ID NO 998
<211> LENGTH: 20
<212> TYPE: RNA
<213> ORGANISM: Homo sapiens

<400> SEQUENCE: 998
ggggaaauca aggaugcuca 20

<210> SEQ ID NO 999
<211> LENGTH: 20
<212> TYPE: RNA
<213> ORGANISM: Mus sp.

<400> SEQUENCE: 999
agguccauca gaaucaggga 20

<210> SEQ ID NO 1000
<211> LENGTH: 20
<212> TYPE: RNA
<213> ORGANISM: Mus sp.

<400> SEQUENCE: 1000
ucagguccau cagaaucagg 20

<210> SEQ ID NO 1001
<211> LENGTH: 20
<212> TYPE: RNA
<213> ORGANISM: Mus sp.

<400> SEQUENCE: 1001
uggagccugu auagcucagc 20

<210> SEQ ID NO 1002
<211> LENGTH: 20
<212> TYPE: RNA
<213> ORGANISM: Mus sp.

<400> SEQUENCE: 1002
acaggcaugg ccuaguaccu 20

<210> SEQ ID NO 1003
<211> LENGTH: 20
<212> TYPE: RNA
<213> ORGANISM: Mus sp.

<400> SEQUENCE: 1003
ccugaaacuu accucuuagc 20

<210> SEQ ID NO 1004
<211> LENGTH: 20
<212> TYPE: RNA

<213> ORGANISM: Mus sp.

<400> SEQUENCE: 1004
ucucagagcc ugaaacuuac 20

<210> SEQ ID NO 1005
<211> LENGTH: 20
<212> TYPE: RNA
<213> ORGANISM: Mus sp.

<400> SEQUENCE: 1005
ugggugagcu cuacauggug 20

<210> SEQ ID NO 1006
<211> LENGTH: 20
<212> TYPE: RNA
<213> ORGANISM: Mus sp.

<400> SEQUENCE: 1006
agagcaagaa gcuaaugccg 20

<210> SEQ ID NO 1007
<211> LENGTH: 20
<212> TYPE: RNA
<213> ORGANISM: Mus sp.

<400> SEQUENCE: 1007
uucccaagcu aagggccuag 20

<210> SEQ ID NO 1008
<211> LENGTH: 20
<212> TYPE: RNA
<213> ORGANISM: Homo sapiens

<400> SEQUENCE: 1008
auagacagug cccuuggugc 20

<210> SEQ ID NO 1009
<211> LENGTH: 20
<212> TYPE: RNA
<213> ORGANISM: Homo sapiens

<400> SEQUENCE: 1009
ggugacgugg uagucacuug 20

<210> SEQ ID NO 1010
<211> LENGTH: 20
<212> TYPE: RNA
<213> ORGANISM: Mus sp.

<400> SEQUENCE: 1010
ugggcugguc auacugucau 20

<210> SEQ ID NO 1011
<211> LENGTH: 20
<212> TYPE: RNA
<213> ORGANISM: Mus sp.

<400> SEQUENCE: 1011
guugggcugg ucauacuguc 20

<210> SEQ ID NO 1012
<211> LENGTH: 20

<212> TYPE: RNA
<213> ORGANISM: Mus sp.

<400> SEQUENCE: 1012
ugaguaaccu gaugaccuga 20

<210> SEQ ID NO 1013
<211> LENGTH: 20
<212> TYPE: RNA
<213> ORGANISM: Mus sp.

<400> SEQUENCE: 1013
gaccucugag uaaccugaug 20

<210> SEQ ID NO 1014
<211> LENGTH: 20
<212> TYPE: RNA
<213> ORGANISM: Mus sp.

<400> SEQUENCE: 1014
uggaucacua aggacuauga 20

<210> SEQ ID NO 1015
<211> LENGTH: 20
<212> TYPE: RNA
<213> ORGANISM: Mus sp.

<400> SEQUENCE: 1015
uuggaucacu aaggacuaug 20

<210> SEQ ID NO 1016
<211> LENGTH: 20
<212> TYPE: RNA
<213> ORGANISM: Mus sp.

<400> SEQUENCE: 1016
acucucaugu uggaacuucu 20

<210> SEQ ID NO 1017
<211> LENGTH: 20
<212> TYPE: RNA
<213> ORGANISM: Homo sapiens

<400> SEQUENCE: 1017
cuuuccaggg gccaauuuug 20

<210> SEQ ID NO 1018
<211> LENGTH: 20
<212> TYPE: RNA
<213> ORGANISM: Homo sapiens

<400> SEQUENCE: 1018
accaccagcu auuggaccuu 20

<210> SEQ ID NO 1019
<211> LENGTH: 20
<212> TYPE: RNA
<213> ORGANISM: Homo sapiens

<400> SEQUENCE: 1019
ugccccauug agaucuuccu 20

<210> SEQ ID NO 1020

<211> LENGTH: 20
<212> TYPE: RNA
<213> ORGANISM: Mus sp.

<400> SEQUENCE: 1020
gaugaccaga uucuguuggg 20

<210> SEQ ID NO 1021
<211> LENGTH: 20
<212> TYPE: RNA
<213> ORGANISM: Mus sp.

<400> SEQUENCE: 1021
cccaccagaa uggaugacca 20

<210> SEQ ID NO 1022
<211> LENGTH: 20
<212> TYPE: RNA
<213> ORGANISM: Mus sp.

<400> SEQUENCE: 1022
uucacuuuua uuaaacagug 20

<210> SEQ ID NO 1023
<211> LENGTH: 20
<212> TYPE: RNA
<213> ORGANISM: Mus sp.

<400> SEQUENCE: 1023
uuucacuuuu auuaaacagu 20

<210> SEQ ID NO 1024
<211> LENGTH: 20
<212> TYPE: RNA
<213> ORGANISM: Mus sp.

<400> SEQUENCE: 1024
cgaagggccu uucacuuuua 20

<210> SEQ ID NO 1025
<211> LENGTH: 20
<212> TYPE: RNA
<213> ORGANISM: Mus sp.

<400> SEQUENCE: 1025
uuugagauga uucgaagggc 20

<210> SEQ ID NO 1026
<211> LENGTH: 20
<212> TYPE: RNA
<213> ORGANISM: Mus sp.

<400> SEQUENCE: 1026
uguaccuuuu gagaugauuc 20

<210> SEQ ID NO 1027
<211> LENGTH: 20
<212> TYPE: RNA
<213> ORGANISM: Mus sp.

<400> SEQUENCE: 1027
gugcacaaug uaccuuuuga 20

<210> SEQ ID NO 1028
<211> LENGTH: 20
<212> TYPE: RNA
<213> ORGANISM: Mus sp.

<400> SEQUENCE: 1028
cugugcacaa uguaccuuuu 20

<210> SEQ ID NO 1029
<211> LENGTH: 20
<212> TYPE: RNA
<213> ORGANISM: Mus sp.

<400> SEQUENCE: 1029
ccugaauuuu aacuuccugu 20

<210> SEQ ID NO 1030
<211> LENGTH: 20
<212> TYPE: RNA
<213> ORGANISM: Homo sapiens

<400> SEQUENCE: 1030
uaaacaguga acuugucugg 20

<210> SEQ ID NO 1031
<211> LENGTH: 20
<212> TYPE: RNA
<213> ORGANISM: Homo sapiens

<400> SEQUENCE: 1031
uuaaacagug aacuugucug 20

<210> SEQ ID NO 1032
<211> LENGTH: 20
<212> TYPE: RNA
<213> ORGANISM: Mus sp.

<400> SEQUENCE: 1032
agggccugaa uuuuaacuuc 20

<210> SEQ ID NO 1033
<211> LENGTH: 20
<212> TYPE: RNA
<213> ORGANISM: Mus sp.

<400> SEQUENCE: 1033
aagggccuga auuuuaacuu 20

<210> SEQ ID NO 1034
<211> LENGTH: 20
<212> TYPE: RNA
<213> ORGANISM: Mus sp.

<400> SEQUENCE: 1034
caagaaaacc aagggccuga 20

<210> SEQ ID NO 1035
<211> LENGTH: 20
<212> TYPE: RNA
<213> ORGANISM: Mus sp.

<400> SEQUENCE: 1035
ugcaagaaaa ccaagggccu 20

<210> SEQ ID NO 1036
<211> LENGTH: 20
<212> TYPE: RNA
<213> ORGANISM: Mus sp.

<400> SEQUENCE: 1036
cugcaagaaa accaagggcc 20

<210> SEQ ID NO 1037
<211> LENGTH: 20
<212> TYPE: RNA
<213> ORGANISM: Mus sp.

<400> SEQUENCE: 1037
uucugcaaga aaaccaaggg 20

<210> SEQ ID NO 1038
<211> LENGTH: 20
<212> TYPE: RNA
<213> ORGANISM: Homo sapiens

<400> SEQUENCE: 1038
auucagaggu cacuucauuu 20

<210> SEQ ID NO 1039
<211> LENGTH: 20
<212> TYPE: RNA
<213> ORGANISM: Homo sapiens

<400> SEQUENCE: 1039
ugauucagag gucacuucau 20

<210> SEQ ID NO 1040
<211> LENGTH: 20
<212> TYPE: RNA
<213> ORGANISM: Homo sapiens

<400> SEQUENCE: 1040
uuagagauga uucagagguc 20

<210> SEQ ID NO 1041
<211> LENGTH: 20
<212> TYPE: RNA
<213> ORGANISM: Homo sapiens

<400> SEQUENCE: 1041
uuuacucuua gagaugauuc 20

<210> SEQ ID NO 1042
<211> LENGTH: 20
<212> TYPE: RNA
<213> ORGANISM: Mus sp.

<400> SEQUENCE: 1042
ugucccagac uuccuuuguc 20

<210> SEQ ID NO 1043
<211> LENGTH: 20
<212> TYPE: RNA
<213> ORGANISM: Homo sapiens

<400> SEQUENCE: 1043
ccgugcauga uuuacucuua 20

<210> SEQ ID NO 1044
<211> LENGTH: 20
<212> TYPE: RNA
<213> ORGANISM: Mus sp.

<400> SEQUENCE: 1044
ggcuuugucc cagacuuccu 20

<210> SEQ ID NO 1045
<211> LENGTH: 20
<212> TYPE: RNA
<213> ORGANISM: Homo sapiens

<400> SEQUENCE: 1045
uuccccgugc augauuuacu 20

<210> SEQ ID NO 1046
<211> LENGTH: 20
<212> TYPE: RNA
<213> ORGANISM: Homo sapiens

<400> SEQUENCE: 1046
uuacaagaaa acaauggggc 20

<210> SEQ ID NO 1047
<211> LENGTH: 20
<212> TYPE: RNA
<213> ORGANISM: Homo sapiens

<400> SEQUENCE: 1047
uuuacaagaa aacaaugggg 20

<210> SEQ ID NO 1048
<211> LENGTH: 20
<212> TYPE: RNA
<213> ORGANISM: Homo sapiens

<400> SEQUENCE: 1048
uuuuacaaga aaacaauggg 20

<210> SEQ ID NO 1049
<211> LENGTH: 20
<212> TYPE: RNA
<213> ORGANISM: Homo sapiens

<400> SEQUENCE: 1049
uucguccuug acgucguuuu 20

<210> SEQ ID NO 1050
<211> LENGTH: 20
<212> TYPE: RNA
<213> ORGANISM: Mus sp.

<400> SEQUENCE: 1050
acgguauuua cagauuggau 20

<210> SEQ ID NO 1051
<211> LENGTH: 20
<212> TYPE: RNA
<213> ORGANISM: Mus sp.

<400> SEQUENCE: 1051
gacgguauuu acagauugga 20

<210> SEQ ID NO 1052
<211> LENGTH: 20
<212> TYPE: RNA
<213> ORGANISM: Mus sp.

<400> SEQUENCE: 1052
acgggaacgu gacgguauuu 20

<210> SEQ ID NO 1053
<211> LENGTH: 20
<212> TYPE: RNA
<213> ORGANISM: Homo sapiens

<400> SEQUENCE: 1053
augguauuca cggacuggau 20

<210> SEQ ID NO 1054
<211> LENGTH: 20
<212> TYPE: RNA
<213> ORGANISM: Homo sapiens

<400> SEQUENCE: 1054
gaugguauuc acggacugga 20

<210> SEQ ID NO 1055
<211> LENGTH: 20
<212> TYPE: RNA
<213> ORGANISM: Homo sapiens

<400> SEQUENCE: 1055
gggaauguga ugguauucac 20

<210> SEQ ID NO 1056
<211> LENGTH: 20
<212> TYPE: RNA
<213> ORGANISM: Homo sapiens

<400> SEQUENCE: 1056
acgggaaugu gaugguauuc 20

<210> SEQ ID NO 1057
<211> LENGTH: 20
<212> TYPE: RNA
<213> ORGANISM: Homo sapiens

<400> SEQUENCE: 1057
guugauaaca gcaagauggc 20

<210> SEQ ID NO 1058
<211> LENGTH: 20
<212> TYPE: RNA
<213> ORGANISM: Homo sapiens

<400> SEQUENCE: 1058
cuguugauaa cagcaagaug 20

<210> SEQ ID NO 1059
<211> LENGTH: 20
<212> TYPE: RNA
<213> ORGANISM: Homo sapiens

<400> SEQUENCE: 1059
ucuggcugug ccaaagcuua 20

<210> SEQ ID NO 1060
<211> LENGTH: 20
<212> TYPE: RNA
<213> ORGANISM: Mus sp.

<400> SEQUENCE: 1060
gguuacuuug aagaaugga 20

<210> SEQ ID NO 1061
<211> LENGTH: 20
<212> TYPE: RNA
<213> ORGANISM: Mus sp.

<400> SEQUENCE: 1061
uguaauagua aauacauaua 20

<210> SEQ ID NO 1062
<211> LENGTH: 20
<212> TYPE: RNA
<213> ORGANISM: Mus sp.

<400> SEQUENCE: 1062
ccaaauguaa uaguaaauac 20

<210> SEQ ID NO 1063
<211> LENGTH: 20
<212> TYPE: RNA
<213> ORGANISM: Mus sp.

<400> SEQUENCE: 1063
cuccaaaugu aauaguaaau 20

<210> SEQ ID NO 1064
<211> LENGTH: 20
<212> TYPE: RNA
<213> ORGANISM: Mus sp.

<400> SEQUENCE: 1064
cgagcccucc aaauguaaua 20

<210> SEQ ID NO 1065
<211> LENGTH: 20
<212> TYPE: RNA
<213> ORGANISM: Mus sp.

<400> SEQUENCE: 1065
gaucgagccc uccaaaugua 20

<210> SEQ ID NO 1066
<211> LENGTH: 20
<212> TYPE: RNA
<213> ORGANISM: Homo sapiens

<400> SEQUENCE: 1066
augucuauga caaccugauc 20

<210> SEQ ID NO 1067
<211> LENGTH: 20
<212> TYPE: RNA
<213> ORGANISM: Mus sp.

<400> SEQUENCE: 1067
ucggacgugu ugaaugcugc 20

<210> SEQ ID NO 1068
<211> LENGTH: 20
<212> TYPE: RNA
<213> ORGANISM: Homo sapiens

<400> SEQUENCE: 1068
aacagcagau augucuauga 20

<210> SEQ ID NO 1069
<211> LENGTH: 20
<212> TYPE: RNA
<213> ORGANISM: Mus sp.

<400> SEQUENCE: 1069
cucggacgug uugaaugcug 20

<210> SEQ ID NO 1070
<211> LENGTH: 20
<212> TYPE: RNA
<213> ORGANISM: Homo sapiens

<400> SEQUENCE: 1070
agaugcaaca gcagauaugu 20

<210> SEQ ID NO 1071
<211> LENGTH: 20
<212> TYPE: RNA
<213> ORGANISM: Mus sp.

<400> SEQUENCE: 1071
ugagaaaggg aagaccucgg 20

<210> SEQ ID NO 1072
<211> LENGTH: 20
<212> TYPE: RNA
<213> ORGANISM: Homo sapiens

<400> SEQUENCE: 1072
auaccuauca uuacucgaug 20

<210> SEQ ID NO 1073
<211> LENGTH: 20
<212> TYPE: RNA
<213> ORGANISM: Homo sapiens

<400> SEQUENCE: 1073
ucagaagugc ugaacgcugc 20

<210> SEQ ID NO 1074
<211> LENGTH: 20
<212> TYPE: RNA
<213> ORGANISM: Homo sapiens

<400> SEQUENCE: 1074
cucagaagug cugaacgcug 20

<210> SEQ ID NO 1075
<211> LENGTH: 20
<212> TYPE: RNA
<213> ORGANISM: Homo sapiens

<400> SEQUENCE: 1075
ccagauaccu aucauuacuc 20

<210> SEQ ID NO 1076
<211> LENGTH: 20
<212> TYPE: RNA
<213> ORGANISM: Homo sapiens

<400> SEQUENCE: 1076
uccagauacc uaucauuacu 20

<210> SEQ ID NO 1077
<211> LENGTH: 20
<212> TYPE: RNA
<213> ORGANISM: Mus sp.

<400> SEQUENCE: 1077
uuggcuuuua augaucuagu 20

<210> SEQ ID NO 1078
<211> LENGTH: 20
<212> TYPE: RNA
<213> ORGANISM: Mus sp.

<400> SEQUENCE: 1078
ugaagcugca gacaccuuug 20

<210> SEQ ID NO 1079
<211> LENGTH: 20
<212> TYPE: RNA
<213> ORGANISM: Mus sp.

<400> SEQUENCE: 1079
aacgacauug cucucaugaa 20

<210> SEQ ID NO 1080
<211> LENGTH: 20
<212> TYPE: RNA
<213> ORGANISM: Homo sapiens

<400> SEQUENCE: 1080
gcagaagccu cugacuuuca 20

<210> SEQ ID NO 1081
<211> LENGTH: 20
<212> TYPE: RNA
<213> ORGANISM: Mus sp.

<400> SEQUENCE: 1081
uucccaucca aauuacgacu 20

<210> SEQ ID NO 1082
<211> LENGTH: 20
<212> TYPE: RNA
<213> ORGANISM: Mus sp.

<400> SEQUENCE: 1082
ggaaguagac accagguaga 20

<210> SEQ ID NO 1083
<211> LENGTH: 20
<212> TYPE: RNA

<213> ORGANISM: Mus sp.

<400> SEQUENCE: 1083
uggaaguaga caccagguag 20

<210> SEQ ID NO 1084
<211> LENGTH: 20
<212> TYPE: RNA
<213> ORGANISM: Mus sp.

<400> SEQUENCE: 1084
uguucuaugg aaguagacac 20

<210> SEQ ID NO 1085
<211> LENGTH: 20
<212> TYPE: RNA
<213> ORGANISM: Homo sapiens

<400> SEQUENCE: 1085
uaugacucca agaccaagaa 20

<210> SEQ ID NO 1086
<211> LENGTH: 20
<212> TYPE: RNA
<213> ORGANISM: Homo sapiens

<400> SEQUENCE: 1086
uucucaucca aauuaugacu 20

<210> SEQ ID NO 1087
<211> LENGTH: 20
<212> TYPE: RNA
<213> ORGANISM: Mus sp.

<400> SEQUENCE: 1087
ugagacaguc ucucauguuc 20

<210> SEQ ID NO 1088
<211> LENGTH: 20
<212> TYPE: RNA
<213> ORGANISM: Mus sp.

<400> SEQUENCE: 1088
cugagacagu cucucauguu 20

<210> SEQ ID NO 1089
<211> LENGTH: 20
<212> TYPE: RNA
<213> ORGANISM: Mus sp.

<400> SEQUENCE: 1089
ugcgggaauu cugagacagu 20

<210> SEQ ID NO 1090
<211> LENGTH: 20
<212> TYPE: RNA
<213> ORGANISM: Homo sapiens

<400> SEQUENCE: 1090
caggucauau ugaacauucc 20

<210> SEQ ID NO 1091
<211> LENGTH: 20

<212> TYPE: RNA
<213> ORGANISM: Homo sapiens

<400> SEQUENCE: 1091
gagacaaucu uucauguucu 20

<210> SEQ ID NO 1092
<211> LENGTH: 20
<212> TYPE: RNA
<213> ORGANISM: Homo sapiens

<400> SEQUENCE: 1092
cgcggcaggu cauauugaac 20

<210> SEQ ID NO 1093
<211> LENGTH: 20
<212> TYPE: RNA
<213> ORGANISM: Homo sapiens

<400> SEQUENCE: 1093
auggcauugg acggcauuug 20

<210> SEQ ID NO 1094
<211> LENGTH: 20
<212> TYPE: RNA
<213> ORGANISM: Homo sapiens

<400> SEQUENCE: 1094
cauggcauug gacggcauuu 20

<210> SEQ ID NO 1095
<211> LENGTH: 45
<212> TYPE: DNA
<213> ORGANISM: Mus sp.

<400> SEQUENCE: 1095
agtgactcat gttcatcccg catggtggtt tctttgcgct gtata 45

<210> SEQ ID NO 1096
<211> LENGTH: 45
<212> TYPE: DNA
<213> ORGANISM: Mus sp.

<400> SEQUENCE: 1096
ctctataaaa aactctacca cagtgactca tgttcatccc gcatg 45

<210> SEQ ID NO 1097
<211> LENGTH: 45
<212> TYPE: DNA
<213> ORGANISM: Mus sp.

<400> SEQUENCE: 1097
ttatgaagct gaatgtgagc tcaggcaacg ttgacctcta taaaa 45

<210> SEQ ID NO 1098
<211> LENGTH: 45
<212> TYPE: DNA
<213> ORGANISM: Homo sapiens

<400> SEQUENCE: 1098
cacagtgatg cctgttcttc aaaagcagtg gtttctttac gctgt 45

<210> SEQ ID NO 1099

<211> LENGTH: 45
<212> TYPE: DNA
<213> ORGANISM: Mus sp.

<400> SEQUENCE: 1099
ctttatgaag ctgaatgtga gctcaggcaa cgttgacctc tataa 45

<210> SEQ ID NO 1100
<211> LENGTH: 45
<212> TYPE: DNA
<213> ORGANISM: Homo sapiens

<400> SEQUENCE: 1100
tctataaaaa actgtaccac agtgatgcct gttcttcaaa agcag 45

<210> SEQ ID NO 1101
<211> LENGTH: 45
<212> TYPE: DNA
<213> ORGANISM: Homo sapiens

<400> SEQUENCE: 1101
aactgaacac aagtgccggc aatgtcgata tctataaaaa actgt 45

<210> SEQ ID NO 1102
<211> LENGTH: 45
<212> TYPE: DNA
<213> ORGANISM: Homo sapiens

<400> SEQUENCE: 1102
atgaaactga acacaagtgc cggcaatgtc gatatctata aaaaa 45

<210> SEQ ID NO 1103
<211> LENGTH: 45
<212> TYPE: DNA
<213> ORGANISM: Mus sp.

<400> SEQUENCE: 1103
gggagagcag catgtaaaga catgggatac aagaacaatt tttat 45

<210> SEQ ID NO 1104
<211> LENGTH: 45
<212> TYPE: DNA
<213> ORGANISM: Homo sapiens

<400> SEQUENCE: 1104
gctataagaa taatttttac tctagccaag gaatagtgga tgaca 45

<210> SEQ ID NO 1105
<211> LENGTH: 45
<212> TYPE: DNA
<213> ORGANISM: Mus sp.

<400> SEQUENCE: 1105
gtctctacgg acaaagcttc atcctccagg tttactcatc tcaga 45

<210> SEQ ID NO 1106
<211> LENGTH: 45
<212> TYPE: DNA
<213> ORGANISM: Mus sp.

<400> SEQUENCE: 1106
gttgtgttcg tctctacgga caaagcttca tcctccaggt ttact 45

<210> SEQ ID NO 1107
<211> LENGTH: 45
<212> TYPE: DNA
<213> ORGANISM: Mus sp.

<400> SEQUENCE: 1107
gtctgagatg gagtgtgggt cttcaggcac atgcatcagc tcttc 45

<210> SEQ ID NO 1108
<211> LENGTH: 45
<212> TYPE: DNA
<213> ORGANISM: Mus sp.

<400> SEQUENCE: 1108
tcttgctttg gaggttctgg gacagcaact gttctacgtc tgaga 45

<210> SEQ ID NO 1109
<211> LENGTH: 45
<212> TYPE: DNA
<213> ORGANISM: Homo sapiens

<400> SEQUENCE: 1109
tgcgactcct caggtacctg catcaacccc tctaactggt gtgat 45

<210> SEQ ID NO 1110
<211> LENGTH: 45
<212> TYPE: DNA
<213> ORGANISM: Mus sp.

<400> SEQUENCE: 1110
tgctgtggct gctgtcttgc tttggaggtt ctgggacagc aactg 45

<210> SEQ ID NO 1111
<211> LENGTH: 45
<212> TYPE: DNA
<213> ORGANISM: Homo sapiens

<400> SEQUENCE: 1111
ctactctgga agttcatggg cagcaagtgc tccaactctg ggata 45

<210> SEQ ID NO 1112
<211> LENGTH: 45
<212> TYPE: DNA
<213> ORGANISM: Mus sp.

<400> SEQUENCE: 1112
gtgcacctca aagtctaaga aatcgctgtg tttagccctc gccct 45

<210> SEQ ID NO 1113
<211> LENGTH: 45
<212> TYPE: DNA
<213> ORGANISM: Mus sp.

<400> SEQUENCE: 1113
aggagcactg tgcacctcaa agtctaagaa atcgctgtgt ttagc 45

<210> SEQ ID NO 1114
<211> LENGTH: 45
<212> TYPE: DNA
<213> ORGANISM: Homo sapiens

<400> SEQUENCE: 1114
gtgcacctca aagactaaga aagcactgtg catcaccttg accct 45

<210> SEQ ID NO 1115
<211> LENGTH: 45
<212> TYPE: DNA
<213> ORGANISM: Mus sp.

<400> SEQUENCE: 1115
gattacaacg caagcctcaa catctgtcat ccacacacat cccaa 45

<210> SEQ ID NO 1116
<211> LENGTH: 45
<212> TYPE: DNA
<213> ORGANISM: Homo sapiens

<400> SEQUENCE: 1116
attgtgaaaa tgaatatcat gcaaataaat tatgcaattt ttttt 45

<210> SEQ ID NO 1117
<211> LENGTH: 45
<212> TYPE: DNA
<213> ORGANISM: Homo sapiens

<400> SEQUENCE: 1117
aattgtgaaa atgaatatca tgcaaataaa ttatgcaatt ttttt 45

<210> SEQ ID NO 1118
<211> LENGTH: 45
<212> TYPE: DNA
<213> ORGANISM: Homo sapiens

<400> SEQUENCE: 1118
ctgtaaagtt caattgtgaa aatgaatatc atgcaaataa attat 45

<210> SEQ ID NO 1119
<211> LENGTH: 45
<212> TYPE: DNA
<213> ORGANISM: Homo sapiens

<400> SEQUENCE: 1119
aactgtaaag ttcaattgtg aaaatgaata tcatgcaaat aaatt 45

<210> SEQ ID NO 1120
<211> LENGTH: 45
<212> TYPE: DNA
<213> ORGANISM: Homo sapiens

<400> SEQUENCE: 1120
ttttaaactg taaagttcaa ttgtgaaaat gaatatcatg caaat 45

<210> SEQ ID NO 1121
<211> LENGTH: 45
<212> TYPE: DNA
<213> ORGANISM: Homo sapiens

<400> SEQUENCE: 1121
tttttaaact gtaaagttca attgtgaaaa tgaatatcat gcaaa 45

<210> SEQ ID NO 1122
<211> LENGTH: 45
<212> TYPE: DNA
<213> ORGANISM: Homo sapiens

<400> SEQUENCE: 1122
gtatcttttt taaactgtaa agttcaattg tgaaaatgaa tatca 45

<210> SEQ ID NO 1123
<211> LENGTH: 45
<212> TYPE: DNA
<213> ORGANISM: Homo sapiens

<400> SEQUENCE: 1123
tttgtatctt ttttaaactg taaagttcaa ttgtgaaaat gaata 45

<210> SEQ ID NO 1124
<211> LENGTH: 45
<212> TYPE: DNA
<213> ORGANISM: Homo sapiens

<400> SEQUENCE: 1124
ttttttgtat cttttttaaa ctgtaaagtt caattgtgaa aatga 45

<210> SEQ ID NO 1125
<211> LENGTH: 45
<212> TYPE: DNA
<213> ORGANISM: Homo sapiens

<400> SEQUENCE: 1125
tttttttgta tcttttttaa actgtaaagt tcaattgtga aaatg 45

<210> SEQ ID NO 1126
<211> LENGTH: 45
<212> TYPE: DNA
<213> ORGANISM: Homo sapiens

<400> SEQUENCE: 1126
ccccttctta tttatgtgaa caactgtttg tctttttttg tatct 45

<210> SEQ ID NO 1127
<211> LENGTH: 45
<212> TYPE: DNA
<213> ORGANISM: Homo sapiens

<400> SEQUENCE: 1127
tgccccttct tatttatgtg aacaactgtt tgtctttttt tgtat 45

<210> SEQ ID NO 1128
<211> LENGTH: 45
<212> TYPE: DNA
<213> ORGANISM: Homo sapiens

<400> SEQUENCE: 1128
ttgccccttc ttatttatgt gaacaactgt ttgtcttttt ttgta 45

<210> SEQ ID NO 1129
<211> LENGTH: 45
<212> TYPE: DNA
<213> ORGANISM: Homo sapiens

<400> SEQUENCE: 1129
attgcccctt cttatttatg tgaacaactg tttgtctttt tttgt 45

<210> SEQ ID NO 1130
<211> LENGTH: 45
<212> TYPE: DNA
<213> ORGANISM: Homo sapiens

<400> SEQUENCE: 1130
ttattgcccc ttcttattta tgtgaacaac tgtttgtctt ttttt 45

<210> SEQ ID NO 1131
<211> LENGTH: 45
<212> TYPE: DNA
<213> ORGANISM: Mus sp.

<400> SEQUENCE: 1131
tgagattcca ctgtgaaata tatgaataaa gtatataatt ctttt 45

<210> SEQ ID NO 1132
<211> LENGTH: 45
<212> TYPE: DNA
<213> ORGANISM: Homo sapiens

<400> SEQUENCE: 1132
ttctttattg ccccttctta tttatgtgaa caactgtttg tcttt 45

<210> SEQ ID NO 1133
<211> LENGTH: 45
<212> TYPE: DNA
<213> ORGANISM: Homo sapiens

<400> SEQUENCE: 1133
acgtcttcct tctttattgc cccttcttat ttatgtgaac aactg 45

<210> SEQ ID NO 1134
<211> LENGTH: 45
<212> TYPE: DNA
<213> ORGANISM: Mus sp.

<400> SEQUENCE: 1134
tgttctgagc tgtgagattc cactgtgaaa tatatgaata aagta 45

<210> SEQ ID NO 1135
<211> LENGTH: 45
<212> TYPE: DNA
<213> ORGANISM: Mus sp.

<400> SEQUENCE: 1135
ctgctttgtg tctgttctga gctgtgagat tccactgtga aatat 45

<210> SEQ ID NO 1136
<211> LENGTH: 45
<212> TYPE: DNA
<213> ORGANISM: Mus sp.

<400> SEQUENCE: 1136
ggttatttcc tgctttgtgt ctgttctgag ctgtgagatt ccact 45

<210> SEQ ID NO 1137
<211> LENGTH: 45
<212> TYPE: DNA
<213> ORGANISM: Homo sapiens

<400> SEQUENCE: 1137
tcctaaaagg tgttgtaatg gtgaaaacgt cttccttctt tattg 45

<210> SEQ ID NO 1138
<211> LENGTH: 45
<212> TYPE: DNA
<213> ORGANISM: Homo sapiens

<400> SEQUENCE: 1138
atcctaaaag gtgttgtaat ggtgaaaacg tcttccttct ttatt 45

<210> SEQ ID NO 1139
<211> LENGTH: 45
<212> TYPE: DNA
<213> ORGANISM: Mus sp.

<400> SEQUENCE: 1139
gttggttggt tatttcctgc tttgtgtctg ttctgagctg tgaga 45

<210> SEQ ID NO 1140
<211> LENGTH: 45
<212> TYPE: DNA
<213> ORGANISM: Mus sp.

<400> SEQUENCE: 1140
tgtctttgct gttggttggt tatttcctgc tttgtgtctg ttctg 45

<210> SEQ ID NO 1141
<211> LENGTH: 45
<212> TYPE: DNA
<213> ORGANISM: Homo sapiens

<400> SEQUENCE: 1141
cttgctcccc aagacacatc ctaaaaggtg ttgtaatggt gaaaa 45

<210> SEQ ID NO 1142
<211> LENGTH: 45
<212> TYPE: DNA
<213> ORGANISM: Homo sapiens

<400> SEQUENCE: 1142
atttgcagga tctgtctgtg cacatgcctc tgtagagagc agcat 45

<210> SEQ ID NO 1143
<211> LENGTH: 45
<212> TYPE: DNA
<213> ORGANISM: Mus sp.

<400> SEQUENCE: 1143
gggaccttct tagatgctgt aaggtaccta catacagact aaatg 45

<210> SEQ ID NO 1144
<211> LENGTH: 45
<212> TYPE: DNA
<213> ORGANISM: Homo sapiens

<400> SEQUENCE: 1144
agtcatgcaa tcccatttgc aggatctgtc tgtgcacatg cctct 45

<210> SEQ ID NO 1145
<211> LENGTH: 45
<212> TYPE: DNA
<213> ORGANISM: Homo sapiens

<400> SEQUENCE: 1145
aatggaaagt catgcaatcc catttgcagg atctgtctgt gcaca 45

<210> SEQ ID NO 1146
<211> LENGTH: 45
<212> TYPE: DNA
<213> ORGANISM: Mus sp.

<400> SEQUENCE: 1146
cctcatgcgt cctctgggac cttcttagat gctgtaaggt accta 45

<210> SEQ ID NO 1147
<211> LENGTH: 45
<212> TYPE: DNA
<213> ORGANISM: Mus sp.

<400> SEQUENCE: 1147
ccctcatgcg tcctctggga ccttcttaga tgctgtaagg tacct 45

<210> SEQ ID NO 1148
<211> LENGTH: 45
<212> TYPE: DNA
<213> ORGANISM: Homo sapiens

<400> SEQUENCE: 1148
gacttaacct tgaaatggaa agtcatgcaa tcccatttgc aggat 45

<210> SEQ ID NO 1149
<211> LENGTH: 45
<212> TYPE: DNA
<213> ORGANISM: Homo sapiens

<400> SEQUENCE: 1149
acagctagga cttaaccttg aaatggaaag tcatgcaatc ccatt 45

<210> SEQ ID NO 1150
<211> LENGTH: 45
<212> TYPE: DNA
<213> ORGANISM: Homo sapiens

<400> SEQUENCE: 1150
tgaaatgaat gattctacag ctaggactta accttgaaat ggaaa 45

<210> SEQ ID NO 1151
<211> LENGTH: 45
<212> TYPE: DNA
<213> ORGANISM: Homo sapiens

<400> SEQUENCE: 1151
gaatgaaatg aatgattcta cagctaggac ttaaccttga aatgg 45

<210> SEQ ID NO 1152
<211> LENGTH: 45
<212> TYPE: DNA
<213> ORGANISM: Homo sapiens

<400> SEQUENCE: 1152
tttgcaagaa tgaaatgaat gattctacag ctaggactta acctt 45

<210> SEQ ID NO 1153
<211> LENGTH: 45
<212> TYPE: DNA
<213> ORGANISM: Homo sapiens

<400> SEQUENCE: 1153
tggccaagca ggctggtttg caagaatgaa atgaatgatt ctaca 45

<210> SEQ ID NO 1154
<211> LENGTH: 45
<212> TYPE: DNA
<213> ORGANISM: Homo sapiens

<400> SEQUENCE: 1154
ggttctgcct cctggccaag caggctggtt tgcaagaatg aaatg 45

<210> SEQ ID NO 1155
<211> LENGTH: 45
<212> TYPE: DNA
<213> ORGANISM: Mus sp.

<400> SEQUENCE: 1155
tcagaaggca gtgaatgggt cataactggg actccatctt tgctg 45

<210> SEQ ID NO 1156
<211> LENGTH: 45
<212> TYPE: DNA
<213> ORGANISM: Mus sp.

<400> SEQUENCE: 1156
agccatgcca gaattaccaa atatgaagta tgaatgtctt accca 45

<210> SEQ ID NO 1157
<211> LENGTH: 45
<212> TYPE: DNA
<213> ORGANISM: Mus sp.

<400> SEQUENCE: 1157
gaaagccatg ccagaattac caaatatgaa gtatgaatgt cttac 45

<210> SEQ ID NO 1158
<211> LENGTH: 45
<212> TYPE: DNA
<213> ORGANISM: Homo sapiens

<400> SEQUENCE: 1158
ttgttttgga ctctctgtgg tcccttccaa tgctgtgggt ttcca 45

<210> SEQ ID NO 1159
<211> LENGTH: 45
<212> TYPE: DNA
<213> ORGANISM: Mus sp.

<400> SEQUENCE: 1159
taccaggaaa gccatgccag aattaccaaa tatgaagtat gaatg 45

<210> SEQ ID NO 1160
<211> LENGTH: 45
<212> TYPE: DNA
<213> ORGANISM: Mus sp.

<400> SEQUENCE: 1160
ataccaggaa agccatgcca gaattaccaa atatgaagta tgaat 45

<210> SEQ ID NO 1161
<211> LENGTH: 45
<212> TYPE: DNA
<213> ORGANISM: Mus sp.

<400> SEQUENCE: 1161
ttataccagg aaagccatgc cagaattacc aaatatgaag tatga 45

<210> SEQ ID NO 1162
<211> LENGTH: 45
<212> TYPE: DNA

<213> ORGANISM: Mus sp.

<400> SEQUENCE: 1162
tgggtttata ccaggaaagc catgccagaa ttaccaaata tgaag 45

<210> SEQ ID NO 1163
<211> LENGTH: 45
<212> TYPE: DNA
<213> ORGANISM: Mus sp.

<400> SEQUENCE: 1163
ttctggccct gggtttatac caggaaagcc atgccagaat tacca 45

<210> SEQ ID NO 1164
<211> LENGTH: 45
<212> TYPE: DNA
<213> ORGANISM: Homo sapiens

<400> SEQUENCE: 1164
gcccatggtg gcggcgaaga agagaaagat gtgttttgtt ttgga 45

<210> SEQ ID NO 1165
<211> LENGTH: 45
<212> TYPE: DNA
<213> ORGANISM: Homo sapiens

<400> SEQUENCE: 1165
aagtgcccat ggtggcggcg aagaagagaa agatgtgttt tgttt 45

<210> SEQ ID NO 1166
<211> LENGTH: 45
<212> TYPE: DNA
<213> ORGANISM: Mus sp.

<400> SEQUENCE: 1166
tcagataaag atgaaagaga ggagatcatt gtcttctgtc ttctt 45

<210> SEQ ID NO 1167
<211> LENGTH: 45
<212> TYPE: DNA
<213> ORGANISM: Mus sp.

<400> SEQUENCE: 1167
tagaagttcc tagcttcaga taaagatgaa agagaggaga tcatt 45

<210> SEQ ID NO 1168
<211> LENGTH: 45
<212> TYPE: DNA
<213> ORGANISM: Mus sp.

<400> SEQUENCE: 1168
atgagattag aagttcctag cttcagataa agatgaaaga gagga 45

<210> SEQ ID NO 1169
<211> LENGTH: 45
<212> TYPE: DNA
<213> ORGANISM: Homo sapiens

<400> SEQUENCE: 1169
tgacaaaatg actggctcct gacttaacgt tctataaatg aatgt 45

<210> SEQ ID NO 1170
<211> LENGTH: 45

<212> TYPE: DNA
<213> ORGANISM: Homo sapiens

<400> SEQUENCE: 1170
ttgacaaaat gactggctcc tgacttaacg ttctataaat gaatg 45

<210> SEQ ID NO 1171
<211> LENGTH: 45
<212> TYPE: DNA
<213> ORGANISM: Homo sapiens

<400> SEQUENCE: 1171
tttgacaaaa tgactggctc ctgacttaac gttctataaa tgaat 45

<210> SEQ ID NO 1172
<211> LENGTH: 45
<212> TYPE: DNA
<213> ORGANISM: Mus sp.

<400> SEQUENCE: 1172
tagactggca atgagattag aagttcctag cttcagataa agatg 45

<210> SEQ ID NO 1173
<211> LENGTH: 45
<212> TYPE: DNA
<213> ORGANISM: Mus sp.

<400> SEQUENCE: 1173
gttctgtaga ctggcaatga gattagaagt tcctagcttc agata 45

<210> SEQ ID NO 1174
<211> LENGTH: 45
<212> TYPE: DNA
<213> ORGANISM: Mus sp.

<400> SEQUENCE: 1174
ttgttctgta gactggcaat gagattagaa gttcctagct tcaga 45

<210> SEQ ID NO 1175
<211> LENGTH: 45
<212> TYPE: DNA
<213> ORGANISM: Homo sapiens

<400> SEQUENCE: 1175
ctatttcagc tgctttgaca aaatgactgg ctcctgactt aacgt 45

<210> SEQ ID NO 1176
<211> LENGTH: 45
<212> TYPE: DNA
<213> ORGANISM: Homo sapiens

<400> SEQUENCE: 1176
gcctatttca gctgctttga caaaatgact ggctcctgac ttaac 45

<210> SEQ ID NO 1177
<211> LENGTH: 45
<212> TYPE: DNA
<213> ORGANISM: Mus sp.

<400> SEQUENCE: 1177
cctcttccag atggttaggt tgttctgtag actggcaatg agatt 45

<210> SEQ ID NO 1178

<211> LENGTH: 45
<212> TYPE: DNA
<213> ORGANISM: Mus sp.

<400> SEQUENCE: 1178
acctcttcca gatggttagg ttgttctgta gactggcaat gagat 45

<210> SEQ ID NO 1179
<211> LENGTH: 45
<212> TYPE: DNA
<213> ORGANISM: Mus sp.

<400> SEQUENCE: 1179
cagacactag acctcttcca gatggttagg ttgttctgta gactg 45

<210> SEQ ID NO 1180
<211> LENGTH: 45
<212> TYPE: DNA
<213> ORGANISM: Homo sapiens

<400> SEQUENCE: 1180
actctttgaa actgtatcat ctttgccaag taagagtggt ggcct 45

<210> SEQ ID NO 1181
<211> LENGTH: 45
<212> TYPE: DNA
<213> ORGANISM: Mus sp.

<400> SEQUENCE: 1181
ctgtgtgatt gtgcctcaga cactagacct cttccagatg gttag 45

<210> SEQ ID NO 1182
<211> LENGTH: 45
<212> TYPE: DNA
<213> ORGANISM: Homo sapiens

<400> SEQUENCE: 1182
cttcatttaa ctctttgaaa ctgtatcatc tttgccaagt aagag 45

<210> SEQ ID NO 1183
<211> LENGTH: 45
<212> TYPE: DNA
<213> ORGANISM: Homo sapiens

<400> SEQUENCE: 1183
accttcattt aactctttga aactgtatca tctttgccaa gtaag 45

<210> SEQ ID NO 1184
<211> LENGTH: 45
<212> TYPE: DNA
<213> ORGANISM: Homo sapiens

<400> SEQUENCE: 1184
agtccacctt catttaactc tttgaaactg tatcatcttt gccaa 45

<210> SEQ ID NO 1185
<211> LENGTH: 45
<212> TYPE: DNA
<213> ORGANISM: Mus sp.

<400> SEQUENCE: 1185
ggagttcacc tgcatttgga ctgtgtgatt gtgcctcaga cacta 45

<210> SEQ ID NO 1186
<211> LENGTH: 45
<212> TYPE: DNA
<213> ORGANISM: Homo sapiens

<400> SEQUENCE: 1186
atgtctccaa gtagtccacc ttcatttaac tctttgaaac tgtat 45

<210> SEQ ID NO 1187
<211> LENGTH: 45
<212> TYPE: DNA
<213> ORGANISM: Homo sapiens

<400> SEQUENCE: 1187
tttgatgtct ccaagtagtc caccttcatt taactctttg aaact 45

<210> SEQ ID NO 1188
<211> LENGTH: 45
<212> TYPE: DNA
<213> ORGANISM: Homo sapiens

<400> SEQUENCE: 1188
cctggaaact tagcttttga tgtctccaag tagtccacct tcatt 45

<210> SEQ ID NO 1189
<211> LENGTH: 45
<212> TYPE: DNA
<213> ORGANISM: Homo sapiens

<400> SEQUENCE: 1189
agtgctcctg gaaacttagc ttttgatgtc tccaagtagt ccacc 45

<210> SEQ ID NO 1190
<211> LENGTH: 45
<212> TYPE: DNA
<213> ORGANISM: Homo sapiens

<400> SEQUENCE: 1190
tgctacctca gtgctcctgg aaacttagct tttgatgtct ccaag 45

<210> SEQ ID NO 1191
<211> LENGTH: 45
<212> TYPE: DNA
<213> ORGANISM: Mus sp.

<400> SEQUENCE: 1191
ttgtgtttct tctcttacta cctcactgca cctggacact agagt 45

<210> SEQ ID NO 1192
<211> LENGTH: 45
<212> TYPE: DNA
<213> ORGANISM: Mus sp.

<400> SEQUENCE: 1192
ttcagtcacc ttgcttctgg gttgtgtttc ttctcttact acctc 45

<210> SEQ ID NO 1193
<211> LENGTH: 45
<212> TYPE: DNA
<213> ORGANISM: Homo sapiens

<400> SEQUENCE: 1193
gtttaaggta cactgtttcc atgttatgtt tctacacatt gctac 45

```
<210> SEQ ID NO 1194
<211> LENGTH: 45
<212> TYPE: DNA
<213> ORGANISM: Homo sapiens

<400> SEQUENCE: 1194

atgctcagtt taaggtacac tgtttccatg ttatgtttct acaca            45

<210> SEQ ID NO 1195
<211> LENGTH: 45
<212> TYPE: DNA
<213> ORGANISM: Homo sapiens

<400> SEQUENCE: 1195

aatcaaggat gctcagttta aggtacactg tttccatgtt atgtt            45

<210> SEQ ID NO 1196
<211> LENGTH: 45
<212> TYPE: DNA
<213> ORGANISM: Homo sapiens

<400> SEQUENCE: 1196

aaatcaagga tgctcagttt aaggtacact gtttccatgt tatgt            45

<210> SEQ ID NO 1197
<211> LENGTH: 45
<212> TYPE: DNA
<213> ORGANISM: Mus sp.

<400> SEQUENCE: 1197

tggaggctca ggtccatcag aatcagggac ttgtgatttc agtca            45

<210> SEQ ID NO 1198
<211> LENGTH: 45
<212> TYPE: DNA
<213> ORGANISM: Homo sapiens

<400> SEQUENCE: 1198

aaattgaggt ccatggggga aatcaaggat gctcagttta aggta            45

<210> SEQ ID NO 1199
<211> LENGTH: 45
<212> TYPE: DNA
<213> ORGANISM: Mus sp.

<400> SEQUENCE: 1199

atcaaatgga ggctcaggtc catcagaatc agggacttgt gattt            45

<210> SEQ ID NO 1200
<211> LENGTH: 45
<212> TYPE: DNA
<213> ORGANISM: Mus sp.

<400> SEQUENCE: 1200

taatcaaatg gaggctcagg tccatcagaa tcagggactt gtgat            45

<210> SEQ ID NO 1201
<211> LENGTH: 45
<212> TYPE: DNA
<213> ORGANISM: Mus sp.

<400> SEQUENCE: 1201

tggcctagta cctgatggag cctgtatagc tcagctaatc aaatg            45
```

<210> SEQ ID NO 1202
<211> LENGTH: 45
<212> TYPE: DNA
<213> ORGANISM: Mus sp.

<400> SEQUENCE: 1202
ctcttagctt tggctacagg catggcctag tacctgatgg agcct 45

<210> SEQ ID NO 1203
<211> LENGTH: 45
<212> TYPE: DNA
<213> ORGANISM: Mus sp.

<400> SEQUENCE: 1203
ctcagcctct cagagcctga aacttacctc ttagctttgg ctaca 45

<210> SEQ ID NO 1204
<211> LENGTH: 45
<212> TYPE: DNA
<213> ORGANISM: Mus sp.

<400> SEQUENCE: 1204
ctgtttctct cagcctctca gagcctgaaa cttacctctt agctt 45

<210> SEQ ID NO 1205
<211> LENGTH: 45
<212> TYPE: DNA
<213> ORGANISM: Mus sp.

<400> SEQUENCE: 1205
tgccggcatg tcccttgggt gagctctaca tggtgttatt cagtc 45

<210> SEQ ID NO 1206
<211> LENGTH: 45
<212> TYPE: DNA
<213> ORGANISM: Mus sp.

<400> SEQUENCE: 1206
ctaggcagat ctctcagagc aagaagctaa tgccggcatg tccct 45

<210> SEQ ID NO 1207
<211> LENGTH: 45
<212> TYPE: DNA
<213> ORGANISM: Mus sp.

<400> SEQUENCE: 1207
agggtgatgg aggctttccc aagctaaggg cctaggcaga tctct 45

<210> SEQ ID NO 1208
<211> LENGTH: 45
<212> TYPE: DNA
<213> ORGANISM: Homo sapiens

<400> SEQUENCE: 1208
ttatggggtg agaatataga cagtgccctt ggtgcgaggg aagca 45

<210> SEQ ID NO 1209
<211> LENGTH: 45
<212> TYPE: DNA
<213> ORGANISM: Homo sapiens

<400> SEQUENCE: 1209
cagcccttca tgggtggtga cgtggtagtc acttgtaagg ggaac    45

<210> SEQ ID NO 1210
<211> LENGTH: 45
<212> TYPE: DNA
<213> ORGANISM: Mus sp.

<400> SEQUENCE: 1210
atctgctgtg caggttgggc tggtcatact gtcatgattt catta    45

<210> SEQ ID NO 1211
<211> LENGTH: 45
<212> TYPE: DNA
<213> ORGANISM: Mus sp.

<400> SEQUENCE: 1211
aaatctgctg tgcaggttgg gctggtcata ctgtcatgat ttcat    45

<210> SEQ ID NO 1212
<211> LENGTH: 45
<212> TYPE: DNA
<213> ORGANISM: Mus sp.

<400> SEQUENCE: 1212
aaggactatg acctctgagt aacctgatga cctgagaaag agtaa    45

<210> SEQ ID NO 1213
<211> LENGTH: 45
<212> TYPE: DNA
<213> ORGANISM: Mus sp.

<400> SEQUENCE: 1213
atcactaagg actatgacct ctgagtaacc tgatgacctg agaaa    45

<210> SEQ ID NO 1214
<211> LENGTH: 45
<212> TYPE: DNA
<213> ORGANISM: Mus sp.

<400> SEQUENCE: 1214
tgctcaggcc ttttttggat cactaaggac tatgacctct gagta    45

<210> SEQ ID NO 1215
<211> LENGTH: 45
<212> TYPE: DNA
<213> ORGANISM: Mus sp.

<400> SEQUENCE: 1215
atgctcaggc cttttttgga tcactaagga ctatgacctc tgagt    45

<210> SEQ ID NO 1216
<211> LENGTH: 45
<212> TYPE: DNA
<213> ORGANISM: Mus sp.

<400> SEQUENCE: 1216
gcagaggagg gtggcactct catgttggaa cttcttttgg gctca    45

<210> SEQ ID NO 1217
<211> LENGTH: 45
<212> TYPE: DNA
<213> ORGANISM: Homo sapiens

<400> SEQUENCE: 1217
tcttcctgct gagtcctttc caggggccaa ttttggatga gcatg 45

<210> SEQ ID NO 1218
<211> LENGTH: 45
<212> TYPE: DNA
<213> ORGANISM: Homo sapiens

<400> SEQUENCE: 1218
tttgaactca gggtcaccac cagctattgg accttactat gaaaa 45

<210> SEQ ID NO 1219
<211> LENGTH: 45
<212> TYPE: DNA
<213> ORGANISM: Homo sapiens

<400> SEQUENCE: 1219
gagaggggtg gaggctgccc cattgagatc ttcctgctga gtcct 45

<210> SEQ ID NO 1220
<211> LENGTH: 45
<212> TYPE: DNA
<213> ORGANISM: Mus sp.

<400> SEQUENCE: 1220
gctcccacca gaatggatga ccagattctg ttgggtttgg gcaca 45

<210> SEQ ID NO 1221
<211> LENGTH: 45
<212> TYPE: DNA
<213> ORGANISM: Mus sp.

<400> SEQUENCE: 1221
gccacttctg cagctcccac cagaatggat gaccagattc tgttg 45

<210> SEQ ID NO 1222
<211> LENGTH: 45
<212> TYPE: DNA
<213> ORGANISM: Mus sp.

<400> SEQUENCE: 1222
tgattcgaag ggcctttcac ttttattaaa cagtgacttg tttga 45

<210> SEQ ID NO 1223
<211> LENGTH: 45
<212> TYPE: DNA
<213> ORGANISM: Mus sp.

<400> SEQUENCE: 1223
atgattcgaa gggcctttca cttttattaa acagtgactt gtttg 45

<210> SEQ ID NO 1224
<211> LENGTH: 45
<212> TYPE: DNA
<213> ORGANISM: Mus sp.

<400> SEQUENCE: 1224
ccttttgaga tgattcgaag ggcctttcac ttttattaaa cagtg 45

<210> SEQ ID NO 1225
<211> LENGTH: 45
<212> TYPE: DNA
<213> ORGANISM: Mus sp.

<400> SEQUENCE: 1225
gtgcacaatg tacctttga gatgattcga agggcctttc acttt 45

<210> SEQ ID NO 1226
<211> LENGTH: 45
<212> TYPE: DNA
<213> ORGANISM: Mus sp.

<400> SEQUENCE: 1226
acttcctgtg cacaatgtac cttttgagat gattcgaagg gcctt 45

<210> SEQ ID NO 1227
<211> LENGTH: 45
<212> TYPE: DNA
<213> ORGANISM: Mus sp.

<400> SEQUENCE: 1227
gaattttaac ttcctgtgca caatgtacct tttgagatga ttcga 45

<210> SEQ ID NO 1228
<211> LENGTH: 45
<212> TYPE: DNA
<213> ORGANISM: Mus sp.

<400> SEQUENCE: 1228
ctgaatttta acttcctgtg cacaatgtac cttttgagat gattc 45

<210> SEQ ID NO 1229
<211> LENGTH: 45
<212> TYPE: DNA
<213> ORGANISM: Mus sp.

<400> SEQUENCE: 1229
caagaaaacc aagggcctga attttaactt cctgtgcaca atgta 45

<210> SEQ ID NO 1230
<211> LENGTH: 45
<212> TYPE: DNA
<213> ORGANISM: Homo sapiens

<400> SEQUENCE: 1230
tcacttcatt tttattaaac agtgaacttg tctggctttg gcact 45

<210> SEQ ID NO 1231
<211> LENGTH: 45
<212> TYPE: DNA
<213> ORGANISM: Homo sapiens

<400> SEQUENCE: 1231
gtcacttcat ttttattaaa cagtgaactt gtctggcttt ggcac 45

<210> SEQ ID NO 1232
<211> LENGTH: 45
<212> TYPE: DNA
<213> ORGANISM: Mus sp.

<400> SEQUENCE: 1232
tctgcaagaa aaccaagggc ctgaatttta acttcctgtg cacaa 45

<210> SEQ ID NO 1233
<211> LENGTH: 45
<212> TYPE: DNA
<213> ORGANISM: Mus sp.

<400> SEQUENCE: 1233
ttctgcaaga aaaccaaggg cctgaatttt aacttcctgt gcaca 45

<210> SEQ ID NO 1234
<211> LENGTH: 45
<212> TYPE: DNA
<213> ORGANISM: Mus sp.

<400> SEQUENCE: 1234
ttcaacaacc ttctgcaaga aaaccaaggg cctgaatttt aactt 45

<210> SEQ ID NO 1235
<211> LENGTH: 45
<212> TYPE: DNA
<213> ORGANISM: Mus sp.

<400> SEQUENCE: 1235
tcttcaacaa ccttctgcaa gaaaaccaag ggcctgaatt ttaac 45

<210> SEQ ID NO 1236
<211> LENGTH: 45
<212> TYPE: DNA
<213> ORGANISM: Mus sp.

<400> SEQUENCE: 1236
gtcttcaaca accttctgca agaaaaccaa gggcctgaat tttaa 45

<210> SEQ ID NO 1237
<211> LENGTH: 45
<212> TYPE: DNA
<213> ORGANISM: Mus sp.

<400> SEQUENCE: 1237
ttgtcttcaa caaccttctg caagaaaacc aagggcctga atttt 45

<210> SEQ ID NO 1238
<211> LENGTH: 45
<212> TYPE: DNA
<213> ORGANISM: Homo sapiens

<400> SEQUENCE: 1238
ttactcttag agatgattca gaggtcactt catttttatt aaaca 45

<210> SEQ ID NO 1239
<211> LENGTH: 45
<212> TYPE: DNA
<213> ORGANISM: Homo sapiens

<400> SEQUENCE: 1239
atttactctt agagatgatt cagaggtcac ttcattttta ttaaa 45

<210> SEQ ID NO 1240
<211> LENGTH: 45
<212> TYPE: DNA
<213> ORGANISM: Homo sapiens

<400> SEQUENCE: 1240
gtgcatgatt tactcttaga gatgattcag aggtcacttc atttt 45

<210> SEQ ID NO 1241
<211> LENGTH: 45
<212> TYPE: DNA

<213> ORGANISM: Homo sapiens

<400> SEQUENCE: 1241
cttccccgtg catgatttac tcttagagat gattcagagg tcact 45

<210> SEQ ID NO 1242
<211> LENGTH: 45
<212> TYPE: DNA
<213> ORGANISM: Mus sp.

<400> SEQUENCE: 1242
taatccacgt ggctttgtcc cagacttcct ttgtcttcaa caacc 45

<210> SEQ ID NO 1243
<211> LENGTH: 45
<212> TYPE: DNA
<213> ORGANISM: Homo sapiens

<400> SEQUENCE: 1243
gctggttttg cttccccgtg catgatttac tcttagagat gattc 45

<210> SEQ ID NO 1244
<211> LENGTH: 45
<212> TYPE: DNA
<213> ORGANISM: Mus sp.

<400> SEQUENCE: 1244
acagctaatc cacgtggctt tgtcccagac ttcctttgtc ttcaa 45

<210> SEQ ID NO 1245
<211> LENGTH: 45
<212> TYPE: DNA
<213> ORGANISM: Homo sapiens

<400> SEQUENCE: 1245
tggggctggt tttgcttccc cgtgcatgat ttactcttag agatg 45

<210> SEQ ID NO 1246
<211> LENGTH: 45
<212> TYPE: DNA
<213> ORGANISM: Homo sapiens

<400> SEQUENCE: 1246
gtccttgacg tcgttttaca agaaaacaat ggggctggtt ttgct 45

<210> SEQ ID NO 1247
<211> LENGTH: 45
<212> TYPE: DNA
<213> ORGANISM: Homo sapiens

<400> SEQUENCE: 1247
cgtccttgac gtcgttttac aagaaaacaa tggggctggt tttgc 45

<210> SEQ ID NO 1248
<211> LENGTH: 45
<212> TYPE: DNA
<213> ORGANISM: Homo sapiens

<400> SEQUENCE: 1248
tcgtccttga cgtcgtttta caagaaaaca atggggctgg ttttg 45

<210> SEQ ID NO 1249
<211> LENGTH: 45

<212> TYPE: DNA
<213> ORGANISM: Homo sapiens

<400> SEQUENCE: 1249
ctaatccaca tggtcttcgt ccttgacgtc gttttacaag aaaac 45

<210> SEQ ID NO 1250
<211> LENGTH: 45
<212> TYPE: DNA
<213> ORGANISM: Mus sp.

<400> SEQUENCE: 1250
gtatacggga acgtgacggt atttacagat tggatctacc agcaa 45

<210> SEQ ID NO 1251
<211> LENGTH: 45
<212> TYPE: DNA
<213> ORGANISM: Mus sp.

<400> SEQUENCE: 1251
agtatacggg aacgtgacgg tatttacaga ttggatctac cagca 45

<210> SEQ ID NO 1252
<211> LENGTH: 45
<212> TYPE: DNA
<213> ORGANISM: Mus sp.

<400> SEQUENCE: 1252
tcagacctgg agtatacggg aacgtgacgg tatttacaga ttgga 45

<210> SEQ ID NO 1253
<211> LENGTH: 45
<212> TYPE: DNA
<213> ORGANISM: Homo sapiens

<400> SEQUENCE: 1253
gtgtacggga atgtgatggt attcacggac tggatttatc gacaa 45

<210> SEQ ID NO 1254
<211> LENGTH: 45
<212> TYPE: DNA
<213> ORGANISM: Homo sapiens

<400> SEQUENCE: 1254
agtgtacggg aatgtgatgg tattcacgga ctggatttat cgaca 45

<210> SEQ ID NO 1255
<211> LENGTH: 45
<212> TYPE: DNA
<213> ORGANISM: Homo sapiens

<400> SEQUENCE: 1255
agaccaggag tgtacgggaa tgtgatggta ttcacggact ggatt 45

<210> SEQ ID NO 1256
<211> LENGTH: 45
<212> TYPE: DNA
<213> ORGANISM: Homo sapiens

<400> SEQUENCE: 1256
acagaccagg agtgtacggg aatgtgatgg tattcacgga ctgga 45

<210> SEQ ID NO 1257

<211> LENGTH: 45
<212> TYPE: DNA
<213> ORGANISM: Homo sapiens

<400> SEQUENCE: 1257
tcattactcg atgctgttga taacagcaag atggctttga actca 45

<210> SEQ ID NO 1258
<211> LENGTH: 45
<212> TYPE: DNA
<213> ORGANISM: Homo sapiens

<400> SEQUENCE: 1258
tatcattact cgatgctgtt gataacagca agatggcttt gaact 45

<210> SEQ ID NO 1259
<211> LENGTH: 45
<212> TYPE: DNA
<213> ORGANISM: Homo sapiens

<400> SEQUENCE: 1259
gatacaagct ggggttctgg ctgtgccaaa gcttacagac cagga 45

<210> SEQ ID NO 1260
<211> LENGTH: 45
<212> TYPE: DNA
<213> ORGANISM: Mus sp.

<400> SEQUENCE: 1260
cagtggaggg ccgctggtta ctttgaagaa tgggatctgg tggct 45

<210> SEQ ID NO 1261
<211> LENGTH: 45
<212> TYPE: DNA
<213> ORGANISM: Mus sp.

<400> SEQUENCE: 1261
atcgagccct ccaaatgtaa tagtaaatac atatacaaca accta 45

<210> SEQ ID NO 1262
<211> LENGTH: 45
<212> TYPE: DNA
<213> ORGANISM: Mus sp.

<400> SEQUENCE: 1262
ccttgatcga gccctccaaa tgtaatagta aatacatata caaca 45

<210> SEQ ID NO 1263
<211> LENGTH: 45
<212> TYPE: DNA
<213> ORGANISM: Mus sp.

<400> SEQUENCE: 1263
acccttgatc gagccctcca aatgtaatag taaatacata tacaa 45

<210> SEQ ID NO 1264
<211> LENGTH: 45
<212> TYPE: DNA
<213> ORGANISM: Mus sp.

<400> SEQUENCE: 1264
catggtaccc ttgatcgagc cctccaaatg taatagtaaa tacat 45

<210> SEQ ID NO 1265
<211> LENGTH: 45
<212> TYPE: DNA
<213> ORGANISM: Mus sp.

<400> SEQUENCE: 1265
tgccatggta cccttgatcg agccctccaa atgtaatagt aaata 45

<210> SEQ ID NO 1266
<211> LENGTH: 45
<212> TYPE: DNA
<213> ORGANISM: Homo sapiens

<400> SEQUENCE: 1266
gatgcaacag cagatatgtc tatgacaacc tgatcacacc agcca 45

<210> SEQ ID NO 1267
<211> LENGTH: 45
<212> TYPE: DNA
<213> ORGANISM: Mus sp.

<400> SEQUENCE: 1267
gagaaaggga agacctcgga cgtgttgaat gctgccatgg taccc 45

<210> SEQ ID NO 1268
<211> LENGTH: 45
<212> TYPE: DNA
<213> ORGANISM: Homo sapiens

<400> SEQUENCE: 1268
gagacacaga gatgcaacag cagatatgtc tatgacaacc tgatc 45

<210> SEQ ID NO 1269
<211> LENGTH: 45
<212> TYPE: DNA
<213> ORGANISM: Mus sp.

<400> SEQUENCE: 1269
tgagaaaggg aagacctcgg acgtgttgaa tgctgccatg gtacc 45

<210> SEQ ID NO 1270
<211> LENGTH: 45
<212> TYPE: DNA
<213> ORGANISM: Homo sapiens

<400> SEQUENCE: 1270
ctcattgaga cacagagatg caacagcaga tatgtctatg acaac 45

<210> SEQ ID NO 1271
<211> LENGTH: 45
<212> TYPE: DNA
<213> ORGANISM: Mus sp.

<400> SEQUENCE: 1271
gtggggggcc acctatgaga aagggaagac ctcggacgtg ttgaa 45

<210> SEQ ID NO 1272
<211> LENGTH: 45
<212> TYPE: DNA
<213> ORGANISM: Homo sapiens

<400> SEQUENCE: 1272
tattgaacat tccagatacc tatcattact cgatgctgtt gataa 45

<210> SEQ ID NO 1273
<211> LENGTH: 45
<212> TYPE: DNA
<213> ORGANISM: Homo sapiens

<400> SEQUENCE: 1273
gagaaaggga agacctcaga agtgctgaac gctgccaagg tgctt 45

<210> SEQ ID NO 1274
<211> LENGTH: 45
<212> TYPE: DNA
<213> ORGANISM: Homo sapiens

<400> SEQUENCE: 1274
ggagaaaggg aagacctcag aagtgctgaa cgctgccaag gtgct 45

<210> SEQ ID NO 1275
<211> LENGTH: 45
<212> TYPE: DNA
<213> ORGANISM: Homo sapiens

<400> SEQUENCE: 1275
gtcatattga acattccaga tacctatcat tactcgatgc tgttg 45

<210> SEQ ID NO 1276
<211> LENGTH: 45
<212> TYPE: DNA
<213> ORGANISM: Homo sapiens

<400> SEQUENCE: 1276
ggtcatattg aacattccag atacctatca ttactcgatg ctgtt 45

<210> SEQ ID NO 1277
<211> LENGTH: 45
<212> TYPE: DNA
<213> ORGANISM: Mus sp.

<400> SEQUENCE: 1277
aagctgcaga cacctttggc ttttaatgat ctagtgaagc cagtg 45

<210> SEQ ID NO 1278
<211> LENGTH: 45
<212> TYPE: DNA
<213> ORGANISM: Mus sp.

<400> SEQUENCE: 1278
acgacattgc tctcatgaag ctgcagacac ctttggcttt taatg 45

<210> SEQ ID NO 1279
<211> LENGTH: 45
<212> TYPE: DNA
<213> ORGANISM: Mus sp.

<400> SEQUENCE: 1279
tctaagacca agaataacga cattgctctc atgaagctgc agaca 45

<210> SEQ ID NO 1280
<211> LENGTH: 45
<212> TYPE: DNA
<213> ORGANISM: Homo sapiens

<400> SEQUENCE: 1280
tgcgctgatg aagctgcaga agcctctgac tttcaacgac ctagt 45

<210> SEQ ID NO 1281
<211> LENGTH: 45
<212> TYPE: DNA
<213> ORGANISM: Mus sp.

<400> SEQUENCE: 1281
ggtagaaaaa gtaatttccc atccaaatta cgactctaag accaa 45

<210> SEQ ID NO 1282
<211> LENGTH: 45
<212> TYPE: DNA
<213> ORGANISM: Mus sp.

<400> SEQUENCE: 1282
tctctcatgt tctatggaag tagacaccag gtagaaaaag taatt 45

<210> SEQ ID NO 1283
<211> LENGTH: 45
<212> TYPE: DNA
<213> ORGANISM: Mus sp.

<400> SEQUENCE: 1283
gtctctcatg ttctatggaa gtagacacca ggtagaaaaa gtaat 45

<210> SEQ ID NO 1284
<211> LENGTH: 45
<212> TYPE: DNA
<213> ORGANISM: Mus sp.

<400> SEQUENCE: 1284
tgagacagtc tctcatgttc tatggaagta gacaccaggt agaaa 45

<210> SEQ ID NO 1285
<211> LENGTH: 45
<212> TYPE: DNA
<213> ORGANISM: Homo sapiens

<400> SEQUENCE: 1285
atttctcatc caaattatga ctccaagacc aagaacaatg acatt 45

<210> SEQ ID NO 1286
<211> LENGTH: 45
<212> TYPE: DNA
<213> ORGANISM: Homo sapiens

<400> SEQUENCE: 1286
agtagaaaaa gtgatttctc atccaaatta tgactccaag accaa 45

<210> SEQ ID NO 1287
<211> LENGTH: 45
<212> TYPE: DNA
<213> ORGANISM: Mus sp.

<400> SEQUENCE: 1287
catttgcggg aattctgaga cagtctctca tgttctatgg aagta 45

<210> SEQ ID NO 1288
<211> LENGTH: 45
<212> TYPE: DNA
<213> ORGANISM: Mus sp.

<400> SEQUENCE: 1288
gcatttgcgg gaattctgag acagtctctc atgttctatg gaagt 45

<210> SEQ ID NO 1289
<211> LENGTH: 45
<212> TYPE: DNA
<213> ORGANISM: Mus sp.

<400> SEQUENCE: 1289
gtactggacg gcatttgcgg gaattctgag acagtctctc atgtt 45

<210> SEQ ID NO 1290
<211> LENGTH: 45
<212> TYPE: DNA
<213> ORGANISM: Homo sapiens

<400> SEQUENCE: 1290
ccgcctggag cgcggcaggt catattgaac attccagata cctat 45

<210> SEQ ID NO 1291
<211> LENGTH: 45
<212> TYPE: DNA
<213> ORGANISM: Homo sapiens

<400> SEQUENCE: 1291
atttgcgggg attttgagac aatctttcat gttctatgga gccgg 45

<210> SEQ ID NO 1292
<211> LENGTH: 45
<212> TYPE: DNA
<213> ORGANISM: Homo sapiens

<400> SEQUENCE: 1292
gagcgccgcc tggagcgcgg caggtcatat tgaacattcc agata 45

<210> SEQ ID NO 1293
<211> LENGTH: 45
<212> TYPE: DNA
<213> ORGANISM: Homo sapiens

<400> SEQUENCE: 1293
acctcttaac aatccatggc attggacggc atttgcgggg atttt 45

<210> SEQ ID NO 1294
<211> LENGTH: 45
<212> TYPE: DNA
<213> ORGANISM: Homo sapiens

<400> SEQUENCE: 1294
aacctcttaa caatccatgg cattggacgg catttgcggg gattt 45

<210> SEQ ID NO 1295
<211> LENGTH: 20
<212> TYPE: RNA
<213> ORGANISM: Homo sapiens

<400> SEQUENCE: 1295
uuguauuuau auaauguaua 20

<210> SEQ ID NO 1296
<211> LENGTH: 20
<212> TYPE: RNA
<213> ORGANISM: Homo sapiens

<400> SEQUENCE: 1296
auuguauuua uauaauguau 20

<210> SEQ ID NO 1297
<211> LENGTH: 20
<212> TYPE: RNA
<213> ORGANISM: Homo sapiens

<400> SEQUENCE: 1297
uauauuguau uuauauaaug 20

<210> SEQ ID NO 1298
<211> LENGTH: 20
<212> TYPE: RNA
<213> ORGANISM: Homo sapiens

<400> SEQUENCE: 1298
uuauauugua uuuauauaau 20

<210> SEQ ID NO 1299
<211> LENGTH: 20
<212> TYPE: RNA
<213> ORGANISM: Homo sapiens

<400> SEQUENCE: 1299
aauauuuaua uuguauuuau 20

<210> SEQ ID NO 1300
<211> LENGTH: 20
<212> TYPE: RNA
<213> ORGANISM: Homo sapiens

<400> SEQUENCE: 1300
aaagaaauau uuauauugua 20

<210> SEQ ID NO 1301
<211> LENGTH: 20
<212> TYPE: RNA
<213> ORGANISM: Homo sapiens

<400> SEQUENCE: 1301
uuaaagaaau auuuauauug 20

<210> SEQ ID NO 1302
<211> LENGTH: 20
<212> TYPE: RNA
<213> ORGANISM: Homo sapiens

<400> SEQUENCE: 1302
uuuuaaagaa auauuuauau 20

<210> SEQ ID NO 1303
<211> LENGTH: 20
<212> TYPE: RNA
<213> ORGANISM: Homo sapiens

<400> SEQUENCE: 1303
ggcuaacuua uacauauuuu 20

<210> SEQ ID NO 1304
<211> LENGTH: 20
<212> TYPE: RNA
<213> ORGANISM: Homo sapiens

<400> SEQUENCE: 1304
uggcuaacuu auacauauuu 20

<210> SEQ ID NO 1305
<211> LENGTH: 20
<212> TYPE: RNA
<213> ORGANISM: Homo sapiens

<400> SEQUENCE: 1305
aaauaaaugg cuaacuuaua 20

<210> SEQ ID NO 1306
<211> LENGTH: 20
<212> TYPE: RNA
<213> ORGANISM: Homo sapiens

<400> SEQUENCE: 1306
ccucaaauaa auggcuaacu 20

<210> SEQ ID NO 1307
<211> LENGTH: 20
<212> TYPE: RNA
<213> ORGANISM: Homo sapiens

<400> SEQUENCE: 1307
accucaaaua aauggcuaac 20

<210> SEQ ID NO 1308
<211> LENGTH: 20
<212> TYPE: RNA
<213> ORGANISM: Homo sapiens

<400> SEQUENCE: 1308
uaccucaaau aaauggcuaa 20

<210> SEQ ID NO 1309
<211> LENGTH: 20
<212> TYPE: RNA
<213> ORGANISM: Homo sapiens

<400> SEQUENCE: 1309
uuaccucaaa uaaauggcua 20

<210> SEQ ID NO 1310
<211> LENGTH: 20
<212> TYPE: RNA
<213> ORGANISM: Homo sapiens

<400> SEQUENCE: 1310
cuuaccucaa auaaauggcu 20

<210> SEQ ID NO 1311
<211> LENGTH: 20
<212> TYPE: RNA
<213> ORGANISM: Homo sapiens

<400> SEQUENCE: 1311
uaggcuuacc ucaaauaaau 20

<210> SEQ ID NO 1312
<211> LENGTH: 20
<212> TYPE: RNA
<213> ORGANISM: Homo sapiens

<400> SEQUENCE: 1312
uggaaagugu aggcuuaccu 20

<210> SEQ ID NO 1313
<211> LENGTH: 20
<212> TYPE: RNA
<213> ORGANISM: Homo sapiens

<400> SEQUENCE: 1313
cuuggaaagu guaggcuuac 20

<210> SEQ ID NO 1314
<211> LENGTH: 20
<212> TYPE: RNA
<213> ORGANISM: Homo sapiens

<400> SEQUENCE: 1314
agagccagau cauuucuugg 20

<210> SEQ ID NO 1315
<211> LENGTH: 20
<212> TYPE: RNA
<213> ORGANISM: Homo sapiens

<400> SEQUENCE: 1315
guuucagagc cagaucauuu 20

<210> SEQ ID NO 1316
<211> LENGTH: 20
<212> TYPE: RNA
<213> ORGANISM: Homo sapiens

<400> SEQUENCE: 1316
gcaguuugaa uauccuuugu 20

<210> SEQ ID NO 1317
<211> LENGTH: 20
<212> TYPE: RNA
<213> ORGANISM: Homo sapiens

<400> SEQUENCE: 1317
aauggaaagu ggcuaugcag 20

<210> SEQ ID NO 1318
<211> LENGTH: 20
<212> TYPE: RNA
<213> ORGANISM: Homo sapiens

<400> SEQUENCE: 1318
gaaauaauaa uggaaagugg 20

<210> SEQ ID NO 1319
<211> LENGTH: 20
<212> TYPE: RNA
<213> ORGANISM: Homo sapiens

<400> SEQUENCE: 1319
uuugaaauaa uaauggaaag 20

<210> SEQ ID NO 1320
<211> LENGTH: 20
<212> TYPE: RNA

<213> ORGANISM: Homo sapiens

<400> SEQUENCE: 1320
uguauuaguu uugaaauaau 20

<210> SEQ ID NO 1321
<211> LENGTH: 20
<212> TYPE: RNA
<213> ORGANISM: Homo sapiens

<400> SEQUENCE: 1321
uauguauuag uuuugaaaua 20

<210> SEQ ID NO 1322
<211> LENGTH: 20
<212> TYPE: RNA
<213> ORGANISM: Homo sapiens

<400> SEQUENCE: 1322
cauuuuaugu auuaguuuug 20

<210> SEQ ID NO 1323
<211> LENGTH: 20
<212> TYPE: RNA
<213> ORGANISM: Homo sapiens

<400> SEQUENCE: 1323
acuugaaaca uuuuauguau 20

<210> SEQ ID NO 1324
<211> LENGTH: 20
<212> TYPE: RNA
<213> ORGANISM: Homo sapiens

<400> SEQUENCE: 1324
accacuugaa acauuuuaug 20

<210> SEQ ID NO 1325
<211> LENGTH: 20
<212> TYPE: RNA
<213> ORGANISM: Homo sapiens

<400> SEQUENCE: 1325
uaccacuuga aacauuuuau 20

<210> SEQ ID NO 1326
<211> LENGTH: 20
<212> TYPE: RNA
<213> ORGANISM: Homo sapiens

<400> SEQUENCE: 1326
guaccacuug aaacauuuua 20

<210> SEQ ID NO 1327
<211> LENGTH: 20
<212> TYPE: RNA
<213> ORGANISM: Homo sapiens

<400> SEQUENCE: 1327
uuaagaagua ccacuugaaa 20

<210> SEQ ID NO 1328
<211> LENGTH: 20

<212> TYPE: RNA
<213> ORGANISM: Homo sapiens

<400> SEQUENCE: 1328
uuuaagaagu accacuugaa 20

<210> SEQ ID NO 1329
<211> LENGTH: 20
<212> TYPE: RNA
<213> ORGANISM: Homo sapiens

<400> SEQUENCE: 1329
uuuuaagaag uaccacuuga 20

<210> SEQ ID NO 1330
<211> LENGTH: 20
<212> TYPE: RNA
<213> ORGANISM: Homo sapiens

<400> SEQUENCE: 1330
uauguaaguc auauuuauau 20

<210> SEQ ID NO 1331
<211> LENGTH: 20
<212> TYPE: RNA
<213> ORGANISM: Homo sapiens

<400> SEQUENCE: 1331
uuauguaagu cauauuuaua 20

<210> SEQ ID NO 1332
<211> LENGTH: 20
<212> TYPE: RNA
<213> ORGANISM: Homo sapiens

<400> SEQUENCE: 1332
aauuuaugua agucauauuu 20

<210> SEQ ID NO 1333
<211> LENGTH: 20
<212> TYPE: RNA
<213> ORGANISM: Homo sapiens

<400> SEQUENCE: 1333
uaauuuaugu aagucauauu 20

<210> SEQ ID NO 1334
<211> LENGTH: 20
<212> TYPE: RNA
<213> ORGANISM: Homo sapiens

<400> SEQUENCE: 1334
uuaauuuaug uaagucauau 20

<210> SEQ ID NO 1335
<211> LENGTH: 20
<212> TYPE: RNA
<213> ORGANISM: Homo sapiens

<400> SEQUENCE: 1335
aguuaauuua uguaagucau 20

<210> SEQ ID NO 1336

<211> LENGTH: 20
<212> TYPE: RNA
<213> ORGANISM: Homo sapiens

<400> SEQUENCE: 1336
gaguuaauuu auguaaguca 20

<210> SEQ ID NO 1337
<211> LENGTH: 20
<212> TYPE: RNA
<213> ORGANISM: Homo sapiens

<400> SEQUENCE: 1337
ugaguuaauu uauguaaguc 20

<210> SEQ ID NO 1338
<211> LENGTH: 20
<212> TYPE: RNA
<213> ORGANISM: Homo sapiens

<400> SEQUENCE: 1338
cugaguuaau uuauguaagu 20

<210> SEQ ID NO 1339
<211> LENGTH: 20
<212> TYPE: RNA
<213> ORGANISM: Homo sapiens

<400> SEQUENCE: 1339
gaagcugagu uaauuuaugu 20

<210> SEQ ID NO 1340
<211> LENGTH: 20
<212> TYPE: RNA
<213> ORGANISM: Homo sapiens

<400> SEQUENCE: 1340
ugaagcugag uuaauuuaug 20

<210> SEQ ID NO 1341
<211> LENGTH: 20
<212> TYPE: RNA
<213> ORGANISM: Homo sapiens

<400> SEQUENCE: 1341
gugaagcuga guuaauuuau 20

<210> SEQ ID NO 1342
<211> LENGTH: 20
<212> TYPE: RNA
<213> ORGANISM: Homo sapiens

<400> SEQUENCE: 1342
augugaagcu gaguuaauuu 20

<210> SEQ ID NO 1343
<211> LENGTH: 20
<212> TYPE: RNA
<213> ORGANISM: Homo sapiens

<400> SEQUENCE: 1343
auaugugaag cugaguuaau 20

<210> SEQ ID NO 1344
<211> LENGTH: 20
<212> TYPE: RNA
<213> ORGANISM: Homo sapiens

<400> SEQUENCE: 1344
uuaaauaugu gaagcugagu 20

<210> SEQ ID NO 1345
<211> LENGTH: 20
<212> TYPE: RNA
<213> ORGANISM: Homo sapiens

<400> SEQUENCE: 1345
uuuaaauaug ugaagcugag 20

<210> SEQ ID NO 1346
<211> LENGTH: 20
<212> TYPE: RNA
<213> ORGANISM: Homo sapiens

<400> SEQUENCE: 1346
auuuaaauau gugaagcuga 20

<210> SEQ ID NO 1347
<211> LENGTH: 20
<212> TYPE: RNA
<213> ORGANISM: Homo sapiens

<400> SEQUENCE: 1347
uaauauuuaa auaugugaag 20

<210> SEQ ID NO 1348
<211> LENGTH: 20
<212> TYPE: RNA
<213> ORGANISM: Homo sapiens

<400> SEQUENCE: 1348
auuaauauuu aaauauguga 20

<210> SEQ ID NO 1349
<211> LENGTH: 20
<212> TYPE: RNA
<213> ORGANISM: Homo sapiens

<400> SEQUENCE: 1349
uuauuaauau uuaaauaugu 20

<210> SEQ ID NO 1350
<211> LENGTH: 20
<212> TYPE: RNA
<213> ORGANISM: Homo sapiens

<400> SEQUENCE: 1350
uaauuuauua auauuuaaau 20

<210> SEQ ID NO 1351
<211> LENGTH: 20
<212> TYPE: RNA
<213> ORGANISM: Homo sapiens

<400> SEQUENCE: 1351
uuuaauuuau uaauauuuaa 20

<210> SEQ ID NO 1352
<211> LENGTH: 20
<212> TYPE: RNA
<213> ORGANISM: Homo sapiens

<400> SEQUENCE: 1352
uaggacacua uuuuaauuau 20

<210> SEQ ID NO 1353
<211> LENGTH: 20
<212> TYPE: RNA
<213> ORGANISM: Homo sapiens

<400> SEQUENCE: 1353
uuaggacacu auuuuaauua 20

<210> SEQ ID NO 1354
<211> LENGTH: 20
<212> TYPE: RNA
<213> ORGANISM: Homo sapiens

<400> SEQUENCE: 1354
guuaggacac uauuuuaauu 20

<210> SEQ ID NO 1355
<211> LENGTH: 20
<212> TYPE: RNA
<213> ORGANISM: Homo sapiens

<400> SEQUENCE: 1355
gcguuaggac acuauuuuaa 20

<210> SEQ ID NO 1356
<211> LENGTH: 20
<212> TYPE: RNA
<213> ORGANISM: Homo sapiens

<400> SEQUENCE: 1356
agcguuagga cacuauuuua 20

<210> SEQ ID NO 1357
<211> LENGTH: 20
<212> TYPE: RNA
<213> ORGANISM: Homo sapiens

<400> SEQUENCE: 1357
gagcguuagg acacuauuuu 20

<210> SEQ ID NO 1358
<211> LENGTH: 20
<212> TYPE: RNA
<213> ORGANISM: Homo sapiens

<400> SEQUENCE: 1358
ugagcguuag gacacuauuu 20

<210> SEQ ID NO 1359
<211> LENGTH: 20
<212> TYPE: RNA
<213> ORGANISM: Homo sapiens

<400> SEQUENCE: 1359
augagcguua ggacacuauu 20

<210> SEQ ID NO 1360
<211> LENGTH: 20
<212> TYPE: RNA
<213> ORGANISM: Homo sapiens

<400> SEQUENCE: 1360
cuaaaaguau gagcguuagg 20

<210> SEQ ID NO 1361
<211> LENGTH: 20
<212> TYPE: RNA
<213> ORGANISM: Homo sapiens

<400> SEQUENCE: 1361
auggagaacu aaaaguauga 20

<210> SEQ ID NO 1362
<211> LENGTH: 20
<212> TYPE: RNA
<213> ORGANISM: Homo sapiens

<400> SEQUENCE: 1362
uucucuaugg agaacuaaaa 20

<210> SEQ ID NO 1363
<211> LENGTH: 20
<212> TYPE: RNA
<213> ORGANISM: Homo sapiens

<400> SEQUENCE: 1363
ugggcacaga acuuauguug 20

<210> SEQ ID NO 1364
<211> LENGTH: 20
<212> TYPE: RNA
<213> ORGANISM: Homo sapiens

<400> SEQUENCE: 1364
guccacuggg cacagaacuu 20

<210> SEQ ID NO 1365
<211> LENGTH: 20
<212> TYPE: RNA
<213> ORGANISM: Homo sapiens

<400> SEQUENCE: 1365
guuguuaaug ggcauuccuu 20

<210> SEQ ID NO 1366
<211> LENGTH: 20
<212> TYPE: RNA
<213> ORGANISM: Homo sapiens

<400> SEQUENCE: 1366
uguagcaugg gcaccucaga 20

<210> SEQ ID NO 1367
<211> LENGTH: 20
<212> TYPE: RNA
<213> ORGANISM: Homo sapiens

<400> SEQUENCE: 1367
cgcagcuuua aggaguuccu 20

<210> SEQ ID NO 1368
<211> LENGTH: 20
<212> TYPE: RNA
<213> ORGANISM: Homo sapiens

<400> SEQUENCE: 1368
ccagcuauga acuccuucuc 20

<210> SEQ ID NO 1369
<211> LENGTH: 20
<212> TYPE: RNA
<213> ORGANISM: Homo sapiens

<400> SEQUENCE: 1369
gacaacucau cucauucugc 20

<210> SEQ ID NO 1370
<211> LENGTH: 20
<212> TYPE: RNA
<213> ORGANISM: Homo sapiens

<400> SEQUENCE: 1370
gagcccagcu augaacuccu 20

<210> SEQ ID NO 1371
<211> LENGTH: 20
<212> TYPE: RNA
<213> ORGANISM: Homo sapiens

<400> SEQUENCE: 1371
augaguacaa aaguccugau 20

<210> SEQ ID NO 1372
<211> LENGTH: 20
<212> TYPE: RNA
<213> ORGANISM: Homo sapiens

<400> SEQUENCE: 1372
gcagaugagu acaaaagucc 20

<210> SEQ ID NO 1373
<211> LENGTH: 20
<212> TYPE: RNA
<213> ORGANISM: Homo sapiens

<400> SEQUENCE: 1373
aggaacaagc cagagcugug 20

<210> SEQ ID NO 1374
<211> LENGTH: 20
<212> TYPE: RNA
<213> ORGANISM: Homo sapiens

<400> SEQUENCE: 1374
cagaacagau uugagaguag 20

<210> SEQ ID NO 1375
<211> LENGTH: 20
<212> TYPE: RNA
<213> ORGANISM: Homo sapiens

<400> SEQUENCE: 1375
ccagaacaga uuugagagua 20

<210> SEQ ID NO 1376
<211> LENGTH: 20
<212> TYPE: RNA
<213> ORGANISM: Homo sapiens

<400> SEQUENCE: 1376
uuggaguuug agguauaccu 20

<210> SEQ ID NO 1377
<211> LENGTH: 20
<212> TYPE: RNA
<213> ORGANISM: Homo sapiens

<400> SEQUENCE: 1377
acuggucuuu uggaguuuga 20

<210> SEQ ID NO 1378
<211> LENGTH: 20
<212> TYPE: RNA
<213> ORGANISM: Homo sapiens

<400> SEQUENCE: 1378
caucacuggu cuuuuggagu 20

<210> SEQ ID NO 1379
<211> LENGTH: 20
<212> TYPE: RNA
<213> ORGANISM: Homo sapiens

<400> SEQUENCE: 1379
gugaaaauca ucacuggucu 20

<210> SEQ ID NO 1380
<211> LENGTH: 20
<212> TYPE: RNA
<213> ORGANISM: Homo sapiens

<400> SEQUENCE: 1380
ugccugguga aaaucaucac 20

<210> SEQ ID NO 1381
<211> LENGTH: 20
<212> TYPE: RNA
<213> ORGANISM: Homo sapiens

<400> SEQUENCE: 1381
uugccuggug aaaaucauca 20

<210> SEQ ID NO 1382
<211> LENGTH: 20
<212> TYPE: RNA
<213> ORGANISM: Homo sapiens

<400> SEQUENCE: 1382
ucaaugagga gacuugccug 20

<210> SEQ ID NO 1383
<211> LENGTH: 20
<212> TYPE: RNA
<213> ORGANISM: Homo sapiens

<400> SEQUENCE: 1383
auucaaugag gagacuugcc 20

<210> SEQ ID NO 1384
<211> LENGTH: 20
<212> TYPE: RNA
<213> ORGANISM: Homo sapiens

<400> SEQUENCE: 1384
gcuuccaauc uggauucaau 20

<210> SEQ ID NO 1385
<211> LENGTH: 20
<212> TYPE: RNA
<213> ORGANISM: Homo sapiens

<400> SEQUENCE: 1385
uggcagaaaa caaccugaac 20

<210> SEQ ID NO 1386
<211> LENGTH: 20
<212> TYPE: RNA
<213> ORGANISM: Homo sapiens

<400> SEQUENCE: 1386
aguaacaugu gugaaagcag 20

<210> SEQ ID NO 1387
<211> LENGTH: 20
<212> TYPE: RNA
<213> ORGANISM: Homo sapiens

<400> SEQUENCE: 1387
uaacaagagu aacaugugug 20

<210> SEQ ID NO 1388
<211> LENGTH: 20
<212> TYPE: RNA
<213> ORGANISM: Homo sapiens

<400> SEQUENCE: 1388
guaacaagag uaacaugugu 20

<210> SEQ ID NO 1389
<211> LENGTH: 20
<212> TYPE: RNA
<213> ORGANISM: Homo sapiens

<400> SEQUENCE: 1389
agacauguaa caagaguaac 20

<210> SEQ ID NO 1390
<211> LENGTH: 20
<212> TYPE: RNA
<213> ORGANISM: Homo sapiens

<400> SEQUENCE: 1390
ggagacaugu aacaagagua 20

<210> SEQ ID NO 1391
<211> LENGTH: 20
<212> TYPE: RNA
<213> ORGANISM: Homo sapiens

<400> SEQUENCE: 1391
uauaauguau aaaugguuuu 20

<210> SEQ ID NO 1392
<211> LENGTH: 20
<212> TYPE: RNA
<213> ORGANISM: Homo sapiens

<400> SEQUENCE: 1392
auauaaugua uaaaugguuu 20

<210> SEQ ID NO 1393
<211> LENGTH: 20
<212> TYPE: RNA
<213> ORGANISM: Homo sapiens

<400> SEQUENCE: 1393
uauauaaugu auaaaugguu 20

<210> SEQ ID NO 1394
<211> LENGTH: 20
<212> TYPE: RNA
<213> ORGANISM: Homo sapiens

<400> SEQUENCE: 1394
uguauuuaua uaauguauaa 20

<210> SEQ ID NO 1395
<211> LENGTH: 20
<212> TYPE: RNA
<213> ORGANISM: Mus sp.

<400> SEQUENCE: 1395
uguuauaugu uauaguuuug 20

<210> SEQ ID NO 1396
<211> LENGTH: 20
<212> TYPE: RNA
<213> ORGANISM: Mus sp.

<400> SEQUENCE: 1396
uugccuauug aaaauuuccu 20

<210> SEQ ID NO 1397
<211> LENGTH: 20
<212> TYPE: RNA
<213> ORGANISM: Mus sp.

<400> SEQUENCE: 1397
uugcuaauuu aaauauguuu 20

<210> SEQ ID NO 1398
<211> LENGTH: 20
<212> TYPE: RNA
<213> ORGANISM: Mus sp.

<400> SEQUENCE: 1398
uaauuuauga uugauauuua 20

<210> SEQ ID NO 1399
<211> LENGTH: 20
<212> TYPE: RNA

<213> ORGANISM: Mus sp.

<400> SEQUENCE: 1399
uaauuuauug auaauuuaaa 20

<210> SEQ ID NO 1400
<211> LENGTH: 20
<212> TYPE: RNA
<213> ORGANISM: Mus sp.

<400> SEQUENCE: 1400
ucaaugaauu gcuaauuuaa 20

<210> SEQ ID NO 1401
<211> LENGTH: 20
<212> TYPE: RNA
<213> ORGANISM: Mus sp.

<400> SEQUENCE: 1401
uaaguuaauu uaugauugau 20

<210> SEQ ID NO 1402
<211> LENGTH: 20
<212> TYPE: RNA
<213> ORGANISM: Mus sp.

<400> SEQUENCE: 1402
uuuaaguuaa uuuaugauug 20

<210> SEQ ID NO 1403
<211> LENGTH: 20
<212> TYPE: RNA
<213> ORGANISM: Mus sp.

<400> SEQUENCE: 1403
aauguuggga cacuauuuua 20

<210> SEQ ID NO 1404
<211> LENGTH: 20
<212> TYPE: RNA
<213> ORGANISM: Mus sp.

<400> SEQUENCE: 1404
guuuaccuca augaauugcu 20

<210> SEQ ID NO 1405
<211> LENGTH: 20
<212> TYPE: RNA
<213> ORGANISM: Mus sp.

<400> SEQUENCE: 1405
uuggaaugua uaaguuuacc 20

<210> SEQ ID NO 1406
<211> LENGTH: 20
<212> TYPE: RNA
<213> ORGANISM: Mus sp.

<400> SEQUENCE: 1406
ugucagguau cugacuuaug 20

<210> SEQ ID NO 1407
<211> LENGTH: 20

<212> TYPE: RNA
<213> ORGANISM: Mus sp.

<400> SEQUENCE: 1407
aaagaaaucu uugugaugua 20

<210> SEQ ID NO 1408
<211> LENGTH: 20
<212> TYPE: RNA
<213> ORGANISM: Mus sp.

<400> SEQUENCE: 1408
uuaauuuauu gauaauuuaa 20

<210> SEQ ID NO 1409
<211> LENGTH: 20
<212> TYPE: RNA
<213> ORGANISM: Mus sp.

<400> SEQUENCE: 1409
guugggacac uauuuuaauu 20

<210> SEQ ID NO 1410
<211> LENGTH: 20
<212> TYPE: RNA
<213> ORGANISM: Mus sp.

<400> SEQUENCE: 1410
uuauaauguu uagacugucu 20

<210> SEQ ID NO 1411
<211> LENGTH: 20
<212> TYPE: RNA
<213> ORGANISM: Mus sp.

<400> SEQUENCE: 1411
uugaaauguu auauguuaua 20

<210> SEQ ID NO 1412
<211> LENGTH: 20
<212> TYPE: RNA
<213> ORGANISM: Mus sp.

<400> SEQUENCE: 1412
aaccaagagg uaaaagauuu 20

<210> SEQ ID NO 1413
<211> LENGTH: 20
<212> TYPE: RNA
<213> ORGANISM: Mus sp.

<400> SEQUENCE: 1413
aaguuaauuu augauugaua 20

<210> SEQ ID NO 1414
<211> LENGTH: 20
<212> TYPE: RNA
<213> ORGANISM: Mus sp.

<400> SEQUENCE: 1414
auugaaaauu uccucugguc 20

<210> SEQ ID NO 1415

-continued

<211> LENGTH: 20
<212> TYPE: RNA
<213> ORGANISM: Mus sp.

<400> SEQUENCE: 1415
ggcuuaauua cacauguucu 20

<210> SEQ ID NO 1416
<211> LENGTH: 20
<212> TYPE: RNA
<213> ORGANISM: Mus sp.

<400> SEQUENCE: 1416
cuaagcauau caguuugugg 20

<210> SEQ ID NO 1417
<211> LENGTH: 20
<212> TYPE: RNA
<213> ORGANISM: Mus sp.

<400> SEQUENCE: 1417
uuugccuauu gaaaauuucc 20

<210> SEQ ID NO 1418
<211> LENGTH: 20
<212> TYPE: RNA
<213> ORGANISM: Mus sp.

<400> SEQUENCE: 1418
aucuauuuga uauaaauauu 20

<210> SEQ ID NO 1419
<211> LENGTH: 20
<212> TYPE: RNA
<213> ORGANISM: Mus sp.

<400> SEQUENCE: 1419
gucacuugaa auguuauaug 20

<210> SEQ ID NO 1420
<211> LENGTH: 20
<212> TYPE: RNA
<213> ORGANISM: Mus sp.

<400> SEQUENCE: 1420
uugauaauuu aaauaaguaa 20

<210> SEQ ID NO 1421
<211> LENGTH: 20
<212> TYPE: RNA
<213> ORGANISM: Mus sp.

<400> SEQUENCE: 1421
auuuaaauaa guaaacuuua 20

<210> SEQ ID NO 1422
<211> LENGTH: 20
<212> TYPE: RNA
<213> ORGANISM: Mus sp.

<400> SEQUENCE: 1422
uuuaaauaag uaaacuuuaa 20

<210> SEQ ID NO 1423
<211> LENGTH: 20
<212> TYPE: RNA
<213> ORGANISM: Mus sp.

<400> SEQUENCE: 1423
uuaaguuaau uuaugauuga 20

<210> SEQ ID NO 1424
<211> LENGTH: 20
<212> TYPE: RNA
<213> ORGANISM: Mus sp.

<400> SEQUENCE: 1424
uaaauaagua aacuuuaagu 20

<210> SEQ ID NO 1425
<211> LENGTH: 20
<212> TYPE: RNA
<213> ORGANISM: Mus sp.

<400> SEQUENCE: 1425
uucaucuuga aaucacuuga 20

<210> SEQ ID NO 1426
<211> LENGTH: 20
<212> TYPE: RNA
<213> ORGANISM: Mus sp.

<400> SEQUENCE: 1426
cugacaauau gaauguuggg 20

<210> SEQ ID NO 1427
<211> LENGTH: 20
<212> TYPE: RNA
<213> ORGANISM: Mus sp.

<400> SEQUENCE: 1427
uucucuacga agaacugaca 20

<210> SEQ ID NO 1428
<211> LENGTH: 20
<212> TYPE: RNA
<213> ORGANISM: Mus sp.

<400> SEQUENCE: 1428
ucagaaaaua uauccuguug 20

<210> SEQ ID NO 1429
<211> LENGTH: 20
<212> TYPE: RNA
<213> ORGANISM: Mus sp.

<400> SEQUENCE: 1429
gaugguuucu uggaauguau 20

<210> SEQ ID NO 1430
<211> LENGTH: 20
<212> TYPE: RNA
<213> ORGANISM: Mus sp.

<400> SEQUENCE: 1430
agugucacuu gaaauguuau 20

<210> SEQ ID NO 1431
<211> LENGTH: 20
<212> TYPE: RNA
<213> ORGANISM: Mus sp.

<400> SEQUENCE: 1431
uuugauauaa auauucuguu 20

<210> SEQ ID NO 1432
<211> LENGTH: 20
<212> TYPE: RNA
<213> ORGANISM: Mus sp.

<400> SEQUENCE: 1432
uuuaaagaaa ucuuugugau 20

<210> SEQ ID NO 1433
<211> LENGTH: 20
<212> TYPE: RNA
<213> ORGANISM: Mus sp.

<400> SEQUENCE: 1433
uuugaaauga uaaccuaaaa 20

<210> SEQ ID NO 1434
<211> LENGTH: 20
<212> TYPE: RNA
<213> ORGANISM: Mus sp.

<400> SEQUENCE: 1434
auaaucagga aauuugccua 20

<210> SEQ ID NO 1435
<211> LENGTH: 20
<212> TYPE: RNA
<213> ORGANISM: Mus sp.

<400> SEQUENCE: 1435
caagagguaa aagauuuaca 20

<210> SEQ ID NO 1436
<211> LENGTH: 20
<212> TYPE: RNA
<213> ORGANISM: Mus sp.

<400> SEQUENCE: 1436
gaaaugagaa aagaguugug 20

<210> SEQ ID NO 1437
<211> LENGTH: 20
<212> TYPE: RNA
<213> ORGANISM: Mus sp.

<400> SEQUENCE: 1437
aaacuuuaag uuaauuuaug 20

<210> SEQ ID NO 1438
<211> LENGTH: 20
<212> TYPE: RNA
<213> ORGANISM: Mus sp.

<400> SEQUENCE: 1438
auugauaauu uaaauaagua 20

<210> SEQ ID NO 1439
<211> LENGTH: 20
<212> TYPE: RNA
<213> ORGANISM: Mus sp.

<400> SEQUENCE: 1439
uaaguaaacu uuaaguuaau 20

<210> SEQ ID NO 1440
<211> LENGTH: 20
<212> TYPE: RNA
<213> ORGANISM: Mus sp.

<400> SEQUENCE: 1440
ugggaaaucg uggaaaugag 20

<210> SEQ ID NO 1441
<211> LENGTH: 20
<212> TYPE: RNA
<213> ORGANISM: Mus sp.

<400> SEQUENCE: 1441
agagauacaa agaaaugaug 20

<210> SEQ ID NO 1442
<211> LENGTH: 20
<212> TYPE: RNA
<213> ORGANISM: Mus sp.

<400> SEQUENCE: 1442
augaauguug ggacacuauu 20

<210> SEQ ID NO 1443
<211> LENGTH: 20
<212> TYPE: RNA
<213> ORGANISM: Mus sp.

<400> SEQUENCE: 1443
aaaacaaucu gaaacuucca 20

<210> SEQ ID NO 1444
<211> LENGTH: 20
<212> TYPE: RNA
<213> ORGANISM: Mus sp.

<400> SEQUENCE: 1444
ugccuauuga aaauuuccuc 20

<210> SEQ ID NO 1445
<211> LENGTH: 20
<212> TYPE: RNA
<213> ORGANISM: Mus sp.

<400> SEQUENCE: 1445
cagaaaauau auccuguugu 20

<210> SEQ ID NO 1446
<211> LENGTH: 20
<212> TYPE: RNA
<213> ORGANISM: Mus sp.

<400> SEQUENCE: 1446
uaaacuuuaa guuaauuuau 20

<210> SEQ ID NO 1447
<211> LENGTH: 20
<212> TYPE: RNA
<213> ORGANISM: Mus sp.

<400> SEQUENCE: 1447
uauaguuuug aaaugauaac 20

<210> SEQ ID NO 1448
<211> LENGTH: 20
<212> TYPE: RNA
<213> ORGANISM: Mus sp.

<400> SEQUENCE: 1448
caauucaucu ugaaaucacu 20

<210> SEQ ID NO 1449
<211> LENGTH: 20
<212> TYPE: RNA
<213> ORGANISM: Mus sp.

<400> SEQUENCE: 1449
augauugaua uuuauuauuu 20

<210> SEQ ID NO 1450
<211> LENGTH: 20
<212> TYPE: RNA
<213> ORGANISM: Mus sp.

<400> SEQUENCE: 1450
auugcuaauu uaaauauguu 20

<210> SEQ ID NO 1451
<211> LENGTH: 20
<212> TYPE: RNA
<213> ORGANISM: Mus sp.

<400> SEQUENCE: 1451
uaccccaauu uccaaugcuc 20

<210> SEQ ID NO 1452
<211> LENGTH: 20
<212> TYPE: RNA
<213> ORGANISM: Mus sp.

<400> SEQUENCE: 1452
cucugcaaga gacuuccauc 20

<210> SEQ ID NO 1453
<211> LENGTH: 20
<212> TYPE: RNA
<213> ORGANISM: Mus sp.

<400> SEQUENCE: 1453
ccaaacugga uauaaucagg 20

<210> SEQ ID NO 1454
<211> LENGTH: 20
<212> TYPE: RNA
<213> ORGANISM: Mus sp.

<400> SEQUENCE: 1454
uuuaauuuau ugauaauuua 20

<210> SEQ ID NO 1455
<211> LENGTH: 20
<212> TYPE: RNA
<213> ORGANISM: Mus sp.

<400> SEQUENCE: 1455
gauggaugcu accaaacugg 20

<210> SEQ ID NO 1456
<211> LENGTH: 20
<212> TYPE: RNA
<213> ORGANISM: Mus sp.

<400> SEQUENCE: 1456
ucuguuaccu agccagaugg 20

<210> SEQ ID NO 1457
<211> LENGTH: 20
<212> TYPE: RNA
<213> ORGANISM: Mus sp.

<400> SEQUENCE: 1457
uuauauguua uaguuuugaa 20

<210> SEQ ID NO 1458
<211> LENGTH: 20
<212> TYPE: RNA
<213> ORGANISM: Mus sp.

<400> SEQUENCE: 1458
caaugaauug cuaauuuaaa 20

<210> SEQ ID NO 1459
<211> LENGTH: 20
<212> TYPE: RNA
<213> ORGANISM: Mus sp.

<400> SEQUENCE: 1459
aaaucacuug aagaauuucu 20

<210> SEQ ID NO 1460
<211> LENGTH: 20
<212> TYPE: RNA
<213> ORGANISM: Mus sp.

<400> SEQUENCE: 1460
aauugcuaau uuaaauaugu 20

<210> SEQ ID NO 1461
<211> LENGTH: 20
<212> TYPE: RNA
<213> ORGANISM: Mus sp.

<400> SEQUENCE: 1461
guuaccuagc cagaugguuu 20

<210> SEQ ID NO 1462
<211> LENGTH: 20
<212> TYPE: RNA
<213> ORGANISM: Mus sp.

<400> SEQUENCE: 1462
uggaauguau aaguuuaccu 20

<210> SEQ ID NO 1463
<211> LENGTH: 20
<212> TYPE: RNA
<213> ORGANISM: Mus sp.

<400> SEQUENCE: 1463
acuugaaaug uuauauguua 20

<210> SEQ ID NO 1464
<211> LENGTH: 20
<212> TYPE: RNA
<213> ORGANISM: Mus sp.

<400> SEQUENCE: 1464
guaaacuuua aguuaauuua 20

<210> SEQ ID NO 1465
<211> LENGTH: 20
<212> TYPE: RNA
<213> ORGANISM: Mus sp.

<400> SEQUENCE: 1465
guuauaguuu ugaaaugaua 20

<210> SEQ ID NO 1466
<211> LENGTH: 20
<212> TYPE: RNA
<213> ORGANISM: Mus sp.

<400> SEQUENCE: 1466
gugcaauggc aauucugauu 20

<210> SEQ ID NO 1467
<211> LENGTH: 20
<212> TYPE: RNA
<213> ORGANISM: Mus sp.

<400> SEQUENCE: 1467
aaucacuuga agaauuucua 20

<210> SEQ ID NO 1468
<211> LENGTH: 20
<212> TYPE: RNA
<213> ORGANISM: Mus sp.

<400> SEQUENCE: 1468
uuuuaauuua uugauaauuu 20

<210> SEQ ID NO 1469
<211> LENGTH: 20
<212> TYPE: RNA
<213> ORGANISM: Mus sp.

<400> SEQUENCE: 1469
uccagagaua caaagaaaug 20

<210> SEQ ID NO 1470
<211> LENGTH: 20
<212> TYPE: RNA
<213> ORGANISM: Mus sp.

<400> SEQUENCE: 1470
cuuuaaguua auuuaugauu 20

<210> SEQ ID NO 1471
<211> LENGTH: 20
<212> TYPE: RNA
<213> ORGANISM: Mus sp.

<400> SEQUENCE: 1471
accucaauga auugcuaauu 20

<210> SEQ ID NO 1472
<211> LENGTH: 20
<212> TYPE: RNA
<213> ORGANISM: Mus sp.

<400> SEQUENCE: 1472
uggucagaaa auauauccug 20

<210> SEQ ID NO 1473
<211> LENGTH: 20
<212> TYPE: RNA
<213> ORGANISM: Mus sp.

<400> SEQUENCE: 1473
uauaaauguu agacugucuu 20

<210> SEQ ID NO 1474
<211> LENGTH: 20
<212> TYPE: RNA
<213> ORGANISM: Mus sp.

<400> SEQUENCE: 1474
uugauauaaa uauucuguua 20

<210> SEQ ID NO 1475
<211> LENGTH: 20
<212> TYPE: RNA
<213> ORGANISM: Mus sp.

<400> SEQUENCE: 1475
uuuaugaagu gucacuugaa 20

<210> SEQ ID NO 1476
<211> LENGTH: 20
<212> TYPE: RNA
<213> ORGANISM: Mus sp.

<400> SEQUENCE: 1476
gcagaaaaca aucugaaacu 20

<210> SEQ ID NO 1477
<211> LENGTH: 20
<212> TYPE: RNA
<213> ORGANISM: Mus sp.

<400> SEQUENCE: 1477
uugggacacu auuuuaauua 20

<210> SEQ ID NO 1478
<211> LENGTH: 20
<212> TYPE: RNA

<213> ORGANISM: Mus sp.

<400> SEQUENCE: 1478
ggauauaauc aggaaauuug 20

<210> SEQ ID NO 1479
<211> LENGTH: 20
<212> TYPE: RNA
<213> ORGANISM: Mus sp.

<400> SEQUENCE: 1479
uuuuauaaug uuuagacugu 20

<210> SEQ ID NO 1480
<211> LENGTH: 20
<212> TYPE: RNA
<213> ORGANISM: Mus sp.

<400> SEQUENCE: 1480
uguucucugg gaaaucgugg 20

<210> SEQ ID NO 1481
<211> LENGTH: 20
<212> TYPE: RNA
<213> ORGANISM: Mus sp.

<400> SEQUENCE: 1481
gaagaauuuc uaaaagucac 20

<210> SEQ ID NO 1482
<211> LENGTH: 20
<212> TYPE: RNA
<213> ORGANISM: Mus sp.

<400> SEQUENCE: 1482
ucaucuugaa aucacuugaa 20

<210> SEQ ID NO 1483
<211> LENGTH: 20
<212> TYPE: RNA
<213> ORGANISM: Mus sp.

<400> SEQUENCE: 1483
uugugcaaug gcaauucuga 20

<210> SEQ ID NO 1484
<211> LENGTH: 20
<212> TYPE: RNA
<213> ORGANISM: Mus sp.

<400> SEQUENCE: 1484
aucuucaacc aagagguaaa 20

<210> SEQ ID NO 1485
<211> LENGTH: 20
<212> TYPE: RNA
<213> ORGANISM: Mus sp.

<400> SEQUENCE: 1485
uuaccuagcc agaugguuuc 20

<210> SEQ ID NO 1486
<211> LENGTH: 20

-continued

<212> TYPE: RNA
<213> ORGANISM: Mus sp.

<400> SEQUENCE: 1486
uaccucaaug aauugcuaau 20

<210> SEQ ID NO 1487
<211> LENGTH: 20
<212> TYPE: RNA
<213> ORGANISM: Mus sp.

<400> SEQUENCE: 1487
cuugaaauca cuugaagaau 20

<210> SEQ ID NO 1488
<211> LENGTH: 20
<212> TYPE: RNA
<213> ORGANISM: Mus sp.

<400> SEQUENCE: 1488
uuaugauuga uauuuauuau 20

<210> SEQ ID NO 1489
<211> LENGTH: 20
<212> TYPE: RNA
<213> ORGANISM: Mus sp.

<400> SEQUENCE: 1489
auuugccuau ugaaaauuuc 20

<210> SEQ ID NO 1490
<211> LENGTH: 20
<212> TYPE: RNA
<213> ORGANISM: Mus sp.

<400> SEQUENCE: 1490
ucuuggaaug uauaaguuua 20

<210> SEQ ID NO 1491
<211> LENGTH: 20
<212> TYPE: RNA
<213> ORGANISM: Mus sp.

<400> SEQUENCE: 1491
uaauuuaaau aaguaaacuu 20

<210> SEQ ID NO 1492
<211> LENGTH: 20
<212> TYPE: RNA
<213> ORGANISM: Mus sp.

<400> SEQUENCE: 1492
ucugaaacuu ccagagauac 20

<210> SEQ ID NO 1493
<211> LENGTH: 20
<212> TYPE: RNA
<213> ORGANISM: Mus sp.

<400> SEQUENCE: 1493
gaggcuuaau uacacauguu 20

<210> SEQ ID NO 1494

<211> LENGTH: 20
<212> TYPE: RNA
<213> ORGANISM: Mus sp.

<400> SEQUENCE: 1494
aguaaacuuu aaguuaauuu 20

<210> SEQ ID NO 1495
<211> LENGTH: 45
<212> TYPE: DNA
<213> ORGANISM: Homo sapiens

<400> SEQUENCE: 1495
aaagaaatat ttatattgta tttatataat gtataaatgg ttttt 45

<210> SEQ ID NO 1496
<211> LENGTH: 45
<212> TYPE: DNA
<213> ORGANISM: Homo sapiens

<400> SEQUENCE: 1496
taaagaaata tttatattgt atttatataa tgtataaatg gtttt 45

<210> SEQ ID NO 1497
<211> LENGTH: 45
<212> TYPE: DNA
<213> ORGANISM: Homo sapiens

<400> SEQUENCE: 1497
ttttaaagaa atatttatat tgtatttata taatgtataa atggt 45

<210> SEQ ID NO 1498
<211> LENGTH: 45
<212> TYPE: DNA
<213> ORGANISM: Homo sapiens

<400> SEQUENCE: 1498
tttttaaaga aatatttata ttgtatttat ataatgtata aatgg 45

<210> SEQ ID NO 1499
<211> LENGTH: 45
<212> TYPE: DNA
<213> ORGANISM: Homo sapiens

<400> SEQUENCE: 1499
acatattttt aaagaaatat ttatattgta tttatataat gtata 45

<210> SEQ ID NO 1500
<211> LENGTH: 45
<212> TYPE: DNA
<213> ORGANISM: Homo sapiens

<400> SEQUENCE: 1500
cttatacata tttttaaaga aatatttata ttgtatttat ataat 45

<210> SEQ ID NO 1501
<211> LENGTH: 45
<212> TYPE: DNA
<213> ORGANISM: Homo sapiens

<400> SEQUENCE: 1501
aacttataca tatttttaaa gaaatattta tattgtattt atata 45

<210> SEQ ID NO 1502
<211> LENGTH: 45
<212> TYPE: DNA
<213> ORGANISM: Homo sapiens

<400> SEQUENCE: 1502
ctaacttata catattttta aagaaatatt tatattgtat ttata 45

<210> SEQ ID NO 1503
<211> LENGTH: 45
<212> TYPE: DNA
<213> ORGANISM: Homo sapiens

<400> SEQUENCE: 1503
ttacctcaaa taaatggcta acttatacat atttttaaag aaata 45

<210> SEQ ID NO 1504
<211> LENGTH: 45
<212> TYPE: DNA
<213> ORGANISM: Homo sapiens

<400> SEQUENCE: 1504
cttacctcaa ataaatggct aacttataca tatttttaaa gaaat 45

<210> SEQ ID NO 1505
<211> LENGTH: 45
<212> TYPE: DNA
<213> ORGANISM: Homo sapiens

<400> SEQUENCE: 1505
gtgtaggctt acctcaaata aatggctaac ttatacatat tttta 45

<210> SEQ ID NO 1506
<211> LENGTH: 45
<212> TYPE: DNA
<213> ORGANISM: Homo sapiens

<400> SEQUENCE: 1506
gaaagtgtag gcttacctca aataaatggc taacttatac atatt 45

<210> SEQ ID NO 1507
<211> LENGTH: 45
<212> TYPE: DNA
<213> ORGANISM: Homo sapiens

<400> SEQUENCE: 1507
ggaaagtgta ggcttacctc aaataaatgg ctaacttata catat 45

<210> SEQ ID NO 1508
<211> LENGTH: 45
<212> TYPE: DNA
<213> ORGANISM: Homo sapiens

<400> SEQUENCE: 1508
tggaaagtgt aggcttacct caaataaatg gctaacttat acata 45

<210> SEQ ID NO 1509
<211> LENGTH: 45
<212> TYPE: DNA
<213> ORGANISM: Homo sapiens

<400> SEQUENCE: 1509
ttggaaagtg taggcttacc tcaaataaat ggctaactta tacat 45

<210> SEQ ID NO 1510
<211> LENGTH: 45
<212> TYPE: DNA
<213> ORGANISM: Homo sapiens

<400> SEQUENCE: 1510
cttggaaagt gtaggcttac ctcaaataaa tggctaactt ataca 45

<210> SEQ ID NO 1511
<211> LENGTH: 45
<212> TYPE: DNA
<213> ORGANISM: Homo sapiens

<400> SEQUENCE: 1511
atttcttgga aagtgtaggc ttacctcaaa taaatggcta actta 45

<210> SEQ ID NO 1512
<211> LENGTH: 45
<212> TYPE: DNA
<213> ORGANISM: Homo sapiens

<400> SEQUENCE: 1512
agccagatca tttcttggaa agtgtaggct tacctcaaat aaatg 45

<210> SEQ ID NO 1513
<211> LENGTH: 45
<212> TYPE: DNA
<213> ORGANISM: Homo sapiens

<400> SEQUENCE: 1513
agagccagat catttcttgg aaagtgtagg cttacctcaa ataaa 45

<210> SEQ ID NO 1514
<211> LENGTH: 45
<212> TYPE: DNA
<213> ORGANISM: Homo sapiens

<400> SEQUENCE: 1514
aatatccttt gtttcagagc cagatcattt cttggaaagt gtagg 45

<210> SEQ ID NO 1515
<211> LENGTH: 45
<212> TYPE: DNA
<213> ORGANISM: Homo sapiens

<400> SEQUENCE: 1515
gtttgaatat cctttgtttc agagccagat catttcttgg aaagt 45

<210> SEQ ID NO 1516
<211> LENGTH: 45
<212> TYPE: DNA
<213> ORGANISM: Homo sapiens

<400> SEQUENCE: 1516
atggaaagtg gctatgcagt ttgaatatcc tttgtttcag agcca 45

<210> SEQ ID NO 1517
<211> LENGTH: 45
<212> TYPE: DNA
<213> ORGANISM: Homo sapiens

<400> SEQUENCE: 1517
tagttttgaa ataataatgg aaagtggcta tgcagtttga atatc 45

<210> SEQ ID NO 1518
<211> LENGTH: 45
<212> TYPE: DNA
<213> ORGANISM: Homo sapiens

<400> SEQUENCE: 1518
ttatgtatta gttttgaaat aataatggaa agtggctatg cagtt 45

<210> SEQ ID NO 1519
<211> LENGTH: 45
<212> TYPE: DNA
<213> ORGANISM: Homo sapiens

<400> SEQUENCE: 1519
attttatgta ttagttttga aataataatg gaaagtggct atgca 45

<210> SEQ ID NO 1520
<211> LENGTH: 45
<212> TYPE: DNA
<213> ORGANISM: Homo sapiens

<400> SEQUENCE: 1520
acttgaaaca ttttatgtat tagttttgaa ataataatgg aaagt 45

<210> SEQ ID NO 1521
<211> LENGTH: 45
<212> TYPE: DNA
<213> ORGANISM: Homo sapiens

<400> SEQUENCE: 1521
ccacttgaaa cattttatgt attagttttg aaataataat ggaaa 45

<210> SEQ ID NO 1522
<211> LENGTH: 45
<212> TYPE: DNA
<213> ORGANISM: Homo sapiens

<400> SEQUENCE: 1522
aagtaccact tgaaacattt tatgtattag ttttgaaata ataat 45

<210> SEQ ID NO 1523
<211> LENGTH: 45
<212> TYPE: DNA
<213> ORGANISM: Homo sapiens

<400> SEQUENCE: 1523
tttttaagaa gtaccacttg aaacatttta tgtattagtt ttgaa 45

<210> SEQ ID NO 1524
<211> LENGTH: 45
<212> TYPE: DNA
<213> ORGANISM: Homo sapiens

<400> SEQUENCE: 1524
atatttttaa gaagtaccac ttgaaacatt ttatgtatta gtttt 45

<210> SEQ ID NO 1525
<211> LENGTH: 45
<212> TYPE: DNA
<213> ORGANISM: Homo sapiens

<400> SEQUENCE: 1525
tatattttta agaagtacca cttgaaacat tttatgtatt agttt 45

<210> SEQ ID NO 1526
<211> LENGTH: 45
<212> TYPE: DNA
<213> ORGANISM: Homo sapiens

<400> SEQUENCE: 1526
ttatattttt aagaagtacc acttgaaaca ttttatgtat tagtt 45

<210> SEQ ID NO 1527
<211> LENGTH: 45
<212> TYPE: DNA
<213> ORGANISM: Homo sapiens

<400> SEQUENCE: 1527
gtcatattta tatttttaag aagtaccact tgaaacattt tatgt 45

<210> SEQ ID NO 1528
<211> LENGTH: 45
<212> TYPE: DNA
<213> ORGANISM: Homo sapiens

<400> SEQUENCE: 1528
agtcatattt atatttttaa gaagtaccac ttgaaacatt ttatg 45

<210> SEQ ID NO 1529
<211> LENGTH: 45
<212> TYPE: DNA
<213> ORGANISM: Homo sapiens

<400> SEQUENCE: 1529
aagtcatatt tatattttta agaagtacca cttgaaacat tttat 45

<210> SEQ ID NO 1530
<211> LENGTH: 45
<212> TYPE: DNA
<213> ORGANISM: Homo sapiens

<400> SEQUENCE: 1530
gaagctgagt taatttatgt aagtcatatt tatattttta agaag 45

<210> SEQ ID NO 1531
<211> LENGTH: 45
<212> TYPE: DNA
<213> ORGANISM: Homo sapiens

<400> SEQUENCE: 1531
tgaagctgag ttaatttatg taagtcatat ttatattttt aagaa 45

<210> SEQ ID NO 1532
<211> LENGTH: 45
<212> TYPE: DNA
<213> ORGANISM: Homo sapiens

<400> SEQUENCE: 1532
atgtgaagct gagttaattt atgtaagtca tatttatatt tttaa 45

<210> SEQ ID NO 1533
<211> LENGTH: 45
<212> TYPE: DNA
<213> ORGANISM: Homo sapiens

<400> SEQUENCE: 1533
tatgtgaagc tgagttaatt tatgtaagtc atatttatat tttta 45

<210> SEQ ID NO 1534
<211> LENGTH: 45
<212> TYPE: DNA
<213> ORGANISM: Homo sapiens

<400> SEQUENCE: 1534
atatgtgaag ctgagttaat ttatgtaagt catatttata ttttt 45

<210> SEQ ID NO 1535
<211> LENGTH: 45
<212> TYPE: DNA
<213> ORGANISM: Homo sapiens

<400> SEQUENCE: 1535
aaatatgtga agctgagtta atttatgtaa gtcatattta tattt 45

<210> SEQ ID NO 1536
<211> LENGTH: 45
<212> TYPE: DNA
<213> ORGANISM: Homo sapiens

<400> SEQUENCE: 1536
taaatatgtg aagctgagtt aatttatgta agtcatattt atatt 45

<210> SEQ ID NO 1537
<211> LENGTH: 45
<212> TYPE: DNA
<213> ORGANISM: Homo sapiens

<400> SEQUENCE: 1537
ttaaatatgt gaagctgagt taatttatgt aagtcatatt tatat 45

<210> SEQ ID NO 1538
<211> LENGTH: 45
<212> TYPE: DNA
<213> ORGANISM: Homo sapiens

<400> SEQUENCE: 1538
tttaaatatg tgaagctgag ttaatttatg taagtcatat ttata 45

<210> SEQ ID NO 1539
<211> LENGTH: 45
<212> TYPE: DNA
<213> ORGANISM: Homo sapiens

<400> SEQUENCE: 1539
aatatttaaa tatgtgaagc tgagttaatt tatgtaagtc atatt 45

<210> SEQ ID NO 1540
<211> LENGTH: 45
<212> TYPE: DNA
<213> ORGANISM: Homo sapiens

<400> SEQUENCE: 1540
taatatttaa atatgtgaag ctgagttaat ttatgtaagt catat 45

<210> SEQ ID NO 1541
<211> LENGTH: 45
<212> TYPE: DNA
<213> ORGANISM: Homo sapiens

<400> SEQUENCE: 1541
ttaatattta aatatgtgaa gctgagttaa tttatgtaag tcata 45

<210> SEQ ID NO 1542
<211> LENGTH: 45
<212> TYPE: DNA
<213> ORGANISM: Homo sapiens

<400> SEQUENCE: 1542
tattaatatt taaatatgtg aagctgagtt aatttatgta agtca 45

<210> SEQ ID NO 1543
<211> LENGTH: 45
<212> TYPE: DNA
<213> ORGANISM: Homo sapiens

<400> SEQUENCE: 1543
tttattaata tttaaatatg tgaagctgag ttaatttatg taagt 45

<210> SEQ ID NO 1544
<211> LENGTH: 45
<212> TYPE: DNA
<213> ORGANISM: Homo sapiens

<400> SEQUENCE: 1544
ttaatttatt aatatttaaa tatgtgaagc tgagttaatt tatgt 45

<210> SEQ ID NO 1545
<211> LENGTH: 45
<212> TYPE: DNA
<213> ORGANISM: Homo sapiens

<400> SEQUENCE: 1545
tttaatttat taatatttaa atatgtgaag ctgagttaat ttatg 45

<210> SEQ ID NO 1546
<211> LENGTH: 45
<212> TYPE: DNA
<213> ORGANISM: Homo sapiens

<400> SEQUENCE: 1546
ttttaattta ttaatattta aatatgtgaa gctgagttaa tttat 45

<210> SEQ ID NO 1547
<211> LENGTH: 45
<212> TYPE: DNA
<213> ORGANISM: Homo sapiens

<400> SEQUENCE: 1547
ttatttttaa tttattaata tttaaatatg tgaagctgag ttaat 45

<210> SEQ ID NO 1548
<211> LENGTH: 45
<212> TYPE: DNA
<213> ORGANISM: Homo sapiens

<400> SEQUENCE: 1548
aattattttt aatttattaa tatttaaata tgtgaagctg agtta 45

<210> SEQ ID NO 1549
<211> LENGTH: 45
<212> TYPE: DNA
<213> ORGANISM: Homo sapiens

<400> SEQUENCE: 1549
ttaattattt ttaatttatt aatatttaaa tatgtgaagc tgagt 45

<210> SEQ ID NO 1550
<211> LENGTH: 45
<212> TYPE: DNA
<213> ORGANISM: Homo sapiens

<400> SEQUENCE: 1550
tattttaatt atttttaatt tattaatatt taaatatgtg aagct 45

<210> SEQ ID NO 1551
<211> LENGTH: 45
<212> TYPE: DNA
<213> ORGANISM: Homo sapiens

<400> SEQUENCE: 1551
actattttaa ttatttttaa tttattaata tttaaatatg tgaag 45

<210> SEQ ID NO 1552
<211> LENGTH: 45
<212> TYPE: DNA
<213> ORGANISM: Homo sapiens

<400> SEQUENCE: 1552
taaaagtatg agcgttagga cactatttta attattttta attta 45

<210> SEQ ID NO 1553
<211> LENGTH: 45
<212> TYPE: DNA
<213> ORGANISM: Homo sapiens

<400> SEQUENCE: 1553
ctaaaagtat gagcgttagg acactatttt aattattttt aattt 45

<210> SEQ ID NO 1554
<211> LENGTH: 45
<212> TYPE: DNA
<213> ORGANISM: Homo sapiens

<400> SEQUENCE: 1554
actaaaagta tgagcgttag gacactattt taattatttt taatt 45

<210> SEQ ID NO 1555
<211> LENGTH: 45
<212> TYPE: DNA
<213> ORGANISM: Homo sapiens

<400> SEQUENCE: 1555
gaactaaaag tatgagcgtt aggacactat tttaattatt tttaa 45

<210> SEQ ID NO 1556
<211> LENGTH: 45
<212> TYPE: DNA
<213> ORGANISM: Homo sapiens

<400> SEQUENCE: 1556
agaactaaaa gtatgagcgt taggacacta ttttaattat tttta 45

<210> SEQ ID NO 1557
<211> LENGTH: 45
<212> TYPE: DNA

<213> ORGANISM: Homo sapiens

<400> SEQUENCE: 1557
gagaactaaa agtatgagcg ttaggacact attttaatta ttttt 45

<210> SEQ ID NO 1558
<211> LENGTH: 45
<212> TYPE: DNA
<213> ORGANISM: Homo sapiens

<400> SEQUENCE: 1558
ggagaactaa aagtatgagc gttaggacac tattttaatt atttt 45

<210> SEQ ID NO 1559
<211> LENGTH: 45
<212> TYPE: DNA
<213> ORGANISM: Homo sapiens

<400> SEQUENCE: 1559
tggagaacta aaagtatgag cgttaggaca ctattttaat tattt 45

<210> SEQ ID NO 1560
<211> LENGTH: 45
<212> TYPE: DNA
<213> ORGANISM: Homo sapiens

<400> SEQUENCE: 1560
gttctctatg gagaactaaa agtatgagcg ttaggacact atttt 45

<210> SEQ ID NO 1561
<211> LENGTH: 45
<212> TYPE: DNA
<213> ORGANISM: Homo sapiens

<400> SEQUENCE: 1561
cttatgttgt tctctatgga gaactaaaag tatgagcgtt aggac 45

<210> SEQ ID NO 1562
<211> LENGTH: 45
<212> TYPE: DNA
<213> ORGANISM: Homo sapiens

<400> SEQUENCE: 1562
acagaactta tgttgttctc tatggagaac taaaagtatg agcgt 45

<210> SEQ ID NO 1563
<211> LENGTH: 45
<212> TYPE: DNA
<213> ORGANISM: Homo sapiens

<400> SEQUENCE: 1563
cagaaacctg tccactgggc acagaactta tgttgttctc tatgg 45

<210> SEQ ID NO 1564
<211> LENGTH: 45
<212> TYPE: DNA
<213> ORGANISM: Homo sapiens

<400> SEQUENCE: 1564
tctggtcaga aacctgtcca ctgggcacag aacttatgtt gttct 45

<210> SEQ ID NO 1565
<211> LENGTH: 45

<212> TYPE: DNA
<213> ORGANISM: Homo sapiens

<400> SEQUENCE: 1565
gcacctcaga ttgttgttgt taatgggcat tccttcttct ggtca 45

<210> SEQ ID NO 1566
<211> LENGTH: 45
<212> TYPE: DNA
<213> ORGANISM: Homo sapiens

<400> SEQUENCE: 1566
gggctcttcg gcaaatgtag catgggcacc tcagattgtt gttgt 45

<210> SEQ ID NO 1567
<211> LENGTH: 45
<212> TYPE: DNA
<213> ORGANISM: Homo sapiens

<400> SEQUENCE: 1567
actcatctca ttctgcgcag ctttaaggag ttcctgcagt ccagc 45

<210> SEQ ID NO 1568
<211> LENGTH: 45
<212> TYPE: DNA
<213> ORGANISM: Homo sapiens

<400> SEQUENCE: 1568
ctcccctcca ggagcccagc tatgaactcc ttctccacaa taccc 45

<210> SEQ ID NO 1569
<211> LENGTH: 45
<212> TYPE: DNA
<213> ORGANISM: Homo sapiens

<400> SEQUENCE: 1569
gtggctgcag gacatgacaa ctcatctcat tctgcgcagc tttaa 45

<210> SEQ ID NO 1570
<211> LENGTH: 45
<212> TYPE: DNA
<213> ORGANISM: Homo sapiens

<400> SEQUENCE: 1570
ctatctcccc tccaggagcc cagctatgaa ctccttctcc acaat 45

<210> SEQ ID NO 1571
<211> LENGTH: 45
<212> TYPE: DNA
<213> ORGANISM: Homo sapiens

<400> SEQUENCE: 1571
gccagagctg tgcagatgag tacaaaagtc ctgatccagt tcctg 45

<210> SEQ ID NO 1572
<211> LENGTH: 45
<212> TYPE: DNA
<213> ORGANISM: Homo sapiens

<400> SEQUENCE: 1572
acaagccaga gctgtgcaga tgagtacaaa agtcctgatc cagtt 45

<210> SEQ ID NO 1573

<211> LENGTH: 45
<212> TYPE: DNA
<213> ORGANISM: Homo sapiens

<400> SEQUENCE: 1573
gatttgagag tagtgaggaa caagccagag ctgtgcagat gagta 45

<210> SEQ ID NO 1574
<211> LENGTH: 45
<212> TYPE: DNA
<213> ORGANISM: Homo sapiens

<400> SEQUENCE: 1574
tacctagagt acctccagaa cagatttgag agtagtgagg aacaa 45

<210> SEQ ID NO 1575
<211> LENGTH: 45
<212> TYPE: DNA
<213> ORGANISM: Homo sapiens

<400> SEQUENCE: 1575
atacctagag tacctccaga acagatttga gagtagtgag gaaca 45

<210> SEQ ID NO 1576
<211> LENGTH: 45
<212> TYPE: DNA
<213> ORGANISM: Homo sapiens

<400> SEQUENCE: 1576
atcatcactg gtcttttgga gtttgaggta tacctagagt acctc 45

<210> SEQ ID NO 1577
<211> LENGTH: 45
<212> TYPE: DNA
<213> ORGANISM: Homo sapiens

<400> SEQUENCE: 1577
ctggtgaaaa tcatcactgg tcttttggag tttgaggtat accta 45

<210> SEQ ID NO 1578
<211> LENGTH: 45
<212> TYPE: DNA
<213> ORGANISM: Homo sapiens

<400> SEQUENCE: 1578
ttgcctggtg aaaatcatca ctggtctttt ggagtttgag gtata 45

<210> SEQ ID NO 1579
<211> LENGTH: 45
<212> TYPE: DNA
<213> ORGANISM: Homo sapiens

<400> SEQUENCE: 1579
gaggagactt gcctggtgaa aatcatcact ggtcttttgg agttt 45

<210> SEQ ID NO 1580
<211> LENGTH: 45
<212> TYPE: DNA
<213> ORGANISM: Homo sapiens

<400> SEQUENCE: 1580
ttcaatgagg agacttgcct ggtgaaaatc atcactggtc ttttg 45

<210> SEQ ID NO 1581
<211> LENGTH: 45
<212> TYPE: DNA
<213> ORGANISM: Homo sapiens

<400> SEQUENCE: 1581
attcaatgag gagacttgcc tggtgaaaat catcactggt ctttt 45

<210> SEQ ID NO 1582
<211> LENGTH: 45
<212> TYPE: DNA
<213> ORGANISM: Homo sapiens

<400> SEQUENCE: 1582
gcttccaatc tggattcaat gaggagactt gcctggtgaa aatca 45

<210> SEQ ID NO 1583
<211> LENGTH: 45
<212> TYPE: DNA
<213> ORGANISM: Homo sapiens

<400> SEQUENCE: 1583
atgcttccaa tctggattca atgaggagac ttgcctggtg aaaat 45

<210> SEQ ID NO 1584
<211> LENGTH: 45
<212> TYPE: DNA
<213> ORGANISM: Homo sapiens

<400> SEQUENCE: 1584
ctgaaaaaga tggatgcttc caatctggat tcaatgagga gactt 45

<210> SEQ ID NO 1585
<211> LENGTH: 45
<212> TYPE: DNA
<213> ORGANISM: Homo sapiens

<400> SEQUENCE: 1585
gcagcaaaga ggcactggca gaaaacaacc tgaaccttcc aaaga 45

<210> SEQ ID NO 1586
<211> LENGTH: 45
<212> TYPE: DNA
<213> ORGANISM: Homo sapiens

<400> SEQUENCE: 1586
gagacatgta acaagagtaa catgtgtgaa agcagcaaag aggca 45

<210> SEQ ID NO 1587
<211> LENGTH: 45
<212> TYPE: DNA
<213> ORGANISM: Homo sapiens

<400> SEQUENCE: 1587
gagaaaggag acatgtaaca agagtaacat gtgtgaaagc agcaa 45

<210> SEQ ID NO 1588
<211> LENGTH: 45
<212> TYPE: DNA
<213> ORGANISM: Homo sapiens

<400> SEQUENCE: 1588
tgagaaagga gacatgtaac aagagtaaca tgtgtgaaag cagca 45

<210> SEQ ID NO 1589
<211> LENGTH: 45
<212> TYPE: DNA
<213> ORGANISM: Homo sapiens

<400> SEQUENCE: 1589
cagccctgag aaaggagaca tgtaacaaga gtaacatgtg tgaaa 45

<210> SEQ ID NO 1590
<211> LENGTH: 45
<212> TYPE: DNA
<213> ORGANISM: Homo sapiens

<400> SEQUENCE: 1590
ctcagccctg agaaaggaga catgtaacaa gagtaacatg tgtga 45

<210> SEQ ID NO 1591
<211> LENGTH: 45
<212> TYPE: DNA
<213> ORGANISM: Homo sapiens

<400> SEQUENCE: 1591
tttatattgt atttatataa tgtataaatg gtttttatac caata 45

<210> SEQ ID NO 1592
<211> LENGTH: 45
<212> TYPE: DNA
<213> ORGANISM: Homo sapiens

<400> SEQUENCE: 1592
atttatattg tatttatata atgtataaat ggtttttata ccaat 45

<210> SEQ ID NO 1593
<211> LENGTH: 45
<212> TYPE: DNA
<213> ORGANISM: Homo sapiens

<400> SEQUENCE: 1593
tatttatatt gtatttatat aatgtataaa tggtttttat accaa 45

<210> SEQ ID NO 1594
<211> LENGTH: 45
<212> TYPE: DNA
<213> ORGANISM: Homo sapiens

<400> SEQUENCE: 1594
aagaaatatt tatattgtat ttatataatg tataaatggt tttta 45

<210> SEQ ID NO 1595
<211> LENGTH: 45
<212> TYPE: DNA
<213> ORGANISM: Mus sp.

<400> SEQUENCE: 1595
aagtgtcact tgaaatgtta tatgttatag ttttgaaatg ataac 45

<210> SEQ ID NO 1596
<211> LENGTH: 45
<212> TYPE: DNA
<213> ORGANISM: Mus sp.

<400> SEQUENCE: 1596
atataatcag gaaatttgcc tattgaaaat ttcctctggt cttct 45

<210> SEQ ID NO 1597
<211> LENGTH: 45
<212> TYPE: DNA
<213> ORGANISM: Mus sp.

<400> SEQUENCE: 1597
gtttacctca atgaattgct aatttaaata tgtttttaaa gaaat 45

<210> SEQ ID NO 1598
<211> LENGTH: 45
<212> TYPE: DNA
<213> ORGANISM: Mus sp.

<400> SEQUENCE: 1598
aagtaaactt taagttaatt tatgattgat atttattatt tttat 45

<210> SEQ ID NO 1599
<211> LENGTH: 45
<212> TYPE: DNA
<213> ORGANISM: Mus sp.

<400> SEQUENCE: 1599
tattttaatt atttttaatt tattgataat ttaaataagt aaact 45

<210> SEQ ID NO 1600
<211> LENGTH: 45
<212> TYPE: DNA
<213> ORGANISM: Mus sp.

<400> SEQUENCE: 1600
atgtataagt ttacctcaat gaattgctaa tttaaatatg ttttt 45

<210> SEQ ID NO 1601
<211> LENGTH: 45
<212> TYPE: DNA
<213> ORGANISM: Mus sp.

<400> SEQUENCE: 1601
taaataagta aactttaagt taatttatga ttgatattta ttatt 45

<210> SEQ ID NO 1602
<211> LENGTH: 45
<212> TYPE: DNA
<213> ORGANISM: Mus sp.

<400> SEQUENCE: 1602
tttaaataag taaactttaa gttaatttat gattgatatt tatta 45

<210> SEQ ID NO 1603
<211> LENGTH: 45
<212> TYPE: DNA
<213> ORGANISM: Mus sp.

<400> SEQUENCE: 1603
agaactgaca atatgaatgt tgggacacta ttttaattat tttta 45

<210> SEQ ID NO 1604
<211> LENGTH: 45
<212> TYPE: DNA
<213> ORGANISM: Mus sp.

<400> SEQUENCE: 1604
tcttggaatg tataagttta cctcaatgaa ttgctaattt aaata 45

<210> SEQ ID NO 1605
<211> LENGTH: 45
<212> TYPE: DNA
<213> ORGANISM: Mus sp.

<400> SEQUENCE: 1605
tagccagatg gtttcttgga atgtataagt ttacctcaat gaatt 45

<210> SEQ ID NO 1606
<211> LENGTH: 45
<212> TYPE: DNA
<213> ORGANISM: Mus sp.

<400> SEQUENCE: 1606
gaaaatatat cctgttgtca ggtatctgac ttatgttgtt ctcta 45

<210> SEQ ID NO 1607
<211> LENGTH: 45
<212> TYPE: DNA
<213> ORGANISM: Mus sp.

<400> SEQUENCE: 1607
tttaaatatg tttttaaaga aatctttgtg atgtattttt ataat 45

<210> SEQ ID NO 1608
<211> LENGTH: 45
<212> TYPE: DNA
<213> ORGANISM: Mus sp.

<400> SEQUENCE: 1608
ctattttaat tatttttaat ttattgataa tttaaataag taaac 45

<210> SEQ ID NO 1609
<211> LENGTH: 45
<212> TYPE: DNA
<213> ORGANISM: Mus sp.

<400> SEQUENCE: 1609
actgacaata tgaatgttgg gacactattt taattatttt taatt 45

<210> SEQ ID NO 1610
<211> LENGTH: 45
<212> TYPE: DNA
<213> ORGANISM: Mus sp.

<400> SEQUENCE: 1610
ctttgtgatg tatttttata atgtttagac tgtcttcaaa caaat 45

<210> SEQ ID NO 1611
<211> LENGTH: 45
<212> TYPE: DNA
<213> ORGANISM: Mus sp.

<400> SEQUENCE: 1611
tttatgaagt gtcacttgaa atgttatatg ttatagtttt gaaat 45

<210> SEQ ID NO 1612
<211> LENGTH: 45
<212> TYPE: DNA
<213> ORGANISM: Mus sp.

<400> SEQUENCE: 1612
ctaattcata tcttcaacca agaggtaaaa gatttacata aaata 45

<210> SEQ ID NO 1613
<211> LENGTH: 45
<212> TYPE: DNA
<213> ORGANISM: Mus sp.

<400> SEQUENCE: 1613
aaataagtaa actttaagtt aatttatgat tgatatttat tattt 45

<210> SEQ ID NO 1614
<211> LENGTH: 45
<212> TYPE: DNA
<213> ORGANISM: Mus sp.

<400> SEQUENCE: 1614
tcaggaaatt tgcctattga aaatttcctc tggtcttctg gagta 45

<210> SEQ ID NO 1615
<211> LENGTH: 45
<212> TYPE: DNA
<213> ORGANISM: Mus sp.

<400> SEQUENCE: 1615
acttcacaag tcggaggctt aattacacat gttctctggg aaatc 45

<210> SEQ ID NO 1616
<211> LENGTH: 45
<212> TYPE: DNA
<213> ORGANISM: Mus sp.

<400> SEQUENCE: 1616
cctagtgcgt tatgcctaag catatcagtt tgtggacatt cctca 45

<210> SEQ ID NO 1617
<211> LENGTH: 45
<212> TYPE: DNA
<213> ORGANISM: Mus sp.

<400> SEQUENCE: 1617
gatataatca ggaaatttgc ctattgaaaa tttcctctgg tcttc 45

<210> SEQ ID NO 1618
<211> LENGTH: 45
<212> TYPE: DNA
<213> ORGANISM: Mus sp.

<400> SEQUENCE: 1618
aatgataacc taaaaatcta tttgatataa atattctgtt accta 45

<210> SEQ ID NO 1619
<211> LENGTH: 45
<212> TYPE: DNA
<213> ORGANISM: Mus sp.

<400> SEQUENCE: 1619
ttatttttat gaagtgtcac ttgaaatgtt atatgttata gtttt 45

<210> SEQ ID NO 1620
<211> LENGTH: 45
<212> TYPE: DNA
<213> ORGANISM: Mus sp.

<400> SEQUENCE: 1620
attattttta atttattgat aatttaaata agtaaacttt aagtt 45

<210> SEQ ID NO 1621
<211> LENGTH: 45
<212> TYPE: DNA
<213> ORGANISM: Mus sp.

<400> SEQUENCE: 1621
tttaatttat tgataattta aataagtaaa ctttaagtta attta 45

<210> SEQ ID NO 1622
<211> LENGTH: 45
<212> TYPE: DNA
<213> ORGANISM: Mus sp.

<400> SEQUENCE: 1622
ttaatttatt gataatttaa ataagtaaac tttaagttaa tttat 45

<210> SEQ ID NO 1623
<211> LENGTH: 45
<212> TYPE: DNA
<213> ORGANISM: Mus sp.

<400> SEQUENCE: 1623
ttaaataagt aaactttaag ttaatttatg attgatattt attat 45

<210> SEQ ID NO 1624
<211> LENGTH: 45
<212> TYPE: DNA
<213> ORGANISM: Mus sp.

<400> SEQUENCE: 1624
aatttattga taatttaaat aagtaaactt taagttaatt tatga 45

<210> SEQ ID NO 1625
<211> LENGTH: 45
<212> TYPE: DNA
<213> ORGANISM: Mus sp.

<400> SEQUENCE: 1625
accaagacca tccaattcat cttgaaatca cttgaagaat ttcta 45

<210> SEQ ID NO 1626
<211> LENGTH: 45
<212> TYPE: DNA
<213> ORGANISM: Mus sp.

<400> SEQUENCE: 1626
gttctctacg aagaactgac aatatgaatg ttgggacact atttt 45

<210> SEQ ID NO 1627
<211> LENGTH: 45
<212> TYPE: DNA
<213> ORGANISM: Mus sp.

<400> SEQUENCE: 1627
atctgactta tgttgttctc tacgaagaac tgacaatatg aatgt 45

<210> SEQ ID NO 1628
<211> LENGTH: 45
<212> TYPE: DNA
<213> ORGANISM: Mus sp.

<400> SEQUENCE: 1628
cattcctcac tgtggtcaga aaatatatcc tgttgtcagg tatct 45

<210> SEQ ID NO 1629
<211> LENGTH: 45
<212> TYPE: DNA
<213> ORGANISM: Mus sp.

<400> SEQUENCE: 1629
tctgttacct agccagatgg tttcttggaa tgtataagtt tacct 45

<210> SEQ ID NO 1630
<211> LENGTH: 45
<212> TYPE: DNA
<213> ORGANISM: Mus sp.

<400> SEQUENCE: 1630
ttattatttt tatgaagtgt cacttgaaat gttatatgtt atagt 45

<210> SEQ ID NO 1631
<211> LENGTH: 45
<212> TYPE: DNA
<213> ORGANISM: Mus sp.

<400> SEQUENCE: 1631
taacctaaaa atctatttga tataaatatt ctgttaccta gccag 45

<210> SEQ ID NO 1632
<211> LENGTH: 45
<212> TYPE: DNA
<213> ORGANISM: Mus sp.

<400> SEQUENCE: 1632
taatttaaat atgtttttaa agaaatcttt gtgatgtatt tttat 45

<210> SEQ ID NO 1633
<211> LENGTH: 45
<212> TYPE: DNA
<213> ORGANISM: Mus sp.

<400> SEQUENCE: 1633
gttatatgtt atagttttga aatgataacc taaaaatcta tttga 45

<210> SEQ ID NO 1634
<211> LENGTH: 45
<212> TYPE: DNA
<213> ORGANISM: Mus sp.

<400> SEQUENCE: 1634
gctaccaaac tggatataat caggaaattt gcctattgaa aattt 45

<210> SEQ ID NO 1635
<211> LENGTH: 45
<212> TYPE: DNA
<213> ORGANISM: Mus sp.

<400> SEQUENCE: 1635
attcatatct tcaaccaaga ggtaaaagat ttacataaaa tagtc 45

<210> SEQ ID NO 1636
<211> LENGTH: 45
<212> TYPE: DNA

<213> ORGANISM: Mus sp.

<400> SEQUENCE: 1636
ctctgggaaa tcgtggaaat gagaaaagag ttgtgcaatg gcaat 45

<210> SEQ ID NO 1637
<211> LENGTH: 45
<212> TYPE: DNA
<213> ORGANISM: Mus sp.

<400> SEQUENCE: 1637
ataatttaaa taagtaaact ttaagttaat ttatgattga tattt 45

<210> SEQ ID NO 1638
<211> LENGTH: 45
<212> TYPE: DNA
<213> ORGANISM: Mus sp.

<400> SEQUENCE: 1638
aattattttt aatttattga taatttaaat aagtaaactt taagt 45

<210> SEQ ID NO 1639
<211> LENGTH: 45
<212> TYPE: DNA
<213> ORGANISM: Mus sp.

<400> SEQUENCE: 1639
tattgataat ttaaataagt aaactttaag ttaatttatg attga 45

<210> SEQ ID NO 1640
<211> LENGTH: 45
<212> TYPE: DNA
<213> ORGANISM: Mus sp.

<400> SEQUENCE: 1640
attacacatg ttctctggga aatcgtggaa atgagaaaag agttg 45

<210> SEQ ID NO 1641
<211> LENGTH: 45
<212> TYPE: DNA
<213> ORGANISM: Mus sp.

<400> SEQUENCE: 1641
caatctgaaa cttccagaga tacaaagaaa tgatggatgc tacca 45

<210> SEQ ID NO 1642
<211> LENGTH: 45
<212> TYPE: DNA
<213> ORGANISM: Mus sp.

<400> SEQUENCE: 1642
cgaagaactg acaatatgaa tgttgggaca ctattttaat tattt 45

<210> SEQ ID NO 1643
<211> LENGTH: 45
<212> TYPE: DNA
<213> ORGANISM: Mus sp.

<400> SEQUENCE: 1643
atgatgcact tgcagaaaac aatctgaaac ttccagagat acaaa 45

<210> SEQ ID NO 1644
<211> LENGTH: 45

<212> TYPE: DNA
<213> ORGANISM: Mus sp.

<400> SEQUENCE: 1644
tataatcagg aaatttgcct attgaaaatt tcctctggtc ttctg 45

<210> SEQ ID NO 1645
<211> LENGTH: 45
<212> TYPE: DNA
<213> ORGANISM: Mus sp.

<400> SEQUENCE: 1645
attcctcact gtggtcagaa aatatatcct gttgtcaggt atctg 45

<210> SEQ ID NO 1646
<211> LENGTH: 45
<212> TYPE: DNA
<213> ORGANISM: Mus sp.

<400> SEQUENCE: 1646
gataatttaa ataagtaaac tttaagttaa tttatgattg atatt 45

<210> SEQ ID NO 1647
<211> LENGTH: 45
<212> TYPE: DNA
<213> ORGANISM: Mus sp.

<400> SEQUENCE: 1647
tgaaatgtta tatgttatag ttttgaaatg ataacctaaa aatct 45

<210> SEQ ID NO 1648
<211> LENGTH: 45
<212> TYPE: DNA
<213> ORGANISM: Mus sp.

<400> SEQUENCE: 1648
aggaccaaga ccatccaatt catcttgaaa tcacttgaag aattt 45

<210> SEQ ID NO 1649
<211> LENGTH: 45
<212> TYPE: DNA
<213> ORGANISM: Mus sp.

<400> SEQUENCE: 1649
actttaagtt aatttatgat tgatatttat tatttttatg aagtg 45

<210> SEQ ID NO 1650
<211> LENGTH: 45
<212> TYPE: DNA
<213> ORGANISM: Mus sp.

<400> SEQUENCE: 1650
agtttacctc aatgaattgc taatttaaat atgtttttaa agaaa 45

<210> SEQ ID NO 1651
<211> LENGTH: 45
<212> TYPE: DNA
<213> ORGANISM: Mus sp.

<400> SEQUENCE: 1651
taaaatagtc cttcctaccc caatttccaa tgctctccta acaga 45

<210> SEQ ID NO 1652

<211> LENGTH: 45
<212> TYPE: DNA
<213> ORGANISM: Mus sp.

<400> SEQUENCE: 1652
cgctatgaag ttcctctctg caagagactt ccatccagtt gcctt 45

<210> SEQ ID NO 1653
<211> LENGTH: 45
<212> TYPE: DNA
<213> ORGANISM: Mus sp.

<400> SEQUENCE: 1653
aaatgatgga tgctaccaaa ctggatataa tcaggaaatt tgcct 45

<210> SEQ ID NO 1654
<211> LENGTH: 45
<212> TYPE: DNA
<213> ORGANISM: Mus sp.

<400> SEQUENCE: 1654
actattttaa ttatttttaa tttattgata atttaaataa gtaaa 45

<210> SEQ ID NO 1655
<211> LENGTH: 45
<212> TYPE: DNA
<213> ORGANISM: Mus sp.

<400> SEQUENCE: 1655
gagatacaaa gaaatgatgg atgctaccaa actggatata atcag 45

<210> SEQ ID NO 1656
<211> LENGTH: 45
<212> TYPE: DNA
<213> ORGANISM: Mus sp.

<400> SEQUENCE: 1656
atttgatata aatattctgt tacctagcca gatggtttct tggaa 45

<210> SEQ ID NO 1657
<211> LENGTH: 45
<212> TYPE: DNA
<213> ORGANISM: Mus sp.

<400> SEQUENCE: 1657
gtgtcacttg aaatgttata tgttatagtt ttgaaatgat aacct 45

<210> SEQ ID NO 1658
<211> LENGTH: 45
<212> TYPE: DNA
<213> ORGANISM: Mus sp.

<400> SEQUENCE: 1658
tgtataagtt tacctcaatg aattgctaat ttaaatatgt tttta 45

<210> SEQ ID NO 1659
<211> LENGTH: 45
<212> TYPE: DNA
<213> ORGANISM: Mus sp.

<400> SEQUENCE: 1659
atccaattca tcttgaaatc acttgaagaa tttctaaaag tcact 45

<210> SEQ ID NO 1660
<211> LENGTH: 45
<212> TYPE: DNA
<213> ORGANISM: Mus sp.

<400> SEQUENCE: 1660
aagtttacct caatgaattg ctaatttaaa tatgttttta aagaa 45

<210> SEQ ID NO 1661
<211> LENGTH: 45
<212> TYPE: DNA
<213> ORGANISM: Mus sp.

<400> SEQUENCE: 1661
tgatataaat attctgttac ctagccagat ggtttcttgg aatgt 45

<210> SEQ ID NO 1662
<211> LENGTH: 45
<212> TYPE: DNA
<213> ORGANISM: Mus sp.

<400> SEQUENCE: 1662
agccagatgg tttcttggaa tgtataagtt tacctcaatg aattg 45

<210> SEQ ID NO 1663
<211> LENGTH: 45
<212> TYPE: DNA
<213> ORGANISM: Mus sp.

<400> SEQUENCE: 1663
tttttatgaa gtgtcacttg aaatgttata tgttatagtt ttgaa 45

<210> SEQ ID NO 1664
<211> LENGTH: 45
<212> TYPE: DNA
<213> ORGANISM: Mus sp.

<400> SEQUENCE: 1664
tgataattta aataagtaaa ctttaagtta atttatgatt gatat 45

<210> SEQ ID NO 1665
<211> LENGTH: 45
<212> TYPE: DNA
<213> ORGANISM: Mus sp.

<400> SEQUENCE: 1665
cttgaaatgt tatatgttat agttttgaaa tgataaccta aaaat 45

<210> SEQ ID NO 1666
<211> LENGTH: 45
<212> TYPE: DNA
<213> ORGANISM: Mus sp.

<400> SEQUENCE: 1666
aatgagaaaa gagttgtgca atggcaattc tgattgtatg aacaa 45

<210> SEQ ID NO 1667
<211> LENGTH: 45
<212> TYPE: DNA
<213> ORGANISM: Mus sp.

<400> SEQUENCE: 1667
tccaattcat cttgaaatca cttgaagaat ttctaaaagt cactt 45

<210> SEQ ID NO 1668
<211> LENGTH: 45
<212> TYPE: DNA
<213> ORGANISM: Mus sp.

<400> SEQUENCE: 1668
cactatttta attattttta atttattgat aatttaaata agtaa 45

<210> SEQ ID NO 1669
<211> LENGTH: 45
<212> TYPE: DNA
<213> ORGANISM: Mus sp.

<400> SEQUENCE: 1669
aaacaatctg aaacttccag agatacaaag aaatgatgga tgcta 45

<210> SEQ ID NO 1670
<211> LENGTH: 45
<212> TYPE: DNA
<213> ORGANISM: Mus sp.

<400> SEQUENCE: 1670
atttaaataa gtaaacttta agttaattta tgattgatat ttatt 45

<210> SEQ ID NO 1671
<211> LENGTH: 45
<212> TYPE: DNA
<213> ORGANISM: Mus sp.

<400> SEQUENCE: 1671
ggaatgtata agtttacctc aatgaattgc taatttaaat atgtt 45

<210> SEQ ID NO 1672
<211> LENGTH: 45
<212> TYPE: DNA
<213> ORGANISM: Mus sp.

<400> SEQUENCE: 1672
ggacattcct cactgtggtc agaaaatata tcctgttgtc aggta 45

<210> SEQ ID NO 1673
<211> LENGTH: 45
<212> TYPE: DNA
<213> ORGANISM: Mus sp.

<400> SEQUENCE: 1673
tttgtgatgt atttttataa tgtttagact gtcttcaaac aaata 45

<210> SEQ ID NO 1674
<211> LENGTH: 45
<212> TYPE: DNA
<213> ORGANISM: Mus sp.

<400> SEQUENCE: 1674
aacctaaaaa tctatttgat ataaatattc tgttacctag ccaga 45

<210> SEQ ID NO 1675
<211> LENGTH: 45
<212> TYPE: DNA
<213> ORGANISM: Mus sp.

<400> SEQUENCE: 1675
ttgatattta ttatttttat gaagtgtcac ttgaaatgtt atatg 45

<210> SEQ ID NO 1676
<211> LENGTH: 45
<212> TYPE: DNA
<213> ORGANISM: Mus sp.

<400> SEQUENCE: 1676
aacgatgatg cacttgcaga aaacaatctg aaacttccag agata 45

<210> SEQ ID NO 1677
<211> LENGTH: 45
<212> TYPE: DNA
<213> ORGANISM: Mus sp.

<400> SEQUENCE: 1677
ctgacaatat gaatgttggg acactatttt aattattttt aattt 45

<210> SEQ ID NO 1678
<211> LENGTH: 45
<212> TYPE: DNA
<213> ORGANISM: Mus sp.

<400> SEQUENCE: 1678
ggatgctacc aaactggata taatcaggaa atttgcctat tgaaa 45

<210> SEQ ID NO 1679
<211> LENGTH: 45
<212> TYPE: DNA
<213> ORGANISM: Mus sp.

<400> SEQUENCE: 1679
atctttgtga tgtattttta taatgtttag actgtcttca aacaa 45

<210> SEQ ID NO 1680
<211> LENGTH: 45
<212> TYPE: DNA
<213> ORGANISM: Mus sp.

<400> SEQUENCE: 1680
aggcttaatt acacatgttc tctgggaaat cgtggaaatg agaaa 45

<210> SEQ ID NO 1681
<211> LENGTH: 45
<212> TYPE: DNA
<213> ORGANISM: Mus sp.

<400> SEQUENCE: 1681
atcttgaaat cacttgaaga atttctaaaa gtcactttga gatct 45

<210> SEQ ID NO 1682
<211> LENGTH: 45
<212> TYPE: DNA
<213> ORGANISM: Mus sp.

<400> SEQUENCE: 1682
ccaagaccat ccaattcatc ttgaaatcac ttgaagaatt tctaa 45

<210> SEQ ID NO 1683
<211> LENGTH: 45
<212> TYPE: DNA
<213> ORGANISM: Mus sp.

<400> SEQUENCE: 1683
gaaatgagaa aagagttgtg caatggcaat tctgattgta tgaac 45

<210> SEQ ID NO 1684
<211> LENGTH: 45
<212> TYPE: DNA
<213> ORGANISM: Mus sp.

<400> SEQUENCE: 1684
gaaactctaa ttcatatctt caaccaagag gtaaaagatt tacat 45

<210> SEQ ID NO 1685
<211> LENGTH: 45
<212> TYPE: DNA
<213> ORGANISM: Mus sp.

<400> SEQUENCE: 1685
gatataaata ttctgttacc tagccagatg gtttcttgga atgta 45

<210> SEQ ID NO 1686
<211> LENGTH: 45
<212> TYPE: DNA
<213> ORGANISM: Mus sp.

<400> SEQUENCE: 1686
tggaatgtat aagtttacct caatgaattg ctaatttaaa tatgt 45

<210> SEQ ID NO 1687
<211> LENGTH: 45
<212> TYPE: DNA
<213> ORGANISM: Mus sp.

<400> SEQUENCE: 1687
gaccatccaa ttcatcttga aatcacttga agaatttcta aaagt 45

<210> SEQ ID NO 1688
<211> LENGTH: 45
<212> TYPE: DNA
<213> ORGANISM: Mus sp.

<400> SEQUENCE: 1688
aaactttaag ttaatttatg attgatattt attattttta tgaag 45

<210> SEQ ID NO 1689
<211> LENGTH: 45
<212> TYPE: DNA
<213> ORGANISM: Mus sp.

<400> SEQUENCE: 1689
ggatataatc aggaaatttg cctattgaaa atttcctctg gtctt 45

<210> SEQ ID NO 1690
<211> LENGTH: 45
<212> TYPE: DNA
<213> ORGANISM: Mus sp.

<400> SEQUENCE: 1690
cctagccaga tggtttcttg gaatgtataa gtttacctca atgaa 45

<210> SEQ ID NO 1691
<211> LENGTH: 45
<212> TYPE: DNA
<213> ORGANISM: Mus sp.

<400> SEQUENCE: 1691
tttttaattt attgataatt taaataagta aactttaagt taatt 45

<210> SEQ ID NO 1692
<211> LENGTH: 45
<212> TYPE: DNA
<213> ORGANISM: Mus sp.

<400> SEQUENCE: 1692
acttgcagaa aacaatctga aacttccaga gatacaaaga aatga 45

<210> SEQ ID NO 1693
<211> LENGTH: 45
<212> TYPE: DNA
<213> ORGANISM: Mus sp.

<400> SEQUENCE: 1693
ccacttcaca agtcggaggc ttaattacac atgttctctg ggaaa 45

<210> SEQ ID NO 1694
<211> LENGTH: 45
<212> TYPE: DNA
<213> ORGANISM: Mus sp.

<400> SEQUENCE: 1694
ttgataattt aaataagtaa actttaagtt aatttatgat tgata 45

<210> SEQ ID NO 1695
<211> LENGTH: 20
<212> TYPE: RNA
<213> ORGANISM: Homo sapiens

<400> SEQUENCE: 1695
auggacauga gauaauguua 20

<210> SEQ ID NO 1696
<211> LENGTH: 20
<212> TYPE: RNA
<213> ORGANISM: Homo sapiens

<400> SEQUENCE: 1696
uuuagaugcu gaugauuugu 20

<210> SEQ ID NO 1697
<211> LENGTH: 20
<212> TYPE: RNA
<213> ORGANISM: Homo sapiens

<400> SEQUENCE: 1697
uuucacuuua gaugcugaug 20

<210> SEQ ID NO 1698
<211> LENGTH: 20
<212> TYPE: RNA
<213> ORGANISM: Homo sapiens

<400> SEQUENCE: 1698
uagaugcuga ugauuuguuu 20

<210> SEQ ID NO 1699
<211> LENGTH: 20
<212> TYPE: RNA
<213> ORGANISM: Homo sapiens

```
<400> SEQUENCE: 1699

gaggauauau uuucacuuug                                           20

<210> SEQ ID NO 1700
<211> LENGTH: 20
<212> TYPE: RNA
<213> ORGANISM: Homo sapiens

<400> SEQUENCE: 1700

ccagcauugc ugguucuauu                                           20

<210> SEQ ID NO 1701
<211> LENGTH: 20
<212> TYPE: RNA
<213> ORGANISM: Homo sapiens

<400> SEQUENCE: 1701

auuuucacuu ugugauuauu                                           20

<210> SEQ ID NO 1702
<211> LENGTH: 20
<212> TYPE: RNA
<213> ORGANISM: Homo sapiens

<400> SEQUENCE: 1702

gccuucauga caacucauuc                                           20

<210> SEQ ID NO 1703
<211> LENGTH: 20
<212> TYPE: RNA
<213> ORGANISM: Homo sapiens

<400> SEQUENCE: 1703

uuugugauua uuucacuuua                                           20

<210> SEQ ID NO 1704
<211> LENGTH: 20
<212> TYPE: RNA
<213> ORGANISM: Homo sapiens

<400> SEQUENCE: 1704

guuugaggau auauuuucac                                           20

<210> SEQ ID NO 1705
<211> LENGTH: 20
<212> TYPE: RNA
<213> ORGANISM: Homo sapiens

<400> SEQUENCE: 1705

uggacaugag auaauguuag                                           20

<210> SEQ ID NO 1706
<211> LENGTH: 20
<212> TYPE: RNA
<213> ORGANISM: Homo sapiens

<400> SEQUENCE: 1706

ucugggaguc cccuuuucuu                                           20

<210> SEQ ID NO 1707
<211> LENGTH: 20
<212> TYPE: RNA
<213> ORGANISM: Homo sapiens
```

<400> SEQUENCE: 1707
uaaacaggcc cagcauugcu 20

<210> SEQ ID NO 1708
<211> LENGTH: 20
<212> TYPE: RNA
<213> ORGANISM: Homo sapiens

<400> SEQUENCE: 1708
caugacaacu cauuccuggg 20

<210> SEQ ID NO 1709
<211> LENGTH: 20
<212> TYPE: RNA
<213> ORGANISM: Homo sapiens

<400> SEQUENCE: 1709
agauaauguu agagguuuua 20

<210> SEQ ID NO 1710
<211> LENGTH: 20
<212> TYPE: RNA
<213> ORGANISM: Homo sapiens

<400> SEQUENCE: 1710
accaaguuca cccucguacu 20

<210> SEQ ID NO 1711
<211> LENGTH: 20
<212> TYPE: RNA
<213> ORGANISM: Homo sapiens

<400> SEQUENCE: 1711
agcagcaaca ggaaccuugg 20

<210> SEQ ID NO 1712
<211> LENGTH: 20
<212> TYPE: RNA
<213> ORGANISM: Homo sapiens

<400> SEQUENCE: 1712
uuuucacuuu gugauuauuu 20

<210> SEQ ID NO 1713
<211> LENGTH: 20
<212> TYPE: RNA
<213> ORGANISM: Homo sapiens

<400> SEQUENCE: 1713
gauaauguua gagguuuuaa 20

<210> SEQ ID NO 1714
<211> LENGTH: 20
<212> TYPE: RNA
<213> ORGANISM: Homo sapiens

<400> SEQUENCE: 1714
uuugcacccc ucccauuagg 20

<210> SEQ ID NO 1715
<211> LENGTH: 20
<212> TYPE: RNA

<213> ORGANISM: Homo sapiens

<400> SEQUENCE: 1715
uagagauuga aaacaccagc 20

<210> SEQ ID NO 1716
<211> LENGTH: 20
<212> TYPE: RNA
<213> ORGANISM: Homo sapiens

<400> SEQUENCE: 1716
aaaggaguga aaccuuuagg 20

<210> SEQ ID NO 1717
<211> LENGTH: 20
<212> TYPE: RNA
<213> ORGANISM: Homo sapiens

<400> SEQUENCE: 1717
cuggguuggu gcacagugau 20

<210> SEQ ID NO 1718
<211> LENGTH: 20
<212> TYPE: RNA
<213> ORGANISM: Homo sapiens

<400> SEQUENCE: 1718
uauauuuuca cuuugugauu 20

<210> SEQ ID NO 1719
<211> LENGTH: 20
<212> TYPE: RNA
<213> ORGANISM: Homo sapiens

<400> SEQUENCE: 1719
uuuaaacagg cccagcauug 20

<210> SEQ ID NO 1720
<211> LENGTH: 20
<212> TYPE: RNA
<213> ORGANISM: Homo sapiens

<400> SEQUENCE: 1720
cccucaaacc uccucuucug 20

<210> SEQ ID NO 1721
<211> LENGTH: 20
<212> TYPE: RNA
<213> ORGANISM: Homo sapiens

<400> SEQUENCE: 1721
cuuuagaugc ugaugauuug 20

<210> SEQ ID NO 1722
<211> LENGTH: 20
<212> TYPE: RNA
<213> ORGANISM: Homo sapiens

<400> SEQUENCE: 1722
gcugguuuug uaagaugcug 20

<210> SEQ ID NO 1723
<211> LENGTH: 20

<212> TYPE: RNA
<213> ORGANISM: Homo sapiens

<400> SEQUENCE: 1723
cacggcauug uggucuccau 20

<210> SEQ ID NO 1724
<211> LENGTH: 20
<212> TYPE: RNA
<213> ORGANISM: Homo sapiens

<400> SEQUENCE: 1724
ucacuuugug auuauuucac 20

<210> SEQ ID NO 1725
<211> LENGTH: 20
<212> TYPE: RNA
<213> ORGANISM: Homo sapiens

<400> SEQUENCE: 1725
gcugguucua uuuaauggac 20

<210> SEQ ID NO 1726
<211> LENGTH: 20
<212> TYPE: RNA
<213> ORGANISM: Homo sapiens

<400> SEQUENCE: 1726
agcaguggca accagaauga 20

<210> SEQ ID NO 1727
<211> LENGTH: 20
<212> TYPE: RNA
<213> ORGANISM: Homo sapiens

<400> SEQUENCE: 1727
cuuggcaggc aauuaugauc 20

<210> SEQ ID NO 1728
<211> LENGTH: 20
<212> TYPE: RNA
<213> ORGANISM: Homo sapiens

<400> SEQUENCE: 1728
agcgaagcca acaacuaugg 20

<210> SEQ ID NO 1729
<211> LENGTH: 20
<212> TYPE: RNA
<213> ORGANISM: Homo sapiens

<400> SEQUENCE: 1729
gaagccaaca acuaugggac 20

<210> SEQ ID NO 1730
<211> LENGTH: 20
<212> TYPE: RNA
<213> ORGANISM: Homo sapiens

<400> SEQUENCE: 1730
ggagacugcu ucccauccua 20

<210> SEQ ID NO 1731

<211> LENGTH: 20
<212> TYPE: RNA
<213> ORGANISM: Homo sapiens

<400> SEQUENCE: 1731
ucauagguca cuggcucucc 20

<210> SEQ ID NO 1732
<211> LENGTH: 20
<212> TYPE: RNA
<213> ORGANISM: Homo sapiens

<400> SEQUENCE: 1732
ugugauuauu ucacuuuaga 20

<210> SEQ ID NO 1733
<211> LENGTH: 20
<212> TYPE: RNA
<213> ORGANISM: Homo sapiens

<400> SEQUENCE: 1733
acuuuagaug cugaugauuu 20

<210> SEQ ID NO 1734
<211> LENGTH: 20
<212> TYPE: RNA
<213> ORGANISM: Homo sapiens

<400> SEQUENCE: 1734
uauuuaaugg acaugagaua 20

<210> SEQ ID NO 1735
<211> LENGTH: 20
<212> TYPE: RNA
<213> ORGANISM: Homo sapiens

<400> SEQUENCE: 1735
uauagcaccg agaaugacgu 20

<210> SEQ ID NO 1736
<211> LENGTH: 20
<212> TYPE: RNA
<213> ORGANISM: Homo sapiens

<400> SEQUENCE: 1736
cauugcuggu ucuauuuaau 20

<210> SEQ ID NO 1737
<211> LENGTH: 20
<212> TYPE: RNA
<213> ORGANISM: Homo sapiens

<400> SEQUENCE: 1737
gacaugagau aauguuagag 20

<210> SEQ ID NO 1738
<211> LENGTH: 20
<212> TYPE: RNA
<213> ORGANISM: Homo sapiens

<400> SEQUENCE: 1738
augauccugg ggccaguuuu 20

<210> SEQ ID NO 1739
<211> LENGTH: 20
<212> TYPE: RNA
<213> ORGANISM: Homo sapiens

<400> SEQUENCE: 1739
gggccuucau gacaacucau 20

<210> SEQ ID NO 1740
<211> LENGTH: 20
<212> TYPE: RNA
<213> ORGANISM: Homo sapiens

<400> SEQUENCE: 1740
uuauuucacu uuagaugcug 20

<210> SEQ ID NO 1741
<211> LENGTH: 20
<212> TYPE: RNA
<213> ORGANISM: Homo sapiens

<400> SEQUENCE: 1741
uuaauggaca ugagauaaug 20

<210> SEQ ID NO 1742
<211> LENGTH: 20
<212> TYPE: RNA
<213> ORGANISM: Homo sapiens

<400> SEQUENCE: 1742
gccaauaaga accucacaug 20

<210> SEQ ID NO 1743
<211> LENGTH: 20
<212> TYPE: RNA
<213> ORGANISM: Homo sapiens

<400> SEQUENCE: 1743
aaagacaucg ggaaacggcu 20

<210> SEQ ID NO 1744
<211> LENGTH: 20
<212> TYPE: RNA
<213> ORGANISM: Homo sapiens

<400> SEQUENCE: 1744
cccauuagga caaucagucc 20

<210> SEQ ID NO 1745
<211> LENGTH: 20
<212> TYPE: RNA
<213> ORGANISM: Homo sapiens

<400> SEQUENCE: 1745
gauggguuua augacugggc 20

<210> SEQ ID NO 1746
<211> LENGTH: 20
<212> TYPE: RNA
<213> ORGANISM: Homo sapiens

<400> SEQUENCE: 1746
aucucagggg cuguuugagg 20

<210> SEQ ID NO 1747
<211> LENGTH: 20
<212> TYPE: RNA
<213> ORGANISM: Homo sapiens

<400> SEQUENCE: 1747
uguaagaugc uggguuggug 20

<210> SEQ ID NO 1748
<211> LENGTH: 20
<212> TYPE: RNA
<213> ORGANISM: Homo sapiens

<400> SEQUENCE: 1748
cugguucuau uuaauggaca 20

<210> SEQ ID NO 1749
<211> LENGTH: 20
<212> TYPE: RNA
<213> ORGANISM: Homo sapiens

<400> SEQUENCE: 1749
uucaccaaca cgugggcugu 20

<210> SEQ ID NO 1750
<211> LENGTH: 20
<212> TYPE: RNA
<213> ORGANISM: Homo sapiens

<400> SEQUENCE: 1750
ugcgcucugg cuuuaguuuu 20

<210> SEQ ID NO 1751
<211> LENGTH: 20
<212> TYPE: RNA
<213> ORGANISM: Homo sapiens

<400> SEQUENCE: 1751
uuccaugugg agaaaggagu 20

<210> SEQ ID NO 1752
<211> LENGTH: 20
<212> TYPE: RNA
<213> ORGANISM: Homo sapiens

<400> SEQUENCE: 1752
ucuauuuaau ggacaugaga 20

<210> SEQ ID NO 1753
<211> LENGTH: 20
<212> TYPE: RNA
<213> ORGANISM: Homo sapiens

<400> SEQUENCE: 1753
uagagguuuu aaagugauua 20

<210> SEQ ID NO 1754
<211> LENGTH: 20
<212> TYPE: RNA
<213> ORGANISM: Homo sapiens

<400> SEQUENCE: 1754
agaagaacca cccggacuug 20

-continued

<210> SEQ ID NO 1755
<211> LENGTH: 20
<212> TYPE: RNA
<213> ORGANISM: Homo sapiens

<400> SEQUENCE: 1755
cuguuugagg auauauuuuc                                          20

<210> SEQ ID NO 1756
<211> LENGTH: 20
<212> TYPE: RNA
<213> ORGANISM: Homo sapiens

<400> SEQUENCE: 1756
auggguuuaa ugacugggcc                                          20

<210> SEQ ID NO 1757
<211> LENGTH: 20
<212> TYPE: RNA
<213> ORGANISM: Homo sapiens

<400> SEQUENCE: 1757
gguuuaauga cugggccuuc                                          20

<210> SEQ ID NO 1758
<211> LENGTH: 20
<212> TYPE: RNA
<213> ORGANISM: Homo sapiens

<400> SEQUENCE: 1758
uuuaucaaag accagagcgc                                          20

<210> SEQ ID NO 1759
<211> LENGTH: 20
<212> TYPE: RNA
<213> ORGANISM: Homo sapiens

<400> SEQUENCE: 1759
ucaggggcug uuugaggaua                                          20

<210> SEQ ID NO 1760
<211> LENGTH: 20
<212> TYPE: RNA
<213> ORGANISM: Homo sapiens

<400> SEQUENCE: 1760
auuucacuuu agaugcugau                                          20

<210> SEQ ID NO 1761
<211> LENGTH: 20
<212> TYPE: RNA
<213> ORGANISM: Homo sapiens

<400> SEQUENCE: 1761
aacaccagcg aagccaacaa                                          20

<210> SEQ ID NO 1762
<211> LENGTH: 20
<212> TYPE: RNA
<213> ORGANISM: Homo sapiens

<400> SEQUENCE: 1762
cuggucuucg ucacugucuu 20

<210> SEQ ID NO 1763
<211> LENGTH: 20
<212> TYPE: RNA
<213> ORGANISM: Homo sapiens

<400> SEQUENCE: 1763
gcagcaacag gaaccuuggu 20

<210> SEQ ID NO 1764
<211> LENGTH: 20
<212> TYPE: RNA
<213> ORGANISM: Homo sapiens

<400> SEQUENCE: 1764
gaagguguac accauggacc 20

<210> SEQ ID NO 1765
<211> LENGTH: 20
<212> TYPE: RNA
<213> ORGANISM: Homo sapiens

<400> SEQUENCE: 1765
gcaaccagaa ugagaagcag 20

<210> SEQ ID NO 1766
<211> LENGTH: 20
<212> TYPE: RNA
<213> ORGANISM: Homo sapiens

<400> SEQUENCE: 1766
cacccugucc uauaaucgcc 20

<210> SEQ ID NO 1767
<211> LENGTH: 20
<212> TYPE: RNA
<213> ORGANISM: Homo sapiens

<400> SEQUENCE: 1767
auugcugguu cuauuuaaug 20

<210> SEQ ID NO 1768
<211> LENGTH: 20
<212> TYPE: RNA
<213> ORGANISM: Homo sapiens

<400> SEQUENCE: 1768
guacacacag augaaugaca 20

<210> SEQ ID NO 1769
<211> LENGTH: 20
<212> TYPE: RNA
<213> ORGANISM: Homo sapiens

<400> SEQUENCE: 1769
caggggcugu uugaggauau 20

<210> SEQ ID NO 1770
<211> LENGTH: 20
<212> TYPE: RNA
<213> ORGANISM: Homo sapiens

<400> SEQUENCE: 1770
gauuauuuca cuuuagaugc 20

<210> SEQ ID NO 1771
<211> LENGTH: 20
<212> TYPE: RNA
<213> ORGANISM: Homo sapiens

<400> SEQUENCE: 1771
uccccuccuu gggcacuuuu 20

<210> SEQ ID NO 1772
<211> LENGTH: 20
<212> TYPE: RNA
<213> ORGANISM: Homo sapiens

<400> SEQUENCE: 1772
uggcaaagcg acggacuaaa 20

<210> SEQ ID NO 1773
<211> LENGTH: 20
<212> TYPE: RNA
<213> ORGANISM: Homo sapiens

<400> SEQUENCE: 1773
uuuggcaacg ugccguggua 20

<210> SEQ ID NO 1774
<211> LENGTH: 20
<212> TYPE: RNA
<213> ORGANISM: Homo sapiens

<400> SEQUENCE: 1774
ggaggccaau aagaaccuca 20

<210> SEQ ID NO 1775
<211> LENGTH: 20
<212> TYPE: RNA
<213> ORGANISM: Homo sapiens

<400> SEQUENCE: 1775
auccacaucu acagugccag 20

<210> SEQ ID NO 1776
<211> LENGTH: 20
<212> TYPE: RNA
<213> ORGANISM: Homo sapiens

<400> SEQUENCE: 1776
ggguuuaaug acugggccuu 20

<210> SEQ ID NO 1777
<211> LENGTH: 20
<212> TYPE: RNA
<213> ORGANISM: Homo sapiens

<400> SEQUENCE: 1777
cuagagauug aaaacaccag 20

<210> SEQ ID NO 1778
<211> LENGTH: 20
<212> TYPE: RNA
<213> ORGANISM: Homo sapiens

```
<400> SEQUENCE: 1778

ccugguugcu auggguggua                                            20

<210> SEQ ID NO 1779
<211> LENGTH: 20
<212> TYPE: RNA
<213> ORGANISM: Homo sapiens

<400> SEQUENCE: 1779

gccaguuuug augucaauga                                            20

<210> SEQ ID NO 1780
<211> LENGTH: 20
<212> TYPE: RNA
<213> ORGANISM: Homo sapiens

<400> SEQUENCE: 1780

auggcgaggu gacagaugca                                            20

<210> SEQ ID NO 1781
<211> LENGTH: 20
<212> TYPE: RNA
<213> ORGANISM: Homo sapiens

<400> SEQUENCE: 1781

uguccuauaa ucgccguggc                                            20

<210> SEQ ID NO 1782
<211> LENGTH: 20
<212> TYPE: RNA
<213> ORGANISM: Homo sapiens

<400> SEQUENCE: 1782

cuccgcagau ggguuuaaug                                            20

<210> SEQ ID NO 1783
<211> LENGTH: 20
<212> TYPE: RNA
<213> ORGANISM: Homo sapiens

<400> SEQUENCE: 1783

gucccucuaa agcaauaaug                                            20

<210> SEQ ID NO 1784
<211> LENGTH: 20
<212> TYPE: RNA
<213> ORGANISM: Homo sapiens

<400> SEQUENCE: 1784

ggaucucagg ggcuguuuga                                            20

<210> SEQ ID NO 1785
<211> LENGTH: 20
<212> TYPE: RNA
<213> ORGANISM: Homo sapiens

<400> SEQUENCE: 1785

ccggacuugg caggcaauua                                            20

<210> SEQ ID NO 1786
<211> LENGTH: 20
<212> TYPE: RNA
<213> ORGANISM: Homo sapiens
```

<400> SEQUENCE: 1786
caggcaauua ugauccuggg 20

<210> SEQ ID NO 1787
<211> LENGTH: 20
<212> TYPE: RNA
<213> ORGANISM: Homo sapiens

<400> SEQUENCE: 1787
agccucggua cacacagaug 20

<210> SEQ ID NO 1788
<211> LENGTH: 20
<212> TYPE: RNA
<213> ORGANISM: Homo sapiens

<400> SEQUENCE: 1788
gcuacaccaa caguaucuac 20

<210> SEQ ID NO 1789
<211> LENGTH: 20
<212> TYPE: RNA
<213> ORGANISM: Homo sapiens

<400> SEQUENCE: 1789
uggucuucgu cacugucuuc 20

<210> SEQ ID NO 1790
<211> LENGTH: 20
<212> TYPE: RNA
<213> ORGANISM: Homo sapiens

<400> SEQUENCE: 1790
uuuguaagau gcugguuugg 20

<210> SEQ ID NO 1791
<211> LENGTH: 20
<212> TYPE: RNA
<213> ORGANISM: Homo sapiens

<400> SEQUENCE: 1791
guucuauuua auggacauga 20

<210> SEQ ID NO 1792
<211> LENGTH: 20
<212> TYPE: RNA
<213> ORGANISM: Homo sapiens

<400> SEQUENCE: 1792
guuagagguu uuaaagugau 20

<210> SEQ ID NO 1793
<211> LENGTH: 20
<212> TYPE: RNA
<213> ORGANISM: Homo sapiens

<400> SEQUENCE: 1793
gcaauuauga uccuggggcc 20

<210> SEQ ID NO 1794
<211> LENGTH: 20
<212> TYPE: RNA

<213> ORGANISM: Homo sapiens

<400> SEQUENCE: 1794
uggggccagu uuugauguca 20

<210> SEQ ID NO 1795
<211> LENGTH: 45
<212> TYPE: DNA
<213> ORGANISM: Homo sapiens

<400> SEQUENCE: 1795
tgctggttct atttaatgga catgagataa tgttagaggt tttaa 45

<210> SEQ ID NO 1796
<211> LENGTH: 45
<212> TYPE: DNA
<213> ORGANISM: Homo sapiens

<400> SEQUENCE: 1796
ttgtgattat ttcactttag atgctgatga tttgtttttg tattt 45

<210> SEQ ID NO 1797
<211> LENGTH: 45
<212> TYPE: DNA
<213> ORGANISM: Homo sapiens

<400> SEQUENCE: 1797
ttcactttgt gattatttca ctttagatgc tgatgatttg ttttt 45

<210> SEQ ID NO 1798
<211> LENGTH: 45
<212> TYPE: DNA
<213> ORGANISM: Homo sapiens

<400> SEQUENCE: 1798
gtgattattt cactttagat gctgatgatt tgtttttgta ttttt 45

<210> SEQ ID NO 1799
<211> LENGTH: 45
<212> TYPE: DNA
<213> ORGANISM: Homo sapiens

<400> SEQUENCE: 1799
tctcaggggc tgtttgagga tatattttca ctttgtgatt atttc 45

<210> SEQ ID NO 1800
<211> LENGTH: 45
<212> TYPE: DNA
<213> ORGANISM: Homo sapiens

<400> SEQUENCE: 1800
gtaatttaaa caggcccagc attgctggtt ctatttaatg gacat 45

<210> SEQ ID NO 1801
<211> LENGTH: 45
<212> TYPE: DNA
<213> ORGANISM: Homo sapiens

<400> SEQUENCE: 1801
gctgtttgag gatatatttt cactttgtga ttatttcact ttaga 45

<210> SEQ ID NO 1802
<211> LENGTH: 45

<212> TYPE: DNA
<213> ORGANISM: Homo sapiens

<400> SEQUENCE: 1802
gggtttaatg actgggcctt catgacaact cattcctggg atgag 45

<210> SEQ ID NO 1803
<211> LENGTH: 45
<212> TYPE: DNA
<213> ORGANISM: Homo sapiens

<400> SEQUENCE: 1803
aggatatatt ttcactttgt gattatttca ctttagatgc tgatg 45

<210> SEQ ID NO 1804
<211> LENGTH: 45
<212> TYPE: DNA
<213> ORGANISM: Homo sapiens

<400> SEQUENCE: 1804
gggatctcag ggctgtttg aggatatatt ttcactttgt gatta 45

<210> SEQ ID NO 1805
<211> LENGTH: 45
<212> TYPE: DNA
<213> ORGANISM: Homo sapiens

<400> SEQUENCE: 1805
gctggttcta tttaatggac atgagataat gttagaggtt ttaaa 45

<210> SEQ ID NO 1806
<211> LENGTH: 45
<212> TYPE: DNA
<213> ORGANISM: Homo sapiens

<400> SEQUENCE: 1806
atcagtcccc tcccatctgg gagtcccctt ttcttttcta cccta 45

<210> SEQ ID NO 1807
<211> LENGTH: 45
<212> TYPE: DNA
<213> ORGANISM: Homo sapiens

<400> SEQUENCE: 1807
ttttttcttg taatttaaac aggcccagca ttgctggttc tattt 45

<210> SEQ ID NO 1808
<211> LENGTH: 45
<212> TYPE: DNA
<213> ORGANISM: Homo sapiens

<400> SEQUENCE: 1808
taatgactgg gccttcatga caactcattc ctgggatgag gatcc 45

<210> SEQ ID NO 1809
<211> LENGTH: 45
<212> TYPE: DNA
<213> ORGANISM: Homo sapiens

<400> SEQUENCE: 1809
tatttaatgg acatgagata atgttagagg ttttaaagtg attaa 45

<210> SEQ ID NO 1810

<211> LENGTH: 45
<212> TYPE: DNA
<213> ORGANISM: Homo sapiens

<400> SEQUENCE: 1810
aactatggga cgctgaccaa gttcaccctc gtactctatg gcacc 45

<210> SEQ ID NO 1811
<211> LENGTH: 45
<212> TYPE: DNA
<213> ORGANISM: Homo sapiens

<400> SEQUENCE: 1811
gttgctatgg gtggtagcag caacaggaac cttggtcctg ctagc 45

<210> SEQ ID NO 1812
<211> LENGTH: 45
<212> TYPE: DNA
<213> ORGANISM: Homo sapiens

<400> SEQUENCE: 1812
ctgtttgagg atatattttc actttgtgat tatttcactt tagat 45

<210> SEQ ID NO 1813
<211> LENGTH: 45
<212> TYPE: DNA
<213> ORGANISM: Homo sapiens

<400> SEQUENCE: 1813
atttaatgga catgagataa tgttagaggt tttaaagtga ttaaa 45

<210> SEQ ID NO 1814
<211> LENGTH: 45
<212> TYPE: DNA
<213> ORGANISM: Homo sapiens

<400> SEQUENCE: 1814
tcttctgacg tgccttttgc acccctccca ttaggacaat cagtc 45

<210> SEQ ID NO 1815
<211> LENGTH: 45
<212> TYPE: DNA
<213> ORGANISM: Homo sapiens

<400> SEQUENCE: 1815
ctggcgagtg ggtcctagag attgaaaaca ccagcgaagc caaca 45

<210> SEQ ID NO 1816
<211> LENGTH: 45
<212> TYPE: DNA
<213> ORGANISM: Homo sapiens

<400> SEQUENCE: 1816
cccttccatg tggagaaagg agtgaaacct ttagggcagc ttgcc 45

<210> SEQ ID NO 1817
<211> LENGTH: 45
<212> TYPE: DNA
<213> ORGANISM: Homo sapiens

<400> SEQUENCE: 1817
tggttttgta agatgctggg ttggtgcaca gtgatttttt tcttg 45

<210> SEQ ID NO 1818
<211> LENGTH: 45
<212> TYPE: DNA
<213> ORGANISM: Homo sapiens

<400> SEQUENCE: 1818
ggggctgttt gaggatatat tttcactttg tgattatttc acttt 45

<210> SEQ ID NO 1819
<211> LENGTH: 45
<212> TYPE: DNA
<213> ORGANISM: Homo sapiens

<400> SEQUENCE: 1819
atttttttct tgtaatttaa acaggcccag cattgctggt tctat 45

<210> SEQ ID NO 1820
<211> LENGTH: 45
<212> TYPE: DNA
<213> ORGANISM: Homo sapiens

<400> SEQUENCE: 1820
tgacctgtca tgcccccctc aaacctcctc ttctgacgtg ccttt 45

<210> SEQ ID NO 1821
<211> LENGTH: 45
<212> TYPE: DNA
<213> ORGANISM: Homo sapiens

<400> SEQUENCE: 1821
tttgtgatta tttcacttta gatgctgatg atttgttttt gtatt 45

<210> SEQ ID NO 1822
<211> LENGTH: 45
<212> TYPE: DNA
<213> ORGANISM: Homo sapiens

<400> SEQUENCE: 1822
ctcgtggcca gcccggctgg ttttgtaaga tgctgggttg gtgca 45

<210> SEQ ID NO 1823
<211> LENGTH: 45
<212> TYPE: DNA
<213> ORGANISM: Homo sapiens

<400> SEQUENCE: 1823
cagggctaca cagggcacgg cattgtggtc tccattctgg acgat 45

<210> SEQ ID NO 1824
<211> LENGTH: 45
<212> TYPE: DNA
<213> ORGANISM: Homo sapiens

<400> SEQUENCE: 1824
tttgaggata tattttcact ttgtgattat ttcactttag atgct 45

<210> SEQ ID NO 1825
<211> LENGTH: 45
<212> TYPE: DNA
<213> ORGANISM: Homo sapiens

<400> SEQUENCE: 1825
aacaggccca gcattgctgg ttctatttaa tggacatgag ataat 45

<210> SEQ ID NO 1826
<211> LENGTH: 45
<212> TYPE: DNA
<213> ORGANISM: Homo sapiens

<400> SEQUENCE: 1826
ctggccacga cctacagcag tggcaaccag aatgagaagc agatc                45

<210> SEQ ID NO 1827
<211> LENGTH: 45
<212> TYPE: DNA
<213> ORGANISM: Homo sapiens

<400> SEQUENCE: 1827
gaagaaccac ccggacttgg caggcaatta tgatcctggg gccag                45

<210> SEQ ID NO 1828
<211> LENGTH: 45
<212> TYPE: DNA
<213> ORGANISM: Homo sapiens

<400> SEQUENCE: 1828
gagattgaaa acaccagcga agccaacaac tatgggacgc tgacc                45

<210> SEQ ID NO 1829
<211> LENGTH: 45
<212> TYPE: DNA
<213> ORGANISM: Homo sapiens

<400> SEQUENCE: 1829
attgaaaaca ccagcgaagc caacaactat gggacgctga ccaag                45

<210> SEQ ID NO 1830
<211> LENGTH: 45
<212> TYPE: DNA
<213> ORGANISM: Homo sapiens

<400> SEQUENCE: 1830
ggaggcaaga ggggtggaga ctgcttccca tcctaccctc gggcc                45

<210> SEQ ID NO 1831
<211> LENGTH: 45
<212> TYPE: DNA
<213> ORGANISM: Homo sapiens

<400> SEQUENCE: 1831
cgccatgccg ggggttcata ggtcactggc tctccaagtg ccaga                45

<210> SEQ ID NO 1832
<211> LENGTH: 45
<212> TYPE: DNA
<213> ORGANISM: Homo sapiens

<400> SEQUENCE: 1832
gatatatttt cactttgtga ttatttcact ttagatgctg atgat                45

<210> SEQ ID NO 1833
<211> LENGTH: 45
<212> TYPE: DNA
<213> ORGANISM: Homo sapiens

<400> SEQUENCE: 1833
ctttgtgatt atttcacttt agatgctgat gatttgtttt tgtat                45

<210> SEQ ID NO 1834
<211> LENGTH: 45
<212> TYPE: DNA
<213> ORGANISM: Homo sapiens

<400> SEQUENCE: 1834
cagcattgct ggttctattt aatggacatg agataatgtt agagg 45

<210> SEQ ID NO 1835
<211> LENGTH: 45
<212> TYPE: DNA
<213> ORGANISM: Homo sapiens

<400> SEQUENCE: 1835
gtcctcgata cgcactatag caccgagaat gacgtggaga ccatc 45

<210> SEQ ID NO 1836
<211> LENGTH: 45
<212> TYPE: DNA
<213> ORGANISM: Homo sapiens

<400> SEQUENCE: 1836
tttaaacagg cccagcattg ctggttctat ttaatggaca tgaga 45

<210> SEQ ID NO 1837
<211> LENGTH: 45
<212> TYPE: DNA
<213> ORGANISM: Homo sapiens

<400> SEQUENCE: 1837
tggttctatt taatggacat gagataatgt tagaggtttt aaagt 45

<210> SEQ ID NO 1838
<211> LENGTH: 45
<212> TYPE: DNA
<213> ORGANISM: Homo sapiens

<400> SEQUENCE: 1838
acttggcagg caattatgat cctggggcca gttttgatgt caatg 45

<210> SEQ ID NO 1839
<211> LENGTH: 45
<212> TYPE: DNA
<213> ORGANISM: Homo sapiens

<400> SEQUENCE: 1839
atgggtttaa tgactgggcc ttcatgacaa ctcattcctg ggatg 45

<210> SEQ ID NO 1840
<211> LENGTH: 45
<212> TYPE: DNA
<213> ORGANISM: Homo sapiens

<400> SEQUENCE: 1840
attttcactt tgtgattatt tcactttaga tgctgatgat ttgtt 45

<210> SEQ ID NO 1841
<211> LENGTH: 45
<212> TYPE: DNA
<213> ORGANISM: Homo sapiens

<400> SEQUENCE: 1841
cattgctggt tctatttaat ggacatgaga taatgttaga ggttt 45

<210> SEQ ID NO 1842
<211> LENGTH: 45
<212> TYPE: DNA
<213> ORGANISM: Homo sapiens

<400> SEQUENCE: 1842
gctctcaccc tggaggccaa taagaacctc acatggcggg acatg 45

<210> SEQ ID NO 1843
<211> LENGTH: 45
<212> TYPE: DNA
<213> ORGANISM: Homo sapiens

<400> SEQUENCE: 1843
atcctcaccg agcccaaaga catcgggaaa cggctcgagg tgcgg 45

<210> SEQ ID NO 1844
<211> LENGTH: 45
<212> TYPE: DNA
<213> ORGANISM: Homo sapiens

<400> SEQUENCE: 1844
gccttttgca cccctcccat taggacaatc agtcccctcc catct 45

<210> SEQ ID NO 1845
<211> LENGTH: 45
<212> TYPE: DNA
<213> ORGANISM: Homo sapiens

<400> SEQUENCE: 1845
catgactact ccgcagatgg gtttaatgac tgggccttca tgaca 45

<210> SEQ ID NO 1846
<211> LENGTH: 45
<212> TYPE: DNA
<213> ORGANISM: Homo sapiens

<400> SEQUENCE: 1846
ctttcccctg tggggatctc aggggctgtt tgaggatata ttttc 45

<210> SEQ ID NO 1847
<211> LENGTH: 45
<212> TYPE: DNA
<213> ORGANISM: Homo sapiens

<400> SEQUENCE: 1847
cagcccggct ggttttgtaa gatgctgggt tggtgcacag tgatt 45

<210> SEQ ID NO 1848
<211> LENGTH: 45
<212> TYPE: DNA
<213> ORGANISM: Homo sapiens

<400> SEQUENCE: 1848
acaggcccag cattgctggt tctatttaat ggacatgaga taatg 45

<210> SEQ ID NO 1849
<211> LENGTH: 45
<212> TYPE: DNA
<213> ORGANISM: Homo sapiens

<400> SEQUENCE: 1849
cagggccaga aggtcttcac caacacgtgg gctgtgcgca tccct 45

<210> SEQ ID NO 1850
<211> LENGTH: 45
<212> TYPE: DNA
<213> ORGANISM: Homo sapiens

<400> SEQUENCE: 1850
tcctggtcct gcagctgcgc tctggcttta gttttcgggg ggtga 45

<210> SEQ ID NO 1851
<211> LENGTH: 45
<212> TYPE: DNA
<213> ORGANISM: Homo sapiens

<400> SEQUENCE: 1851
caccctcagc accccttcca tgtggagaaa ggagtgaaac cttta 45

<210> SEQ ID NO 1852
<211> LENGTH: 45
<212> TYPE: DNA
<213> ORGANISM: Homo sapiens

<400> SEQUENCE: 1852
cccagcattg ctggttctat ttaatggaca tgagataatg ttaga 45

<210> SEQ ID NO 1853
<211> LENGTH: 45
<212> TYPE: DNA
<213> ORGANISM: Homo sapiens

<400> SEQUENCE: 1853
gacatgagat aatgttagag gttttaaagt gattaaacgt gcaga 45

<210> SEQ ID NO 1854
<211> LENGTH: 45
<212> TYPE: DNA
<213> ORGANISM: Homo sapiens

<400> SEQUENCE: 1854
tggacgatgg catcgagaag aaccacccgg acttggcagg caatt 45

<210> SEQ ID NO 1855
<211> LENGTH: 45
<212> TYPE: DNA
<213> ORGANISM: Homo sapiens

<400> SEQUENCE: 1855
tggggatctc aggggctgtt tgaggatata ttttcacttt gtgat 45

<210> SEQ ID NO 1856
<211> LENGTH: 45
<212> TYPE: DNA
<213> ORGANISM: Homo sapiens

<400> SEQUENCE: 1856
atgactactc cgcagatggg tttaatgact gggccttcat gacaa 45

<210> SEQ ID NO 1857
<211> LENGTH: 45
<212> TYPE: DNA
<213> ORGANISM: Homo sapiens

<400> SEQUENCE: 1857
actactccgc agatgggttt aatgactggg ccttcatgac aactc 45

<210> SEQ ID NO 1858
<211> LENGTH: 45
<212> TYPE: DNA
<213> ORGANISM: Homo sapiens

<400> SEQUENCE: 1858
ggcgagagga ccgcctttat caaagaccag agcgccctct gatga 45

<210> SEQ ID NO 1859
<211> LENGTH: 45
<212> TYPE: DNA
<213> ORGANISM: Homo sapiens

<400> SEQUENCE: 1859
tcccctgtgg ggatctcagg ggctgtttga ggatatattt tcact 45

<210> SEQ ID NO 1860
<211> LENGTH: 45
<212> TYPE: DNA
<213> ORGANISM: Homo sapiens

<400> SEQUENCE: 1860
tttcactttg tgattatttc actttagatg ctgatgattt gtttt 45

<210> SEQ ID NO 1861
<211> LENGTH: 45
<212> TYPE: DNA
<213> ORGANISM: Homo sapiens

<400> SEQUENCE: 1861
gtcctagaga ttgaaaacac cagcgaagcc aacaactatg ggacg 45

<210> SEQ ID NO 1862
<211> LENGTH: 45
<212> TYPE: DNA
<213> ORGANISM: Homo sapiens

<400> SEQUENCE: 1862
tgcgccttca tcgtgctggt cttcgtcact gtcttcctgg tcctg 45

<210> SEQ ID NO 1863
<211> LENGTH: 45
<212> TYPE: DNA
<213> ORGANISM: Homo sapiens

<400> SEQUENCE: 1863
ttgctatggg tggtagcagc aacaggaacc ttggtcctgc tagca 45

<210> SEQ ID NO 1864
<211> LENGTH: 45
<212> TYPE: DNA
<213> ORGANISM: Homo sapiens

<400> SEQUENCE: 1864
tagttttcgg ggggtgaagg tgtacaccat ggaccgtggc ctcat 45

<210> SEQ ID NO 1865
<211> LENGTH: 45
<212> TYPE: DNA
<213> ORGANISM: Homo sapiens

<400> SEQUENCE: 1865
cgacctacag cagtggcaac cagaatgaga agcagatcgt gacga 45

<210> SEQ ID NO 1866
<211> LENGTH: 45
<212> TYPE: DNA
<213> ORGANISM: Homo sapiens

<400> SEQUENCE: 1866
cgctcaggcg cggctcaccc tgtcctataa tcgccgtggc gacct 45

<210> SEQ ID NO 1867
<211> LENGTH: 45
<212> TYPE: DNA
<213> ORGANISM: Homo sapiens

<400> SEQUENCE: 1867
ttaaacaggc ccagcattgc tggttctatt taatggacat gagat 45

<210> SEQ ID NO 1868
<211> LENGTH: 45
<212> TYPE: DNA
<213> ORGANISM: Homo sapiens

<400> SEQUENCE: 1868
tgacccccag cctcggtaca cacagatgaa tgacaacagg cacgg 45

<210> SEQ ID NO 1869
<211> LENGTH: 45
<212> TYPE: DNA
<213> ORGANISM: Homo sapiens

<400> SEQUENCE: 1869
cccctgtggg gatctcaggg gctgtttgag gatatatttt cactt 45

<210> SEQ ID NO 1870
<211> LENGTH: 45
<212> TYPE: DNA
<213> ORGANISM: Homo sapiens

<400> SEQUENCE: 1870
atattttcac tttgtgatta tttcacttta gatgctgatg atttg 45

<210> SEQ ID NO 1871
<211> LENGTH: 45
<212> TYPE: DNA
<213> ORGANISM: Homo sapiens

<400> SEQUENCE: 1871
accccctcaa gccaatcccc tccttgggca ctttttaatt cacca 45

<210> SEQ ID NO 1872
<211> LENGTH: 45
<212> TYPE: DNA
<213> ORGANISM: Homo sapiens

<400> SEQUENCE: 1872
ggctggaaca gcaggtggca aagcgacgga ctaaacggga cgtgt 45

<210> SEQ ID NO 1873
<211> LENGTH: 45
<212> TYPE: DNA

<213> ORGANISM: Homo sapiens

<400> SEQUENCE: 1873
agcagcgcca cgcagtttgg caacgtgccg tggtacagcg aggcc 45

<210> SEQ ID NO 1874
<211> LENGTH: 45
<212> TYPE: DNA
<213> ORGANISM: Homo sapiens

<400> SEQUENCE: 1874
cattgctctc accctggagg ccaataagaa cctcacatgg cggga 45

<210> SEQ ID NO 1875
<211> LENGTH: 45
<212> TYPE: DNA
<213> ORGANISM: Homo sapiens

<400> SEQUENCE: 1875
ctgaacccca accacatcca catctacagt gccagctggg gcccc 45

<210> SEQ ID NO 1876
<211> LENGTH: 45
<212> TYPE: DNA
<213> ORGANISM: Homo sapiens

<400> SEQUENCE: 1876
gactactccg cagatgggtt taatgactgg gccttcatga caact 45

<210> SEQ ID NO 1877
<211> LENGTH: 45
<212> TYPE: DNA
<213> ORGANISM: Homo sapiens

<400> SEQUENCE: 1877
tctggcgagt gggtcctaga gattgaaaac accagcgaag ccaac 45

<210> SEQ ID NO 1878
<211> LENGTH: 45
<212> TYPE: DNA
<213> ORGANISM: Homo sapiens

<400> SEQUENCE: 1878
ccatggagct gaggccctgg ttgctatggg tggtagcagc aacag 45

<210> SEQ ID NO 1879
<211> LENGTH: 45
<212> TYPE: DNA
<213> ORGANISM: Homo sapiens

<400> SEQUENCE: 1879
aattatgatc ctggggccag ttttgatgtc aatgaccagg accct 45

<210> SEQ ID NO 1880
<211> LENGTH: 45
<212> TYPE: DNA
<213> ORGANISM: Homo sapiens

<400> SEQUENCE: 1880
gggtgcgcat gctggatggc gaggtgacag atgcagtgga ggcac 45

<210> SEQ ID NO 1881
<211> LENGTH: 45

<212> TYPE: DNA
<213> ORGANISM: Homo sapiens

<400> SEQUENCE: 1881
aggcgcggct caccctgtcc tataatcgcc gtggcgacct ggcca 45

<210> SEQ ID NO 1882
<211> LENGTH: 45
<212> TYPE: DNA
<213> ORGANISM: Homo sapiens

<400> SEQUENCE: 1882
caggccacat gactactccg cagatgggtt taatgactgg gcctt 45

<210> SEQ ID NO 1883
<211> LENGTH: 45
<212> TYPE: DNA
<213> ORGANISM: Homo sapiens

<400> SEQUENCE: 1883
ctcttgccct tccctgtccc tctaaagcaa taatggtccc atcca 45

<210> SEQ ID NO 1884
<211> LENGTH: 45
<212> TYPE: DNA
<213> ORGANISM: Homo sapiens

<400> SEQUENCE: 1884
tgctttcccc tgtggggatc tcaggggctg tttgaggata tattt 45

<210> SEQ ID NO 1885
<211> LENGTH: 45
<212> TYPE: DNA
<213> ORGANISM: Homo sapiens

<400> SEQUENCE: 1885
atcgagaaga accacccgga cttggcaggc aattatgatc ctggg 45

<210> SEQ ID NO 1886
<211> LENGTH: 45
<212> TYPE: DNA
<213> ORGANISM: Homo sapiens

<400> SEQUENCE: 1886
accacccgga cttggcaggc aattatgatc ctggggccag ttttg 45

<210> SEQ ID NO 1887
<211> LENGTH: 45
<212> TYPE: DNA
<213> ORGANISM: Homo sapiens

<400> SEQUENCE: 1887
aggaccctga cccccagcct cggtacacac agatgaatga caaca 45

<210> SEQ ID NO 1888
<211> LENGTH: 45
<212> TYPE: DNA
<213> ORGANISM: Homo sapiens

<400> SEQUENCE: 1888
gctgcaactg cgacggctac accaacagta tctacacgct gtcca 45

<210> SEQ ID NO 1889

```
<211> LENGTH: 45
<212> TYPE: DNA
<213> ORGANISM: Homo sapiens

<400> SEQUENCE: 1889

gcgccttcat cgtgctggtc ttcgtcactg tcttcctggt cctgc           45

<210> SEQ ID NO 1890
<211> LENGTH: 45
<212> TYPE: DNA
<213> ORGANISM: Homo sapiens

<400> SEQUENCE: 1890

gccagcccgg ctggttttgt aagatgctgg gttggtgcac agtga           45

<210> SEQ ID NO 1891
<211> LENGTH: 45
<212> TYPE: DNA
<213> ORGANISM: Homo sapiens

<400> SEQUENCE: 1891

ggcccagcat tgctggttct atttaatgga catgagataa tgtta           45

<210> SEQ ID NO 1892
<211> LENGTH: 45
<212> TYPE: DNA
<213> ORGANISM: Homo sapiens

<400> SEQUENCE: 1892

tggacatgag ataatgttag aggttttaaa gtgattaaac gtgca           45

<210> SEQ ID NO 1893
<211> LENGTH: 45
<212> TYPE: DNA
<213> ORGANISM: Homo sapiens

<400> SEQUENCE: 1893

acccggactt ggcaggcaat tatgatcctg gggccagttt tgatg           45

<210> SEQ ID NO 1894
<211> LENGTH: 45
<212> TYPE: DNA
<213> ORGANISM: Homo sapiens

<400> SEQUENCE: 1894

aggcaattat gatcctgggg ccagttttga tgtcaatgac cagga           45

<210> SEQ ID NO 1895
<211> LENGTH: 20
<212> TYPE: RNA
<213> ORGANISM: Homo sapiens

<400> SEQUENCE: 1895

uuggauuuca uaccaugugg                                       20

<210> SEQ ID NO 1896
<211> LENGTH: 20
<212> TYPE: RNA
<213> ORGANISM: Homo sapiens

<400> SEQUENCE: 1896

ugucaaaacu augacucugu                                       20
```

<210> SEQ ID NO 1897
<211> LENGTH: 20
<212> TYPE: RNA
<213> ORGANISM: Homo sapiens

<400> SEQUENCE: 1897
ccuagcauug gaaaauguug 20

<210> SEQ ID NO 1898
<211> LENGTH: 20
<212> TYPE: RNA
<213> ORGANISM: Homo sapiens

<400> SEQUENCE: 1898
auguaaaugu uaauuucaug 20

<210> SEQ ID NO 1899
<211> LENGTH: 20
<212> TYPE: RNA
<213> ORGANISM: Homo sapiens

<400> SEQUENCE: 1899
ucuguuucuu aauaaggauu 20

<210> SEQ ID NO 1900
<211> LENGTH: 20
<212> TYPE: RNA
<213> ORGANISM: Homo sapiens

<400> SEQUENCE: 1900
caggaguuga cauagauacu 20

<210> SEQ ID NO 1901
<211> LENGTH: 20
<212> TYPE: RNA
<213> ORGANISM: Homo sapiens

<400> SEQUENCE: 1901
aaugauuacu cauucauucg 20

<210> SEQ ID NO 1902
<211> LENGTH: 20
<212> TYPE: RNA
<213> ORGANISM: Homo sapiens

<400> SEQUENCE: 1902
aucgauauua gcaaaggaga 20

<210> SEQ ID NO 1903
<211> LENGTH: 20
<212> TYPE: RNA
<213> ORGANISM: Homo sapiens

<400> SEQUENCE: 1903
caugguauag aaaauauaag 20

<210> SEQ ID NO 1904
<211> LENGTH: 20
<212> TYPE: RNA
<213> ORGANISM: Homo sapiens

<400> SEQUENCE: 1904
uuugaaacca agaaucuccu 20

<210> SEQ ID NO 1905
<211> LENGTH: 20
<212> TYPE: RNA
<213> ORGANISM: Homo sapiens

<400> SEQUENCE: 1905
augggaguga uagugguugg 20

<210> SEQ ID NO 1906
<211> LENGTH: 20
<212> TYPE: RNA
<213> ORGANISM: Homo sapiens

<400> SEQUENCE: 1906
uugaagagau uaaaccauua 20

<210> SEQ ID NO 1907
<211> LENGTH: 20
<212> TYPE: RNA
<213> ORGANISM: Homo sapiens

<400> SEQUENCE: 1907
uuuguuguau guaaauguua 20

<210> SEQ ID NO 1908
<211> LENGTH: 20
<212> TYPE: RNA
<213> ORGANISM: Homo sapiens

<400> SEQUENCE: 1908
uucaugguau agaaaauaua 20

<210> SEQ ID NO 1909
<211> LENGTH: 20
<212> TYPE: RNA
<213> ORGANISM: Homo sapiens

<400> SEQUENCE: 1909
cucuggauuu gacuucuguu 20

<210> SEQ ID NO 1910
<211> LENGTH: 20
<212> TYPE: RNA
<213> ORGANISM: Homo sapiens

<400> SEQUENCE: 1910
uaaaccauua uaugaacauc 20

<210> SEQ ID NO 1911
<211> LENGTH: 20
<212> TYPE: RNA
<213> ORGANISM: Homo sapiens

<400> SEQUENCE: 1911
uuccucuuga ggugauuuug 20

<210> SEQ ID NO 1912
<211> LENGTH: 20
<212> TYPE: RNA
<213> ORGANISM: Homo sapiens

<400> SEQUENCE: 1912
cauuaaaugu caaaacuaug 20

<210> SEQ ID NO 1913
<211> LENGTH: 20
<212> TYPE: RNA
<213> ORGANISM: Homo sapiens

<400> SEQUENCE: 1913
ggagaaaaua auccaggauu 20

<210> SEQ ID NO 1914
<211> LENGTH: 20
<212> TYPE: RNA
<213> ORGANISM: Homo sapiens

<400> SEQUENCE: 1914
uggccaagga gagagcaucu 20

<210> SEQ ID NO 1915
<211> LENGTH: 20
<212> TYPE: RNA
<213> ORGANISM: Homo sapiens

<400> SEQUENCE: 1915
ucagggauaa ucuaaaugua 20

<210> SEQ ID NO 1916
<211> LENGTH: 20
<212> TYPE: RNA
<213> ORGANISM: Homo sapiens

<400> SEQUENCE: 1916
uucaagaaga caaugaaaca 20

<210> SEQ ID NO 1917
<211> LENGTH: 20
<212> TYPE: RNA
<213> ORGANISM: Homo sapiens

<400> SEQUENCE: 1917
aggacccuuu accaauucca 20

<210> SEQ ID NO 1918
<211> LENGTH: 20
<212> TYPE: RNA
<213> ORGANISM: Homo sapiens

<400> SEQUENCE: 1918
uguaggagca aagaacauga 20

<210> SEQ ID NO 1919
<211> LENGTH: 20
<212> TYPE: RNA
<213> ORGANISM: Homo sapiens

<400> SEQUENCE: 1919
aggagcaaag aacaugaaug 20

<210> SEQ ID NO 1920
<211> LENGTH: 20
<212> TYPE: RNA
<213> ORGANISM: Homo sapiens

<400> SEQUENCE: 1920
uggagaaaau ccuuaugccu 20

<210> SEQ ID NO 1921
<211> LENGTH: 20
<212> TYPE: RNA
<213> ORGANISM: Homo sapiens

<400> SEQUENCE: 1921
ggugauuuug uuguauguaa 20

<210> SEQ ID NO 1922
<211> LENGTH: 20
<212> TYPE: RNA
<213> ORGANISM: Homo sapiens

<400> SEQUENCE: 1922
uucugcagcc acaccuaagc 20

<210> SEQ ID NO 1923
<211> LENGTH: 20
<212> TYPE: RNA
<213> ORGANISM: Homo sapiens

<400> SEQUENCE: 1923
aaaacuauga cucuguucag 20

<210> SEQ ID NO 1924
<211> LENGTH: 20
<212> TYPE: RNA
<213> ORGANISM: Homo sapiens

<400> SEQUENCE: 1924
aucuaaaugu aaaugucugu 20

<210> SEQ ID NO 1925
<211> LENGTH: 20
<212> TYPE: RNA
<213> ORGANISM: Homo sapiens

<400> SEQUENCE: 1925
uuagucuagg gaaagucauu 20

<210> SEQ ID NO 1926
<211> LENGTH: 20
<212> TYPE: RNA
<213> ORGANISM: Homo sapiens

<400> SEQUENCE: 1926
ggagcaagug uuggaucuug 20

<210> SEQ ID NO 1927
<211> LENGTH: 20
<212> TYPE: RNA
<213> ORGANISM: Homo sapiens

<400> SEQUENCE: 1927
uuugacuucu guucuguuuc 20

<210> SEQ ID NO 1928
<211> LENGTH: 20
<212> TYPE: RNA
<213> ORGANISM: Homo sapiens

<400> SEQUENCE: 1928
uuuuguauua gaguauauua 20

<210> SEQ ID NO 1929
<211> LENGTH: 20
<212> TYPE: RNA
<213> ORGANISM: Homo sapiens

<400> SEQUENCE: 1929
gaggccauua uaugaagagu 20

<210> SEQ ID NO 1930
<211> LENGTH: 20
<212> TYPE: RNA
<213> ORGANISM: Homo sapiens

<400> SEQUENCE: 1930
ccaagaaucu ccuuuaauuu 20

<210> SEQ ID NO 1931
<211> LENGTH: 20
<212> TYPE: RNA
<213> ORGANISM: Homo sapiens

<400> SEQUENCE: 1931
gaugauguuc agaccuccuu 20

<210> SEQ ID NO 1932
<211> LENGTH: 20
<212> TYPE: RNA
<213> ORGANISM: Homo sapiens

<400> SEQUENCE: 1932
ucuggauuug acuucuguuc 20

<210> SEQ ID NO 1933
<211> LENGTH: 20
<212> TYPE: RNA
<213> ORGANISM: Homo sapiens

<400> SEQUENCE: 1933
uccaccauug aggaacaggc 20

<210> SEQ ID NO 1934
<211> LENGTH: 20
<212> TYPE: RNA
<213> ORGANISM: Homo sapiens

<400> SEQUENCE: 1934
uuauuacuug aaccagguuu 20

<210> SEQ ID NO 1935
<211> LENGTH: 20
<212> TYPE: RNA
<213> ORGANISM: Homo sapiens

<400> SEQUENCE: 1935
ugaaccaggu uugaaugaaa 20

<210> SEQ ID NO 1936
<211> LENGTH: 20
<212> TYPE: RNA
<213> ORGANISM: Homo sapiens

<400> SEQUENCE: 1936
ugugggaugg aguaccgacu 20

<210> SEQ ID NO 1937
<211> LENGTH: 20
<212> TYPE: RNA
<213> ORGANISM: Homo sapiens

<400> SEQUENCE: 1937
ugaggugauu uuguuguaug 20

<210> SEQ ID NO 1938
<211> LENGTH: 20
<212> TYPE: RNA
<213> ORGANISM: Homo sapiens

<400> SEQUENCE: 1938
uguauuugcu cacaguguuu 20

<210> SEQ ID NO 1939
<211> LENGTH: 20
<212> TYPE: RNA
<213> ORGANISM: Homo sapiens

<400> SEQUENCE: 1939
auuacuugaa ccagguuuga 20

<210> SEQ ID NO 1940
<211> LENGTH: 20
<212> TYPE: RNA
<213> ORGANISM: Homo sapiens

<400> SEQUENCE: 1940
auggcaagag caaaucauua 20

<210> SEQ ID NO 1941
<211> LENGTH: 20
<212> TYPE: RNA
<213> ORGANISM: Homo sapiens

<400> SEQUENCE: 1941
uggacagaaa ccaaacauag 20

<210> SEQ ID NO 1942
<211> LENGTH: 20
<212> TYPE: RNA
<213> ORGANISM: Homo sapiens

<400> SEQUENCE: 1942
uguauuagag uauauuaggg 20

<210> SEQ ID NO 1943
<211> LENGTH: 20
<212> TYPE: RNA
<213> ORGANISM: Homo sapiens

<400> SEQUENCE: 1943
auaucauugg agcaaguguu 20

<210> SEQ ID NO 1944
<211> LENGTH: 20
<212> TYPE: RNA
<213> ORGANISM: Homo sapiens

<400> SEQUENCE: 1944
guaaauguua auuucauggu 20

<210> SEQ ID NO 1945
<211> LENGTH: 20
<212> TYPE: RNA
<213> ORGANISM: Homo sapiens

<400> SEQUENCE: 1945
cuuaauaagg auuuuguauu 20

<210> SEQ ID NO 1946
<211> LENGTH: 20
<212> TYPE: RNA
<213> ORGANISM: Homo sapiens

<400> SEQUENCE: 1946
cccaaguuca aaggcugaua 20

<210> SEQ ID NO 1947
<211> LENGTH: 20
<212> TYPE: RNA
<213> ORGANISM: Homo sapiens

<400> SEQUENCE: 1947
ucugccauuu acuuacaugu 20

<210> SEQ ID NO 1948
<211> LENGTH: 20
<212> TYPE: RNA
<213> ORGANISM: Homo sapiens

<400> SEQUENCE: 1948
aaggccacug cucaacuacu 20

<210> SEQ ID NO 1949
<211> LENGTH: 20
<212> TYPE: RNA
<213> ORGANISM: Homo sapiens

<400> SEQUENCE: 1949
gggacgaugu caagcucuuc 20

<210> SEQ ID NO 1950
<211> LENGTH: 20
<212> TYPE: RNA
<213> ORGANISM: Homo sapiens

<400> SEQUENCE: 1950
cacgaagccg aagaccuguu 20

<210> SEQ ID NO 1951
<211> LENGTH: 20
<212> TYPE: RNA
<213> ORGANISM: Homo sapiens

<400> SEQUENCE: 1951
acaagaaauu cagaaucuca 20

<210> SEQ ID NO 1952
<211> LENGTH: 20
<212> TYPE: RNA

<213> ORGANISM: Homo sapiens

<400> SEQUENCE: 1952
ugugucugau aucauuccua 20

<210> SEQ ID NO 1953
<211> LENGTH: 20
<212> TYPE: RNA
<213> ORGANISM: Homo sapiens

<400> SEQUENCE: 1953
cagggauaau cuaaauguaa 20

<210> SEQ ID NO 1954
<211> LENGTH: 20
<212> TYPE: RNA
<213> ORGANISM: Homo sapiens

<400> SEQUENCE: 1954
cugauagaaa cucauuucua 20

<210> SEQ ID NO 1955
<211> LENGTH: 20
<212> TYPE: RNA
<213> ORGANISM: Homo sapiens

<400> SEQUENCE: 1955
uaugauaugg cauaugcugc 20

<210> SEQ ID NO 1956
<211> LENGTH: 20
<212> TYPE: RNA
<213> ORGANISM: Homo sapiens

<400> SEQUENCE: 1956
cacgauuguu gggacucugc 20

<210> SEQ ID NO 1957
<211> LENGTH: 20
<212> TYPE: RNA
<213> ORGANISM: Homo sapiens

<400> SEQUENCE: 1957
gauguucaga ccuccuuuua 20

<210> SEQ ID NO 1958
<211> LENGTH: 20
<212> TYPE: RNA
<213> ORGANISM: Homo sapiens

<400> SEQUENCE: 1958
auaagaugau aaagauauca 20

<210> SEQ ID NO 1959
<211> LENGTH: 20
<212> TYPE: RNA
<213> ORGANISM: Homo sapiens

<400> SEQUENCE: 1959
ugauaaagau aucauuaaau 20

<210> SEQ ID NO 1960
<211> LENGTH: 20

<212> TYPE: RNA
<213> ORGANISM: Homo sapiens

<400> SEQUENCE: 1960
guuucuuaau aaggauuuug 20

<210> SEQ ID NO 1961
<211> LENGTH: 20
<212> TYPE: RNA
<213> ORGANISM: Homo sapiens

<400> SEQUENCE: 1961
uuuguauuag aguauauuag 20

<210> SEQ ID NO 1962
<211> LENGTH: 20
<212> TYPE: RNA
<213> ORGANISM: Homo sapiens

<400> SEQUENCE: 1962
cuuggaauua uaacaccaau 20

<210> SEQ ID NO 1963
<211> LENGTH: 20
<212> TYPE: RNA
<213> ORGANISM: Homo sapiens

<400> SEQUENCE: 1963
agccguauca augaugcuuu 20

<210> SEQ ID NO 1964
<211> LENGTH: 20
<212> TYPE: RNA
<213> ORGANISM: Homo sapiens

<400> SEQUENCE: 1964
auuucugucu cuggauuuga 20

<210> SEQ ID NO 1965
<211> LENGTH: 20
<212> TYPE: RNA
<213> ORGANISM: Homo sapiens

<400> SEQUENCE: 1965
gagcacaaag cagacacuca 20

<210> SEQ ID NO 1966
<211> LENGTH: 20
<212> TYPE: RNA
<213> ORGANISM: Homo sapiens

<400> SEQUENCE: 1966
aaagauauca uuaaauguca 20

<210> SEQ ID NO 1967
<211> LENGTH: 20
<212> TYPE: RNA
<213> ORGANISM: Homo sapiens

<400> SEQUENCE: 1967
gugaccuuga cugaguuuug 20

<210> SEQ ID NO 1968

<211> LENGTH: 20
<212> TYPE: RNA
<213> ORGANISM: Homo sapiens

<400> SEQUENCE: 1968
uguggaacau accuuugaag 20

<210> SEQ ID NO 1969
<211> LENGTH: 20
<212> TYPE: RNA
<213> ORGANISM: Homo sapiens

<400> SEQUENCE: 1969
uaugcuauga ggcaguacuu 20

<210> SEQ ID NO 1970
<211> LENGTH: 20
<212> TYPE: RNA
<213> ORGANISM: Homo sapiens

<400> SEQUENCE: 1970
uuccauaugg cugauuguuu 20

<210> SEQ ID NO 1971
<211> LENGTH: 20
<212> TYPE: RNA
<213> ORGANISM: Homo sapiens

<400> SEQUENCE: 1971
acuacaauga gaggcucugg 20

<210> SEQ ID NO 1972
<211> LENGTH: 20
<212> TYPE: RNA
<213> ORGANISM: Homo sapiens

<400> SEQUENCE: 1972
auuugaaacc aagaaucucc 20

<210> SEQ ID NO 1973
<211> LENGTH: 20
<212> TYPE: RNA
<213> ORGANISM: Homo sapiens

<400> SEQUENCE: 1973
uguugaauuu cugaaguuga 20

<210> SEQ ID NO 1974
<211> LENGTH: 20
<212> TYPE: RNA
<213> ORGANISM: Homo sapiens

<400> SEQUENCE: 1974
cccagucucu uaaaucuuuu 20

<210> SEQ ID NO 1975
<211> LENGTH: 20
<212> TYPE: RNA
<213> ORGANISM: Homo sapiens

<400> SEQUENCE: 1975
gaugggagug auagugguug 20

<210> SEQ ID NO 1976
<211> LENGTH: 20
<212> TYPE: RNA
<213> ORGANISM: Homo sapiens

<400> SEQUENCE: 1976
ugaugauguu cagaccuccu 20

<210> SEQ ID NO 1977
<211> LENGTH: 20
<212> TYPE: RNA
<213> ORGANISM: Homo sapiens

<400> SEQUENCE: 1977
ugcuucuugg aauuauaaca 20

<210> SEQ ID NO 1978
<211> LENGTH: 20
<212> TYPE: RNA
<213> ORGANISM: Homo sapiens

<400> SEQUENCE: 1978
cuaaauguaa augucuguug 20

<210> SEQ ID NO 1979
<211> LENGTH: 20
<212> TYPE: RNA
<213> ORGANISM: Homo sapiens

<400> SEQUENCE: 1979
aaugcugggg acaaaugguc 20

<210> SEQ ID NO 1980
<211> LENGTH: 20
<212> TYPE: RNA
<213> ORGANISM: Homo sapiens

<400> SEQUENCE: 1980
uuuucaagaa gacaaugaaa 20

<210> SEQ ID NO 1981
<211> LENGTH: 20
<212> TYPE: RNA
<213> ORGANISM: Homo sapiens

<400> SEQUENCE: 1981
ucuuggagau aaagcauaug 20

<210> SEQ ID NO 1982
<211> LENGTH: 20
<212> TYPE: RNA
<213> ORGANISM: Homo sapiens

<400> SEQUENCE: 1982
aaugaaaugu accuguuccg 20

<210> SEQ ID NO 1983
<211> LENGTH: 20
<212> TYPE: RNA
<213> ORGANISM: Homo sapiens

<400> SEQUENCE: 1983
aauauaagau gauaaagaua 20

<210> SEQ ID NO 1984
<211> LENGTH: 20
<212> TYPE: RNA
<213> ORGANISM: Homo sapiens

<400> SEQUENCE: 1984
uguucuguuu cuuaauaagg 20

<210> SEQ ID NO 1985
<211> LENGTH: 20
<212> TYPE: RNA
<213> ORGANISM: Homo sapiens

<400> SEQUENCE: 1985
uuugccuaca gugauguuug 20

<210> SEQ ID NO 1986
<211> LENGTH: 20
<212> TYPE: RNA
<213> ORGANISM: Homo sapiens

<400> SEQUENCE: 1986
aaucucauga ggagguuuua 20

<210> SEQ ID NO 1987
<211> LENGTH: 20
<212> TYPE: RNA
<213> ORGANISM: Homo sapiens

<400> SEQUENCE: 1987
uaagaugaua aagauaucau 20

<210> SEQ ID NO 1988
<211> LENGTH: 20
<212> TYPE: RNA
<213> ORGANISM: Homo sapiens

<400> SEQUENCE: 1988
gauguuugga aucgaucaug 20

<210> SEQ ID NO 1989
<211> LENGTH: 20
<212> TYPE: RNA
<213> ORGANISM: Homo sapiens

<400> SEQUENCE: 1989
ccacacuugc ccaaauguau 20

<210> SEQ ID NO 1990
<211> LENGTH: 20
<212> TYPE: RNA
<213> ORGANISM: Homo sapiens

<400> SEQUENCE: 1990
gagacuauga aguaaauggg 20

<210> SEQ ID NO 1991
<211> LENGTH: 20
<212> TYPE: RNA
<213> ORGANISM: Homo sapiens

<400> SEQUENCE: 1991
cuucauugac auugcuuuca 20

<210> SEQ ID NO 1992
<211> LENGTH: 20
<212> TYPE: RNA
<213> ORGANISM: Homo sapiens

<400> SEQUENCE: 1992
aaaugucugu ugaauuucug 20

<210> SEQ ID NO 1993
<211> LENGTH: 20
<212> TYPE: RNA
<213> ORGANISM: Homo sapiens

<400> SEQUENCE: 1993
uguagcugca aggauugaga 20

<210> SEQ ID NO 1994
<211> LENGTH: 20
<212> TYPE: RNA
<213> ORGANISM: Homo sapiens

<400> SEQUENCE: 1994
guugacauag auacucuuug 20

<210> SEQ ID NO 1995
<211> LENGTH: 20
<212> TYPE: RNA
<213> ORGANISM: Homo sapiens

<400> SEQUENCE: 1995
uguccaaaac augaauaaug 20

<210> SEQ ID NO 1996
<211> LENGTH: 20
<212> TYPE: RNA
<213> ORGANISM: Homo sapiens

<400> SEQUENCE: 1996
gaugauaaag auaucauuaa 20

<210> SEQ ID NO 1997
<211> LENGTH: 20
<212> TYPE: RNA
<213> ORGANISM: Homo sapiens

<400> SEQUENCE: 1997
uuguauuaga guauauuagg 20

<210> SEQ ID NO 1998
<211> LENGTH: 20
<212> TYPE: RNA
<213> ORGANISM: Homo sapiens

<400> SEQUENCE: 1998
uucacaguaa cucaguucaa 20

<210> SEQ ID NO 1999
<211> LENGTH: 20
<212> TYPE: RNA
<213> ORGANISM: Homo sapiens

<400> SEQUENCE: 1999
ucaggaguug acauagauac 20

<210> SEQ ID NO 2000
<211> LENGTH: 20
<212> TYPE: RNA
<213> ORGANISM: Homo sapiens

<400> SEQUENCE: 2000
uguacucuuu gacaguuccc 20

<210> SEQ ID NO 2001
<211> LENGTH: 20
<212> TYPE: RNA
<213> ORGANISM: Homo sapiens

<400> SEQUENCE: 2001
ggagcuaaug aaggauucca 20

<210> SEQ ID NO 2002
<211> LENGTH: 20
<212> TYPE: RNA
<213> ORGANISM: Homo sapiens

<400> SEQUENCE: 2002
ugagcccuua uuuaccuggc 20

<210> SEQ ID NO 2003
<211> LENGTH: 20
<212> TYPE: RNA
<213> ORGANISM: Homo sapiens

<400> SEQUENCE: 2003
ugcuaugagg caguacuuuu 20

<210> SEQ ID NO 2004
<211> LENGTH: 20
<212> TYPE: RNA
<213> ORGANISM: Homo sapiens

<400> SEQUENCE: 2004
guauguaaau guuaauuuca 20

<210> SEQ ID NO 2005
<211> LENGTH: 20
<212> TYPE: RNA
<213> ORGANISM: Homo sapiens

<400> SEQUENCE: 2005
ucuucauuga cauugcuuuc 20

<210> SEQ ID NO 2006
<211> LENGTH: 20
<212> TYPE: RNA
<213> ORGANISM: Homo sapiens

<400> SEQUENCE: 2006
uuuggucuca caggcuguuc 20

<210> SEQ ID NO 2007
<211> LENGTH: 20
<212> TYPE: RNA
<213> ORGANISM: Homo sapiens

<400> SEQUENCE: 2007
uaagagagaa aaucucauga 20

<210> SEQ ID NO 2008
<211> LENGTH: 20
<212> TYPE: RNA
<213> ORGANISM: Homo sapiens

<400> SEQUENCE: 2008
caugagaugg ggcauaucca 20

<210> SEQ ID NO 2009
<211> LENGTH: 20
<212> TYPE: RNA
<213> ORGANISM: Homo sapiens

<400> SEQUENCE: 2009
uucuaaugau uacucauuca 20

<210> SEQ ID NO 2010
<211> LENGTH: 20
<212> TYPE: RNA
<213> ORGANISM: Homo sapiens

<400> SEQUENCE: 2010
guaucaauga ugcuuuccgu 20

<210> SEQ ID NO 2011
<211> LENGTH: 20
<212> TYPE: RNA
<213> ORGANISM: Homo sapiens

<400> SEQUENCE: 2011
guugaaaaca aggauauauc 20

<210> SEQ ID NO 2012
<211> LENGTH: 20
<212> TYPE: RNA
<213> ORGANISM: Homo sapiens

<400> SEQUENCE: 2012
gaagaugugg aacauaccuu 20

<210> SEQ ID NO 2013
<211> LENGTH: 20
<212> TYPE: RNA
<213> ORGANISM: Homo sapiens

<400> SEQUENCE: 2013
uuugaagaga uuaaaccauu 20

<210> SEQ ID NO 2014
<211> LENGTH: 20
<212> TYPE: RNA
<213> ORGANISM: Homo sapiens

<400> SEQUENCE: 2014
agaacaagaa uucuuuugug 20

<210> SEQ ID NO 2015
<211> LENGTH: 20
<212> TYPE: RNA
<213> ORGANISM: Homo sapiens

<400> SEQUENCE: 2015
uagcaaagga gaaaauaauc 20

<210> SEQ ID NO 2016
<211> LENGTH: 20
<212> TYPE: RNA
<213> ORGANISM: Homo sapiens

<400> SEQUENCE: 2016
gaaaacaagg auauaucauu 20

<210> SEQ ID NO 2017
<211> LENGTH: 20
<212> TYPE: RNA
<213> ORGANISM: Homo sapiens

<400> SEQUENCE: 2017
caugcuuucu ucaaggugac 20

<210> SEQ ID NO 2018
<211> LENGTH: 20
<212> TYPE: RNA
<213> ORGANISM: Homo sapiens

<400> SEQUENCE: 2018
aacccaaguu caaaggcuga 20

<210> SEQ ID NO 2019
<211> LENGTH: 20
<212> TYPE: RNA
<213> ORGANISM: Homo sapiens

<400> SEQUENCE: 2019
augaacaucu ucaugccuau 20

<210> SEQ ID NO 2020
<211> LENGTH: 20
<212> TYPE: RNA
<213> ORGANISM: Homo sapiens

<400> SEQUENCE: 2020
acugggauca gagaucggaa 20

<210> SEQ ID NO 2021
<211> LENGTH: 20
<212> TYPE: RNA
<213> ORGANISM: Homo sapiens

<400> SEQUENCE: 2021
ucuucaaggu gacaggucua 20

<210> SEQ ID NO 2022
<211> LENGTH: 20
<212> TYPE: RNA
<213> ORGANISM: Homo sapiens

<400> SEQUENCE: 2022
ucagcaaaau gggucuucag 20

<210> SEQ ID NO 2023
<211> LENGTH: 20
<212> TYPE: RNA
<213> ORGANISM: Homo sapiens

<400> SEQUENCE: 2023
gcaaacaguu uagacuacaa 20

<210> SEQ ID NO 2024
<211> LENGTH: 20
<212> TYPE: RNA
<213> ORGANISM: Homo sapiens

<400> SEQUENCE: 2024
aaaccauuau augaacaucu 20

<210> SEQ ID NO 2025
<211> LENGTH: 20
<212> TYPE: RNA
<213> ORGANISM: Homo sapiens

<400> SEQUENCE: 2025
ucuguacucu uugacaguuc 20

<210> SEQ ID NO 2026
<211> LENGTH: 20
<212> TYPE: RNA
<213> ORGANISM: Homo sapiens

<400> SEQUENCE: 2026
uuugacaguu cccuuuggac 20

<210> SEQ ID NO 2027
<211> LENGTH: 20
<212> TYPE: RNA
<213> ORGANISM: Homo sapiens

<400> SEQUENCE: 2027
gaaacagaaa uaaacuuccu 20

<210> SEQ ID NO 2028
<211> LENGTH: 20
<212> TYPE: RNA
<213> ORGANISM: Homo sapiens

<400> SEQUENCE: 2028
caguauuuau uucugucucu 20

<210> SEQ ID NO 2029
<211> LENGTH: 20
<212> TYPE: RNA
<213> ORGANISM: Homo sapiens

<400> SEQUENCE: 2029
caguucaagu acuaugguga 20

<210> SEQ ID NO 2030
<211> LENGTH: 20
<212> TYPE: RNA
<213> ORGANISM: Homo sapiens

<400> SEQUENCE: 2030
guccaaaaca ugaauaaugc 20

<210> SEQ ID NO 2031
<211> LENGTH: 20
<212> TYPE: RNA

<213> ORGANISM: Homo sapiens

<400> SEQUENCE: 2031
uugaugaaug ccuauccuuc 20

<210> SEQ ID NO 2032
<211> LENGTH: 20
<212> TYPE: RNA
<213> ORGANISM: Homo sapiens

<400> SEQUENCE: 2032
ugcauaugcu augaggcagu 20

<210> SEQ ID NO 2033
<211> LENGTH: 20
<212> TYPE: RNA
<213> ORGANISM: Homo sapiens

<400> SEQUENCE: 2033
uaugccucca ucgauauuag 20

<210> SEQ ID NO 2034
<211> LENGTH: 20
<212> TYPE: RNA
<213> ORGANISM: Homo sapiens

<400> SEQUENCE: 2034
aguugacaua gauacucuuu 20

<210> SEQ ID NO 2035
<211> LENGTH: 20
<212> TYPE: RNA
<213> ORGANISM: Homo sapiens

<400> SEQUENCE: 2035
uuuagucuag ggaaagucau 20

<210> SEQ ID NO 2036
<211> LENGTH: 20
<212> TYPE: RNA
<213> ORGANISM: Homo sapiens

<400> SEQUENCE: 2036
uccacacuug cccaaaugua 20

<210> SEQ ID NO 2037
<211> LENGTH: 20
<212> TYPE: RNA
<213> ORGANISM: Homo sapiens

<400> SEQUENCE: 2037
ucuucuguca cccgauuuuc 20

<210> SEQ ID NO 2038
<211> LENGTH: 20
<212> TYPE: RNA
<213> ORGANISM: Homo sapiens

<400> SEQUENCE: 2038
auagaaaaua uaagaugaua 20

<210> SEQ ID NO 2039
<211> LENGTH: 20

<212> TYPE: RNA
<213> ORGANISM: Homo sapiens

<400> SEQUENCE: 2039
uaugcugcac aaccuuuucu 20

<210> SEQ ID NO 2040
<211> LENGTH: 20
<212> TYPE: RNA
<213> ORGANISM: Homo sapiens

<400> SEQUENCE: 2040
uggauuugac uucuguucug 20

<210> SEQ ID NO 2041
<211> LENGTH: 20
<212> TYPE: RNA
<213> ORGANISM: Homo sapiens

<400> SEQUENCE: 2041
gacuucuguu cuguuucuua 20

<210> SEQ ID NO 2042
<211> LENGTH: 20
<212> TYPE: RNA
<213> ORGANISM: Homo sapiens

<400> SEQUENCE: 2042
cuuucauuua auccauuguc 20

<210> SEQ ID NO 2043
<211> LENGTH: 20
<212> TYPE: RNA
<213> ORGANISM: Homo sapiens

<400> SEQUENCE: 2043
aaggaugaca ugcuuucuuc 20

<210> SEQ ID NO 2044
<211> LENGTH: 20
<212> TYPE: RNA
<213> ORGANISM: Homo sapiens

<400> SEQUENCE: 2044
agguagagga cauugcuuuu 20

<210> SEQ ID NO 2045
<211> LENGTH: 20
<212> TYPE: RNA
<213> ORGANISM: Homo sapiens

<400> SEQUENCE: 2045
uuuguaucug uuggucuucc 20

<210> SEQ ID NO 2046
<211> LENGTH: 20
<212> TYPE: RNA
<213> ORGANISM: Homo sapiens

<400> SEQUENCE: 2046
auucccaaag accaguggau 20

<210> SEQ ID NO 2047

<211> LENGTH: 20
<212> TYPE: RNA
<213> ORGANISM: Homo sapiens

<400> SEQUENCE: 2047
aagaccagaa caagaauucu 20

<210> SEQ ID NO 2048
<211> LENGTH: 20
<212> TYPE: RNA
<213> ORGANISM: Homo sapiens

<400> SEQUENCE: 2048
uaaagcauau gaauggaacg 20

<210> SEQ ID NO 2049
<211> LENGTH: 20
<212> TYPE: RNA
<213> ORGANISM: Homo sapiens

<400> SEQUENCE: 2049
cuggauuuga cuucuguucu 20

<210> SEQ ID NO 2050
<211> LENGTH: 20
<212> TYPE: RNA
<213> ORGANISM: Homo sapiens

<400> SEQUENCE: 2050
uagggaaagu guguauuugg 20

<210> SEQ ID NO 2051
<211> LENGTH: 20
<212> TYPE: RNA
<213> ORGANISM: Homo sapiens

<400> SEQUENCE: 2051
gcaugcauua gcucacuuuc 20

<210> SEQ ID NO 2052
<211> LENGTH: 20
<212> TYPE: RNA
<213> ORGANISM: Homo sapiens

<400> SEQUENCE: 2052
uuggucuucc uaauaugacu 20

<210> SEQ ID NO 2053
<211> LENGTH: 20
<212> TYPE: RNA
<213> ORGANISM: Homo sapiens

<400> SEQUENCE: 2053
guuucuaaug auuacucauu 20

<210> SEQ ID NO 2054
<211> LENGTH: 20
<212> TYPE: RNA
<213> ORGANISM: Homo sapiens

<400> SEQUENCE: 2054
uuacacaagg acccuuuacc 20

<210> SEQ ID NO 2055
<211> LENGTH: 20
<212> TYPE: RNA
<213> ORGANISM: Homo sapiens

<400> SEQUENCE: 2055
uugaaaccaa gaaucuccuu 20

<210> SEQ ID NO 2056
<211> LENGTH: 20
<212> TYPE: RNA
<213> ORGANISM: Homo sapiens

<400> SEQUENCE: 2056
ucugauauca uuccuagaac 20

<210> SEQ ID NO 2057
<211> LENGTH: 20
<212> TYPE: RNA
<213> ORGANISM: Homo sapiens

<400> SEQUENCE: 2057
agugccuggg aacuggugua 20

<210> SEQ ID NO 2058
<211> LENGTH: 20
<212> TYPE: RNA
<213> ORGANISM: Homo sapiens

<400> SEQUENCE: 2058
ugagaauggc augcauuagc 20

<210> SEQ ID NO 2059
<211> LENGTH: 20
<212> TYPE: RNA
<213> ORGANISM: Homo sapiens

<400> SEQUENCE: 2059
ugcauuagcu cacuuucauu 20

<210> SEQ ID NO 2060
<211> LENGTH: 20
<212> TYPE: RNA
<213> ORGANISM: Homo sapiens

<400> SEQUENCE: 2060
ucacccucug aaguggguac 20

<210> SEQ ID NO 2061
<211> LENGTH: 20
<212> TYPE: RNA
<213> ORGANISM: Homo sapiens

<400> SEQUENCE: 2061
ugaggagguu uuagucuagg 20

<210> SEQ ID NO 2062
<211> LENGTH: 20
<212> TYPE: RNA
<213> ORGANISM: Homo sapiens

<400> SEQUENCE: 2062
uuugcuuggu gauauguggg 20

<210> SEQ ID NO 2063
<211> LENGTH: 20
<212> TYPE: RNA
<213> ORGANISM: Homo sapiens

<400> SEQUENCE: 2063
uggggcauau ccaguaugau 20

<210> SEQ ID NO 2064
<211> LENGTH: 20
<212> TYPE: RNA
<213> ORGANISM: Homo sapiens

<400> SEQUENCE: 2064
auaugaaugg aacgacaaug 20

<210> SEQ ID NO 2065
<211> LENGTH: 20
<212> TYPE: RNA
<213> ORGANISM: Homo sapiens

<400> SEQUENCE: 2065
uuucauggua uagaaaauau 20

<210> SEQ ID NO 2066
<211> LENGTH: 20
<212> TYPE: RNA
<213> ORGANISM: Homo sapiens

<400> SEQUENCE: 2066
uacugaagag aauguccaaa 20

<210> SEQ ID NO 2067
<211> LENGTH: 20
<212> TYPE: RNA
<213> ORGANISM: Homo sapiens

<400> SEQUENCE: 2067
ggcaagagca aaucauuaug 20

<210> SEQ ID NO 2068
<211> LENGTH: 20
<212> TYPE: RNA
<213> ORGANISM: Homo sapiens

<400> SEQUENCE: 2068
ugcugcacaa ccuuuucugc 20

<210> SEQ ID NO 2069
<211> LENGTH: 20
<212> TYPE: RNA
<213> ORGANISM: Homo sapiens

<400> SEQUENCE: 2069
aaagaccaga acaagaauuc 20

<210> SEQ ID NO 2070
<211> LENGTH: 20
<212> TYPE: RNA
<213> ORGANISM: Homo sapiens

<400> SEQUENCE: 2070
aacgacaaug aaauguaccu 20

<210> SEQ ID NO 2071
<211> LENGTH: 20
<212> TYPE: RNA
<213> ORGANISM: Homo sapiens

<400> SEQUENCE: 2071
ugugcgagug gcuaauuuga 20

<210> SEQ ID NO 2072
<211> LENGTH: 20
<212> TYPE: RNA
<213> ORGANISM: Homo sapiens

<400> SEQUENCE: 2072
uuagcaaagg agaaaauaau 20

<210> SEQ ID NO 2073
<211> LENGTH: 20
<212> TYPE: RNA
<213> ORGANISM: Homo sapiens

<400> SEQUENCE: 2073
ggaacaggua gaggacauug 20

<210> SEQ ID NO 2074
<211> LENGTH: 20
<212> TYPE: RNA
<213> ORGANISM: Homo sapiens

<400> SEQUENCE: 2074
cuuaaaucuu uuguauuugc 20

<210> SEQ ID NO 2075
<211> LENGTH: 20
<212> TYPE: RNA
<213> ORGANISM: Homo sapiens

<400> SEQUENCE: 2075
uauccacuac aagaaauuca 20

<210> SEQ ID NO 2076
<211> LENGTH: 20
<212> TYPE: RNA
<213> ORGANISM: Homo sapiens

<400> SEQUENCE: 2076
aaaccaaaca uagauguuac 20

<210> SEQ ID NO 2077
<211> LENGTH: 20
<212> TYPE: RNA
<213> ORGANISM: Homo sapiens

<400> SEQUENCE: 2077
caaggauucu gggaaaauuc 20

<210> SEQ ID NO 2078
<211> LENGTH: 20
<212> TYPE: RNA
<213> ORGANISM: Homo sapiens

<400> SEQUENCE: 2078

```
accagaacaa gaauucuuuu                                               20

<210> SEQ ID NO 2079
<211> LENGTH: 20
<212> TYPE: RNA
<213> ORGANISM: Homo sapiens

<400> SEQUENCE: 2079

auguuaauuu caugguauag                                               20

<210> SEQ ID NO 2080
<211> LENGTH: 20
<212> TYPE: RNA
<213> ORGANISM: Homo sapiens

<400> SEQUENCE: 2080

gauaucauua aaugucaaaa                                               20

<210> SEQ ID NO 2081
<211> LENGTH: 20
<212> TYPE: RNA
<213> ORGANISM: Homo sapiens

<400> SEQUENCE: 2081

uuaaauguca aaacuaugac                                               20

<210> SEQ ID NO 2082
<211> LENGTH: 20
<212> TYPE: RNA
<213> ORGANISM: Homo sapiens

<400> SEQUENCE: 2082

caggcuguuc agggauaauc                                               20

<210> SEQ ID NO 2083
<211> LENGTH: 20
<212> TYPE: RNA
<213> ORGANISM: Homo sapiens

<400> SEQUENCE: 2083

ugucaaggau gacaugcuuu                                               20

<210> SEQ ID NO 2084
<211> LENGTH: 20
<212> TYPE: RNA
<213> ORGANISM: Homo sapiens

<400> SEQUENCE: 2084

auggugauuu gccuacagug                                               20

<210> SEQ ID NO 2085
<211> LENGTH: 20
<212> TYPE: RNA
<213> ORGANISM: Homo sapiens

<400> SEQUENCE: 2085

uuggacaaau cuguacucuu                                               20

<210> SEQ ID NO 2086
<211> LENGTH: 20
<212> TYPE: RNA
<213> ORGANISM: Homo sapiens

<400> SEQUENCE: 2086
```

ucaagaagca cuuugucaag 20

<210> SEQ ID NO 2087
<211> LENGTH: 20
<212> TYPE: RNA
<213> ORGANISM: Homo sapiens

<400> SEQUENCE: 2087
uuuaauuucu uugucacugc 20

<210> SEQ ID NO 2088
<211> LENGTH: 20
<212> TYPE: RNA
<213> ORGANISM: Homo sapiens

<400> SEQUENCE: 2088
gcaaggauug agaauggcau 20

<210> SEQ ID NO 2089
<211> LENGTH: 20
<212> TYPE: RNA
<213> ORGANISM: Homo sapiens

<400> SEQUENCE: 2089
uuggaaucga ucaugcuuuc 20

<210> SEQ ID NO 2090
<211> LENGTH: 20
<212> TYPE: RNA
<213> ORGANISM: Homo sapiens

<400> SEQUENCE: 2090
ucucaugagg agguuuuagu 20

<210> SEQ ID NO 2091
<211> LENGTH: 20
<212> TYPE: RNA
<213> ORGANISM: Homo sapiens

<400> SEQUENCE: 2091
cauuauauga agaguaugug 20

<210> SEQ ID NO 2092
<211> LENGTH: 20
<212> TYPE: RNA
<213> ORGANISM: Homo sapiens

<400> SEQUENCE: 2092
ucugggaaaa uuccaugcua 20

<210> SEQ ID NO 2093
<211> LENGTH: 20
<212> TYPE: RNA
<213> ORGANISM: Homo sapiens

<400> SEQUENCE: 2093
uucaggaucc uuaugugcac 20

<210> SEQ ID NO 2094
<211> LENGTH: 20
<212> TYPE: RNA
<213> ORGANISM: Homo sapiens

<400> SEQUENCE: 2094
aggcccucug cacaaaugug 20

<210> SEQ ID NO 2095
<211> LENGTH: 45
<212> TYPE: DNA
<213> ORGANISM: Homo sapiens

<400> SEQUENCE: 2095
tgacatagat actctttgga tttcatacca tgtggaggct ttctt 45

<210> SEQ ID NO 2096
<211> LENGTH: 45
<212> TYPE: DNA
<213> ORGANISM: Homo sapiens

<400> SEQUENCE: 2096
aaagatatca ttaaatgtca aaactatgac tctgttcaga aaaaa 45

<210> SEQ ID NO 2097
<211> LENGTH: 45
<212> TYPE: DNA
<213> ORGANISM: Homo sapiens

<400> SEQUENCE: 2097
atcagaaccc tggaccctag cattggaaaa tgttgtagga gcaaa 45

<210> SEQ ID NO 2098
<211> LENGTH: 45
<212> TYPE: DNA
<213> ORGANISM: Homo sapiens

<400> SEQUENCE: 2098
aggtgatttt gttgtatgta aatgttaatt tcatggtata gaaaa 45

<210> SEQ ID NO 2099
<211> LENGTH: 45
<212> TYPE: DNA
<213> ORGANISM: Homo sapiens

<400> SEQUENCE: 2099
ggatttgact tctgttctgt ttcttaataa ggattttgta ttaga 45

<210> SEQ ID NO 2100
<211> LENGTH: 45
<212> TYPE: DNA
<213> ORGANISM: Homo sapiens

<400> SEQUENCE: 2100
atggctacag aggatcagga gttgacatag atactctttg gattt 45

<210> SEQ ID NO 2101
<211> LENGTH: 45
<212> TYPE: DNA
<213> ORGANISM: Homo sapiens

<400> SEQUENCE: 2101
ctgttccatg tttctaatga ttactcattc attcgatatt acaca 45

<210> SEQ ID NO 2102
<211> LENGTH: 45
<212> TYPE: DNA
<213> ORGANISM: Homo sapiens

<400> SEQUENCE: 2102
aatccttatg cctccatcga tattagcaaa ggagaaaata atcca 45

<210> SEQ ID NO 2103
<211> LENGTH: 45
<212> TYPE: DNA
<213> ORGANISM: Homo sapiens

<400> SEQUENCE: 2103
tgtaaatgtt aatttcatgg tatagaaaat ataagatgat aaaga 45

<210> SEQ ID NO 2104
<211> LENGTH: 45
<212> TYPE: DNA
<213> ORGANISM: Homo sapiens

<400> SEQUENCE: 2104
tgtgcgagtg gctaatttga aaccaagaat ctcctttaat ttctt 45

<210> SEQ ID NO 2105
<211> LENGTH: 45
<212> TYPE: DNA
<213> ORGANISM: Homo sapiens

<400> SEQUENCE: 2105
gtttttggag ttgtgatggg agtgatagtg gttggcattg tcatc 45

<210> SEQ ID NO 2106
<211> LENGTH: 45
<212> TYPE: DNA
<213> ORGANISM: Homo sapiens

<400> SEQUENCE: 2106
atgtggaaca tacctttgaa gagattaaac cattatatga acatc 45

<210> SEQ ID NO 2107
<211> LENGTH: 45
<212> TYPE: DNA
<213> ORGANISM: Homo sapiens

<400> SEQUENCE: 2107
tcctcttgag gtgattttgt tgtatgtaaa tgttaatttc atggt 45

<210> SEQ ID NO 2108
<211> LENGTH: 45
<212> TYPE: DNA
<213> ORGANISM: Homo sapiens

<400> SEQUENCE: 2108
tatgtaaatg ttaatttcat ggtatagaaa atataagatg ataaa 45

<210> SEQ ID NO 2109
<211> LENGTH: 45
<212> TYPE: DNA
<213> ORGANISM: Homo sapiens

<400> SEQUENCE: 2109
agtatttatt tctgtctctg gatttgactt ctgttctgtt tctta 45

<210> SEQ ID NO 2110
<211> LENGTH: 45
<212> TYPE: DNA

<213> ORGANISM: Homo sapiens

<400> SEQUENCE: 2110
tacctttgaa gagattaaac cattatatga acatcttcat gccta 45

<210> SEQ ID NO 2111
<211> LENGTH: 45
<212> TYPE: DNA
<213> ORGANISM: Homo sapiens

<400> SEQUENCE: 2111
gaaaaatcta tgtttttcct cttgaggtga ttttgttgta tgtaa 45

<210> SEQ ID NO 2112
<211> LENGTH: 45
<212> TYPE: DNA
<213> ORGANISM: Homo sapiens

<400> SEQUENCE: 2112
agatgataaa gatatcatta aatgtcaaaa ctatgactct gttca 45

<210> SEQ ID NO 2113
<211> LENGTH: 45
<212> TYPE: DNA
<213> ORGANISM: Homo sapiens

<400> SEQUENCE: 2113
atcgatatta gcaaaggaga aaataatcca ggattccaaa acact 45

<210> SEQ ID NO 2114
<211> LENGTH: 45
<212> TYPE: DNA
<213> ORGANISM: Homo sapiens

<400> SEQUENCE: 2114
tgtccaaaga caacatggcc aaggagagag catcttcatt gacat 45

<210> SEQ ID NO 2115
<211> LENGTH: 45
<212> TYPE: DNA
<213> ORGANISM: Homo sapiens

<400> SEQUENCE: 2115
ggtctcacag gctgttcagg gataatctaa atgtaaatgt ctgtt 45

<210> SEQ ID NO 2116
<211> LENGTH: 45
<212> TYPE: DNA
<213> ORGANISM: Homo sapiens

<400> SEQUENCE: 2116
ttctgtcacc cgattttcaa gaagacaatg aaacagaaat aaact 45

<210> SEQ ID NO 2117
<211> LENGTH: 45
<212> TYPE: DNA
<213> ORGANISM: Homo sapiens

<400> SEQUENCE: 2117
attcgatatt acacaaggac cctttaccaa ttccagtttc aagaa 45

<210> SEQ ID NO 2118
<211> LENGTH: 45

<212> TYPE: DNA
<213> ORGANISM: Homo sapiens

<400> SEQUENCE: 2118
agcattggaa aatgttgtag gagcaaagaa catgaatgta aggcc 45

<210> SEQ ID NO 2119
<211> LENGTH: 45
<212> TYPE: DNA
<213> ORGANISM: Homo sapiens

<400> SEQUENCE: 2119
attggaaaat gttgtaggag caaagaacat gaatgtaagg ccact 45

<210> SEQ ID NO 2120
<211> LENGTH: 45
<212> TYPE: DNA
<213> ORGANISM: Homo sapiens

<400> SEQUENCE: 2120
aaataaagca agaagtggag aaaatcctta tgcctccatc gatat 45

<210> SEQ ID NO 2121
<211> LENGTH: 45
<212> TYPE: DNA
<213> ORGANISM: Homo sapiens

<400> SEQUENCE: 2121
tgtttttcct cttgaggtga ttttgttgta tgtaaatgtt aattt 45

<210> SEQ ID NO 2122
<211> LENGTH: 45
<212> TYPE: DNA
<213> ORGANISM: Homo sapiens

<400> SEQUENCE: 2122
ggaaatcatg tcactttctg cagccacacc taagcattta aaatc 45

<210> SEQ ID NO 2123
<211> LENGTH: 45
<212> TYPE: DNA
<213> ORGANISM: Homo sapiens

<400> SEQUENCE: 2123
atatcattaa atgtcaaaac tatgactctg ttcagaaaaa aaatt 45

<210> SEQ ID NO 2124
<211> LENGTH: 45
<212> TYPE: DNA
<213> ORGANISM: Homo sapiens

<400> SEQUENCE: 2124
ggctgttcag ggataatcta aatgtaaatg tctgttgaat ttctg 45

<210> SEQ ID NO 2125
<211> LENGTH: 45
<212> TYPE: DNA
<213> ORGANISM: Homo sapiens

<400> SEQUENCE: 2125
tctcatgagg aggttttagt ctagggaaag tcattcagtg gatgt 45

<210> SEQ ID NO 2126

<211> LENGTH: 45
<212> TYPE: DNA
<213> ORGANISM: Homo sapiens

<400> SEQUENCE: 2126
caaggatata tcattggagc aagtgttgga tcttgtatgg aatat 45

<210> SEQ ID NO 2127
<211> LENGTH: 45
<212> TYPE: DNA
<213> ORGANISM: Homo sapiens

<400> SEQUENCE: 2127
atttctgtct ctggatttga cttctgttct gtttcttaat aagga 45

<210> SEQ ID NO 2128
<211> LENGTH: 45
<212> TYPE: DNA
<213> ORGANISM: Homo sapiens

<400> SEQUENCE: 2128
gtttcttaat aaggattttg tattagagta tattagggaa agtgt 45

<210> SEQ ID NO 2129
<211> LENGTH: 45
<212> TYPE: DNA
<213> ORGANISM: Homo sapiens

<400> SEQUENCE: 2129
ggtcggcaag cagctgaggc cattatatga agagtatgtg gtctt 45

<210> SEQ ID NO 2130
<211> LENGTH: 45
<212> TYPE: DNA
<213> ORGANISM: Homo sapiens

<400> SEQUENCE: 2130
gtggctaatt tgaaaccaag aatctccttt aatttctttg tcact 45

<210> SEQ ID NO 2131
<211> LENGTH: 45
<212> TYPE: DNA
<213> ORGANISM: Homo sapiens

<400> SEQUENCE: 2131
ggattccaaa acactgatga tgttcagacc tccttttaga aaaat 45

<210> SEQ ID NO 2132
<211> LENGTH: 45
<212> TYPE: DNA
<213> ORGANISM: Homo sapiens

<400> SEQUENCE: 2132
gtatttattt ctgtctctgg atttgacttc tgttctgttt cttaa 45

<210> SEQ ID NO 2133
<211> LENGTH: 45
<212> TYPE: DNA
<213> ORGANISM: Homo sapiens

<400> SEQUENCE: 2133
gtaactgctg ctcagtccac cattgaggaa caggccaaga cattt 45

<210> SEQ ID NO 2134
<211> LENGTH: 45
<212> TYPE: DNA
<213> ORGANISM: Homo sapiens

<400> SEQUENCE: 2134
aatccacaag aatgcttatt acttgaacca ggtttgaatg aaata 45

<210> SEQ ID NO 2135
<211> LENGTH: 45
<212> TYPE: DNA
<213> ORGANISM: Homo sapiens

<400> SEQUENCE: 2135
agaatgctta ttacttgaac caggtttgaa tgaaataatg gcaaa 45

<210> SEQ ID NO 2136
<211> LENGTH: 45
<212> TYPE: DNA
<213> ORGANISM: Homo sapiens

<400> SEQUENCE: 2136
gaacaagaat tcttttgtgg gatggagtac cgactggagt ccata 45

<210> SEQ ID NO 2137
<211> LENGTH: 45
<212> TYPE: DNA
<213> ORGANISM: Homo sapiens

<400> SEQUENCE: 2137
ctatgttttt cctcttgagg tgattttgtt gtatgtaaat gttaa 45

<210> SEQ ID NO 2138
<211> LENGTH: 45
<212> TYPE: DNA
<213> ORGANISM: Homo sapiens

<400> SEQUENCE: 2138
gtctcttaaa tcttttgtat ttgctcacag tgtttgagca gtgct 45

<210> SEQ ID NO 2139
<211> LENGTH: 45
<212> TYPE: DNA
<213> ORGANISM: Homo sapiens

<400> SEQUENCE: 2139
tccacaagaa tgcttattac ttgaaccagg tttgaatgaa ataat 45

<210> SEQ ID NO 2140
<211> LENGTH: 45
<212> TYPE: DNA
<213> ORGANISM: Homo sapiens

<400> SEQUENCE: 2140
gtcttgaaaa atgagatggc aagagcaaat cattatgagg actat 45

<210> SEQ ID NO 2141
<211> LENGTH: 45
<212> TYPE: DNA
<213> ORGANISM: Homo sapiens

<400> SEQUENCE: 2141
tttgacagtt ccctttggac agaaaccaaa catagatgtt actga 45

<210> SEQ ID NO 2142
<211> LENGTH: 45
<212> TYPE: DNA
<213> ORGANISM: Homo sapiens

<400> SEQUENCE: 2142
tcttaataag gattttgtat tagagtatat tagggaaagt gtgta 45

<210> SEQ ID NO 2143
<211> LENGTH: 45
<212> TYPE: DNA
<213> ORGANISM: Homo sapiens

<400> SEQUENCE: 2143
gttgaaaaca aggatatatc attggagcaa gtgttggatc ttgta 45

<210> SEQ ID NO 2144
<211> LENGTH: 45
<212> TYPE: DNA
<213> ORGANISM: Homo sapiens

<400> SEQUENCE: 2144
gtgattttgt tgtatgtaaa tgttaatttc atggtataga aaata 45

<210> SEQ ID NO 2145
<211> LENGTH: 45
<212> TYPE: DNA
<213> ORGANISM: Homo sapiens

<400> SEQUENCE: 2145
acttctgttc tgtttcttaa taaggatttt gtattagagt atatt 45

<210> SEQ ID NO 2146
<211> LENGTH: 45
<212> TYPE: DNA
<213> ORGANISM: Homo sapiens

<400> SEQUENCE: 2146
ttgaatagcg cccaacccaa gttcaaaggc tgataagaga gaaaa 45

<210> SEQ ID NO 2147
<211> LENGTH: 45
<212> TYPE: DNA
<213> ORGANISM: Homo sapiens

<400> SEQUENCE: 2147
cacgattgtt gggactctgc catttactta catgttagag aagtg 45

<210> SEQ ID NO 2148
<211> LENGTH: 45
<212> TYPE: DNA
<213> ORGANISM: Homo sapiens

<400> SEQUENCE: 2148
aaagaacatg aatgtaaggc cactgctcaa ctactttgag ccctt 45

<210> SEQ ID NO 2149
<211> LENGTH: 45
<212> TYPE: DNA
<213> ORGANISM: Homo sapiens

<400> SEQUENCE: 2149
gatcttggct cacaggggac gatgtcaagc tcttcctggc tcctt 45

<210> SEQ ID NO 2150
<211> LENGTH: 45
<212> TYPE: DNA
<213> ORGANISM: Homo sapiens

<400> SEQUENCE: 2150
ttggacaagt ttaaccacga agccgaagac ctgttctatc aaagt 45

<210> SEQ ID NO 2151
<211> LENGTH: 45
<212> TYPE: DNA
<213> ORGANISM: Homo sapiens

<400> SEQUENCE: 2151
ccaaatgtat ccactacaag aaattcagaa tctcacagtc aagct 45

<210> SEQ ID NO 2152
<211> LENGTH: 45
<212> TYPE: DNA
<213> ORGANISM: Homo sapiens

<400> SEQUENCE: 2152
cactgcacct aaaaatgtgt ctgatatcat tcctagaact gaagt 45

<210> SEQ ID NO 2153
<211> LENGTH: 45
<212> TYPE: DNA
<213> ORGANISM: Homo sapiens

<400> SEQUENCE: 2153
gtctcacagg ctgttcaggg ataatctaaa tgtaaatgtc tgttg 45

<210> SEQ ID NO 2154
<211> LENGTH: 45
<212> TYPE: DNA
<213> ORGANISM: Homo sapiens

<400> SEQUENCE: 2154
actcccagag catgcctgat agaaactcat ttctactgtt ctcta 45

<210> SEQ ID NO 2155
<211> LENGTH: 45
<212> TYPE: DNA
<213> ORGANISM: Homo sapiens

<400> SEQUENCE: 2155
atggggcata tccagtatga tatggcatat gctgcacaac ctttt 45

<210> SEQ ID NO 2156
<211> LENGTH: 45
<212> TYPE: DNA
<213> ORGANISM: Homo sapiens

<400> SEQUENCE: 2156
gctcaaacaa gcactcacga ttgttgggac tctgccattt actta 45

<210> SEQ ID NO 2157
<211> LENGTH: 45
<212> TYPE: DNA
<213> ORGANISM: Homo sapiens

<400> SEQUENCE: 2157

-continued ttccaaaaca ctgatgatgt tcagacctcc ttttagaaaa atcta 45

<210> SEQ ID NO 2158
<211> LENGTH: 45
<212> TYPE: DNA
<213> ORGANISM: Homo sapiens

<400> SEQUENCE: 2158
catggtatag aaaatataag atgataaaga tatcattaaa tgtca 45

<210> SEQ ID NO 2159
<211> LENGTH: 45
<212> TYPE: DNA
<213> ORGANISM: Homo sapiens

<400> SEQUENCE: 2159
atagaaaata taagatgata aagatatcat taaatgtcaa aacta 45

<210> SEQ ID NO 2160
<211> LENGTH: 45
<212> TYPE: DNA
<213> ORGANISM: Homo sapiens

<400> SEQUENCE: 2160
tttgacttct gttctgtttc ttaataagga ttttgtatta gagta 45

<210> SEQ ID NO 2161
<211> LENGTH: 45
<212> TYPE: DNA
<213> ORGANISM: Homo sapiens

<400> SEQUENCE: 2161
tttcttaata aggattttgt attagagtat attagggaaa gtgtg 45

<210> SEQ ID NO 2162
<211> LENGTH: 45
<212> TYPE: DNA
<213> ORGANISM: Homo sapiens

<400> SEQUENCE: 2162
aaagttcact tgcttcttgg aattataaca ccaatattac tgaag 45

<210> SEQ ID NO 2163
<211> LENGTH: 45
<212> TYPE: DNA
<213> ORGANISM: Homo sapiens

<400> SEQUENCE: 2163
atcaggatgt cccggagccg tatcaatgat gctttccgtc tgaat 45

<210> SEQ ID NO 2164
<211> LENGTH: 45
<212> TYPE: DNA
<213> ORGANISM: Homo sapiens

<400> SEQUENCE: 2164
ttgctttcag tatttatttc tgtctctgga tttgacttct gttct 45

<210> SEQ ID NO 2165
<211> LENGTH: 45
<212> TYPE: DNA
<213> ORGANISM: Homo sapiens

<400> SEQUENCE: 2165
tgtttgagca gtgctgagca caaagcagac actcaataaa tgcta 45

<210> SEQ ID NO 2166
<211> LENGTH: 45
<212> TYPE: DNA
<213> ORGANISM: Homo sapiens

<400> SEQUENCE: 2166
aaaatataag atgataaaga tatcattaaa tgtcaaaact atgac 45

<210> SEQ ID NO 2167
<211> LENGTH: 45
<212> TYPE: DNA
<213> ORGANISM: Homo sapiens

<400> SEQUENCE: 2167
ctttcttact tccacgtgac cttgactgag ttttgaatag cgccc 45

<210> SEQ ID NO 2168
<211> LENGTH: 45
<212> TYPE: DNA
<213> ORGANISM: Homo sapiens

<400> SEQUENCE: 2168
ccagttgatt gaagatgtgg aacatacctt tgaagagatt aaacc 45

<210> SEQ ID NO 2169
<211> LENGTH: 45
<212> TYPE: DNA
<213> ORGANISM: Homo sapiens

<400> SEQUENCE: 2169
cgatcatctg ttgcatatgc tatgaggcag tactttttaa aagta 45

<210> SEQ ID NO 2170
<211> LENGTH: 45
<212> TYPE: DNA
<213> ORGANISM: Homo sapiens

<400> SEQUENCE: 2170
taaccagccc cctgtttcca tatggctgat tgtttttgga gttgt 45

<210> SEQ ID NO 2171
<211> LENGTH: 45
<212> TYPE: DNA
<213> ORGANISM: Homo sapiens

<400> SEQUENCE: 2171
tggcaaacag tttagactac aatgagaggc tctgggcttg ggaaa 45

<210> SEQ ID NO 2172
<211> LENGTH: 45
<212> TYPE: DNA
<213> ORGANISM: Homo sapiens

<400> SEQUENCE: 2172
atgtgcgagt ggctaatttg aaaccaagaa tctcctttaa tttct 45

<210> SEQ ID NO 2173
<211> LENGTH: 45
<212> TYPE: DNA
<213> ORGANISM: Homo sapiens

<400> SEQUENCE: 2173
ctaaatgtaa atgtctgttg aatttctgaa gttgaaaaca aggat 45

<210> SEQ ID NO 2174
<211> LENGTH: 45
<212> TYPE: DNA
<213> ORGANISM: Homo sapiens

<400> SEQUENCE: 2174
cctctgaagt gggtacccag tctcttaaat cttttgtatt tgctc 45

<210> SEQ ID NO 2175
<211> LENGTH: 45
<212> TYPE: DNA
<213> ORGANISM: Homo sapiens

<400> SEQUENCE: 2175
tgtttttgga gttgtgatgg gagtgatagt ggttggcatt gtcat 45

<210> SEQ ID NO 2176
<211> LENGTH: 45
<212> TYPE: DNA
<213> ORGANISM: Homo sapiens

<400> SEQUENCE: 2176
aggattccaa aacactgatg atgttcagac ctccttttag aaaaa 45

<210> SEQ ID NO 2177
<211> LENGTH: 45
<212> TYPE: DNA
<213> ORGANISM: Homo sapiens

<400> SEQUENCE: 2177
ctatcaaagt tcacttgctt cttggaatta taacaccaat attac 45

<210> SEQ ID NO 2178
<211> LENGTH: 45
<212> TYPE: DNA
<213> ORGANISM: Homo sapiens

<400> SEQUENCE: 2178
ctgttcaggg ataatctaaa tgtaaatgtc tgttgaattt ctgaa 45

<210> SEQ ID NO 2179
<211> LENGTH: 45
<212> TYPE: DNA
<213> ORGANISM: Homo sapiens

<400> SEQUENCE: 2179
gtccaaaaca tgaataatgc tggggacaaa tggtctgcct tttta 45

<210> SEQ ID NO 2180
<211> LENGTH: 45
<212> TYPE: DNA
<213> ORGANISM: Homo sapiens

<400> SEQUENCE: 2180
tcttctgtca cccgattttc aagaagacaa tgaaacagaa ataaa 45

<210> SEQ ID NO 2181
<211> LENGTH: 45
<212> TYPE: DNA
<213> ORGANISM: Homo sapiens

<400> SEQUENCE: 2181
aagcctaaaa tcagctcttg gagataaagc atatgaatgg aacga 45

<210> SEQ ID NO 2182
<211> LENGTH: 45
<212> TYPE: DNA
<213> ORGANISM: Homo sapiens

<400> SEQUENCE: 2182
tatgaatgga acgacaatga aatgtacctg ttccgatcat ctgtt 45

<210> SEQ ID NO 2183
<211> LENGTH: 45
<212> TYPE: DNA
<213> ORGANISM: Homo sapiens

<400> SEQUENCE: 2183
tttcatggta tagaaaatat aagatgataa agatatcatt aaatg 45

<210> SEQ ID NO 2184
<211> LENGTH: 45
<212> TYPE: DNA
<213> ORGANISM: Homo sapiens

<400> SEQUENCE: 2184
tctggatttg acttctgttc tgtttcttaa taaggatttt gtatt 45

<210> SEQ ID NO 2185
<211> LENGTH: 45
<212> TYPE: DNA
<213> ORGANISM: Homo sapiens

<400> SEQUENCE: 2185
caagtactat ggtgatttgc ctacagtgat gtttggaatc gatca 45

<210> SEQ ID NO 2186
<211> LENGTH: 45
<212> TYPE: DNA
<213> ORGANISM: Homo sapiens

<400> SEQUENCE: 2186
gctgataaga gagaaaatct catgaggagg ttttagtcta gggaa 45

<210> SEQ ID NO 2187
<211> LENGTH: 45
<212> TYPE: DNA
<213> ORGANISM: Homo sapiens

<400> SEQUENCE: 2187
atggtataga aaatataaga tgataaagat atcattaaat gtcaa 45

<210> SEQ ID NO 2188
<211> LENGTH: 45
<212> TYPE: DNA
<213> ORGANISM: Homo sapiens

<400> SEQUENCE: 2188
tgatttgcct acagtgatgt ttggaatcga tcatgctttc ttcaa 45

<210> SEQ ID NO 2189
<211> LENGTH: 45
<212> TYPE: DNA

<213> ORGANISM: Homo sapiens

<400> SEQUENCE: 2189
ttttaaagga acagtccaca cttgcccaaa tgtatccact acaag 45

<210> SEQ ID NO 2190
<211> LENGTH: 45
<212> TYPE: DNA
<213> ORGANISM: Homo sapiens

<400> SEQUENCE: 2190
gggattattg gagaggagac tatgaagtaa atggggtaga tggct 45

<210> SEQ ID NO 2191
<211> LENGTH: 45
<212> TYPE: DNA
<213> ORGANISM: Homo sapiens

<400> SEQUENCE: 2191
ccaaggagag agcatcttca ttgacattgc tttcagtatt tattt 45

<210> SEQ ID NO 2192
<211> LENGTH: 45
<212> TYPE: DNA
<213> ORGANISM: Homo sapiens

<400> SEQUENCE: 2192
ggataatcta aatgtaaatg tctgttgaat ttctgaagtt gaaaa 45

<210> SEQ ID NO 2193
<211> LENGTH: 45
<212> TYPE: DNA
<213> ORGANISM: Homo sapiens

<400> SEQUENCE: 2193
gtgcctggga actggtgtag ctgcaaggat tgagaatggc atgca 45

<210> SEQ ID NO 2194
<211> LENGTH: 45
<212> TYPE: DNA
<213> ORGANISM: Homo sapiens

<400> SEQUENCE: 2194
tacagaggat caggagttga catagatact ctttggattt catac 45

<210> SEQ ID NO 2195
<211> LENGTH: 45
<212> TYPE: DNA
<213> ORGANISM: Homo sapiens

<400> SEQUENCE: 2195
tattactgaa gagaatgtcc aaaacatgaa taatgctggg gacaa 45

<210> SEQ ID NO 2196
<211> LENGTH: 45
<212> TYPE: DNA
<213> ORGANISM: Homo sapiens

<400> SEQUENCE: 2196
gtatagaaaa tataagatga taaagatatc attaaatgtc aaaac 45

<210> SEQ ID NO 2197
<211> LENGTH: 45

<212> TYPE: DNA
<213> ORGANISM: Homo sapiens

<400> SEQUENCE: 2197
ttcttaataa ggattttgta ttagagtata ttagggaaag tgtgt 45

<210> SEQ ID NO 2198
<211> LENGTH: 45
<212> TYPE: DNA
<213> ORGANISM: Homo sapiens

<400> SEQUENCE: 2198
ggatgacatg ctttcttcac agtaactcag ttcaagtact atggt 45

<210> SEQ ID NO 2199
<211> LENGTH: 45
<212> TYPE: DNA
<213> ORGANISM: Homo sapiens

<400> SEQUENCE: 2199
catggctaca gaggatcagg agttgacata gatactcttt ggatt 45

<210> SEQ ID NO 2200
<211> LENGTH: 45
<212> TYPE: DNA
<213> ORGANISM: Homo sapiens

<400> SEQUENCE: 2200
gattttggac aaatctgtac tctttgacag ttccctttgg acaga 45

<210> SEQ ID NO 2201
<211> LENGTH: 45
<212> TYPE: DNA
<213> ORGANISM: Homo sapiens

<400> SEQUENCE: 2201
tttctgctaa gaaatggagc taatgaagga ttccatgaag ctgtt 45

<210> SEQ ID NO 2202
<211> LENGTH: 45
<212> TYPE: DNA
<213> ORGANISM: Homo sapiens

<400> SEQUENCE: 2202
actgctcaac tactttgagc ccttatttac ctggctgaaa gacca 45

<210> SEQ ID NO 2203
<211> LENGTH: 45
<212> TYPE: DNA
<213> ORGANISM: Homo sapiens

<400> SEQUENCE: 2203
atcatctgtt gcatatgcta tgaggcagta ctttttaaaa gtaaa 45

<210> SEQ ID NO 2204
<211> LENGTH: 45
<212> TYPE: DNA
<213> ORGANISM: Homo sapiens

<400> SEQUENCE: 2204
tgaggtgatt ttgttgtatg taaatgttaa tttcatggta tagaa 45

<210> SEQ ID NO 2205

<211> LENGTH: 45
<212> TYPE: DNA
<213> ORGANISM: Homo sapiens

<400> SEQUENCE: 2205
gccaaggaga gagcatcttc attgacattg ctttcagtat ttatt 45

<210> SEQ ID NO 2206
<211> LENGTH: 45
<212> TYPE: DNA
<213> ORGANISM: Homo sapiens

<400> SEQUENCE: 2206
tagggaaagt gtgtatttgg tctcacaggc tgttcaggga taatc 45

<210> SEQ ID NO 2207
<211> LENGTH: 45
<212> TYPE: DNA
<213> ORGANISM: Homo sapiens

<400> SEQUENCE: 2207
aagttcaaag gctgataaga gagaaaatct catgaggagg tttta 45

<210> SEQ ID NO 2208
<211> LENGTH: 45
<212> TYPE: DNA
<213> ORGANISM: Homo sapiens

<400> SEQUENCE: 2208
ttcctgacag ctcatcatga gatggggcat atccagtatg atatg 45

<210> SEQ ID NO 2209
<211> LENGTH: 45
<212> TYPE: DNA
<213> ORGANISM: Homo sapiens

<400> SEQUENCE: 2209
atctctgttc catgtttcta atgattactc attcattcga tatta 45

<210> SEQ ID NO 2210
<211> LENGTH: 45
<212> TYPE: DNA
<213> ORGANISM: Homo sapiens

<400> SEQUENCE: 2210
ggatgtcccg gagccgtatc aatgatgctt tccgtctgaa tgaca 45

<210> SEQ ID NO 2211
<211> LENGTH: 45
<212> TYPE: DNA
<213> ORGANISM: Homo sapiens

<400> SEQUENCE: 2211
tgttgaattt ctgaagttga aaacaaggat atatcattgg agcaa 45

<210> SEQ ID NO 2212
<211> LENGTH: 45
<212> TYPE: DNA
<213> ORGANISM: Homo sapiens

<400> SEQUENCE: 2212
cgcggccagt tgattgaaga tgtggaacat acctttgaag agatt 45

<210> SEQ ID NO 2213
<211> LENGTH: 45
<212> TYPE: DNA
<213> ORGANISM: Homo sapiens

<400> SEQUENCE: 2213
gatgtggaac atacctttga agagattaaa ccattatatg aacat          45

<210> SEQ ID NO 2214
<211> LENGTH: 45
<212> TYPE: DNA
<213> ORGANISM: Homo sapiens

<400> SEQUENCE: 2214
cctggctgaa agaccagaac aagaattctt ttgtgggatg gagta          45

<210> SEQ ID NO 2215
<211> LENGTH: 45
<212> TYPE: DNA
<213> ORGANISM: Homo sapiens

<400> SEQUENCE: 2215
tgcctccatc gatattagca aaggagaaaa taatccagga ttcca          45

<210> SEQ ID NO 2216
<211> LENGTH: 45
<212> TYPE: DNA
<213> ORGANISM: Homo sapiens

<400> SEQUENCE: 2216
tgaatttctg aagttgaaaa caaggatata tcattggagc aagtg          45

<210> SEQ ID NO 2217
<211> LENGTH: 45
<212> TYPE: DNA
<213> ORGANISM: Homo sapiens

<400> SEQUENCE: 2217
atgtttggaa tcgatcatgc tttcttcaag gtgacaggtc taaag          45

<210> SEQ ID NO 2218
<211> LENGTH: 45
<212> TYPE: DNA
<213> ORGANISM: Homo sapiens

<400> SEQUENCE: 2218
ttttgaatag cgcccaaccc aagttcaaag gctgataaga gagaa          45

<210> SEQ ID NO 2219
<211> LENGTH: 45
<212> TYPE: DNA
<213> ORGANISM: Homo sapiens

<400> SEQUENCE: 2219
agattaaacc attatatgaa catcttcatg cctatgtgag ggcaa          45

<210> SEQ ID NO 2220
<211> LENGTH: 45
<212> TYPE: DNA
<213> ORGANISM: Homo sapiens

<400> SEQUENCE: 2220
gtcatcctga tcttcactgg gatcagagat cggaagaaga aaaat          45

<210> SEQ ID NO 2221
<211> LENGTH: 45
<212> TYPE: DNA
<213> ORGANISM: Homo sapiens

<400> SEQUENCE: 2221
gaatcgatca tgctttcttc aaggtgacag gtctaaagag agaag 45

<210> SEQ ID NO 2222
<211> LENGTH: 45
<212> TYPE: DNA
<213> ORGANISM: Homo sapiens

<400> SEQUENCE: 2222
tcagctgcag gctcttcagc aaaatgggtc ttcagtgctc tcaga 45

<210> SEQ ID NO 2223
<211> LENGTH: 45
<212> TYPE: DNA
<213> ORGANISM: Homo sapiens

<400> SEQUENCE: 2223
ttgaatgaaa taatggcaaa cagtttagac tacaatgaga ggctc 45

<210> SEQ ID NO 2224
<211> LENGTH: 45
<212> TYPE: DNA
<213> ORGANISM: Homo sapiens

<400> SEQUENCE: 2224
acctttgaag agattaaacc attatatgaa catcttcatg cctat 45

<210> SEQ ID NO 2225
<211> LENGTH: 45
<212> TYPE: DNA
<213> ORGANISM: Homo sapiens

<400> SEQUENCE: 2225
tagattttgg acaaatctgt actctttgac agttcccttt ggaca 45

<210> SEQ ID NO 2226
<211> LENGTH: 45
<212> TYPE: DNA
<213> ORGANISM: Homo sapiens

<400> SEQUENCE: 2226
gacaaatctg tactctttga cagttccctt tggacagaaa ccaaa 45

<210> SEQ ID NO 2227
<211> LENGTH: 45
<212> TYPE: DNA
<213> ORGANISM: Homo sapiens

<400> SEQUENCE: 2227
tttcaagaag acaatgaaac agaaataaac ttcctgctca aacaa 45

<210> SEQ ID NO 2228
<211> LENGTH: 45
<212> TYPE: DNA
<213> ORGANISM: Homo sapiens

<400> SEQUENCE: 2228
cattgacatt gctttcagta tttatttctg tctctggatt tgact 45

<210> SEQ ID NO 2229
<211> LENGTH: 45
<212> TYPE: DNA
<213> ORGANISM: Homo sapiens

<400> SEQUENCE: 2229
ttcttcacag taactcagtt caagtactat ggtgatttgc ctaca 45

<210> SEQ ID NO 2230
<211> LENGTH: 45
<212> TYPE: DNA
<213> ORGANISM: Homo sapiens

<400> SEQUENCE: 2230
attactgaag agaatgtcca aaacatgaat aatgctgggg acaaa 45

<210> SEQ ID NO 2231
<211> LENGTH: 45
<212> TYPE: DNA
<213> ORGANISM: Homo sapiens

<400> SEQUENCE: 2231
tatgtgaggg caaagttgat gaatgcctat ccttcctata tcagt 45

<210> SEQ ID NO 2232
<211> LENGTH: 45
<212> TYPE: DNA
<213> ORGANISM: Homo sapiens

<400> SEQUENCE: 2232
gttccgatca tctgttgcat atgctatgag gcagtacttt ttaaa 45

<210> SEQ ID NO 2233
<211> LENGTH: 45
<212> TYPE: DNA
<213> ORGANISM: Homo sapiens

<400> SEQUENCE: 2233
agtggagaaa atccttatgc ctccatcgat attagcaaag gagaa 45

<210> SEQ ID NO 2234
<211> LENGTH: 45
<212> TYPE: DNA
<213> ORGANISM: Homo sapiens

<400> SEQUENCE: 2234
ctacagagga tcaggagttg acatagatac tctttggatt tcata 45

<210> SEQ ID NO 2235
<211> LENGTH: 45
<212> TYPE: DNA
<213> ORGANISM: Homo sapiens

<400> SEQUENCE: 2235
atctcatgag gaggttttag tctagggaaa gtcattcagt ggatg 45

<210> SEQ ID NO 2236
<211> LENGTH: 45
<212> TYPE: DNA
<213> ORGANISM: Homo sapiens

<400> SEQUENCE: 2236
tttttaaagg aacagtccac acttgcccaa atgtatccac tacaa 45

<210> SEQ ID NO 2237
<211> LENGTH: 45
<212> TYPE: DNA
<213> ORGANISM: Homo sapiens

<400> SEQUENCE: 2237
tttaaaatcc attggtcttc tgtcacccga ttttcaagaa gacaa 45

<210> SEQ ID NO 2238
<211> LENGTH: 45
<212> TYPE: DNA
<213> ORGANISM: Homo sapiens

<400> SEQUENCE: 2238
tgttaatttc atggtataga aaatataaga tgataaagat atcat 45

<210> SEQ ID NO 2239
<211> LENGTH: 45
<212> TYPE: DNA
<213> ORGANISM: Homo sapiens

<400> SEQUENCE: 2239
cagtatgata tggcatatgc tgcacaacct tttctgctaa gaaat 45

<210> SEQ ID NO 2240
<211> LENGTH: 45
<212> TYPE: DNA
<213> ORGANISM: Homo sapiens

<400> SEQUENCE: 2240
atttatttct gtctctggat ttgacttctg ttctgtttct taata 45

<210> SEQ ID NO 2241
<211> LENGTH: 45
<212> TYPE: DNA
<213> ORGANISM: Homo sapiens

<400> SEQUENCE: 2241
tctgtctctg gatttgactt ctgttctgtt tcttaataag gattt 45

<210> SEQ ID NO 2242
<211> LENGTH: 45
<212> TYPE: DNA
<213> ORGANISM: Homo sapiens

<400> SEQUENCE: 2242
gcatgcatta gctcactttc atttaatcca ttgtcaagga tgaca 45

<210> SEQ ID NO 2243
<211> LENGTH: 45
<212> TYPE: DNA
<213> ORGANISM: Homo sapiens

<400> SEQUENCE: 2243
atttaatcca ttgtcaagga tgacatgctt tcttcacagt aactc 45

<210> SEQ ID NO 2244
<211> LENGTH: 45
<212> TYPE: DNA
<213> ORGANISM: Homo sapiens

<400> SEQUENCE: 2244
aagaatccag ggaacaggta gaggacattg ctttttcact tccaa 45

<210> SEQ ID NO 2245
<211> LENGTH: 45
<212> TYPE: DNA
<213> ORGANISM: Homo sapiens

<400> SEQUENCE: 2245
gaggccgaga agttctttgt atctgttggt cttcctaata tgact 45

<210> SEQ ID NO 2246
<211> LENGTH: 45
<212> TYPE: DNA
<213> ORGANISM: Homo sapiens

<400> SEQUENCE: 2246
gtctttaaag gggaaattcc caaagaccag tggatgaaaa agtgg 45

<210> SEQ ID NO 2247
<211> LENGTH: 45
<212> TYPE: DNA
<213> ORGANISM: Homo sapiens

<400> SEQUENCE: 2247
tatttacctg gctgaaagac cagaacaaga attcttttgt gggat 45

<210> SEQ ID NO 2248
<211> LENGTH: 45
<212> TYPE: DNA
<213> ORGANISM: Homo sapiens

<400> SEQUENCE: 2248
atcagctctt ggagataaag catatgaatg gaacgacaat gaaat 45

<210> SEQ ID NO 2249
<211> LENGTH: 45
<212> TYPE: DNA
<213> ORGANISM: Homo sapiens

<400> SEQUENCE: 2249
tatttatttc tgtctctgga tttgacttct gttctgtttc ttaat 45

<210> SEQ ID NO 2250
<211> LENGTH: 45
<212> TYPE: DNA
<213> ORGANISM: Homo sapiens

<400> SEQUENCE: 2250
tgtattagag tatattaggg aaagtgtgta tttggtctca caggc 45

<210> SEQ ID NO 2251
<211> LENGTH: 45
<212> TYPE: DNA
<213> ORGANISM: Homo sapiens

<400> SEQUENCE: 2251
caaggattga gaatggcatg cattagctca ctttcattta atcca 45

<210> SEQ ID NO 2252
<211> LENGTH: 45
<212> TYPE: DNA
<213> ORGANISM: Homo sapiens

<400> SEQUENCE: 2252
agttctttgt atctgttggt cttcctaata tgactcaagg attct 45

<210> SEQ ID NO 2253
<211> LENGTH: 45
<212> TYPE: DNA
<213> ORGANISM: Homo sapiens

<400> SEQUENCE: 2253
gcatctctgt tccatgtttc taatgattac tcattcattc gatat 45

<210> SEQ ID NO 2254
<211> LENGTH: 45
<212> TYPE: DNA
<213> ORGANISM: Homo sapiens

<400> SEQUENCE: 2254
ctcattcatt cgatattaca caaggaccct ttaccaattc cagtt 45

<210> SEQ ID NO 2255
<211> LENGTH: 45
<212> TYPE: DNA
<213> ORGANISM: Homo sapiens

<400> SEQUENCE: 2255
gtgcgagtgg ctaatttgaa accaagaatc tcctttaatt tcttt 45

<210> SEQ ID NO 2256
<211> LENGTH: 45
<212> TYPE: DNA
<213> ORGANISM: Homo sapiens

<400> SEQUENCE: 2256
gcacctaaaa atgtgtctga tatcattcct agaactgaag ttgaa 45

<210> SEQ ID NO 2257
<211> LENGTH: 45
<212> TYPE: DNA
<213> ORGANISM: Homo sapiens

<400> SEQUENCE: 2257
atcacttgta aggacagtgc ctgggaactg gtgtagctgc aagga 45

<210> SEQ ID NO 2258
<211> LENGTH: 45
<212> TYPE: DNA
<213> ORGANISM: Homo sapiens

<400> SEQUENCE: 2258
tgtagctgca aggattgaga atggcatgca ttagctcact ttcat 45

<210> SEQ ID NO 2259
<211> LENGTH: 45
<212> TYPE: DNA
<213> ORGANISM: Homo sapiens

<400> SEQUENCE: 2259
ggattgagaa tggcatgcat tagctcactt tcatttaatc cattg 45

<210> SEQ ID NO 2260
<211> LENGTH: 45
<212> TYPE: DNA
<213> ORGANISM: Homo sapiens

<400> SEQUENCE: 2260
attccaactg tatgttcacc ctctgaagtg ggtacccagt ctctt 45

<210> SEQ ID NO 2261
<211> LENGTH: 45
<212> TYPE: DNA
<213> ORGANISM: Homo sapiens

<400> SEQUENCE: 2261
agagagaaaa tctcatgagg aggttttagt ctagggaaag tcatt 45

<210> SEQ ID NO 2262
<211> LENGTH: 45
<212> TYPE: DNA
<213> ORGANISM: Homo sapiens

<400> SEQUENCE: 2262
atgcctccct gctcatttgc ttggtgatat gtggggtaga ttttg 45

<210> SEQ ID NO 2263
<211> LENGTH: 45
<212> TYPE: DNA
<213> ORGANISM: Homo sapiens

<400> SEQUENCE: 2263
cagctcatca tgagatgggg catatccagt atgatatggc atatg 45

<210> SEQ ID NO 2264
<211> LENGTH: 45
<212> TYPE: DNA
<213> ORGANISM: Homo sapiens

<400> SEQUENCE: 2264
tcttggagat aaagcatatg aatggaacga caatgaaatg tacct 45

<210> SEQ ID NO 2265
<211> LENGTH: 45
<212> TYPE: DNA
<213> ORGANISM: Homo sapiens

<400> SEQUENCE: 2265
gtatgtaaat gttaatttca tggtatagaa aatataagat gataa 45

<210> SEQ ID NO 2266
<211> LENGTH: 45
<212> TYPE: DNA
<213> ORGANISM: Homo sapiens

<400> SEQUENCE: 2266
ttataacacc aatattactg aagagaatgt ccaaaacatg aataa 45

<210> SEQ ID NO 2267
<211> LENGTH: 45
<212> TYPE: DNA
<213> ORGANISM: Homo sapiens

<400> SEQUENCE: 2267
cttgaaaaat gagatggcaa gagcaaatca ttatgaggac tatgg 45

<210> SEQ ID NO 2268
<211> LENGTH: 45
<212> TYPE: DNA

<213> ORGANISM: Homo sapiens

<400> SEQUENCE: 2268
gtatgatatg gcatatgctg cacaaccttt tctgctaaga aatgg 45

<210> SEQ ID NO 2269
<211> LENGTH: 45
<212> TYPE: DNA
<213> ORGANISM: Homo sapiens

<400> SEQUENCE: 2269
ttatttacct ggctgaaaga ccagaacaag aattcttttg tggga 45

<210> SEQ ID NO 2270
<211> LENGTH: 45
<212> TYPE: DNA
<213> ORGANISM: Homo sapiens

<400> SEQUENCE: 2270
aaagcatatg aatggaacga caatgaaatg tacctgttcc gatca 45

<210> SEQ ID NO 2271
<211> LENGTH: 45
<212> TYPE: DNA
<213> ORGANISM: Homo sapiens

<400> SEQUENCE: 2271
ttttggggag gaggatgtgc gagtggctaa tttgaaacca agaat 45

<210> SEQ ID NO 2272
<211> LENGTH: 45
<212> TYPE: DNA
<213> ORGANISM: Homo sapiens

<400> SEQUENCE: 2272
atgcctccat cgatattagc aaaggagaaa ataatccagg attcc 45

<210> SEQ ID NO 2273
<211> LENGTH: 45
<212> TYPE: DNA
<213> ORGANISM: Homo sapiens

<400> SEQUENCE: 2273
gagagaagaa tccagggaac aggtagagga cattgctttt tcact 45

<210> SEQ ID NO 2274
<211> LENGTH: 45
<212> TYPE: DNA
<213> ORGANISM: Homo sapiens

<400> SEQUENCE: 2274
gtgggtaccc agtctcttaa atcttttgta tttgctcaca gtgtt 45

<210> SEQ ID NO 2275
<211> LENGTH: 45
<212> TYPE: DNA
<213> ORGANISM: Homo sapiens

<400> SEQUENCE: 2275
acacttgccc aaatgtatcc actacaagaa attcagaatc tcaca 45

<210> SEQ ID NO 2276
<211> LENGTH: 45

<212> TYPE: DNA
<213> ORGANISM: Homo sapiens

<400> SEQUENCE: 2276
gttccctttg gacagaaacc aaacatagat gttactgatg caatg 45

<210> SEQ ID NO 2277
<211> LENGTH: 45
<212> TYPE: DNA
<213> ORGANISM: Homo sapiens

<400> SEQUENCE: 2277
cttcctaata tgactcaagg attctgggaa aattccatgc taacg 45

<210> SEQ ID NO 2278
<211> LENGTH: 45
<212> TYPE: DNA
<213> ORGANISM: Homo sapiens

<400> SEQUENCE: 2278
ttacctggct gaaagaccag aacaagaatt cttttgtggg atgga 45

<210> SEQ ID NO 2279
<211> LENGTH: 45
<212> TYPE: DNA
<213> ORGANISM: Homo sapiens

<400> SEQUENCE: 2279
ttttgttgta tgtaaatgtt aatttcatgg tatagaaaat ataag 45

<210> SEQ ID NO 2280
<211> LENGTH: 45
<212> TYPE: DNA
<213> ORGANISM: Homo sapiens

<400> SEQUENCE: 2280
atataagatg ataaagatat cattaaatgt caaaactatg actct 45

<210> SEQ ID NO 2281
<211> LENGTH: 45
<212> TYPE: DNA
<213> ORGANISM: Homo sapiens

<400> SEQUENCE: 2281
atgataaaga tatcattaaa tgtcaaaact atgactctgt tcaga 45

<210> SEQ ID NO 2282
<211> LENGTH: 45
<212> TYPE: DNA
<213> ORGANISM: Homo sapiens

<400> SEQUENCE: 2282
gtgtatttgg tctcacaggc tgttcaggga taatctaaat gtaaa 45

<210> SEQ ID NO 2283
<211> LENGTH: 45
<212> TYPE: DNA
<213> ORGANISM: Homo sapiens

<400> SEQUENCE: 2283
tttcatttaa tccattgtca aggatgacat gctttcttca cagta 45

<210> SEQ ID NO 2284

<211> LENGTH: 45
<212> TYPE: DNA
<213> ORGANISM: Homo sapiens

<400> SEQUENCE: 2284
ctcagttcaa gtactatggt gatttgccta cagtgatgtt tggaa 45

<210> SEQ ID NO 2285
<211> LENGTH: 45
<212> TYPE: DNA
<213> ORGANISM: Homo sapiens

<400> SEQUENCE: 2285
tatgtggggt agattttgga caaatctgta ctctttgaca gttcc 45

<210> SEQ ID NO 2286
<211> LENGTH: 45
<212> TYPE: DNA
<213> ORGANISM: Homo sapiens

<400> SEQUENCE: 2286
ttaccaattc cagtttcaag aagcactttg tcaagcagct aaaca 45

<210> SEQ ID NO 2287
<211> LENGTH: 45
<212> TYPE: DNA
<213> ORGANISM: Homo sapiens

<400> SEQUENCE: 2287
aaaccaagaa tctcctttaa tttctttgtc actgcaccta aaaat 45

<210> SEQ ID NO 2288
<211> LENGTH: 45
<212> TYPE: DNA
<213> ORGANISM: Homo sapiens

<400> SEQUENCE: 2288
ggaactggtg tagctgcaag gattgagaat ggcatgcatt agctc 45

<210> SEQ ID NO 2289
<211> LENGTH: 45
<212> TYPE: DNA
<213> ORGANISM: Homo sapiens

<400> SEQUENCE: 2289
tgcctacagt gatgtttgga atcgatcatg ctttcttcaa ggtga 45

<210> SEQ ID NO 2290
<211> LENGTH: 45
<212> TYPE: DNA
<213> ORGANISM: Homo sapiens

<400> SEQUENCE: 2290
tgataagaga gaaaatctca tgaggaggtt ttagtctagg gaaag 45

<210> SEQ ID NO 2291
<211> LENGTH: 45
<212> TYPE: DNA
<213> ORGANISM: Homo sapiens

<400> SEQUENCE: 2291
gcaagcagct gaggccatta tatgaagagt atgtggtctt gaaaa 45

<210> SEQ ID NO 2292
<211> LENGTH: 45
<212> TYPE: DNA
<213> ORGANISM: Homo sapiens

<400> SEQUENCE: 2292
atatgactca aggattctgg gaaaattcca tgctaacgga cccag 45

<210> SEQ ID NO 2293
<211> LENGTH: 45
<212> TYPE: DNA
<213> ORGANISM: Homo sapiens

<400> SEQUENCE: 2293
ctggggaagg gcgacttcag gatccttatg tgcacaaagg tgaca 45

<210> SEQ ID NO 2294
<211> LENGTH: 45
<212> TYPE: DNA
<213> ORGANISM: Homo sapiens

<400> SEQUENCE: 2294
agcagctaaa catgaaggcc ctctgcacaa atgtgacatc tcaaa 45

<210> SEQ ID NO 2295
<211> LENGTH: 20
<212> TYPE: RNA
<213> ORGANISM: Homo sapiens

<400> SEQUENCE: 2295
ugugaaaaug aauaucaugc 20

<210> SEQ ID NO 2296
<211> LENGTH: 20
<212> TYPE: RNA
<213> ORGANISM: Homo sapiens

<400> SEQUENCE: 2296
accuucauuu aacucuuuga 20

<210> SEQ ID NO 2297
<211> LENGTH: 20
<212> TYPE: RNA
<213> ORGANISM: Homo sapiens

<400> SEQUENCE: 2297
ucguccuuga cgucguuuua 20

<210> SEQ ID NO 2298
<211> LENGTH: 20
<212> TYPE: RNA
<213> ORGANISM: Homo sapiens

<400> SEQUENCE: 2298
ggagccggau accaaguaga 20

<210> SEQ ID NO 2299
<211> LENGTH: 20
<212> TYPE: RNA
<213> ORGANISM: Homo sapiens

<400> SEQUENCE: 2299
uaccacagug augccuguuc 20

<210> SEQ ID NO 2300
<211> LENGTH: 20
<212> TYPE: RNA
<213> ORGANISM: Homo sapiens

<400> SEQUENCE: 2300
ucaugcaaau aaauuaugca 20

<210> SEQ ID NO 2301
<211> LENGTH: 20
<212> TYPE: RNA
<213> ORGANISM: Homo sapiens

<400> SEQUENCE: 2301
uugaaacugu aucaucuuug 20

<210> SEQ ID NO 2302
<211> LENGTH: 20
<212> TYPE: RNA
<213> ORGANISM: Homo sapiens

<400> SEQUENCE: 2302
gccggcaaug ucgauaucua 20

<210> SEQ ID NO 2303
<211> LENGTH: 20
<212> TYPE: RNA
<213> ORGANISM: Homo sapiens

<400> SEQUENCE: 2303
uguaauggug aaaacgucuu 20

<210> SEQ ID NO 2304
<211> LENGTH: 20
<212> TYPE: RNA
<213> ORGANISM: Homo sapiens

<400> SEQUENCE: 2304
gguggccuau uucagcugcu 20

<210> SEQ ID NO 2305
<211> LENGTH: 20
<212> TYPE: RNA
<213> ORGANISM: Homo sapiens

<400> SEQUENCE: 2305
acagcuagga cuuaaccuug 20

<210> SEQ ID NO 2306
<211> LENGTH: 20
<212> TYPE: RNA
<213> ORGANISM: Homo sapiens

<400> SEQUENCE: 2306
caguuuaagg uacacuguuu 20

<210> SEQ ID NO 2307
<211> LENGTH: 20
<212> TYPE: RNA
<213> ORGANISM: Homo sapiens

<400> SEQUENCE: 2307
gccgccagag caggauugug 20

<210> SEQ ID NO 2308
<211> LENGTH: 20
<212> TYPE: RNA
<213> ORGANISM: Homo sapiens

<400> SEQUENCE: 2308
ccagccauga ucugugccgg 20

<210> SEQ ID NO 2309
<211> LENGTH: 20
<212> TYPE: RNA
<213> ORGANISM: Homo sapiens

<400> SEQUENCE: 2309
uccaucauca cccccgagug 20

<210> SEQ ID NO 2310
<211> LENGTH: 20
<212> TYPE: RNA
<213> ORGANISM: Homo sapiens

<400> SEQUENCE: 2310
augaucugug ccggcuuccu 20

<210> SEQ ID NO 2311
<211> LENGTH: 20
<212> TYPE: RNA
<213> ORGANISM: Homo sapiens

<400> SEQUENCE: 2311
gcuuugaacu cagggucacc 20

<210> SEQ ID NO 2312
<211> LENGTH: 20
<212> TYPE: RNA
<213> ORGANISM: Homo sapiens

<400> SEQUENCE: 2312
aggagaaagg gaagaccuca 20

<210> SEQ ID NO 2313
<211> LENGTH: 20
<212> TYPE: RNA
<213> ORGANISM: Homo sapiens

<400> SEQUENCE: 2313
ccuggcaggu cagccugcac 20

<210> SEQ ID NO 2314
<211> LENGTH: 20
<212> TYPE: RNA
<213> ORGANISM: Homo sapiens

<400> SEQUENCE: 2314
gaggagaaag ggaagaccuc 20

<210> SEQ ID NO 2315
<211> LENGTH: 20
<212> TYPE: RNA
<213> ORGANISM: Homo sapiens

<400> SEQUENCE: 2315
caggucagcc ugcacgucca 20

<210> SEQ ID NO 2316
<211> LENGTH: 20
<212> TYPE: RNA
<213> ORGANISM: Homo sapiens

<400> SEQUENCE: 2316
cauuggacgg cauuugcggg 20

<210> SEQ ID NO 2317
<211> LENGTH: 20
<212> TYPE: RNA
<213> ORGANISM: Homo sapiens

<400> SEQUENCE: 2317
gaggcuccau caucaccccc 20

<210> SEQ ID NO 2318
<211> LENGTH: 20
<212> TYPE: RNA
<213> ORGANISM: Homo sapiens

<400> SEQUENCE: 2318
caugaucugu gccggcuucc 20

<210> SEQ ID NO 2319
<211> LENGTH: 20
<212> TYPE: RNA
<213> ORGANISM: Homo sapiens

<400> SEQUENCE: 2319
accagccaug aucugugccg 20

<210> SEQ ID NO 2320
<211> LENGTH: 20
<212> TYPE: RNA
<213> ORGANISM: Mus sp.

<400> SEQUENCE: 2320
uuugucuuca acaaccuucu 20

<210> SEQ ID NO 2321
<211> LENGTH: 20
<212> TYPE: RNA
<213> ORGANISM: Mus sp.

<400> SEQUENCE: 2321
ugcacaaugu accuuuugag 20

<210> SEQ ID NO 2322
<211> LENGTH: 20
<212> TYPE: RNA
<213> ORGANISM: Mus sp.

<400> SEQUENCE: 2322
ugggacagca acuguucuac 20

<210> SEQ ID NO 2323
<211> LENGTH: 20
<212> TYPE: RNA
<213> ORGANISM: Mus sp.

<400> SEQUENCE: 2323
uuccacugug aaauauauga 20

<210> SEQ ID NO 2324
<211> LENGTH: 20
<212> TYPE: RNA
<213> ORGANISM: Mus sp.

<400> SEQUENCE: 2324
ucaggcaacg uugaccucua 20

<210> SEQ ID NO 2325
<211> LENGTH: 20
<212> TYPE: RNA
<213> ORGANISM: Mus sp.

<400> SEQUENCE: 2325
gggaacguga cgguauuuac 20

<210> SEQ ID NO 2326
<211> LENGTH: 20
<212> TYPE: RNA
<213> ORGANISM: Mus sp.

<400> SEQUENCE: 2326
ucugcaagaa aaccaagggc 20

<210> SEQ ID NO 2327
<211> LENGTH: 20
<212> TYPE: RNA
<213> ORGANISM: Mus sp.

<400> SEQUENCE: 2327
uuuggcuuuu aaugaucuag 20

<210> SEQ ID NO 2328
<211> LENGTH: 20
<212> TYPE: RNA
<213> ORGANISM: Mus sp.

<400> SEQUENCE: 2328
uaagcgagaa cuggaguagg 20

<210> SEQ ID NO 2329
<211> LENGTH: 20
<212> TYPE: RNA
<213> ORGANISM: Mus sp.

<400> SEQUENCE: 2329
guugacauga cggcccuuuc 20

<210> SEQ ID NO 2330
<211> LENGTH: 20
<212> TYPE: RNA
<213> ORGANISM: Mus sp.

<400> SEQUENCE: 2330
ugcuucuggg uuguguuucu 20

<210> SEQ ID NO 2331
<211> LENGTH: 45
<212> TYPE: DNA
<213> ORGANISM: Homo sapiens

<400> SEQUENCE: 2331
actgtaaagt tcaattgtga aaatgaatat catgcaaata aatta 45

<210> SEQ ID NO 2332
<211> LENGTH: 45
<212> TYPE: DNA
<213> ORGANISM: Homo sapiens

<400> SEQUENCE: 2332
gtctccaagt agtccacctt catttaactc tttgaaactg tatca 45

<210> SEQ ID NO 2333
<211> LENGTH: 45
<212> TYPE: DNA
<213> ORGANISM: Homo sapiens

<400> SEQUENCE: 2333
taatccacat ggtcttcgtc cttgacgtcg ttttacaaga aaaca 45

<210> SEQ ID NO 2334
<211> LENGTH: 45
<212> TYPE: DNA
<213> ORGANISM: Homo sapiens

<400> SEQUENCE: 2334
tctttcatgt tctatggagc cggataccaa gtagaaaaag tgatt 45

<210> SEQ ID NO 2335
<211> LENGTH: 45
<212> TYPE: DNA
<213> ORGANISM: Homo sapiens

<400> SEQUENCE: 2335
atctataaaa aactgtacca cagtgatgcc tgttcttcaa aagca 45

<210> SEQ ID NO 2336
<211> LENGTH: 45
<212> TYPE: DNA
<213> ORGANISM: Homo sapiens

<400> SEQUENCE: 2336
ttgtgaaaat gaatatcatg caaataaatt atgcaatttt ttttt 45

<210> SEQ ID NO 2337
<211> LENGTH: 45
<212> TYPE: DNA
<213> ORGANISM: Homo sapiens

<400> SEQUENCE: 2337
ccttcattta actctttgaa actgtatcat ctttgccaag taaga 45

<210> SEQ ID NO 2338
<211> LENGTH: 45
<212> TYPE: DNA
<213> ORGANISM: Homo sapiens

<400> SEQUENCE: 2338
aaactgaaca caagtgccgg caatgtcgat atctataaaa aactg 45

<210> SEQ ID NO 2339
<211> LENGTH: 45
<212> TYPE: DNA
<213> ORGANISM: Homo sapiens

<400> SEQUENCE: 2339
catcctaaaa ggtgttgtaa tggtgaaaac gtcttccttc tttat 45

<210> SEQ ID NO 2340
<211> LENGTH: 45
<212> TYPE: DNA
<213> ORGANISM: Homo sapiens

<400> SEQUENCE: 2340
ttgccaagta agagtggtgg cctatttcag ctgctttgac aaaat 45

<210> SEQ ID NO 2341
<211> LENGTH: 45
<212> TYPE: DNA
<213> ORGANISM: Homo sapiens

<400> SEQUENCE: 2341
gaaatgaatg attctacagc taggacttaa ccttgaaatg gaaag 45

<210> SEQ ID NO 2342
<211> LENGTH: 45
<212> TYPE: DNA
<213> ORGANISM: Homo sapiens

<400> SEQUENCE: 2342
gaaatcaagg atgctcagtt taaggtacac tgtttccatg ttatg 45

<210> SEQ ID NO 2343
<211> LENGTH: 45
<212> TYPE: DNA
<213> ORGANISM: Homo sapiens

<400> SEQUENCE: 2343
tcaacttgaa ctcaagccgc cagagcagga ttgtgggcgg cgaga 45

<210> SEQ ID NO 2344
<211> LENGTH: 45
<212> TYPE: DNA
<213> ORGANISM: Homo sapiens

<400> SEQUENCE: 2344
gacaacctga tcacaccagc catgatctgt gccggcttcc tgcag 45

<210> SEQ ID NO 2345
<211> LENGTH: 45
<212> TYPE: DNA
<213> ORGANISM: Homo sapiens

<400> SEQUENCE: 2345
cacgtgtgcg gaggctccat catcaccccc gagtggatcg tgaca 45

<210> SEQ ID NO 2346
<211> LENGTH: 45
<212> TYPE: DNA
<213> ORGANISM: Homo sapiens

<400> SEQUENCE: 2346
ctgatcacac cagccatgat ctgtgccggc ttcctgcagg ggaac 45

<210> SEQ ID NO 2347
<211> LENGTH: 45
<212> TYPE: DNA

<213> ORGANISM: Homo sapiens

<400> SEQUENCE: 2347
gataacagca agatggcttt gaactcaggg tcaccaccag ctatt 45

<210> SEQ ID NO 2348
<211> LENGTH: 45
<212> TYPE: DNA
<213> ORGANISM: Homo sapiens

<400> SEQUENCE: 2348 ggtgggggc caccgaggag aaagggaaga cctcagaagt gctga 45

<210> SEQ ID NO 2349
<211> LENGTH: 45
<212> TYPE: DNA
<213> ORGANISM: Homo sapiens

<400> SEQUENCE: 2349
tcccgggggc ctggccctgg caggtcagcc tgcacgtcca gaacg 45

<210> SEQ ID NO 2350
<211> LENGTH: 45
<212> TYPE: DNA
<213> ORGANISM: Homo sapiens

<400> SEQUENCE: 2350
gggtgggggg ccaccgagga gaaagggaag acctcagaag tgctg 45

<210> SEQ ID NO 2351
<211> LENGTH: 45
<212> TYPE: DNA
<213> ORGANISM: Homo sapiens

<400> SEQUENCE: 2351
ggggcctggc cctggcaggt cagcctgcac gtccagaacg tccac 45

<210> SEQ ID NO 2352
<211> LENGTH: 45
<212> TYPE: DNA
<213> ORGANISM: Homo sapiens

<400> SEQUENCE: 2352
cttaacaatc catggcattg gacggcattt gcggggattt tgaga 45

<210> SEQ ID NO 2353
<211> LENGTH: 45
<212> TYPE: DNA
<213> ORGANISM: Homo sapiens

<400> SEQUENCE: 2353
acgtccacgt gtgcggaggc tccatcatca cccccgagtg gatcg 45

<210> SEQ ID NO 2354
<211> LENGTH: 45
<212> TYPE: DNA
<213> ORGANISM: Homo sapiens

<400> SEQUENCE: 2354
cctgatcaca ccagccatga tctgtgccgg cttcctgcag gggaa 45

<210> SEQ ID NO 2355
<211> LENGTH: 45

<212> TYPE: DNA
<213> ORGANISM: Homo sapiens

<400> SEQUENCE: 2355
tgacaacctg atcacaccag ccatgatctg tgccggcttc ctgca 45

<210> SEQ ID NO 2356
<211> LENGTH: 45
<212> TYPE: DNA
<213> ORGANISM: Mus sp.

<400> SEQUENCE: 2356
ttgtcccaga cttcctttgt cttcaacaac cttctgcaag aaaac 45

<210> SEQ ID NO 2357
<211> LENGTH: 45
<212> TYPE: DNA
<213> ORGANISM: Mus sp.

<400> SEQUENCE: 2357
aattttaact tcctgtgcac aatgtacctt ttgagatgat tcgaa 45

<210> SEQ ID NO 2358
<211> LENGTH: 45
<212> TYPE: DNA
<213> ORGANISM: Mus sp.

<400> SEQUENCE: 2358
ttgctttgga ggttctggga cagcaactgt tctacgtctg agatg 45

<210> SEQ ID NO 2359
<211> LENGTH: 45
<212> TYPE: DNA
<213> ORGANISM: Mus sp.

<400> SEQUENCE: 2359
ttctgagctg tgagattcca ctgtgaaata tatgaataaa gtata 45

<210> SEQ ID NO 2360
<211> LENGTH: 45
<212> TYPE: DNA
<213> ORGANISM: Mus sp.

<400> SEQUENCE: 2360
aagctgaatg tgagctcagg caacgttgac ctctataaaa aactc 45

<210> SEQ ID NO 2361
<211> LENGTH: 45
<212> TYPE: DNA
<213> ORGANISM: Mus sp.

<400> SEQUENCE: 2361
agacctggag tatacgggaa cgtgacggta tttacagatt ggatc 45

<210> SEQ ID NO 2362
<211> LENGTH: 45
<212> TYPE: DNA
<213> ORGANISM: Mus sp.

<400> SEQUENCE: 2362
tgtcttcaac aaccttctgc aagaaaacca agggcctgaa tttta 45

<210> SEQ ID NO 2363

<211> LENGTH: 45
<212> TYPE: DNA
<213> ORGANISM: Mus sp.

<400> SEQUENCE: 2363
gaagctgcag acacctttgg cttttaatga tctagtgaag ccagt 45

<210> SEQ ID NO 2364
<211> LENGTH: 45
<212> TYPE: DNA
<213> ORGANISM: Mus sp.

<400> SEQUENCE: 2364
ccgcctccgg agatttaagc gagaactgga gtaggtcgtg tactt 45

<210> SEQ ID NO 2365
<211> LENGTH: 45
<212> TYPE: DNA
<213> ORGANISM: Mus sp.

<400> SEQUENCE: 2365
cttgctctcc tgcatgttga catgacggcc ctttccaagg gtgat 45

<210> SEQ ID NO 2366
<211> LENGTH: 45
<212> TYPE: DNA
<213> ORGANISM: Mus sp.

<400> SEQUENCE: 2366
tgatttcagt caccttgctt ctgggttgtg tttcttctct tacta 45

<210> SEQ ID NO 2367
<211> LENGTH: 20
<212> TYPE: RNA
<213> ORGANISM: Homo sapiens

<400> SEQUENCE: 2367
uuggaaagug uaggcuuacc 20

<210> SEQ ID NO 2368
<211> LENGTH: 20
<212> TYPE: RNA
<213> ORGANISM: Mus sp.

<400> SEQUENCE: 2368
cuugaaaugu uauauguuau 20

<210> SEQ ID NO 2369
<211> LENGTH: 20
<212> TYPE: RNA
<213> ORGANISM: Mus sp.

<400> SEQUENCE: 2369
uaugauugau auuuauuauu 20

<210> SEQ ID NO 2370
<211> LENGTH: 20
<212> TYPE: RNA
<213> ORGANISM: Mus sp.

<400> SEQUENCE: 2370
uuaaauaagu aaacuuuaag 20

<210> SEQ ID NO 2371
<211> LENGTH: 20
<212> TYPE: RNA
<213> ORGANISM: Mus sp.

<400> SEQUENCE: 2371
gacacuauuu uaauuauuuu 20

<210> SEQ ID NO 2372
<211> LENGTH: 20
<212> TYPE: RNA
<213> ORGANISM: Mus sp.

<400> SEQUENCE: 2372
ggacacuauu uuaauuauuu 20

<210> SEQ ID NO 2373
<211> LENGTH: 20
<212> TYPE: RNA
<213> ORGANISM: Mus sp.

<400> SEQUENCE: 2373
ugggacacua uuuuaauuau 20

<210> SEQ ID NO 2374
<211> LENGTH: 20
<212> TYPE: RNA
<213> ORGANISM: Mus sp.

<400> SEQUENCE: 2374
guggacauuc cucacugugg 20

<210> SEQ ID NO 2375
<211> LENGTH: 20
<212> TYPE: RNA
<213> ORGANISM: Mus sp.

<400> SEQUENCE: 2375
ugaagaauuu cuaaaaguca 20

<210> SEQ ID NO 2376
<211> LENGTH: 20
<212> TYPE: RNA
<213> ORGANISM: Homo sapiens

<400> SEQUENCE: 2376
augggcaccu cagauuguug 20

<210> SEQ ID NO 2377
<211> LENGTH: 20
<212> TYPE: RNA
<213> ORGANISM: Homo sapiens

<400> SEQUENCE: 2377
ucggcaaaug uagcaugggc 20

<210> SEQ ID NO 2378
<211> LENGTH: 20
<212> TYPE: RNA
<213> ORGANISM: Mus sp.

<400> SEQUENCE: 2378
gauauaauca ggaaauuugc 20

<210> SEQ ID NO 2379
<211> LENGTH: 20
<212> TYPE: RNA
<213> ORGANISM: Homo sapiens

<400> SEQUENCE: 2379
ugagguauac cuagaguacc 20

<210> SEQ ID NO 2380
<211> LENGTH: 20
<212> TYPE: RNA
<213> ORGANISM: Homo sapiens

<400> SEQUENCE: 2380
ggugaaaauc aucacugguc 20

<210> SEQ ID NO 2381
<211> LENGTH: 20
<212> TYPE: RNA
<213> ORGANISM: Homo sapiens

<400> SEQUENCE: 2381
cuugccuggu gaaaaucauc 20

<210> SEQ ID NO 2382
<211> LENGTH: 20
<212> TYPE: RNA
<213> ORGANISM: Mus sp.

<400> SEQUENCE: 2382
ugugcaaugg caauucugau 20

<210> SEQ ID NO 2383
<211> LENGTH: 20
<212> TYPE: RNA
<213> ORGANISM: Homo sapiens

<400> SEQUENCE: 2383
ugaaccuucc aaagauggcu 20

<210> SEQ ID NO 2384
<211> LENGTH: 20
<212> TYPE: RNA
<213> ORGANISM: Homo sapiens

<400> SEQUENCE: 2384
acuggcagaa aacaaccuga 20

<210> SEQ ID NO 2385
<211> LENGTH: 20
<212> TYPE: RNA
<213> ORGANISM: Homo sapiens

<400> SEQUENCE: 2385
gaaagcagca aagaggcacu 20

<210> SEQ ID NO 2386
<211> LENGTH: 20
<212> TYPE: RNA
<213> ORGANISM: Homo sapiens

<400> SEQUENCE: 2386
ucagcccuga gaaaggagac 20

<210> SEQ ID NO 2387
<211> LENGTH: 20
<212> TYPE: RNA
<213> ORGANISM: Mus sp.

<400> SEQUENCE: 2387
ugcuaauuua aauauguuuu 20

<210> SEQ ID NO 2388
<211> LENGTH: 20
<212> TYPE: RNA
<213> ORGANISM: Mus sp.

<400> SEQUENCE: 2388
cuuggaaugu auaaguuuac 20

<210> SEQ ID NO 2389
<211> LENGTH: 45
<212> TYPE: DNA
<213> ORGANISM: Homo sapiens

<400> SEQUENCE: 2389
gagccagatc atttcttgga aagtgtaggc ttacctcaaa taaat 45

<210> SEQ ID NO 2390
<211> LENGTH: 45
<212> TYPE: DNA
<213> ORGANISM: Mus sp.

<400> SEQUENCE: 2390
ttttatgaag tgtcacttga aatgttatat gttatagttt tgaaa 45

<210> SEQ ID NO 2391
<211> LENGTH: 45
<212> TYPE: DNA
<213> ORGANISM: Mus sp.

<400> SEQUENCE: 2391
aactttaagt taatttatga ttgatattta ttatttttat gaagt 45

<210> SEQ ID NO 2392
<211> LENGTH: 45
<212> TYPE: DNA
<213> ORGANISM: Mus sp.

<400> SEQUENCE: 2392
taatttattg ataatttaaa taagtaaact ttaagttaat ttatg 45

<210> SEQ ID NO 2393
<211> LENGTH: 45
<212> TYPE: DNA
<213> ORGANISM: Mus sp.

<400> SEQUENCE: 2393
caatatgaat gttgggacac tattttaatt atttttaatt tattg 45

<210> SEQ ID NO 2394
<211> LENGTH: 45
<212> TYPE: DNA
<213> ORGANISM: Mus sp.

<400> SEQUENCE: 2394
acaatatgaa tgttgggaca ctattttaat tatttttaat ttatt 45

<210> SEQ ID NO 2395
<211> LENGTH: 45
<212> TYPE: DNA
<213> ORGANISM: Mus sp.

<400> SEQUENCE: 2395
tgacaatatg aatgttggga cactatttta attattttta attta 45

<210> SEQ ID NO 2396
<211> LENGTH: 45
<212> TYPE: DNA
<213> ORGANISM: Mus sp.

<400> SEQUENCE: 2396
taagcatatc agtttgtgga cattcctcac tgtggtcaga aaata 45

<210> SEQ ID NO 2397
<211> LENGTH: 45
<212> TYPE: DNA
<213> ORGANISM: Mus sp.

<400> SEQUENCE: 2397
catcttgaaa tcacttgaag aatttctaaa agtcactttg agatc 45

<210> SEQ ID NO 2398
<211> LENGTH: 45
<212> TYPE: DNA
<213> ORGANISM: Homo sapiens

<400> SEQUENCE: 2398
ttcggcaaat gtagcatggg cacctcagat tgttgttgtt aatgg 45

<210> SEQ ID NO 2399
<211> LENGTH: 45
<212> TYPE: DNA
<213> ORGANISM: Homo sapiens

<400> SEQUENCE: 2399
cagcctgagg gctcttcggc aaatgtagca tgggcacctc agatt 45

<210> SEQ ID NO 2400
<211> LENGTH: 45
<212> TYPE: DNA
<213> ORGANISM: Mus sp.

<400> SEQUENCE: 2400
gatgctacca aactggatat aatcaggaaa tttgcctatt gaaaa 45

<210> SEQ ID NO 2401
<211> LENGTH: 45
<212> TYPE: DNA
<213> ORGANISM: Homo sapiens

<400> SEQUENCE: 2401
tggtcttttg gagtttgagg tatacctaga gtacctccag aacag 45

<210> SEQ ID NO 2402
<211> LENGTH: 45
<212> TYPE: DNA
<213> ORGANISM: Homo sapiens

<400> SEQUENCE: 2402
tgaggagact tgcctggtga aaatcatcac tggtcttttg gagtt 45

<210> SEQ ID NO 2403
<211> LENGTH: 45
<212> TYPE: DNA
<213> ORGANISM: Homo sapiens

<400> SEQUENCE: 2403
gattcaatga ggagacttgc ctggtgaaaa tcatcactgg tcttt 45

<210> SEQ ID NO 2404
<211> LENGTH: 45
<212> TYPE: DNA
<213> ORGANISM: Mus sp.

<400> SEQUENCE: 2404
aaatgagaaa agagttgtgc aatggcaatt ctgattgtat gaaca 45

<210> SEQ ID NO 2405
<211> LENGTH: 45
<212> TYPE: DNA
<213> ORGANISM: Homo sapiens

<400> SEQUENCE: 2405
tggcagaaaa caacctgaac cttccaaaga tggctgaaaa agatg 45

<210> SEQ ID NO 2406
<211> LENGTH: 45
<212> TYPE: DNA
<213> ORGANISM: Homo sapiens

<400> SEQUENCE: 2406
aagcagcaaa gaggcactgg cagaaaacaa cctgaacctt ccaaa 45

<210> SEQ ID NO 2407
<211> LENGTH: 45
<212> TYPE: DNA
<213> ORGANISM: Homo sapiens

<400> SEQUENCE: 2407
aagagtaaca tgtgtgaaag cagcaaagag gcactggcag aaaac 45

<210> SEQ ID NO 2408
<211> LENGTH: 45
<212> TYPE: DNA
<213> ORGANISM: Homo sapiens

<400> SEQUENCE: 2408
atcctcgacg gcatctcagc cctgagaaag gagacatgta acaag 45

<210> SEQ ID NO 2409
<211> LENGTH: 45
<212> TYPE: DNA
<213> ORGANISM: Mus sp.

<400> SEQUENCE: 2409
tttacctcaa tgaattgcta atttaaatat gtttttaaag aaatc 45

<210> SEQ ID NO 2410
<211> LENGTH: 45
<212> TYPE: DNA
<213> ORGANISM: Mus sp.

<400> SEQUENCE: 2410
ctagccagat ggtttcttgg aatgtataag tttacctcaa tgaat 45

<210> SEQ ID NO 2411
<211> LENGTH: 20
<212> TYPE: RNA
<213> ORGANISM: Homo sapiens

<400> SEQUENCE: 2411
caacccaagu ucaaaggcug 20

<210> SEQ ID NO 2412
<211> LENGTH: 20
<212> TYPE: RNA
<213> ORGANISM: Homo sapiens

<400> SEQUENCE: 2412
ucuaucaaag uucacuugcu 20

<210> SEQ ID NO 2413
<211> LENGTH: 20
<212> TYPE: RNA
<213> ORGANISM: Homo sapiens

<400> SEQUENCE: 2413
acuugcuucu uggaauuaua 20

<210> SEQ ID NO 2414
<211> LENGTH: 20
<212> TYPE: RNA
<213> ORGANISM: Homo sapiens

<400> SEQUENCE: 2414
uuggaauuau aacaccaaua 20

<210> SEQ ID NO 2415
<211> LENGTH: 20
<212> TYPE: RNA
<213> ORGANISM: Homo sapiens

<400> SEQUENCE: 2415
aauccacaag aaugcuuauu 20

<210> SEQ ID NO 2416
<211> LENGTH: 20
<212> TYPE: RNA
<213> ORGANISM: Homo sapiens

<400> SEQUENCE: 2416
gauggcaaga gcaaaucauu 20

<210> SEQ ID NO 2417
<211> LENGTH: 20
<212> TYPE: RNA
<213> ORGANISM: Homo sapiens

<400> SEQUENCE: 2417
gaagagauua aaccauuaua 20

<210> SEQ ID NO 2418
<211> LENGTH: 20
<212> TYPE: RNA
<213> ORGANISM: Homo sapiens

<400> SEQUENCE: 2418
agauuuugga caaaucugua 20

<210> SEQ ID NO 2419
<211> LENGTH: 20
<212> TYPE: RNA
<213> ORGANISM: Homo sapiens

<400> SEQUENCE: 2419
uuggacagaa accaaacaua 20

<210> SEQ ID NO 2420
<211> LENGTH: 20
<212> TYPE: RNA
<213> ORGANISM: Homo sapiens

<400> SEQUENCE: 2420
ccuaauauga cucaaggauu 20

<210> SEQ ID NO 2421
<211> LENGTH: 20
<212> TYPE: RNA
<213> ORGANISM: Homo sapiens

<400> SEQUENCE: 2421
ucugcuaaga aauggagcua 20

<210> SEQ ID NO 2422
<211> LENGTH: 20
<212> TYPE: RNA
<213> ORGANISM: Homo sapiens

<400> SEQUENCE: 2422
ggggaaauca ugucacuuuc 20

<210> SEQ ID NO 2423
<211> LENGTH: 20
<212> TYPE: RNA
<213> ORGANISM: Homo sapiens

<400> SEQUENCE: 2423
ugaaacagaa auaaacuucc 20

<210> SEQ ID NO 2424
<211> LENGTH: 20
<212> TYPE: RNA
<213> ORGANISM: Homo sapiens

<400> SEQUENCE: 2424
ucacgauugu ugggacucug 20

<210> SEQ ID NO 2425
<211> LENGTH: 20
<212> TYPE: RNA
<213> ORGANISM: Homo sapiens

<400> SEQUENCE: 2425
guggaggugg auggucuuua 20

<210> SEQ ID NO 2426
<211> LENGTH: 20
<212> TYPE: RNA

<213> ORGANISM: Homo sapiens

<400> SEQUENCE: 2426
cuaaugauua cucauucauu 20

<210> SEQ ID NO 2427
<211> LENGTH: 20
<212> TYPE: RNA
<213> ORGANISM: Homo sapiens

<400> SEQUENCE: 2427
uucgauauua cacaaggacc 20

<210> SEQ ID NO 2428
<211> LENGTH: 20
<212> TYPE: RNA
<213> ORGANISM: Homo sapiens

<400> SEQUENCE: 2428
cuuuaccaau uccaguuuca 20

<210> SEQ ID NO 2429
<211> LENGTH: 20
<212> TYPE: RNA
<213> ORGANISM: Homo sapiens

<400> SEQUENCE: 2429
cugcacaaau gugacaucuc 20

<210> SEQ ID NO 2430
<211> LENGTH: 20
<212> TYPE: RNA
<213> ORGANISM: Homo sapiens

<400> SEQUENCE: 2430
uagaaaauau aagaugauaa 20

<210> SEQ ID NO 2431
<211> LENGTH: 20
<212> TYPE: RNA
<213> ORGANISM: Homo sapiens

<400> SEQUENCE: 2431
auggccaagg agagagcauc 20

<210> SEQ ID NO 2432
<211> LENGTH: 20
<212> TYPE: RNA
<213> ORGANISM: Homo sapiens

<400> SEQUENCE: 2432
auugacauug cuuucaguau 20

<210> SEQ ID NO 2433
<211> LENGTH: 20
<212> TYPE: RNA
<213> ORGANISM: Homo sapiens

<400> SEQUENCE: 2433
uucaguauuu auuucugucu 20

<210> SEQ ID NO 2434
<211> LENGTH: 20

<212> TYPE: RNA
<213> ORGANISM: Homo sapiens

<400> SEQUENCE: 2434
uuuggaaucg aucaugcuuu 20

<210> SEQ ID NO 2435
<211> LENGTH: 45
<212> TYPE: DNA
<213> ORGANISM: Homo sapiens

<400> SEQUENCE: 2435
gttttgaata gcgcccaacc caagttcaaa ggctgataag agaga 45

<210> SEQ ID NO 2436
<211> LENGTH: 45
<212> TYPE: DNA
<213> ORGANISM: Homo sapiens

<400> SEQUENCE: 2436
aagccgaaga cctgttctat caaagttcac ttgcttcttg gaatt 45

<210> SEQ ID NO 2437
<211> LENGTH: 45
<212> TYPE: DNA
<213> ORGANISM: Homo sapiens

<400> SEQUENCE: 2437
gttctatcaa agttcacttg cttcttggaa ttataacacc aatat 45

<210> SEQ ID NO 2438
<211> LENGTH: 45
<212> TYPE: DNA
<213> ORGANISM: Homo sapiens

<400> SEQUENCE: 2438
aagttcactt gcttcttgga attataacac caatattact gaaga 45

<210> SEQ ID NO 2439
<211> LENGTH: 45
<212> TYPE: DNA
<213> ORGANISM: Homo sapiens

<400> SEQUENCE: 2439
gtttgtaacc cagataatcc acaagaatgc ttattacttg aacca 45

<210> SEQ ID NO 2440
<211> LENGTH: 45
<212> TYPE: DNA
<213> ORGANISM: Homo sapiens

<400> SEQUENCE: 2440
ggtcttgaaa aatgagatgg caagagcaaa tcattatgag gacta 45

<210> SEQ ID NO 2441
<211> LENGTH: 45
<212> TYPE: DNA
<213> ORGANISM: Homo sapiens

<400> SEQUENCE: 2441
gtggaacata cctttgaaga gattaaacca ttatatgaac atctt 45

<210> SEQ ID NO 2442

<211> LENGTH: 45
<212> TYPE: DNA
<213> ORGANISM: Homo sapiens

<400> SEQUENCE: 2442
ggtgatatgt ggggtagatt ttggacaaat ctgtactctt tgaca 45

<210> SEQ ID NO 2443
<211> LENGTH: 45
<212> TYPE: DNA
<213> ORGANISM: Homo sapiens

<400> SEQUENCE: 2443
ctttgacagt tccctttgga cagaaaccaa acatagatgt tactg 45

<210> SEQ ID NO 2444
<211> LENGTH: 45
<212> TYPE: DNA
<213> ORGANISM: Homo sapiens

<400> SEQUENCE: 2444
gtatctgttg gtcttcctaa tatgactcaa ggattctggg aaaat 45

<210> SEQ ID NO 2445
<211> LENGTH: 45
<212> TYPE: DNA
<213> ORGANISM: Homo sapiens

<400> SEQUENCE: 2445
tgctgcacaa ccttttctgc taagaaatgg agctaatgaa ggatt 45

<210> SEQ ID NO 2446
<211> LENGTH: 45
<212> TYPE: DNA
<213> ORGANISM: Homo sapiens

<400> SEQUENCE: 2446
ttccatgaag ctgttgggga aatcatgtca ctttctgcag ccaca 45

<210> SEQ ID NO 2447
<211> LENGTH: 45
<212> TYPE: DNA
<213> ORGANISM: Homo sapiens

<400> SEQUENCE: 2447
ttttcaagaa gacaatgaaa cagaaataaa cttcctgctc aaaca 45

<210> SEQ ID NO 2448
<211> LENGTH: 45
<212> TYPE: DNA
<213> ORGANISM: Homo sapiens

<400> SEQUENCE: 2448
tgctcaaaca agcactcacg attgttggga ctctgccatt tactt 45

<210> SEQ ID NO 2449
<211> LENGTH: 45
<212> TYPE: DNA
<213> ORGANISM: Homo sapiens

<400> SEQUENCE: 2449
ttacatgtta gagaagtgga ggtggatggt ctttaaaggg gaaat 45

-continued

<210> SEQ ID NO 2450
<211> LENGTH: 45
<212> TYPE: DNA
<213> ORGANISM: Homo sapiens

<400> SEQUENCE: 2450
ctctgttcca tgtttctaat gattactcat tcattcgata ttaca 45

<210> SEQ ID NO 2451
<211> LENGTH: 45
<212> TYPE: DNA
<213> ORGANISM: Homo sapiens

<400> SEQUENCE: 2451
atgattactc attcattcga tattacacaa ggacccttta ccaat 45

<210> SEQ ID NO 2452
<211> LENGTH: 45
<212> TYPE: DNA
<213> ORGANISM: Homo sapiens

<400> SEQUENCE: 2452
tattacacaa ggacccttta ccaattccag tttcaagaag cactt 45

<210> SEQ ID NO 2453
<211> LENGTH: 45
<212> TYPE: DNA
<213> ORGANISM: Homo sapiens

<400> SEQUENCE: 2453
aaacatgaag gccctctgca caaatgtgac atctcaaact ctaca 45

<210> SEQ ID NO 2454
<211> LENGTH: 45
<212> TYPE: DNA
<213> ORGANISM: Homo sapiens

<400> SEQUENCE: 2454
gttaatttca tggtatagaa aatataagat gataaagata tcatt 45

<210> SEQ ID NO 2455
<211> LENGTH: 45
<212> TYPE: DNA
<213> ORGANISM: Homo sapiens

<400> SEQUENCE: 2455
ttgtccaaag acaacatggc caaggagaga gcatcttcat tgaca 45

<210> SEQ ID NO 2456
<211> LENGTH: 45
<212> TYPE: DNA
<213> ORGANISM: Homo sapiens

<400> SEQUENCE: 2456
ggagagagca tcttcattga cattgctttc agtatttatt tctgt 45

<210> SEQ ID NO 2457
<211> LENGTH: 45
<212> TYPE: DNA
<213> ORGANISM: Homo sapiens

<400> SEQUENCE: 2457
ttcattgaca ttgctttcag tatttatttc tgtctctgga tttga 45

<210> SEQ ID NO 2458
<211> LENGTH: 45
<212> TYPE: DNA
<213> ORGANISM: Homo sapiens

<400> SEQUENCE: 2458
ttgcctacag tgatgtttgg aatcgatcat gctttcttca aggtg 45

<210> SEQ ID NO 2459
<211> LENGTH: 20
<212> TYPE: RNA
<213> ORGANISM: Homo sapiens

<400> SEQUENCE: 2459
ucaaccuggg ccagaucuuc 20

<210> SEQ ID NO 2460
<211> LENGTH: 20
<212> TYPE: RNA
<213> ORGANISM: Homo sapiens

<400> SEQUENCE: 2460
auuaccacuu cuggcaucga 20

<210> SEQ ID NO 2461
<211> LENGTH: 20
<212> TYPE: RNA
<213> ORGANISM: Homo sapiens

<400> SEQUENCE: 2461
gcaggcaauu augauccugg 20

<210> SEQ ID NO 2462
<211> LENGTH: 20
<212> TYPE: RNA
<213> ORGANISM: Homo sapiens

<400> SEQUENCE: 2462
uuugauguca augaccagga 20

<210> SEQ ID NO 2463
<211> LENGTH: 20
<212> TYPE: RNA
<213> ORGANISM: Homo sapiens

<400> SEQUENCE: 2463
gaggccaaua agaaccucac 20

<210> SEQ ID NO 2464
<211> LENGTH: 20
<212> TYPE: RNA
<213> ORGANISM: Homo sapiens

<400> SEQUENCE: 2464
uucaugacaa cucauuccug 20

<210> SEQ ID NO 2465
<211> LENGTH: 20
<212> TYPE: RNA
<213> ORGANISM: Homo sapiens

<400> SEQUENCE: 2465
ugggacgcug accaaguuca 20

<210> SEQ ID NO 2466
<211> LENGTH: 20
<212> TYPE: RNA
<213> ORGANISM: Homo sapiens

<400> SEQUENCE: 2466
ugaccaaguu cacccucgua 20

<210> SEQ ID NO 2467
<211> LENGTH: 20
<212> TYPE: RNA
<213> ORGANISM: Homo sapiens

<400> SEQUENCE: 2467
uuuuaauuca ccaaaguauu 20

<210> SEQ ID NO 2468
<211> LENGTH: 20
<212> TYPE: RNA
<213> ORGANISM: Homo sapiens

<400> SEQUENCE: 2468
uuuaauucac caaaguauuu 20

<210> SEQ ID NO 2469
<211> LENGTH: 20
<212> TYPE: RNA
<213> ORGANISM: Homo sapiens

<400> SEQUENCE: 2469
uguuugagga uauauuuuca 20

<210> SEQ ID NO 2470
<211> LENGTH: 20
<212> TYPE: RNA
<213> ORGANISM: Homo sapiens

<400> SEQUENCE: 2470
uuugaggaua uauuuucacu 20

<210> SEQ ID NO 2471
<211> LENGTH: 20
<212> TYPE: RNA
<213> ORGANISM: Homo sapiens

<400> SEQUENCE: 2471
ugaggauaua uuuucacuuu 20

<210> SEQ ID NO 2472
<211> LENGTH: 20
<212> TYPE: RNA
<213> ORGANISM: Homo sapiens

<400> SEQUENCE: 2472
uuucacuuug ugauuauuuc 20

<210> SEQ ID NO 2473
<211> LENGTH: 20
<212> TYPE: RNA
<213> ORGANISM: Homo sapiens

<400> SEQUENCE: 2473
uauuucacuu uagaugcuga 20

<210> SEQ ID NO 2474
<211> LENGTH: 20
<212> TYPE: RNA
<213> ORGANISM: Homo sapiens

<400> SEQUENCE: 2474
uuagaugcug augauuuguu 20

<210> SEQ ID NO 2475
<211> LENGTH: 20
<212> TYPE: RNA
<213> ORGANISM: Homo sapiens

<400> SEQUENCE: 2475
cugguuuugu aagaugcugg 20

<210> SEQ ID NO 2476
<211> LENGTH: 20
<212> TYPE: RNA
<213> ORGANISM: Homo sapiens

<400> SEQUENCE: 2476
uggguuggug cacagugauu 20

<210> SEQ ID NO 2477
<211> LENGTH: 20
<212> TYPE: RNA
<213> ORGANISM: Homo sapiens

<400> SEQUENCE: 2477
cuuguaauuu aaacaggccc 20

<210> SEQ ID NO 2478
<211> LENGTH: 20
<212> TYPE: RNA
<213> ORGANISM: Homo sapiens

<400> SEQUENCE: 2478
uuaaacaggc ccagcauugc 20

<210> SEQ ID NO 2479
<211> LENGTH: 20
<212> TYPE: RNA
<213> ORGANISM: Homo sapiens

<400> SEQUENCE: 2479
cccagcauug cugguucuau 20

<210> SEQ ID NO 2480
<211> LENGTH: 20
<212> TYPE: RNA
<213> ORGANISM: Homo sapiens

<400> SEQUENCE: 2480
ugagauaaug uuagagguuu 20

<210> SEQ ID NO 2481
<211> LENGTH: 20
<212> TYPE: RNA
<213> ORGANISM: Homo sapiens

<400> SEQUENCE: 2481
gagauaaugu uagagguuuu 20

<210> SEQ ID NO 2482
<211> LENGTH: 20
<212> TYPE: RNA
<213> ORGANISM: Homo sapiens

<400> SEQUENCE: 2482
uuagagguuu uaaagugauu 20

<210> SEQ ID NO 2483
<211> LENGTH: 45
<212> TYPE: DNA
<213> ORGANISM: Homo sapiens

<400> SEQUENCE: 2483
ggaagcatgg gttcctcaac ctgggccaga tcttcgggga ctatt 45

<210> SEQ ID NO 2484
<211> LENGTH: 45
<212> TYPE: DNA
<213> ORGANISM: Homo sapiens

<400> SEQUENCE: 2484
agatcttcgg ggactattac cacttctggc atcgaggagt gacga 45

<210> SEQ ID NO 2485
<211> LENGTH: 45
<212> TYPE: DNA
<213> ORGANISM: Homo sapiens

<400> SEQUENCE: 2485
aaccacccgg acttggcagg caattatgat cctggggcca gtttt 45

<210> SEQ ID NO 2486
<211> LENGTH: 45
<212> TYPE: DNA
<213> ORGANISM: Homo sapiens

<400> SEQUENCE: 2486
gatcctgggg ccagttttga tgtcaatgac caggaccctg acccc 45

<210> SEQ ID NO 2487
<211> LENGTH: 45
<212> TYPE: DNA
<213> ORGANISM: Homo sapiens

<400> SEQUENCE: 2487
attgctctca ccctggaggc caataagaac ctcacatggc gggac 45

<210> SEQ ID NO 2488
<211> LENGTH: 45
<212> TYPE: DNA
<213> ORGANISM: Homo sapiens

<400> SEQUENCE: 2488
tttaatgact gggccttcat gacaactcat tcctgggatg aggat 45

<210> SEQ ID NO 2489
<211> LENGTH: 45
<212> TYPE: DNA
<213> ORGANISM: Homo sapiens

<400> SEQUENCE: 2489
cgaagccaac aactatggga cgctgaccaa gttcaccctc gtact 45

<210> SEQ ID NO 2490
<211> LENGTH: 45
<212> TYPE: DNA
<213> ORGANISM: Homo sapiens

<400> SEQUENCE: 2490
acaactatgg gacgctgacc aagttcaccc tcgtactcta tggca 45

<210> SEQ ID NO 2491
<211> LENGTH: 45
<212> TYPE: DNA
<213> ORGANISM: Homo sapiens

<400> SEQUENCE: 2491
ccctccttgg gcacttttta attcaccaaa gtattttttt atctt 45

<210> SEQ ID NO 2492
<211> LENGTH: 45
<212> TYPE: DNA
<213> ORGANISM: Homo sapiens

<400> SEQUENCE: 2492
cctccttggg cactttttaa ttcaccaaag tattttttta tcttg 45

<210> SEQ ID NO 2493
<211> LENGTH: 45
<212> TYPE: DNA
<213> ORGANISM: Homo sapiens

<400> SEQUENCE: 2493
ggggatctca ggggctgttt gaggatatat tttcactttg tgatt 45

<210> SEQ ID NO 2494
<211> LENGTH: 45
<212> TYPE: DNA
<213> ORGANISM: Homo sapiens

<400> SEQUENCE: 2494
ggatctcagg ggctgtttga ggatatattt tcactttgtg attat 45

<210> SEQ ID NO 2495
<211> LENGTH: 45
<212> TYPE: DNA
<213> ORGANISM: Homo sapiens

<400> SEQUENCE: 2495
atctcagggg ctgtttgagg atatattttc actttgtgat tattt 45

<210> SEQ ID NO 2496
<211> LENGTH: 45
<212> TYPE: DNA
<213> ORGANISM: Homo sapiens

<400> SEQUENCE: 2496
tgtttgagga tatattttca ctttgtgatt atttcacttt agatg 45

<210> SEQ ID NO 2497
<211> LENGTH: 45
<212> TYPE: DNA
<213> ORGANISM: Homo sapiens

<400> SEQUENCE: 2497
ttttcacttt gtgattattt cactttagat gctgatgatt tgttt 45

<210> SEQ ID NO 2498
<211> LENGTH: 45
<212> TYPE: DNA
<213> ORGANISM: Homo sapiens

<400> SEQUENCE: 2498
tgtgattatt tcactttaga tgctgatgat ttgtttttgt atttt 45

<210> SEQ ID NO 2499
<211> LENGTH: 45
<212> TYPE: DNA
<213> ORGANISM: Homo sapiens

<400> SEQUENCE: 2499
tcgtggccag cccggctggt tttgtaagat gctgggttgg tgcac 45

<210> SEQ ID NO 2500
<211> LENGTH: 45
<212> TYPE: DNA
<213> ORGANISM: Homo sapiens

<400> SEQUENCE: 2500
ggttttgtaa gatgctgggt tggtgcacag tgattttttt cttgt 45

<210> SEQ ID NO 2501
<211> LENGTH: 45
<212> TYPE: DNA
<213> ORGANISM: Homo sapiens

<400> SEQUENCE: 2501
cacagtgatt tttttcttgt aatttaaaca ggcccagcat tgctg 45

<210> SEQ ID NO 2502
<211> LENGTH: 45
<212> TYPE: DNA
<213> ORGANISM: Homo sapiens

<400> SEQUENCE: 2502
ttttttcctt gtaatttaaa caggcccagc attgctggtt ctatt 45

<210> SEQ ID NO 2503
<211> LENGTH: 45
<212> TYPE: DNA
<213> ORGANISM: Homo sapiens

<400> SEQUENCE: 2503
tgtaatttaa acaggcccag cattgctggt tctatttaat ggaca 45

<210> SEQ ID NO 2504
<211> LENGTH: 45
<212> TYPE: DNA
<213> ORGANISM: Homo sapiens

<400> SEQUENCE: 2504
tctatttaat ggacatgaga taatgttaga ggttttaaag tgatt 45

<210> SEQ ID NO 2505
<211> LENGTH: 45
<212> TYPE: DNA

<213> ORGANISM: Homo sapiens

<400> SEQUENCE: 2505
ctatttaatg gacatgagat aatgttagag gttttaaagt gatta 45

<210> SEQ ID NO 2506
<211> LENGTH: 45
<212> TYPE: DNA
<213> ORGANISM: Homo sapiens

<400> SEQUENCE: 2506
ggacatgaga taatgttaga ggttttaaag tgattaaacg tgcag 45

<210> SEQ ID NO 2507
<211> LENGTH: 20
<212> TYPE: RNA
<213> ORGANISM: Homo sapiens

<400> SEQUENCE: 2507
ugagucaugu gcgaguggga 20

<210> SEQ ID NO 2508
<211> LENGTH: 20
<212> TYPE: RNA
<213> ORGANISM: Homo sapiens

<400> SEQUENCE: 2508
agagccggaa gacaaugcca 20

<210> SEQ ID NO 2509
<211> LENGTH: 20
<212> TYPE: RNA
<213> ORGANISM: Homo sapiens

<400> SEQUENCE: 2509
cucagcaaug uuguuuguga 20

<210> SEQ ID NO 2510
<211> LENGTH: 20
<212> TYPE: RNA
<213> ORGANISM: Homo sapiens

<400> SEQUENCE: 2510
gcucuuggug aggaaguuuc 20

<210> SEQ ID NO 2511
<211> LENGTH: 20
<212> TYPE: RNA
<213> ORGANISM: Homo sapiens

<400> SEQUENCE: 2511
agugucggga gcaaguucag 20

<210> SEQ ID NO 2512
<211> LENGTH: 20
<212> TYPE: RNA
<213> ORGANISM: Homo sapiens

<400> SEQUENCE: 2512
uucagcaaaa cucaaaccuu 20

<210> SEQ ID NO 2513
<211> LENGTH: 20

```
<212> TYPE: RNA
<213> ORGANISM: Homo sapiens

<400> SEQUENCE: 2513

ucaaaccuuu caggguugug                                               20

<210> SEQ ID NO 2514
<211> LENGTH: 20
<212> TYPE: RNA
<213> ORGANISM: Homo sapiens

<400> SEQUENCE: 2514

uucaggguug uggaaucuug                                               20

<210> SEQ ID NO 2515
<211> LENGTH: 20
<212> TYPE: RNA
<213> ORGANISM: Homo sapiens

<400> SEQUENCE: 2515

cacuccugga acucaucuuu                                               20

<210> SEQ ID NO 2516
<211> LENGTH: 20
<212> TYPE: RNA
<213> ORGANISM: Homo sapiens

<400> SEQUENCE: 2516

acuccuggaa cucaucuuuc                                               20

<210> SEQ ID NO 2517
<211> LENGTH: 20
<212> TYPE: RNA
<213> ORGANISM: Homo sapiens

<400> SEQUENCE: 2517

gguuugagcu cagauaucgg                                               20

<210> SEQ ID NO 2518
<211> LENGTH: 20
<212> TYPE: RNA
<213> ORGANISM: Homo sapiens

<400> SEQUENCE: 2518

ucagauaucg ggcugaacgg                                               20

<210> SEQ ID NO 2519
<211> LENGTH: 20
<212> TYPE: RNA
<213> ORGANISM: Homo sapiens

<400> SEQUENCE: 2519

cugaacgguc aaagacauuc                                               20

<210> SEQ ID NO 2520
<211> LENGTH: 20
<212> TYPE: RNA
<213> ORGANISM: Homo sapiens

<400> SEQUENCE: 2520

aaagacauuc acaacaugga                                               20

<210> SEQ ID NO 2521
```

<211> LENGTH: 20
<212> TYPE: RNA
<213> ORGANISM: Homo sapiens

<400> SEQUENCE: 2521
uccagcauca cugugucauc 20

<210> SEQ ID NO 2522
<211> LENGTH: 20
<212> TYPE: RNA
<213> ORGANISM: Homo sapiens

<400> SEQUENCE: 2522
uuggacagaa ggucuccuga 20

<210> SEQ ID NO 2523
<211> LENGTH: 20
<212> TYPE: RNA
<213> ORGANISM: Homo sapiens

<400> SEQUENCE: 2523
ccugagaggg ucacugcaaa 20

<210> SEQ ID NO 2524
<211> LENGTH: 20
<212> TYPE: RNA
<213> ORGANISM: Homo sapiens

<400> SEQUENCE: 2524
cacugcaaaa gagaaucucg 20

<210> SEQ ID NO 2525
<211> LENGTH: 20
<212> TYPE: RNA
<213> ORGANISM: Homo sapiens

<400> SEQUENCE: 2525
ugcaaaagag aaucucguuc 20

<210> SEQ ID NO 2526
<211> LENGTH: 20
<212> TYPE: RNA
<213> ORGANISM: Homo sapiens

<400> SEQUENCE: 2526
guggaccacg ccuaaacuaa 20

<210> SEQ ID NO 2527
<211> LENGTH: 20
<212> TYPE: RNA
<213> ORGANISM: Homo sapiens

<400> SEQUENCE: 2527
uggaccacgc cuaaacuaau 20

<210> SEQ ID NO 2528
<211> LENGTH: 20
<212> TYPE: RNA
<213> ORGANISM: Homo sapiens

<400> SEQUENCE: 2528
ugugccagcu ggagugauga 20

<210> SEQ ID NO 2529
<211> LENGTH: 45
<212> TYPE: DNA
<213> ORGANISM: Homo sapiens

<400> SEQUENCE: 2529
gaccgtccgc cgctctgagt catgtgcgag tgggaagtcg cactg 45

<210> SEQ ID NO 2530
<211> LENGTH: 45
<212> TYPE: DNA
<213> ORGANISM: Homo sapiens

<400> SEQUENCE: 2530
gacctgcccg ggggtagagc cggaagacaa tgccactgtt cactg 45

<210> SEQ ID NO 2531
<211> LENGTH: 45
<212> TYPE: DNA
<213> ORGANISM: Homo sapiens

<400> SEQUENCE: 2531
ttccggaaga gccccctcag caatgttgtt tgtgagtggg gtcct 45

<210> SEQ ID NO 2532
<211> LENGTH: 45
<212> TYPE: DNA
<213> ORGANISM: Homo sapiens

<400> SEQUENCE: 2532
gacgacaaag gctgtgctct tggtgaggaa gtttcagaac agtcc 45

<210> SEQ ID NO 2533
<211> LENGTH: 45
<212> TYPE: DNA
<213> ORGANISM: Homo sapiens

<400> SEQUENCE: 2533
atgtgcgtcg ccagtagtgt cgggagcaag ttcagcaaaa ctcaa 45

<210> SEQ ID NO 2534
<211> LENGTH: 45
<212> TYPE: DNA
<213> ORGANISM: Homo sapiens

<400> SEQUENCE: 2534
agtgtcggga gcaagttcag caaaactcaa acctttcagg gttgt 45

<210> SEQ ID NO 2535
<211> LENGTH: 45
<212> TYPE: DNA
<213> ORGANISM: Homo sapiens

<400> SEQUENCE: 2535
caagttcagc aaaactcaaa cctttcaggg ttgtggaatc ttgca 45

<210> SEQ ID NO 2536
<211> LENGTH: 45
<212> TYPE: DNA
<213> ORGANISM: Homo sapiens

<400> SEQUENCE: 2536
gcaaaactca aacctttcag ggttgtggaa tcttgcagcc tgatc 45

<210> SEQ ID NO 2537
<211> LENGTH: 45
<212> TYPE: DNA
<213> ORGANISM: Homo sapiens

<400> SEQUENCE: 2537
acctggcaag acccccactc ctggaactca tctttctaca gacta 45

<210> SEQ ID NO 2538
<211> LENGTH: 45
<212> TYPE: DNA
<213> ORGANISM: Homo sapiens

<400> SEQUENCE: 2538
cctggcaaga cccccactcc tggaactcat ctttctacag actac 45

<210> SEQ ID NO 2539
<211> LENGTH: 45
<212> TYPE: DNA
<213> ORGANISM: Homo sapiens

<400> SEQUENCE: 2539
ctttctacag actacggttt gagctcagat atcgggctga acggt 45

<210> SEQ ID NO 2540
<211> LENGTH: 45
<212> TYPE: DNA
<213> ORGANISM: Homo sapiens

<400> SEQUENCE: 2540
gactacggtt tgagctcaga tatcgggctg aacggtcaaa gacat 45

<210> SEQ ID NO 2541
<211> LENGTH: 45
<212> TYPE: DNA
<213> ORGANISM: Homo sapiens

<400> SEQUENCE: 2541
agctcagata tcgggctgaa cggtcaaaga cattcacaac atgga 45

<210> SEQ ID NO 2542
<211> LENGTH: 45
<212> TYPE: DNA
<213> ORGANISM: Homo sapiens

<400> SEQUENCE: 2542
tcgggctgaa cggtcaaaga cattcacaac atggatggtc aagga 45

<210> SEQ ID NO 2543
<211> LENGTH: 45
<212> TYPE: DNA
<213> ORGANISM: Homo sapiens

<400> SEQUENCE: 2543
ggatggtcaa ggacctccag catcactgtg tcatccacga cgcct 45

<210> SEQ ID NO 2544
<211> LENGTH: 45
<212> TYPE: DNA
<213> ORGANISM: Homo sapiens

<400> SEQUENCE: 2544
ggccatgggc acgccttgga cagaaggtct cctgagaggg tcact 45

<210> SEQ ID NO 2545
<211> LENGTH: 45
<212> TYPE: DNA
<213> ORGANISM: Homo sapiens

<400> SEQUENCE: 2545
ttggacagaa ggtctcctga gagggtcact gcaaaagaga atctc 45

<210> SEQ ID NO 2546
<211> LENGTH: 45
<212> TYPE: DNA
<213> ORGANISM: Homo sapiens

<400> SEQUENCE: 2546
gtctcctgag agggtcactg caaaagagaa tctcgttcca acctc 45

<210> SEQ ID NO 2547
<211> LENGTH: 45
<212> TYPE: DNA
<213> ORGANISM: Homo sapiens

<400> SEQUENCE: 2547
tcctgagagg gtcactgcaa aagagaatct cgttccaacc tccct 45

<210> SEQ ID NO 2548
<211> LENGTH: 45
<212> TYPE: DNA
<213> ORGANISM: Homo sapiens

<400> SEQUENCE: 2548
cctgtcaatc tgaacgtgga ccacgcctaa actaattttt gactg 45

<210> SEQ ID NO 2549
<211> LENGTH: 45
<212> TYPE: DNA
<213> ORGANISM: Homo sapiens

<400> SEQUENCE: 2549
ctgtcaatct gaacgtggac cacgcctaaa ctaatttttg actgc 45

<210> SEQ ID NO 2550
<211> LENGTH: 45
<212> TYPE: DNA
<213> ORGANISM: Homo sapiens

<400> SEQUENCE: 2550
ctaatttttg actgctgtgc cagctggagt gatgataggc tcact 45

<210> SEQ ID NO 2551
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2551
gcaagtgaac tttgat 16

<210> SEQ ID NO 2552
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2552
aaaggcagac catttg 16

<210> SEQ ID NO 2553
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2553
ggcctcagct gcttgc 16

<210> SEQ ID NO 2554
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2554
gccgcggctg tagtca 16

<210> SEQ ID NO 2555
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2555
atcaactggc cgcggc 16

<210> SEQ ID NO 2556
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2556
taccccacat atcacc 16

<210> SEQ ID NO 2557
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2557
aggcctggtc caccat 16

<210> SEQ ID NO 2558
<211> LENGTH: 16
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 2558
tcttcttgaa aatcgg 16

<210> SEQ ID NO 2559
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2559
aagaccatcc acctcc 16

<210> SEQ ID NO 2560
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2560
gggtcacagt atgttt 16

<210> SEQ ID NO 2561
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2561
gatgtcacat ttgtgc 16

<210> SEQ ID NO 2562
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2562
gagttcacgg aggccc 16

<210> SEQ ID NO 2563
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2563
ccggggctga ctggtg 16

<210> SEQ ID NO 2564
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2564
aagatctggc ccaggt 16

<210> SEQ ID NO 2565
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2565
gtcacctcgc catcca 16

<210> SEQ ID NO 2566
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2566
tcatcctcgg ggcccc 16

<210> SEQ ID NO 2567
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2567
cgcagttgca gctgtc 16

<210> SEQ ID NO 2568
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2568
tggcgctgct gatgga 16

<210> SEQ ID NO 2569
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2569
tgatgccggc tgctaa 16

<210> SEQ ID NO 2570
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2570 gctgggggc cactgt 16

<210> SEQ ID NO 2571
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2571
cacatgaggc gtggca 16

<210> SEQ ID NO 2572
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2572
gtggcacatg aggcgt 16

<210> SEQ ID NO 2573
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2573
agggcgctct ggtctt 16

<210> SEQ ID NO 2574
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2574
tcagagggcg ctctgg 16

<210> SEQ ID NO 2575
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 2575
ugaaaguuca aucauucuuu u 21

<210> SEQ ID NO 2576
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 2576
aaugauugaa cuuuca 16

<210> SEQ ID NO 2577
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2577
ugaaauuugg aucuuuguuu u 21

<210> SEQ ID NO 2578
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2578
aaagauccaa auuuca 16

<210> SEQ ID NO 2579
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2579
uaagcuuaaa gaaugucuuu u 21

<210> SEQ ID NO 2580
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2580
acauucuuua agcuua 16

<210> SEQ ID NO 2581
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2581
ucaaauacga cucugucuuu u 21

<210> SEQ ID NO 2582
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2582

-continued acagagucgu auuuga 16

<210> SEQ ID NO 2583
<211> LENGTH: 20
<212> TYPE: DNA
<213> ORGANISM: Severe acute respiratory syndrome coronavirus 2

<400> SEQUENCE: 2583
tttgctaaca aacatgctga 20

<210> SEQ ID NO 2584
<211> LENGTH: 20
<212> TYPE: DNA
<213> ORGANISM: Severe acute respiratory syndrome-related coronavirus

<400> SEQUENCE: 2584
tttgcaaata aacatgctgg 20

<210> SEQ ID NO 2585
<211> LENGTH: 19
<212> TYPE: DNA
<213> ORGANISM: Middle East respiratory syndrome-related coronavirus

<400> SEQUENCE: 2585
tttgctaata agcaccggt 19

<210> SEQ ID NO 2586
<211> LENGTH: 20
<212> TYPE: DNA
<213> ORGANISM: Human coronavirus NL63

<400> SEQUENCE: 2586
gttcgtaatg tttttgataa 20

<210> SEQ ID NO 2587
<211> LENGTH: 20
<212> TYPE: DNA
<213> ORGANISM: Human coronavirus 229E

<400> SEQUENCE: 2587
gtcagaaacg tttttgaaaa 20

<210> SEQ ID NO 2588
<211> LENGTH: 20
<212> TYPE: DNA
<213> ORGANISM: Human coronavirus HKU1

<400> SEQUENCE: 2588
tttgctaata aatttttcca 20

<210> SEQ ID NO 2589
<211> LENGTH: 20
<212> TYPE: DNA
<213> ORGANISM: Unknown
<220> FEATURE:
<223> OTHER INFORMATION: Description of Unknown:
Human coronavirus OC43 sequence

<400> SEQUENCE: 2589
ttcgctaaca aatttgaaca 20

<210> SEQ ID NO 2590
<211> LENGTH: 20

<212> TYPE: DNA
<213> ORGANISM: Severe acute respiratory syndrome coronavirus 2

<400> SEQUENCE: 2590
ggtaactggt atgatttcgg 20

<210> SEQ ID NO 2591
<211> LENGTH: 20
<212> TYPE: DNA
<213> ORGANISM: Severe acute respiratory syndrome-related coronavirus

<400> SEQUENCE: 2591
gggaactggt acgatttcgg 20

<210> SEQ ID NO 2592
<211> LENGTH: 20
<212> TYPE: DNA
<213> ORGANISM: Middle East respiratory syndrome-related coronavirus

<400> SEQUENCE: 2592
ggcaagtggt atgattttgg 20

<210> SEQ ID NO 2593
<211> LENGTH: 20
<212> TYPE: DNA
<213> ORGANISM: Human coronavirus NL63

<400> SEQUENCE: 2593
ggtaactttt atgattttgg 20

<210> SEQ ID NO 2594
<211> LENGTH: 20
<212> TYPE: DNA
<213> ORGANISM: Human coronavirus 229E

<400> SEQUENCE: 2594
gggaatttct atgacttcgg 20

<210> SEQ ID NO 2595
<211> LENGTH: 20
<212> TYPE: DNA
<213> ORGANISM: Human coronavirus HKU1

<400> SEQUENCE: 2595
ggtcaatggt atgattttgg 20

<210> SEQ ID NO 2596
<211> LENGTH: 20
<212> TYPE: DNA
<213> ORGANISM: Unknown
<220> FEATURE:
<223> OTHER INFORMATION: Description of Unknown:
Human coronavirus OC43 sequence

<400> SEQUENCE: 2596
ggtaaatggt atgattttgg 20